US011638762B2

(12) United States Patent
Neumann et al.

(10) Patent No.: US 11,638,762 B2
(45) Date of Patent: May 2, 2023

(54) TARGETED DELIVERY OF NICOTINAMIDE ADENINE DINUCLEOTIDE SALVAGE PATHWAY INHIBITORS

(71) Applicant: Seagen Inc., Bothell, WA (US)

(72) Inventors: Christopher Scott Neumann, Seattle, WA (US); Kathleen Olivas, Tacoma, WA (US)

(73) Assignee: Seagen Inc., Bothell, WA (US)

( * ) Notice: Subject to any disclaimer, the term of this patent is extended or adjusted under 35 U.S.C. 154(b) by 835 days.

(21) Appl. No.: 16/343,140

(22) PCT Filed: Oct. 18, 2017

(86) PCT No.: PCT/US2017/057116
§ 371 (c)(1),
(2) Date: Apr. 18, 2019

(87) PCT Pub. No.: WO2018/075600
PCT Pub. Date: Apr. 26, 2018

(65) Prior Publication Data
US 2019/0314519 A1    Oct. 17, 2019

Related U.S. Application Data

(60) Provisional application No. 62/409,765, filed on Oct. 18, 2016.

(51) Int. Cl.
| *A61K 47/68* | (2017.01) |
| *A61K 47/54* | (2017.01) |
| *A61P 35/00* | (2006.01) |
| *A61K 31/4468* | (2006.01) |
| *A61K 31/4545* | (2006.01) |
| *A61K 47/51* | (2017.01) |
| *C07K 5/02* | (2006.01) |

(52) U.S. Cl.
CPC ...... *A61K 47/6889* (2017.08); *A61K 31/4468* (2013.01); *A61K 31/4545* (2013.01); *A61K 47/51* (2017.08); *A61K 47/54* (2017.08); *A61K 47/545* (2017.08); *A61K 47/549* (2017.08); *A61K 47/6849* (2017.08); *A61K 47/6851* (2017.08); *A61P 35/00* (2018.01); *C07K 5/0202* (2013.01)

(58) Field of Classification Search
CPC ............ A61K 47/6889; A61K 31/4468; A61K 31/4545; A61K 47/549; A61K 47/6849; A61K 47/6851; A61K 47/51; A61K 47/54; A61K 47/545; A61K 47/6899; A61K 9/0019; A61K 9/08; A61P 35/00; A61P 35/02; A61P 43/00; C07K 5/0202
See application file for complete search history.

(56) References Cited

U.S. PATENT DOCUMENTS

| 4,816,397 | A | 3/1989 | Boss et al. |
| 4,816,567 | A | 3/1989 | Cabilly et al. |
| 5,225,539 | A | 7/1993 | Winter |
| 5,585,089 | A | 12/1996 | Queen et al. |
| 6,214,345 | B1 | 4/2001 | Firestone et al. |
| 6,451,816 | B1 | 9/2002 | Biedermann et al. |
| 7,091,186 | B2 | 8/2006 | Senter et al. |
| 7,498,298 | B2 | 3/2009 | Doronina et al. |
| 7,553,816 | B2 | 6/2009 | Senter et al. |
| 7,754,681 | B2 | 7/2010 | Feng |
| 7,968,687 | B2 | 6/2011 | McDonagh et al. |
| 7,989,434 | B2 | 8/2011 | Feng |
| 8,163,888 | B2 | 4/2012 | Steeves et al. |
| 8,257,706 | B2 | 9/2012 | McDonagh et al. |
| 8,324,165 | B2 | 12/2012 | Penta et al. |
| 10,010,547 | B2 | 7/2018 | Boyle |
| 10,272,072 | B2 | 4/2019 | Bair et al. |
| 2005/0256030 | A1 | 11/2005 | Feng |
| 2009/0018086 | A1 | 1/2009 | Doronina et al. |
| 2009/0111756 | A1 | 4/2009 | Doronina et al. |
| 2009/0274713 | A1 | 11/2009 | Charti et al. |
| 2011/0288024 | A1 | 11/2011 | Penta et al. |
| 2012/0122842 | A1 | 5/2012 | Curtin et al. |
| 2012/0270900 | A1* | 10/2012 | Olesen ................. A61K 31/455 514/318 |
| 2013/0259860 | A1 | 10/2013 | Smith et al. |
| 2013/0309223 | A1 | 11/2013 | Sutherland et al. |
| 2014/0357599 | A1 | 12/2014 | Christensen et al. |

(Continued)

FOREIGN PATENT DOCUMENTS

| EP | 0012023 | A1 | 6/1980 |
| EP | 0012023 | | 11/1980 |

(Continued)

OTHER PUBLICATIONS

Wei et al. Review of various NAMPT inhibitors for the treatment of cancer. Front. Pharmacol., Sep. 7, 2022, pp. 1-23. (Year: 2022).*
Alouane et al., "Self-immolative spacers: kinetic aspects, structure-property relationships, and applications," Angewandte Chemie International Edition, Jun. 22, 2015, 54(26):7492-509.
Beidler et al., "Cloning and high level expression of a chimeric antibody with specificity for human carcinoembryonic antigen," The Journal of Immunology, Dec. 1, 1988, 141(11):4053-60.
Better et al., "*Escherichia coli* secretion of an active chimeric antibody fragment," Science, May 20, 1988, 240(4855):1041-3.

(Continued)

*Primary Examiner* — Marcela M Cordero Garcia
(74) *Attorney, Agent, or Firm* — Morrison & Foerster LLP

(57) ABSTRACT

Compounds and compositions are disclosed in which a NAMPT Drug Unit is linked to a targeting Ligand Unit through a Unit from which a NAMPT inhibitor compound or derivative thereof is released at the targeted site of action. Methods for treating diseases characterized by the targeted abnormal cells, such as cancer or an autoimmune disease, using the compounds and compositions of the invention are also disclosed.

20 Claims, 3 Drawing Sheets

Specification includes a Sequence Listing.

(56) References Cited

U.S. PATENT DOCUMENTS

| | | | |
|---|---|---|---|
| 2017/0247412 A1* | 8/2017 | Burke | A61K 47/545 |
| 2020/0197524 A1 | 6/2020 | Neumann et al. | |

FOREIGN PATENT DOCUMENTS

| | | |
|---|---|---|
| EP | 0171496 | 2/1986 |
| EP | 0171496 A2 | 2/1986 |
| EP | 0173494 | 3/1986 |
| EP | 0173494 A2 | 3/1986 |
| EP | 0184187 | 6/1986 |
| EP | 0184187 A2 | 6/1986 |
| JP | 2012529467 A | 11/2012 |
| TW | 201625316 A | 7/2016 |
| WO | 198601533 A1 | 3/1986 |
| WO | WO 86/01533 | 3/1986 |
| WO | 198702671 A1 | 5/1987 |
| WO | WO 87/02671 | 5/1987 |
| WO | 199734631 A1 | 9/1997 |
| WO | WO 97/34631 | 9/1997 |
| WO | WO97/48397 | 12/1997 |
| WO | WO98/54144 | 12/1998 |
| WO | WO00/61559 | 10/2000 |
| WO | 2003097602 A1 | 11/2003 |
| WO | WO 2003/097602 | 11/2003 |
| WO | 2004010957 A2 | 2/2004 |
| WO | WO 2004/010957 | 2/2004 |
| WO | 2004010957 A3 | 6/2004 |
| WO | 2007038658 A2 | 4/2007 |
| WO | WO 2007/038658 | 4/2007 |
| WO | 2007038658 A3 | 10/2007 |
| WO | WO2009/086835 A1 | 7/2009 |
| WO | WO 2009/099741 | 8/2009 |
| WO | WO2009/156421 A1 | 12/2009 |
| WO | WO 2010/023307 | 3/2010 |
| WO | WO2010/142735 A1 | 12/2010 |
| WO | 2011006988 A1 | 1/2011 |
| WO | WO 2011/006988 | 1/2011 |
| WO | WO2012/031196 A1 | 3/2012 |
| WO | WO2012/031197 A1 | 3/2012 |
| WO | WO2012/067963 A1 | 5/2012 |
| WO | WO2012/067965 A1 | 5/2012 |
| WO | WO2012/150952 A1 | 11/2012 |
| WO | WO2012/154194 A1 | 11/2012 |
| WO | 2012177782 A1 | 12/2012 |
| WO | WO2012/177782 A1 | 12/2012 |
| WO | WO2013/067710 A1 | 5/2013 |
| WO | WO2013/082150 A1 | 6/2013 |
| WO | 2013123152 A2 | 8/2013 |
| WO | WO 2013/123152 | 8/2013 |
| WO | 2013127268 A1 | 9/2013 |
| WO | WO2013/130935 A1 | 9/2013 |
| WO | WO2013/130943 A1 | 9/2013 |
| WO | 2013170191 A1 | 11/2013 |
| WO | WO2013/170112 A1 | 11/2013 |
| WO | WO2013/170113 A1 | 11/2013 |
| WO | WO2013/170115 A1 | 11/2013 |
| WO | WO2013/170118 A1 | 11/2013 |
| WO | WO2013/170191 A1 | 11/2013 |
| WO | WO 2014/068443 | 5/2014 |
| WO | WO2014/074715 A1 | 5/2014 |
| WO | WO2014/111871 A1 | 7/2014 |
| WO | 2013123152 A3 | 11/2014 |
| WO | WO2014/178001 A1 | 11/2014 |
| WO | WO2015/054060 A1 | 4/2015 |
| WO | WO 2015/095755 | 6/2015 |
| WO | WO2015/161142 A1 | 10/2015 |
| WO | WO2015/179759 A1 | 11/2015 |
| WO | WO2016/012958 A1 | 1/2016 |
| WO | 2016040684 A1 | 3/2016 |
| WO | WO2016/040684 A1 | 3/2016 |
| WO | WO2016/095581 A1 | 6/2016 |
| WO | WO2016/118565 A1 | 7/2016 |
| WO | WO2018/075600 A1 | 4/2018 |
| WO | WO 2018/201087 | 11/2018 |

OTHER PUBLICATIONS

Blencowe et al., "Self-immolative linkers in polymeric delivery systems," Polymer Chemistry, Nov. 18, 2010, 2(4):773-90.

Burke et al., "Development of novel quaternary ammonium linkers for antibody-drug conjugates," Molecular Cancer Therapeutics, May 1, 2016, 15(5):938-45.

Fridkin et al., "Peptide synthesis," Annual Review of Biochemistry, 1974, 43(1):419-43.

Gaertner et al., "Chemo-enzymic backbone engineering of proteins. Site-specific incorporation of synthetic peptides that mimic the 64-74 disulfide loop of granulocyte colony-stimulating factor," Journal of Biological Chemistiy, Mar. 11, 1994, 269(10):7224-30.

Greenwald et al., "Drug delivery systems employing 1, 4-or 1, 6-elimination: poly (ethylene glycol) prodmgs of amine-containing compounds," Journal of Medicinal Chemistry, Sep. 9, 1999, 42(18):3657-67.

Han et al., "Recent development of peptide coupling reagents in organic synthesis," Tetrahedron, Mar. 8, 2004, 60(11):2447-67.

Hasmann et al., FK866, A Highly Specific Noncompetitive Inhibitor of Nicotinamide Phosphoribosyltransferase, Represents a Novel Mechanism for Induction of Tumor Cell Apoptosis, Cancer Research, 2003, 63:7634-7442.

Hay et al., "A 2-nitroimidazole carbamate prodrug of 5-amino-1-(chloromethyl)-3-[(5, 6, 7-trimethoxyindol-2-yl) carbonyl]-1, 2-dihydro-3H-benz [e] indole (amino-seco-CBI-TMI) for use with ADEPT and GDEPT," Bioorganic & Medicinal Chemistry Letters, Aug. 2, 1999. 9(15):2237-42.

International Union of Pure and Applied Chemistry, "Definitive rules for nomenclature of organic chemistiy," Journal of American Chemical Society, Nov. 1, 1960, 82(21):5545-74.

Jain et al., "ADC linker chemistry," Pharmaceutical Research, Nov. 1, 2015, 32(11):3526-40.

Jones et al., "Replacing the complementarity-determining regions in a human antibody with those from a mouse," Nature, May 1986, 321(6069):522-5.

Kabat, "Origins of antibody complementarity and specificity—hypervariable regions and minigene hypothesis," The Journal of Immunology, Sep. 1, 1980, 125(3):961-969.

Kozbor et al., "The production of monoclonal antibodies from human lymphocytes," Immunology Today, Mar. 1, 1983, 4(3):72-9.

Laguzza et al., "New antitumor monoclonal antibody-vinca conjugates LY203725 and related compounds: design, preparation, and representative in vivo activity," Journal of Medicinal Chemistiy, Mar. 1989, 32(3):548-55.

Liu et al., "Chimeric mouse-human IgG1 antibody that can mediate lysis of cancer cells," Proceedings of the National Academy of Sciences, May 1, 1987, 84(10):3439-43.

Liu et al., "Production of a mouse-human chimeric monoclonal antibody to CD20 with potent Fc-dependent biologic activity," The Journal of Immunology, Nov. 15, 1987, 139(10):3521-6.

Morrison, "Transfectomas provide novel chimeric antibodies," Science, Sep. 20, 1985, 229(4719):1202-7.

Nishimura et al., "Recombinant human-mouse chimeric monoclonal antibody specific for common acute lymphocytic leukemia antigen," Cancer Research, Feb. 15, 1987, 47(4):999-1005.

Oi et al., "Chimeric antibodies," BioTechniques, 1986, 4(3):214-221.

Olsson et al., "Human-human monoclonal antibody-producing hybridomas: Technical aspects," Methods in Enzymology, Jan. 1, 1983, 92:3-16.

PCT Application No. PCT/US2018/030018, International Preliminary Report on Patentability, 8 pages, dated Nov. 7, 2019.

PCT Application No. PCT/US2018/030018, Search Report and Written Opinion, 14 pages, dated Jul. 4, 2018.

PCT International Search Report and Written Opinion in International Appln. No. 11201903013S, dated Aug. 27, 2020, 8 pages.

Rose et al., "Preparation of well-defined protein conjugates using enzyme-assisted reverse proteolysis," Bioconjugate Chemistry, May 1, 1991, 2(3):154-9.

Schmidt et al., "A modeling analysis of the effects of molecular size and binding affinity on tumor targeting," Molecular Cancer Therapeutics, Oct. 1, 2009, 8(10):2861-71.

(56) References Cited

OTHER PUBLICATIONS

Schwarz et al., "[15] Enzymatic C-terminal biotinylation of proteins," Methods in Enzymology, Jan. 1, 1990; 184:160-2.
Shaw et al., "Mouse/human chimeric antibodies to a tumor-associated antigen: biologic activity of the four human IgG subclasses," JNCI: Journal of the National Cancer Institute, Dec. 7, 1988, 80(19):1553-9.
Sun et al., "Chimeric antibody with human constant regions and mouse variable regions directed against carcinoma-associated antigen 17-1A," Proceedings of the National Academy of Sciences, Jan. 1, 1987, 84(1):214-8.
Teng et al., "Construction and testing of mouse-human heteromyelomas for human monoclonal antibody production," Proceedings of the National Academy of Sciences, Dec. 1, 1983, 80(23):7308-12.
Verhoeyen et al., "Reshaping human antibodies: grafting an antilysozyme activity," Science, Mar. 25, 1988, 239(4847):1534-6.
Veronese et al., PEGylation, successful approach to drug delivery, Drug Discovery Today, 2005, 10(21):1451-1458.
Wood et al., "The synthesis and in vivo assembly of functional antibodies in yeast," Nature, Apr. 4, 1985, 314(6010):446-9.
Hasmann, M. et al. (Nov. 1, 2003). "FK866, A Highly Specific Noncompetitive Inhibitor of Nicotinamide Phosphorisbosyltransferase, Represents a Novel Mechanism For Induction of Tumor Cell Apoptosis," Cancer Research 63:7436-7442.
Jeffrey, S.C. et al. (May-Jun. 2006, e-pub. May 3, 2006). "Development and Properties of β-Glucuronide Linkers for Monoclonal Antibody-Drug Conjugates," American Chemical Society 17(3):831-840.
Lyon, R.P. et al. (Jul. 2015; e-pub. Jun. 15, 2015). "Reducing Hydrophobicity of Homogeneous Antibody-Drug Conjugates Improves Pharmacokinetics and Therapeutic Index," Nat Biotechnol 33(7):733-735.
Lyon, R.P. et al. (Oct. 2014, e-pub. Sep. 7, 2014). "Self-hydrolyzing Maleimides Improve the Stability and Pharmacological Properties of Antibody-Drug Conjugates," Nat Biotechnol 32(10): 1059-1062.
NCBI Accession No. NP_005737.1, "nicotinamide phosphoribosyltransferase precursor [*Homo sapiens*]," Apr. 9, 2017, 3 pages.
Alouane, A. et al. (Jun. 22, 2015, e-pub. Jun. 5, 2015). "Self-Immolative Spacers: Kinetic Aspects, Structure-Property 15 Relationships, And Applications," Angew. Chem. Int. Ed. 54(26):7492-7509. (Abstract Only).
Beidler, C.B. et al. (Dec. 1, 1988). "Cloning and High Level Expression Of A Chimeric Antibody With Specificity For Human Carcinoembryonic Antigen," J. Immunol. 141(11):4053-4060.
Better, M. et al. (May 20, 1988). "*Escherichia coli* Secretion of An Active Chimerica Antibody Fragment," Science 240:1041-1043.
Blencowe, C.A. et al. (2011). "Self-immolative Linkers in Polymeric Delivery Systems," Polymer Chem 2:773-790.
Burke, P.J. et al. (May 2016). "Development of Novel Quaternary Ammonium linkers for Antibody-Drug Conjugates", Molecular Cancer Therapy, 15(5):938-945.
Christensen, M.K. et al. (2013) "Nicotinamide Phosphoribosyltransferase Inhibitors, Design, Preparation, and Structure-Activity Relationships," J. Med. Chem. 56:9071-9088, 57 pages.
Colombano, G. et al. (2009, e-pub. Dec. 4, 2009). "A Novel Potent Nicotinamide Phosphoribosyltransferase Inhibitor Synthesized By Click Chemistry," J. Med. Chem. 53:616-623.
Dragovich, P.S. et al. (Feb. 1, 2014, e-pub. Dec. 21, 2013). "Fragment-Based Design Of 3-Aminopyridine-Derived Amides As Potent Inhibitors Of Human Nicotinamide Phosphoribosyltransferase (NAMPT)," Bioorg. Med. Chem. Lett. 24:954-962.
Fridkin, M. et al. (1974). "Peptide Synthesis," Ann. Rev. Biochem. 43:419-443.
Gaertner, H.F. et al. (Mar. 11, 1994). "Chemo-Enzymic Backbone Engineering of Proteins," J. Biol. Chem. 269(10):7224-7230.
Galli, U. et al. (2008) "Synthesis and Biological Evaluation Of Isosteric Analogues Of FK866, An Inhibitor Of NAD Salvage," Chem. Med. Chem. 3:771-779.

Galli, U. et al. (2013) "Medicinal Chemistry Of Nicotinamide Phosphoribosyltransferase (NAMPT) Inhibitors," J. Med. Chem. 56:6279-6296, 19 pages.
Giannetti, A.M. et al. (Feb. 13, 2014, e-pub. Jan. 22, 2014) "Fragment-Based Identification Of Amides Derived From Trans-2-(Pyridin-3-yl)Cyclopropane Carboxylic Acid As Potent Inhibitors Of Human Nicotinamide Phosphoribosyltransferase (NAMPT)," J. Med. Chem. 57:770-792.
Greenwald, R.B. et al. (1999, e-pub. Aug. 13, 1999). "Drug Delivery Systems Employing 1,4- Or 1,6-Elimination: Poly(Ethylene Glycol) Prodrugs Of Amine-Containing Compounds," J. Med. Chem. 42:3657-3667.
Gunzner-Toste, J. et al. (Jun. 15, 2013, e-pub. Apr. 25, 2013). "Discovery of Potent and Efficacious Urea-Containing Nicotinamide Phosphoribosyltransferase (NAMPT) Inhibitors With Reduced CYP2C9 Inhibition Properties," Bioorg. Med. Chem. Lett. 23:3531-3538.
Han, S.-Y. et al. (2004). "Recent Development Of Peptide Coupling Agents In Organic Synthesis," Tet. 60:2447-2476.
Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," Bioorganic & Medicinal Chemistry Letters 9(15):2237-2242.
International Preliminary Report on Patentability, dated Apr. 23, 2019, for PCT Application No. PCT/US2017/057116, filed Oct. 18, 2017, 12 pages.
International Preliminary Report on Patentability, dated Oct. 29, 2019, for PCT Application No. PCT/US2017/030018, filed Apr. 27, 2018, 7 pages.
International Search Report and Written Opinion, dated Feb. 12, 2018, for PCT Application No. PCT/US2017/057116, filed Oct. 18, 2017, 12 pages.
International Search Report and Written Opinion, dated Jul. 4, 2018, for PCT Application No. PCT/US2017/030018, filed Apr. 27, 2018, 10 pages.
INTERNATIONAL Union of Pure and Applied Chemistry (Nov. 5, 1960). "Definitive Rules for Nomenclature of Organic Chemistry," J. Am. Chem. Soc. 82:5545-5473, 30 pages.
Jain, N. et al. (Nov. 2015, e-pub. Mar. 11, 2015). "Current ADC Linker Chemistry," Pharma Res 32(11):3526-3540.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th Ed. Public Health Service, National Institutes of Health, Bethesda MD., Table of Contents, 21 pages.
Kabat, E.A. et al. (Sep. 1980). "Origins of Antibody Complementarity and Specificity-Hypervariable Regions and the Minigene Hypothesis," J Immunology 125(3):961-969.
Kolakowski, R. V. et al. (Jul. 4, 2016, e-pub. May 20, 2016). "The Methylene Alkoxy Carbamate Self-Immolative Unit: Utilization for the Targeted Delivery of Alcohol-Containing Payloads with Antibody-Drug Conjugates," Angewandte Chemie 55(28):7948-7951.
Kozbor, D. et al. (1983). "The Production of Monoclonal Antibodies From Human Lymphocytes," Immunology Today 4(3):72-79.
Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3):548-555.
Liu, A.Y. et al. (May 1987). "Chimeric Mouse-Human IgG1 Antibody That Can Mediate Lysis of Cancer Cells," Proc. Natl. Acad. Sci. USA 84:3439-3443.
Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.
Lockman, J.W. et al. (Dec. 23, 2010, e-pub. Nov. 16, 2010). "Analogues of 44(7-bromo-2-methyl-4-oxo-3H-quinazolin-6-yl)methylprop-2-ynylaminol-N-(3-pyridylmethypbenzamide (CB-30865) As Potent Inhibitors Of Nicotinamide Phosphoribosyltransferase (NAMPT)," J. Med. Chem. 53:8734-8746.
Morrison, S.L. (Sep. 1985). "Transfectomas Provide Novel Chimeric Antibodies," Science 229(4719):1202-1207.

(56) References Cited

OTHER PUBLICATIONS

Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4):999-1005.
Oi, V.T. et al. (1986). "Chimeric Antibodies," Bio Techniques 4(3):214-219.
Olsson, L. et al. (1983), "Human-Human Monoclonal Antibody-Producing Hybridomas: Technical Aspects," Meth Enzymol. 92:3-16.
Rose, K. et al. (May-Jun. 1991). "Preparation Of Well-Defined Protein Conjugates Using Enzyme-Assisted Reverse Proteolysis," Bioconjugate Chem. 2(3):154-159.
Roulston, A. et al. (2016, e-pub. Jan. 2016) "New Strategies to Maximize Therapeutic Opportunities For NAMPT Inhibitors In Oncology," Mol. Cell. Oncol. 3(1):e1052180, 13 pages.
Sampath, D. et al. (Jul. 2015, e-pub. Feb. 21, 2015) "Inhibition of Nicotinamide Phosphoribosyl-20 Transferase (NAMPT) As a Therapeutic Strategy," Pharmacol Ther. 151:16-31, 17 pages.
Schmidt, M.M. et al. (Oct. 2009). "A Modeling Analysis of the Effects of Molecular Size and Binding Affinity on Tumor Targeting," Mol. Cancer Ther. 8(10):2861-2871.
Schwarz, A. et al. (1990). "Enzymatic C-Terminal Biotinylation of Proteins," Methods Enzymol. 184:160-162. (Abstract Only).
Shaw, D.R. et al. (Dec. 7, 1988). "Mouse/Human Chimeric Antibodies To A Tumor-Associated Antigen: Biologic Activity Of The Four Human IgG Subclasses," J. Natl. Cancer Inst. 80(19):1553-1559.
Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.
Teng, N.N.H. et al. (Dec. 1983). "Construction and Testing of Mouse-Human Heteromyelomas For Human Monoclonal Antibody Production," Proc. Natl. Acad. Sci. USA. 80:7308-7312.
Verhoeyan, M. et al. (Mar. 25, 1988). "Reshaping Human Antibodies: Grafting an Antilysozyme Activity," Science 239:1534-1536.
Wood, C.R. et al. (Apr. 4, 1985). "The Synthesis and in vivo Assembly of Functional Antibodies In Yeast," Nature 314(6010):446-449.
You, H. et al. (Apr. 2011, e-pub. Jan. 31, 2011) "Design, Synthesis and X-Ray Crystallographic Study of NAmPRTase Inhibitors As Anti-Cancer Agents," Eur. J. Med. Chem. 46:1153-1164.
Zak, M. et al. (Feb. 1, 2015, e-pub. Dec. 17, 2014) "Identification of Nicotinamide Phosphoribosyltransferase (NAMPT) Transferase Inhibitors With No Evidence of CYP3A4 Time-Dependent Inhibition and Improved Aqueous Solubility," Bioorg. Med. Chem. Lett. 25(3):529-541.
Zheng, X. (Aug. 22, 2013, e-pub. Jul. 31, 2013). "Structure-Based Discovery of Novel Amide-Containing Nicotinamide Phosphoribosyltransferase (NAMPT) Inhibitors," J. Med. Chem. 56:6413-6433.
PCT Application No. PCT/US2017/057116, Search Report and Written Opinion, 14 pages, dated Feb. 12, 2018.
PCT Application No. PCT/US2017/057116, International Preliminary Reporton Patentability, 10 pages, dated May 2, 2019.
Chandra, et al., "Virtual screening, identification and experimental testing of novel inhibitors of PBEF1/Visfatin/NMPRTase for glioma therapy", Journal of Clinical Bio, 1:5, (2011).
Chen, et al., "Dual NAMPT/HDAC Inhibitors as a New Strategy for Multitargeting Antitumor Drug Discovery", ASC Medical Chemistry Letters, 9, 34-38, (2018).
Christensen, et al., "Nicotinamide Phosphoribosyltransferase Inhibitors, Design, Preparation, and Structure-Activity Relationship", Journal of Medicinal Chemistry, 56, 9071-9088, (2013).
Colombano, et al., "A Novel Potent Nicotinamide Phosphoribosyltransferase Inhibitor Synthesized via Click Chemistry", Journal of Medicinal Chemistry, 53, 616-623, (2010).
Dragovich, et al., "Fragment-based design of 3-aminopyridine-derived amides as potent inhibitors of human nicotinamide phosphoribosyltransferase (NAMPT)", Bioorganic & Medicinal Chemistry Letter, 24, 954-962, (2014).
Galli, et al., "Synthesis and Biological Evaluation of Isosteric Analogues of FK866, an Inhibitorof NAD Salvage", Chem Med Chem, 3, 771-779, (2008).
Galli, et al., "Medicinal Chemistry of Nicotinamide Phosphoribosyltransferase (NAMPT) Inhibitors", Journal of Medicinal Chemistry, 56, 6279-6296, (2013).
Giannetti, et al., "Fragment-Based Identification of Amides Derived from trans-2-(Pyridin-3-yl)cyclopropanecarboxylic Acid as Potent Inhibitors of Human Nicotinamide Phosphoribosyltransferase (NAMPT)", Journal of Medicinal Chemistry, 57, 770-792, (2014).
Gunzner, et al., "Discovery of potent and efficacious urea-containing nicotinamide phosphoribosyltransferase (NAMPT) inhibitors with reduced CYP2C9 inhibition properties", Bioorganic & Medicinal Chemistry Letters, 23, 3531-3538, (2013).
Karpov, et al., "Nicotinamide Phosphoribosyltransferase Inhibitor as a Novel Payload for Antibody-Drug Conjugates", ACS Medicinal Chemistry Letters, pp. A-E, (2018).
Kolakowski, et al., "The Methylene Alkoxy Carbamate Self-Immolative Unit: Utilization for the Targeted Delivery of Alcohol-Containing Payloads with Antibody-Drug Conjugates", Angew. Chem., 128, 8080-8083, (2016).
Lockman, et al., "Analogues of 4-[(7-Bromo-2-methyl-4-oxo-3H-quinazolin-6-yl)methylprop-2-ynylamino]-N-(3-pyridylmethyl)benzamide (CB-30865) as Potent Inhibitors of Nicotinamide Phosphoribosyltransferase (Nampt)", Journal of Medicinal Chemistry, 53, 8734-8746, (2010).
Roulston, et al., "New strategies to maximize therapeutic opportunities for NAMPT inhibitors in oncology", Molecular & Cellular Oncology, vol. 3, No. 1, 12 pgs., (2016).
Sadrerafi, et al., "Clickable prodrugs bearing potent and hydrolytically cleavable nicotinamide phosphoribosyltransferase inhibitors" Drug Design, Development and Therapy, 12, 987-995, (2018).
Sampath, et al., "Inhibition of nicotinamide phosphoribosyltransferase (NAMPT) as a therapeutic strategy in cancer", Pharmacology & Therapeutics, 151, 16-31, (2015).
You, et al., "Design, synthesis and X-ray crystallographic study of NAmPRTase inhibitors as anti-cancer agents", European Journal of Medicinal Chemistry, 46, 1153-1164, (2011).
Zak, et al., "Identification of nicotinamide phosphoribosyltransferase (NAMPT) inhibitors with no evidence of CYP3A4 time-dependent inhibition and improved aqueous solubility", Bioorganic & Medicinal Chemistry Letters, 25, 529-541, (2015).
Zheng, et al., "Structure-Based Discovery of Novel Amide-Containing Nicotinamide Phosphoribosyltransferase (Nampt) Inhibitors", Journal of Medicinal Chemistry, 56, 6413-6433, (2013).
EP Patent Application No. 17862746.9, Supplemental European Search Report and Search Opinion, 6 pages, dated May 25, 2020.

* cited by examiner

TARGETED DELIVERY OF NICOTINAMIDE ADENINE DINUCLEOTIDE SALVAGE PATHWAY INHIBITORS

CROSS REFERENCE TO RELATED APPLICATIONS

This application is a U.S. national stage filing under 35 USC § 371 of International Application No. PCT/US2017/057116, filed Oct. 18, 2017, which claims the benefit of provisional U.S. Appl. Ser. No. 62/409,765, filed Oct. 18, 2016, all of which are incorporated herein in their entirety for all purposes.

REFERENCE TO SEQUENCE LISTING

This application includes a sequence listing as a text file, named 5000-00111PC_Sequence_Listing_ST25.txt" created Oct. 10, 2017 and containing 4.39 k bytes. The material contained in this text file is incorporated by reference in its entirety for all purposes.

BACKGROUND OF THE INVENTION

The invention relates to Ligand-Drug Conjugates for targeted delivery of compounds that inhibit intracellular production of nicotinamide adenine dinucleotide (NAD) within abnormal cells associated with a given disease state. Abnormal cells have increased energy demands in comparison to normal cells due to their persistent or heightened metabolic activity. The ATP levels for meeting those demands are reliant on commensurate levels of NAD for shuttling electrons in the oxidative phosphorylation and glycolytic pathways, both of which contribute to ATP production in eukaryotic cells. In addition to meeting the increased energy demand, continuous production of NAD is required due to turnover of that cofactor by various intracellular enzymes, including poly (ADP ribose) polymerases (PARPs), mono (ADP ribose) transferases (ARTs) and sirturins. Cancer cells are thought to be particularly sensitive to disruptions in maintaining intracellular concentrations of NAD for supporting their energy demands due to significantly increased turnover of that cofactor. That greater sensitivity may also be attributed to greater reliance of those abnormal cells on the glycolytic pathway for producing ATP instead of oxidative phosphorylation, the former of which is less efficient at that task, even when those cancer cells are not under hypoxic conditions.

Intracellular concentrations of NAD in eukaryotic cells are produced either by a de novo pathway starting from tryptophan or more efficiently through salvage pathways by uptake of pyridine-containing precursors, such as nicotinic acid, nicotinamide and nicotinamide ribose, from the diet or reuse of these compounds subsequent to the activities of NAD-consuming enzymes. Nicotinamide is salvaged preferentially over nicotinic acid in mammalian cells for intracellular replenishment of NAD, the rate limiting enzyme for which is nicotinamide phosphoribosyltransferase (NAMPT). NAMPT synthesizes nicotinamide mononucleotide (NMN) from nicotinamide and 5-phospho-alpha-D-ribose 1-diphosphate (PRPP), which is followed by conversion of NMN to NAD by nicotinamide mononucleotide adenylyl transferase. Inhibition of NAD synthesis through the salvage pathway should deplete intracellular NAD due to its consumption by the aforementioned enzymes that use it as a substrate. Inhibition of NAMPT in cancer cells to a sufficient extent should then cause a drop in intracellular concentration of ATP to levels that are no longer sufficient for sustaining the continued metabolic activity of these abnormal cells, which should then lead to their death.

Due to its central role in the salvage pathway and the greater sensitivity of cancer cells to disruptions in intracellular concentrations of NAD, which interferes with maintaining sufficient levels of ATP for supporting their heightened or persistent metabolic activity, targeting of NAMPT by small molecule mimetics of nicotinamide has been explored for the treatment of cancer. As with cancer cells, inflammatory cells, such as polymorphonucleate cells (PMNC) and neutrophils, having persistent activation in inflammatory disease states, such as rheumatoid arthritis, lupus erythematosus and inflammatory bowel diseases, also show elevated NAMPT mRNA and/or protein levels for maintaining sufficient levels of NAD to support the continued metabolic activities of these abnormal cells. Thus, NAMPT inhibitors may also be useful in treating those diseases. However, cytotoxicity towards normal cells, including thrombocytopenia, anemia, hyperglycemia and electrolyte dysfunction, has resulted in repeated failures in developing NAMPT inhibitors as therapeutic agents for treating any disease state.

Therefore, there is a long-standing unmet need in the art for improving the therapeutic index of NAMPT inhibitor compounds for treatment of disease states attributable to abnormal cells that have a heightened and/or continual demand for ATP, which are supported by commensurate intracellular concentrations of NAD. Ligand Drug Conjugates described herein having a NAMPT inhibitor compound or derivative thereof as a Drug Unit and whose Ligand Unit targets those abnormal cells, or the vicinity of such cells, address that unmet need.

SUMMARY OF THE INVENTION

Principle embodiments of the invention are Ligand Drug Conjugate (LDC) compositions that are represented by Formula 1:

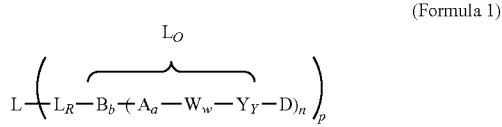

(Formula 1)

or a pharmaceutically acceptable salt thereof, wherein L is a Ligand Unit; D is a NAMPT Drug Unit represented by the general structure of:

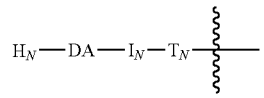

or a pharmaceutically acceptable salt thereof, wherein the wavy line indicates the site of covalent attachment to $L_O$ or $L_R$, depending on the presence or absence of $L_O$; $H_N$ is a NAMPT Head Unit, wherein the NAMPT Head Unit is a $C_5$-$C_{24}$ heteroaryl or partially aromatic $C_9$-$C_{24}$ heterocyclyl, optionally substituted, wherein the $C_5$-$C_{24}$ heteroaryl or partially aromatic $C_9$-$C_{24}$ heterocyclyl is comprised of an optionally substituted 5- or 6-membered nitrogen-containing heteroaromatic ring system corresponding to the heterocycle of nicotinamide, and is capable of interacting with enzymatically competent NAMPT homodimer at its nicotinamide mononucleotide binding site when the NAMPT Drug Unit is released from a Ligand Drug Conjugate compound of the composition as a NAMPT inhibitor (NAMPTi) compound or derivative thereof;

DA is a Donor-Acceptor Unit wherein the Donor-Acceptor Unit is or is comprised of a hydrogen bond donor acceptor functional group and is bonded to a carbon skeletal atom at position 2 or 3 of the 5-membered nitrogen-containing heteroaromatic ring system or at position 3 or 4 of the 6-membered nitrogen-containing heteroaromatic ring system, with optional formal cyclization of DA back to an adjacent skeletal carbon atom of the 6-membered nitrogen-containing heteroaromatic ring system through an introduced optionally substituted non-aromatic carbon atom or an optionally substituted nitrogen, oxygen or sulfur atom resulting in a partially aromatic or fully aromatic fused 6,5- or 6,6-ring system, wherein said bonding of DA is in relation to a skeletal nitrogen atom of the 5- or 6 membered nitrogen-containing heteroaromatic ring system and wherein said formal cyclization to the adjacent carbon atom of the 6-membered nitrogen-containing heteroaromatic ring system substantially retains the hydrogen bonding capability of the donor acceptor functional group of DA in absence of said cyclization;

$I_N$ is an Interconnecting Unit, wherein the Interconnecting Unit is or is comprised of $-X^1-[C(=O)]_{0,1}-$, $-X^1-[S(=O)]_{1,2}-$, $-X^2-C_6-C_{24}$ arylene-$[C(=O)]_{0,1}-$, $-X^2-C_6-C_{24}$ arylene-$[S(=O)]_{1,2}]_{0,1}$, $-X^2-C_6-C_{24}$ arylene-O—, $-X^2-C_5-C_{24}$ heteroarylene-$[C(=O)_{0,1}]-$, $-X^2-C_5-C_{24}$ heteroarylene-$[S(=O)]_{1,2}]_{0,1}$, $-X^2-C_5-C_{24}$ heteroarylene-O— or $-X^2-C_3-C_{20}$ heterocyclo-$[C(=O)_{0,1}]-$, wherein the arylene, heteroarylene and heterocyclo are optionally substituted; $X^1$ is optionally substituted $C_5$-$C_7$ alkylene; $X^2$ is absent or is an optionally substituted $C_1$-$C_4$ alkylene;

$T_N$ is a NAMPT Tail Unit, wherein the NAMPT Tail Unit is or is comprised of an optionally substituted amino-alcohol residue or a carboxylic acid-alcohol residue, the —O— or optionally substituted nitrogen of which is the site of covalent attachment to $L_O$, or or $L_R$, depending on the presence or absence of $L_O$, or $T_N$ is or is comprised of an optionally substituted benzamide moiety, the amide nitrogen atom of which is bonded to $I_N$ with optional cyclization of that atom back to $I_N$ or to the remainder of $T_N$, and the aromatic ring of which is at least substituted with a hydroxyl, thiol or amino residue, the —O—, —S— or optionally substituted nitrogen atom of which at position 3 or 4 relative to the site at which the amide carbonyl carbon atom is attached is the site of covalent attachment to $L_O$ or $L_R$, depending on the presence or absence of $L_O$, or $T_N$ is or is comprised of an optionally substituted aryl or biaryl moiety, an aromatic skeletal atom of which is bonded to $I_N$, or to the remainder of $T_N$, and wherein an aromatic ring of which is at least substituted with a hydroxyl, thiol or an amino residue, the —O—, —S— or optionally substituted nitrogen of which is the site of covalent attachment to $L_O$ or $L_R$, depending on the presence or absence of $L_O$, respectively; and wherein $T_N$ or the remainder thereof is bonded to $I_N$, wherein said remainder is an optionally substituted $C_2$-$C_7$ heteroalkylene or an optionally substituted $C_5$-$C_6$ heterocyclo, $L_R$ is a primary linker, which interconnects the Ligand Unit and Drug Unit optionally through $L_O$, as indicated, which is an optional secondary linker; subscripts a and b independently are 0 or 1, indicating the absence or presence, respectively, of A or B; subscript n is 1, 2, 3 or 4; A is an first optional Stretcher; and B is a Branching Unit, when subscript b is 1 and subscript n is 2, 3 or 4, or B is absent, so that subscript b is 0, when subscript n is 1, wherein each of A and B is an independently selected single unit or is optionally comprised or consists of at least two, three or four independently selected subunits;

Y is a Spacer Unit; and subscript y is 0, 1 or 2, indicating the absence or presence of one or two of Y, respectively, provided that when subscript y is 1, Y is a Spacer Unit covalently attached to a heteroatom or moiety thereof of $T_N$ selected from the group consisting of —O—, —S— and optionally substituted nitrogen, provided that when subscript y is 2 so that $Y_y$ is —Y—Y, Y is a first Spacer Unit and Y' is a second Spacer Unit or a functional group comprised of the optionally substituted heteroatom from $T_N$; and provided that subscript y is 1 or 2 when W is a Glucuronide Unit of formula Y(W'), in which instance subscript y is inclusive of a first Spacer Unit Y, wherein that Spacer Unit is a required self-immolative Spacer Unit; and subscript w is 0 or 1, indicating the absence or presence, respectively, of W; wherein when subscript w is 1, W is a Peptide Cleavable Unit or said Glucuronide Unit in which W' represents a carbohydrate moiety with glycosidic bonding to the required self-immolative Spacer Unit through a optionally substituted heteroatom, wherein enzymatic or non-enzymatic cleavage of either Unit initiates release of the NAMPT Drug Unit as a NAMPTi compound or derivative thereof from a drug linker moiety of a compound comprising the Ligand Drug Conjugate composition; and when subscript w is 0, which indicates the absence of a Cleavable Unit, enzymatic or non-enzymatic cleavage of the bond between $L_R$ and $L_O$, when $L_O$ is present, or the bond between $L_R$ and D, when $L_O$ is absent, initiates release of the NAMPT Drug Unit as a NAMPTi compound or derivative thereof; and subscript p is an average drug linker moiety loading when subscript n is other than 1 or an average drug loading when subscript n is 1, wherein subscript p in either instance is a number ranging from about 1 to about 24; and wherein a compound comprising the Ligand Drug Conjugate composition corresponds in structure(s) to that of Formula 1 or Formula 2 in which p is replaced by p', wherein p' is an integer ranging from 1 to 24.

In some aspects, W is a Peptide Cleavable Unit and subscript y is 0, 1 or 2, or W is a Glucuronide Unit of structure —Y(W')—, so that subscript y is 1 or 2, wherein Y is a self-immolative Spacer Unit and W' is a carbohydrate moiety (Su) with attachment to Y by glycosidic bonding through an optionally substituted heteroatom (E') wherein D is attached directly to Y when subscript y is 1 or D is attached indirectly to Y through Y' when subscript y is 2.

In some aspects in which subscript y is 2, Y and Y' are both self-immolative Spacer Units, which undergo self-immolation upon enzymatic processing of the Peptide Cleavable Unit or Glucuronide Unit as, for example, when one self-immolative Spacer Unit (Y) is capable of 1,4- or 1,6-elimination and the other self-immolative Spacer Unit (Y') is a methylene carbamate unit or a carbamate functional group as described herein.

In other aspects, when subscript y is 1, Y undergoes self-immolation upon conditional enzymatic processing of the Peptide or Glucuronide Unit to release D as a NAMPTi compound or derivative thereof, or releases Y'-D, when subscript y is 2 and Y bonded to Y' undergoes self-immolation. In some of those aspects Y' of —Y'-D so released also can undergo self-immolation to release D as a NAMPTi compound or derivative thereof. In still other aspects, W is a Cleavable Unit that is not reliant upon enzymatic cleavage for release of the NAMPTi compound or derivative thereof and in some instances is acted upon non-enzymatically for that release.

In other aspects, the Ligand Unit of a Ligand Drug Conjugate composition is that of an antibody, thereby defining an Antibody Drug Conjugate (ADC) composition, and the targeted moiety recognized by its targeting antibody Ligand Unit is an cell-surface antigen of abnormal cells, wherein the targeted antigen so bound from said recognition is capable of cellular internalization of a Ligand Drug Conjugate compound of the composition, wherein the antigen is typically present on the abnormal cells in greater copy number in comparison to that of normal cells.

In still other aspects, the antibody Ligand Unit of a Ligand Drug Conjugate composition recognizes an antigen present within the vicinity of abnormal cells in which the antigen is typically present in greater copy number in comparison to that of normal cells or the vicinity of these cells distant from the site of the abnormal cells, wherein bonding to the targeted antigen culminates in release of the NAMPT Drug Unit in proximity to the abnormal cells, which is followed by entry of the NAMPTi compound or its derivative from that release into the abnormal cells.

In any one of those aspects, a NAMPT Drug Unit is released from a Ligand Drug Conjugate compound of the composition as a NAMPTi compound or derivative thereof within abnormal cells, or is released in the vicinity of the abnormal cells targeted by the Ligand Drug Conjugate, to exert a therapeutic effect due intracellular inhibition of NAMPT in the abnormal cells.

Those and other aspects of Ligand Drug Conjugates and NAMPT Drug Units therein are further described by the embodiments of the invention.

Other principle embodiments of the invention provide for compounds having the structure of Formula I:

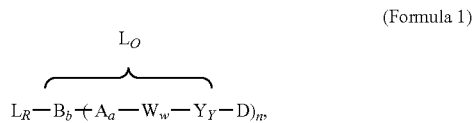

(Formula 1)

or a salt thereof, wherein $L_R$ is a primary linker having a functional group capable of forming a covalent bond to a targeting moeity that becomes the Ligand Unit of a Ligand Drug Conjugate of Formula 1 wherein the other variable groups of Formula I are as defined for Formula 1.

DETAILED DESCRIPTION OF THE INVENTION

Definitions

Figure 1:
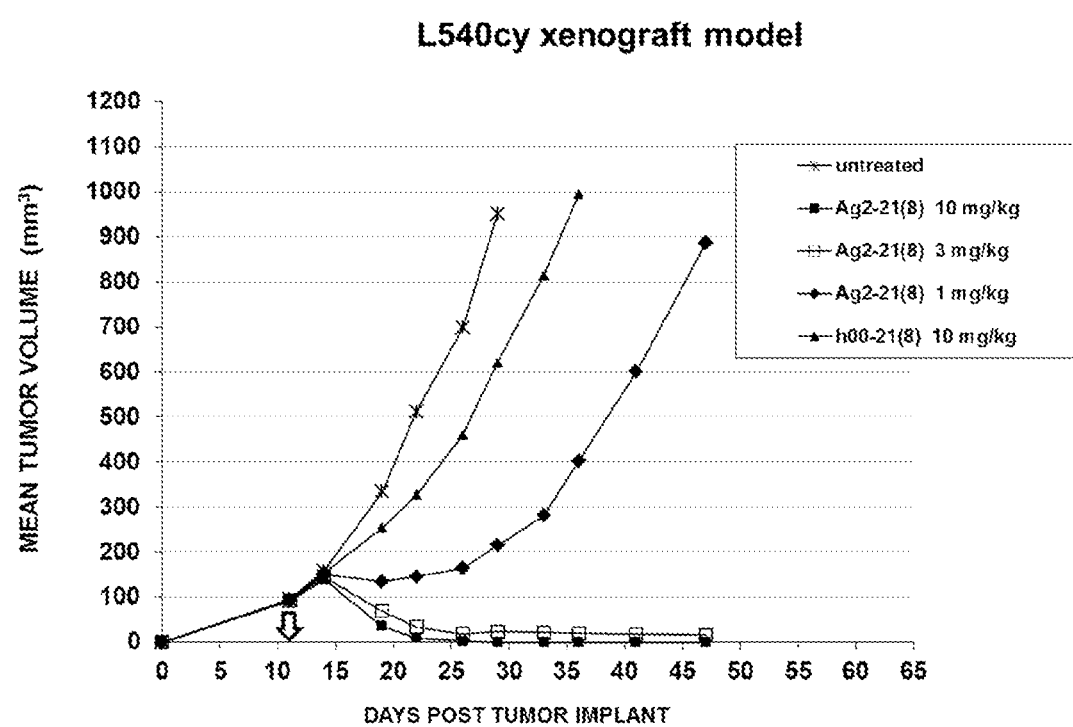
FIG. 1 shows variation over time (days) in tumor volume (mm$^3$) in a L450cy xenograft model post tumor implant in untreated SCID mice in comparison to those treated with 1, 3 or 10 mg/Kg (i.p.) of an Antibody Drug Conjugate (8 NAMPT Drug Units/Ab) prepared from chimeric antibody cAC10, which targets Ag2 (CD30) expressed by the implanted L450cy tumor cells, and Drug Linker compound 21.

As used herein and unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as used in the specification and the appended claims, the singular forms "a," "an" and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are, or that consist of, or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist or a component or step are closed and they would not include or read on those compositions or methods having appreciable amounts of" an additional component(s) or an additional step(s). Furthermore, use of the term "including" as well as other forms, such as "include", "includes," and "included," is not limiting. Finally, the term "consisting essentially of" admits for the inclusion of unrecited elements that have no material effect on the functionality of the disclosed compositions, devices, articles of manufacture or methods for its intended purpose as further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques and pharmacology are employed.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values may vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.01% of the recited value or range of values, typically by 10% to 0.5%, more typically by 5% to 1%, while still describing the particular property.

"Essentially retains", "essentially retaining" and like terms as used herein refers to a property, characteristic, function or activity of a compound or composition or moiety thereof that has not detectably changed or is within experimental error of determination of that same activity, characteristic or property of a compound or composition or moiety of related structure.

"Substantially retains", "substantially retaining" and like terms as used herein refers to a measured value of a physical property or characteristic of a compound or composition or moiety thereof that may be statistically different from the determination of that same physical property of another compound or composition or moiety of related structure, but which such difference does not translate to a statistically significant or meaningful difference in biological activity or pharmacological property in a suitable biological test system for evaluating that activity or property (i.e., biological activity or property is essentially retained). Thus the phrase "substantially retains" is made in reference to the effect that a physical property or characteristic of a compound or composition has on a physiochemical or pharmacological property or biological activity that is explicitly associated with that physical property or characteristic.

"Negligibly" or "negligible" as used herein is an amount of an impurity below the level of quantification by HPLC analysis and if present represents from about 0.5% to about 0.1 w/w % of the composition that it contaminates. Depending on context those terms may alternatively mean that no statistically significant difference is observed between measured values or outcomes or are within experimental error of the instrumentation used to obtain those values. Negligible differences in values of a parameter determined experimentally do not imply that an impurity characterized by that parameter is present in negligible amount.

"Predominately containing", "predominately having" and like terms as used herein refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

The term "electron-withdrawing group" as the term is used herein refers to a functional group or electronegative atom that draws electron density away from an atom to which it is bonded either inductively and/or through resonance, whichever is more dominant (i.e. a functional group or atom may be electron donating through resonance but may overall be electron withdrawing inductively), and tends to stabilize anions or electron rich moieties. The electron withdrawing effect is typically transmitted inductively, albeit in attenuated form, to other atoms attached to the bonded atom that has been made electron deficient by the electron withdrawing group (EWG) thus affecting the electrophilicity of a more remote reactive center.

Exemplary electron withdrawing groups include, but are not limited to —C(=O), —CN, —NO$_2$, —CX$_3$, —X, —C(=O)OR', —C(=O)NH$_2$, —C(=O)N(R')R$^{op}$, —C(=O)R', —C(=O)X, —S(=O)$_2$R$^{op}$, —S(=O)$_2$OR', —SO$_3$H$_2$, —S(=O)$_2$NH$_2$, —S(=O)$_2$N(R')R$^{op}$, —PO$_3$H$_2$, —P(=O)(OR')(OR$^{op}$)$_2$, —NO, —NH$_2$, —N(R')(R$^{op}$), —N(R$^{op}$)$_3^+$, and salts thereof, wherein X is —F, —Br, —Cl, or —I, and R$^{op}$ is, at each occurrence, independently selected from a group previously described for optional substituents and in some aspects are independently selected from the group consisting of C$_1$-C$_6$ alkyl and phenyl, and wherein R' is hydrogen or R$^{op}$ selected from a group as described elsewhere for optional substituents and in some aspects is a C$_1$-C$_{12}$ alkyl or C$_1$-C$_6$ alkyl. Exemplary EWGs can also include aryl groups (e.g., phenyl) depending on substitution and certain heteroaryl groups (e.g., pyridine). Thus, the term "electron withdrawing groups" also includes aryls or heteroaryls that are further substituted with electron withdrawing groups. Typically, electron withdrawing groups are —C(=O), —CN, —NO$_2$, —CX$_3$, and —X, wherein X is halogen. Depending on its substituents, an optionally substituted alkyl moiety may also be an electron withdrawing group. In some aspects an electron withdrawing group is a substituent of a Glucuronide Unit that increases the glycosidase cleavage rate of that Unit in a Drug Linker compound or Ligand Drug Conjugate when measured in a suitable in vitro enzyme assay in comparison to a corresponding Drug Linker compound or Conjugate in which the EWG is not present as a Glucuronide Unit substituent.

"Electron donating group" as the term is used herein refers to a functional group or electropositive atom that increases electron density of an atom to which it is bonded either inductively and/or through resonance, whichever is more dominant (i.e., a functional group or atom may be electron withdrawing inductively but may overall be electron donating through resonance), and tends to stabilize cations or electron poor systems. The electron donating effect is typically transmitted through resonance to other atoms attached to the bonded atom that has been made electron rich by the electron donating group (EDG) thus affecting the nucleophilicity of a more remote reactive center. Exemplary electron donating groups include, but are not limited to, —OH, —OR', —NH$_2$, —NHR' and N(R')$_2$, wherein each R' is an independently selected C$_1$-C$_{12}$ alkyl, typically C$_1$-C$_6$ alkyl. Depending on their substituents, an aryl, heteroaryl or unsaturated alkyl moiety may also be an electron donating group.

"Moiety" as used herein means a specified segment, fragment or functional group of a molecule or compound. Chemical moieties are sometimes indicated as chemical entities that are embedded in or appended to (i.e., a substituent or variable group) a molecule, compound or chemical formula.

For any substituent group or moiety described herein by a given range of carbon atoms, the designated range means that any individual number of carbon atoms is described. Thus, reference to, e.g., "optionally substituted C$_1$-C$_4$ alkyl", "optionally substituted alkenyl C$_2$-C$_6$ alkenyl specifically means that a 1, 2, 3 or 4 carbon alkyl moiety, optionally substituted, as defined herein is present, or a 2, 3, 4, 5 or 6 carbon alkenyl, or a 3, 4, 5, 6, 7 or 8 carbon alkenyl moiety, optionally substituted, as defined herein is present. All such numerical designations are expressly intended to disclose all of the individual carbon atom groups; and thus "optionally substituted C$_1$-C$_4$ alkyl" includes, methyl, ethyl, 3 carbon alkyls, and 4 carbon alkyls, including all of their positional isomers, whether substituted or unsubstituted. Thus, when an alkyl moiety is substituted, the numerical designations refer to an unsubstituted base moiety and are not intended to include carbon atoms that may be present in the substituents of that base moiety. For esters, carbonates, carbamates and ureas as defined herein that are identified by a given range of carbon atoms, the designated range includes the carbonyl carbon of the respective functional group. Thus, a C$_1$ ester refers to a formate ester and a C$_2$ ester refers to an acetate ester.

The organic substituents, moieties and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are referred to as carbocyclyls as defined herein.

When referring to an alkyl moiety or group as an alkyl substituent, that alkyl substituent to a Markush structure or another organic moiety with which it is associated is methyl or that chain of contiguous carbon atoms covalently attached to the structure or moiety through a $sp^3$ carbon of the alkyl substituent. An alkyl substituent, as used herein, therefore contains at least one saturated moiety and may also contain one or more unsaturated moieties or groups. Thus, an alkyl substituent may additionally contain one, two, three or more independently selected double and/or triple bonds to define an unsaturated alkyl substituent, and may be substituted (i.e., optionally substituted) by other moieties that include optional substituents as described herein. A saturated, unsubstituted alkyl substituent contains saturated carbon atoms (i.e., $sp^3$ carbons) and no $sp^2$ or sp carbon atoms.

Unless otherwise indicated or implied by context, the term "alkyl" will indicate a saturated, non-cyclic hydrocarbon radical, wherein the hydrocarbon radical has the indicated number of covalently linked saturated carbon atoms (e.g., "$C_1$-$C_6$ alkyl" or "C1-C6 alkyl" means an alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to an alkyl moiety or group having 1 saturated carbon atom or 2, 3, 4, 5, 6, 7 or 8 contiguous saturated, non-cyclic carbon atoms. The number of saturated carbon atoms in an alkyl moiety or group can vary and typically is 1-50, 1-30 or 1-20, and more typically is 1-8 or 1-6. Typically, alkyl will refer to a saturated $C_1$-$C_8$ alkyl moiety, or more typically is a $C_1$-$C_6$ or $C_1$-$C_4$ alkyl moiety with the latter sometimes referred to as lower alkyl. When the number of carbon atoms is not indicated, the alkyl moiety or group has from 1 to 8 carbon atoms.

When an alkyl substituent, moiety or group is specified, species include those derived from removing a hydrogen atom from a parent alkane (i.e., is monovalent) and include without limitation methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear and branch chain alkyl moieties.

"Alkylene," as used herein, by itself or as part of another term, unless otherwise stated or implied by context, refers to a saturated, branched, cyclic or straight chain hydrocarbon diradical, substituted or unsubstituted, wherein one or more of the carbon atoms is unsaturated (i.e., is comprised of one or more $sp^3$ carbons), of the stated number of carbon atoms, typically 1-10 carbon atoms, and having two radical centers (i.e., is divalent) derived by the removal of two hydrogen atoms from the same or two different saturated (i.e., $sp^3$) carbon atoms of a parent alkane. Alkylene moieties further include alkyl radicals as described herein in which a hydrogen atom has been removed from another of its saturated carbons or from the radical carbon of an alkyl radical to form a diradical. Typically, alkylene moieties include, but are not limited to, divalent moieties derived from removing a hydrogen atom from a saturated carbon atom of a parent alkyl moiety and are exemplified without limitation by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. Typically, an alkylene is a branched or straight chain hydrocarbon containing only $sp^3$ carbons (i.e., is fully saturated notwithstanding the radical carbon atoms).

"Carbocyclyl" as used herein, by itself of as part of another term, unless otherwise stated or implied by context, refers to a radical of a monocyclic, bicyclic or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more $sp^3$ carbons). Thus, a carbocyclyl is a cyclic arrangement of saturated carbons but may also contain unsaturated carbon atom(s) and therefore its carbocyclic ring may be saturated or partially unsaturated or may be fused with an aromatic moiety, wherein the points of fusion to the cycloalkyl and aromatic rings are to adjacent unsaturated carbons of the carbocyclyl moiety and adjacent aromatic carbons of the aromatic moiety.

Unless otherwise specified, a carbocyclyl may be substituted (i.e. optionally substituted) with moieties described for alkyl, alkenyl, alkynyl, aryl, arylalkyl, alkylaryl and the like or can be substituted with another cycloalkyl moiety. Cycloalkyl moieties, groups or substituents include without limitation cyclopropyl, cyclopentyl, cyclohexyl, adamantly and other cyclic moieties that have only carbon atoms in their cyclic ring systems.

When carbocyclyl is used as a Markush group (i.e., a substituent) the carbocyclyl is attached to a Markush formula or another organic moiety with which it is associated through a carbon atom that is involved in the carbocyclic ring system of the carbocyclyl moiety provided that carbon atom is not aromatic. When an unsaturated carbon of an alkene moiety comprising the carbocyclyl substituent is attached to a Markush formula with which it is associated that carbocyclyl is sometimes referred to as a cycloalkenyl substituent. The number of carbon atoms in a carbocyclyl substituent is defined by the total number of skeletal atoms of its carbocyclic ring system. That number can vary and typically ranges from 3 to 50, 1-30 or 1-20, and more typically 3-8 or 3-6 unless otherwise specified, e.g., $C_3$-$C_8$ carbocyclyl means an carbocyclyl substituent, moiety or group containing 3, 4, 5, 6, 7 or 8 carbocyclic carbon atoms and $C_3$-$C_6$ carbocyclyl means an carbocyclyl substituent, moiety or group containing 3, 4, 5 or 6 carbocyclic carbon atoms. A carbocyclyl may be derived by the removal of one hydrogen atom from a ring atom of a parent cycloalkane or cycloalkene. Representative $C_3$-$C_8$ carbocyclyls include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups typically have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share one (i.e., is a spiro ring system) or two carbon atoms and a tricyclic ring system may share a total of 2, 3 or 4 carbon atoms, typically 2 or 3.

"Carbocyclo," by itself or as part of another term, unless otherwise stated or implied by context, refers to a carbocyclyl as defined above wherein another hydrogen atom of its cycloalkyl ring has been removed (i.e., it is divalent) and typically is a $C_3$-$C_{10}$ carbocycle or a $C_3$-$C_8$ carbocyclo.

"Alkenyl" as the terms are used herein, by itself or as part of another term, unless otherwise stated or implied by context, refers to an organic moiety, substituent or group that comprises one or more double bond functional groups (e.g., a —CH=CH— moiety) or 1, 2, 3, 4, 5 or 6 or more, typically 1, 2 or 3 of such functional groups and may be substituted (i.e., optionally substituted) with an aryl moiety or group such as phenyl, or linked normal, secondary, tertiary or cyclic carbon atoms, i.e., linear, branched, cyclic or any combination thereof unless the alkenyl substituent, moiety or group is a vinyl moiety (e.g., a —CH=CH$_2$ moiety). An alkenyl moiety, group or substituent having multiple double bonds may have the double bonds arranged contiguously (i.e., a 1,3 butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

When an alkenyl moiety, group or substituent is specified, species include, by way of example and not limitation, any of the optionally substituted alkyl or carbocyclyl, groups moieties or substituents described herein that has an one or more endo double bonds and monovalent moieties derived from removal of a hydrogen atom from a $sp^2$ carbon of a parent alkene compound. Such monovalent moieties without limitation typically include vinyl (—CH=CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, and other linear, cyclic and branched chained, all carbon-containing moieties containing at least one double bond functional group. When alkenyl is used as a Markush group (i.e., is a substituent) the alkenyl is attached to a Markush formula or another organic moiety with which it is associated through a double-bonded carbon (i.e., a $sp^2$ carbon) of its alkene functional group. The number of carbon atoms in an alkenyl substituent is defined by the number of $sp^2$ carbon atoms of the alkene functional group that defines it as an alkenyl substituent and the total number of contiguous non-aromatic carbon atoms appended to each of these $sp^2$ carbons not including any carbon atom of the larger moiety or Markush structure for which the alkenyl moiety is a variable group. That number can vary and unless otherwise specified ranges from 1 to 50, e.g., typically 1 to 30 or 1 to 20, more typically 1 to 8 or 1 to 6, when the double bond functional group is doubly bonded to a Markush structure (e.g. =CH$_2$), or can vary and unless otherwise specified ranges from 2 to 50, typically 2 to 30 or 2 to 20, more typically 2 to 8 or 2 to 6, when the double bond functional group is singly bonded to the Markush structure (e.g., —CH=CH$_2$). For example, $C_2$-$C_8$ alkenyl or $C_2$-$C_8$ alkenyl means an alkenyl moiety containing 2, 3, 4, 5, 6, 7 or 8 carbon atoms in which at least two are $sp^2$ carbons in conjugation with each other and $C_2$-$C_6$ alkenyl or $C_2$-$C_6$ alkenyl means an alkenyl moiety containing 2, 3, 4, 5 or 6 carbon atoms in which at least two are $sp^2$ carbons that are in conjugation with each other. Typically, an alkenyl substituent is a $C_2$-$C_6$ or $C_2$-$C_4$ alkenyl moiety having two $sp^2$ carbons that are in conjugation with each other.

"Alkenylene" as used herein, by itself of as part of another term, unless otherwise stated or implied by context, refers to an organic moiety, substituent or group that comprises one or more double bond moieties, as previously described for alkenyl, of the stated number of carbon atoms, typically 2 to 10 carbon atoms and has two radical centers derived by the removal of two hydrogen atoms from the same or two different $sp^2$ carbon atoms of an alkene functional group in a parent alkene. Alkenylene moieties also include alkenyl radicals as described herein in which a hydrogen atom has been removed from the same or different $sp^2$ carbon atom of a double bond functional group of an alkenyl radical, or from a $sp^2$ carbon from a different double bonded moiety to provide a diradical. Typically, alkenylene moieties include diradicals containing the structure of —C=C— or —C=C—X'—C=C— wherein X' is absent or is an alkylene as defined herein. The number of carbon atoms in an alkenylene moiety is defined by the number of $sp^2$ carbon atoms of its alkene functional group(s) that defines it as an alkenylene moiety and the total number of contiguous non-aromatic carbon atoms appended to each of its $sp^2$ carbons not including any carbon atoms of the larger moiety or Markush structure in which the alkenyl moiety is a present as a variable group. That number can vary and unless otherwise specified ranges from 2 to 50, typically 2-30 or 2-20, more typically 2 to 8 or 2-6. For example, $C_2$-$C_8$ alkenylene or $C_2$-$C_8$ alkenylene means an alkenylene moiety containing 2, 3, 4, 5, 6, 7 or 8 carbon atoms in which at least two are $sp^2$ carbons in conjugation with each other and $C_2$-$C_6$ alkenylene or $C_2$-$C_6$ alkenylene means an alkenyl moiety containing 2, 3, 4, 5 or 6 carbon atoms in which at least two are $sp^2$ carbons that are in conjugation with each other. Typically, an alkenylene substituent is a $C_2$-$C_6$ or $C_2$-$C_4$ alkenylene having two $sp^2$ carbons that are in conjugation with each other.

"Aryl" as the terms are used herein, by itself or as part of another term, unless otherwise stated or implied by context, refers to an organic moiety, substituent or group defined by an aromatic ring system or a fused ring system with no ring heteroatoms comprising 1, 2, 3 or 4 to 6 aromatic rings, typically 1 to 3 aromatic rings, wherein the rings are composed of only carbon atoms that participate in a cyclically conjugated system of 4n+2 electrons (Hückel rule), typically 6, 10 or 14 electrons some of which may additionally participate in exocyclic conjugation with a heteroatom (cross-conjugated, e.g., quinone). Aryl substituents, moieties or groups are typically formed by six, eight, ten or more aromatic carbon atoms. Aryl substituents, moieties or groups are optionally substituted. Exemplary aryls include $C_6$-$C_{10}$ aryls such as phenyl and naphthalenyl and phenanthryl. As aromaticity in a neutral aryl moiety requires an even number or electrons it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Arylene," or "heteroarylene" as used herein, by itself or as part of another term, unless otherwise stated or implied by context, is an aromatic diradical moiety that forms two covalent bonds (i.e., it is divalent) within a larger moiety, which can be in the ortho, meta, or para configurations or an. Arylene and heteroarylenes include divalent species by removal of a hydrogen atom from a parent aryl moiety or group as defined herein. Heteroarylene further include those in which heteroatom(s) replaces one or more but not all of the aromatic carbon atoms of a parent arylene. Exemplary arylenes include, but are not limited to, phenyl-1,2-ene, phenyl-1,3-ene, and phenyl-1,4-ene as shown in the following structures:

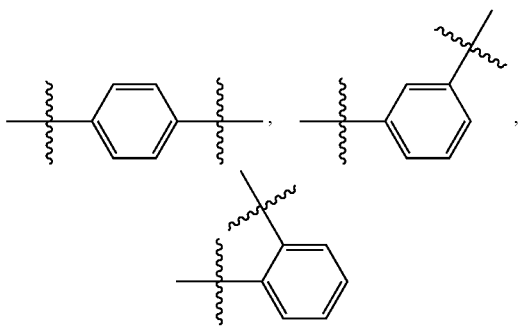

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above, for example, but without limitation, by $C_6H_5$—$CH_2$—, $C_6H_5$—$CH(CH_3)CH_2$— or $C_6H_5$—$CH_2$—$CH(CH_2CH_2CH_3)$—. When (hetero)arylalkyl is used as a Markush group (i.e., a substituent) the alkyl moiety of the (hetero)arylalkyl is attached to a Markush formula with which it is associated through a sp$^3$ carbon of its alkyl moiety.

"Alkylaryl" or "alkylheteroaryl" as the terms are used herein, by itself or as part of another term, unless otherwise stated or implied by context, refers to an alkyl moiety bonded to an aryl or heteroaryl moiety, i.e., -(hetero)aryl-alkyl, where (hetero)aryl and alkyl groups are as described above, for example, but without limitation, by —$C_6H_4$—$CH_3$ or —$C_6H_4$—$CH_2CH(CH_3)$. When alkyl(hetero)aryl is used as a Markush group (i.e., a substituent) the (hetero)aryl moiety of the alkyl(hetero)aryl is attached to a Markush formula with which it is associated through a sp$^2$ carbon of its aryl or heteroaryl moiety.

"Heterocyclyl" as the terms is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms, optionally substituted where permitted, including without limitation N/NH, O, S, Se, B, Si and P, wherein two or more heteroatoms may be adjacent to each other or separated by one or more carbon atoms within the same ring system, typically by 1 to 3 atoms. Those heteroatoms typically include N/NH, O and S. A heterocyclyl typically contains a total of one to ten heteroatoms in the heterocyclic ring system provided that not all of the skeletal atoms of any one ring in the heterocyclic ring system are heteroatoms, wherein each heteroatom in the ring(s), optionally substituted where permitted, is independently selected from the group consisting of N/NH, O and S, with the proviso that any one ring does not contain two adjacent O or S atoms. Exemplary heterocyclyls and heteroaryls, which are defined below, are collectively referred to as heterocycles, are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 1960, 82:5545-5473 particularly 5566-5573).

When heterocyclyl is used as a Markush group (i.e., a substituent) a saturated or partially unsaturated heterocycle ring system of the heterocyclyl is attached to a Markush formula or larger moiety with which it is associated through a carbon or a heteroatom of that heterocycle ring, where such attachment does not result in an unstable or disallowed formal oxidation state of that carbon or heteroatom. A heterocyclyl in that context is a monovalent moiety in which the heterocyclic ring system defining it as a heterocyclyl is non-aromatic, but may be fused with a carbocyclic, aryl or heteroaryl ring and includes phenyl- (i.e., benzo) fused heterocycloalkyl moieties.

Typically, a heterocyclyl is a carbocyclyl wherein 1, 2 or 3 carbons of its cycloalkyl ring is replaced along with its attached hydrogens with a heteroatom selected from the group consisting of optionally substituted N/NH, O and S and is a $C_3$-$C_{24}$ heterocycloalkyl, more typically a $C_3$-$C_{12}$ or $C_5$-$C_{12}$ heterocycloalkyl in which the subscript indicates the total number of skeletal atoms (inclusive of its carbon atoms and heteroatoms) of the heterocyclic ring system of the heterocyclyl. Non-limiting heterocyclyls may contain 0 to 2 N atoms, 0 to 2 O atoms or 0 to 1 S atoms or some combination thereof provided at least one of said heteroatoms is present in the cyclic ring system which may be substituted at a carbon atom with one or two oxo (=O) moieties, as in pyrrolidin-2-one, or at a heteroatom so as to contain an oxidized moeity such as, but not limited to, —N(=O), —S(=O)— or —S(=O)$_2$—. More typically, heterocycloalkyls include pyrrolidinyl, piperidinyl, morpholinyl and piperazinyl.

"Heteroaryl" as the term is used herein, by itself or as part of another term, unless otherwise stated or implied by context, refers to an aryl moiety, group or substituent as defined herein in which one or more but not all of the aromatic carbons of an aromatic ring of the aryl is replaced by a heteroatom. A heteroaryl typically contains a total one to four heteroatoms in the ring(s) of the heteroaryl ring system, provided that not all of the skeletal atoms of any one ring system in the heteroaryl are heteroatoms, optionally substituted where permitted, and have 0 to 3 N atoms, 1 to 3 N atoms or 0 to 3 N atoms, typically 0 to 1 O atoms and/or 0 to 1 S atoms, provided that at least one heteroatom is present. A heteroaryl may be monocyclic, bicyclic or polycyclic. Monocyclic heteroaryls include $C_5$-$C_{24}$ heteroaryls, typically $C_5$-$C_{12}$ or $C_5$-$C_6$ heteroaryls, in which the subscript indicates the total number of skeletal atoms (inclusive of its carbon atoms and heteroatoms) of the aromatic ring system(s) of the heteroaryl. In some aspects a heteroaryl is an aryl moiety wherein one 1, 2 or 3 of the carbon atoms of the aromatic ring(s) and their attached hydrogen atoms of a parent aryl moiety are replaced by a heteroatom, optionally substituted where permitted, including N/NH, O and S, provided that not all of the skeletal atoms of any one aromatic ring system in the aryl moiety are replaced by heteroatoms and more typically are replaced by oxygen (—O—), sulfur (—S—) nitrogen (=N—) or —NR— wherein R is —H, a protecting group or $C_1$-$C_{20}$ alkyl, $C_6$-$C_{24}$ aryl, or is nitrogen substituted with another organic moiety in a manner which retains the cyclic conjugated system, wherein the nitrogen, sulfur or oxygen heteroatom participates in the conjugated system either through pibonding with an adjacent atom in the ring system or through a lone pair of electrons on the heteroatom. In other aspects, a heteroaryl is a heterocyclyl as defined herein that is aromatized.

Typically, a heteroaryl is monocyclic which in some aspects has a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic $C_6$ heteroaryl containing 1 to 5 aromatic carbon atoms and the requisite number of aromatic heteroatoms within its heteroaromatic ring system. Heteroaryls that are 5-membered have four, three, two or one aromatic heteroatom(s), and heteroaryls that are 6-membered include heteroaryls having five, four, three, two or one aromatic heteroatom(s). $C_5$-heteroaryls are monovalent moieties derived from removing a hydrogen atom from an aromatic carbon or an electron from an aromatic heteroatom, where permitted, from a parent heterocycle compound including pyrrole, furan, thiophene, oxazole, isoxazole, thiazole, isothiazole, imidazole, pyrazole, triazole and tetrazole. $C_6$ heteroaryls, which are 6-membered, are exemplified by monovalent moieties derived from removing a hydrogen atom from an aromatic carbon or an electron from an aromatic heteroatom, where permitted, from a parent aromatic heterocycle compound including without limitation pyridine, pyridazine, pyrimidine, and a triazine.

A "5-membered nitrogen-containing heteroaryl" as the terms are used herein, by itself or as part of another term, unless otherwise stated or implied by context, refers to an optionally substituted 5-membered heteroaromatic system that is monovalent and contains a skeletal aromatic nitrogen atom and is typically a monocyclic heteroaryl or is fused to an aryl or another heteroaryl ring system to typically form a 6,5-fused ring system in which the 5-membered heteroaromatic moiety may contain one or more other independently selected heteroatoms such as N/NH, O or S, optionally substituted where permitted. Exemplary 5-membered heteroaryls include thiazole, pyrrole, imidazole, oxazole, and triazole.

A "6-membered nitrogen-containing heteroaryl" as the terms are used herein, by itself or as part of another term, unless otherwise stated or implied by context, refers to an optionally substituted 6-membered heteroaromatic system that is monovalent and contains a skeletal aromatic nitrogen atom and is typically a monocyclic heteroaryl or is fused to an aryl or another heteroaryl ring system to typically form a 6,5- or 6,6-fused ring system in which the 6-membered heteroaromatic moiety may contain one or more other independently selected heteroatoms such as N/NH, O or S, optionally substituted where permitted. Exemplary 6-membered heteroaryls include without limitation pyridine, pyrimidine and pyrazine.

"Heterocyclo", as the term is used herein, by itself or as part of another term, unless otherwise stated or implied by context, refers to a heterocyclyl moiety, group or substituent as defined above wherein a hydrogen atom or an electron, where permitted, from a different carbon atom or an electron from a nitrogen ring atom if present is removed to provide a divalent moiety.

"Heteroarylene", as the term is used herein, by itself or as part of another term, unless otherwise stated or implied by context refers to heteroaryl moiety, group or substituent as defined above wherein a hydrogen atom or an electron, where permitted, from a different aromatic carbon atom or an electron from an aromatic nitrogen ring atom if present is removed to provide a divalent moiety. A "5-membered nitrogen-containing heteroarylene contains at least one aromatic nitrogen atom in its heteroaromatic ring system and is divalent and is similarly related in structure to a 5-membered nitrogen-containing heteroaryl as described above. Likewise, a "6-membered nitrogen-containing heteroarylene is divalent and is similarly related in structure to a 6-membered nitrogen heteroaryl as described above.

"Heteroalkyl," as used herein by itself or in combination with another term, unless otherwise stated or implied by context, refers to an optionally substituted straight or branched chain hydrocarbon, fully saturated or containing from 1 to 3 degrees of unsaturation, consisting of 1 to 20 carbon atom and from 1 to 10 heteroatoms, typically from 1 to 5 heteroatoms, selected from the group consisting of O, N, Si and S (typically O, N, and S), optionally substituted where permitted, and wherein each nitrogen and sulfur atom is optionally oxidized to an N-oxide, a sulfoxide or sulfone, or wherein one of the nitrogen atoms is optionally quaternized. The heteroatom(s) O, N, S and/or Si may be placed at any interior position of the heteroalkyl group or at a terminal position of the optionally substituted alkyl group of the heteroalkyl. Non-limiting examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, as for example, but not limitation, by —$CH_2$—NH—OCH$_3$ and —$CH_2$—O—Si($CH_3$)$_3$. In some aspects, a heteroalkyl is fully saturated. A heteroalkyl is typically denoted by the number of its contiguous heteroatom(s) and non-aromatic carbon atoms of its alkyl moiety unless indicated otherwise or by context. Thus, —$CH_2$—$CH_2$—O—$CH_3$ and —$CH_2$—$CH_2$—S(O)—$CH_3$ are both $C_4$-heteroalkyls and —$CH_2$—CH=N—O—$CH_3$, and —CH=CH—N($CH_3$)—$CH_3$ are both $C_5$ heteroalkyl.

"Heteroalkylene" as used herein by itself or in combination with another term, unless otherwise stated or implied by context, means a divalent group derived from heteroalkyl (as discussed above), by removal of a hydrogen atom or an heteroatom electron form a parent heteroalkyl to provide a divalent moeity exemplified by, but not limited to —$CH_2$—$CH_2$—S—$CH_2$—$CH_2$— and —$CH_2$—S—$CH_2$—$CH_2$—NH—$CH_2$—. For a heteroalkylene, heteroatom(s) thereof may be interior to or may occupy either or both termini of its optionally substituted alkyl chain. When a heteroalkylene is a component of a Linker Unit both orientations of that component within the Linker Unit is permitted unless indicated or implied by context.

"Aminoalkyl" as used herein by itself or in combination with another term, unless otherwise stated or implied by context, refers to a moiety, group or substituent having a basic nitrogen bonded to one radical terminus of an alkylene moiety as defined above to provide a primary amine in which the basic nitrogen is not further substituted, or to provide a secondary or tertiary amine in which the basic amine is further substituted by one or two alkyl moieties, respectively, as described above, which in some aspects together with the nitrogen to which both moieties are attached define a $C_3$-$C_8$ heterocyclyl containing the basic nitrogen as a skeletal atom, typically a $C_3$-$C_6$ heterocyclyl. When aminoalkyl is used as a Markush group (i.e., a substituent) the alkylene moiety of the aminoalkyl is attached to a Markush formula with which it is associated through a spa carbon of that moiety (i.e., the other radical terminus of the aforementioned alkylene). In some aspects, an aminoalkyl when part of a self-stabilizing Linker Unit ($L_{SS}$) or self-stabilized Linker Unit ($L_S$) is an exemplary acyclic Basic Unit. An aminoalkyl is typically denoted by the number of contiguous carbon atoms of its alkylene moiety. Thus, a $C_1$ aminoalkyl includes without limitation —$CH_2NH_2$, —$CH_2NHCH_3$ and —$CH_2N(CH_3)_2$ and a $C_2$ amino alkyl includes —$CH_2CH_2NH_2$, —$CH_2CH_2NHCH_3$ and —$CH_2CH_2N(CH_3)_2$.

"Optionally substituted alkyl", "optionally substituted alkenyl", "optionally substituted alkynyl", "optionally substituted alkylaryl", "optionally substituted arylalkyl", "optionally substituted heterocycle", "optionally substituted aryl", "optionally substituted heteroaryl", "optionally substituted alkylheteroaryl", "optionally substituted heteroarylalkyl" and like terms refer to an alkyl, alkenyl, alkynyl, alkylaryl, arylalkyl heterocycle, aryl, heteroaryl, alkylheteroaryl, heteroarylalkyl, or other substituent, moiety or group as defined or disclosed herein wherein hydrogen atom(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects an alkene function group replaces two contiguous sp3 carbon atoms of an alkyl substituent, provided that the radical carbon of the alkyl moiety is not replaced, so that the optionally substituted alkyl becomes an unsaturated alkyl substituent.

Optional substituent replacing hydrogen(s) in any one of the foregoing substituents, moieties or groups is independently selected from the group consisting of aryl, heteroaryl, hydroxyl, alkoxy, aryloxy, cyano, halogen, nitro, fluoroalkoxy, and amino, including mono-, di- and tri-substituted amino groups, and the protected derivatives thereof, or is selected from the group consisting of —X, —OR', —SR', —$NH_2$, —N(R')($R^{op}$), —N($R^{op}$)$_3$, =NR', —$CX_3$, —CN, —$NO_2$, —NR'C(=O)H, —NR'C(=O)$R^{op}$, —NR'C(=O)$R^{op}$, —C(=O)R', —C(=O)$NH_2$, —C(=O)N(R')$R^{op}$, —S(=O)$_2R^{op}$, —S(=O)$_2NH_2$, —S(=O)$_2$N(R')$R^{op}$, —S(=O)$_2NH_2$, —S(=O)$_2$N(R')$R^{op}$, —S(=O)$_2$OR', —S(=O)$R^{op}$, —OP(=O)(OR')(O$R^{op}$), —OP(OH)$_3$, —P(=O)(OR')(O$R^{op}$), —P$O_3H_2$, —C(=O)R', —C(=S)$R^{op}$, —$CO_2R'$, —C(=S)O$R^{op}$, —C(=O)SR', —C(=S)SR', —C(=S)$NH_2$, —C(=S)N(R')($R^{op}$)$_2$, —C(=NR')$NH_2$, —C(=NR')N(R')$R^{op}$, and salts thereof, wherein each X is independently selected from the group consisting of a halogen: —F, —Cl, —Br, and —I; and wherein each $R^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl, $C_5$-$C_{24}$ heteroaryl, a protecting group, and a prodrug moiety or two of $R^{op}$ together with the heteroatom to which they are attached defines a heterocyclyl; and R' is hydrogen or $R^{op}$, wherein $R^{op}$ is selected from the group consisting of $C_1$-$C_{20}$ alkyl, $C_6$-$C_{24}$ aryl, $C_3$-$C_{24}$ heterocyclyl, $C_5$-$C_{24}$ heteroaryl, and a protecting group.

Typically, optional substituents are selected from the group consisting of —X, —OH, —O$R^{op}$, —SH, —S$R^{op}$, —$NH_2$, —NH($R^{op}$), —NR'($R^{op}$)$_2$, —N($R^{op}$)$_3$, =NH, =N$R^{op}$, —$CX_3$, —CN, —$NO_2$, —NR'C(=O)H, NR'C(=O)$R^{op}$, —$CO_2H$, —C(=O)H, —C(=O)$R^{op}$, —C(=O)$NH_2$, —C(=O)NR'$R^{op}$, —S(=O)$_2R^{op}$, —S(=O)$_2NH_2$, —S(=O)$_2$N(R') $R^{op}$, —S(=O)$_2NH_2$, —S(=O)$_2$N(R')($R^{op}$), —S(=O)$_2$OR', —S(=O)$R^{op}$, —C(=S)$R^{op}$, —C(=S)$NH_2$, —C(=S)N(R')$R^{op}$, —C(=NR')N($R^{op}$)$_2$, and salts thereof, wherein each X is independently selected from the group consisting of —F and —Cl, $R^{op}$ is typically selected from the group consisting of $C_1$-$C_6$ alkyl, $C_6$-$C_{10}$ aryl, $C_3$-$C_{10}$ heterocyclyl, $C_5$-$C_{10}$ heteroaryl, and a protecting group; and R' is independently selected from the group typically consisting of hydrogen, $C_1$-$C_6$ alkyl, $C_6$-$C_{10}$ aryl, $C_3$-$C_{10}$ heterocyclyl, $C_5$-$C_{10}$ heteroaryl, and a protecting group, independently selected from $R^{op}$. More typically, substituents are selected from the group consisting of —X, —$R^{op}$, —OH, —O$R^{op}$, —$NH_2$, —NH($R^{op}$), —N($R^{op}$)$_2$, —N($R^{op}$)$_3$, —$CX_3$, —$NO_2$, —NHC(=O)H, —NHC(=O) $R^{op}$, —C(=O)$NH_2$, —C(=O)NH$R^{op}$, —C(=O)N($R^{op}$)$_2$, —$CO_2H$, —$CO_2R^{op}$, —C(=O)H, —C(=O)$R^{op}$, —C(=O) $NH_2$, —C(=O)NH($R^{op}$), —C(=O)N($R^{op}$)$_2$, —C(=NR') $NH_2$, —C(=NR')NH($R^{op}$), —C(=NR')N($R^{op}$)$_2$, a protecting group and salts thereof, wherein each X is —F, $R^{op}$ is independently selected from the group consisting of $C_1$-$C_6$ alkyl, $C_6$-$C_{10}$ aryl, $C_5$-$C_{10}$ heteroaryl and a protecting group; and R' is selected from the group consisting of hydrogen, $C_1$-$C_6$ alkyl and a protecting group, independently selected from $R^{op}$.

In some aspects, an alkyl substituent is selected from the group consisting —$NH_2$, —NH($R^{op}$), —N($R^{op}$)$_2$, —N($R^{op}$)$_3$, —C(=NR')$NH_2$, —C(=NR')NH($R^{op}$), and —C(=NR')N($R^{op}$)$_2$, wherein R' and $R^{op}$ is as defined for any one of the R' or $R^{op}$ groups above. In some of those aspects the R' and/or $R^{op}$ substituents provide for a Basic Unit (BU) (i.e., the basic functional group of BU) as when $R^{op}$ is independently selected from the group consisting of hydrogen and $C_1$-$C_6$ alkyl. Alkylene, carbocyclyl, carbocyclo, aryl, arylene, heteroalkyl, heteroalkylene, heterocyclyl, heterocyclo, heteroaryl, and heteroarylene groups as described above may also be similarly substituted.

"Optionally substituted heteroatom" as used herein, unless otherwise stated or implied by context, refers to a heteroatom within a functional group or other organic moiety in which the heteroatom is not further substitution and/or refers to —NH— within a functional group or other organic in which the hydrogen is retained or is replaced by a substituent that suitably retains the localization of the lone pair electrons on the nitrogen atom. Therefore, such substituents include optionally substituted alkyl, arylalkyl, and heteroarylalkyl, and may further include optionally substituted alkenyl, alkynyl, aryl, alkylaryl, and arylheteroalkyl, as those terms are defined herein, but whose inclusion is dependent on the amount of delocalization of the nitrogen lone pair electrons into these substituents, and in some aspects excludes carbonyl-containing substituents in which the carbonyl functional group of that substituent is bonded to the nitrogen atom. In some aspects, when variable group J' of a PAB or PAB-type moiety, as described by the embodiments of the invention, is optionally substituted —NH—, the nitrogen atom so substituted suitably retains the localization of its nitrogen lone pair electrons when cleavage of the Linker Unit to release J' which allows for self-immolation of the PAB or PAB-type moiety. In other aspects, when variable group E' of a glycosidic bond been W' and Y of a Glucuronide Unit, as described by the embodiments of the invention, is an optionally substituted —NH— moiety, the nitrogen atom so substituted suitably retains the localization of its nitrogen lone pair electrons in its participation in the glycosidic bond between Y and W and provides for a recognition site for a glycosidase cleavage so that cleavage of the glycosidic bond effectively competes with spontaneous hydrolysis of that bond.

In some aspect, an optional substituent replacing carbon in an acyclic carbon chain provides for a heteroalkyl or heteroalkylene and for that purpose is typically selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O, in which —NH— is optionally substituted.

"O-linked moiety", "O-linked substituent" and like terms as used herein, unless otherwise stated or implied by context, refers to a group or substituent that is attached to another moiety with which it is associated directly through an oxygen atom of the group or substituent. An O-linked group may be monovalent including without limitation groups such as —OH, acetoxy (i.e., —OC(=O)CH$_3$), acyloxy (i.e., —OC(=O)R$^b$, wherein R$^b$ is —H, optionally substituted C$_1$-C$_{20}$ alkyl, optionally substituted C$_3$-C$_{20}$ cycloalkyl, optionally substituted C$_3$-C$_{20}$ alkenyl, optionally substituted C$_2$-C$_{20}$ alkynyl, optionally substituted C$_6$-C$_{24}$ aryl, optionally substituted C$_5$-C$_{24}$ heteroaryl or optionally substituted C$_3$-C$_{24}$ heterocyclyl, and further include monovalent groups such as, but without limitation, C$_1$-C$_{20}$ alkyloxy (i.e., C$_1$-C$_{20}$ aliphatic ether), optionally substituted, wherein the alkyl moiety is saturated or unsaturated, and other ethers including C$_6$-C$_{24}$ aryloxy (Aryl-O—), phenoxy (Ph-O—), C$_5$-C$_{20}$ heteroaryloxy (heteroaryl-O—), optionally substituted, and silyloxy, (i.e., R$_3$SiO—, wherein each R independently is C$_1$-C$_{20}$ alkyl or C$_6$-C$_{24}$ aryl, or C$_5$-C$_{24}$ heteroaryl, optionally substituted), and —ORPR, wherein R$^{PR}$ is a protecting group as previously defined, or an O-linked group may be divalent including without limitation =O or —X—(CH$_2$)$_n$—Y—, wherein X and Y independently are S and O and subscript n is 2 to 3, to form a spiro ring system with the carbon to which X and Y are both attached.

Typically, a O-linked substituent is a monovalent moiety selected from the group consisting of —OH, —OC(=O) CH$_3$), —OC(=O)R$^b$, C$_1$-C$_6$ saturated alkyl ether and C$_2$-C$_6$ unsaturated ether, wherein R$^b$ is typically C$_1$-C$_6$ saturated alkyl, C$_3$-C$_6$ unsaturated alkyl, C$_2$-C$_6$ alkenyl, or phenyl, optionally substituted, or is selected from that group excluding —OH. Other exemplary O-linked substituent are provided by definitions for carbamate, ether and carbonate as disclosed herein in which the monovalent oxygen atom of the carbamate, ether and carbonate functional group is bonded to the Markush structure or larger organic moiety with which it is associated.

"Halogen" as used herein, unless otherwise stated or implied by context, refers to fluorine, chlorine, bromine or iodine and is typically —F or —Cl.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (1999), "Protective groups in organic synthesis, 3$^{rd}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —ORPR, wherein R$^{PR}$ is a protecting group for hydroxyl, wherein hydroxyl is typically protected as an ester (e.g., acetate, propionate or benzoate). Other protecting groups for hydroxyl avoid its interference with the nucleophilicity of organometallic reagents or other highly basic reagents, for which purpose hydroxyl is typically protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$—, wherein least one of R$^{PR}$ is a nitrogen atom protecting group or both R$^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. By way of example and not limitation, a suitable protecting group may include those previously described for protecting functional groups. In some aspects a suitable protecting group is typically a protecting group used in peptide coupling reactions. For example, a suitable protecting group for nitrogen is an acid-labile carbamate protecting group such as t-butyloxycarbonyl (BOC).

"Ester" as used herein, unless otherwise stated or implied by context, refers to a substituent, moiety or group having the structure of —C(=O)—O— to define an ester functional group in which the carbonyl carbon atom of that structure is not directly connected to another heteroatom but is directly connected to hydrogen or another carbon atom of an organic moiety with which it is associated, and wherein the monovalent oxygen atom is either attached to the same organic moiety to a different carbon atom to provide a lactone or to some other organic moiety. Typically, esters in addition to the ester functional group comprise or consist of an organic moiety containing 1 to 50 carbon atoms, typically 1 to 20 carbon atoms or more typically 1 to 8 carbon atoms and 0 to 10 independently selected heteroatoms (e.g., O, S, N, P, Si, but usually O, S and N), typically 0 to 2 where the organic moieties are bonded through the —C(=O)—O— structure (i.e., through the ester functional group). When an ester is a substituent or variable group of a Markush structure that substituent is bonded to the structure with which it is associated through the monovalent oxygen atom of the ester functional group. In those instances the organic moiety attached to the carbonyl carbon of the ester functional group comprises any one of the organic groups described herein, e.g., C$_1$-C$_{20}$ alkyl, C$_2$-C$_{20}$ alkenyl, C$_2$-C$_{20}$ alkynyl, C$_6$-C$_{24}$ aryl, C$_5$-C$_{24}$ heteroaryl, C$_3$-C$_{24}$ heterocyclyl or substituted derivatives of any of these, e.g., comprising 1, 2, 3, 4 or more substituents, where each substituent as defined herein for optional substituent is independently chosen. Exemplary esters include, by way of example and not limitation, acetate, propionate, isopropionate, isobutyrate, butyrate, valerate, isovalerate, caproate, isocaproate, hexanoate, heptanoate, octanoate, phenylacetate esters and benzoate esters or have the structure of —OC(=O)R$^b$ wherein R$^b$ is as defined for acyloxy O-linked substituents and is typically selected from the group consisting of methyl, ethyl, propyl, iso-propyl, 3-methyl-prop-1-yl, 3,3-dimethyl-prop-1-yl and vinyl. Ester substituents as described herein are exemplary monovalent O-linked substituents.

"Ether" as used herein, unless otherwise stated or implied by context, refers to an organic moiety, group or substituent that comprises 1, 2, 3, 4 or more —O— (i.e., oxy) moieties that are not bonded to carbonyl moiety(ies), typically 1 or 2, wherein no two —O— moieties are immediately adjacent (i.e., directly attached) to each other. Typically, an ether structure is comprised or consists of the formula —O-organic moiety wherein organic moiety is as described for an organic moiety bonded to an ester functional group. More typically, an ether moiety, group or substituent has the formula of —O-organic moiety wherein the organic moiety is as described herein for an optionally substituted alkyl group. When ether is used as a Markush group (i.e., an ether substituent) the oxygen of the ether functional group is attached to a Markush formula with which it is associated. When ether is a used as substituent in a Markush group it is sometimes designated as an "alkoxy" group, which is an exemplary O-linked substituent. $C_1$-$C_{20}$ alkoxy includes $C_1$-$C_4$ ether substituents such as, by way of example and not limitation, methoxy, ethoxy, propoxy, iso-propoxy, butoxy and allyloxy (i.e., —OCH$_2$CH=CH$_2$).

"Amide" as used herein, unless otherwise stated or implied by context, refers to a moiety having an optionally substituted functional group of structure R—C(=O)N(R$^c$)— or —C(=O)N(R$^c$)$_2$ to which no other heteroatom is directly attached to the carbonyl carbon and wherein R$^c$, independently selected, is hydrogen, a protecting group or an organic moiety wherein the organic moiety is as described herein for an organic moiety bonded to an ester functional group and is typically an optionally substituted $C_1$-$C_{20}$ alkyl. Typically, hydrogen or an organic moiety, independently selected from R$^c$, is bonded to the amide functional group, wherein the organic moiety is also as described herein for an organic moiety bonded to an ester functional group. When bonded to an organic moiety the resulting structure is represented by organic moiety-C(=O)N(R$^c$)$_2$, or R$^c$—C(=O)N(R$^c$)— organic moiety. When an amide is recited as a variable for a Markush structure, the amide nitrogen atom or carbonyl carbon atom of the amide functional group is bonded to that structure. Amides are typically prepared by condensing an acid halide, such an acid chloride, with a molecule containing a primary or secondary amine. Alternatively, amide coupling reactions well-known in the art of peptide synthesis, which oftentimes proceed through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem.* (1974) 43: 419-443. Reagents used in the preparation of activated carboxylic acids is provided in Han, et al. "Recent development of peptide coupling agents in organic synthesis" *Tet.* (2004) 60: 2447-2476.

"Carbonate" as used here means a substituent, moiety or group that contains a —O—C(=O)—O— structure, which defines a carbonate functional group. Typically, carbonate groups as used herein are comprised of an organic moiety, wherein the organic moiety is as described herein for an organic moiety bonded to an ester functional group, bonded through the —O—C(=O)—O— structure, e.g., organic moiety-O—C(=O)—O—. When carbonate is used as a Markush group (i.e., a substituent) one of the monovalent oxygen atoms of the carbonate functional group is attached to a Markush formula with which it is associated and the other is bonded to a carbon atom of an organic moiety as previously described for an organic moiety bonded to an ester functional group. In such instances carbonate is an exemplary O-linked substituent.

"Carbamate" as used here means a substituent, moiety or group that contains a optionally substituted carbamate functional group structure represented by —O—C(=O)N(R$^c$)— or —O—C(=O)N(R$^c$)$_2$, or —O—C(=O)NH(optionally substituted alkyl) or —O—C(=O)N(optionally substituted alkyl)$_2$ in which the optionally substituted alkyl(s) are exemplary carbamate functional group substituents, wherein R$^c$ and optionally substituted alkyl are independently selected wherein independently selected R$^c$, is hydrogen, a protecting group or an organic moiety, wherein the organic moiety is as described herein for an organic moiety bonded to an ester functional group and is typically an optionally substituted alkyl. Typically, carbamate groups as used herein are additionally comprised of an organic moiety, independently selected from R$^c$, wherein the organic moiety is as described herein for an organic moiety bonded to an ester functional group, bonded through the —O—C(=O)—N(R$^c$)— structure, wherein the resulting structure has the formula of organic moiety-O—C(=O)—N(R$^c$)— or —O—C(=O)—N(R$^c$)-organic moiety. When carbamate is used as a Markush group (i.e., a substituent), the monovalent oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked substituents. In some aspects a carbamate functional group interconnects a Drug Unit and a PAB or PAB-type self-immolative moiety of a self-immolative Spacer Unit and functions as a second self-immolative Spacer Unit by undergoing spontaneous decomposition to release CO$_2$ and D as a drug compound subsequent to self-immolation of the first Spacer Unit.

"Antibody" as used herein, unless otherwise stated or implied by context, refers to is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment has the requisite number of sites for covalent attachment to the requisite number of drug-linker moieties. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system (see, e.g., Janeway et al., (2001), "Immunol. Biology, 5th ed.", Garland Publishing, New York). An antibody can be of any type (e.g., IgG, IgE, IgM, IgD, and IgA), class (e.g., IgG$_1$, IgG$_2$, IgG$_3$, IgG$_4$, IgA$_1$ and IgA$_2$) or subclass. The antibody can be derived from any suitable species. In some embodiments, the antibody is of human or murine origin. An antibody can be, for example, human, humanized or chimeric. An antibody or antibody fragment thereof, is an exemplary targeting agent that is incorporated as a Ligand Unit into an LDC of the present invention and in these instances is sometimes referred to as an antibody Ligand Unit.

In some aspects an antibody selectively and specifically binds to an epitope on hyper-proliferating or hyper-stimulated mammalian cells (i.e., abnormal cells), wherein the epitope is preferentially displayed by or is more characteristic the abnormal cells in contrast to normal cells, or is preferentially displayed within and is peculiar to the vicinity of the abnormal cells or is more characteristic of normal cells in the vicinity of abnormal cells in contrast to normal cells not localized to the abnormal cells. In those aspects the mammalian cells are typically human cells.

"Monoclonal antibody" as used herein, unless otherwise stated or implied by context, refers to an antibody obtained from a population of substantially homogeneous antibodies, i.e., the individual antibodies comprising the population are identical except for possible naturally-occurring mutations that may be present in minor amounts or differences in glycosylation patterns. A monoclonal antibody (mAb) is highly specific, being directed against a single antigenic site. The modifier "monoclonal" indicates the character of the antibody as being obtained from a substantially homogeneous population of antibodies, and is not to be construed as requiring production of the antibody by any particular method.

"Antibody fragment" as used herein, unless otherwise stated or implied by context, refers to a portion of an intact antibody that is comprised of the antigen-binding site or variable region of the intact antibody and remains capable of binding to the cognate antigen of the intact antibody. Examples of antibody fragments include Fab, Fab', $F(ab')_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically binds to a target antigen (e.g., a cancer cell antigen, an immune cell antigen, a viral antigen or a microbial antigen).

"Cytotoxic activity" as used herein, unless otherwise stated or implied by context, refers to a cell-killing effect or anti-survival effect of a NAMPTi compound or derivative thereof, or refers to a Ligand-Drug Conjugate, or an intracellular metabolite of a Ligand Drug Conjugate, having a NAMPT Drug Unit. Cytotoxic activity may be expressed as an $IC_{50}$ value, which is the concentration (molar or mass) per unit volume at which half the cells survive after incubation of the cells for a defined time period in the presence of the NAMPTi compound or its derivative or in the presence of a Ligand-Drug Conjugate having a NAMPT Drug Unit.

"Cytostatic activity" as used herein, unless otherwise stated or implied by context, refers to an anti-proliferative effect of a NAMPTi compound, a Ligand-Drug Conjugate, or an intracellular metabolite of a Ligand-Drug Conjugate having a NAMPT Drug Unit whose biological effectiveness is not dependent on cell killing but whose effect is due to inhibition of cell division of hyper-proliferating cells, hyperstimulated immune cells or other abnormal or unwanted cells.

"Specific binding" and "specifically binds" as the terms are used herein, unless otherwise stated or implied by context, refers to an antibody, a fragment thereof, or an antibody Ligand Unit as the targeting moiety in a Ligand Drug Conjugate that is capable of binding in a immunologically selective manner with its corresponding targeted antigen and not with a multitude of other antigens. Typically, the antibody or fragment thereof binds its targeted antigen with an affinity of at least about $1 \times 10^{-7}$ M, and preferably about $1 \times 10^{-8}$ M to $1 \times 10^{-9}$ M, $1 \times 10^{-10}$ M, or $1 \times 10^{-11}$ M and binds to that predetermined antigen with an affinity that is at least two-fold greater than its affinity for binding to a non-specific antigen (e.g., BSA, casein) other than for a closely-related antigen, wherein said affinities are substantially retained when incorporated into a Ligand Drug Conjugate as an antibody Ligand Unit.

"Ligand-Drug Conjugate" as the term is used herein, unless otherwise stated or implied by context, refers to a compound, or a collection of such compounds comprised of a Ligand Unit derived from a targeting agent, and a NAMPT Drug Unit (D), which upon release from a Ligand Drug Conjugate compounds provides a NAMPTi compound or derivative thereof, wherein the targeting Ligand Unit of the Ligand Drug Conjugate selectively binds to its cognate targeted moiety. In some instances a collection of Ligand Drug Conjugate compounds is referred to as a Ligand Drug Conjugate composition in which the individual Ligand Drug Conjugate compounds differing primarily by the number of NAMPT Drug Units bonded to each Ligand Unit or the locations on the Ligand Unit at which the NAMPT Drug Units are bound. In other instances the term Ligand Drug Conjugate applies to an individual member (i.e., a Ligand Drug Conjugate compound) of the composition.

"Targeting agent" are used herein, unless otherwise stated or implied by context, refers to an agent that that is capable of selectively binding to a targeted moeity and which substantially retains that capability when incorporated as a Ligand Unit into a Ligand Drug Conjugate or when the Ligand Unit of a Ligand Drug Conjugate corresponds in structure to the targeting agent, so that the targeting Ligand Unit is the targeting moeity of the Conjugate. In some aspects the targeting agent is an antibody that specifically binds to an accessible antigen characteristic of an abnormal cell or is an accessible antigen that is particular to the surrounding environment in which these cells are found. In other aspects the targeting agent is a receptor ligand that specifically binds to an accessible receptor characteristic of, or in greater abundance on, abnormal cells or other unwanted cells, or to an accessible receptor that is particular to cells of the surrounding environment in which abnormal cells are found. Typically a targeting agent is an antibody as defined herein that binds selectively to a targeted moiety of an abnormal mammalian cell, more typically a targeted moiety of an abnormal human cell.

"Targeted moeity" as defined herein is a moeity to be selectively recognized by a targeting agent or targeting moeity of a Ligand Drug Conjugate, which is its Ligand Unit. In some aspects a targeted moiety is present on, within, or in the vicinity of abnormal cells and is typically present in greater abundance or copy number in comparison to normal cells or the environment of such cells in which abnormal cells are typically not present. In some aspects the targeted moiety is an antigen accessible to selective binding by an antibody, which is an exemplary targeting agent that is incorporated as an antibody Ligand Unit or which corresponds in structure to the Ligand Unit in a Ligand Drug Conjugate. In other aspects, the targeting moiety is that of a ligand for an extracellularly accessible cell membrane receptor, which may be internalized upon binding of the cognate targeting moiety provided by the Ligand Unit of a Ligand Drug Conjugate that incorporates or corresponds in structure to the receptor ligand, or is capable of passive or facilitative transport of the Ligand Drug Conjugate compound subsequent to binding of the cell-surface receptor. In some aspects, the targeted moiety is present on abnormal mammalian cells or on mammalian cells characteristic of the environment of such abnormal cells. In some aspects the targeted moeity is an antigen of an abnormal mammalian cell, more typically a targeted moiety of an abnormal human cell.

"Target cells", "targeted cells", or like terms as used herein, unless otherwise stated or implied by context, are the intended cells to which Ligand Drug Conjugate is designed to interact in order to inhibit the proliferation or other unwanted activity of abnormal cells. In some aspects, the targeted cells are hyper-proliferating cells or hyper-activated immune cells, which are exemplary abnormal cells. Typically, those abnormal cells are mammalian cells and more typically are human cells. In other aspects the targeted cells are within the vicinity of the abnormal cells so that action of the Ligand Drug Conjugate on the nearby cells has an intended effect on the abnormal or unwanted cells. For example, the nearby cells may be epithelial cells that are characteristic of the abnormal vasculature of a tumor. Targeting of those vascular cells by a Ligand Drug Conjugate compound or a composition of such compounds will either have a cytotoxic or a cytostatic effect on these cells which is believed to inhibit nutrient delivery to the nearby abnormal cells of the tumor so as to indirectly have a cytotoxic or cytostatic effect on these cells, and/or will have a direct cytotoxic or cytostatic effect on the nearby abnormal cells by releasing its NAMPT Drug Unit as a NAMPTi compound or derivative in the vicinity of these cells.

"Antigen" as the term is used herein, unless otherwise stated or implied by context, is a moiety that is capable of selective binding by an unconjugated antibody or a fragment thereof or to an Antibody Drug Conjugate compound, which is comprised of an antibody Ligand Unit, which incorporates or corresponds in structure to the unconjugated antibody. In some aspects, the antigen is an extracellularly-accessible cell-surface protein, glycoprotein, or carbohydrate preferentially displayed by abnormal cells in comparison to normal cells. In some instances, the abnormal cells displaying the antigen are hyper-proliferating cells in a mammal. In other instances, the abnormal cells displaying the antigen are hyper-activated immune cells in a mammal. In other aspects, the antigen to be specifically bound by an antibody Ligand Unit of an Antibody Drug Conjugate compound is present in the particular environment of hyper-proliferating cells or hyper-activated immune cells in a mammal in contrast to the environment typically experienced by normal cells in the absence of such abnormal cells. In still other aspects, the cell-surface antigen is capable of internalization upon selective binding by a compound of an Antibody Drug Conjugate composition. Antigens associated with hyper-proliferating cells that are cell-surface accessible to an ADC include by way of example and not limitation CD19, CD70, CD30, CD33, NTB-A, $\alpha v \beta 6$, and CD123.

"Antibody Drug Conjugate" as the term is used herein, unless otherwise stated or implied by context, refers to a Ligand Drug Conjugate wherein the targeting moiety of the Conjugate is that of an antibody, wherein the antibody in the form of an antibody Ligand Unit that is covalently associated with a NAMPT Drug Unit D, typically through an intervening Linker Unit. In some aspects the term refers to a collection (i.e., population or plurality) of Conjugate compounds having the same antibody Ligand Unit, except for previously described variations in antibody sequence and structure, NAMPT Drug Unit, and Linker Unit, but having variable loading or a distribution of the linker-drug moieties for each antibody (as for example when the number of NAMPT Drug Units in any two Antibody Drug Conjugate compounds in a plurality of such compound is the same but the location of their sites of attachment to the targeting moiety differ). In those aspects an Antibody Drug Conjugate is described by the averaged drug linker or NAMPT Drug Unit loading per antibody Ligand Unit of the conjugate compounds of the Antibody Drug Conjugate composition, depending on the presence or absence, respectively, of branching within the Linker Units. An Antibody Drug Conjugate composition obtained from the methods described herein have the general formula of Ab-$(L_R$-$L_O$-$D)_p$, wherein Ab is an antibody Ligand Unit, subscript p is the average number of drug linker moieties or NAMPT Drug Units connected to the antibody Ligand Unit and $L_R$-$L_O$ defines the Linker Unit, wherein $L_R$ is a primary linker, and is so named because that component is required to be present in a Linker Unit of an Antibody Drug Conjugate, and wherein $L_O$ is an optional secondary linker that when present is susceptible to enzymatic (e.g., protease or glycosidase) or non-enzymatic (e.g., reductive or hydrolytic) cleavage to effect release of the NAMPT Drug Unit as a NAMPTi compound or derivative thereof. In some aspects that cleavage is enhanced in the environment of abnormal or occurs subsequent to intracellular internalization of an Antibody Drug Conjugate compound of the composition on binding of its targeting antibody Ligand Unit to its cognate antigen. In the generalized Antibody Drug Conjugate structures disclosed herein, D is a NAMPT Drug Unit, wherein the NAMPT Drug Unit is released subsequent to enzymatic or non-enzymatic action on $L_O$ as a NAMPTi compound or derivative thereof when $L_O$ is present or of the bond between $L_R$ and D when $L_O$ is absent and subscript p is a number ranging from about 2 to about 20 or about 2 to about 16 or about 2 to about 10 and in some aspects is about 2, about 4, or about 8. An Antibody Drug Conjugate compound of the composition is described by the same general formula in which subscript p is replaced by p', wherein p' is an integer ranging 2 to 20 or 2 to 16 or 2 to 10 and in some aspects is 2, 4, or 8.

The average number of NAMPT Drugs Units or drug linker moieties per Ligand Unit in a preparation from a conjugation reaction may be characterized by conventional means such as mass spectroscopy, ELISA assay, HIC and/or HPLC. In some instances, separation, purification, and characterization of homogeneous Ligand-Drug Conjugates, where p is a certain value (i.e., p becomes p') from Ligand Drug Conjugate compounds with other drug loadings may be achieved by means such as reverse phase HPLC or electrophoresis.

"Ligand Unit" as the term is used herein, unless otherwise stated or implied by context, refers to a targeting moiety of a Ligand Drug Conjugate that binds selectively to its cognate targeted moiety and incorporates the structure of a targeting agent. A Ligand Unit (L) includes without limitation those of receptor ligands, antibodies to cell-surface antigens, and transporter substrates. In some aspects, the receptor, antigen or transporter to be bound by a Ligand Drug Conjugate compound is present in greater abundance on abnormal cells in contrast to normal cells. In other aspects the receptor, antigen or transporter to be bound by a Ligand Drug Conjugate compound is present in greater abundance on normal cells that are in the vicinity of abnormal cells in contrast to normal cells that are distant from the site of the abnormal cells. Various aspects of Ligand Units, including antibody Ligand Units, are further described by embodiments of the invention.

"Linker Unit" as the term is used herein, unless otherwise stated or implied by context, refers to an organic moiety in a Ligand Drug Conjugate intervening between and covalently attached to a NAMPT Drug Unit (D) and a Ligand Unit (L) as those terms are defined herein. A Linker Unit (LU) is comprised of a primary linker ($L_R$), which is a required component of that Unit, and an optional secondary linker ($L_O$), which in some aspects is present and intervenes between $L_R$ and D within a drug linker moiety of Ligand Drug Conjugate compound or a Drug Linker compound. In some aspects, $L_R$ is comprised of succinimide ($M^2$) or a succinic acid amide ($M^3$) moiety and is sometimes further comprised of a Basic Unit within a Linker Unit of a Ligand Drug Conjugate, and in other aspects $L_R$ is comprised of a maleimide ($M^1$) moiety and is sometimes further comprised of an Basic Unit within a Linker Unit of a Drug Linker compound. As a Drug Linker compound as described herein is sometimes comprised of a maleimide ($M^1$) moiety, attachment of a targeting agent, which results in a Ligand Unit, occurs to such a Drug Linker compound through a reactive thiol functional group of the targeting agent by way of Michael addition of its thiol functional group to the maleimide ring system of $M^1$. When the targeting agent is an antibody, the reactive thiol in some aspects is provided by a cysteine thiol group of the antibody. As a result of that addition, a Linker Unit of a Ligand Drug Conjugate compound contains a succinimide ($M^2$) moiety having a thio-substituted succinimide ring system. Subsequent hydrolysis of that ring system under controlled conditions due to the presence of an acyclic or cyclic Basic Unit as part of a self-stabilizing linker ($L_{SS}$) in which $L_R$ within a Ligand Drug Conjugate is $L_{SS}$, results in a succinic acid-amide ($M^3$) moiety, which is a component of self-stabilized linker ($L_S$), as further described herein. As a result $L_{SS}$ in an Ligand Drug Conjugate compound is hydrolyzed so that $L_R$ becomes $L_S$. That hydrolysis is controllable due to the Basic Unit (BU), as further described herein, being in appropriate proximity to the succinimide ring system.

"Primary linker" as the term is used herein, unless otherwise stated or implied by context, refers to a required component of Linker Unit (LU), and for Ligand Drug Conjugates and Drug Linker compounds of the present invention are either a self-stabilizing ($L_{SS}$) linker or a self-stabilized ($L_S$) linker, as further described herein. A $L_{SS}$ primary linker in a Drug Conjugate compound or Ligand Drug Conjugate (LDC) is characterized by a maleimide ($M^1$) or succinimide ($M^2$) moiety, respectively, while a $L_S$ primary linker in a LDC is characterized by a succinic acid amide ($M^3$) moiety. An $L_{SS}$ or $L_S$ primary linker of the present invention is also characterized by a $C_1$-$C_{12}$ alkylene moiety bonded to the imide nitrogen of the maleimide or succinimide ring system of $M^1$ or $M^2$ or the amide nitrogen of $M^3$, wherein the alkylene moiety in some aspects is substituted by an acyclic Basic Unit and may be further substituted by optional substituents or in other aspects incorporates a cyclic Basic Unit and is optionally substituted. Drug Linker compounds having a $L_{SS}$ primary linker are typically represented in general as $L_{SS}$-$L_O$-D while Ligand Drug Conjugates having a $L_{SS}$ primary linker are typically represented in general as L-($L_{SS}$-$L_O$-D)$_p$ in which the variable groups are as previously defined herein.

A maleimide ($M^1$) moiety of $L_{SS}$ in a Drug Linker Compound is capable of reacting with a thiol functional group of a targeting agent to form a thio-substituted succinimide moiety ($M^2$) in a $L_{SS}$ primary linker of a Ligand Drug Conjugate, wherein the thio-substituent is a Ligand Unit incorporating or corresponding to the structure of the targeting agent, wherein the Ligand Unit is bonded to $M^2$ through a sulfur atom from one of the targeting agent's thiol functional groups. As a result of that reaction, the targeting agent becomes covalently bonded to the primary linker ($L_R$) as a Ligand Unit. Subsequent hydrolysis of $M^2$ results in a $L_S$ primary linker in which $M^2$ is a succinic acid amide moiety ($M^3$). That linker moiety may exist as a mixture of two regioisomers ($M^{3A}$ and $M^{3B}$), depending on the relative reactivity of the two carbonyls of the succinimide ring system to hydrolysis. A Ligand Drug Conjugate having a $L_S$ primary linker is typically represented in general as L-($L_S$-$L_O$-D)$_p$, wherein the variable groups are as previously described herein.

"Secondary linker" as used herein, unless otherwise stated or implied by context, refers to an organic moiety in a Linker Unit (LU), wherein the secondary linker ($L_O$) is an optional component of that Unit that interconnects a Drug Unit to a primary linker ($L_R$) which is some aspects is a self-stabilizing ($L_{SS}$) linker of a Drug Linker compound or of a Ligand Drug Conjugate or a self-stabilized ($L_S$) linker of a Ligand Drug Conjugate upon hydrolysis of $L_{SS}$. Typically, $L_R$ is attached to $L_O$, when present, through a heteroatom or functional group shared between the two Linker Unit components. For some aspects of a Ligand Drug Conjugate or Drug Linker compound, $L_O$ is present and is covalently attached to $L_R$ and a NAMPT Drug Unit (D). For some of those aspects, $L_O$ is comprised of a self-immolative Spacer Unit (Y) having a PAB or PAB-type moiety, and a Peptide Cleavable Unit. In those aspects W, Y and D are arranged in linear configuration, as represented by —W—$Y_y$-D, wherein W is the Peptide Cleavable Unit, subscript y 1 or 2, wherein Y bonded to W is the PAB or PAB-type self-immolative Spacer Unit. In other aspects involving a PAB or PAB-type moiety, $L_O$ is further comprised of a Glucuronide Unit, in which the self-immolative Spacer Unit having the PAB or PAB-type self-immolative moiety is attached to a carbohydrate moiety (Su) through a glycoside cleavable bond in which the carbohydrate moiety and the glycosidic heteroatom (E') that attaches Su to Y is sometimes referred to as W' so that W', Y and D are arranged in an orthogonal configuration, as represented by —$Y_y$(W')-D, in which Y(W')— is W, wherein W is the Glucuronide Unit an subscript y is 1 or 2, and Y bonded to W' is the self-immolative Spacer Unit.

In either of those aspects, a secondary linker is further comprised of a first optional Stretcher Unit (A) and/or a Branching Unit (B) when LU is attached to more than one Drug Unit. When present, a first optional Stretcher Unit (A), interconnects $L_R$ with the remainder of the secondary linker, optionally through intermediacy of B, depending on its presence or absence, or interconnects $L_R$ when $L_R$ is $L_{SS}$ or $L_S$ with D optionally by way of $A_O$ in which $A_O$ is a component of $L_{SS}$ or $L_S$ through —W—$Y_y$— or —$Y_y$(W')— wherein Y of $Y_y$ is covalently attached to W or W' and is a self-immolative Spacer Unit having a PAB or PAB-type moiety.

In other aspects, a PAB or PAB-type self-immolative Spacer Unit is absent, as for example when D is directly attached to W, and W is a Peptide Cleavable Unit so that LU has the structure of -$A_a$-W—$Y_y$-D in which subscript y is 0, wherein $Y_y$ is replaced by an optionally substituted heteroatom from the NAMPT Drug Unit component attached to LU, or subscript y is 1, wherein Y is an optionally substituted heteroatom or functional group in which the latter may be capable of self-immolation and thus would be considered a self-immolative Spacer Unit or Y is a Spacer Unit that does not undergo self-immolation subsequent to protease action on W, or subscript y is 2 wherein $Y_y$ is —Y—Y'— and is combination of independently selected Y components from those recited for subscript y is 1. In still other aspects in which W is a Peptide Cleavable Unit or a Glucuronide Unit (i.e., W is —Y(W')—) wherein Y is a PAB-type self-immolative Spacer Unit, a second Spacer Unit (Y') is absent or may be present, which for the latter in some aspects may either be a functional group, which may be capable of self-immolation and thus considered as a self-immolative Spacer Unit, or a second self-immolative Spacer Unit having a PAB or PAB-type self-immolative moiety, so that LU, for example, has the structure -$A_a$-W—Y—Y'-D, or -$A_a$-Y(W')—Y'-D in which W is a Peptide Cleavable Unit cleavable by a protease and W' is a carbohydrate moiety (Su) bonded to Y through a heteroatom (E') of a glycosidic bond cleavable by a glucosidase. Sometimes that second self-immolative Spacer Unit (Y') is other than a PAB or PAB-type self-immolative Spacer Unit such as a carbamate functional group or a methylene carbamate unit as described elsewhere, both of which are capable of self-immolation. In other aspects the second Spacer Unit (Y') does not undergo self-immolation so that a NAMPTi derivative of structure Y'-D is released, which can undergo further enzymatic or non-enzymatic processing to release D as the NAMPTi compound. In all of those aspects, LU in general is represented by -$A_a$-W—$Y_y$-D in which W is a Peptide Cleavable Unit and subscript y is 0, 1 or 2 or W is a Glucuronide Unit of formula —Y(W')— and subscript y is 1 or 2, wherein one Y of $Y_y$ is present in —Y(W')—.

In some aspects, $L_O$ within a LDC or Drug Linker compound is comprised of a self-immolative Spacer Unit that is covalently attached directly to a NAMPT Drug Unit through a shared optionally substituted heteroatom or indirectly through a functional group acting as a second Spacer Unit, wherein that Spacer Unit may or may not also undergo self-immolation, such that cleavage of W as a Peptide Cleavable Unit or W' of a Glucuronide Unit under conditions more likely experienced within or in the vicinity of abnormal cells in comparison to normal cells distant from the abnormal cells or the environment of such normal cells. Since W as a Peptide Cleavable Unit or W' of a Glucuronide Unit is attached to a first self-immolative Spacer Unit, enzymatic action on W/W' results in fragmentation of the first self-immolating Spacer Unit, which is followed by fragmentation of the second Spacer Unit if that unit is also capable of self-immolation, with concomitant release of Y'-D or D as a NAMPTi compound or derivative thereof.

$L_O$ in other aspects of an Ligand Drug Conjugate or Drug Linker compound is comprised of a second self-immolative Spacer Unit that is covalently attached to a first self-immolative Spacer Unit such that cleavage of W in the form of a Peptide Cleavable Unit or W' of a Glucuronide Unit under conditions more likely experienced within abnormal cells distant from the abnormal cells results in sequential fragmentation of the first and second self-immolating Spacer Units resulting in release of D as a NAMPTi compound or derivative thereof. Alternatively, that cleavage may be occur in the vicinity of those cells, in comparison to the environment of normal cells distant from the site of the abnormal cells. Typically, that fragmentation of the first self-immolative Spacer Unit occurs through a 1,6-elimination of its PAB or PAB-type moiety as described herein and is followed by fragmentation of a carbamate functional group or a methylene carbamate (MAC) unit, as described herein, wherein that functional group or MAC Unit serves as the second self-immolative Spacer Unit.

A secondary linker ($L_O$) when bonded to D in a Linker Unit attached to only one NAMPT Drug Unit is typically represented by the structure of (1) or (2):

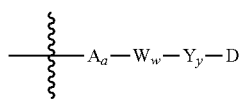
(1)

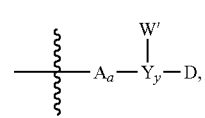

wherein the variable groups are as defined herein. In some aspects of the invention, $Y_y$ in structure (1) is comprised or consists of a PAB or PAB-type self-immolative Spacer Unit (Y) as described herein, wherein its PAB or PAB-type moiety is substituted with W in the form of a Peptide Cleavable Unit and D. In other aspects of the invention, $Y_y$ in structure (2) is comprised or consists of a PAB or PAB-type moiety of a self-immolating Spacer Unit as described herein wherein its PAB or PAB-type moiety is substituted with W' of a Glucuronide Unit and D, and in a Ligand Drug Conjugate or Drug Linker compound that moiety is further substituted with -$L_R$-$A_a$- with $L_R$ bonded to a Ligand Unit (L) or $L_R$-$A_a$-, respectively.

Typically, secondary linkers with structure (1) in which subscripts a is 0 or 1, and subscript y and w are each 1 and subscript y is 1 or 2 are represented by:

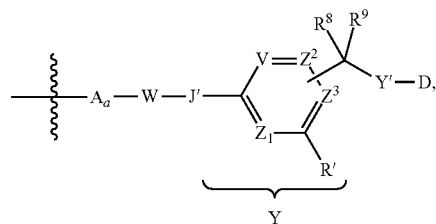

wherein if subscript y is 1, Y' of the above formula is replaced with an optionally substituted heteroatom from the NAMPT component bonded to LU comprised of structure (1) and secondary linkers with structure (2) in which subscripts a is 0 or 1 and subscript y is 1 or 2 are represented by:

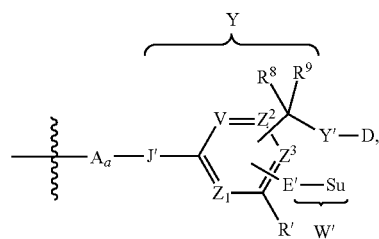

wherein if subscript y is 1, Y' of the above formula is replaced with an optionally substituted heteroatom from the NAMPT component bonded to LU comprised of structure and when subscript y is 2, Y' is an optionally substituted functional group shared between Y and D, or a second self-immolative moiety, as when the shared functional group is an optionally substituted carbamate or Y' is a MAC Unit, and wherein J', V, $Z^1$, $Z^2$, $Z^3$, R', $R^8$ and $R^9$ are as defined in embodiments for PAB or PAB-type self-immolative Spacer Units, and E' and Su are as defined in embodiments for Glucuronide Units of formula —Y(W')—, wherein the $A_a$-W-J'— and —C($R^8$)($R^9$)—Y'-D substituents on the central (hetero)arylene in a secondary linker of structure (1) are ortho or para to each other or the -E'-Su (i.e., W') and —C(R⁸)(R⁹)—Y'-D substituents on the central (hetero) arylene in secondary linker of structure (2) are ortho or para to each other.

"Maleimide moiety" as used herein, unless otherwise stated or implied by context, refers to is a component of a primary linker ($L_R$) when $L_R$ is self-stabilizing linker ($L_{SS}$). A maleimide moiety ($M^1$) is capable of participating in Michael addition (i.e., 1,4-conjugate addition) by a reactive thiol functional group of a targeting agent to provide a thio-substituted succinimide ($M^2$) moiety, wherein the thio substituent is a Ligand Unit that incorporates or correspond to the structure of the targeting agent as described herein in an Ligand Drug Conjugate composition or Conjugate compound thereof. An $M^1$ moiety of a Drug Linker compound is attached to the remainder of the primary linker ($L_R$), through its imide nitrogen. Other than the imide nitrogen, an $M^1$ moiety is typically unsubstituted, but may be asymmetrically substituted at the cyclic double bond of its maleimide ring system. Such substitution can result in regiochemically preferred conjugate addition of a reactive thiol of a targeting agent to the less hindered or more electronically deficient double bond carbon (dependent on the more dominant contribution) of the maleimide ring system. Typically, that conjugate addition results in a succinimide ($M^2$) moiety, which is thio-substituted by a Ligand Unit though a sulfur atom from a thiol functional group provided by the targeting agent.

When present in a self-stabilizing linker ($L_{SS}$), controlled hydrolysis of the succinimide ring system of the thio-substituted succinimide ($M^2$) moiety can provide regiochemical isomers of succinic acid-amide ($M^3$) moieties in a self-stabilized linker ($L_S$) due to its asymmetric substitution by the thio substituent. The relative amounts of those isomers will be due at least in part to differences in reactivity of the two carbonyl carbons of $M^2$, which can be partially attributed to any substituent(s) that were present in the $M^1$ precursor.

"Succinimide moiety" as used herein, unless otherwise stated or implied by context, refers to a component of a self-stabilizing linker ($L_{SS}$), which in turn is a component of a Linker Unit of a Ligand Drug Conjugate and results from Michael addition of an thiol functional group of a targeting agent to the maleimide ring system of a maleimide moiety ($M^1$) in a Drug Linker compound. A succinimide ($M^2$) moiety is therefore comprised of a thio-substituted succinimide ring system that has its imide nitrogen substituted with the remainder of the primary linker through its optionally substituted $C_1$-$C_{12}$ alkylene moiety, wherein that moiety incorporates a cyclic Basic Unit or is substituted by an acyclic Basic Unit as described elsewhere, and is optionally substituted with substituent(s) that may have been present on the $M^1$ precursor.

"Succinic acid-amide moiety" as used herein, unless otherwise stated or implied by context, refers to component of a self-stabilized linker ($L_S$) of a Linker Unit within a Ligand Drug Conjugate and has the structure of a succinic amide hemi-acid having substitution of its amide nitrogen by another component of $L_S$ wherein that component is an optionally substituted $C_1$-$C_{12}$ alkylene moiety, which incorporates cyclic Basic Unit or is substituted by an acyclic Basic Unit, and having further substitution by L-S—, wherein L is Ligand Unit incorporating a targeting agent and S is a sulfur atom from that targeting agent. Thus a succinic acid-amide moiety has a free carboxylic acid functional group and an amide functional group whose nitrogen heteroatom is attached to the remainder of the primary linker, and is substituted by L-S— at the carbon that is alpha to that carboxylic acid or amide functional group. A succinic acid-amide ($M^3$) moiety results from the thio-substituted succinimide ring system of a succinimide ($M^2$) moiety in self-stabilizing primary linker having undergone breakage of one of its carbonyl-nitrogen bonds by hydrolysis, which is assisted by the Basic Unit. Without being bound by theory, it is believed the aforementioned hydrolysis, which results in a succinic acid-amide ($M^3$) moiety, provides a Linker Unit in a Ligand Drug Conjugate that is less likely to suffer premature loss from the Conjugate of its targeting Ligand Unit through elimination of the thio substituent.

"Self-stabilizing linker" as used herein, unless otherwise stated or implied by context, refers to a $M^2$-containing component in a primary linker of a Linker Unit in a Ligand Drug Conjugate or is an $M^1$-containing component of a Linker Unit in a Drug Conjugate compound wherein that component is a precursor to a $M^2$-containing component of a self-stabilized linker ($L_S$) by conversion under controlled hydrolysis conditions of the corresponding self-stabilizing linker ($L_{SS}$). That hydrolysis is facilitated by the Basic Unit component of $L_{SS}$, such that a Ligand Drug Conjugate initially comprised of $L_{SS}$ becomes more resistant to premature loss of its Ligand Unit, by virtue of its Linker Unit (LU), which is now comprised of $L_S$. The $L_{SS}$ moiety, in addition to its $M^1$ or $M^2$ moiety, is comprised of $A_R$, which is a required Stretcher Unit, and optionally in combination with $A_O$ in some aspects is comprised of an optionally substituted $C_1$-$C_{12}$ alkylene moiety that incorporates a cyclic Basic Unit or is substituted by an acyclic Basic Unit to which $M^1$ or $M^2$ and the remainder of LU are covalently attached.

In the context of the present invention, $L_{SS}$ of a Drug Linker compound prior to its incorporation into a Ligand Drug Conjugate compound as a drug linker moiety contains a maleimide ($M^1$) moiety, through which a targeting agent is to be attached as a Ligand Unit, and $A_R$. In some aspects, the $C_1$-$C_{12}$ alkylene moiety of BU is attached to the imide nitrogen of the maleimide ring system of $M^1$ in a Drug Linker compound and to the remainder of the Linker Unit the latter of which optionally occurs through $A_O$ of $L_{SS}$. In some of those aspects $A_O$ consists or is comprised of an optionally substituted electron withdrawing heteroatom or functional group, referred herein as a Hydrolysis-Enhancing (HE) Unit, which in some aspects, in addition to BU, may enhance the hydrolysis rate of the $M^2$ moiety in the corresponding $L_{SS}$ of a Ligand Drug Conjugate compound. After incorporation of the Drug Linker compound into a Ligand Drug Conjugate compound, $L_{SS}$ now contains a maleimide ($M^2$) moiety that is thio-substituted by the Ligand Unit (i.e., Ligand Unit attachment occurs through Michael addition of a targeting agent's reactive thiol to the maleimide ring system of $M^1$).

In some aspects, a cyclized Basic unit (cBU) corresponds in structure to an acyclic Basic Unit through formal cyclisation to the basic nitrogen of that Unit so that the cyclic Basic Unit structure is incorporated into $A_R$ as a spiro $C_4$-$C_{12}$ heterocyclo. In such constructs the spiro carbon is attached to the maleimide imide nitrogen of M', and hence to that nitrogen in $M^2$, and is further attached to the remainder of the Linker Unit optionally through $A_O$, which in some aspects is a Hydrolysis-enhancing (HE) Unit. In that aspect, a cyclic BU assists in the hydrolysis of the succinimide moiety of $M^2$ to its corresponding ring-opened form(s) represented by $M^3$ in qualitatively similar manner to that of an acyclic Basic Unit, which may also be enhanced by HE.

In some aspects, a $L_{SS}$ moiety in a Drug Linker compound or a Ligand Drug Conjugate, according to the present invention, can be represented by the general formula of $M^1$-$A_R$(BU)-$A_O$- or -$M^2$-$A_R$(BU)-$A_O$-, respectively, wherein $A_R$(BU) is a required Stretcher Unit ($A_R$) incorporating a cyclic Basic Unit or substituted by an acyclic Basic Unit, $M^1$ and $M^2$ are maleimide and succinimide moieties, respectively, and $A_O$ is an second optional Stretcher Unit, which in some aspects consists or is comprised of HE.

Exemplary $L_{SS}$ structures are those of general Formula 1A, wherein these structures are present in exemplary Ligand Drug Conjugates compounds, as represented by:

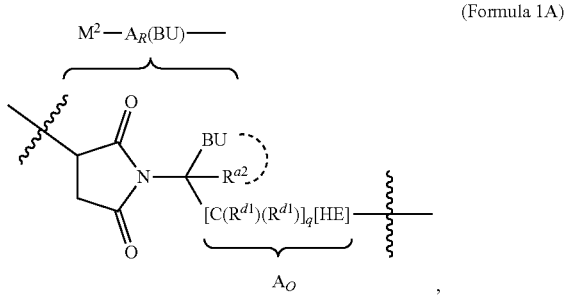

(Formula 1A)

wherein the dotted curved line indicates optional cyclization so that when present BU is a cyclic Basic Unit or when BU is an acyclic Basic Unit, the $[C(R^{d1})R^{d1})]_q$—[HE] moiety is $A_O$ of Formula 1 in which $A_O$ is present, wherein HE is an optional Hydrolysis-enhancing Unit, subscript q is 0 or an integer ranging from 1 to 6; each $R^{d1}$ is independently selected from the group consisting of hydrogen and optionally substituted $C_1$-$C_6$ alkyl, or two of $R^{d1}$, the carbon atom(s) to which they are attached and any intervening carbon atoms define an optionally substituted $C_3$-$C_8$ carbocyclo, and the remaining $R^{d1}$, if any, are independently hydrogen or optionally substituted $C_1$-$C_6$; and $R^{a2}$ is an optionally substituted $C_1$-$C_{12}$, alkyl, which in a cyclic Basic Unit along with the carbon atom to which BU and $R^{a2}$ are attached define an optionally substituted spiro $C_4$-$C_{12}$ heterocycle having a skeletal secondary or tertiary basic nitrogen atom, such that the cyclic Basic Unit is capable of increasing the rate of hydrolysis of the shown succinimide ($M^2$) moiety to provide succinic acid amide ($M^3$) moieties at a suitable pH in comparison to the corresponding Conjugate in which $R^{a2}$ is hydrogen and BU is replaced by hydrogen, and/or substantially retains the increase in the rate of hydrolysis of the corresponding Conjugate in which in which $R^{a2}$ is hydrogen and BU is an acyclic BU over the aforementioned Conjugate in which $R^{a2}$ is hydrogen and BU is replaced by hydrogen.

Other exemplary $L_{SS}$ structures are those of general Formula 1B, which are present in Drug Linker compounds typically used intermediates in the preparation of Ligand Drug Conjugate compositions represented by Formula I:

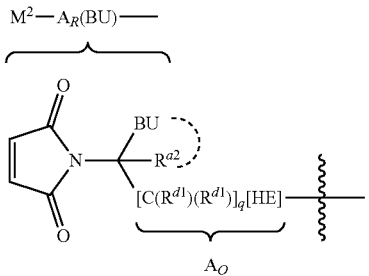

(Formula 1B)

wherein BU is as defined for the structure of Formula 1A and the other variable groups are as defined for Formula 1A and in the embodiments for that and other exemplary $L_{SS}$ structures. When a Drug Linker compound having Formula 1B is used in the preparation of a Ligand Drug Conjugate Formula 1B is converted to Formula 1A.

"Self-stabilized linker" is an organic moiety derived from an $M^2$-containing moiety of a self-stabilizing linker ($L_{SS}$) in an LDC that has undergone hydrolysis under controlled conditions so as to provide a corresponding $M^3$-moiety of an self-stabilized linker ($L_S$) wherein that LU component is less likely to reverse the condensation reaction of a targeting moiety with a NV-containing moiety that provided the original $M^2$-containing $L_{SS}$ moiety. In addition to the $M^3$ moiety, a self-stabilized linker ($L_S$) is comprised of $A_R$ incorporating a cyclic Basic Unit or substituted by an acyclic Basic Unit wherein $A_R$ is covalently attached $M^3$ and the remainder of the Linker Unit in which $L_S$ is a component. The $M^3$ moiety is obtained from conversion of a succinimide moiety ($M^2$) of $L_{SS}$ in a Ligand Drug Conjugate, wherein the $M^2$ moiety has a thio-substituted succinimide ring system resulting from Michael addition of a sulfhydryl group of a targeting moiety to the maleimide ring system of NV of a $L_{SS}$ moiety in a Drug Linker compound, wherein that $M^2$-derived moiety has reduced reactivity for elimination of its thio-substituent in comparison to the corresponding substituent in $M^2$. In those aspects, the $M^2$-derived moiety has the structure of a succinic acid-amide ($M^3$) moiety corresponding to $M^2$ wherein $M^2$ has undergone hydrolysis of one of its carbonyl-nitrogen bonds of its succinimide ring system, which is assisted by the basic functional group of BU due to its appropriate proximity as a result of that attachment. The product of that hydrolysis therefore has a carboxylic acid functional group and an amide functional group substituted at its amide nitrogen, which corresponds to the imide nitrogen in the $M^2$-containing $L_{SS}$ precursor, with the remainder of LU. In some aspects the basic functional group is a primary, secondary or tertiary amine of an acyclic Basic Unit or secondary or tertiary amine of an cyclic Basic Unit. In other aspects, the basic nitrogen of BU is a heteroatom of an optionally substituted basic functional group as in a guanidino moiety. In either aspect the reactivity of the basic functional group of BU for base-catalyzed hydrolysis is controlled by pH.

Thus, a self-stabilized linker ($L_S$) typically has the structure of an $M^3$ moiety covalently bond $A_R$ incorporating a cyclic Basic Unit or substituted by an acyclic Basic Unit, wherein $A_R$ in turn is covalently bonded to the secondary linker $L_O$. $L_S$ with its $M^3$, $A_R$, $A_O$ and BU components and $L_O$ arranged in the manner so indicated is represented by the formula of $M^3$-$A_R$(BU)-$A_O$-$L_O$- or $M^3$-$A_R$(BU)-$A_O$-$L_O$-, wherein BU represents either type of Basic Unit (cyclic or acyclic).

Exemplary non-limiting structures of $L_{SS}$ and $L_S$ moieties with $M^2$ or $M^3$, and $A_R(BU)$, $A_O$ and $L_O$ arranged in the manner indicated above in which BU is acyclic is shown by way of example but not limitation by:

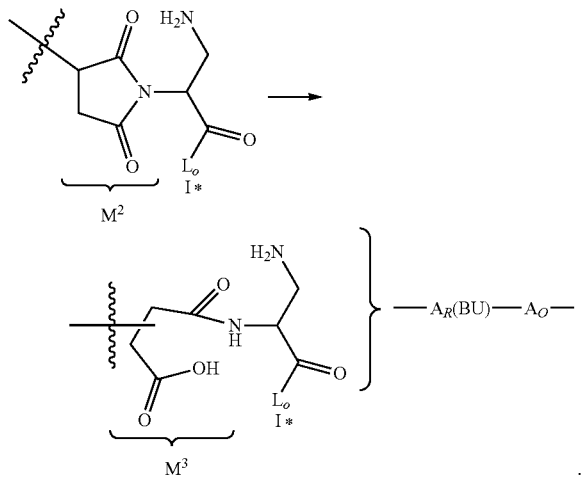

wherein the indicated —CH(CH$_2$NH$_2$)C(=O)— moiety is -$A_R$(BU)-$A_O$-, wherein BU is an acyclic Basic Unit in which $A_R$ is covalently bonded to the imide or amide nitrogen of $M^2$ or $M^3$, respectively, and is substituted by the acyclic Basic Unit, —CH$_2$NH$_2$, and wherein $A_O$ is [HE], which is bonded to $L_O$, wherein [HE] is —C(=O)—. Those exemplary structures contain a succinimide ($M^2$) moiety or a succinic acid-amide ($M^3$) moiety from succinimide ring hydrolysis of $M^2$ in the conversion of $L_{SS}$ to $L_S$.

Exemplary structures of $L_{SS}$ and $L_S$ moieties with $M^2$ or $M^3$, and $A_R$(BU) and $A_O$ components bonded to $L_O$ in the manner indicated above in which BU is incorporated into $A_R$ as a cyclic Basic Unit is shown by way of example but not limitation by:

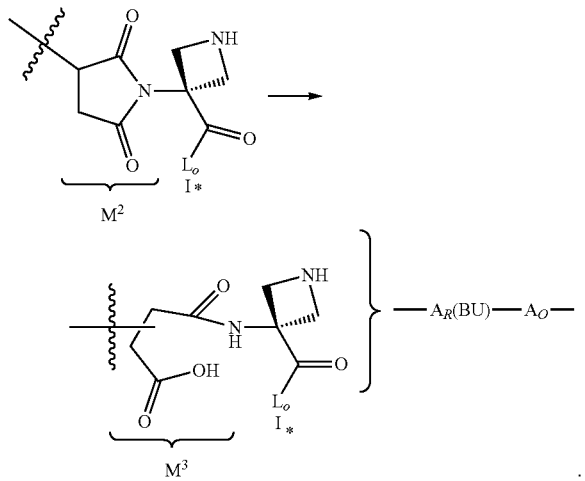

In the above $A_R$(BU)-$A_O$ moieties, BU is a heterocyclo cyclic Basic Unit, the structure of which corresponds to the aminoalkyl of an acyclic Basic Unit in the $A_R$(BU) moiety in which the basic nitrogen of an acyclic Basic Unit has been formally cyclized back to the carbon alpha through $R^{\alpha 2}$ to the succinimide nitrogen of $M^2$ to which the acyclic Basic Unit is attached. The wavy line in each of the above $L_{SS}$ and $L_S$ moieties indicates the site of covalent attachment of a sulfur atom of a Ligand Unit derived from a thiol functional group of a targeting agent upon Michael addition of that thiol group to the maleimide ring system of an $M^1$ moiety in a corresponding Drug Linker compound. The asterisk in each of the above structures indicate the site of covalent attachment of a Drug Unit to the -$L_{SS}$-$L_O$- and $L_S$-$L_O$- structures of $M^2/M^3$-$A_R$(BU)-$A_O$-$L_O$- in which BU is cyclic or acyclic. Since the succinimide ring system of $M^2$ is asymmetrically substituted due to its thio substituent, regiochemical isomers of succinic acid-amide ($M^3$) moieties as defined herein differing in position relative to the liberated carboxylic acid group may result on $M^2$ hydrolysis. In the above structures, the carbonyl functional group attached to $L_O$ exemplifies a hydrolysis enhancer [HE] as defined herein in which [HE] is the indicated $A_O$ component of $L_{SS}$ or $L_S$ that is covalently attached to -$A_R$(BU) and $L_O$.

The -$M^3$-$A_R$(BU)— moieties wherein BU is acyclic or cyclic Basic Unit represent exemplary structures of self-stabilized linker ($L_S$) moieties, since these structures are less likely to eliminate the thio substituent of the Ligand Unit, and thus cause loss of that targeting moiety, in comparison to the corresponding $L_{SS}$ moieties of formula $M^2$-$A_R$(BU). Without being bound by theory, it is believed the increased stability results from the greater conformational flexibility in $M^3$ in comparison to $M^2$, which no longer constrains the thio substituent in a conformation favorable for E2 elimination.

"Basic Unit" as used herein, unless otherwise stated or implied by context, refers to an organic moiety within a self-stabilizing linker ($L_{SS}$) moiety, as described herein, which is carried forward into a corresponding $L_S$ moiety by BU participating in base catalyzed hydrolysis of the succinimide ring system within a $M^2$ moiety comprising $L_{SS}$ (i.e., catalyzes addition of a water molecule to one of the succinimide carbonyl-nitrogen bonds). In some aspects the base-catalyzed hydrolysis is initiated under controlled conditions tolerable by the targeting Ligand Unit attached to $L_{SS}$. In other aspects the base-catalyzed hydrolysis is initiated on contact of the Drug Linker compound comprised of $L_{SS}$ with a targeting agent in which Michael addition of the reactive thiol of the targeting agent effectively competes with hydrolysis of the $L_{SS}$ $M^1$ moeity of the Drug Linker compound. Without being bound by theory, the following aspect described various considerations for design of a suitable Basic Unit. In one such aspect, the basic functional group of an acyclic Basic Unit and its relative position in $L_{SS}$ with respect to its $M^2$ component are selected for the ability of BU to hydrogen bond to a carbonyl group of $M^2$, which effectively increases its electrophilicity and hence its susceptibility to water attack. In another such aspect, those selections are made so that a water molecule, whose nucleophilicity is increased by hydrogen bonding to the basic functional group of BU, is directed to an $M^2$ carbonyl group. In a third such aspect, those selections are made so the basic nitrogen on protonation increases the electrophilicity of the succinimide carbonyls by inductive electron withdrawing. In a final such aspect, some combination of those mechanisms contributes to catalysis for hydrolysis of $L_{SS}$ to $L_S$.

Typically, an acyclic Basic Unit, which may act through any of the above mechanistic aspects, is comprised of 1 carbon atom or 2 to 6 contiguous carbon atoms, more typically of 1 carbon atom or 2 or 3 contiguous carbon atoms, wherein the carbon atom(s) connect the basic amino functional group of the acyclic Basic Unit to the remainder of the $L_{SS}$ moiety to which it is attached. In order for that basic amine nitrogen to be in the required proximity to assist in the hydrolysis of a succinimide ($M^2$) moiety to its corresponding ring-opened succinic acid amide ($M^3$) moiety, the amine-bearing carbon chain of an acyclic Basic Unit is typically attached to $A_R$ of $L_{SS}$ at the alpha carbon of that moiety relative to the site of attachment of $A_R$ to the succinimide nitrogen of $M^2$ (and hence to the maleimide nitrogen of its corresponding $M^1$-$A_R$ structure). Typically, that alpha carbon in an acyclic Basic Unit has the (S) stereochemical configuration or the configuration corresponding to that of the alpha carbon of 1-amino acids.

As previously described, BU in acyclic form or BU in cyclized form is typically connected to $M^1$ or $M^2$ of $L_{SS}$ or $M^3$ of $L_S$ through an optionally substituted $C_1$-$C_{12}$ alkylene moiety in which that moiety incorporates the cyclized Basic Unit or is substituted by the acyclic Basic Unit and is bonded to the maleimide or succinimide nitrogen of $M^1$ or $M^2$, respectively, or the amide nitrogen of $M^3$. In some aspects the $C_1$—$C_{12}$ alkylene moiety incorporating the cyclic Basic Unit is covalently bonded to $L_O$ when that Linker Unit component is present and typically occurs through intermediacy of an ether, ester, carbonate, urea, disulfide, amide carbamate or other functional group, more typically through an ether, amide or carbamate functional group. Likewise, BU in acyclic form is typically connected to $M^1$ or $M^2$ of $L_{SS}$ or $M^3$ of $L_S$ through an optionally substituted $C_1$-$C_{12}$ alkylene moiety which is substituted by the acyclic Basic unit at the same carbon of the alkylene moiety that is attached to the imino nitrogen atom of the maleimide or succinimide ring system of $M^1$ or $M^2$ or the amide nitrogen of $M^3$ subsequent to hydrolysis of the succinimide ring system of $M^2$.

In some aspects, a cyclic Basic Unit incorporates the structure of an acyclic BU by formally cyclizing an acyclic Basic Unit to an optionally substituted $C_1$-$C_{12}$ alkyl ($R^{a2}$) bonded to the same alpha carbon as the acyclic Basic Unit, thus forming a spirocyclic ring system so that a cyclic Basic Unit is incorporated into the structure of $A_R$ rather than being a substituent of $A_R$ as when BU is acyclic. In those aspects, the formal cyclization is to the basic amine nitrogen of an acyclic Basic Unit thus providing a cyclic Basic Unit as an optionally substituted symmetrical or asymmetrical spiro $C_4$-$C_{12}$ heterocyclo, depending on the relative carbon chain lengths in the two alpha carbon substituents, in which the basic nitrogen is now a basic skeletal heteroatom. In order for that cyclization to substantially retain the basic properties of the acyclic Basic Unit in an cyclic Basic Unit, the basic nitrogen atom of the acyclic Basic Unit nitrogen should be that of a primary or secondary amine and not a tertiary amine since that would result in a quaternized skeletal nitrogen in the heterocyclo of the cyclic Basic Unit. In that aspect of formal cyclization of an acyclic Basic Unit to a cyclic Basic Unit, in order to substantially retain the ability of the basic nitrogen to assist in hydrolysis of $M^2$ to $M^3$ in conversion of $L_{SS}$ to $L_S$, the resulting structure of the cyclic Basic Unit in these primary linkers will typically have its basic nitrogen located so that no more than three, and typically one or two, intervening carbon atoms are between the basic nitrogen atom and the spiro alpha carbon of the $A_R$ component. Cyclic Basic Units incorporated into $A_R$ and the $L_{SS}$ and $L_S$ moieties having those as components are further described by the embodiments of the invention.

"Hydrolysis-enhancing Unit" as used herein, unless otherwise stated or implied by context, refers to is electron withdrawing group or moiety that is an optional substituent of an $L_{SS}$ moiety and its hydrolysis product $L_S$. When present, a Hydrolysis-enhancing Unit (HE) is a second Stretcher Unit, which is attached to $A_R$ as another component of $L_{SS}$, wherein $A_R$ is bonded to the imide nitrogen of an $M^2$ moiety, so that its electron withdrawing effects can increase the electrophilicity of the succinimide carbonyl groups in that moiety for its conversion to a $M^3$ moiety of $L_S$. With $A_R$ incorporating or substituted by a cyclic Basic Unit or an acyclic Basic Unit, respectively, the potential effect of HE on the carbonyl groups of $M^2$ for increasing the hydrolysis rate to $M^3$ by induction and the aforementioned effect (s) of either type of BU, are adjusted so that premature hydrolysis of $M^1$ does not occur to an appreciable extent during preparation of an Ligand Drug Conjugate from a Drug Linker compound having the structure of $M^1$-$A_R$(BU)—[HE]-. Instead, the combined effects of BU and [HE] to promote hydrolysis (i.e., conversion of an -$M^2$-$A_R$(BU[HE]- moiety of an Ligand Drug Conjugate compound to its corresponding -$M^3$-$A_R$(BU[HE]- moiety) under controlled conditions (as when pH is purposely increased) are such that an undue molar excess of Drug Linker compound to compensate for hydrolysis of its $M^1$ moiety is not required. Therefore, Michael addition of the reactive thiol of the targeting agent to the maleimide ring system of $M^1$, which provides a targeting Ligand Unit attached to a succinimide ring system of $M^2$, typically occurs at a rate that effectively competes with $M^1$ hydrolysis. Without being bound by theory, it is believed that at low pH, as for example when the basic amine of BU is in the form of a TFA salt, premature hydrolysis of $M^1$ in a Drug Linker product is much slower than when the pH is raised to that suitable for base catalysis using an appropriate buffering agent and that use of an acceptable molar excess of Drug Linker compound can compensate for any loss due to premature $M^1$ hydrolysis that does occur during the time course for completion of the Michael addition of a targeting agent's reactive thiol functional group to a Drug Linker compound's $M^1$ moiety.

As previously discussed, enhancement of carbonyl hydrolysis by either type of Basic Unit is dependent on the basicity of its functional group and the distance of that basic functional group in relation to the $M^1/M^2$ carbonyl groups. Typically, the HE Unit is a carbonyl moiety (i.e., ketone or —C(=O)—) or other carbonyl-containing functional group located distal to the end of $A_R$ that is bonded to $M^2$, or $M^3$ derived therefrom, and that also provides for covalent attachment of $L_{SS}$ or $L_S$ to the secondary linker ($L_O$). Carbonyl-containing functional groups other than ketone include esters, carbamates, carbonates and ureas. When HE is a carbonyl-containing functional group other than ketone the carbonyl moiety of that functional group is typically bonded to the remainder of $A_R$. In some aspects, the HE Unit may be sufficiently distant within $A_R$ from the imide nitrogen to which the remainder of $A_R$ is covalently bonded so that no discernable or minor effect on hydrolytic sensitivity of the succinimide carbonyl-nitrogen bonds of an $M^2$-containing moiety is observable, but instead is driven primarily from BU.

"Stretcher Unit" as used herein, unless otherwise stated or implied by context, refers to an organic moiety in a primary or secondary linker of a Linker Unit that physically separates the targeting Ligand Unit from other intervening components of the Linker Unit that are more proximal to the Drug Unit. An $A_R$ Stretcher Unit is a required component in a $L_{SS}$ or $L_S$ primary linker since it provides the Basic Unit. The presence of a first optional Stretcher Unit (A) and/or second optional Stretcher Unit ($A_O$) may be required when there is insufficient steric relief from the Ligand Unit provided by an $L_{SS}$ primary linker absent of one or both of those optional Stretcher Units to allow for efficient processing of a Linker Unit in a drug linker moiety of a Ligand Drug Conjugate for release of its Drug Unit as a NAMPTi compound derivative thereof. Alternatively, or in addition to steric relief, those optional components may be included for synthetic ease in preparing a Drug Linker compound. A first or second optional Stretcher Unit (A or $A_O$) can each be a single unit or can contain multiple subunits. Typically, A or $A_O$ is one distinct unit or has 2 to 4 distinct subunits. In some aspects A or $A_O$, or a subunit of, has the formula of -$L^P$(PEG)-.

In some aspects, in addition to covalent attachment to $M^1$ of a Drug Linker compound or $M^2/M^3$ of a Ligand Drug Conjugate compound, $A_R$ is bonded to a secondary linker optionally through $A_O$ wherein $A_O$ as a component of $L_{SS}/L_S$ is a carbonyl-containing functional group, which can serve as a Hydrolysis-enhancing (HE) Unit for improving the rate of conversion of $L_{SS}$ to $L_S$, which is catalyzed by an cyclic Basic Unit as incorporated into $A_R$ or by an acyclic Basic Unit as a substituent of $A_R$. In some of those aspects $A_R$ is bonded to a secondary linker ($L_O$) through a Branching Unit of $L_O$, if in Formula 1, Formula 2 or Formula I, subscript n is 2 or more requiring that subscript b is 1, or if in these formulae subscript n is 1 so that subscript b is 0, then $A_R$ is bonded to a secondary linker through an optional second Stretcher Unit ($A_O$) of $L_{SS}$ or $L_S$, or $A_R$ or $A_O$ is bonded to a secondary linker ($L_O$) through a first optional Stretcher Unit (A) of $L_O$, when subscript a is 1, or through W when subscript a is 0 and components W, Y and D are arranged linearly, wherein subscript w is 1 and W is a Peptide Cleavable Unit (i.e., arranged as —W—$Y_y$-D, wherein subscript y is 0, 1 or 2), or $A_R$ or $A_O$ when subscript a is 0 or A, when subscript a is 1 is bonded to Y of $Y_y$, as is W', in formula —Y(W')— of a Glucuronide Unit, so that W, $Y_y$ and D are arranged orthogonally (i.e., arranged as —$Y_y$(W')-D, wherein subscript y is 1 or 2). Finally, $A_R$ or $A_O$ in Formula 1, Formula 2 or Formula I is bonded $Y_y$-D when subscript a is 0 and subscript w is 0.

Some Linker Units in an LDC or Drug Linker compound contain the formula of -$L^P$(PEG)-$W_w$—$Y_y$, in which subscript a is 1 and A, or a subunit thereof, in Formula 1, Formula 2 or Formula I is -$L^P$(PEG)-, and wherein subscript w is 1 and W is a Peptide Cleavable Unit, or contain the formula -$L^P$(PEG)-$Y_y$(W')— in which subscript a is 1 and A, or a subunit thereof, in Formula 1, Formula 2 or Formula I is -$L^P$(PEG)-, wherein —Y(W')— in $Y_y$(W')— is a Glucuronide Unit and subscript y is 1 or 2.

Typically, a first optional Stretcher Unit (A), has one carbon atom or two to six contiguous carbon atoms that connects A to $A_R$ or to a second optional Stretcher Unit ($A_O$), depending on the presence or absence of $A_O$, of the primary linker, when subscript b is 0 or to B when subscript b is 1, through one functional group and connects A to W, Y, or D, depending on the presence or absence W and/or Y and the configuration of A, W, and Y within the secondary linker through another functional group. In some aspects of Formula 1, Formula 2 or Formula I, subscript a is 0, so that no first Stretcher Unit is present, or subscript a is 1 wherein A is an α-amino acid, a β-amino acid or other amine-containing acid residue so that A is bonded $A_R$, $A_O$ or B, and to W, Y or D through amide functional groups. In other aspects, A is bonded to $A_O$, when $A_O$ is present and consists or is comprised of a Hydrolysis-enhancing Unit (HE).

"Branching Unit" as used herein, unless otherwise stated or implied by context, refers to a tri-functional organic moiety that is an optional component of a Linker Unit (LU). A Branching Unit (B) is present when more than one Drug Unit (D), typically 2, 3 or 4, are attached to a Linker Unit (LU) of a drug linker moiety in a Ligand Drug Conjugate compound or Drug Linker compound. In a Ligand Drug Conjugate of Formula 1 or Formula 2 or a Drug Linker compound of Formula I, the presence of a Branching Unit is indicated when subscript b of Bb is 1, which occurs when subscript n greater than 1 in any of these structural formulae. A Branching Unit is trifunctional in order to be incorporated into a secondary linker unit ($L_O$). In aspects where n is 1, a Branching Unit is not present, as indicated when subscript b is 0. Drug Linker or Ligand Drug Conjugate compounds with a Branching Unit due to multiple D units per LU have Linker Units containing formula —B-$A_a$-$W_w$—$Y_y$—, wherein subscripts a and w are independently 0 or 1 and subscript y is 0, 1 or 2, and W is a Peptide Cleavable Unit, or have Linker Units containing formula —B-$A_a$-$Y_y$(W')—, wherein subscript a is 0 or 1 and subscript y is 1 or 2, wherein —Y(W') within that formula is a Glucuronide Unit. As A can contain formula -$L^P$(PEG)-, in these instances Linker Units can contain formula -$L^P$(PEG)-$W_w$—$Y_y$ or -$L^P$(PEG)-$Y_y$(W')— when subscript b is 0.

In some aspects a natural or un-natural amino acid or other amine-containing acid compound having a functionalized side chain serves as a Branching unit. In some aspects B is a lysine, glutamic acid or aspartic acid moiety in the L- or D-configuration in which the epsilon-amino, gamma-carboxylic acid or beta-carboxylic acid functional group, respectively, interconnects B to the remainder of LU.

"Cleavable Unit" as used herein, unless otherwise stated or implied by context, refers to an organic moiety that provides for a reactive site within a Linker Unit wherein reactivity towards that site is greater within or surrounding abnormal cell such as hyper-proliferating cell or a hyper-stimulated immune cell, which in some aspects is due to a greater amount enzymatic or non-enzymatic activity in these locations, in comparison to a normal cells that are not typically present at the site or are distant from the site of the abnormal cells such that action upon the reactive site of the Linker Unit results in preferential exposure of the abnormal cells to a NAMPTi compound or derivative thereof released from a Ligand Drug Conjugate compound having that Linker Unit. The exposure from release of the NAMPTi or its derivative is initiated by enzymatic or non-enzymatic action on the Linker Unit having that Cleavable Unit. In some aspects of the invention, a Cleavable Unit or component thereof (W or W') contains a reactive site cleavable by an enzyme (i.e., W or W' provides for an enzyme substrate) whose activity or abundance is greater within or surrounding the hyper-proliferating, immune-stimulating or other abnormal cells compared to normal cells or the vicinity of normal cells that are distant from the site of the abnormal cells. In some of those aspects of the invention, the Cleavable Unit is a substrate for a protease, which in some aspects is a regulatory protease, or a hydrolase or glycosidase, wherein the protease, hydrolase or glycosidase is located intracellularly in targeted cells (i.e., the reactive site of the Cleavable Unit is a peptide bond or glycoside bond, respectively, cleavable by the protease, hydrolase or glycosidase). In those aspects, the peptide or glycoside bond of the Cleavable Unit is capable of selective cleavage by an intracellular regulatory protease, hydrolase or glycosidase in comparison to serum proteases, hydrolases, or glycosidases.

In other aspects, a Cleavable Unit is comprised of a reactive site cleavable by other mechanisms (i.e., non-enzymatic) more likely operable within or in the surrounding environment of abnormal cells targeted by a Ligand Unit of a Ligand Drug Conjugate in comparison to the environment of normal cells in which abnormal cells are typically not present or are distant from the site of the targeted cells.

In some of those aspects, the reactive site is more likely operated upon enzymatically or non-enzymatically subsequent to cellular internalization of an Ligand Drug Conjugate compound into a targeted abnormal cell.

Alternatively, W provides for a functional group that when incorporated into an Ligand Drug Conjugate composition is susceptible to the acidic environment of lysozymes upon preferential internalization of a compound of that composition into an abnormal cell, or is susceptible to the greater reductive environment in or around such cells in comparison to the environment of normal cells where abnormal cells are usually not present, such that release of D from that Ligand Drug Conjugate compound as a NAMPTi compound or derivative thereof preferentially exposes the abnormal cell to that released compound in comparison to the normal cells Functional groups that provide for cleavable bonds include, by way of example and not limitation, include (a) sulfhydryl groups that form a disulfide bond, which are susceptible to the greater reductive conditions of abnormal cells in comparison to normal cells, or excess glutathione produced under hypoxic conditions experienced by the abnormal cells, (b) aldehyde, ketone, or hydrazine groups that form a Schiff base or hydrazone functional groups, which are susceptible to the acidic conditions of lysozymes upon selective internalization of an Ligand Drug Conjugate compound having a Linker Unit with that cleavable bond into an abnormal cell in comparison to internalization into normal cells, (c) carboxylic or amino groups that form an amide bond, as in peptide bonds, that are susceptible to enzymatic cleavage by proteases produced or excreted preferentially by abnormal cells in comparison to normal cells or by a regulatory protease within a targeted cell, and (d) amino or hydroxyl groups that form certain urea or carbamate groups or carboxylic or hydroxy groups that form ester or carbonate groups that are susceptible to enzymatic cleavage by hydrolases or esterases that are produced or excreted preferentially by abnormal cells in comparison to normal cells.

Still other functional groups that provide for cleavable bonds are found in sugars or carbohydrates having a glycosidic linkage that are substrates for glycosides which sometimes may be produced preferentially by abnormal cells in comparison to normal cells. Alternatively, the protease, hydrolase or glycosidase enzyme required for processing of the Linker Unit to release a NAMPTi compound or derivative thereof need not be produced preferentially by abnormal cells in comparison to normal cells provided the processing enzyme is not excreted by normal cells to an extent that would cause undesired side effects from premature release of the NAMPTi compound or derivative thereof. In other instances, the required protease, hydrolase or glycosidase enzyme may be excreted, but to avoid undesired premature release of drug, some aspects of the invention typically require the processing enzyme be excreted in the vicinity of abnormal cells and remain localized to that environment, whether produced by abnormal cells or nearby normal cells in response to the abnormal environment caused by the abnormal cells. In that respect W as a Peptide Cleavable Unit or W' of a Glucuronide Unit in which W has the formula of —Y(W')— is selected to be preferentially acted upon by a protease, hydrolase or glycosidase in or within the environment of abnormal cells in contrast to freely circulating enzymes. In those instances a Ligand Drug Conjugate compound is less likely to release a NAMPTi compound or derivative thereof in the vicinity of normal cells nor would it be internalized to any appreciable extent into normal cells that do intracellularly produce but do not excrete the enzyme intended to be acted upon by the internalized Ligand Drug Conjugate compound since such cells are less likely to display a targeted moiety required for entry by that compound or have sufficient copy number of that targeted moeity.

In some aspects, W is a Peptide Cleavable Unit comprised of an amino acid or is comprised or consists of one or more sequences of amino acids that provide a substrate for a protease present within abnormal cells or a protease localized to the environment of these abnormal cells. Thus, W may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a self-immolative moiety of a self-immolative Spacer Unit Y wherein that moiety provides a recognition sequence for that protease. In other aspects, W is a Glucuronide Unit of formula —Y(W')— wherein W' is a carbohydrate moiety (Su) attached to a self-immolative moiety of the Glucuronide's self-immolative Spacer Unit (Y) by a glycosidic bond through a optionally substituted heteroatom (E') that is cleavable by a glycosidase preferentially produced by abnormal cells, or is found in such cells to which an Ligand Drug Conjugate compound having that Spacer Unit and carbohydrate moiety has selective entry due to the presence of the targeted moiety on the abnormal cells.

"Spacer Unit" as used herein, unless otherwise stated or implied by context, refers to a moiety in a secondary linker ($L_O$) within a Linker Unit of a Ligand Drug Conjugate or Drug Linker compound that is covalently bonded to a NAMPT Drug Unit (D), or to another such moiety (Y') covalently bonded to D, and in some aspects the Spacer Unit (Y) is also covalently bonded to a first optional Stretcher Unit (A) if subscript b is 0 in Formula 1, Formula 2 or Formula I or to a Branching Unit (B) if subscript b is 1 in either one of these formulae or to a second optional Stretcher Unit ($A_O$), if A and B are absent (i.e., subscripts a and b are both 0), or to $A_R$ if none of these other Linker Unit components are present. In other aspects, Y is covalently bonded to W and D or another Spacer Unit (Y'), which is bonded to D, as when W is a Peptide Cleavable Unit. Each Y of $Y_y$, in Formula 1, Formula 2 or Formula I is independently selected from the group consisting of an optionally substituted heteroatom, an optionally substituted functional group, which may be capable of self-immolation, a non-self-immolative Spacer Unit and a self-immolative Spacer Unit. When W in any one of those formulae is a Peptide Cleavable Unit the Y bonded to W may be a self-immolative Spacer Unit and when W is a Glucuronide Unit of formula —Y(W'), then Y bonded to W' is required to be a self-immolative Spacer Unit in order for D to be released as a NAMPTi compound or derivative thereof subsequent to cleavage of the glycosidic bond in W'.

Typically, in one configuration W, $Y_y$, and D are arranged linearly with D bonded to $Y_y$, wherein W is a Peptide Cleavable Unit and subscript y is 1 or 2, so that protease action upon W initiates release D as a NAMPTi compound or derivative thereof. When subscript y is 2 then protease cleavage of W releases —Y—Y'-D, which may be capable of NAMPT inhibition in its own right, or Y in that released moiety is a self-immolative Spacer Unit so that Y'-D, which also may be capable of NAMPT inhibition, is subsequently released. Finally, both Spacer Units (Y and Y') are capable of self-immolation so that protease cleavage of W to release —Y—Y'-D is followed by sequential self-immolative events to release D as a NAMPTi compound or derivative thereof.

Typically in another configuration in which a Ligand Drug Conjugate contains a Glucuronide Unit of formula —Y(W')— within a secondary linker ($L_O$), subscript y in Formula 1, Formula 2 or Formula I is 1 or 2 and W' of the Glucuronide Unit and D or —Y'-D are covalently bonded Y, wherein Y is a self-immolative Spacer Unit or Y and Y' are each capable of self-immolation upon glycosidase action upon the Glucuronide Unit, and Y in turn is also bonded to A, B, $A_O$ or $L_R$, depending on the presence or absence of A, B and $A_O$, so that W' is orthogonal to the remainder of $L_O$. As before, glycosidase action is followed by self-immolation of Y to release D or —Y'-D, which in the latter case when Y' is capable of self-immolation D is eventually released as a NAMPTi compound or derivative thereof, or D is released as a derivative of the NAMPTi compound in which Y' or a fragment thereof is retained so as to exert a therapeutic effect. In either configuration, $Y_y$ may serve to separate the cleavage site of the Peptide Cleavable Unit or Glucuronide from D to avoid steric interactions from that Unit that would interfere with cleavage of W/W' which could occur when that cleavage is preformed through enzymatic action.

Typically, a Spacer Unit bonded to a NAMPT Drug Unit (D) is comprised or consists of a self-immolating moiety as defined herein wherein that moiety defines a self-immolative Spacer Unit and is covalently bonded to a Cleavage Unit (W) so that enzymatic processing of the Cleavable Unit activates the self-immolative moiety for self-destruction thus initiating release of the NAMPT Drug Unit as NAMPTi compound or derivative thereof. In some aspects, that self-immolative moiety of Y is covalently bonded to W when W is a Peptide Cleavable Unit through an amide (or anilide) functional group.

In those aspects in which a self-immolative Space Unit is covalent attached to W as a Peptide Cleavable Unit and subscript y is 2 that self-immolative Spacer is covalently bonded to D through a functional group comprised of an optionally substituted heteroatom from the NAMPT Drug Unit component attached to LU so that $Y_y$ is —Y—Y'— wherein Y is the self-immolative Spacer and Y' is the optionally substituted functional group. In other such aspects in which subscript y is 1, the optionally substituted heteroatom of the NAMPT Drug Unit component is directly attached to the self-immolative moiety of the Spacer Unit. For either aspect the optionally substituted heteroatom is provided by a component of the NAMPTi Drug Unit other than the head group component, which is capable of interacting with enzymatically competent NAMPT homodimer at the binding site occupied by the nicotinamide heterocycle, when the NAMPT Drug Unit is released from a Ligand Drug Conjugate compound as a NAMPTi compound or derivative thereof. In some of those aspects in which subscript y is 1, the heteroatom of the NAMPT Drug Unit component replacing Y' is sometimes designated $X^a$ in which $X^a$ is O or S and in some instances is provided by the NAMPT Tail ($T_N$) Unit of a NAMPTi compound or derivative thereof. In other aspects in which Y' is an optionally substituted functional group, the optionally substituted heteroatom comprising that group provided by the NAMPT Drug Unit component is sometimes optionally substituted NH, O or S. In any one of the above aspects, $Y_y$ is bonded to the NAMPT Drug Unit (D) such that spontaneous self-destruction of the self-immolative moiety of Y initiated by enzymatic action on the amide or anilide functional group, which binds together W as a Peptide Cleavable Unit and the PAB or PAB-type self-immolative moiety of Y as self-immolative Spacer Unit initiates release of a NAMPTi compound or derivative thereof, which in some aspects has the formula of H—$X^a$-$T_N$-$I_N$-DA-$H_N$, wherein $T_N$, $I_N$, DA and $H_N$ are as defined for NAMPTi compounds or NAMPT Drug Units.

In other of those aspects the self-immolative Spacer Unit is also covalently attached to D through another self-immolative Spacer Unit so that $Y_y$ is —Y—Y'— wherein Y is a first self-immolative Spacer and Y' is second self-immolative Spacer Unit which in some aspects is comprised of an optionally substituted heteroatom, sometimes designated as $X^b$. In some of those aspects $X^b$ is provided by a Tail ($T_N$) Unit of a NAMPTi compound or derivative thereof. In either instance, $Y_y$ is bonded to the NAMPT Drug Unit (D) such that spontaneous self-destruction of the first self-immolative Spacer Unit Y initiated by enzymatic action on the amide or anilide functional group releases Y'-D, which then spontaneously decomposes to a NAMPTi compound or derivative thereof. In those instances the resulting NAMPTi compound or derivative thereof has the formula of H—$X^b$-$T_N$-$I_N$-DA-$H_N$, wherein $T_N$, $I_N$, DA and $H_N$ are as defined for NAMPTi compounds or NAMPT Drug Units.

In other aspects, the self-immolative moiety of a self-immolative Spacer Unit Y in $Y_y$ is attached to W' of a Glucuronide Unit through a glycosidic bond so that cleavage of that bond initiates release of Y'-D or D so as to provide a NAMPTi compound or derivative thereof. As before, Y' may be a second self immolative Spacer Unit, when subscript y is 2 or may be replaced by optionally substituted heteroatom, sometimes designated as $X^a$, of a component of the NAMPT Drug Unit when subscript y is 1. In other aspects in which subscript y is 2, Y' is a functional group comprised of an optionally substituted heteroatom provided by a component of the NAMPT Drug Unit, and is sometimes designated as $X^b$. In some aspects that functional group serves as a second self-immolative Space Unit when it is capable of spontaneous decomposition upon release from a Ligand Drug Conjugate compound or Drug Linker compound. When $X^a$ or $X^b$ is provided by the NAMPT Tail ($T_N$) of a NAMPTi compound or derivative thereof the compound eventually released has the formula of H—$X^a$-$T_N$-$I_N$-DA-$H_N$ or H—$X^b$-$T_N$-$I_N$-DA-$H_N$, respectively, for which typically $X^a$ is O or S, $X^b$ is optionally substituted NH, O or S, and $T_N$, $I_N$, DA and $H_N$ are as defined for NAMPTi compounds or NAMPT Drug Units.

"Self-immolating moiety" as used herein refers to a bifunctional moiety within a Spacer Unit (Y) wherein the self-immolative moiety is covalently attached to D through a shared heteroatom or functional group, optionally substituted where permitted, and is also covalently attached to a peptide of W when W is a Peptide Cleavable Unit through another heteroatom (J'), optionally substituted where permitted, or to a glycosidic heteroatom (E') bonded to the carbohydrate moiety (Su) of W' when W is a Glucuronide Unit of formula —Y(W')— so that the self-immolative moiety incorporates these drug linker components into a normally stable tripartite molecule unless activated.

On activation the covalent bond to the Peptide Cleavable Unit W or the glycosidic bond of W' in a Glucuronide Unit of formula —Y(W')— is cleaved so that D or —Y'-D, when subscript y is 1 or 2, respectively, spontaneously separates from the tripartite molecule by self-destruction of the self-immolative moiety of its self-immolative Spacer Unit resulting in release a NAMPTi compound or derivative thereof. In some aspects in some aspects in which subscript y is 1 Y' is replaced by optionally substituted heteroatom designated $X^a$ so that the NAMPTi compound or its derivative released from the Conjugate has the formula H—$X^a$-$T_N$-$I_N$-DA-$H_N$ when the Drug Unit is conjugated through its Tail ($T_N$) Unit. In other aspects, when subscript y is 2 Y' is a functional group comprised of an optionally substituted heteroatom designated as $X^b$ and if that functional group is also capable of spontaneous decomposition it becomes a second self-immolative Spacer Unit that upon that decomposition provides the NAMPTi compound or its derivative having the formula of $X^b$-$T_N$-$I_N$-DA-$H_N$ when the Drug Unit is conjugated through its Tail ($T_N$) Unit. In either of those aspects, self-destruction of Y or Y and Y' occurs in some instances after cellular internalization of a Ligand Drug Conjugate compound comprised of a NAMPT Drug Unit (D) and a Linker Unit having a Spacer Unit in which its self-immolating moiety is bonded to Y'-D or D.

In some aspects in which W is a Peptide Cleavable Unit, a component of self-immolative moeity Spacer Unit intervening between Y'-D or D and the optionally substituted the heteroatom J' of Y bonded to W, or a component of a self-immolative Spacer Unit in which W is a Glucuronide Unit of formula —Y(W')— between Y'-D or D and the optionally substituted heteroatom E' in W' has the formula of —$C_6$-$C_{24}$ arylene-C($R^8$)($R^9$)—, —$C_5$-$C_{24}$ heteroarylene-C($R^8$)($R^9$)—, —$C_6$-$C_{24}$ arylene-C($R^8$)=C($R^9$)— or —$C_5$-$C_{24}$ heteroarylene-C($R^8$)=C($R^9$)—, optionally substituted, wherein $R^8$ and $R^9$ are as described by the embodiments of the invention, and typically is $C_6$-$C_{10}$ arylene-$CH_2$— or $C_5$-$C_{10}$ heteroarylene-$CH_2$—, in which the (hetero)arylene is optionally substituted, wherein the component of the self-immolative moeity Spacer Unit is capable of undergoing fragmentation to form a imino-quinone methide or related structure by 1,4 or 1,6-elimination with concomitant release of D or Y'-D on cleavage of the protease cleavable bond between J' and W or on cleavage of the glycosidase cleavable bond of W'. In some aspects, a self-immolative Spacer Unit having the aforementioned component bonded to J' is exemplified by an optionally substituted p-aminobenzyl alcohol (PAB) moiety, ortho or para-aminobenzylacetals, or other aromatic compounds that are electronically similar to the PAB group (i.e., PAB-type) such as 2-aminoimidazol-5-methanol derivatives (see, e.g., Hay et al., 1999, Bioorg. Med. Chem. Lett. 9:2237) or those in which the phenyl group of the p-aminobenzyl alcohol (PAB) moiety is replaced by a heteroarylene.

Without being bound by theory an aromatic carbon of an arylene or heteroarylene group of a PAB or PAB-type moiety of a self-immolative Spacer Unit that is incorporated into a Linker Unit is substituted by J' wherein the electron-donating heteroatom of J' is attached to the cleavage site of W so that the electron-donating capacity of that heteroatom attenuated (i.e., EDG ability is masked by incorporation of a self-immolative moiety of a Self-immolative Spacer Unit into a Linker Unit). The other substituent of the hetero (arylene) is a benzylic carbon that is attached to an optionally substituted second functional group or heteroatom or a second Spacer Unit (Y') bonded to the NAMPT Drug Unit (D), wherein the benzylic carbon is attached to another aromatic carbon atom of the central arylene or heteroarylene, wherein the aromatic carbon bearing the attenuated electron-donating heteroatom is adjacent to (i.e., 1,2-relationship), or two additional positions removed (i.e., 1,4-relationship) from that benzylic carbon atom. The functionalized EDG heteroatom is chosen so that upon processing of the cleavage site of W the electron-donating capacity of the masked heteroatom is restored thus triggering a 1,4- or 1,6-elimination to expel -D or —Y'-D as a NAMPTi compound or derivative thereof from the benzylic substituent, or when Y'-D is released that compound may be capable of exerting a therapeutic effect through NAMPT inhibition or subsequent self-immolation of Y' may be required to provide a NAMPTi compound or its derivative in order to elicit a therapeutic effect. Exemplary self-immolative moieties and self-immolative Spacer Unit having those self-immolative moieties are exemplified by the embodiments of the invention.

"Methylene Carbamate Unit" as used herein, unless otherwise stated or implied by context, refers to an organic moiety capable of self-immolation and intervenes between a first self-immolative Spacer Unit and a Drug Unit within a Linker Unit of a Ligand Drug Conjugate or Drug linker compound and as such is an exemplary second Spacer Unit.

A Methylene Carbamate (MAC) Unit bonded to a Drug Unit is represented by formula III:

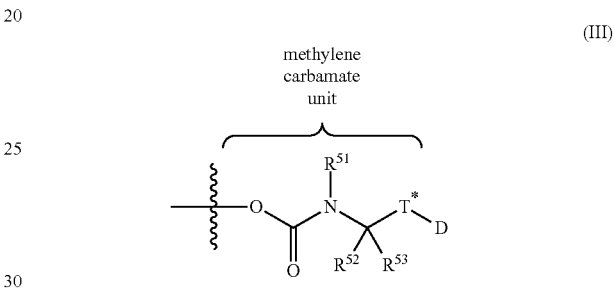

(III)

or a pharmaceutically acceptable salt thereof, wherein the wavy line indicates covalent attachment of the methylene carbamate unit to a first self-immolative Spacer Unit (Y); D is a Drug Unit having a functional group (e.g., hydroxyl, thiol, amide or amine functional group) that is incorporated into the methylene carbamate unit; T* is a heteroatom from said functional group, which includes oxygen, sulfur, or nitrogen (i.e, optionally substituted —NH—) and is sometimes designated as $X^b$, which is provided by a component of the NAMPT Drug Unit; and $R^{51}$, $R^{52}$ and $R^{53}$ are exemplified by the embodiments of the invention. Upon cleavage of a Linker Unit comprised of a MAC Unit, a first self-immolative Spacer Unit (Y) bonded to that MAC Unit as the second self-immolative Spacer Unit (Y') undergoes fragmentation to release —Y'-D of formula III. The MAC Unit then spontaneously decomposes to release D as a NAMPTi compound or derivative thereof, the presumed mechanism for which is indicated by the embodiments of the invention. When the NAMPT Drug Unit is conjugated through $X^b$ of its NAMPT ($T_N$) Tail Unit, that compound or its derivative has the formula of $X^b$-$T_N$-$I_N$-DA-$H_N$, wherein $T_N$, $I_N$, DA and $H_N$ are as defined for NAMPTi compounds and NAMPT Drug Units.

"NAMPTi compound" as used herein, unless otherwise stated or implied by context, refers to a compound capable of exerting a therapeutic effect by inhibition of intracellular nicotinamide phosphoribosyltransferase (NAMPT), which is present in its active form as a homodimer. A NAMPTi compound or its derivative typically binds to a narrow tunnel (15×6 angstroms) in the interface between the two monomers of the NAMPT dimer in which the amino acid sequences of the monomers are arranged anti-parallel to each other, and is typically divided into four components: a NAMPT Head Unit ($H_N$), a Donor-Acceptor Unit (DA), an Interconnecting Unit ($I_N$) and a Tail Unit ($T_N$) arranged in the order as given. In some aspects a NAMPTi compound has or is derivatized to have a functional group in the NAMPT Tail Unit that can serve as a conjugation handle for its incorporation as a NAMPT Drug Unit into a Ligand Drug Conjugate or Drug Linker compound. In other aspects a NAMPTi compound precursor having that Tail Unit is first conjugated through said functional group to form an intermediate Drug Linker compound followed by elaboration of the precursor Drug Unit of the intermediate so formed to a NAMPT Drug Unit within a Drug Linker compound.

NAMPTi compounds useful for adaptable for use in practicing the invention include those described in Roulston, A. and Shore, G. C. (2016) "New Strategies to maximize therapeutic opportunities for NAMPT inhibitors in oncology" *Mol. Cell. Oncol.* 3(1): e1052180; Sampath, D. et al. (2015) "Inhibition of nicotinamide phosphoribosyl-transferase (NAMPT) as a therapeutic strategy" *Pharmacol Ther.* 151: 16-31; Zak, M. et al. (2015) "Identification of nicotinamide phosphoribosyltransferase (NAMPT) transferase inhibitors with no evidence of CYP3A4 time-dependent inhibition and improved aqueous solubility" *Bioorg. Med. Chem. Lett.* 25: 529-541; Giannetti, A. M. et al. (2014) "Fragment-based identification of amides derived from trans-2-(pyridin-3-yl)cyclopropanecarboxylic acid as potent inhibitors of human nicotinamide phosphoribosyltransferase (NAMPT)" *J. Med. Chem.* 57: 770-792; Christensen, M. K. et al. (2013) "Nicotinamide phosphoribosyltransferase inhibitors, design, preparation, and structure-activity relationships" *J. Med. Chem.* 56: 9071-9088; Dragovich, P. S. et al. "Fragment-based design of 3-aminopyridine-derived amides as potent inhibitors of human nicotinamide phosphoribosyltransferase (NAMPT)" *Bioorg. Med. Chem. Lett.* 24: 954-962; Zheng, X. (2013) "Structure-based discovery of novel amide-containing nicotinamide phosphoribosyltransferase (NAMPT) inhibitors" *J. Med. Chem.* 56: 6413-6433; Galli, U. et al. (2013) "Medicinal chemistry of nicotinamide phosphoribosyltransferase (NAMPT) inhibitors" *J. Med. Chem.* 56: 6279-6296; Gunzner-Toste, J. et al. (2013) "Discovery of potent and efficacious urea-containing nicotinamide phosphoribosyltransferase (NAMPT) inhibitors with reduced $CYP2C_9$ inhibition properties" *Bioorg. Med. Chem. Lett.* 23: 3531-3538; You, H. et al. (2011) "Design, synthesis and X-ray crystallographic study of NAmPRTase inhibitors as anti-cancer agents" *Eur. J. Med. Chem.* 46: 1153-1164; Lockman, J. W. et al. (2010) "Analogues of 4-[(7-bromo-2-methyl-4-oxo-3H-quinazolin-6-yl)methyl-prop-2-ynylamino]-N-(3-pyridylmethyl)benzamide (CB-30865) as potent inhibitors of nicotinamide phosphoribosyltransferase (NAMPT)" *J. Med. Chem.* 53: 8734-8746; Colombano, G. et al. "A novel potent nicotinamide phosphoribosyltransferase inhibitor synthesized by click chemistry" *J. Med. Chem.* 53: 616-623; Galli, U. et al. (2008) "Synthesis and biological evaluation of isosteric analogues of FK866, an inhibitor of NAD salvage" *Chem Med Chem* 3: 771-779, the structure of which are specifically incorporated by reference herein, some of which have been unexpectedly found to already have a suitable functional group for attachment to a Linker Unit to allow for its conjugation as a Drug Unit in Ligand Drug Conjugate or may be modified to introduce such a handle for conjugation, either by addition of the requisite substituent to the pre-existing Tail Unit of a NAMPTi compound or by replacement of its Tail Unit in its entirety with a structurally different Tail Unit.

In some of those aspects a known NAMPTi compound is derivatized to allow for its attachment to a Linker Unit, so that release of D from a Ligand Drug Conjugate compound would be in the form of a derivative of the known NAMPTi compound, which includes those described in the above publication list. In other aspects a derivatized NAMPTi compound is selectively delivered initially to the desired site of action due to release of a Y'-D moiety from a Ligand Drug Conjugate compound, which may exert the desired therapeutic effect alone or may do so in combination with D if Y'-D is biologically active as an inhibitor of NAMPT in its own right and can be subsequently degraded to produce the parent NAMPTi compound. In such aspects derivatization of a NAMPTi compound is typically to the NAMPT Tail Unit as described herein, but may occur to other components other than the head group which is responsible for binding to the site occupied by the nicotinamide heterocycle in a enzymatically competent NAMPT homodimer.

"NAMPT Drug Unit" as used herein, unless otherwise stated or implied by context, refers to a component of a Ligand Drug Conjugate or Drug Linker compound that is covalently attached to a Linker Unit of the Ligand Drug Conjugate or Drug Linker compound and is released from that Ligand Drug Conjugate or Drug Linker compound upon enzymatic or non-enzymatic action on the Linker Unit. In some aspects the NAMPT Drug Unit is released as the parent NAMPTi compound that was incorporated into the Ligand Drug Conjugate or Drug Linker compound as a Drug Unit. In other aspects the released NAMPT Drug Unit retains a fragment of the Linker Unit so that a derivatized NAMPTi compound results from enzymatic on non-enzymatic action upon the Linker Unit of a Ligand Drug Conjugate or Drug Linker compound. That derivatized NAMPTi compound may exert a therapeutic effect in its own right by inhibiting NAMPT and/or may undergo further enzymatic or non-enzymatic action(s) to eventually release the parent NAMPTi compound.

"NAMPT Head Unit" as used herein, unless otherwise stated or implied by context, refers to a component of NAMPTi compound or derivative thereof or of a NAMPT Drug Unit of that compound or derivative that is covalently attached to or incorporates the Donor Acceptor Unit of that compound and is capable of interacting with the binding site of NAMPT normally occupied by the nicotinamide heterocycle prior to its enzymatic conversion to nicotinamide mononucleotide (NMN) and is typically a $C_5$-$C_{24}$ heteroaryl or partially aromatic $C_8$-$C_{24}$ heterocyclyl, optionally substituted, wherein both are comprised of an optionally substituted 5- or 6-membered nitrogen-containing heteroaromatic ring system. In those aspects in which the NAMPT Head ($H_N$) Unit incorporates part of the Donor Acceptor (DA) Unit, such incorporation takes the form of a 5- or 6-membered aromatic or non-aromatic ring system in which a DA Unit is cyclized back to that ring system, so as to define a $H_N$-DA Unit having a partially or fully aromatic fused ring system. Typically, in such instances when $H_N$ is an optionally substituted 6-membered nitrogen-containing heteroaromatic ring system cyclization of DA back to that ring system provides a $H_N$-DA moeity in the form of a partially or fully aromatic 6,5- or 6,6-fused ring system.

In some aspects, the $H_N$ Unit is capable of interacting with Phe 193 on one monomer of NAMPT and/or Tyr 18' of the other monomer when these monomer form an enzymatically competent NAMPT homodimer and wherein each NAMPT monomer has the amino acid sequence of NCBI Reference Sequence NP_005737.1. That interaction typically occurs by a π-π offset stacking interaction with one or both aromatic side chains of those two amino acid residues. The nitrogen-containing $C_5$-$C_{24}$ heteroaryl or partially aromatic $C_9$-$C_{24}$ heterocyclyl is typically weakly basic or remains uncharged under normal physiological conditions. Accordingly, a $H_N$ Unit typically has a pKa ranging from about −2 to about 7 and includes a pyridine mimetic as described herein Those and other $H_N$ Units are further described by the embodiments of the invention.

"Pyridine mimetic" as used herein, unless otherwise stated or implied by context, refers to a NAMPT Head Unit ($H_N$) in which the optionally substituted $C_5$-$C_{24}$ heteroaryl or partially aromatic $C_8$-$C_{24}$ heterocyclyl of that Unit has a pKa of between about −2 to about 7, and is therefore weakly basic, and is capable of interacting with the nicotinamide binding site of enzymatically competent NAMPT homodimer by interactions that include those engaged by the pyridine moiety of nicotinamide. Pyridine mimetics as $H_N$ Units include pyridin-3-yl and pyridin-4-yl, optionally substituted and/or optionally fused to an optionally substituted $C_5$ heteroaryl or a $C_6$ hetero(aryl) where appropriate, wherein the pyridinyl is attached to the Donor Acceptor (DA) Unit by a skeletal aromatic carbon atom of that moeity. In some aspects, that Unit is optionally cyclized back to the pyridine mimetic, which is typically comprised of an aromatic 6-membered nitrogen-containing ring system, at an adjacent skeletal carbon atom of that ring system through a heteroatom of DA, or through an oxygen, sulfur or nitrogen heteroatom, optionally substituted, introduced between $H_N$ and DA. In either instance as a result of that formal cyclization, part of the Donor Acceptor (DA) Unit is incorporated into $H_N$ typically in the form of an optionally substituted 5-membered heteroaromatic ring system or an optionally substituted 6-membered non-aromatic ring system so as to define $H_N$-DA typically having a fully aromatic 6,5-fused ring system or partially aromatic 6,6-fused ring system, optionally substituted. In those instances, the optionally substituted heteroatom introduced for that formal cyclization includes, —NR—, wherein R is hydrogen, optionally substituted alkyl, optionally substituted $C_6$-$C_{24}$ aryl and optionally substituted $C_5$-$C_{24}$ heteroaryl, $S(=O)_{0-2}$ and —O—. In other aspects, that Unit is optionally cyclized back to the pyridine mimetic, which typically is comprised a optionally substituted 6-membered nitrogen-containing aromatic ring system, at an adjacent skeletal carbon atom of that ring system through an optionally substituted methylene introduced between $H_N$ and DA. That formal cyclization also results in partial incorporation of the Donor Acceptor (DA) Unit into $H_N$ but does so typically in the form of a optionally substituted non-aromatic 5-membered ring system so as to define a $H_N$-DA moiety typically having an optionally substituted, partially aromatic 6,5 fused ring system. Those and other pyridine mimetics are further described by the embodiments of the invention.

"NAMPT Donor-Acceptor Unit" as used herein, unless otherwise stated or implied by context, refers to a component of a NAMPTi compound or derivative thereof, or of a NAMPT Drug Unit of that compound or derivative, that is bonded to or incorporated at least in part into that compound's Head Unit ($H_N$) and is also bonded to an interconnecting Unit ($I_N$). Combinations of $H_N$ and DA with or without said incorporation by cyclization is represented by the formula of $H_N$-DA. A Donor-Acceptor (DA) Unit is comprised of an optionally substituted hydrogen bond donor acceptor functional group, wherein a heteroatom of that functional group is attached to $H_N$, or DA is an organic moeity comprised of that functional wherein a carbon atom of that organic moeity is covalently bonded to $H_N$, which in some aspects is the carbon atom to which the hydrogen bond donor acceptor functional group is attached. In those aspects the attachment of the heteroatom or carbon atom of DA is to a skeletal carbon atom at position 2 or 3 of the 5-membered nitrogen-containing heteroaromatic ring system of $H_N$ or at position 3 or 4 of the 6-membered nitrogen-containing heteroaromatic ring system of $H_N$, with optional formal cyclization of the Donor-Acceptor (DA) Unit back to an adjacent skeletal carbon atom of either nitrogen-containing heteroaromatic ring system through a heteroatom of DA or through an optionally substituted non-aromatic carbon atom or an introduced optionally substituted nitrogen, oxygen or sulfur atom. Typically, said formal cyclization is to an optionally substituted 6-membered nitrogen-containing ring system of $H_N$ to define a $H_N$-DA moiety typically having an optionally substituted, partially aromatic or fully aromatic fused 6,5 or 6,6-ring system. In any one of those aspects said bonding of DA to $H_N$ is in relation to a skeletal nitrogen atom of the 5- or 6-membered nitrogen-containing aromatic ring system and wherein said optional cyclization of DA to $H_N$ is typically to the adjacent carbon atom of the 6-membered nitrogen-containing heteroaromatic ring system. In any of the above aspects of formal cyclization of DA to $H_N$ said formal cyclization occurs to substantially retain the hydrogen bonding ability of the donor acceptor functional group of DA existing prior to that cyclization.

In some aspects, the hydrogen bond donor acceptor functional group is or is comprised of an optionally substituted amide functional group so that DA is capable of interacting at the nicotinamide binding site with one or more of the same interactions as the amide functional group of nicotinamide and is thus capable of interacting with Ser 275 of an NAMPT monomer of an enzymatically competent NAMPT homodimer wherein each NAMPT monomer has the amino acid sequence of NCBI Reference Sequence NP_005737.1. That interaction typically occurs with the hydroxyl side chain of that amino acid residue through hydrogen bonding, and/or is capable of interacting with one or more amino acid residues selected from the group consisting of Asp 219, Ser 241, and Val 242 either directly by hydrogen bonding or indirectly through hydrogen bonding network(s) involving the intermediacy of water molecule(s). Those and other DA Units are further described by the embodiments of the invention.

"Acrylamide Donor-Acceptor" as used herein, unless otherwise stated or implied by context, refers to a subset of Donor Acceptor (DA) Units within a NAMPTi compound or derivative thereof, or of a NAMPT Drug Unit of that compound or derivative, having an optionally substituted $C_2$-$C_{20}$ alkenylene in which one of the sp$^2$ carbons defining it as an alkenylene moiety is bonded to the carbonyl carbon of an optionally substituted amide functional group, the nitrogen atom of which is the site of attachment to the NAMPT Interconnecting ($I_N$) Unit, and in which another sp$^2$ carbon of the alkenylene moiety distal to the amide functional group is the site of covalent attachment of that DA Unit to the optionally substituted 5- or 6-membered nitrogen-containing heteroaromatic ring system of the NAMPT Head ($H_N$) Unit When an acrylamide DA Unit is cyclized back to an adjacent skeletal carbon atom of the optionally substituted nitrogen-containing heteroaromatic ring system of $H_N$ it typically does so to a 6-membered heteroaromatic ring system of $H_N$ through the sp$^2$ carbon atom of the alkenylene moiety proximal to the amide functional group through an oxygen, sulfur or nitrogen heteroatom, optionally substituted, introduced between that proximal sp$^2$ carbon atom and the adjacent carbon atom so as to define a 5-membered heteroaromatic ring system fused to the 6-membered nitrogen-containing heteroaromatic ring system of $H_N$. Bioisosteres of such Donor Acceptor Units are included in the definition of an acrylamide Donor-Acceptor Unit and is an organic moeity that is sterically and functionally equivalent to that type of DA Unit by joining together the $H_N$ and $I_N$ Units while retaining a plurality of interactions attributable to the amide functional group of the parent structure within the interface of an enzymatically competent NAMPT homodimer.

"Nicotinamide mimetic" as used herein, unless otherwise stated or implied by context, refers to $H_N$-DA- of a NAMPTi compound or derivative thereof, or of a NAMPT Drug Unit of that compound or derivative, in which DA is bonded to an a Interconnecting Unit of that compound and in which $H_N$ is a pyridine mimetic and DA is bonded to position 3 relative to the weakly basic skeletal nitrogen atom of the pyridine mimetic and wherein the pyridine mimetic and the hydrogen bond donor acceptor functional group of DA is capable of interacting at the nicotinamide binding site of an enzymatically competent NAMPT homodimer with one or more of the same interactions as the pyridine and amide functional groups of nicotinamide as previously described.

"NAMPT Tail Unit" as used herein, unless otherwise stated or implied by context, refers to an component of a NAMPTi compound or derivative thereof, or of a NAMPT Drug Unit of that compound or derivative, that is bonded to that compound's Interconnecting ($I_N$) Unit and in a NAMPTi compound or its derivative provides a functional group capable of forming a covalent bond to a Linker Unit of a Ligand Drug Conjugate or Drug Linker compound for bonding to a NAMPT Tail ($T_N$) Unit or incorporation of the NAMPTi compound or its derivative as a NAMPT Drug Unit. For that purpose $T_N$ in some aspects typically is or is comprised of an optionally substituted amino-alcohol residue or an optionally substituted carboxylic acid-alcohol residue, the amino nitrogen or carbonyl carbon atom of which is bonded to $I_N$ or the remainder of $T_N$ that is bonded to $I_N$.

In other aspects $T_N$ is or is comprised of an optionally substituted benzamide moiety, the amide nitrogen atom of which is bonded to $I_N$ or the remainder of $T_N$ that is bonded to $I_N$, with optional cyclization of that atom back to $I_N$ or to the remainder of $T_N$ in which either optional cyclization is included within the formula of $I_N$-$T_N$, and the aromatic ring of which is at least substituted with a hydroxyl, thiol or amino residue at position 3 or 4 relative to the site at which the amide carbonyl carbon atom is attached. In still other aspects $T_N$ is or is comprised of an aryl or biaryl moiety, an aromatic ring which is at least substituted with a hydroxyl, thiol or amino residue. In those aspects the hydroxyl oxygen atom of the amino alcohol or carboxylic acid-alcohol residue, or the oxygen, sulfur or nitrogen atom of the hydroxyl, thiol or amino residue of the benzamide, aryl or biaryl moiety, is the site of covalent attachment of $T_N$ to $L_R$ or $L_O$, depending on the absence or present of $L_O$, respectively. $T_N$ aryl moieties include those having either a $C_6$-$C_{24}$ arylene or a $C_5$-$C_{24}$ heteroarylene and $T_N$ biaryl moieties include those having independently selected $C_6$-$C_{24}$ arylenes or $C_5$-$C_{24}$ heteroarylenes or a combination thereof. In any of the above aspects in which a remainder of $T_N$ is bonded to $I_N$ that remainder is typically an optionally substituted $C_2$-$C_{20}$ heteroalkylene or an optionally substituted $C_3$-$C_{20}$ heterocyclo or a combination thereof, more typically a $C_2$-$C_7$ heteroalkylene or a $C_5$-$C_6$ heterocyclo or a combination thereof. In those aspects the $C_3$-$C_{20}$ heterocyclo or $C_5$-$C_6$ heterocyclo is typically saturated or partially unsaturated.

In some aspects, $T_N$ or —$I_N$-$T_N$- is capable of engaging in one or more interactions with a hydrophobic cleft region formed by Ile 309, Pro 307, Val 350, Ile 378 and Ala 379 and/or is capable of interacting with one or more amino acid residues selected from the group consisting of Tyr 188, Lys 189, Ala 379, Asn 377, Glu 376, Val 350, Arg 349 and Pro 307 of an NAMPT monomer of an enzymatically competent NAMPT homodimer wherein each NAMPT monomer has the amino acid sequence of NCBI Reference Sequence NP_005737.1. Those and other $T_N$ Units are further described by the embodiments of the invention.

"NAMPT Interconnecting Unit" as used herein, unless otherwise stated or implied by context, refers to a component of a NAMPTi compound or derivative thereof, or of a NAMPT Drug Unit of that compound or derivative, that interconnect its Donor Acceptor (DA) and Tail ($T_N$) Units. In some aspects, $I_N$ engages in Van der Waals interactions with hydrophobic side amino acid side chains that line the tunnel in the region between the DA and Tail Units and allows for the Tail Unit to engage in one or more of the aforementioned interactions to anchor the NAMPTi compound into the dimer interface. Typically, the length of the Interconnecting Unit is also selected to allow projection of the hydroxyl or amino residue substituent of $T_N$ towards solvent accessible space on binding of a NAMPTi compound to an enzymatically competent NAMPT dimer in order for that moiety, when introduced as a handle for its conjugation as a NAMPTi Drug Unit in a Ligand Drug Conjugate, does not unduly interfere with, and in some instances may enhance, binding of the NAMPTi compound to that NAMPT homodimer. For that purpose $I_N$ typically has or is comprised of a hydrophobic residue selected from the group consisting of $C_1$-$C_8$ alkylene, $C_6$-$C_{24}$ arylene or a combination thereof, in which the terminus of the hydrophobic residue distal to the site of attachment to $H_N$-DA is optionally functionalized for attachment to $T_N$ Unit. Those functionalities include —O—, —S($=$O)$_{1,2}$, and —C($=$O)—. In some aspects, $I_N$ is additionally comprised of an optionally substituted $C_2$-$C_{12}$ heteroalkylene or an optionally substituted $C_5$-$C_{20}$ heterocyclo, which in some aspects is optionally functionalized for covalent attachment to $T_N$. Although the hydrophobic residue of $I_N$ may be capable of hydrophobic interactions in the enzymatically competent dimer interface between two NAMPT monomers, those interactions may not contribute meaningfully to binding of an NAMPTi compound or derivative to the enzyme, therefore the capability of $I_N$ in a released NAMPT Drug Unit for those interactions is considered optional. $I_N$ Units are further described by the embodiments of the invention.

"Cytotoxic drug" as used herein, unless otherwise stated or implied by context, refers to compound or a metabolite derived from an Ligand Drug Conjugate that exerts an anti-survival effect on hyper-proliferating cells, hyper-activated immune cells or other abnormal cells. In some aspects the cytotoxic drug acts directly upon those cells or indirectly by acting upon the abnormal vasculature that supports the survival and/or growth of the hyper-proliferating or other abnormal or unwanted cells, or the cytotoxic drug acts within sites of infiltrating hyper-activated immune cells. Typically, the abnormal or unwanted cells acted upon by the cytotoxic drug are mammalian cells, more typically human cells. Cytotoxic activity of a cytotoxic drug may be expressed as an $IC_{50}$ value, which is the effective concentration, typically molar amount per unit volume, at which half the cancer cells in an in vitro cell model system survive exposure to the cytotoxic agent. Thus, an $IC_{50}$ value is model-dependent. Typically, a cytotoxic agent incorporated into an LDC will have an $IC_{50}$ value in an in vitro cell model comprised of hyper-proliferating cells of between 100 nM to 0.1 pM or more typically about 10 nM to 1 pM. A highly toxic cytotoxic drug typically has an $IC_{50}$ value in such models of about 100 pM or lower. Although compounds that reverse resistance to cytotoxic or cytostatic drugs in abnormal compounds having the MDR phenotype are not cytotoxic in their own right they are sometimes included as cytotoxic drugs as are cytostatic drugs, which exert an anti-proliferative effect that is not dependent on cell killing but whose effect remains due to inhibition of cell division of hyper-proliferating cells, hyper-stimulated immune cells or other abnormal or unwanted cells. As unconjugated free drugs NAMPTi compounds typically exhibit steep dose-response curves indicating that a threshold amount of NAD depletion is necessary for cytotoxicity. Furthermore, for maximal cytotoxicity a sustained exposure to the NAMPTi compound is typically necessary in order to deplete intracellular ATP to an amount from which there is no escape from cell death as would occur if NAD levels were allowed to rebound.

"Hematological malignancy" as used herein, unless otherwise stated or implied by context, refers to a blood cell tumor that originates from cells of lymphoid or myeloid origin and is synonymous with the term "liquid tumor". Hematological malignancies may be categorized as indolent, moderately aggressive or highly aggressive.

"Lymphoma" as used herein, unless otherwise stated or implied by context, refers to is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sézary's disease, peripheral T-cell lymphomas not otherwise specified, nodular sclerosis of Hodgkin lymphoma, and mixed-cellularity subtype of Hodgkin lymphoma.

"Leukemia" as used herein, unless otherwise stated or implied by context, refers to a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocytic leukemia (AMoL). Other leukemias include hairy cell leukemia (HCL), T-cell lymphatic leukemia (T-PLL), large granular lymphocytic leukemia and adult T-cell leukemia.

"Hyper-proliferating cells" as used herein, unless otherwise stated or implied by context, refer to abnormal cells that are characterized by unwanted cellular proliferation or an abnormally high rate or persistent state of cell division or other cellular activity that is unrelated or uncoordinated with that of the surrounding normal tissues. Typically, hyper-proliferating cells are mammalian cells. In some aspects hyper-proliferating cells are hyper-stimulated immune cells as defined herein whose persistent state of cell division or activation occurs after the cessation of the stimulus that may have initially evoked the change in their cell division. In other aspects the hyper-proliferating cells are transformed normal cells or cancer cells and their uncontrolled and progressive state of cell proliferation may result in a tumor that is benign, potentially malignant (premalignant) or frankly malignant. Hyperproliferation conditions resulting from transformed normal cells or cancer cells include but are not limited to those characterized as a precancer, hyperplasia, dysplasia, adenoma, sarcoma, blastoma, carcinoma, lymphoma, leukemia or papilloma. Precancers are usually defined as lesions that exhibit histological changes which are associated with an increased risk of cancer development and sometimes have some, but not all, of the molecular and phenotypic properties that characterize the cancer. Hormone associated or hormone sensitive precancers include, prostatic intraepithelial neoplasia (PIN), particularly high-grade PIN (HGPIN), atypical small acinar proliferation (ASAP), cervical dysplasia and ductal carcinoma in situ. Hyperplasias generally refers to the proliferation of cells within an organ or tissue beyond that which is ordinarily seen that may result in the gross enlargement of an organ or in the formation of a benign tumor or growth. Hyperplasias include, but are not limited to endometrial hyperplasia (endometriosis), benign prostatic hyperplasia and ductal hyperplasia.

"Normal cells" as used herein, unless otherwise stated or implied by context, refer to cells undergoing coordinated cell division related to maintenance of cellular integrity of normal tissue or replenishment of circulating lymphatic or blood cells that is required by regulated cellular turnover, or tissue repair necessitated by injury, or to a regulated immune or inflammatory response resulting from pathogen exposure or other cellular insult, where the provoked cell division or immune response terminates on completion of the necessary maintenance, replenishment or pathogen clearance. Normal cells include normally proliferating cells, normal quiescent cells and normally activated immune cells.

"Normal quiescent cells" as used herein, unless otherwise stated or implied by context, refer to are noncancerous cells in their resting $G_o$ state and have not been stimulated by stress or a mitogen or are immune cells that are normally inactive or have not been activated by pro-inflammatory cytokine exposure.

"Hyper-stimulated immune cells" as used herein, unless otherwise stated or implied by context, refer to cells involved in innate or adaptive immunity characterized by an abnormally persistent proliferation or inappropriate state of stimulation that occurs after the cessation of the stimulus that may have initially evoked the change in proliferation or stimulation or that occurs in the absence of any external insult. Oftentimes, the persistent proliferation or inappropriate state of stimulation results in a chronic state of inflammation characteristic of a disease state or condition. In some instances the stimulus that may have initially evoked the change in proliferation or stimulation is not attributable to an external insult but is internally derived as in an autoimmune disease. In some aspects a hyper-stimulated immune cells is a pro-inflammatory immune cell that has been hyper-activated through chronic pro-inflammatory cytokine exposure.

In some aspects of the invention a Ligand Drug Conjugate compound of an LDC composition binds to an antigen preferentially displayed by pro-inflammatory immune cells that are abnormally proliferating or are inappropriately or persistently activated. Those immune cells include classically activated macrophages or Type 1 T helper (Th1) cells, which produce interferon-gamma (INF-γ), interleukin-2 (IL-2), interleukin-10 (IL-10), and tumor necrosis factor-beta (TNF-β), which are cytokines that are involved in macrophage and CD8+ T cell activation.

"Glycosidase" as used herein, unless otherwise stated or implied by context, refers to a protein capable of enzymatic cleavage of a glycosidic bond. Typically, the glycosidic bond to be cleaved is present in a Glucuronide Unit as the Cleavable Unit of Ligand Drug Conjugate or Drug Linker compound. Sometimes the glycosidase acting upon a Ligand Drug Conjugate is present intracellularly in hyper-proliferating cells, hyper-activated immune cells or other abnormal cells to which the LDC has preferential access in comparison to normal cells, which is attributable to the targeting capability of its Ligand Unit. Sometimes the glycosidase is more specific to the abnormal or unwanted cells or is preferentially excreted by abnormal or unwanted cells in comparison to normal cells or is present in greater amount in the vicinity of abnormal cells in comparison to amounts of the glycosidase typically found in serum of an intended subject to whom the LDC is to be administered. Typically, the glycosidic bond within a Glucuronide Unit, which has the formula of —W'(Y)—, acted upon by a glycosidase connects the anomeric carbon of a carbohydrate moiety (Su) to a self-immolative Stretcher Unit (Y) through an optionally substituted heteroatom (E') so that W' is Su-E'-. In some aspects E', which forms the glycosidic bond to the carbohydrate moiety (Su), is a phenolic oxygen atom of a self-immolating moiety in a self-immolative Stretcher Unit Y such that glycosidic cleavage of that bond triggers 1,4- or 1,6-elimination of D or Y'-D as NAMPTi compound or derivative thereof.

In some aspects, Drug Linker compounds or Ligand Drug Conjugates are represented by formula $L_{SS}$-$B_b$-$(A_a$-$Y_y(W')$-$D)_n$ or L-$(L_S$-$B_b$-$(A_a$-$Y_y(W')$-$D)_n)_p$, in which $L_{SS}$ is $M^1$-$A_R$(BU)-$A_O$- and $L_S$ is $M^2$-$A_R$(BU)-$A_O$ or $M^3$-$A_R$(BU)-$A_O$-, wherein $A_O$ is an second optionally Stretcher Unit, which in some aspects serves as Hydrolysis-enhancing (HE) Unit and A is a first optionally Stretcher Unit, wherein in some aspects A or a subunit thereof has the formula of -$L^P$(PEG)-, wherein -$L^P$ and PEG are as defined herein for parallel connector units and PEG Units, respectively; BU represents an acyclic or cyclic Basic Unit, and subscripts a and b are independently 0 or 1, and subscript n is 1, 2, 3 or 4, wherein B is a Branching Unit, and is present when subscript n is 2, 3 or 4 so that subscript b is 1 and wherein A is a first Stretcher Unit, when subscript a is 1, and subscript y is 1 or 2.

In those aspects —Y(W')— typically is of the formula -(Su-O')—Y—, wherein Su is a carbohydrate moiety, Y is a self-immolative Spacer Unit having a PAB or PAB-type self-immolative moiety with glycosidic bonding to Su, wherein O' represents the oxygen atom of the glycosidic bond cleavable by a glycosidase and a NAMPT Drug (D) Unit is bonded directly to the self-immolative moiety of Y through its NAMPT Tail ($T_N$) Unit so that subscript y is 1, or D is bonded to that self-immolative moiety through Y' so that subscript y is 2, wherein Y' is a second Spacer Unit, which may or may not be capable of self-immolation, or an optionally substituted heteroatom or functional group provided by the Tail Unit of a NAMPTi compound or its derivative the latter of which may also be capable of self-immolation upon release of Y'-D to provide D as a NAMPTi compound or derivative thereof, or Y' is a methylene carbamate unit, wherein Su-O'— is attached to the optionally substituted (hetero)arylene of the self-immolative moiety and D or —Y'-D are attached to that (hetero)arylene through an optionally substituted benzylic carbon such that self-immolative release of D or —Y'-D is initiated, thereby providing a NAMPTi compound or derivative thereof. Although such —Y(W')— moieties are referred to as Glucuronide Units, Su of W' is not limited to a glucuronic acid residue.

Typically, a Glucuronide Unit having the formula of -(Su-O'—Y)— (where —O'-represents the oxygen of the glycosidic bond and Su is a carbohydrate moiety) is represented by a structure described for a self-immolating Spacer Unit (Y) in which E' bonded to the central (hetero)arylene moiety of a PAB or PAB-type moiety of Y is an oxygen atom with that heteroatom bonded to the carbohydrate moiety (Su) through that moiety's anomeric carbon atom.

In some aspects such moieties attached to D include those of formula -(Su-O')—Y—Y'-D having the structure of:

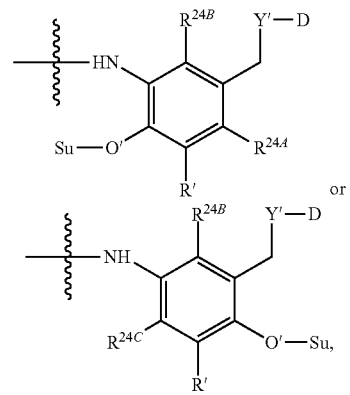

wherein Y' is replaced an optionally substituted heteroatom of the NAMPT Tail ($T_N$) Unit of a NAMPT compound or derivative thereof, including but not limited to NH—, O, and S, when subscript y is 1, which in some aspects is $X^a$, wherein $X^a$ is O or S, or Y' is a functional group comprised of an optionally substituted heteroatom, in some instances in which subscript y is 2, wherein the functional group may be capable of self-immolation as when Y' is a carbamate functional group, which in some aspects has the formula of —OC(=O)—$X^b$—, wherein $X^b$ is optionally substituted NH, O or S of the optionally substituted heteroatom of the NAMPT Tail ($T_N$) Unit, or Y' is a second Spacer Unit in other instances when subscript y is 2, which may also be capable of self-immolation as when Y' is a methylene carbamate unit; $R^{24A}$, $R^{24B}$ and $R^{24C}$ are independently selected from the group consisting of hydrogen, $C_1$-$C_6$ alkyl, $C_1$-$C_6$ alkoxy, other EDGs, halogen, nitro and other EWGs or $R^{24}$ and R' in the left-hand structure or $R^{24C}$ and R' in the right-hand structure together with the aromatic carbons to which they are attached define an benzo-fused $C_5$-$C_6$ carbocycle, and are selected so that the electron donating ability of the phenolic —OH released from the glycosidic bond by enzymatic action of a glycosidase, the sensitivity to selective cleavage by the glycosidase, and the stability of the iminoquinone methide intermediate resulting from fragmentation by 1,4- or 1,6-elimination is balanced with the leaving ability of D or —Y'D so that a suitably efficient release of a NAMPTi compound or derivative thereof occurs. The -(Su-O')—Y'— moieties in the above —$Y_y(W')$-D structures are representative Glucuronide Units. When the glycosidic bond is to a glucuronic acid, the glycosidase capable of enzymatic cleavage of that glycosidic bond is a glucuronidase.

In some of those aspects -(Su-O')—Y—Y'-D has the structure of:

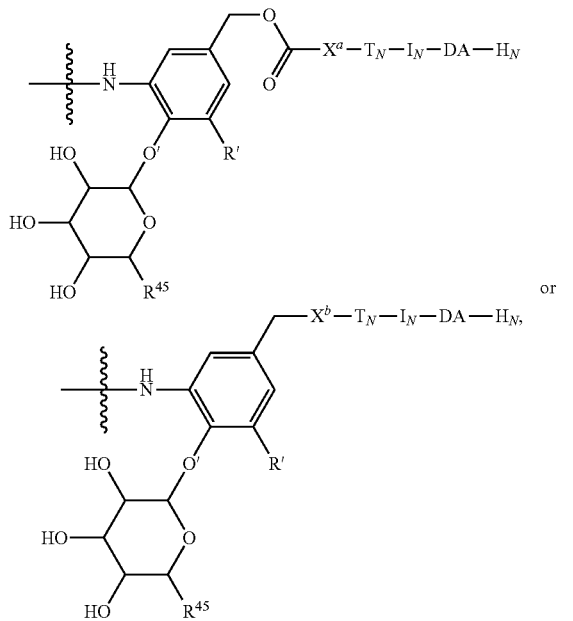

wherein Y' is —OC(=O)—X$^b$—, in some instances in which subscript y is 2, wherein X$^b$ is a nitrogen atom from a primary or secondary amine functional group of an NAMPT Tail (T$_N$) Unit of a NAMPTi compound or derivative thereof, or Y' is replaced by X$^b$ when subscript y is 1, wherein X$^b$ is an oxygen atom from an alcohol functional group or a sulfur atom of a thiol functional group of T$_N$; R$^{45}$ is —OH or —CO$_2$H and the remaining variable groups are as defined for NAMPTi compounds and NAMPT Drug Units. Further descriptions of those and other Glucuronide Units are provided by the embodiments of the invention.

"Carbohydrate moiety" as used herein, unless otherwise stated or implied by context, refers to a monovalent radical of a monosaccharide having the empirical formula of C$_m$(H$_2$O)$_n$, wherein n is equal to m, containing an aldehyde moiety in its hemiacetal form or a derivative thereof in which a CH$_2$OH moiety within that formula has been oxidized to a carboxylic acid (e.g., glucuronic acid from oxidation of the CH$_2$OH group in glucose). Typically, a carbohydrate moiety (Su) is a monovalent radical of cyclic hexose, such as a pyranose, or a cyclic pentose, such as a furanose. Usually, the pyranose is a glucuronide or hexose in the β-D conformation. In some instances, the pyranose is a β-D-glucuronide moiety (i.e., β-D-glucuronic acid linked to the self-immolative moiety of a self-immolative Spacer Unit via a glycosidic bond that is cleavable by β-glucuronidase). Sometimes, the carbohydrate moiety is unsubstituted (e.g., is a naturally occurring cyclic hexose or cyclic pentose). Other times, the carbohydrate moiety can be a β-D-glucuronide derivative, e.g., glucuronic acid in which one or more, typically 1 or 2 of its hydroxyl moieties are independently replaced with moieties selected from the group consisting of halogen and C$_1$-C$_4$ alkoxy.

"Protease" as used herein, unless otherwise stated or implied by context, refers to a protein capable of enzymatic cleavage of a carbonyl-nitrogen bond such as an amide bond typically found in a peptide. Proteases are classified into major six classes: serine proteases, threonine proteases, cysteine proteases, glutamic acid proteases, aspartic acid proteases and metalloproteases so named for the catalytic residue in the active site that is primarily responsible for cleaving the carbonyl-nitrogen bond of its substrate. Proteases are characterized by various specificities, which are dependent of identities of the residues at the N-terminal and/or C-terminal side of the carbonyl-nitrogen bond.

When W is a Peptide Cleavable Unit bonded to a self-immolative Spacer Y when subscript y is 1 or 2, or to a NAMPT Drug Unit when subscript y is 0 in Formula 1, Formula 2 or Formula I, through an amide or other carbonyl-nitrogen containing functional group cleavable by a protease that cleavage site is oftentimes limited to those recognized by proteases that are found in abnormal cells including hyper-proliferating cells and hyper-stimulated immune cells or within cells particular to the environment in which these abnormal cells are present. In those instances, the protease may or may not be preferentially present or found in greater abundance within cells targeted by a Ligand Drug Conjugate having that Peptide Cleavable Unit since it will have poorer access to cells that do not have the targeted moiety or have insufficient copy number of the targeted moiety to which its Ligand Unit is directed to have an adverse effect due to immunologically specific uptake of the Conjugate. Other times, the protease is preferentially excreted by abnormal cells or by cells in the environment in which those abnormal cells are found in comparison to normal cells or in comparison to typical environments in which those normal cells are found in the absence of abnormal cells. Thus, in those instances where the protease is excreted, the protease is typically required to be preferentially present or found in greater abundance in the vicinity of cells targeted by the Ligand Drug Conjugate in comparison to that of normal cells.

When incorporated into a Ligand Drug Conjugate composition, a peptide that comprises W and which is bonded to Y or D, dependent on the presence or absence of Y, through a carbon-nitrogen bond will present a recognition sequence to a protease that cleaves that bond resulting in fragmentation of the Linker Unit whereby release of a NAMPTi compound or derivative thereof from a Conjugate compound of the composition occurs. Sometimes, the recognition sequence is selectively recognized for the purpose of appropriately delivering a NAMPTi compound or derivative thereof to the desired site of action by an intracellular protease present in abnormal cells to which the Ligand Drug Conjugate has preferred access in comparison to normal cells due to targeting of the abnormal cells by its Ligand Unit, or is preferentially produced by abnormal cells in comparison to normal cells. In some aspects, the peptide is resistant to circulating proteases in order to minimize premature release of the NAMPTi compound or its derivative and thus minimize unwanted systemic exposure to the released compound. In some of those aspects, the peptide will have one or more unnatural or non-classical amino acids in its sequence order to have that resistance. In that and other aspects, the amide bond that is specifically cleaved by a protease is produced by or present within an abnormal cell and is sometimes an anilide bond wherein the nitrogen of that anilide is a nascent electron-donating heteroatom (i.e., J') of an self-immolative moiety having one the previously defined structures for such moieties. Thus, protease action on such a peptide sequence in W results in release of a NAMPT Drug Unit as a NAMPTi compound or derivative thereof from Linker Unit fragmentation occurring by 1,4- or 1,6-elimination through the central (hetero)arylene moiety of a PAB or PAB-type self-immolative Spacer Unit.

Regulatory proteases are typically located intracellularly and are required for the regulation of cellular activities, including cellular maintenance, proliferation or other intracellular activity, that sometimes becomes aberrant or dysregulated in abnormal cells. In some instances, when W is directed to a protease preferentially present intracellularly in comparison its extracellularly presence, that protease is typically a regulatory protease. In some instances, those proteases include cathepsins. Cathepsins include the serine proteases, Cathepsin A, Cathepsin G, aspartic acid proteases Cathepsin D, Cathepsin E and the cysteine proteases, Cathepsin B, Cathepsin C, Cathepsin F, Cathepsin H, Cathepsin K, Cathepsin L1, Cathepsin L2, Cathepsin O, Cathepsin S, Cathepsin W and Cathepsin Z.

In other instances, when W is directed to a protease that is preferentially distributed extracellularly in the vicinity of abnormal cells, such as hyper-proliferating or hyper-stimulated immune cells, in comparison to normal cells distant from the abnormal cells, that distribution is due to preferential excretion by the abnormal cells or by neighboring cells whose excretion of the protease is peculiar to the environment of hyper-proliferating or hyper-stimulated immune cells. In some of those instances the protease is a metalloprotease. Typically, those proteases are involved in tissue remodeling, which aids in the invasiveness of hyper-proliferating cells or undesired accumulation of hyper-activated immune cells, which often results in further recruitment of such cells.

"Intracellularly cleaved", "intracellular cleavage" and like terms used herein refer to a metabolic process or reaction within a targeted cell occurring upon an Ligand Drug Conjugate or the like, whereby covalent attachment through its Linker Unit between the NAMPT Drug Unit and the Ligand Unit of the Conjugate is broken, resulting in release of a NAMPTi compound or derivative thereof or other metabolite(s) of the Conjugate within the targeted cell. The moieties from that cleavage are thus intracellular metabolites of the Ligand Drug Conjugate.

"Bioavailability" unless otherwise stated or implied by context, refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

"Subject" unless otherwise stated or implied by context, refers to a human, non-human primate or mammal having a hyper-proliferation, inflammatory or immune disorder or other disorder attributable to abnormal cells or is prone to such a disorder who would benefit from administering an effective amount of a Ligand Drug Conjugate. Non-limiting examples of a subject include human, rat, mouse, guinea pig, monkey, pig, goat, cow, horse, dog, cat, bird and fowl. Typically, the subject is a human, non-human primate, rat, mouse or dog.

The term "inhibit" or "inhibition of" unless otherwise stated or implied by context, means to reduce by a measurable amount, or to prevent entirely an undesired activity or outcome. In some aspects the undesired outcome or activity is related to abnormal cells and includes hyper-proliferation, or hyper-stimulation or other dysregulated cellular activity underlying a disease state. Inhibition of such a dysregulated cellular activity by a Ligand Drug Conjugate is typically determined relative to untreated cells (sham treated with vehicle) in a suitable test system as in cell culture (in vitro) or in a xenograft model (in vivo). Typically, a Ligand Drug Conjugate that targets an antigen that is not present or has low copy number on the abnormal cells of interest or is genetically engineered to not recognize any known antigen is used as a negative control.

The term "therapeutically effective amount" unless otherwise stated or implied by context, refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic or cytotoxic. For cancer therapy, efficacy can, for example, be measured by assessing the time to disease progression (TTP) determining the response rate (RR) and/or overall survival (OS).

In the case of immune disorders resulting from hyper-stimulated immune cells, a therapeutically effective amount of the drug may reduce the number of hyper-stimulated immune cells, the extent of their stimulation and/or infiltration into otherwise normal tissue and/or relieve to some extent one or more of the symptoms associated with a dysregulated immune system due to hyper-stimulated immune cells. For immune disorders due to hyper-stimulated immune cells, efficacy can, for example, be measured by assessing one or more inflammatory surrogates, including one or more cytokines levels such as those for IL-1β, TNFα, INFγ and MCP-1, or numbers of classically activated macrophages.

In some aspects of the invention, the Ligand Drug Conjugate compound associates with an antigen on the surface of a target cell (i.e., an abnormal cell such as a hyper-proliferating cell or a hyper-stimulated immune cell), and the Conjugate compound is then taken up inside a target cell through receptor-mediated endocytosis. Once inside the cell, one or more Cleavage Units within a Linker Unit of the Conjugate are cleaved, resulting in release of D as a NAMPTi compound or derivative thereof. The released compound is then free to migrate within the cytosol and induce cytotoxic or cytostatic activities, or in the case of hyper-stimulated immune cells may alternatively inhibit pro-inflammatory signal transduction. In another aspect of the invention, the NAMPT Drug Unit (D) is released from a Ligand Drug Conjugate compound outside the targeted cell but within the vicinity of the targeted cell so that the released NAMPTi compound or its derivative is able to subsequently penetrate the cell rather than being prematurely released at distal sites.

"Carrier" unless otherwise stated or implied by context refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a subject, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

"Treat", "treatment," and like terms, unless otherwise indicated by context, refer to therapeutic treatment or prophylactic measures to prevent relapse, wherein the object is to inhibit or slow down (lessen) an undesired physiological change or disorder, such as the development or spread of cancer or tissue damage from chronic inflammation. Typically, beneficial or desired clinical results of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The term can also mean prolonging survival or quality of like of a subject as compared to expected survival or quality of life for a subject not receiving treatment. Those in need of treatment include those already having the condition or disorder as well as those prone to have the condition or disorder.

In the context of cancer or a disease state related to chronic inflammation, the term includes any or all of inhibiting growth of tumor cells, cancer cells, or of a tumor; inhibiting replication of tumor cells or cancer cells, inhibiting dissemination of tumor cells or cancer cell, lessening of overall tumor burden or decreasing the number of cancerous cells, inhibiting replication or stimulation of pro-inflammatory immune cells, inhibiting or decreasing the chronic inflammatory state of a dysregulated immune system or decreasing the frequency and/or intensity of flares experienced by subjects having an autoimmune condition or disease or ameliorating one or more symptoms associated with cancer or a hyper-immune stimulated disease or condition.

"Salt form" as used herein, unless otherwise indicated by context, refers to a charged compound in ionic association with a countercation(s) and/or counteranions so as to form an overall neutral species. Accordingly, salt forms include a protonated form of a compound in ionic association with a counteranion. Such a salt forms may result from interaction of a basic functional group and an acid functional group within the same compound or involve inclusion of a negatively charged molecule such as an acetate ion, a succinate ion or other counteranion. In some aspects, a salt form of a compound occurs through interaction of the parent compound's basic or acid functional group with an external acid or base, respectively. In other aspects the charged atom of the compound that is associated with a counteranion is permanent in the sense that spontaneous disassociation to a neural species cannot occur without altering the structural integrity of the parent compound. The counterion may be any charged organic or inorganic moiety that stabilizes an opposite charge on the parent compound. Furthermore, a compound in salt form may have more than one charged atoms in its structure. In instances where multiple charged atoms of the parent compound are part of the salt form, that salt from of the compound can have multiple counter ions. Hence, a salt form of a compound can have one or more charged atoms and/or one or more counterions.

A salt form of a compound not involving a quaternized nitrogen atom is typically obtained when a basic functional group of a compound, such as a primary, secondary or tertiary amine or other basic amine functional group interacts with an organic or inorganic acid of suitable pKa for protonation of the basic functional group, or when an acid functional group of a compound with a suitable pKa, such as a carboxylic acid, interacts with a hydroxide salt, such as NaOH or KOH, or an organic base of suitable strength, such as triethylamine, for deprotonation of the acid functional group. In some aspects, a compound in salt form contains at least one basic amine functional group, and accordingly acid addition salts can be formed with this amine group, which includes the basis amine functional group of a cyclic or acyclic Basic Unit.

"Pharmaceutically acceptable salt" as used herein, unless otherwise indicated by context, refers to a salt form of a compound in which its counterion is acceptable for administration of the salt form to an intended subject and include inorganic and organic countercations and counteranions. Exemplary pharmaceutically acceptable counteranions for basic amine functional groups, such as those in cyclic or acyclic Basic Units, include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, mesylate, besylate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Typically, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability as when in a lyophilized formulation under accelerated conditions (i.e., for determining degradation or solid-state changes when stored at 40° C. and 75% relative humidity).

"Loading", "drug loading", "payload loading" or like terms as used herein, unless otherwise indicated by context, refer to the average number of payloads ("payload" and "drug" is used interchangeable herein with "biologically active compound or its derivative) in an population of Ligand Drug Conjugate compounds of a LDC composition. The drug loading of that composition, which can also include species lacking conjugated drug, is characterized by a distribution of attached D/D$^+$ Units or drug linker moieties per Ligand Unit. Other species may include those Conjugate compounds having the same number of NAMPT Drug Units or drug linker moieties per Ligand Unit but differ by the attachment sites of their respective drug linker moieties to the Linker Unit, but otherwise have substantially the structure with respect to the Ligand Unit, which allows for variations in glycosylation and mutational differences in peptide sequences. Drug loading may range from 1 to 24 NAMPT Drug Units (D) or drug linker moieties comprising D per Ligand Unit and is sometimes referred to as the DAR, or drug to targeting moiety ratio, wherein the targeting moiety of a Ligand Drug Conjugate is its Ligand Unit. Ligand Drug Conjugate compositions described herein typically have DAR values ranging from 1 to 24, and in some aspects range from 1 to about 10, from about 2 to about 8, from about 2 to about 6, from about 2 to about 5 or from about 2 to about 4. Typically, DAR values are about 2, about 4, about 6, about 8 or about 10. The average number of conjugated drugs per Ligand Unit, or DAR value, of a Ligand Drug Conjugate composition may be characterized by conventional means such as UV/visible spectroscopy, mass spectrometry, ELISA assay, and HPLC. A quantitative DAR value may also be determined. In some instances, separation, purification, and characterization of homogeneous Ligand Drug Conjugate compounds having a particular DAR value may be achieved by methods using reverse phase HPLC or electrophoresis. DAR may be limited by the number of attachment sites on a targeting agent that is to be incorporated into a Ligand Drug Conjugate as its Ligand Unit.

For example, when the targeting agent is an antibody and the attachment site is a cysteine thiol functional group, the antibody may have only one or several that are sufficiently reactive towards the maleimide ring system of a $M^1$-$A_R$ (BU)-containing moiety, such as a Drug Linker compound, so as to undergo Michael addition. Sometimes, the cysteine thiol functional group is from of a cysteine residue that participated in an interchain disulfide bond of an antibody. Other times, the cysteine thiol functional group is that of a cysteine residue that did not participate in an interchain disulfide bond, but was introduced through genetic engineering. Sometimes, less than the theoretical maximum of NAMPT Drug Units or drug linker moieties having these Units is conjugated to an antibody during a conjugation reaction.

I. Embodiments

Provided herein are Ligand Drug Conjugate compositions and compounds, and their Drug Linker compound precursors and Intermediates thereof, wherein a Ligand Drug Conjugate compound of the composition is capable of preferential delivery of a NAMPTi compound or derivative thereof to a hyperproliferating cells or hyper-activated immune cell or is capable of preferential delivery of that compound or its derivative to the vicinity of such abnormal cells including preferential delivery to nearby normal cells in comparison to normal cells or the vicinity of normal cells that are distant from these abnormal cells and are thus useful for treating diseases and conditions characterized by these abnormal cells.

1.1 General

A Ligand Drug Conjugate has three major components: (1) a Ligand Unit, which incorporates a targeting agent that selectively binds to a targeted moiety present on, within or in the vicinity of abnormal cells or other unwanted cells in comparison to other moieties present on, within, or in the vicinity of normal cells where these abnormal or unwanted cells are typically not present, or the targeted moiety is present on, within, or in the vicinity of abnormal or other unwanted cells in greater copy number in comparison to normal cells or the environment of normal cells where abnormal or unwanted cells are typically not present, (2) a Drug Unit (D) incorporating the structure of a NAMPTi compound or derivative thereof, and (3) a Linker Unit, which interconnects D and the Ligand Unit and is capable of conditionally releasing D as a NAMPTi compound or derivative thereof, wherein said release is preferably within or in the vicinity of abnormal cells or within or in the vicinity of targeted normal cells that are peculiar to the environment of the abnormal cells as opposed to normal cells distant from the site of the abnormal cells.

A NAMPTi compound or derivative thereof to be used in the present invention is one that primarily or selectively exerts its biological effect (e.g., cytotoxic or cytostatic effect) on mammalian cells by inhibiting intracellular NAMPT. In some embodiments the NAMPT compound or its derivative competes competitively with the nicotinamide binding site of NAMPT and in these instances may undergo phospho-ribosylation by the enzyme to form a mononucleotide. Without being bound by theory, the mononucleotide metabolite so formed may be more slowly released from NAMPT than nicotinamide mononucleotide (NMN), thus causing product inhibition of the enzyme and/or when released may inhibit nicotinamide mononucleotide adenylyl transferase (NMNAT) in its conversion of NMN to NAD. The inhibition at either of those steps of the NAD salvage pathway may be more prolonged due to intracellular trapping of the mononucleotide metabolite due to its 5′-phosphate group, which inhibits efflux from the cell targeted by a Ligand Drug Conjugate compound having a corresponding NAMPT Drug Unit.

In some aspects, the targeted moiety, which is recognized by the targeting Ligand Unit of the Conjugate, is an epitope of an extracellular displayed membrane protein and is preferentially found on abnormal or unwanted cells in comparison to normal cells. Specificity towards the abnormal (i.e., the targeted cells) results from the Ligand (L) Unit of the Ligand Drug Conjugate. In some embodiments, the Ligand Unit is that of an antibody, for which the antibody is an exemplary targeting agent, wherein the Ligand Unit substantially retains the antibody's ability to recognize the abnormal mammalian cells. Such a Ligand Unit is sometimes referred to as an antibody Ligand Unit.

In some embodiments, it is preferred that the membrane protein targeted by the Ligand Unit have sufficient copy number and be internalized upon binding of a Ligand Drug Conjugate compound through its Ligand Unit in order to intracellularly deliver an effective amount of the NAMPTi compound to exert a cytotoxic, cytostatic, immune-suppressive or anti-inflammatory effect.

A NAMPTi compound or its derivative for incorporation into a Drug Unit may exhibit adverse peripheral effects when administered in unconjugated form. Due to selective delivery when in the form of NAMPT Drug Unit in a Ligand Drug Conjugate, such compounds may be better tolerated. For that purpose the Linker Unit of a Ligand Drug Conjugate is not merely a passive structure that serves as a bridge between a targeting Ligand Unit and a NAMPT Drug Unit but must be carefully engineered to have sufficient stability from the site of administration of the Ligand Drug Conjugate until its delivery to the targeted site to prevent premature release of the NAMPT Drug Unit and then should efficiently release it as the free NAMPTi compound or derivative thereof. To accomplish that task, a targeting agent having a reactive thiol or thiol-containing functional group is preferably reacted with a $L_{SS}$-containing moiety of a Drug Linker compound comprising the formula $M_1$-$A_R$(BU)-$A_O$- to form a $L_{SS}$-containing moiety comprising the formula of $M^2$-$A_R$(BU)-$A_O$- within a Ligand Drug Conjugate, which under controlled hydrolysis conditions is convertible to a $L_S$-containing moiety comprising the formula $M^3$-$A_R$(BU)-$A_O$-, wherein BU is a cyclic or acyclic Basic Unit, $M^1$, $M^2$ and $M^3$ are a maleimide, succinimide and succinic acid amide moiety, respectively, and $A_R$ is a required Stretcher Unit and $A_O$ is a second optional Stretcher Unit. Thus preferred Ligand Drug Conjugate are comprised of a targeting Ligand Unit, a NAMPT Drug Unit and an intervening Linker Unit having $L_{SS}$ or $L_S$ as a primary linker ($L_R$), in which $L_R$ is bonded to the Ligand Unit and either directly to D or through a secondary linker ($L_O$) so that one component of $L_O$ is attached to $L_R$ and the same or different component of $L_O$ is attached to D.

1.1 Primary Linker ($L_R$) with Basic Unit (BU)

A primary linker ($L_R$) is a component of a Linker Unit of a Ligand Drug Conjugate, a Drug Linker compound, or other Intermediate and preferably has a cyclic or acyclic Basic Unit, thus defining $L_R$ as a self-stabilizing linker ($L_{SS}$) or self-stabilized linker ($L_S$). In such Ligand Drug Conjugates $L_R$ is attached to a Ligand Unit through a succinimide ($M^2$) moiety when $L_R$ is $L_{SS}$ or through a succinic acid amide ($M^3$) moiety when $L_R$ is $L_S$, in which the latter primary linker from hydrolysis of the $M^2$ moiety mediated by its Basic Unit (BU), or $L_R$ is capable of that attachment through interaction of a reactive thiol functional group of a targeting agent with a maleimide ($M^1$) moiety of $L_{SS}$ as $L_R$ in a Drug Linker compound or other Intermediate.

1.1.1 Acyclic Basic Unit

In some embodiments, $L_R$- is a $L_{SS}$ moiety in a Drug Linker compound that has the formula $M^1$-$A_R$(BU)-$A_O$-, wherein BU is an acyclic Basic Unit. Exemplary $L_{SS}$ primary linkers of that formula in which $A_O$ is a Hydrolysis-enhancing (HE) Unit are represented by the substructure in Formula I of:

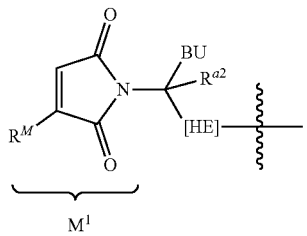

wherein the indicated $M^1$ moiety is a maleimide moiety, BU is acyclic Basic Unit, the wavy line indicates covalent binding to -D, if $L_O$ is absent, or -$L_O$-D if $L_O$ is present, $R^M$ is hydrogen or optionally substituted $C_1$-$C_6$ alkyl, HE is an optional Hydrolysis-enhancing Unit, and $R^{a2}$ is hydrogen or an optionally substituted $C_1$-$C_8$ alkyl. An acyclic Basic Unit is typically comprised of an optionally substituted $C_1$-$C_6$ alkylene in which one of its radical centers is bonded to the same carbon as $R^{a2}$, wherein that carbon is in the alpha position relative to the imide nitrogen of the $M^1$ moiety, and the other radical center is bonded to a basic amine functional group of BU. To avoid premature hydrolysis of the maleimide ring system by base catalysis, the basic nitrogen of the basic amine functional group is typically protonated as a salt form, or the basic amine of the basic amine functional group is protected with an acid labile protecting group so that deprotection results in a protonated BU. For the former strategy to preclude premature hydrolysis, the basic amine of the basic functional group may be a primary, secondary or tertiary amine, while for the latter strategy, the basic amine of the basic functional group may be a primary or secondary amine.

On interaction with an reactive thiol functional group of a targeting agent, the $L_{SS}$ moiety of formula $M^1$-$A_R$(BU)— in Drug Linker compound is converted to an L-$L_{SS}$-substructure of formula L-$M^2$-$A_R$(BU)-$A_O$- in a drug linker moeity bonded to L of a Ligand Drug Conjugate of Formula 1 as exemplified by substructures:

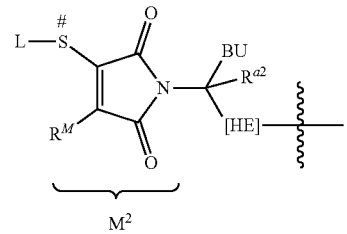

wherein HE as $A_O$ in a Hydrolysis-enhancing Unit, and the indicated $M^2$ moiety is a succinimide moiety, wherein that moiety is thio-substituted with L-S—; and wherein L is a Ligand Unit incorporating or corresponding to the targeting agent and the indicated (#) sulfur atom is derived from a reactive thiol or thiol-containing functional group of the targeting agent; the wavy line indicates the site of covalent attachment to $L_O$ or D depending on the presence or absence of $L_O$, respectively; BU is an acyclic Basic Unit, and the remaining variable groups are as defined for the corresponding $M^1$-$A_R$(BU)-substructure above in which BU is an acyclic Basic Unit, On controlled hydrolysis of the succinimide ring system mediated by the acyclic Basic Unit, the L-$L_{SS}$- moiety having the above L-$M^2$-$A_R$(BU)-$A_O$- substructure is converted to one having a $L_S$-containing moiety as exemplified by substructure(s):

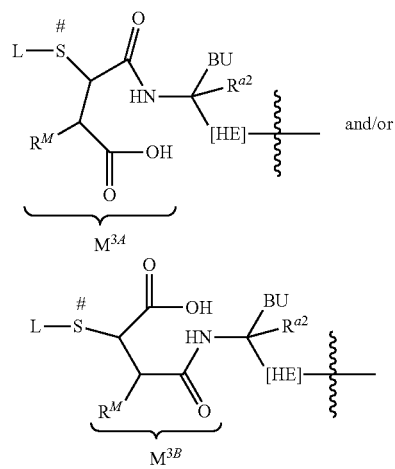

wherein the drug linker moieties of Conjugate compounds of the Ligand Drug Conjugate composition of Formula 2 may be represented as having a single one of the above $L_S$ primary linkers bonded to L or as having a mixture of both, collectively referred to as L-$M^3$-$A_R$(BU)-$A_O$-, wherein BU is an acyclic Basic Unit and the remaining variable groups are as previously defined for their $M^2$-containing precursor, wherein the indicated $M^{3A}$ and $M^3$B moieties are succinic acid amide ($M^3$) moieties thio-substituted by L-S—, and wherein the contribution of the above L-$M^{3A}$-$A_R$(BU)-$A_O$- and L-$M^{3B}$-$A_R$(BU)-$A_O$-constituents to the Conjugate compound mixture is dependent on the relative reactivity of the two carbonyl carbons of the succinimide ring system of the succinic acid ($M^2$) moiety of the L-$M^2$-$A_R$(BU)-$A_O$- precursor to base catalyzed hydrolysis.

In preferred embodiments, $R^{a2}$ in any one of the above $M^1$-$A_R$(BU)-$A_O$-, L-$M^2$-$A_R$(BU)-$A_O$- and L-$M^3$-$A_R$(BU)-

$A_O$- substructures is —H, —CH$_3$, —CH$_2$CH$_3$, or —CH$_2$CH$_2$CH$_3$. In other preferred embodiments, [HE] as $A_O$ in any one of those structures is —C(=O)—. In any one of those embodiments, BU preferably has the formula of —[C(R$^{a1}$)(R$^{a1}$)]—[C(R$^{a1}$)(R$^{a1}$)]$_x$—N(R$^{a3}$)(R$^{a3}$) wherein subscript x is 0, 1, 2 or 3, each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^{a3}$ independently are hydrogen, optionally substituted C$_1$-C$_6$ alkyl or a nitrogen protecting group, or together with the nitrogen atom to which they are attached define a C$_3$-C$_6$ heterocycloalkyl or both R$^{a3}$ together define a nitrogen protecting group.

In more preferred embodiments an acyclic BU is of formula —(CH$_2$)$_x$NH$_2$, —(CH$_2$)$_x$NHR$^{a3}$, or —(CH$_2$)$_x$N(R$^{a3}$)$_2$, wherein subscript x is an integer ranging from 1 to 4, with 1 or 2 particularly preferred; and R$^{a1}$, at each instance, is independently hydrogen, —CH$_3$ or —CH$_2$CH$_3$, or both R$^{a1}$ together with the nitrogen to which they are attached define an azetidinyl, pyrrolidinyl or piperidinyl heterocyclyl, in which a basic primary, secondary or tertiary amine so defined is optionally protonated or is in a salt form, preferably as a pharmaceutically acceptable salt form.

In some of those more preferred embodiments R$^{a2}$ is hydrogen and in this, and any of the above embodiments an acyclic BU having the structure of —CH$_2$—NH$_2$ or —CH$_2$CH$_2$—NH$_2$ is particularly preferred. A Ligand Drug Conjugate of Formula 2 wherein R$^{a2}$ is hydrogen and the acyclic Basic Unit is —CH$_2$—NH$_2$ may be used as a comparator to a corresponding Conjugate in which BU is a cyclic Basic Unit, the structure of which is incorporated into that of $A_R$ and is formally derived by cyclization of an acyclic BU to R$^{a2}$ in any one of the above L$_{SS}$ or L$_S$ structures, wherein R$^{a2}$ is other than hydrogen, as described herein. In any one of those more preferred embodiments, R$^M$ is preferably hydrogen or C$_1$-C$_4$ alkyl, more preferably hydrogen.

In particularly preferred embodiments, L$_{SS}$ and L$_{SS}$ primary linkers having an acyclic Basic Unit are represented by substructures:

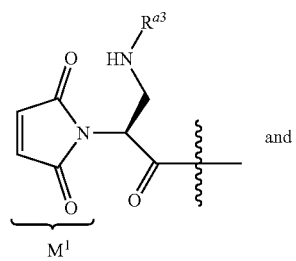

M$^1$

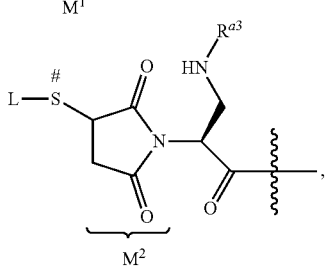

M$^2$ within Formula I and for a Ligand Unit bonded to a drug linker moiety of Formula 1, respectively, wherein R$^{a1}$ is preferably hydrogen, C$_1$-C$_4$ alkyl or a nitrogen protecting group and wherein the basic nitrogen atom to which R$^{a1}$ is attached is optionally protonated or in pharmaceutically acceptable salt when R$^{a1}$ is hydrogen, C$_1$-C$_4$ alkyl.

L$_S$ primary linkers derived from hydrolysis by the cyclic Basic Unit under controlled conditions of those L$_{SS}$ primary linkers are exemplified by substructure(s) for a Ligand Unit bonded to a drug linker moeity of Formula 2:

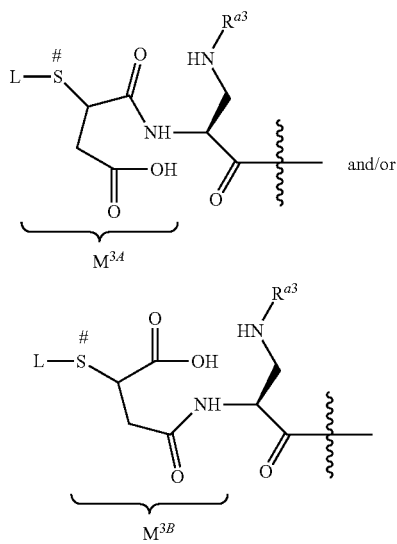

M$^{3A}$ and/or

M$^{3B}$ wherein the thio substituent L-S— is bonded to the carbon alpha to the carboxylic acid functional group or the amide functional group of the succinic acid (M$^3$) amide moiety or is a mixture of the two regioisomers and wherein R$^{a1}$ is hydrogen, C$_1$-C$_4$ alkyl or a nitrogen protecting group and wherein the basic nitrogen atom to which R$^{a1}$ is attached is optionally protonated or in pharmaceutically acceptable salt form when R$^{a1}$ is hydrogen, C$_1$-C$_4$ alkyl.

In particularly preferred embodiments R$^{a1}$ is hydrogen, wherein the basic nitrogen atom to which R$^{a1}$ is attached is protonated or in a pharmaceutically acceptable salt form, or R$^{a1}$ is —C(=O)O-t-Bu (BOC).

1.1.2 Cyclic Basic Unit

As mentioned above, a L$_{SS}$ moiety or L-L$_{SS}$ or L-L$_S$-substructure having a cyclic Basic Unit will, in some embodiments, correspond to any one of the above M$^1$-A$_R$(BU)-A$_O$-, L-M$^2$-A$_R$(BU)-A$_O$- and L-M$^3$-A$_R$(BU)-A$_O$- formulae in which R$^{a2}$ is an optionally substituted C$_1$-C$_6$ alkyl, as exemplified by substructures of:

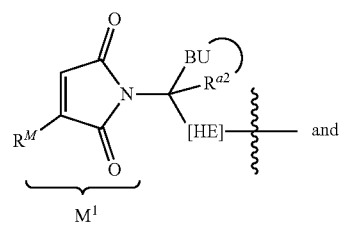

M$^1$ and

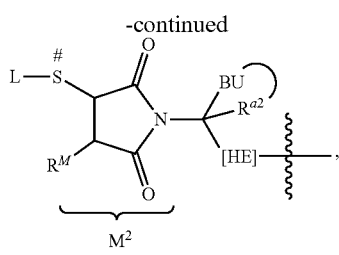

within Formula I and a drug linker moiety bonded to L within Formula 1, respectively, and as exemplified by substructure(s) of:

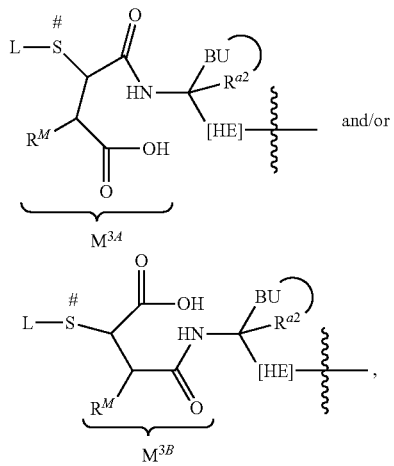

for a Ligand Unit bonded to a drug linker moiety of Formula 2 wherein BU is cyclized onto $R^{a2}$, as indicated by the solid curved line, and the remaining variable groups are as defined in the corresponding $L_{SS}$ and $L_S$ moieties in which BU is acyclic, so as to provide a cyclic Basic Unit.

Preferably the basic nitrogen of a cyclic BU is capable of increasing the rate of hydrolysis of the shown succinimide ($M^2$) moiety of Formula 1 to provide the shown succinic acid amide ($M^3$) moiety(ies) of Formula 2 at a suitable pH in comparison to a corresponding Conjugate in which $R^{a2}$ is hydrogen and BU is absent. More preferably the enhancement of hydrolysis provided a corresponding Conjugate in which BU is an acyclic Basic Unit is substantially retained by the Conjugate having an acyclic Basic Unit formally derived from that acyclic BU Formally, a cyclic Basic Unit in one group of embodiments includes those derived from removing a hydrogen atom from a basic nitrogen atom of a primary or secondary basic amine functional group of an acyclic Basic Unit and by removing a hydrogen atom from a carbon in the optionally substituted $C_1$-$C_{12}$ alkyl carbon chain of $R^{a2}$ to form an alkylene moiety and then combining the basic amino and alkylene moieties at their radical centers so as to form a corresponding spiro $C_4$-$C_{12}$ heterocyclo in which the radical nitrogen atom becomes a basic skeletal heteroatom of the heterocyclo, thereby resulting in a basic secondary or tertiary amine.

Preferably, the basic skeletal nitrogen atom of the spiro $C_4$-$C_{12}$ heterocyclo is one or two carbon atoms removed from the imide nitrogen of $M^1$/$M^2$ and is thus preferably removed from the corresponding amide nitrogen of $M^3$ by the same number of carbon atoms subsequent to controlled hydrolysis of $M^2$.

$L_{SS}$ or $L_{SS}$ primary linkers in which BU is cyclic Basic Unit having a spiro heterocyclo in which the basic nitrogen atom of the basic amine functional group of BU is a skeletal atom are exemplified by substructures within Formula I and for a Ligand Unit bonded to a drug linker moiety of Formula 1:

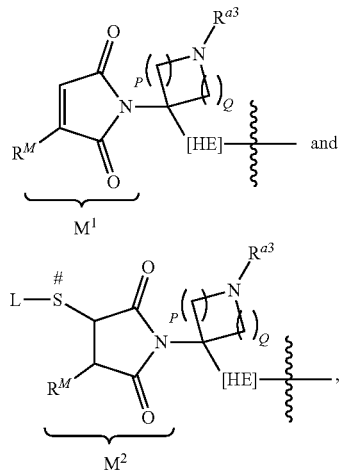

respectively, as exemplified for occurrences in which subscript p is 1, and $L_S$ primary linkers in which BU is cyclic Basic Unit having a spiro heterocyclo in which the basic nitrogen of the basic amine functional group is a skeletal atom are exemplified by substructures of:

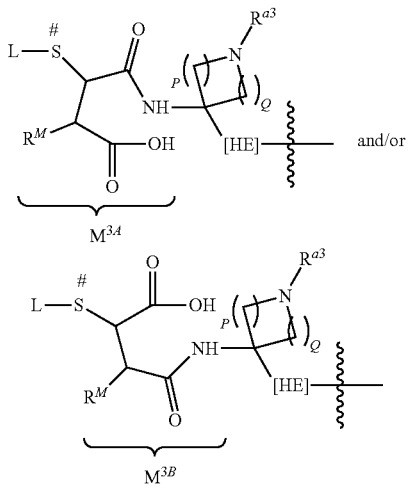

for a Ligand Unit bonded to a drug linker moiety of Formula 2, wherein $R^M$ is hydrogen or optionally substituted $C_1$-$C_6$ alkyl; subscript P is 1 or 2; subscript Q ranges from 1 to 6; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated or is in a salt form, preferably a pharmaceutically acceptable salt form, or $R^{a3}$ is a nitrogen protecting group such as a suitable acid-labile protecting group, and the remaining variable groups are as previously defined for $L_{SS}$ and $L_S$ primary linkers having the corresponding acyclic Basic Units. In preferred embodiments subscript P is 1 and subscript Q is 1, 2 or 3 or subscript P is 2 and subscript Q is 1 or 2.

A suitable acid-labile protecting group for a basic amine nitrogen of a primary or secondary amine include —C(=O)O-t-Bu (BOC). In any one of the above structures in which BU is a cyclic basic Unit, [HE] is preferably —C(=O)—. In any one of those preferred embodiments, $R^M$ is preferably hydrogen or $C_1$-$C_4$ alkyl, more preferably hydrogen.

In more preferred embodiments $L_{SS}$ and $L_{SS}$ primary linker having a cyclic Basic Unit are exemplified by substructures of:

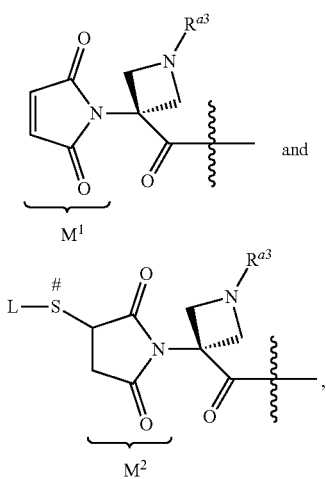

within Formula I and for a Ligand Unit bonded to a drug linker moeity of Formula 1, respectively.

$L_S$ primary linkers derived from hydrolysis by the cyclic Basic Unit under controlled conditions of those $L_{SS}$-containing moieties are exemplified by substructure(s) of Formula 2, for occurrences of Formula 2 in which subscript p is 1 of:

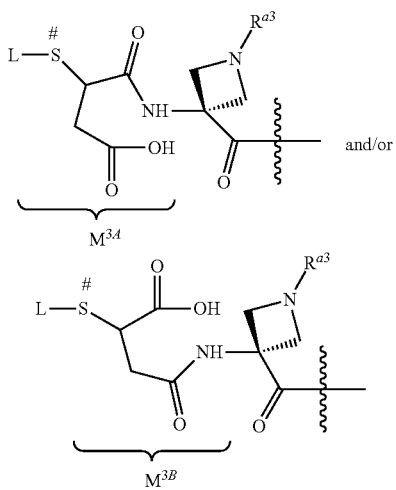

wherein the thio substituent L-S— is bonded to the carbon alpha to the carboxylic acid functional group or the amide functional group of the succinic acid ($M^3$) amide moiety or is a mixture of the two regioisomers. In particularly preferred embodiments $R^{a3}$ is hydrogen, wherein the secondary amine so defined is protonated or in a pharmaceutically acceptable salt form, or $R^{a3}$ is —C(=O)O-t-Bu (BOC).

1.2 Secondary Linkers ($L_O$)

Secondary linkers in a Linker Unit of Ligand Drug Conjugate or a Drug Linker compound or an Intermediate thereof, is an optional organic moiety situated between a primary linker ($L_R$) and a NAMPT Drug Unit (D). When present, a secondary linker ($L_O$) is subject to enzymatic or non-enzymatic processing so as to release D as a NAMPTi compound or derivative thereof. In some embodiments, a Cleavable Unit is present in $L_O$ to allow for that processing. In preferred embodiments when subscript w is 1 in Formula 1, Formula 2 or Formula I, W is a Peptide Cleavable Unit so that $L_O$ presents a cleavage site for enzymatic processing by a protease to initiate release of D as a NAMPTi compound or derivative thereof. In some of those embodiments, Spacer Unit(s) intervene between W and the Drug Unit so that subscript y is 1 or 2 in Formula 1, Formula 2 or Formula I, wherein Y of $Y_y$ attached to W is a PAB or PAB-type self-immolative Spacer Unit. In other preferred embodiments when subscript w is 1 in Formula 1, Formula 2 or Formula I, W is a Glucuronide Unit of formula —Y(W')—, wherein W' is a carbohydrate moiety bonded to a self-immolative Spacer Unit (Y) through a glycosidic bond, wherein that bond allows for enzymatic processing of $L_O$ by a glycosidase to initiate release of D as a NAMPTi compound or derivative thereof.

In some embodiments W is a Peptide Cleavable Unit that provides a substrate for a protease present within or in the vicinity of hyper-proliferating cells, hyper-activated immune cells or other abnormal cells. Preferred are Peptide Cleavable Units that are not recognized or are poorly recognized by proteases that may be excreted by normal cells distant from the site of the targeted abnormal cells. Other preferred Peptide Cleavable Units are not recognized or are poorly recognized by proteases having systemic circulation so as to minimize non-targeted release of Drug Unit from its Ligand Drug Conjugate that would result in systemic exposure of a NAMPTi compound or derivative thereof that was conjugated as a Drug Unit. More preferred are those Peptide Cleavable Units that are recognized as substrates by proteases that are regulatory proteases or proteases found in lysosomes, which are cellular compartments to which a Ligand Drug Conjugate is sometimes delivered upon internalization of a membrane-surface receptor to which the Ligand Unit of a ligand Drug Conjugate compound has specifically bound. Regulatory and lysosomal proteases are exemplary intracellular proteases.

In one embodiment a Peptide Cleavable Unit (W) within a secondary linker is comprised or consists of a dipeptide moiety having the structure of:

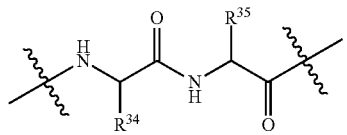

wherein the wavy lines indicate the sites of covalent attachment within a Linker Unit comprised of that secondary linker and $R^{34}$ is benzyl, methyl, isopropyl, isobutyl, sec-butyl, —CH(OH)CH$_3$ or $R^{34}$ has the structure of

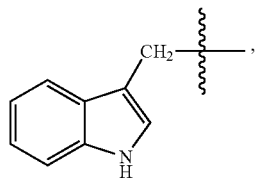 [SMILES: *Cc1c[nH]c2ccccc12]

wherein the wavy line indicates the site of covalent attachment to the dipeptide backbone, and $R^{35}$ is methyl, $-(CH_2)_4-NH_2$, $-(CH_2)_3NH(C=O)NH_2$, $-(CH_2)_3NH(C=NH)NH_2$, or $-(CH_2)_2CO_2H$, wherein the dipeptide moiety provides for a recognition site for a protease, preferably a regulatory or lysosomal protease.

In preferred embodiments the dipeptide is valine-alanine (val-ala). In another embodiment, W is comprised or consists of the dipeptide valine-citrulline (val-cit). In another embodiment W is comprised or consists of the dipeptide threonine-glutamic acid (thr-glu). In any one of those embodiments, the dipeptide moiety is covalently attached to a self-immolative moiety of a self-immolative Spacer Unit (Y) through an amide bond (i.e., a carbonyl-nitrogen bond). In some of those embodiments that amide bond is between the carbonyl carbon of the carboxylic acid functional group of alanine or citrulline and an optionally substituted amine, the nitrogen atom of which is bonded to the optionally substituted central (hetero)arylene of the PAB or PAB-type self-immolative moeity. In other preferred embodiments that amide bond is between the carbonyl carbon of the alpha carboxylic acid functional group of glutamate and a optionally substituted amine, the nitrogen atom of which is bonded to the central optionally substituted (hetero)arylene in the PAB or PAB-type self-immolative moiety. Thus, in those embodiments a self-immolative moiety is comprised of an optionally substituted arylamine or heteroarylamine moiety of a self-immolative Spacer Unit to which the aforementioned carboxylic acid functional group of a dipeptide moiety is attached through an anilide bond with the amino nitrogen bonded to that (hetero)arylamine moiety.

In another embodiment, a Cleavable Unit is a Glucuronide Unit of formula $-Y(W')-$ within a secondary linker and is comprised of a glycoside-bonded carbohydrate moiety (W') having a recognition site for an glycosidase. In preferred embodiments the glycosidase is intracellularly located with cells targeted by a Ligand Drug Conjugate comprised of that Glucuronide Unit. In those embodiments W' is a carbohydrate moiety (Su) bonded to a glycosidic heteroatom (E') in which the bond between Su and E' is a glycosidic bond, wherein Su-E' provides a recognition site for cleavage of that bond by a glycosidase. In those embodiments W' preferably has the structure of

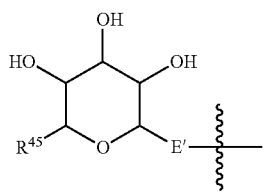

wherein $R^{45}$ is $-CH_2OH$ or $-CO_2H$ and E' is a heteroatom moiety such as $-O-$, $-S-$ or optionally substituted $-NH-$, which is bonded to the carbohydrate moiety (Su) and to a self-immolative moiety of a self-immolative Spacer Unit Y (as indicated by the wavy line) wherein the bond to the carbohydrate moiety provides for a recognition site for a glycosidase. Preferably that site is recognized by a lysosome glycosidase. In some embodiments the glycosidase is a glucuronidase so that $R^{45}$ is $-CO_2H$.

In some preferred embodiments a secondary linker ($L_O$), in addition to a Peptide Cleavable Unit as W is also comprised of one or two Spacer Units (Y or Y—Y') and a first Stretcher Unit (A). In other preferred embodiments $L_O$, in addition to a Peptide Cleavable Unit as W, is also comprised of a first Stretcher Unit (A) but has no Spacer Units. In either of those embodiment A or a subunit thereof is -$L^P$(PEG)-. In other preferred embodiments, in addition to a Glucuronide Unit as the Cleavable Unit, $L_O$ is comprised of a first Stretcher Unit (A) and may be additionally comprised of an additional Spacer Unit (Y'). When W is a Peptide Cleavable Unit, A, W and Y are arranged in a linear relationship with respect to D as represented within -$L_O$-D structures of (1a). When W is a Glucuronide Unit, which has the formula $-Y(W')-$, A, W' and Y/Y' are arranged in an orthogonal relationship with respect to D as represented within -$L_O$-D structures of (1b).

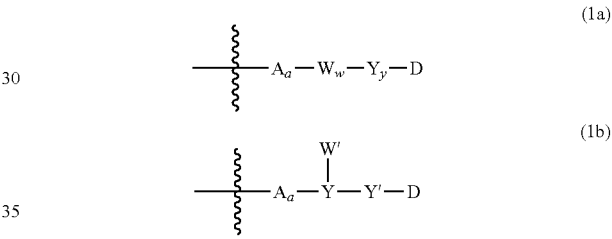

wherein the wavy line in either structure indicates the site of covalent bonding to $L_R$ in a Ligand Drug Conjugate or Drug Linker compound, subscript a is 0 or 1, subscript w is 1, subscript y is 0, 1 or 2 and Y' is an optional second Spacer Unit, which may or may not be capable of self-immolation, wherein in both formulae Y is a self-immolative Spacer Unit. When a is 1, the wavy line before A indicates covalent bonding of that $L_O$ subunit to a primary linker ($L_R$), preferably to $L_{SS}$ or $L_S$ as $L_R$. When subscript a is 0 that wavy line indicates covalent binding to $L_R$ by the Peptide Cleavable Unit in formula 1a, or to Y of the Glucuronide Unit of formula 1b.

In preferred embodiments subscript a is 1 in formula (1a) or (1b). In some of those embodiments -$A_O$ is also present, which is covalently attached to A. In some of those preferred embodiments A or a subunit thereof is -$L^P$(PEG)-. In other preferred embodiments of formula (1a), subscript y is 2 wherein the Spacer Unit attached to D (Y') is a methylene carbamate (MAC) unit, which is capable of self-immolation, and the Spacer Unit (Y) attached to Y' is also capable of self-immolation. In other preferred embodiments of formula (1a) when subscript y is 2 the Spacer Unit bonded to D is a carbamate functional group, which is capable of self-immolation and therefore is a second self-immolative Spacer Unit (Y') and the Spacer Unit bonded to Y' is also capable of self-immolation and therefore is a first self-immolative Spacer Unit (Y). In other preferred embodiments -$L_O$-D has the structure of formula (1b) in which Y' is present and $-Y(W')-$ is a Glucuronide Unit, wherein Y is a self-immolative Spacer Unit and Y' is a carbamate functional group or a methylene carbamate Unit, both of which are capable of self-immolation. In either one of those preferred embodiments of formula (1a) or formula (1b), the Spacer Unit (Y) bonded to W or W' is a self-immolative Spacer Unit comprised of a PAB or PAB-type self-immolative moiety.

In some embodiments in which subscript w is 1 in $L_O$ of formula (1a), subscript y is 0 so that D is directly attached to W through a optionally substituted heteroatom provided by the Tail Unit of a NAMPTi compound or derivative thereof, which in some embodiments is designated as $X^b$, wherein $X^b$ is preferably —NH, O or S. In those embodiments $Y_y$ of Formula 1, Formula and Formula I is replaced by $X^b$ and the W—$X^b$ bond is cleavable by a protease to release D as a NAMPTi compound or derivative thereof. In preferred embodiments D is bonded through the Tail Unit so that the NAMPTi compound or derivative thereof resulting from protease cleavage of the W—$X^b$ bond has the formula of H—$X^b$-$T_N$-$I_N$-DA-$H_N$, wherein the variable groups $T_N$, $I_N$, DA and $H_N$ are as defined for embodiments of NAMPTi compounds or NAMPT Drug Units. In other embodiments in which subscript w is 1 in $L_O$ of formula (1a), subscript y is 1 so that D is bonded to $L_O$ through Y, wherein Y bonded to D is a Spacer Unit that does not undergo self-immolation or is an optionally substituted functional group, which is some embodiments remains with D upon its release as a biologically active inhibitor of NAMPT. In those embodiments the W—Y bond is cleavable by a protease to release Y-D, which may be an inhibitor of NAMPT in its own right or may undergo further enzymatic or non-enzymatic processing to release D as a NAMPTi compound or derivative thereof. In still other embodiments in which subscript w is 1 in $L_O$ of formula (1a), subscript y is 2 so that D is bonded to $L_O$ through its Y and Y' components, wherein Y' bonded to D is a Spacer Unit that does not undergo self-immolation or is an optionally substituted functional group, which is some embodiments remains with D upon its release as an NAMPTi compound or derivative thereof. In those embodiments the W—Y bond is cleavable by a protease to release Y-'Y-D, which may be an inhibitor of NAMPT in its own right or may undergo further enzymatic or non-enzymatic processing to release Y'-D or D as a NAMPTi compound or derivative thereof.

In some embodiments in which subscript w is 1 in $L_O$ of formula (1b), subscript y is 1 so that D is directly attached to Y. In those embodiments the W'—Y bond is cleavable by a glucosidase to release D as a NAMPTi compound or derivative thereof. In other embodiments of formula (1b), subscript y is 2 so that D is bonded to $L_O$ through the intermediacy of Y and Y', wherein Y' bonded to D is a Spacer Unit that does not undergo self-immolation or is an optionally substituted functional group, which is some embodiments remains with D upon its release as a NAMPTi compound or derivative thereof. In those embodiments the W'—Y bond is cleavable by a glucosidase to release Y'-D, which may be an inhibitor of NAMPT in its own right or may undergo further enzymatic or non-enzymatic processing to release D as a NAMPTi compound or derivative thereof.

In still other embodiments for formula (1a) or formula (1b) in which subscript y is 2, Y attached to W or W' and Y' attached to D are both self-immolative Spacer Units that undergo sequential self-immolation on cleavage of the W—Y or W'—Y bond, respectively to release D as a NAMPTi compound or derivative thereof. In some of those embodiments Y contains a PAB or PAB-type self-immolative moiety and Y' is a methylene carbamate (MAC) Unit or a carbamate functional group as defined herein.

Structures of some exemplary $A/A_O$, W and Y moieties in $L_O$ and their substituents are described in WO 2004/010957, WO 2007/038658, U.S. Pat. Nos. 6,214,345, 7,498,298, 7,968,687 and 8,163,888, and US Pat. Publ. Nos. 2009-0111756, 2009-0018086 and 2009-0274713 and these disclosures are specifically incorporated by reference herein.

In some embodiments A, or subunits thereof, has the structure of

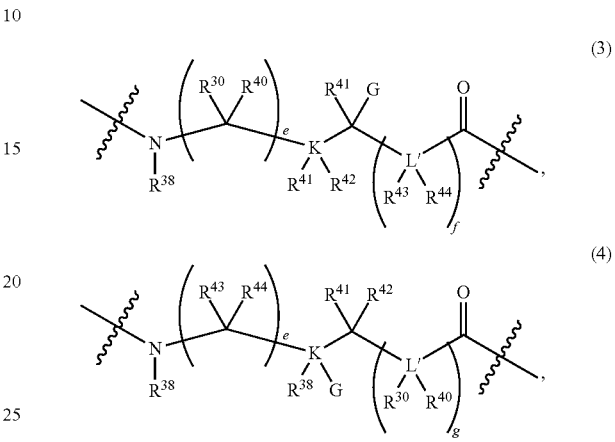

wherein the wavy lines indicate covalent attachment within the remainder of a Linker Unit, and wherein the wavy line to the carbonyl moiety of either structure represents the site of covalent attachment to the amino terminus of a dipeptide moiety comprising W wherein W is a Peptide Cleavable Unit and A W and Y are arranged linearly with respect to D or to a self-immolating moiety of a self-immolative Spacer Unit described herein wherein W is a Glucuronide Unit in which W' is bonded to Y and A, W' and Y are arranged orthogonal with respect to D, and wherein the wavy line to the amino moiety of either structures represents the site of covalent attachment to a carbonyl-containing functional group of another subunit of A or to $L_R$, preferably through $A_O$; and wherein K and L' independently are C, N, O or S, provided that when K or L' is O or S, $R^{41}$ and $R^{42}$ to K or $R^{43}$ and $R^{44}$ to L' are absent, and when K or L are N, one of $R^{41}$, $R^{42}$ to K or one of $R^{42}$, $R^{43}$ to L' are absent, and provided that no two adjacent L' are independently selected as N, O, or S;

wherein subscripts e and f are independently selected integers that range from 0 to 12, and subscript g is an integer ranging from 1 to 12:

wherein G is hydrogen, optionally substituted $C_1$-$C_6$ alkyl, —OH, —OR', —$CO_2$H, $CO_2R^{PR}$, wherein $R^{PR}$ is a suitable protecting, —N($R^{PR}$)($R^{PR}$), wherein $R^{PR}$ are independently a protecting group or $R^{PR}$ together form a suitable protecting group, or —N($R^{45}$)($R^{46}$) wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^{44}$ together with L' to which they are attached when L' is C comprise a $C_3$-$C_6$ cycloalkyl, or $R^{49}$ and $R^{41}$, or $R^{49}$ and $R^{43}$, or $R^{41}$ and $R^{43}$ to together with the carbon or heteroatom to which they are attached and the atoms intervening between those carbon and/or heteroatoms comprise a 5- or 6-membered carbocyclo or heterocyclo, provided that when K is O or S, $R^{41}$ and $R^{42}$ are absent, when K is N, one of $R^{41}$, $R^{42}$ is absent, when L' is O or S, $R^{43}$ and $R^{44}$ are absent, and when L' is N, one of $R^{43}$, $R^{44}$ is absent.

In some embodiments $R^{38}$ of formula (3) or formula (4) is hydrogen. In other embodiments —K($R^{41}$)($R^{42}$) is —(CH$_2$)—. In other embodiments when subscript e is not 0, $R^{39}$ and $R^{49}$ are hydrogen in each occurrence. In other embodiments when subscript f is not 0, -L($R^{43}$)($R^{44}$)— is —CH$_2$— in each occurrence.

In preferred embodiments G is —CO$_2$H. In other preferred embodiments K and/or L are C. In other preferred embodiments subscript e or f is 0. In still other preferred embodiments subscripts e+f is an integer ranging from 1 to 4.

In some embodiments $A_O$, A, or a subunit thereof has the structure of —NH—C$_1$-C$_{10}$ alkylene-C(=O)—, —NH—C$_1$-C$_{10}$ alkylene-NH—C(=O)—C$_1$-C$_{10}$ alkylene-C(=O)—, —NH—C$_1$-C$_{10}$ alkylene-C(=O)—NH—C$_1$-C$_{10}$ alkylene (C=O)—, —NH—(CH$_2$CH$_2$O), —CH$_2$ (C=O)—, —NH—(C$_3$-C$_8$ carbocyclo)(C=O)—, —NH— (C$_6$-C$_{10}$ arylene-)—C(=O)—, and —NH—(C$_3$-C$_8$ heterocyclo-) C(=O).

In other embodiments A, or a subunit thereof, has the structure of

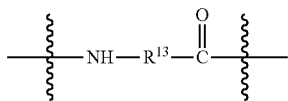

wherein $R^{13}$ is —C$_1$-C$_{10}$ alkylene-, —C$_3$-C$_8$ carbocyclo-, —C$_6$-C$_{10}$ arylene-, —C$_1$-C$_{30}$ heteroalkylene-, —C$_3$-C$_8$ heterocyclo-, —C$_1$-C$_{10}$ alkylene-C$_6$-C$_{10}$ arylene-, —C$_6$-C$_{10}$ arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_1$-C$_{10}$ alkylene-(C$_3$-C$_8$ heterocyclo)-, —(C$_3$-C$_8$ heterocyclo)-C$_1$-C$_{10}$ alkylene-, —(CH$_2$CH$_2$O)$_{1-10}$ (—CH$_2$)$_{1-3}$—, or —(CH$_2$CH$_2$NH)$_{1-10}$(—CH$_2$)$_{1-3}$—. In some embodiments, $R^{13}$ is —C$_1$-C$_{10}$ alkylene- or —C$_1$-C$_{30}$ heteroalkylene-. In some embodiments, $R^{13}$ is —C$_1$-C$_{10}$ alkylene-, —(CH$_2$CH$_2$O)$_{1-10}$—(CH$_2$)$_{1-3}$—, or —(CH$_2$CH$_2$NH)$_{1-10}$— (CH$_2$)$_{1-3}$—. In some embodiments, $R^{13}$ is —C$_1$-C$_{10}$ alkylene-polyethylene glycol, or -polyethyleneimine.

In more preferred embodiments A, or a subunit thereof, corresponds in structure to an alpha-amino acid-, a beta-amino acid moiety, or other amine-containing acid residue. Other embodiments of A as a single unit or having subunits $A_{1-4}$ are described in embodiments for Linker Units that have the formula of -L$_R$-L$_O$-.

In some embodiments, a self-immolative Spacer Unit is capable of undergoing a 1,4- or 1,6-elimination reaction subsequent to enzymatic processing of W/W' when WAY' is covalently bonded to a PAB or PAB-type self-immolative moiety of a self-immolative Spacer Unit Y. In some embodiments when W is a Peptide Cleavable Unit, W and Y are arranged linearly within $L_O$ of the Linker Unit with respect to —Y-D or —Y—Y'-D so that —Y-D or —Y—Y'-D has the structure of:

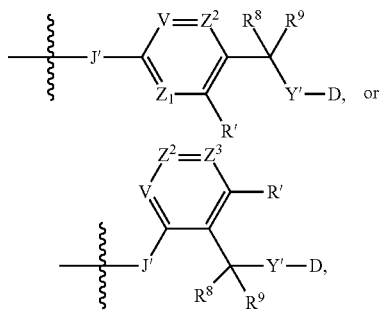

wherein when subscript y is 1 in Formula 1, Formula 2 or Formula I, Y' in the above structures is replaced by an optionally substituted heteroatom, which is some embodiments is designated as $X^a$, wherein preferably $X^a$ is O or S, or when subscript y in either one of those formula is 2, Y' is a carbamate functional group of formula —OC(=O)—$X^b$—, or a MAC Unit incorporating $X^b$, wherein preferably $X^b$ is optionally substituted NH, O or S of a NAMPT Drug Unit. In preferred embodiments the NAMPT Drug Unit is attached to $L_O$ through its NAMPT Tail ($T_N$) Unit so that $X^a$ or $X^b$ is provided by $T_N$ resulting in release of a NAMPTi compound or derivative thereof of formula H—$X^a$-$T_N$-$I_N$-DA-$H_N$ or H—$X^b$-$T_N$-$I_N$-DA-$H_N$, wherein variable groups $T_N$, $I_N$, DA and $H_N$ are as defined for embodiments of NAMPTi compounds, derivatives thereof or NAMPT Drug Units; and V, $Z^1$, $Z^2$ and $Z^3$ independently are —C($R^{24}$)= or —N=;

$R^{24}$ independently are hydrogen, halogen, —NO$_2$, —CN, —OR$^{25}$, —SR$^{26}$, —N($R^{27}$)($R^{28}$), optionally substituted C$_1$-C$_6$ alkyl, or —C($R^{29}$)=C($R^{30}$)—$R^{31}$, wherein $R^{25}$ is hydrogen, optionally substituted C$_1$-C$_6$ alkyl, optionally substituted C$_6$-C$_{10}$ aryl or optionally substituted C$_6$-C$_{10}$ heteroaryl, $R^{26}$ is optionally substituted C$_1$-C$_6$ alkyl, optionally substituted C$_6$-C$_{10}$ aryl or optionally substituted C$_5$-C$_{10}$ heteroaryl, $R^{27}$ and $R^{28}$ independently are hydrogen, optionally substituted C$_1$-C$_6$ alkyl, optionally substituted C$_6$-C$_{10}$ aryl or optionally substituted C$_5$-C$_{10}$ heteroaryl or both $R^{27}$ and $R^{28}$ together with the nitrogen to which they are attached define a 5- or 6-membered heterocyclyl, $R^{29}$ and $R^{30}$ independently are hydrogen, or optionally substituted C$_1$-C$_6$ alkyl, and $R^{3'}$ is hydrogen, optionally substituted C$_1$-C$_6$ alkyl, optionally substituted C$_6$-C$_{10}$ aryl, optionally substituted C$_5$-C$_{10}$ heteroaryl, —C(=O)OR$^{32}$ or —C(=O)NR$^{32}$, wherein $R^{32}$ is hydrogen, optionally substituted C$_1$-C$_6$ alkyl, optionally substituted C$_6$-C$_{24}$ aryl, or optionally substituted C$_5$-C$_{24}$ heteroaryl, $R^8$ and $R^9$ independently are hydrogen, optionally substituted C$_1$-C$_6$ alkyl, or together with the benzylic carbon to which they are attached define an optionally substituted C$_3$-C$_6$ carbocyclo or one of $R^8$, $R^9$ is hydrogen or optionally substituted C$_1$-C$_6$ alkyl and the other is optionally substituted C$_5$-C$_{10}$ aryl or C$_5$-C$_{10}$ heteroaryl; and R' is hydrogen or is halogen, —NO$_2$, —CN or other electron withdrawing group or is —CH$_3$ or other an electron donating group; and J' is —O—, S—, or optionally substituted NH, including —N($R^{33}$)—, wherein $R^{33}$ is as defined for $R^{32}$, and is preferably hydrogen or methyl, wherein the wavy line to J' represents covalent bonding of that optionally substituted heteroatom to a functional group of W so as to inhibit the electron donating ability of J' to suitably stabilize the central (hetero)arylene component of the self-immolative Spacer Unit and wherein enzymatic processing of W by a protease results in dis-inhibition of that ability, as when J' is bonded to the carbonyl moiety of a carbonyl-containing functional group of W. As a result of that processing, release of the aforementioned benzylic substituent of the central (hetero)arylene component, D or —Y'-D, is initiated to provide a NAMPTi compound or derivative thereof, which in some embodiments has the formula of H—$X^a$-$T_N$-$I_N$-DA-$H_N$ or H—$X^b$-$T_N$-$I_N$-DA-$H_N$, wherein variable groups $T_N$, $I_N$, DA and $H_N$ are as described for NAMPTi compounds, derivatives thereof or NAMPT Drug Units.

In preferred embodiments no more than two of $R^{24}$ are other than hydrogen. In other preferred embodiments R' is hydrogen. In other preferred embodiments one or both of W and $R^9$ are hydrogen or J' is —NH—. In still other preferred embodiments V, Z', $Z^2$ and $Z^3$ are each =CH—. In more preferred embodiments V, $Z^1$, $Z^2$ and $Z^3$ are each =CH— and R' is hydrogen or $R^8$ and $R^9$ are each hydrogen. In more preferred embodiments V, $Z^1$, $Z^2$ and $Z^3$ are each =CH—, R' is hydrogen or $R^8$ and $R^9$ are each hydrogen and J' is —NH—.

In other embodiments W is a Glucuronide Unit of formula —Y(W')—, wherein W' and Y are arranged orthogonally within $L_O$ of the Linker Unit with respect to —Y'-D or -D, wherein Y is self-immolative Spacer Unit having its self-immolative moiety bonded to a glycoside-bonded carbohydrate (Su) moiety through an optionally substituted heteroatom (E') so as to display a recognition site for a glycosidase. In those embodiments the orthogonal arrangement of Y and W' with respect to —Y'-D or -D is represented by the structure of:

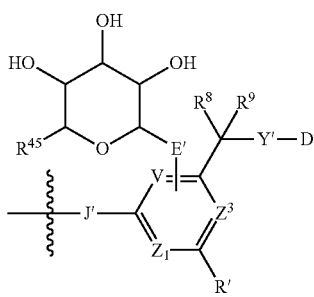

wherein when subscript y in Formula 1, Formula 2 or Formula I is 1, Y' is replaced by optionally substituted heteroatom provided by the NAMPT Drug Unit, preferably by its NAMPT Tail ($T_N$) Unit, which in some embodiments is designated $X^a$ wherein $X^a$ is O or S, or Y' is a functional group comprised of that optionally substituted heteroatom, wherein the functional group may be capable of self-immolation as when Y is a carbamate functional group, which is some embodiments is of formula —O(C=O)—$X^b$—, wherein $X^b$ is optionally substituted NH, O or S, or Y' is a second Spacer Unit, which may also be capable of self-immolation as when Y' is a methylene carbamate unit; J' and E' are independently selected from the group consisting of —O—, S—, and optionally substituted NH, including —N($R^{33}$)—, wherein $R^{33}$ is as defined for $R^{32}$, preferably hydrogen or methyl;

V, $Z^1$ and $Z^3$ independently are —C($R^{24}$)= or —N=; $R^{24}$ independently are selected from the group consisting of hydrogen, halogen, —$NO_2$, —CN, —$OR^{25}$, —$SR^{26}$, —N($R^{27}$)($R^{28}$), —C($R^{29}$)=C($R^{30}$)—$R^{31}$, W' and optionally substituted $C_1$-$C_6$ alkyl;

provided that E' of W' is bonded to one of V, $Z^1$, $Z^3$, in which that variable group is defined as =C($R^{24}$)— (i.e., one of $R^{24}$ is W'— of formula Su-E'-) provided and the other V, $Z^1$, $Z^2$ is defined by =N— or =C($R^{24}$)— wherein $R^{24}$ is other than W'; and $R^{45}$ is —$CH_2OH$ or —$CO_2H$; and wherein $R^{25}$ is hydrogen, optionally substituted $C_1$-$C_6$ alkyl, optionally substituted $C_6$-$C_{10}$ aryl or optionally substituted $C_5$-$C_{10}$ heteroaryl; $R^{26}$ is optionally substituted $C_1$-$C_6$ alkyl, optionally substituted $C_6$-$C_{10}$ aryl or optionally substituted $C_5$-$C_{10}$ heteroaryl, and $R^{27}$ and $R^{28}$ independently are hydrogen, optionally substituted $C_1$-$C_6$ alkyl, optionally substituted $C_6$-$C_{10}$ aryl or optionally substituted $C_5$-$C_{10}$ heteroaryl or both $R^{27}$ and $R^{28}$ together with the nitrogen to which they are attached define a 5- or 6-membered heterocyclyl, $R^{29}$ and $R^{30}$ independently are hydrogen, or optionally substituted $C_1$-$C_6$ alkyl, and $R^{31}$ is hydrogen, optionally substituted $C_1$-$C_6$ alkyl, optionally substituted $C_6$-$C_{10}$ aryl, optionally substituted $C_5$-$C_{10}$ heteroaryl, —CN, —C(=O)$R^{32}$ or —C(=O)$NR^{32}$; wherein $R^{32}$ is hydrogen, optionally substituted $C_1$-$C_6$ alkyl, optionally substituted a $C_6$-$C_{10}$ aryl, or optionally substituted $C_6$-$C_{10}$ heteroaryl;

$R^8$ and $R^9$ independently are hydrogen or optionally substituted $C_1$-$C_6$ alkyl or together with the benzylic carbon to which both are attached define an optionally substituted $C_3$-$C_6$ carbocyclo or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; R' is hydrogen or is halogen, —$NO_2$, —CN or other electron withdrawing group, or is an electron donating group; $R^{45}$ is —$CH_2OH$ or —$CO_2H$; E' is —O— or optionally substituted —NH—; J is —NH—; and Y' is an optional second Spacer Unit, or otherwise is an optionally substituted heteroatom, a carbamate functional group or a methylene carbamate (MAC) Unit; and wherein the wavy line to J' represents covalent bonding off to a functional group of A if subscript a is 1 or to $A_O$ if subscript a is 0 and $A_O$ is present (e.g., when J' is bonded to the carbonyl moiety of a carbonyl-containing functional group of A of $L_O$ or $A_O$ of $L_R$), or to $A_R$ if A and $A_O$ are both absent;

and wherein enzymatic processing of W'-E' by a glycosidase results in dis-inhibition of the ability of E' as an electron donating group to trigger 1,4- or 1,6-elimination of the benzylic substituent from the central (hetero)arylene of the PAB or PAB-type self-immolative Spacer Unit Y. As a result releases of that processing release of D or —Y'-D as a NAMPTi compound or derivative thereof is initiated, which in preferred embodiments has the formula of H—$X^a$-$T_N$-$I_N$-DA-$H_N$ or H—$X^b$-$T_N$-$I_N$-DA-$H_N$, wherein variable groups $T_N$, $I_N$, DA and $H_N$ are as described for NAMPTi compounds, derivatives thereof or NAMPT Drug.

In preferred embodiments, the orthogonal arrangement involving the self-immolative moiety of Y bonded to W' and D through Y' is represented by the structure of:

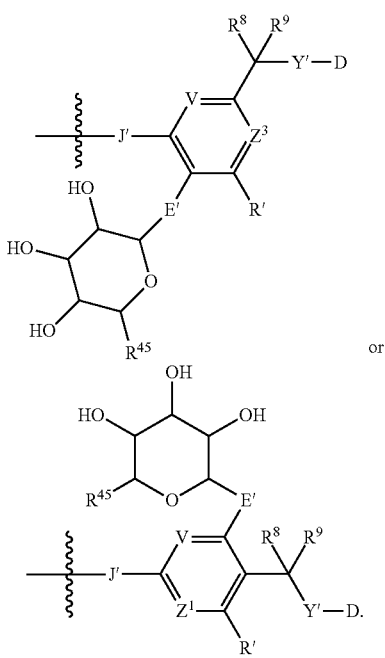

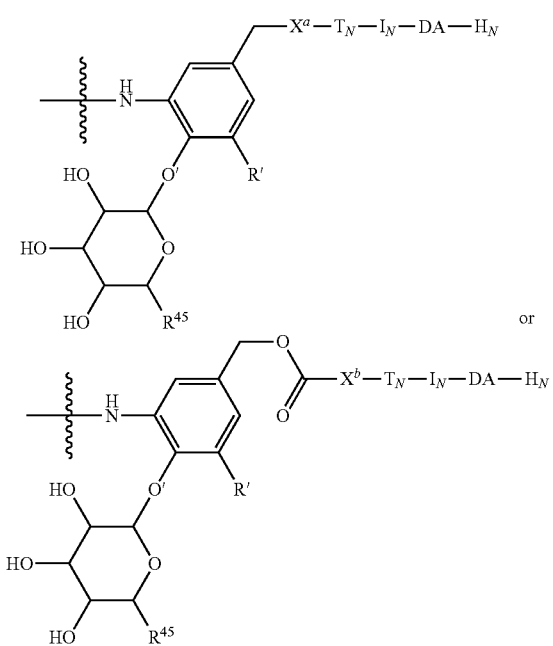

In more preferred embodiments of the above orthogonal arrangement -E'- is —O— or —NH—, wherein oxygen as the glycosidic bonded heteroatom is represented by O', and V or $Z^3$ is $=C(R^{24})$, wherein $R^{24}$ is hydrogen or an electron withdrawing group. In other preferred embodiments $R^8$ and $R^9$ are hydrogen and V, $Z^1$ or $Z^2$ is =CH—. In other preferred embodiments -J- is —NH, V, $Z^1$ or $Z^2$ is =CH— and R' is hydrogen or an electron withdrawing group, preferably —$NO_2$.

In particularly preferred embodiments —$Y_y$(W')-D, in which subscript y is 1 or 2, has the structure of:

wherein $X^b$ is a nitrogen atom from a primary or secondary amine functional group of an NAMPT Tail ($T_N$) Unit of a NAMPTi compound or derivative thereof so that Y' is a self-immolative Spacer Unit of formula —C(=O)—$X^b$—, or $X^a$ replacing Y', when subscript y is 1, is an oxygen atom from an alcohol functional group or a sulfur atom of a thiol functional group of $T_N$ of a NAMPTi compound or derivative thereof (i.e., $X^a$ is O or S); $R^{45}$ is —OH or —$CO_2$H; R' is hydrogen or —$NO_2$ or Y' is a carbamate functional group; and the remaining variable groups are as defined for NAMPTi compounds, derivatives thereof and NAMPT Drug Units.

In other particularly preferred embodiments —$Y_y$(W')-D, in which subscript y is 2, has the structure of:

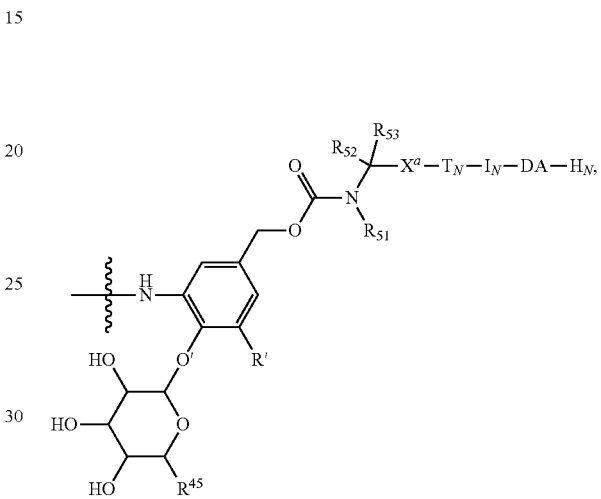

wherein $X^a$ is an oxygen atom from an alcohol functional group or a sulfur atom of a thiol functional group of $T_N$; $R^{45}$ is —OH or —$CO_2$H; R' is hydrogen or —$NO_2$; $R^{51}$, $R^{52}$ and $R^{53}$ are as defined for a MAC Unit and the remaining variable groups are as defined for NAMPTi compounds, derivatives thereof and NAMPT Drug Units.

1.3 $L_R$-$L_O$ as Linker Units

In one group of embodiments the NAMPT Drug Unit (D) in any of the —W—$Y_y$-D or —$Y_y$(W')-D structures disclosed herein represents a NAMPTi compound or derivative thereof in which an optionally substituted heteroatom is provided by the NAMPT Drug Unit preferably by its NAMPT Tail ($T_N$) Unit and is attached to the benzylic position of a PAB or PAB-type moiety in a self-immolative Spacer Unit when subscript y is 1 or is attached to that benzylic position through Y' when subscript y is 2 wherein Y' is a functional group or a second self-immolative Spacer Unit comprised of the optionally substituted heteroatom of the $T_N$ Unit.

In some of those embodiments, -$L_{SS}$-$L_O$-D of a drug linker moiety within a Ligand Drug Conjugate composition or Conjugate compound thereof and its hydrolysis product -$L_S$-$L_O$-D, whose formation in preferred embodiments is catalyzed by an acyclic or cyclic Basic Unit, has the structures of:

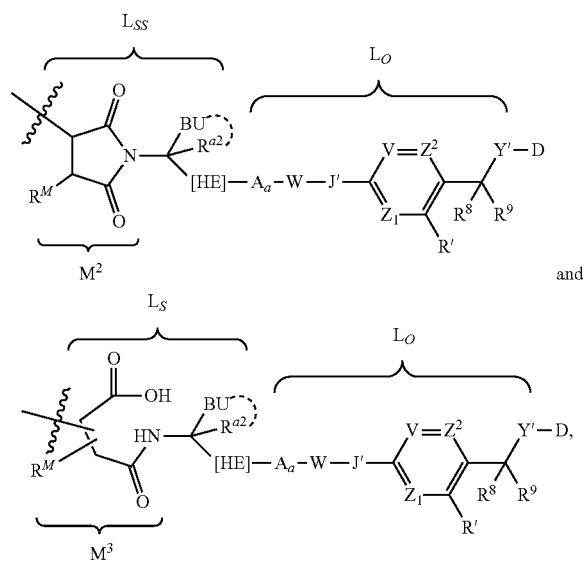

and respectively, wherein the wavy line indicates covalent bonding of a Ligand Unit, which for the $M^3$ moiety in $L_S$ is to the carbon atom that is adjacent to its acid or amide functional group with $R^M$ bonded to the carbon adjacent to the remaining functional group; the dotted curved line indicates optional cyclization so that when absent BU is an acyclic Basic Unit and $R^{a2}$ is optionally substituted $C_1$-$C_6$ alkyl, and when present BU and $R^{a2}$ together with the carbon atom to which both are attached define a cyclic Basic Unit; W is a Peptide Cleavable Unit; A is an optional first Stretcher Unit; subscript a is 0 or 1, indicating the absence or presence of A, respectively; [HE] is an optional Hydrolysis-enhancing Unit; $R^M$ is hydrogen or $C_1$-$C_4$ alkyl; V, $Z^1$ and $Z^2$ are independently =N— or =C($R^{24}$)—, wherein $R^{24}$, independently selected, is hydrogen, optionally substituted $C_1$-$C_6$ alkyl or an electron donating group; $R^8$ and $R^9$ independently are hydrogen or optionally substituted $C_1$-$C_6$ alkyl or together with the benzylic carbon to which they are attached define an optionally substituted $C_3$-$C_6$ carbocyclo, or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; J' is an optionally substituted heteroatom, such as —O— or optionally substituted —NH—, which includes —N($R^{33}$), wherein $R^{33}$ is hydrogen or optionally substituted $C_1$-$C_6$ alkyl; and Y' is an optional second Spacer Unit and is absent when subscript y is 1 in which instance Y' in the above -$L_{SS}$-$L_O$-D structures is replaced by an optionally substituted heteroatom provided by the NAMPT Tail ($T_N$) Unit of a NAMPTi compound or derivative thereof, which in some preferred embodiments is designated as $X^a$, wherein $X^a$ is —O— or —S—, and Y' is present when subscript y is 2, in which instance Y' is a second Spacer Unit or functional group comprised of that optionally substituted heteroatom, in which the second Spacer Unit or functional group may also be capable of self-immolation so that Y' is a second self-immolative Spacer Unit, which in the latter case for some preferred embodiment occurs when Y' is —OC(=O)—$X^b$— wherein $X^b$ is the optionally substituted heteroatom provided by the Tail ($T_N$) Unit of a NAMPTi compound or derivative thereof, wherein $X^b$ is —NH—, —O— or —S—, and in the former case occurs when Y' is methylene carbamate (MAC) Unit.

In preferred embodiments, two of V, $Z^1$, $Z^2$ are =CH— and the other is =N— or =CH— or $R^8$ and $R^9$ are independently hydrogen or $C_1$-$C_4$ alkyl. In other preferred embodiments, is —NH—. In more preferred embodiments V, $Z^1$, $Z^2$ are each =CH— and $R^8$ and $R^9$ are independently selected from the group consisting of hydrogen, —$CH_3$ and —$CH_2CH_3$; and is —NH—. In those embodiments, the indicated $M^2$ and $M^3$ residues represent a succinimide moiety and a succinic acid amide moiety, respectively.

In other embodiments, a Drug Linker compound of formula $L_{SS}$-$L_O$-D having $L_O$ of formula (1a) in which subscript y is 1 or 2 and having an acyclic or cyclic Basic Unit is exemplified by the structure of:

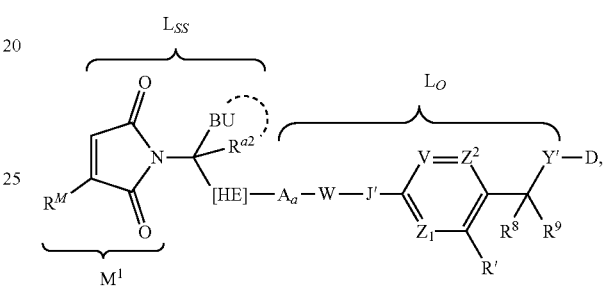

wherein the dotted curved line and variable groups are as previously described for drug linker moieties in Ligand Drug Conjugates having an acyclic or cyclic Basic Unit and a peptide cleavable secondary linker. In those embodiments the indicated $M^1$ residue represents a maleimide moiety.

In other such embodiments, preferably V, $Z^1$ and $Z^2$ are each =CH—, or one of $R^8$, $R^9$ is hydrogen and the other is hydrogen, $C_1$-$C_4$ alkyl or optionally substituted phenyl. In still other such embodiments, preferably [HE] is —C(=O)—, R' is hydrogen or $R^8$ and $R^9$ are both hydrogen.

In other group of embodiments $L_O$ in $L_{SS}$-$L_O$-D of a drug linker moiety within a Ligand Drug Conjugate composition or Conjugate compound and its hydrolysis product -$L_S$-$L_O$-D have formula (1a) in which subscript w is 0 or 1, wherein W is a Peptide Cleavable Unit when subscript w is 1, and subscript y is 0, wherein $Y_y$ in Formula 1, Formula 2 and Formula I is replaced by an optionally substituted heteroatom, designated as $X^b$, provided by the NAMPT Tail ($T_N$) Unit of NAMPTi compound or derivative thereof so that the NAMPTi compound or its derivative is bonded directly to W through that heteroatom. In those embodiments in which subscript w is 1 the W-J' bond is cleavable by a protease to release D, which is a NAMPTi compound or derivative thereof having the formula H—$X^b$-$T_N$-$I_N$-DA-$H_N$, wherein $X^b$ preferably —NH—, —S— or —O—, as provided by $T_N$, and the other variable groups are as defined. In those embodiments a drug linker moiety of formula -$L_{SS}$-$L_O$-D and -$L_S$-$L_O$- in a Ligand Drug Conjugate composition or a Conjugate compound thereof in which subscript y is 0, wherein $X^b$ replacing $Y_y$ is an optionally substituted heteroatom of $T_N$, have the structures of:

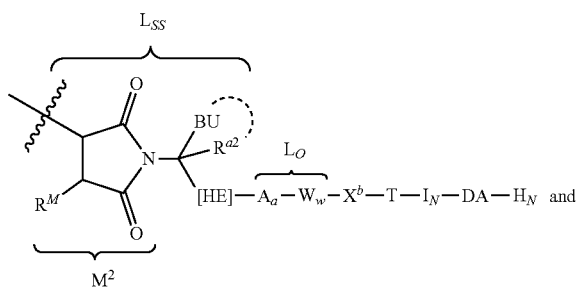

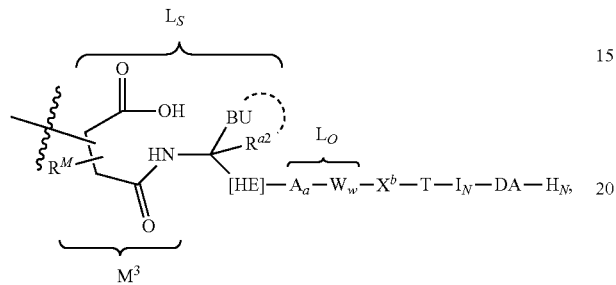

respectively, and corresponding Drug Linker Compounds have the structure of:

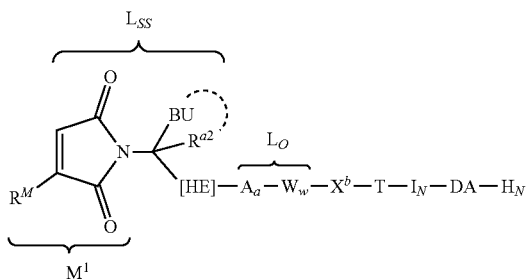

wherein the dotted curved line and other variable groups are as previously described for drug linker moieties in Ligand Drug Conjugates having an acyclic or cyclic Basic Unit and a peptide cleavable secondary linker.

In preferred embodiments, -L$_{SS}$-L$_O$-D of a drug linker moiety within a Ligand Drug Conjugate composition or Conjugate compound thereof and its hydrolysis product -L$_S$-L$_O$-D in which L$_O$ is of formula (1a), wherein W is a Peptide Cleavable Unit and subscript y is 1 or 2 so that A, W and Y/Y' are in a linear configuration with respect to D, are represented by:

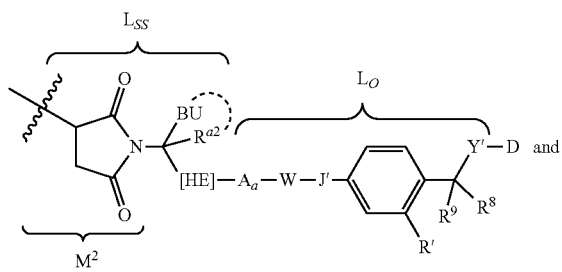

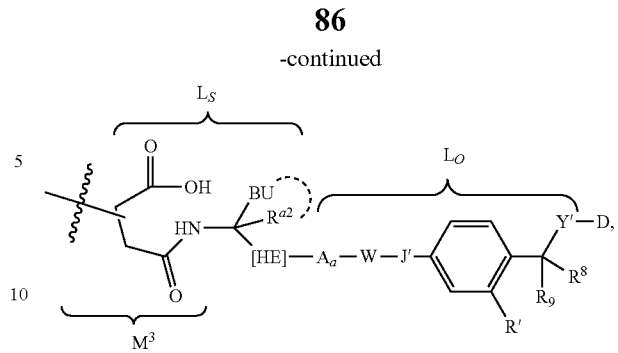

respectively, and corresponding Drug Linker compounds are represented by:

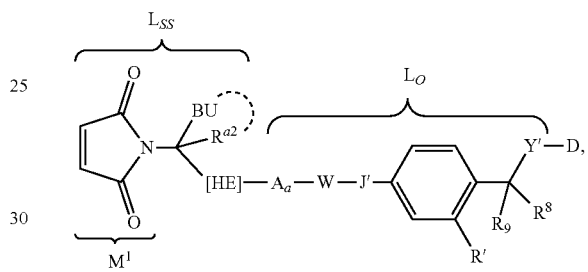

wherein the dotted curved line and variable groups are as previously described for drug linker moieties in Ligand Drug Conjugates having an acyclic or cyclic Basic Unit in peptide-cleavable secondary linkers, and when subscript y is 1, Y' in the above -L$_{SS}$-L$_O$-D embodiments is replaced with an optionally substituted heteroatom, designated as X$^a$, provided by the NAMPT Tail (T$_N$) Unit of a NAMPTi compound or derivative thereof, wherein X$^a$ is —O— or —S—.

In those drug linker moieties and Drug Linker compounds, preferably J' is —NH—. More preferred embodiments in which A, W and Y/Y' in L$_O$ are in a linear configuration with respect to D, a drug linker moiety within a Ligand Drug Conjugate composition or Conjugate compound thereof of formula -L$_{SS}$-L$_O$-D and it hydrolysis product of formula -L$_{SS}$-L$_O$-D have the structures of:

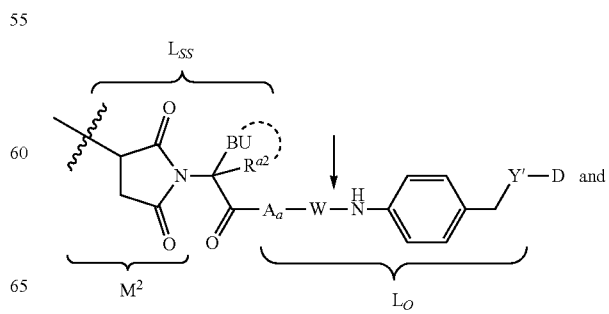

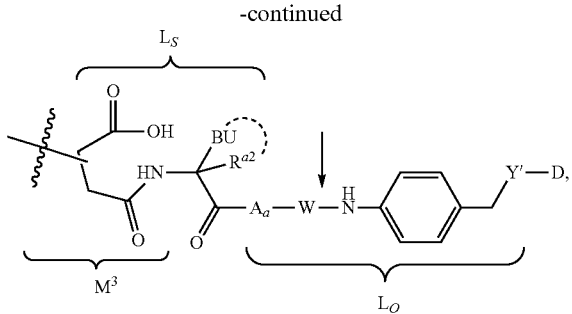

respectively, and corresponding Drug Linker compounds of formula $L_{SS}$-$L_O$-D have the structure of:

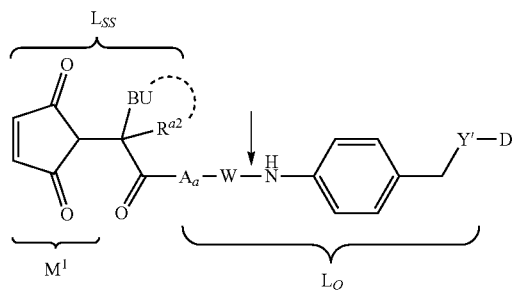

wherein W consists or is comprised of a dipeptide wherein the dipeptide subunit is at the distal end of W and the indicated bond is an amide bond specifically cleavable by an intracellular protease in comparison to freely circulating serum proteases and wherein the remaining variable groups are as previously defined for drug linker moieties in Ligand Drug Conjugates and Drug Linker compounds having an acyclic or cyclic Basic Unit and a peptide cleavable secondary linker.

In any one of the above embodiments in which W is comprised of a dipeptide that dipeptide is recognized by a intracellular protease. Preferably that protease is a cathepsin protease in which preferred dipeptides recognized by the cathepsin protease have the structure of

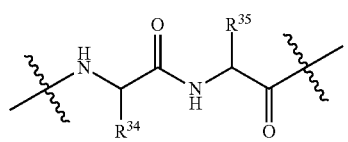

wherein $R^{34}$ is benzyl, methyl, isopropyl, isobutyl, sec-butyl, —CH(OH)CH$_3$ or has the structure of

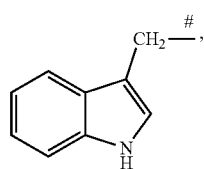

wherein the hash tag indicates the site of covalent attachment to the dipeptide backbone and $R^{35}$ is methyl, —(CH$_2$)$_4$—NH$_2$, —(CH$_2$)$_3$NH(C=O)NH$_2$, (CH$_2$)$_3$NH(C=NH)NH$_2$, or —(CH$_2$)$_2$CO$_2$H, wherein the wavy line at the dipeptide N-terminal indicates the site of covalent binding to A or $A_O$ or to $L_{SS}$ or $L_S$, depending on the presence or absence of A and $A_O$, and the wavy line at the dipeptide C-terminal indicates the site of covalent binding to J' or —NH— as J'.

In other embodiments a drug linker moeity of a Ligand Drug Conjugate in which W is a Glucuronide Unit of formula —Y(W')— so that $L_O$ is of formula 1b, which has A, W' and Y/Y' in an orthogonal configuration with respect to D, -$L_{SS}$-$L_O$-D of a drug linker moiety within a Ligand Drug Conjugate compound and its hydrolysis product -$L_S$-$L_O$-D, whose formation is catalyzed by an acyclic or cyclic Basic Unit, have structures of:

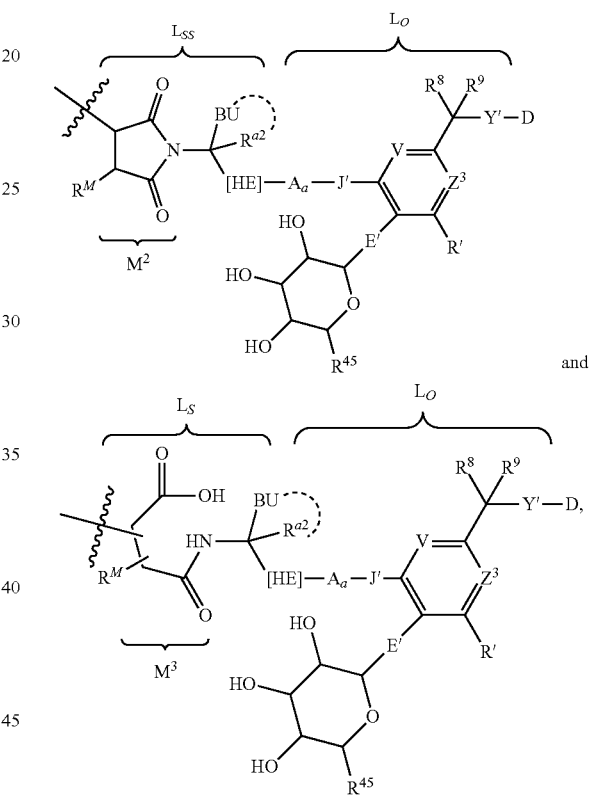

respectively, wherein the dotted curved line indicates optional cyclization so that when absent BU is an acyclic Basic Unit and $R^{a2}$ is optionally substituted C$_1$-C$_6$ alkyl, and when present BU and $R^{a2}$ together with the carbon atom to which both are attached define a cyclic Basic Unit; the wavy line indicates covalent bonding of a Ligand Unit, which for the $M^3$ moiety in $L_S$ is to the carbon atom that is adjacent to its acid or amide functional group with $R^M$ bonded to the carbon atom adjacent to the remaining functional group; A is an optional first Stretcher Unit; subscript a is 0 or 1, indicating the absence or presence of A, respectively; [HE] is an optional Hydrolysis Enhancer Unit; $R^M$ is hydrogen or C$_1$-C$_4$ alkyl; V and $Z^3$ are independently =N— or C($R^{24}$), wherein $R^{24}$, independently selected, is hydrogen, optionally substituted C$_1$-C$_6$ alkyl or an electron withdrawing group; $R^8$ and $R^9$ independently are hydrogen or optionally substituted C$_1$-C$_6$ alkyl or together with the benzylic carbon to which both are attached define an optionally substituted $C_3$-$C_6$ carbocyclo, or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; J' and E' are independently selected optionally substituted heteroatoms, such as —O— or optionally substituted —NH—, which includes —N($R^{33}$), wherein each $R^{33}$ is independently hydrogen or optionally substituted $C_1$-$C_6$ alkyl;

Y' is an optional second Spacer Unit and is absent when subscript y is 1 in which instance Y' in the above -$L_{SS}$-$L_O$-D structures is replaced by an optionally substituted heteroatom provided by the NAMPT Tail ($T_N$) Unit of a NAMPTi compound or derivative thereof, which in some preferred embodiments is designated as $X^a$, wherein $X^a$ is —O— or —S—, and Y' is present when subscript y is 2, in which instance Y' is a second Spacer Unit or functional group comprised of that optionally substituted heteroatom, in which the second Spacer Unit or functional group may also be capable of self-immolation so that Y' is a second self-immolative Spacer Unit, which in the latter case for some preferred embodiment occurs when Y' is —OC(=O)—$X^b$— wherein $X^b$ is the optionally substituted heteroatom provided by the Tail ($T_N$) Unit of a NAMPTi compound or derivative thereof, wherein $X^b$ is —NH—, —O— or —S—, and in the former case occurs when Y' is methylene carbamate (MAC) Unit;

$R^{45}$ is —$CH_2OH$ or —$CO_2H$; and the wavy line indicates covalent bonding of a Ligand Unit, which for the $M^3$ moiety in $L_S$ is to the carbon atom that is alpha to the acid or amide functional group with $R^M$ bonded to the remaining beta carbon. In preferred embodiments, V and $Z^2$ are =CH— or $R^8$ and $R^9$ are independently hydrogen or $C_1$-$C_4$ alkyl. In other preferred embodiments, J' is —NH—. In more preferred embodiments, $R^8$ and $R^9$ are independently selected from the group consisting of hydrogen, —$CH_3$ and —$CH_2CH_3$; and J' is —NH—. In those embodiments the indicated $M^2$ and $M^3$ residues represent a succinimide moiety and a succinic acid amide moiety, respectively.

In other embodiments, a Drug Linker compound of formula $L_{SS}$-$L_O$-D having an acyclic or cyclic Basic Unit and a Glucuronide Unit is exemplified by the structure of:

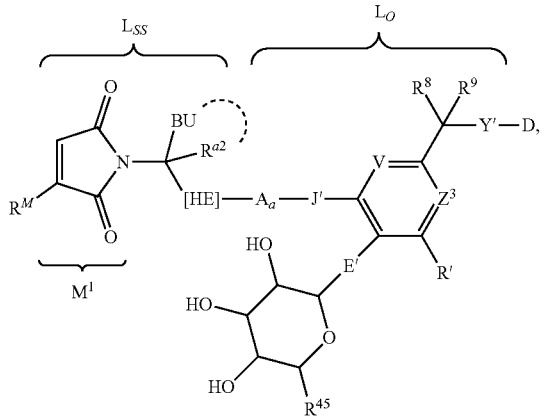

wherein the variable groups are as previously described for Glucuronide-based drug linker moieties in Ligand Drug Conjugates and Drug Linker compounds.

In preferred embodiments, -$L_{SS}$-$L_O$-D and its hydrolysis product -$L_S$-$L_O$-D, in which W is a Glucuronide Unit of formula —Y(W')— have $L_O$ of formula (1b), so that A, W' and Y are in an orthogonal configuration with respect to D, are represented by:

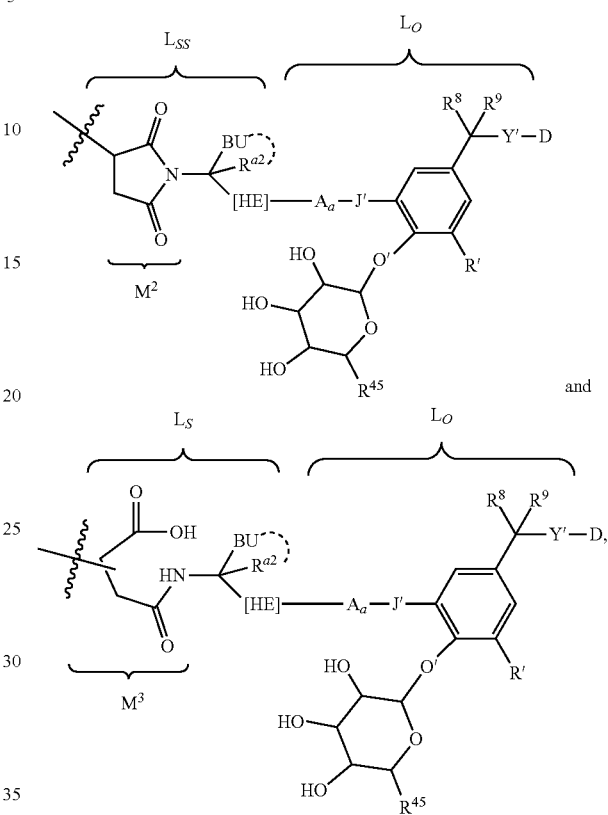

respectively, and corresponding Drug Linker compounds are represented by:

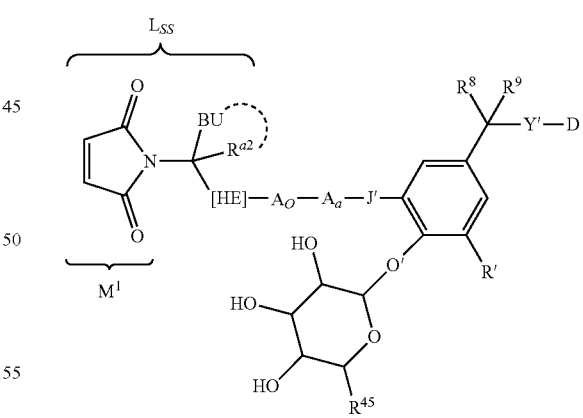

wherein O' represents a glycosidic-bonded oxygen, the bond to which is cleavable by a glycosidase and wherein the variable groups are as previously described for Glucuronide-based drug linker moieties in Ligand Drug Conjugates and Drug Linker compounds.

In those drug linker moieties and Drug Linker compounds, preferably one of $R^8$, $R^9$ is hydrogen and the other is hydrogen, $C_1$-$C_4$ alkyl or optionally substituted phenyl. In other such embodiments preferably J' is —O— or —N($R^{33}$), wherein $R^{33}$ is hydrogen or $C_1$-$C_4$ alkyl or R' is hydrogen or an electron withdrawing group. In more preferred embodiments J is —NH— and R' is hydrogen or —$NO_2$.

In more preferred embodiments in which A, W' and Y in $L_O$ are in an orthogonal configuration with respect to D, a drug linker moiety of a Ligand Drug Conjugate compound of formula -$L_{SS}$-$L_O$-D and it hydrolysis product of formula -$L_{SS}$-$L_O$-D have the structures of:

respectively, and corresponding Drug Linker compounds are represented by:

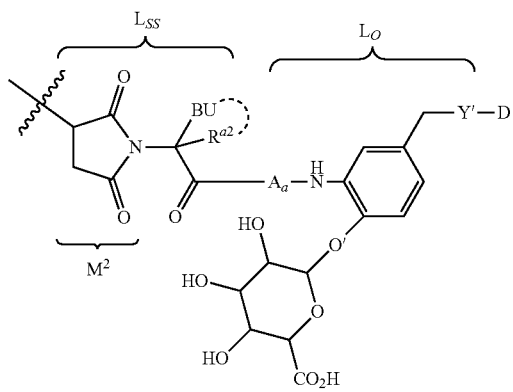

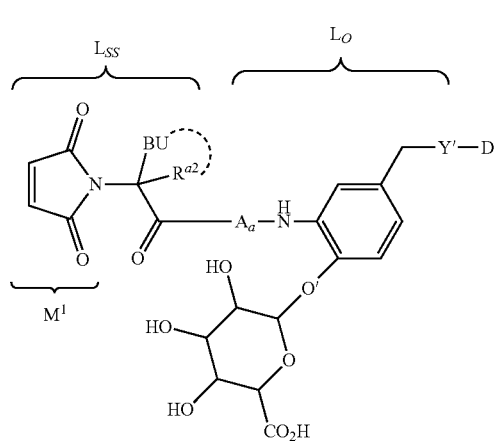

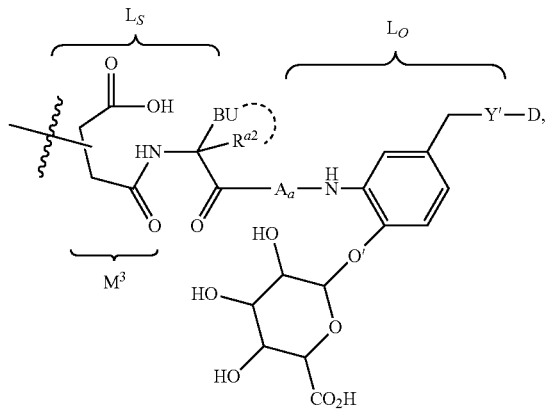

wherein the variable groups are as previously described for Glucuronide-based drug linker moieties in Ligand Drug Conjugates and Drug Linker compounds.

In other preferred embodiments the -$L_{SS}$ and -$L_S$ containing drug linker moieties of a Ligand Drug Conjugate compound having $L_O$ of formula (1a) in which W is a Peptide Cleavable Unit and subscript y is 1 or 2 and having a heterocyclo cyclic Basic Unit are represented by:

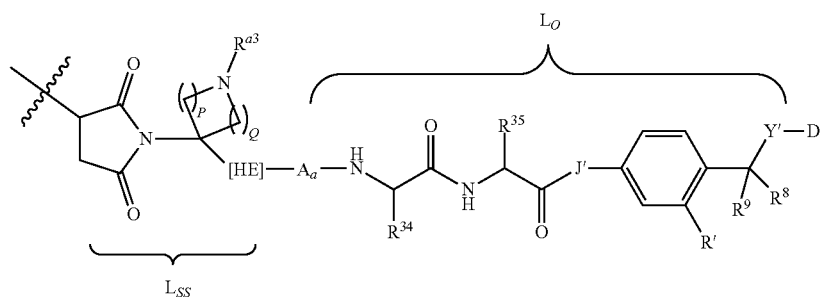

and

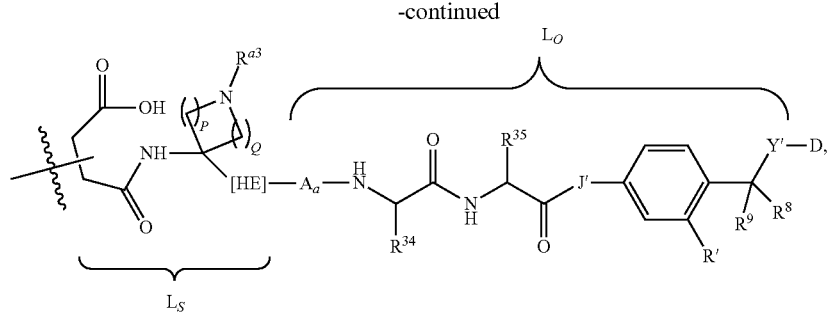

respectively, and corresponding Drug Linker compounds are represented by:

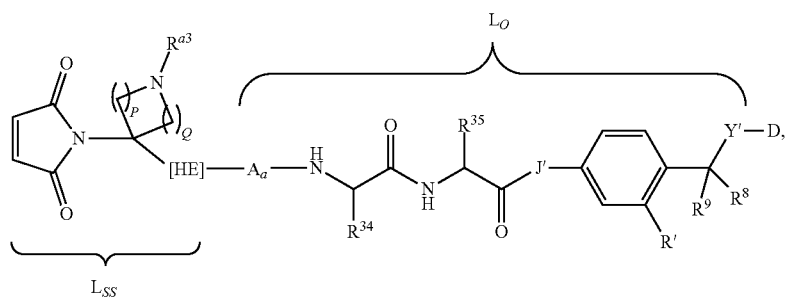

wherein subscript P is 1 or 2; subscript Q ranges from 1 to 6; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated or is in a salt form, preferably in a pharmaceutically acceptable salt form, or $R^{a3}$ is a nitrogen protecting group such as a suitable acid-labile protecting group; and -$L_{SS}$ and -$L_S$ containing drug linker moieties of a Ligand Drug Conjugate compound having $L_O$ of formula (1a) in which W is a Peptide Cleavable Unit and subscript y is 1 or 2 and having a acyclic Basic Unit are represented by:

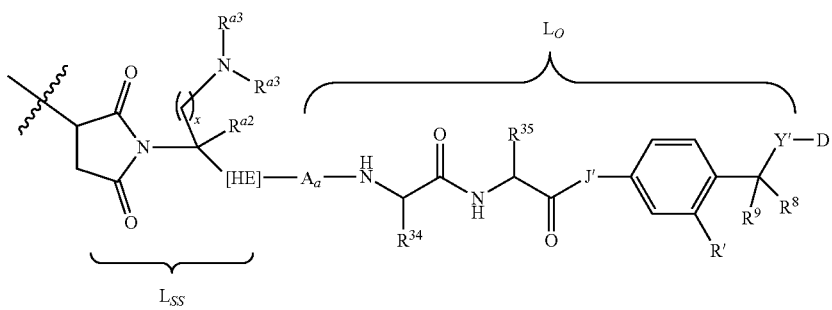

and

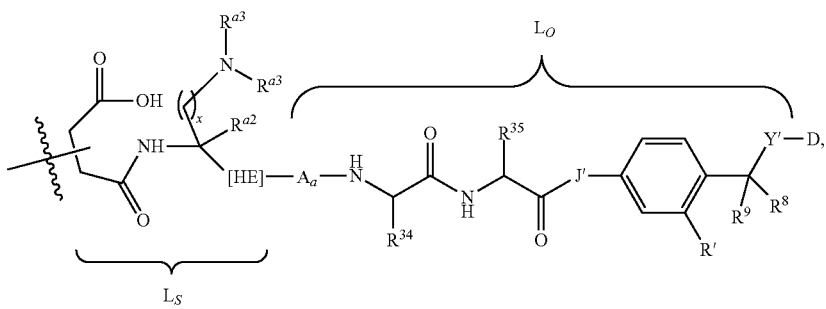

respectively, and corresponding Drug Linker compounds are represented by:

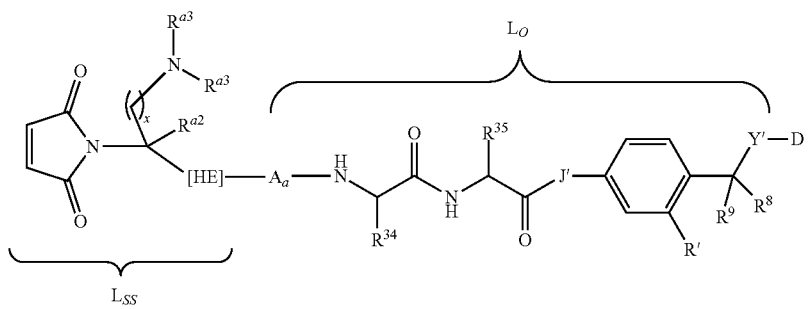

wherein HE is an optional Hydrolysis Enhancing Unit, A is an optional first Stretcher Unit, subscript a is 0 or 1, indicating the absence or presence of A, respectively; subscript x is 1 or 2, $R^{a2}$ is hydrogen or —$CH_3$ or —$CH_2CH_3$; $R^{a3}$, at each instance, is independently hydrogen, —$CH_3$ or —$CH_2CH_3$, or both $R^{a1}$ together with the nitrogen to which they are attached define an azetidinyl, pyrrolidinyl or piperidinyl heterocyclyl, in which a basic primary, secondary or tertiary amine so defined is optionally protonated or is in a salt form, preferably a pharmaceutically acceptable salt form;

Y' is an optional second Spacer Unit and is absent when subscript y is 1 in which instance Y' in the above -$L_{SS}$-$L_O$-D structures is replaced by an optionally substituted heteroatom provided by the NAMPT Tail ($T_N$) Unit of a NAMPTi compound or derivative thereof, which in some preferred embodiments is designated as $X^a$, wherein $X^a$ is —O— or —S—, and Y' is present when subscript y is 2, in which instance Y' is a second Spacer Unit or functional group comprised of that optionally substituted heteroatom, in which the second Spacer Unit or functional group may also be capable of self-immolation so that Y' is a second self-immolative Spacer Unit, which in the latter case for some preferred embodiment occurs when Y' is —OC(=O)—$X^b$— wherein $X^b$ is the optionally substituted heteroatom provided by the Tail ($T_N$) Unit of a NAMPTi compound or derivative thereof, wherein $X^b$ is —NH—, —O— or —S—, and in the former case occurs when Y' is methylene carbamate (MAC) Unit;

$R^{34}$ and $R^{35}$ are as previously defined for Peptide Cleavable Units and the remaining variable groups are as previously defined for drug linker moieties and Drug Linker compounds comprised of these Peptide Cleavable Units.

In other preferred embodiments the -$L_{SS}$ and -$L_S$ containing drug linker moieties of a Ligand Drug Conjugate compound having $L_O$ of formula (1a) in which W is a Peptide Cleavable Unit and subscript y is 0 or 1 and having a heterocyclo cyclic Basic Unit are represented by:

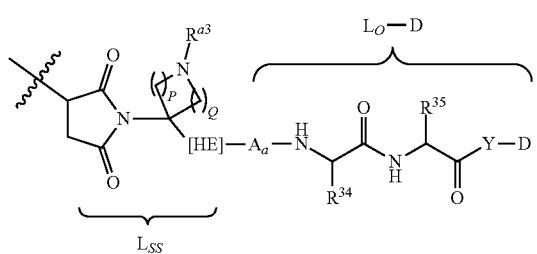

-continued

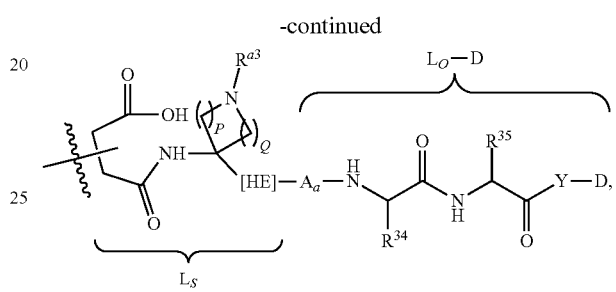

respectively, and corresponding Drug Linker compounds are represented by:

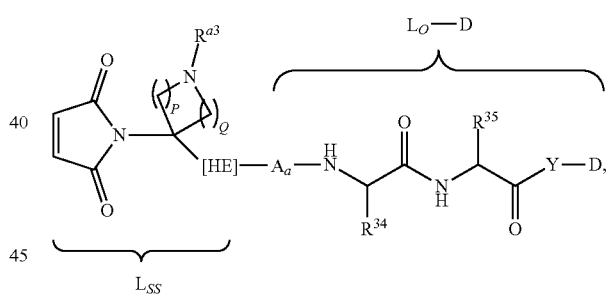

and -$L_{SS}$ and -$L_S$ containing drug linker moieties of a Ligand Drug Conjugate compound having $L_O$ of formula (1a) in which W is a Peptide Cleavable Unit and subscript y is 0 or 1 and having an acyclic Basic Unit are represented by:

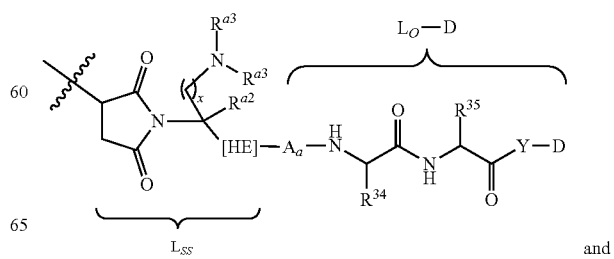

and

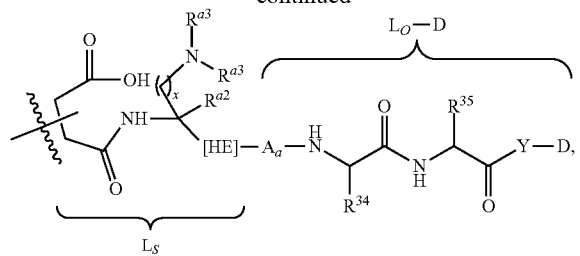

respectively, and corresponding Drug Linker compounds are represented by:

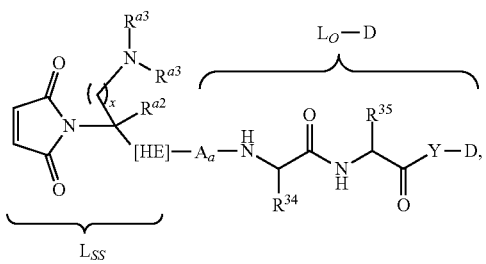

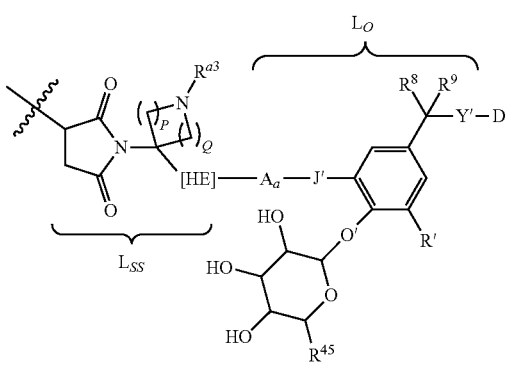

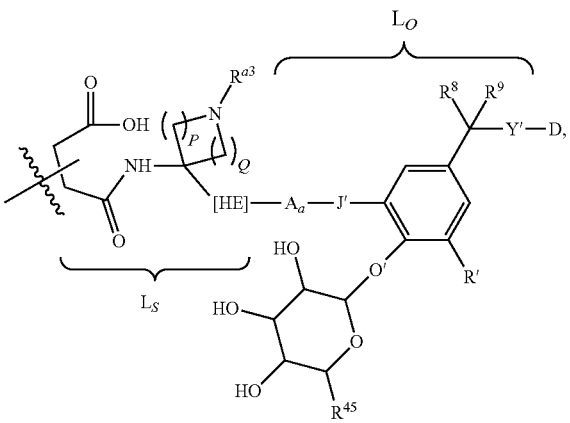

respectively, and corresponding Drug Linker compounds are represented by:

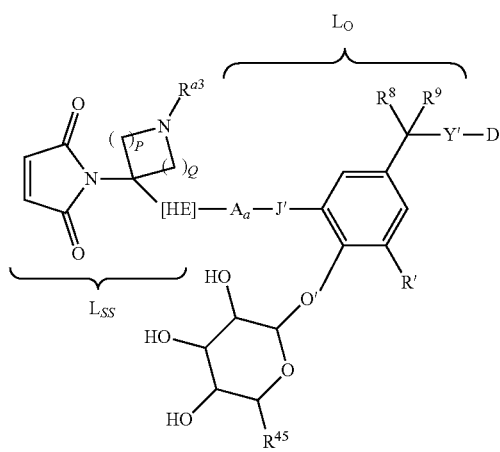

wherein when subscript y is 0, Y is replaced by an optionally substituted heteroatom provided by the NAMPT Tail ($T_N$) Unit of a NAMPTi compound or derivative thereof, which in some preferred embodiments is designated as $X^a$, wherein $X^a$ is —O— or —S—, and when subscript y is 1, Y is a second Spacer Unit or functional group comprised of that optionally substituted heteroatom, wherein the second Spacer Unit or functional group may also be capable of self-immolation so that Y is a self-immolative Spacer Unit other than a PAB or PAB-type self-immolative Spacer Unit, which in some preferred embodiment occurs when Y is —OC(=O)—$X^b$— wherein $X^b$ is the optionally substituted heteroatom provided by the Tail ($T_N$) Unit of a NAMPTi compound or derivative thereof, wherein $X^b$ is —NH—, —O— or —S—, wherein protease cleavage of the W—Y bond within $L_O$ when Y is present or the W-D bond when Y is absent releases a NAMPTi compound or its derivative, which in preferred embodiments have the formula H—$X^a$-$T_N$-$I_N$-DA-$H_N$ or H—$X^b$-$T_N$-$I_N$-DA-$H_N$; and wherein $T_N$, $I_N$, DA and $H_N$ are as defined for NAMPTi compounds, derivatives thereof, or NAMPT Drug Units, the basic nitrogen to which $R^{a1}$ is bonded is optionally protonated when $R^{a1}$ is other than a nitrogen protecting group, and $R^{34}$ and $R^{35}$ are as previously defined for Peptide Cleavable Units and the remaining variable groups are as previously defined for drug linker moieties and Drug Linker compounds having a peptide cleavage secondary linker.

In other preferred embodiments the $L_{SS}$- and $L_S$-containing drug linker moieties having a Glucuronide Unit in which $L_O$ is of formula (1b), and a heterocyclo cyclic Basic Unit within a Ligand Drug Conjugate compound have the structure of:

and $L_{SS}$- and $L_S$-containing drug linker moieties having a Glucuronide Unit in which $L_O$ is of formula 1b, and an acyclic Basic Unit within a Ligand Drug Conjugate compound have the structure of:

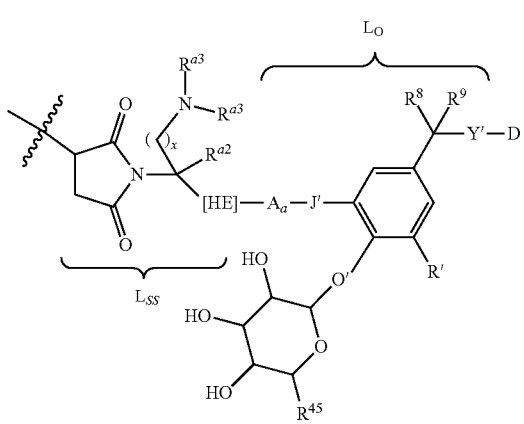

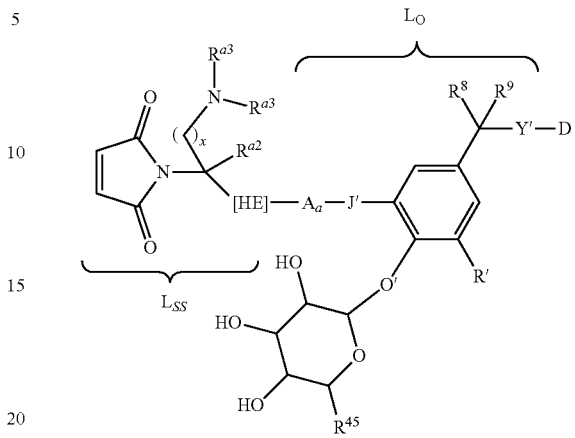

and

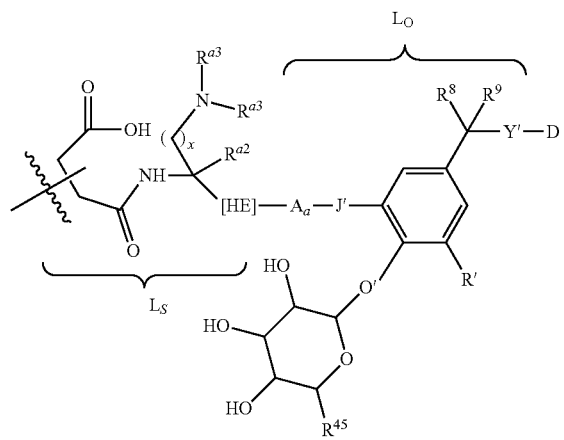

respectively, and corresponding Drug Linker compounds are represented by:

wherein subscript x is 1 or 2, $R^{a2}$ is hydrogen or —CH$_3$ or —CH$_2$CH$_3$; $R^{a3}$, at each instance, is independently hydrogen, —CH$_3$ or —CH$_2$CH$_3$, or both $R^{a1}$ together with the nitrogen to which they are attached define an azetidinyl, pyrrolidinyl or piperidinyl heterocyclyl, wherein the basic primary, secondary or tertiary amine so defined is optionally protonated or is in a salt form, preferably a pharmaceutically acceptable salt form, and wherein O' represents a glycosidic-bonded oxygen, the bond to which is cleavable by a glycosidase; and the other variable groups are as previously described for Glucuronide-based drug linker moieties in Ligand Drug Conjugates and Drug Linker compounds.

In more preferred embodiments the -L$_{SS}$ containing drug linker moieties within a Ligand Drug Conjugate compound having L$_O$ of formula (1a), wherein W is a Peptide Cleavable Unit and subscript y is 1 or 2, and having a heterocyclo cyclic Basic Unit or an acyclic Basic Unit are represented by:

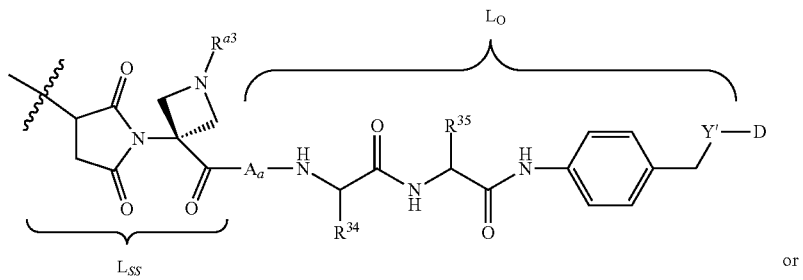

or

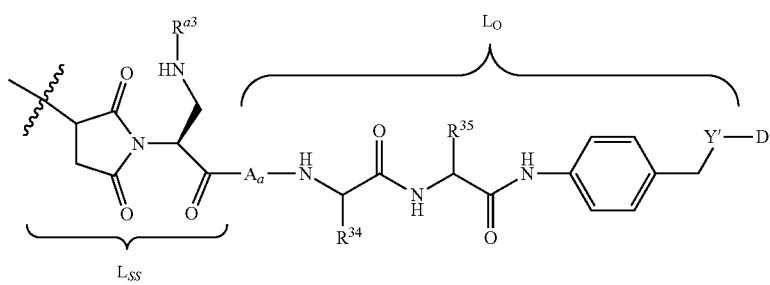

and more preferred $L_S$-containing drug linker moieties from controlled hydrolysis of the above drug linker moieties are represented by:

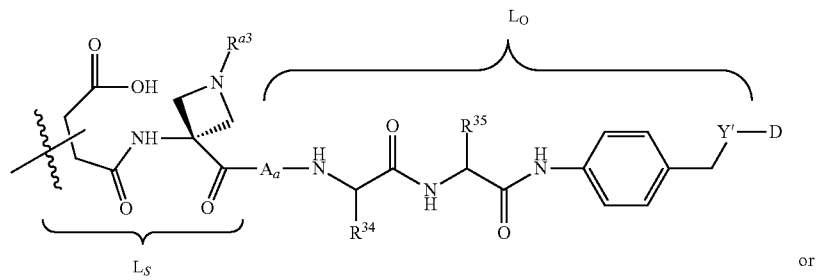

or

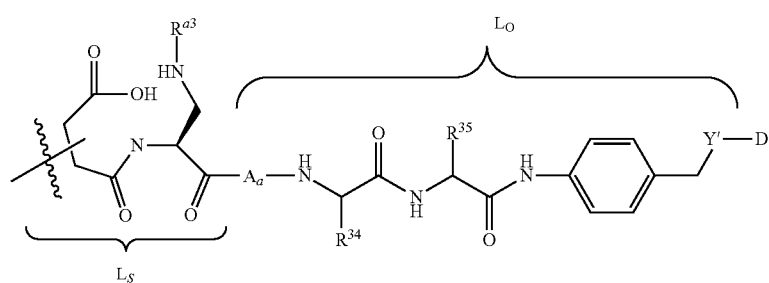

and corresponding more preferred Drug Linker compounds are represented by:

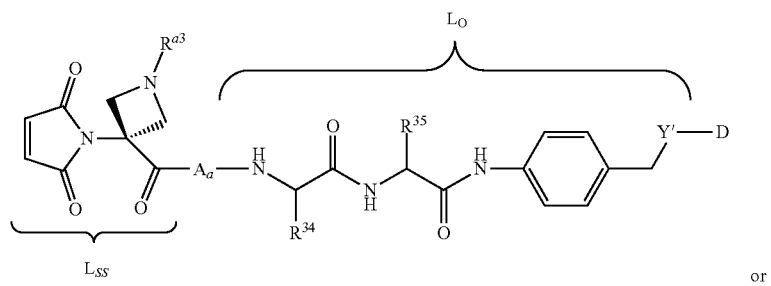

or

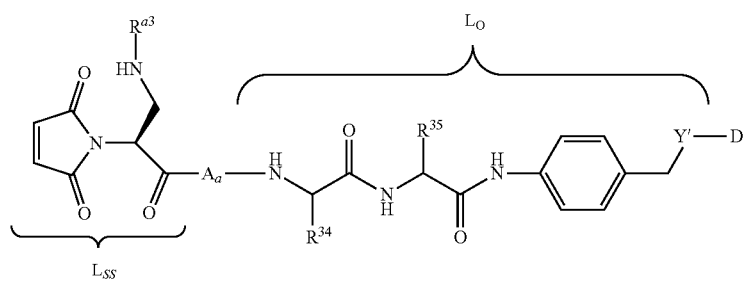

wherein the variable groups are as previously described for drug linker moieties and Drug Linker compounds having a heterocyclo cyclic Basic Unit or an acyclic Basic Unit and a peptide cleavable secondary linker in Ligand Drug Conjugates and Drug Linker compounds and wherein the nitrogen atom to which $R^{a3}$ is bonded is optionally protonated or in a salt form, preferably a pharmaceutically acceptable salt from, when $R^{a3}$ is other than a nitrogen protecting group.

In other more preferred embodiments $L_{SS}$-containing drug linker moieties of a Ligand Drug Conjugate compound having $L_O$ of formula (1a) in which W is a Peptide Cleavable Unit and subscript y is 0 or 1 and having a heterocyclo cyclic Basic Unit or acyclic Basic Unit are represented by:

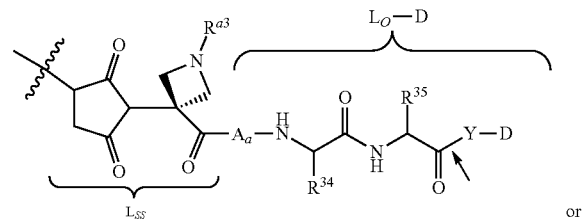

or

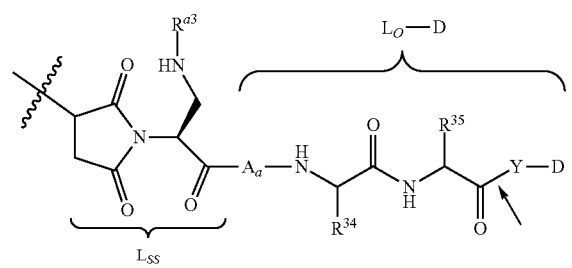

, and $L_S$-containing drug linker moieties from controlled hydrolysis of the above drug linker moieties are represented by:

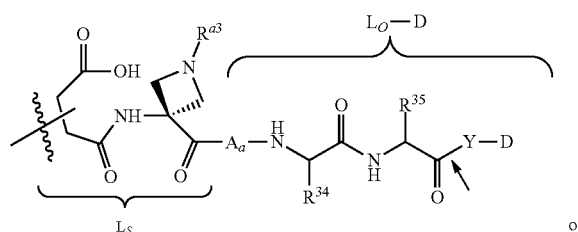

or

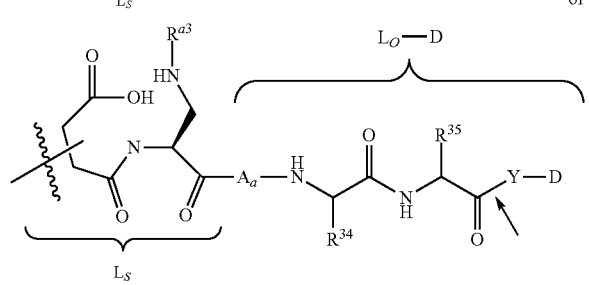

and corresponding Drug Linker compounds are represented by:

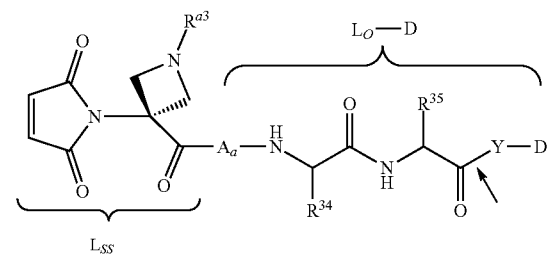

or

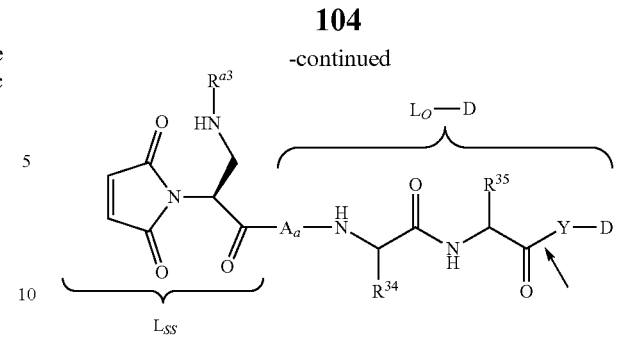

wherein Y is absent when subscript y is 0 in which instance Y is replaced by an optionally substituted heteroatom provided by the NAMPT Tail ($T_N$) Unit of a NAMPTi compound or derivative thereof, which in some more preferred embodiments is designated as $X^a$, wherein $X^a$ is —O— or —S—, or Y is present when subscript y is 1, wherein Y is a functional group comprised of an optionally substituted heteroatom provided by the NAMPT Tail ($T_N$) Unit of a NAMPTi compound or derivative thereof, which in some more preferred embodiments that optionally substituted heteroatom is designated as $X^b$, wherein $X^a$ is —NH—, —O— or —S—, or Y is a Spacer Unit other than a PAB or PAB-type self-immolative Spacer Unit; and wherein protease cleavage of the indicated W—Y bond within $L_O$ when subscript 1 so that Y is present or the W-D bond when subscript y is 0 so that Y is absent releases a NAMPT compound or its derivative of formula H—$X^a$-$T_N$-$I_N$-DA-$H_N$, H—$X^b$-$T_N$-$I_N$-DA-$H_N$ or H—Y-$T_N$-$I_N$-DA-$H_N$ wherein $T_N$, $I_N$, DA and $H_N$ are as defined for NAMPTi compounds, derivatives thereof, or NAMPT Drug Units and wherein the other variable groups are as previously described for drug linker moieties and Drug Linker compounds having a heterocyclo cyclic Basic Unit or an acyclic Basic Unit and a peptide cleavable secondary linker in Ligand Drug Conjugates and Drug Linker compounds and wherein the basic nitrogen atom to which $R^{a3}$ is bonded is optionally protonated or in a salt form, preferably a pharmaceutically acceptable salt from, when $R^{a3}$ is other than a nitrogen protecting group.

In other more preferred embodiments the -$L_{SS}$ containing drug linker moieties having a Glucuronide Unit in which $L_O$ is of formula (1b) and having a heterocyclo cyclic Basic Unit or an acyclic Basic Unit within a Ligand Drug Conjugate are represented by:

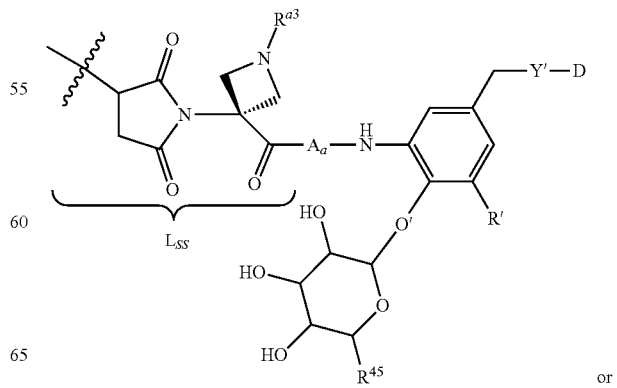

or

-continued

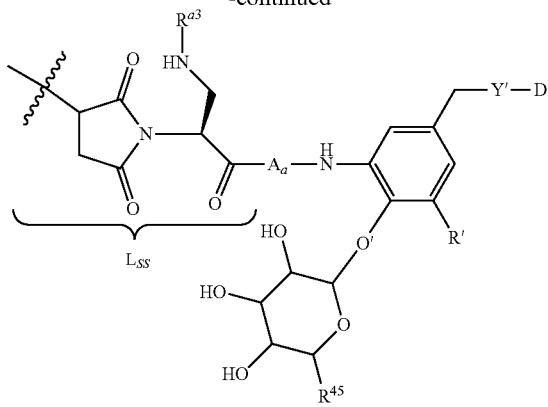

and the $L_S$-containing drug linker moieties from controlled hydrolysis of the above LSS-containing drug linker moieties have the structures of:

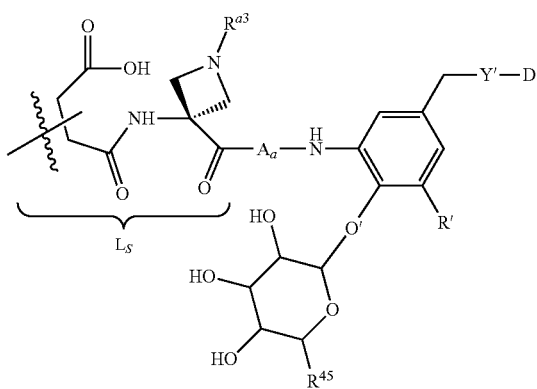

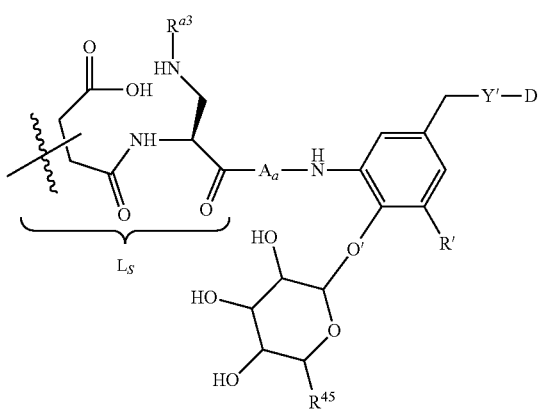

and corresponding Drug Linker compounds are represented by:

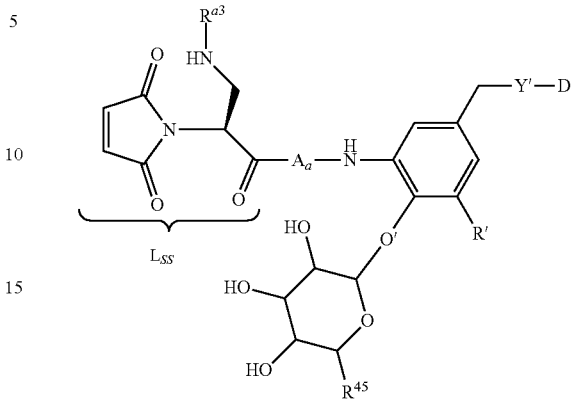

wherein the other variable groups are as previously described for drug linker moieties and Drug Linker compounds having a heterocyclo cyclic Basic Unit or an acyclic Basic Unit and a Glucuronide-based secondary linker in Ligand Drug Conjugates and Drug Linker compounds and wherein the nitrogen atom to which $R^{a3}$ is bonded is optionally protonated or in a salt form, preferably a pharmaceutically acceptable salt from, when $R^{a3}$ is other than a nitrogen protecting group.

In the above preferred and more preferred embodiments, the $L_{SS}$ and $L_S$ components within a drug linker moiety of a Ligand Drug Conjugate exemplify the general formula of $M^2$-$A_R$(BU)-$A_O$- and $M^3$-$A_R$(BU)-$A_O$-, respectively, wherein BU is a cyclic Basic Unit and in which [HE] as $A_O$ is —C(=O)—, wherein $M^2$ is succinimide moiety and $M^3$ is succinic acid amide moiety, and $L_{SS}$ of a Drug Linker compound exemplify the general formula of $M^1$-$A_R$(BU)-$A_O$-, wherein BU is a cyclic Basic Unit which is a precursor to representative $L_{SS}$ moieties of a Ligand Drug Conjugates comprised of a cyclic Basic Unit, wherein $M^1$ is a maleimide moiety and [HE] as $A_O$ is —C(=O)—.

In some of the above embodiments A, or a subunit thereof, when subscript a is 1 and is bonded to $A_O$ in any one of the above $L_R$-$L_o$-D structures in which $L_R$ is either $L_{SS}$ or $L_S$, preferably has a structure corresponding to an independently selected amine-containing acid (e.g., an amino acid residue) wherein the carboxylic acid terminus of the amine-containing acid is bonded to W as an ester or amide, preferably as an amide, and its N-terminus is bonded to $L_{SS}$ of formulae $M^1$-$A_R$(BU)-$A_O$- or $M^2$-$A_R$(BU)-$A_O$- or $L_S$ of formula $M^3$-$A_R$(BU)-$A_O$-, wherein BU is a cyclic Basic Unit, through a carbonyl-containing functional group. In several of those embodiments $A_O$ is [HE] or is comprised of [HE], wherein HE is a carbonyl-containing functional group so that its carbonyl carbon is bonded to the N-terminus of W.

In other embodiments A, or a subunit thereof, has the formula of -$L^P$(PEG)-, wherein $L^P$ is a Parallel Connector Unit and PEG is a PEG Unit. In those embodiments, the PEG Unit contains a total of 2 to 36 ethyleneoxy monomer units and $L^P$ is comprised of an amine-containing acid residue, preferably an amino acid residue, covalently attached to W. In more preferred embodiments the covalent attachment of $L^P$ within the Linker Unit of a drug linker moiety of Ligand Drug Conjugate or of a Drug Linker compound is through amide functional groups. In other more preferred embodiments the PEG Unit contains a total of 4 to 24 contiguous ethyleneoxy monomer units.

In any one of the above -$L_{SS}$-$L_O$-D and -$L_S$-$L_O$-D Ligand Drug Conjugate sub-structures and the $L_{SS}$-$L_O$-D Drug Linker compound structures having a heterocyclo cyclic Basic Unit or a acyclic Basic Unit and a protease cleavable Peptide Cleavable Unit, preferably $R^{34}$ is methyl, isopropyl or —CH(OH)CH$_3$ and $R^{35}$ is methyl, —(CH$_2$)$_3$NH(C=O)NH$_2$ or —(CH$_2$)$_2$CO$_2$H. In any one of the above -L$_{SS}$-L$_O$-D and -L$_S$-L$_O$-D Ligand Drug Conjugate sub-structures and L$_{SS}$-L$_O$-D Drug Linker compound structures having a heterocyclo cyclic Basic Unit or an acyclic Basic Unit and a glycosidase cleavable Glucuronide Unit preferably $R^{45}$ is —CO$_2$H.

In preferred embodiments in which A, W', Y are in an orthogonal configuration with respect to D, a first Stretcher Unit (A) is present and has the structure previously defined for formula (3) or formula (4) or has the structure of formula (3a) or formula (4a):

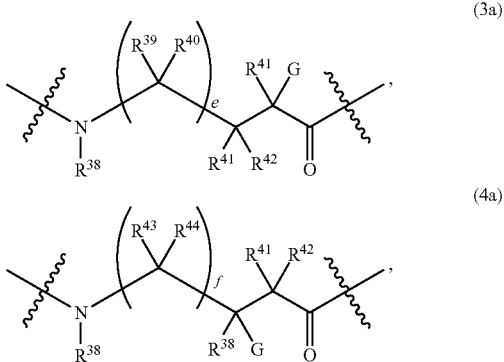

wherein subscript e or f is 0 or 1 and G and $R^{39}$-$R^{44}$ are as previously defined and the wavy line to the carbonyl moiety of any one of the formula (3), (3a), (4) and (4a) structures represents the site of attachment of A to J' preferably through an amide functional group and wherein the wavy line to the amino moiety of either one of these structures represents the site of attachment to a carbonyl-containing functional group of a second Stretcher Unit A$_O$ or to the carbonyl carbon of [HE] as A$_O$. In preferred embodiments of formula (3) or formula (4) L' is absent (i.e., subscript q is 0) and G is hydrogen, —CO$_2$H or —NH$_2$ or the side chain of a naturally occurring amino acid such as aspartic acid, glutamic acid or lysine. In other preferred embodiments, L' and K are carbon and $R^{41}$, $R^{42}$, $R^{43}$ and $R^{44}$ in each occurrence is hydrogen. In other preferred embodiments $R^{38}$-$R^{44}$ in each occurrence is hydrogen. Other preferred embodiments have formula (3) wherein K is nitrogen and one of $R^{41}$, $R^{42}$ is absent and the other is hydrogen. Other preferred embodiments have formula (4) wherein subscript r is 1, K is nitrogen and one of $R^{41}$, $R^{42}$ is absent and the other is hydrogen. In other preferred embodiments subscripts p and q of structure (3) are both 0 or subscripts q and r of structure (4) are both 0. Other preferred embodiments have structure (3) wherein subscripts p and q are both 0 and K together with $R^{41}$ and $R^{42}$ is —C(=O)—. Other preferred embodiments have structure (4) wherein subscript q is 1 and L' together with $R^{43}$ and $R^{44}$ is —C(=O)—.

In preferred embodiments in which A, W, Y are in a linear configuration with respect to D, a first Stretcher Unit (A) is present having the same variable group preferences as described above for preferred embodiments in which W', Y and D are in an orthogonal configuration. In such preferred embodiments, the wavy line to the carbonyl moiety of any one of the formula (3), (3a), (4) and (4a) structures represents the site of attachment of A to the N-terminus of the Peptide Cleavable Unit (W) and the wavy line to the amino moiety of either one of these structures represents the site of attachment to a carbonyl-containing functional group of a second Stretcher Unit A$_O$ or to the carbonyl carbon of [HE] as A$_O$.

In other preferred embodiments A and A$_O$ are both present A is selected from formula (3), (3a), (4) and (4a). In more preferred embodiments A is an alpha-amino, beta-amino or other amine-containing acid residue. In more preferred embodiment A is an alpha-amino, beta-amino or other amine-containing acid residue.

In any one of the above -L$_R$-L$_O$-D, -L$_{SS}$-L$_O$-D and -L$_S$-L$_O$-D Ligand Drug Conjugate sub-structures and the L$_{SS}$-L$_O$-D Drug Linker compound structures in which a first optional Stretcher Unit is present and which have an acyclic Basic Unit or heterocyclo cyclic Basic Unit particularly, preferred amine-containing acids that correspond to A have the structure of NH$_2$—X$^1$—CO$_2$H wherein X$^1$ is an optionally substituted C$_1$-C$_6$-alkylene.

Particularly preferred Ligand Drug Conjugates are represented by any one of the above -L$_R$-L$_O$-D, -L$_{SS}$-L$_O$-D and -L$_S$-L$_O$-D Ligand Drug Conjugate sub-structures bonded to L in which L is an antibody Ligand Unit bonded to the L$_R$, L$_{SS}$ or L$_S$ moiety.

1.3.1 Ligand Unit

In some embodiments of the invention, a Ligand Unit is present. The Ligand Unit (L) is a targeting moiety of a Ligand Drug Conjugate that specifically binds to a targeted moiety. The Ligand Unit can specifically bind to a cell component (a Cell Binding Agent), which serves as the targeted moiety, or to other target molecules of interest. The Ligand Unit acts to target and present the Drug Unit of the Ligand Drug Conjugate to the particular target cell population with which the Ligand Unit interacts in order to selectively release D as a NAMPTi compound or derivative thereof. Targeting agents that provide for Ligand Units include, but are not limited to, proteins, polypeptides and peptides. Exemplary Ligand Units include, but are not limited to, those provided by proteins, polypeptides and peptides such as antibodies, e.g., full-length antibodies and antigen binding fragments thereof, interferons, lymphokines, hormones, growth factors and colony-stimulating factors. Other suitable Ligand Units are those from vitamins, nutrient-transport molecules, or any other cell binding molecule or substance. In some embodiments a Ligand Unit is from non-antibody protein targeting agent. In other embodiments, a Ligand Unit is from protein targeting agent such as an antibody. Preferred targeting agents are larger molecular weight proteins, e.g., Cell Binding Agents having a molecular weight of at least about 80 Kd.

A targeting agent reacts with a L$_{SS}$ moiety of a Drug Linker compound to form a Ligand Unit covalently attached to drug-linker moiety wherein the drug-linker moiety has the formula -L$_{SS}$-D. The targeting agent has or is modified to have to have the appropriate number of attachment sites to accommodate the requisite number of drug-linker moieties, defined by subscript p, whether they be naturally occurring or non-naturally occurring (e.g., engineered). For example, in order for the value of subscript p to be from 6 to 14, a targeting agent has to be capable of forming a bond to 6 to 14 drug-linker moieties. The attachment sites can be naturally-occurring or engineered into the targeting agent. A targeting agent can form a bond to the L$_{SS}$ moiety of the Linker unit of a Drug Linker compound via a reactive or activatable heteroatom or a heteroatom-containing functional group of the targeting agent. Reactive or activatable heteroatoms or a heteroatom-containing functional groups that may be present on a targeting agent include sulfur (in one embodiment, from a thiol functional group of an targeting agent), C=O or (in one embodiment, from a carbonyl, carboxyl or hydroxyl group of a targeting agent) and nitrogen (in one embodiment, from a primary or secondary amino group of a targeting agent). Those heteroatoms can be present on the targeting agent in the targeting agent's natural state, for example a naturally-occurring antibody, or can be introduced into the targeting agent via chemical modification or genetic engineering.

In one embodiment, a targeting agent has a thiol functional group and the Ligand Unit therefrom is attached to a drug linker moiety of a Ligand Drug Conjugate compound via the thiol functional group's sulfur atom.

In another embodiment, the targeting agent has lysine residues that can react with an activated ester, including but are not limited to, N-hydroxysuccinimide, pentafluorophenyl, and p-nitrophenyl esters), of $L_{SS}$ of the Linker Unit of a Drug Linker compound and thus results in an amide bond between the nitrogen atom from the Ligand Unit and the C=O functional group from the Linker Unit of the Drug Linker compound.

In yet another embodiment, the targeting agent has one or more lysine residues that can be chemically modified to introduce one or more thiol functional groups. The Ligand Unit from that targeting agent is attached to the Linker Unit via the introduced thiol functional group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the targeting agent can have one or more carbohydrate groups that can be chemically modified to have one or more thiol functional groups. The Ligand Unit from that targeting agent is attached to the Linker Unit via the introduced thiol functional group's sulfur atom, or the targeting agent can have one or more carbohydrate groups that can be oxidized to provide an aldehyde (—CHO) group (see, e.g., Laguzza, et al., 1989, *J. Med. Chem.* 32(3):548-55). The corresponding aldehyde can then react with a $L_{SS}$ moiety of a Drug Linker compound having nucleophilic nitrogen. Other reactive sites on $L_{SS}$ that can react with a carbonyl group on a targeting agent include, but are not limited to, hydrazine and hydroxylamine Other protocols for the modification of proteins for the attachment of drug linker moieties are described in Coligan et al., *Current Protocols in Protein Science*, vol. 2, John Wiley & Sons (2002) (incorporated herein by reference).

In preferred embodiments, the reactive group of $L_{SS}$ of a Drug Linker compound is a maleimide ($M^1$) moiety and covalent attachment of L to $L_{SS}$ is accomplished through a thiol functional group of a targeting agent so that a thio-substituted succinimide ($M^2$) moiety is formed through Michael addition. The thiol functional group can be present on the targeting agent in the targeting agent's natural state, for example a naturally-occurring residue, or can be introduced into the targeting agent via chemical modification and/or genetic engineering.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker to a ligand can affect the ability of the conjugated drug-linker moiety to undergo an elimination reaction and for the drug linker moiety to be transferred from the Ligand Unit of a bioconjugate to an alternative reactive thiol present in the milieu of the bioconjugate, such as, for example, a reactive thiol in albumin, free cysteine, or glutathione when in plasma. Such sites include, for example, the interchain disulfides as well as select cysteine engineered sites. The Ligand-Drug Conjugates described herein can be conjugated to thiol residues at sites that are less susceptible to the elimination reaction (e.g., positions 239 according to the EU index as set forth in Kabat) in addition to other sites.

In yet another embodiment, the targeting agent is that of an antibody and the thiol functional group is chemically introduced into the antibody, for example by introduction of a cysteine residue. Accordingly, in some embodiments, the Linker Unit of a Ligand Drug Conjugate compound is conjugated to a drug linker moiety through an introduced cysteine residue.

Thus, in more preferred embodiments, the targeting agent is an antibody and the thiol functional group is generated by reduction of an interchain disulfide, or the Linker Unit is conjugated to cysteine residue(s) of the reduced interchain disulfides of the Ligand Unit. In other more preferred embodiments, the targeting agent is an antibody and the thiol functional group is from cysteine residue(s) of reduced interchain disulfides of the Ligand Unit and cysteine residue(s) introduced by genetic engineering.

When the conjugates comprise non-immunoreactive protein, polypeptide, or peptide ligands instead of an antibody, useful non-immunoreactive protein, polypeptide, or peptide ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred targeting agents are antibodies, including intact antibodies. In fact, in any of the embodiments described herein, the Ligand Unit can be that of an antibody. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immuno-specifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety). Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety). Such chimeric and humanized monoclonal antibodies can be produced by recombinant DNA techniques known in the art, for example using methods, each of which is specifically incorporated herein by reference, as described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., *Science* (1988) 240:1041-1043; Liu et al., *Proc. Natl. Acad. Sci.* (USA) (1987) 84:3439-3443; Liu et al., *J. Immunol.* (1987) 139: 3521-3526; Sun et al. *Proc. Natl. Acad. Sci.* (USA) (1987) 84:214-218; Nishimura et al. *Cancer. Res.* (1987) 47:999-1005; Wood et al., *Nature* (1985) 314:446-449; Shaw et al., *J. Natl. Cancer Inst.* (1988) 80:1553-1559; Morrison, *Science* (1985) 229:1202-1207; Oi et al. *BioTechniques* (1986) 4:214; U.S. Pat. No. 5,225,539; Jones et al., *Nature* 1986) (321:552-525; Verhoeyan et al., *Science* (1988) 239:1534; and Beidler et al., *J. Immunol.* (1988) 141:4053-4060.

Completely human antibodies are particularly preferred and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

In a specific embodiment, known antibodies for the treatment of cancer can be used. In another specific embodiment, antibodies for the treatment of an autoimmune disease are used in accordance with the compositions and methods of the invention.

In certain embodiments, useful antibodies can bind to a receptor a receptor complex expressed on an activated lymphocyte. The receptor receptor complex can comprise an immunoglobulin gene superfamily member, a TNF receptor superfamily member, an integrin, a cytokine receptor, a chemokine receptor, a major histocompatibility protein, a lectin, or a complement control protein.

In some embodiments, the antibody will specifically bind to CD19, CD20, CD30, CD33, CD70, alpha-v-beta-6, or Lewis Y antigen.

The antibody can be a humanized anti-CD33 antibody (US 2013/0309223 incorporated by reference herein in its entirety and for all purposes), a humanized anti-Beta6 antibody (see, e.g., WO 2013/123152 incorporated by reference herein in its entirety and for all purposes), a humanized anti-Liv-1 antibody (see, e.g., US 2013/0259860 incorporated by reference herein in its entirety and for all purposes), or a humanized AC10 antibody (see, e.g., U.S. Pat. No. 8,257,706 incorporated by reference herein in its entirety and for all purposes). Exemplary attachment of the Linker Unit to the antibody Ligand Unit is via thioether linkages. The thioether linkages can be via interchain disulfide bonds, introduced cysteines resides, and combinations thereof.

1.3.2 Parallel Connector Unit

In some embodiments A or $A_O$ is a Parallel Connector Unit ($L^P$) having the structure of Formula A or Formula B:

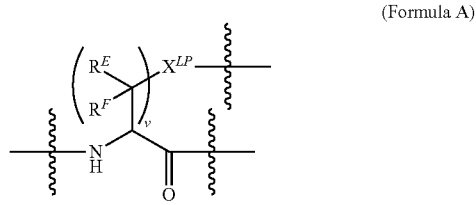
(Formula A)

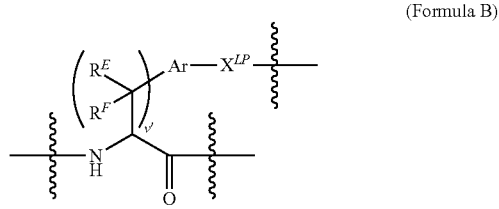
(Formula B)

wherein subscript v is an integer ranging from 1 to 4; subscript v' is an integer ranging from 0 to 4; $X^{LP}$ is provided by a natural or un-natural amino acid side chain or is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, and —N(R$^{LP}$)C(=NR$^{LP}$)N(R$^{LP}$)—, or heterocyclo wherein each R$^{LP}$ is independently selected from the group consisting of hydrogen and optionally substituted C$_1$-C$_{12}$ alkyl, preferably hydrogen and optionally substituted $C_1$-$C_6$ alkyl or two of $R^{LP}$ together along with their intervening atoms define an optionally substituted $C_3$-$C_{20}$ heterocyclyl, preferably optionally substituted $C_3$-$C_6$ heterocyclyl and any remaining $R^{LP}$ are as previously defined; Ar is an optionally substituted $C_6$-$C_{24}$ arylene or optionally substituted $C_5$-$C_{24}$ heteroarylene, preferably optionally substituted phenylene; each $R^E$ and $R^F$ is independently selected from the group consisting of —H, optionally substituted $C_1$-$C_{12}$ alkyl, optionally substituted $C_6$-$C_{24}$ aryl and optionally substituted $C_5$-$C_{24}$ heteroaryl, preferably hydrogen and optionally substituted phenyl, or $R^E$ and $R^F$ together with the same carbon to which they are attached, or $R^E$ and $R^F$ from adjacent carbons together with these carbons, defines a optionally substituted $C_3$-$C_{20}$ carbocyclo, preferably optionally substituted $C_3$-$C_6$ carbocyclo with any remaining $R^E$ and $R^F$ substituents as previously defined; and wherein the wavy lines indicates covalent attachment of the Formula A or Formula B structure within a Ligand Drug Conjugate or Drug Linker compound structure.

In some embodiments -$L^P$(PEG)- has the structure of Formula A1 or A2:

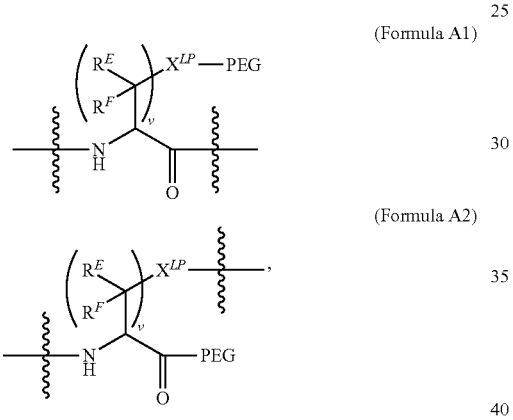

(Formula A1)

(Formula A2)

wherein the variable groups are as defined in Formula A.

In preferred embodiments, $L^P$ has the structure of Formula A1 wherein $X^{LP}$ is provided by a natural or un-natural amino acid side chain.

In preferred embodiments of Formula A, Formula A1, Formula A2 or Formula B, $R^E$ and $R^F$ are independently selected from the group consisting of —H, and —$C_1$-$C_4$ alkyl. In preferred embodiments of Formula A, Formula A1 or Formula A2, $X^{LP}$ is selected from the group consisting of —O—, —NH, —S— and —C(=O)—.

In some embodiments, $L^P$ is selected from the group consisting of lysine, glutamic acid, aspartic acid, cysteine, penicillamine, serine and threonine each of which is in D- or L-stereochemical configuration.

In other embodiments, $L^P$ is selected from the group consisting of lysine, glutamic acid, aspartic acid, cysteine, and penicillamine each of which is in D- or l-stereochemical configuration.

In other embodiments, $L^P$ is a thiol containing amino acid residue in the D- or L-stereochemical configuration. The thiol containing amino acid is preferably cysteine, homocysteine, or penicillamine.

In other embodiments, $L^P$ is an aminoalkanedioic acid residue. Preferred aminoalkanedioic acids are N-alkylaminoalkanedioic acids, 2-aminohexanedioic acid, 2-aminoheptanedioic acid and 2-aminooctanedioic acid (H-Asu-OH).

In other embodiments, $L^P$ is a diaminoalkanoic acid residue. Preferred diaminoalkanoic acids are N-alkyl-diamino-alkanoic acids, N,N-dialkylamino-alkanoic acids, α,γ-diaminobutyric acid (H-Dab-OH), and α,β-diaminopropionic acid.

In preferred embodiments lysine, cysteine or penicillamine amino acid residues for $L^P$ are shown below:

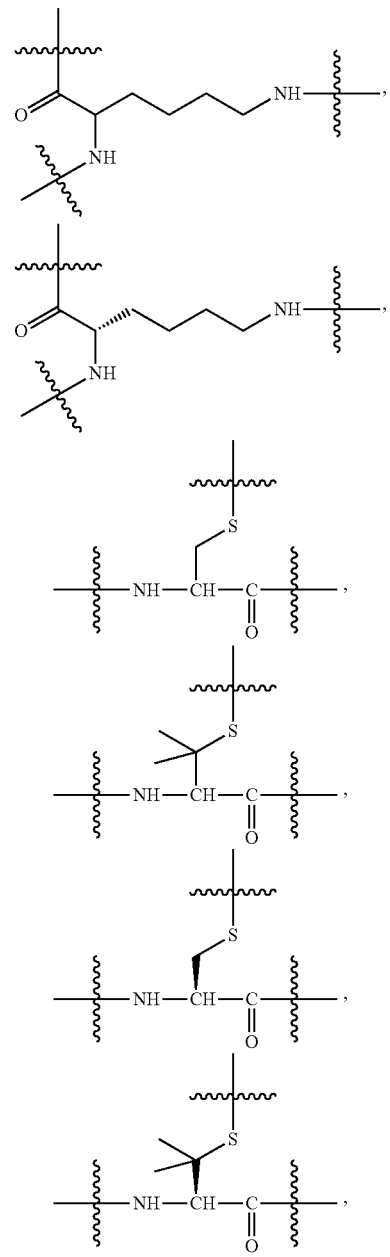

wherein the wavy lines indicate the points of covalent attachment to PEG and $L^P$ of $L^P$(PEG)- within a Linker Unit of a drug linker moiety or a Drug Linker compound.

Preferred Ligand-Drug Conjugates having lysine as the $L^P$ unit are shown below wherein L, $L_S$, A, $A_O$, W, W', Y, Y', D, PEG, subscript y is 0, 1 or 2 and subscripts a and p are as described herein. (R)- and (S)-stereoisomers at the indicated (*) position are suitable for use herein.

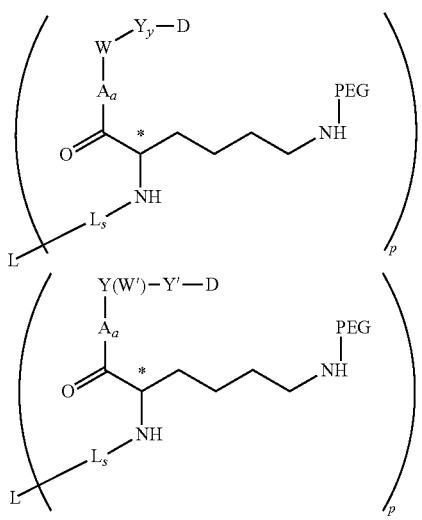

1.3.3 PEG Unit

The PEG Units as taught herein are designed to impart an suitable level of hydrophobicity masking of hydrophobic NAMPT Drug Units(s) and other hydrophobic components of a drug-linker moiety within a Ligand Drug Conjugate. For that reason, the incorporation of PEG Unit as taught herein is particularly suitable for hydrophobic NAMPT Drug Units that negatively impact the pharmacokinetics of the resultant Ligand Drug Conjugate as compared to the unconjugated targeting agent that is incorporated into its Ligand Unit. Those poorer pharmokinetics include greater plasma clearance, which can be attributed to the hydrophobicity of a hydrophobic NAMPTi compound or derivative thereof incorporated into or corresponding to the NAMPT Drug Unit the Ligand Drug Conjugate. Thus, Ligand Drug Conjugates having a hydrophobic NAMPT Drug Unit that display significantly greater plasma clearance and correspondingly lower plasma exposure relative to the unconjugated targeting agent will benefit by a Linker Unit to which that hydrophobic NAMPT Drug Unit is attached having a Stretcher Unit or subunit thereof of formula $-L^P(PEG)-$, wherein $L^P$ is a Parallel Connector Unit and PEG is a PEG Unit. Ligand-Drug Conjugates whose Linker Units are comprised of such Stretcher Units will have those more favorable pharmokinetic properties due to the parallel orientation within a hydrophobic drug-linker moiety of a hydrophobic NAMPT Drug Unit and the PEG Unit attached to $L^P$, whereby the negative impact of hydrophobicity of the hydrophobic NAMPT Drug Unit, which may be further aggravated by other hydrophobic components of the drug-linker moiety, on plasma clearance is sufficiently reduced or is essentially eliminated (i.e., hydrophobicity of a drug-linker moiety is masked).

The PEG Unit will be directly attached to the Ligand-Drug Conjugate (or Intermediate thereof) at the Parallel Connector Unit. The other terminus (or termini) of the PEG Unit will be free and untethered and may take the form of a methoxy, carboxylic acid, alcohol or other suitable functional group. The methoxy, carboxylic acid, alcohol or other suitable functional group acts as a cap for the terminal PEG subunit of the PEG Unit. The skilled artisan will understand that the PEG Unit in addition to comprising repeating polyethylene glycol subunits may also contain non-PEG material (e.g., to facilitate coupling of multiple PEG chains to each other or to facilitate coupling to the Parallel Connector Unit). Non-PEG material refers to the atoms in the PEG Unit that are not part of the repeating $-CH_2CH_2O-$ subunits. In embodiments provided herein, the PEG Unit can comprise two monomeric PEG chains linked to each other via non-PEG elements.

Thus in some embodiment, the PEG Unit is covalently bound to an amino acid residue via a reactive functional group. Reactive functional groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) may also be used as a reactive functional group for attaching PEG. In addition, enzyme-assisted methods for introducing activated groups (e.g., hydrazide, aldehyde, and aromatic-amino groups) specifically at the C-terminus of a polypeptide have been described (see Schwarz, et al. (1990) *Methods Enzymol.* 184:160; Rose, et al. (1991) *Bioconjugate Chem.* 2:154; and Gaertner et al. (1994) *J. Biol. Chem.* 269:7224].

The addition of the PEG Unit may have two potential impacts upon the pharmacokinetics of the resulting Ligand-Drug Conjugate. The desired impact is the decrease in clearance (and consequent in increase in exposure) that arises from the reduction in non-specific interactions induced by the exposed hydrophobic elements of the drug-linker. The second impact may be undesired and is dues to the decrease in volume and rate of distribution that may arise from the increase in the molecular weight of the Ligand-Drug Conjugate. Increasing the number of PEG subunits increases the hydrodynamic radius of a conjugate, resulting in decreased diffusivity. In turn, decreased diffusivity may diminish the ability of the Ligand-Drug Conjugate to penetrate into a tumor (Schmidt and Wittrup, *Mol. Cancer Ther.* (2009) 8:2861-2871). Because of these two competing pharmacokinetic effects, it is desirable to use a PEG that is sufficiently large to decrease the clearance of Ligand Drug Conjugate compounds of an administered Conjugate composition thus increasing plasma exposure, but not so large as to greatly diminish its diffusivity, which may reduce the ability of the Ligand-Drug Conjugate compound to reach the intended target cell population.

In preferred embodiments, the PEG Unit is a derivatized linear single PEG chain having from 2 to 72, 2 to 60, 2 to 48, 2 to 36 or 2 to 24 subunits, or from 4 to 72, 4 to 60, 4 to 48, 4 to 36 or 4 to 24 subunits or from 6 to 72, 6 to 60, 6 to 48, 6 to 36 or 6 to 24 subunits, or from 8 to 72, 8 to 60, 8 to 48, 8 to 36 or 8 to 24 subunits, or from 12 to 72, 12 to 60, 12 to 48, 12 to 36 or 12 to 24 subunits, or from 8 to 36, 8 to 24 or 8 to 12 subunits.

Preferred linear PEG Units for use in any of the embodiments provided herein are as follows:

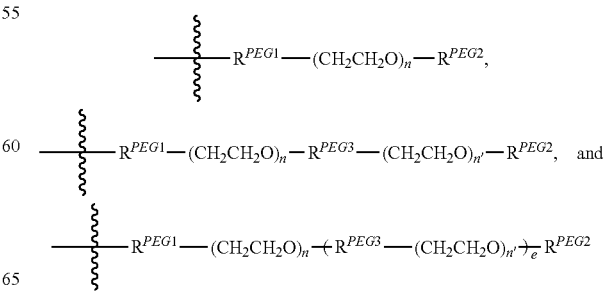

wherein the wavy line indicates site of attachment to the Parallel Connector Unit to $L^P$; $R^{PEG1}$ is a PEG Attachment Unit, $R^{PEG2}$ is a PEG Capping Unit; $R^{PEG3}$ is an PEG Coupling Unit (i.e., for coupling multiple PEG subunit chains together), subscript n is selected from 2 to 72, preferably from 4 to 72, more preferably from 6 to 72, from 8 to 72, from 10 to 72, from 12 to 72, from 6 to 24 or from 8 to 24, with 8 to 12 particularly preferred; subscript e is 2 to 5; and each subscript n' is independently selected from 1 to 72.

In more preferred embodiments, there are no more than 72 or 36 PEG subunits in a PEG Unit. In other more preferred embodiments, subscript n is 8 or about 8, 12 or about 12, or 24 or about 24.

The PEG Attachment Unit ($R^{PEG1}$) is part of a PEG Unit and acts to connect the PEG Unit to the Parallel Connector Unit ($L^P$) through a functional group of the PEG Unit. Functional groups for attachment of the PEG Unit to $L^P$ include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, the PEG Unit in some embodiment is attached to $L^P$ via disulfide, thioether, hydrazone, oxime, peptide, ester, sulfonamide, carbamate, or amide bonds.

In some embodiments, $R^{PEG1}$ is —C(O)—, —O—, —S—, —S(O)—, —NH—, —C(O)O—, —C(O)$C_1$-$C_{10}$alkyl, —C(O)$C_1$-$C_{10}$alkyl-O—, —C(O)$C_1$-$C_{10}$alkyl-CO$_2$—, —C(O)$C_1$-$C_{10}$alkyl-NH—, —C(O)$C_1$-$C_{10}$alkyl-S—, —C(O)$C_1$-$C_{10}$alkyl-C(O)—NH—, —C(O)$C_1$-$C_{10}$alkyl-NH—C(O)—, —$C_1$-$C_{10}$alkyl, —$C_1$-$C_{10}$alkyl-O—, —$C_1$-$C_{10}$alkyl-CO$_2$—, —$C_1$-$C_{10}$alkyl-NH—, —$C_1$-$C_{10}$alkyl-S—, —$C_1$-$C_{10}$alkyl-C(O)—NH—, —$C_1$-$C_{10}$alkyl-NH—C(O)—, —CH$_2$CH$_2$SO$_2$—$C_1$-$C_{10}$alkyl-, —CH$_2$C(O)—$C_1$-$C_{10}$ alkyl-, =N—(O or NH)—$C_1$-$C_{10}$alkyl-O—, =N—(O or NH)—$C_1$-$C_{10}$alkyl-NH—, =N—(O or NH)—$C_1$-$C_{10}$alkyl-CO$_2$—, =N—(O or NH)—$C_1$-$C_{10}$alkyl-S—,

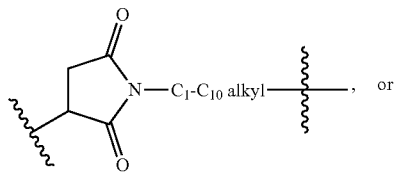, or

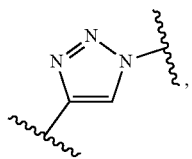, wherein in each instance $C_1$-$C_{10}$ is optionally substituted.

In preferred embodiments, $R^{PEG1}$ is —NH—, —C(=O)—, triazole-linked groups, or —S—, or maleimido-linked groups such as

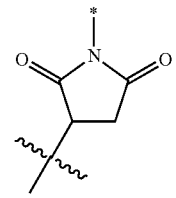

wherein the wavy line indicates the site of attachment to $L^P$ and the asterisk indicates the site of attachment within the PEG Unit.

The PEG Capping Unit ($R^{PEG2}$) is part of the PEG Unit and acts to terminate a PEG Unit at its untethered end, which is distal to the tethered end of the PEG Unit.

In exemplary embodiments $R^{PEG2}$ is independently —$C_1$-$C_{10}$ alkyl, —$C_2$-$C_{10}$ alkyl-CO$_2$H, —$C_2$-$C_{10}$ alkyl-OH, —$C_2$-$C_{10}$ alkyl-NH$_2$, —$C_2$-$C_{10}$ alkyl-NH($C_1$-$C_3$ alkyl), or —$C_2$-$C_{10}$ alkyl-N($C_1$-$C_3$ alkyl)$_2$, wherein each $C_1$-$C_3$ alkyl is independently selected and wherein $C_1$-$C_{10}$, $C_2$-$C_{10}$ and $C_1$-$C_3$ are optionally substituted.

$R^{PEG3}$ is part of a PEG Unit when there two linear sequences of contiguous PEG subunits contained within the PEG Unit and acts to join these sequences together into a single linear chain. In exemplary embodiments $R^{PEG3}$ is —$C_1$-$C_{10}$ alkyl-C(O)—NH—, —$C_1$-$C_{10}$ alkyl-NH—C(O)—, —$C_2$-$C_{10}$ alkyl-NH—, —$C_2$-$C_{10}$ alkyl-O—, —$C_1$-$C_{10}$ alkyl-S—, or —$C_2$-$C_{10}$ alkyl-NH—, wherein $C_1$-$C_{10}$ alkyl and $C_2$-$C_{10}$ alkyl are optionally substituted.

Preferred linear PEG Units that can be used in any of the embodiments provided herein are as follows:

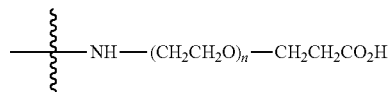

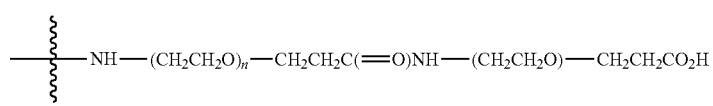

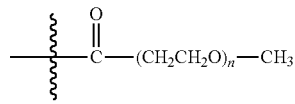

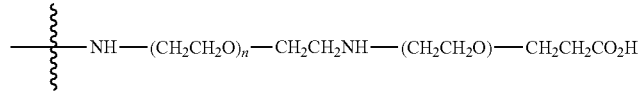

wherein the wavy line indicates site of covalent attachment to $L^P$, and each subscript n is independently selected from 4 to 72, 6 to 72, 8 to 72, 10 to 72, 12 to 72, 6 to 24, or 8 to 24. In some aspects, subscript n is about 8, about 12, or about 24.

It will be appreciated that when referring to PEG subunits, and depending on context, the number of subunits can represent an average number, e.g., when referring to a population of Ligand-Drug Conjugates or Intermediate Compounds (e.g., Drug Linker compounds), and/or when using polydisperse PEGs.

1.3.4 Cleavable Unit

A Cleavable Unit (W) is a component of a secondary linker within a drug linker moiety of a Ligand Drug Conjugate or is a component of a Linker Unit of a Drug Linker compound wherein W provides for a reactive site that when acted upon enzymatically or non-enzymatically results in breaking of a covalent bond within the secondary linker to initiate release of a drug compound or active drug moiety. In some embodiments, reactivity to that site is greater within or surrounding a hyper-proliferating cell or a hyper-stimulated immune cell (i.e., an abnormal cell) in comparison to a normal cell such that action upon that site results in preferential exposure to the abnormal cell of the released drug compound or active drug moiety. In some of those embodiments, a Cleavable Unit or component thereof (W or W') contains a reactive site cleavable by an enzyme (i.e., W or W' provides for an enzyme substrate) whose activity or abundance is greater within or surrounding the hyper-proliferating, immune-stimulating or other abnormal or unwanted cell compared to normal cells or whose activity or abundance is greater the vicinity of normal cells that are distant from the site of the abnormal or unwanted cells. In other embodiments, a Cleavable Unit is comprised of a reactive site cleavable by other mechanisms (i.e., non-enzymatic) more likely operable within abnormal cells targeted by a Ligand Unit of a Ligand Drug Conjugate or in the surrounding environment of abnormal cells in comparison to the environment of normal cells in which abnormal cells are typically not present or are distant from the site of the targeted cells. In some of those embodiments, the reactive site is more likely operated upon enzymatically or non-enzymatically subsequent to cellular internalization of a Ligand Drug Conjugate compound into a targeted abnormal cell. That internalization more likely occurs in those cells in comparison to normal cells due to greater presentation of the targeted moiety recognized by the targeting moiety (i.e., the Ligand Unit) of the Ligand Drug Conjugate compound on the cellular membrane of the targeted abnormal cells. Therefore, the targeted cells will more likely be exposed intracellularly to a NAMPTi compound or its derivative liberated from the Ligand Drug Conjugate compound on release of its NAMPT Drug Unit. The Cleavable Unit can comprise one or multiple sites susceptible to cleavage under conditions of the targeted site or within the targeted cells, but in some embodiments has only one such site.

In some embodiments, the Cleavable Unit is a substrate for a protease, preferably a regulatory protease, or a hydrolase or glycosidase, wherein the protease, hydrolase or glycosidase is located intracellularly in targeted cells (i.e., the reactive site of the Cleavable Unit is a peptide bond or glycoside bond, respectively, cleavable by the protease, hydrolase or glycosidase). In those embodiments the peptide or glycoside bond of the Cleavable Unit is capable of selective cleavage by an intracellular regulatory protease, hydrolase or glycosidase in comparison to serum proteases, hydrolases, or glycosidases. Those intracellular regulatory proteases, hydrolases or glycosidases in more preferred embodiment are more specific to the targeted abnormal cells in comparison to normal cells distant from the site of the abnormal cells. In other embodiments, a Cleavable Unit is a substrate for a protease, hydrolase or glycosidase excreted in greater amounts by the targeted abnormal or other unwanted cells in comparison to normal cells distant from the site of the abnormal cells so that W or W' is capable of selective cleavage by the excreted protease, hydrolase or glycosidase. In still other aspects the Cleavable Unit is a substrate for a protease, hydrolase or glycosidase, present within or preferentially excreted by normal cells that are peculiar to the environment of the abnormal cells in comparison to other normal cells in the periphery.

Alternatively, W provides for a functional group that when incorporated into an Ligand Drug Conjugate composition is susceptible to the acidic environment of lysozymes upon preferential internalization of a compound of that composition into an abnormal cell, or is susceptible to the greater reductive environment in or around such cells in comparison to the environment of normal cells where abnormal cells are usually not present, such that eventual release of D from that Ligand Drug Conjugate compound as a NAMPTi compound or derivative thereof, which is initiated by action on the susceptible functional group, exposes the abnormal cell preferentially to that drug compound or its derivative in comparison to the normal cells. In other embodiments, a Ligand Drug Conjugate compound is preferentially internalized into targeted normal cells that are peculiar to the environment of abnormal cells in comparison to normal cells in the periphery such that enzymatic or non-enzymatic action upon the Cleavable Unit of the Conjugate compound will release a NAMPT Drug Unit thereby preferentially exposing the nearby abnormal cells to a NAMPTi compound or derivative thereof.

In some embodiments, a Cleavable Unit in a Drug Linker or Ligand Drug Conjugate compound is covalently attached to a Spacer Unit (Y) that is comprised or consists of a self-immolating moiety such that enzymatic action on the Cleavable Unit or component thereof (W or W') triggers self-destruction of that Unit within Y-D of —W—Y-D or —Y(W')-D, of that Drug Linker or Ligand Drug Conjugate compound to release D as a NAMPTi compound or derivative thereof, wherein W represents a Peptide Cleavable Unit and —Y(W')— is a Glucuronide Unit.

Functional groups that provide for cleavable bonds include, by way of example and not limitation, (a) sulfhydryl groups that form a disulfide bond, which are susceptible to the greater reductive conditions of abnormal cells in comparison to normal cells or excess glutathione produced under hypoxic conditions experienced by the abnormal cells, (b) aldehyde, ketone, or hydrazine groups that form a Schiff base or hydrazone functional groups, which are susceptible to the acidic conditions of lysozymes upon selective internalization of an LDC compound having a Linker Unit with that cleavable bond into an abnormal cell in comparison to internalization into normal cells, (c) carboxylic or amino groups that form an amide bond, as in peptide bonds, that are susceptible to enzymatic cleavage by proteases produced or excreted preferentially by abnormal cells in comparison to normal cells or by a regulatory protease within a targeted cell (d) amino or hydroxyl groups that form certain urea or carbamate groups or carboxylic or hydroxy groups that form ester or carbonate groups that are susceptible to enzymatic cleavage by hydrolases or esterases that are produced or excreted preferentially by abnormal cells in comparison to normal cells.

Still other functional groups that provide for cleavable bonds are found in sugars or carbohydrates having a glycosidic linkage that are substrates for glycosides which sometimes may be produced preferentially by abnormal cells in comparison to normal cells. Alternatively, the protease, hydrolase or glycosidase enzyme required for processing of the Linker Unit to release a drug compound or active drug moeity need not be produced preferentially by abnormal cells in comparison to normal cells provided the processing enzyme is not excreted by normal cells to an extent that would cause undesired side effects from premature release of the drug compound or moeity. In other instances the required protease, hydrolase or glycosidase enzyme may be excreted, but to avoid undesired premature release of drug, it is preferred that the processing enzyme be excreted in the vicinity of abnormal cells and remain localized to that environment, whether produced by abnormal cells or nearby normal cells in response to the abnormal environment caused by the abnormal cells. In that respect W as a Peptide Cleavable Unit or W' of a Glucuronide Unit in which W is —Y(W')— is selected to be preferentially acted upon by a protease, hydrolase or glycosidase in or within the environment of abnormal cells in contrast to freely circulating enzymes. In those instances a Ligand Drug Conjugate compound is less likely to release its Drug Unit as a drug compound or active drug moeity in the vicinity of normal cells nor would it be internalized into normal cells that do intracellularly produce but do not excrete the enzyme intended for action upon the Ligand Drug Conjugate compound since such cells are less likely to display a targeted moiety required for entry by the Ligand Drug Conjugate compound.

In some embodiments, W is a Peptide Cleavable Unit comprised of an amino acid or is comprised or consists of one or more sequences of amino acids that provide a substrate for a protease present within abnormal cells or a protease localized to the environment of these abnormal cells. Thus, W may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a self-immolative moiety of a self-immolative Y wherein that moiety is a recognition sequence for that protease. In other aspects, W is a Glucuronide Unit of formula —Y(W')—, wherein W' is a carbohydrate moiety (Su) having a glycosidic bond to a heteroatom (E') attached to a self-immolative moiety of the Glucuronide's self-immolative Spacer Unit (Y) wherein the glycosidic bond is cleavable by a glycosidase preferentially produced by abnormal cells, or is found in such cells to which an LDC having that Spacer Unit and carbohydrate moiety, has selective entry due to the presence of the targeted moiety on the abnormal cells.

1.3.4 Spacer Units

A secondary linker ($L_O$) when bonded to a NAMPT Drug Unit (D) in a Linker Unit attached to only one Drug Unit and having a PAB or PAB-related self-immolative Spacer Unit is in preferred embodiments is represented by the structure of (1) or (2):

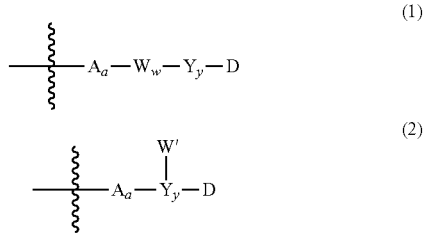

wherein in formula (1) subscript w is 0 or 1, indicating the absence or presence of W, respectively, wherein when present W is a Peptide Cleavable Unit, Y of $Y_y$ is the PAB or PAB-type Spacer Unit and the peptide bond between W and Y is cleavable by a protease to initiate release of D as a NAMPTi compound or derivative thereof and wherein formula (2) is related to formula (1) by replacing $W_w$ with a Glucuronide Unit of formula —Y(W')—, wherein Y of $Y_y$ is the PAB or PAB-type Spacer Unit and W' is glycosidic-bonded carbohydrate wherein the glycosidic bond between W' and Y is cleavable by a glycosidase to initiate to initiate release of D as a NAMPTi compound or derivative thereof, and wherein in either formula subscript y is 1 or 2, A is an optional first Stretcher Unit and subscript a is 0 or 1 indicating the absence or presence of A, respectively.

In those embodiment in which a second Spacer Unit (Y') is present so that subscript y is 2, formula (1) and formula (2) is represented by formula (1a) and formula (1b) as previously described for secondary linkers. In formulae (1a) or (1b) when Y' is present, Y' is sometimes another Spacer Unit that is also capable of spontaneous decomposition subsequent to self-immolation of the first Spacer Unit, which is the PAB or PAB-type self-immolative Spacer Unit, and is some preferred embodiments that second self-immolative Spacer Unit is a carbamate functional group represented by —OC(=O)—$X^b$—, wherein $X^b$ is a optionally substituted heteroatom provided by the NAMPT Drug Unit, preferably by its Tail ($T_N$) Unit and is preferably —NH—, —O—, or —S—. In formula (1a) or (1b) when Y' is absent (i.e., subscript y is formula (1) or formula (2) is 1), Y' is replaced by a optionally substituted heteroatom, which in preferred embodiments is provided by the NAMPT Tail ($T_N$) Unit of a NAMPTi compound or derivative thereof, which in some of these embodiments is designated as $X^a$, wherein $X^a$ is preferably —O— or —S—.

Exemplary PAB or PAB-related self-immolative moieties when present in a secondary linker bonded to -D or —Y'-D, in which subscript y is 1 or 2, respectively, have a central arylene or heteroarylene substituted by a masked electron donating group (EDG) and a benzylic carbon bonded directly to D through a heteroatom or shared functional group, or is bonded to D indirectly through an intervening second Spacer Unit (Y'), wherein the masked EDG and benzylic carbon substituents are ortho or para to each other (i.e., 1,2 or 1,4 substitution pattern). In some of those embodiments the second Spacer Unit (Y') when present is capable of self-immolation or is absent.

Exemplary structures of self-immolative Spacer Units having a PAB or PAB-related self-immolative moiety in which the central (hetero)arylene has the requisite 1,2 or 1,4 substitution pattern that allows for 1,4- or 1,6-fragmentation to release D or —Y'-D as a NAMPTi compound or derivative thereof or precursor thereto, as when Y' of released Y'-D is capable of self-immolation, are represented by:

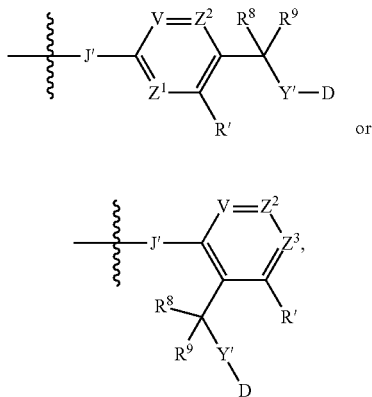

wherein the wavy line to J' indicates the site of covalent attachment to a primary linker ($L_R$), preferably $L_{SS}$ or $L_S$) or the remainder the secondary linker through J' or through a functional group comprising J', wherein J' is a heteroatom, optionally substituted where permitted (i.e., optionally substituted —NH—), D is a NAMPT Drug Unit, Y' when present is a functional group or a second self-immolative moiety, such as a carbamate functional group or a MAC Unit, or Y' is absent and is replaced in the above formulae by an optionally substituted heteroatom from the NAMPT Drug Unit, preferably from its Tail ($T_N$) Unit, and wherein V, $Z^1$, $Z^2$, $Z^3$ are independently =N or =C($R^{24}$)—, wherein each $R^{24}$ is independently selected from the group consisting of hydrogen and $C_1$-$C_{12}$ alkyl, $C_2$-$C_{12}$ alkenyl, $C_2$-$C_{12}$ alkynyl, $C_6$-$C_{24}$ aryl, ($C_6$-$C_{24}$ aryl)-$C_1$-$C_{12}$ alkyl-, $C_5$-$C_{24}$ heteroaryl and ($C_5$-$C_{24}$ heteroaryl)-$C_1$-$C_{12}$ alkyl-, optionally substituted, and halogen and other electron withdrawing groups; R' is hydrogen or $C_1$-$C_{12}$ alkyl, $C_2$-$C_{12}$ alkenyl, $C_2$-$C_{12}$ alkynyl, $C_6$-$C_{24}$ aryl, ($C_6$-$C_{24}$ aryl)-$C_1$-$C_{12}$ alkyl-, $C_5$-$C_{24}$ heteroaryl, or $C_5$-$C_{24}$ heteroaryl)-$C_1$-$C_{12}$ alkyl, optionally substituted, or an electron donating group; and $R^8$ and $R^9$ are independently selected from the group consisting of hydrogen, $C_1$-$C_{12}$ alkyl, $C_2$-$C_{12}$ alkenyl, $C_2$-$C_{12}$ alkynyl, $C_6$-$C_{24}$ aryl and $C_5$-$C_{24}$ heteroaryl, optionally substituted, or both $R^8$ and $R^9$ together with the carbon atom to which they are attached define a $C_3$-$C_{20}$ carbocyclo. In preferred embodiments, one or more of V, $Z^1$, $Z^2$ or one or more of V, $Z^2$, $Z^3$ is =CH—. In other preferred embodiments R' is hydrogen or an electron donating group, including $C_1$-$C_6$ ethers such as —$OCH_3$ and —$OCH_2CH_3$, or one of $R^8$, $R^9$ is hydrogen and the other is hydrogen or $C_1$-$C_4$ alkyl. In more preferred embodiments two or more of V, $Z^1$ and $Z^2$ are =CH— or two or more of V, $Z^2$ and $Z^3$ are =CH—. In other more preferred embodiments $R^8$, $R^9$ and R' are each hydrogen.

In some embodiments, —W—$Y_y$-D, as shown in structure (1) in which subscript y is 2, and wherein W is a Peptide Cleavable Unit, has the structure of:

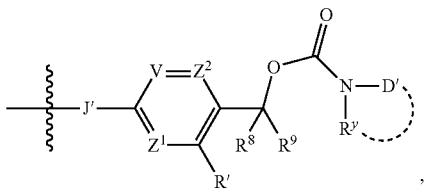

wherein —N($R^y$)D' represents D, wherein D' is the remainder of D, and wherein the dotted line indicates optional cyclization of $R^y$ to D', wherein $R^y$ is hydrogen or $R^y$ is optionally substituted $C_1$-$C_6$ alkyl in absence of cyclization to D' or optionally substituted $C_1$-$C_6$ alkylene when cyclized to D'; -J'- is an optionally substituted heteroatom where permitted, including O, S and optionally substituted —NH—, wherein J' or a functional group comprised of J' is bonded to W as indicated by the adjacent wavy line, wherein cleavage of that bond initiates release of D as a primary or secondary amine-containing NAMPTi compound or derivative thereof from a compound of a Ligand Drug Conjugate composition and wherein the remaining variable groups are as defined above. Those variables are selected so that reactivity of J' when released from processing of Peptide Cleavable Unit W at the targeted site is balanced with the reactivity of Y'-D or D eliminated from the PAB or PAB-type self-immolative moiety and the stability of the quinone-methide type intermediate resulting from that elimination.

In those embodiments, the intervening moiety between D and the benzylic carbon (—C($R^8$)($R^9$)—) of the PAB or PAB-related self-immolative moiety of the first self-immolative Spacer Unit Y is Y' so that a carbamate functional group is shared between Y and D. In such embodiments fragmentation of the Spacer Unit Y with expulsion of —Y'-D is followed by loss of $CO_2$ for release of D as NAMPTi compound or derivative thereof having a primary or secondary amine whose nitrogen atom was bonded to the secondary linker comprised of the PAB or PAB-related self-immolative moiety.

In some embodiments, a self-immolative Spacer Unit having a PAB or PAB-type moiety bound to —Y'-D has the structure of:

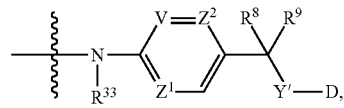

wherein the wavy line adjacent to the nitrogen atom indicates the site of covalent attachment to W, wherein that bond to W is cleavable by a protease, and $R^{33}$ is hydrogen or optionally substituted $C_1$-$C_6$ alkyl, preferably hydrogen or $C_1$-$C_4$ alkyl, more preferably hydrogen, —$CH_3$ or —$CH_2CH_3$. In more preferred embodiments V, $Z^1$ and $Z^2$ are each =CH— and $R^{33}$ is hydrogen.

Without being bound by theory, the sequential self-immolation of Y in which $R^{33}$ is —H and Y' is a carbamate functional group is illustrated for Ligand Drug Conjugates and Drug Linker compounds having a Peptide Cleavable Unit as:

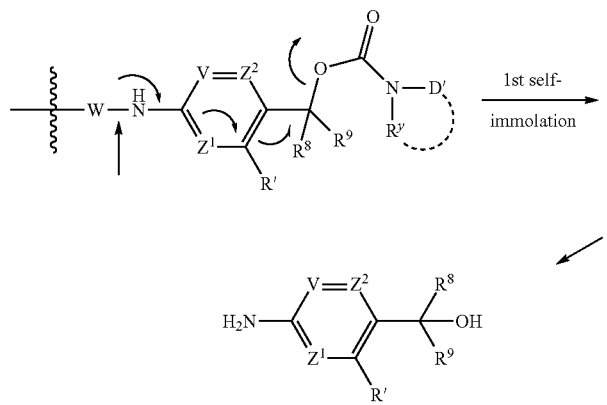

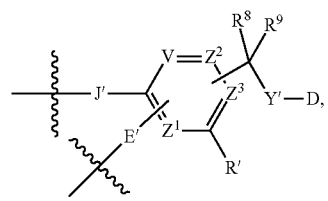

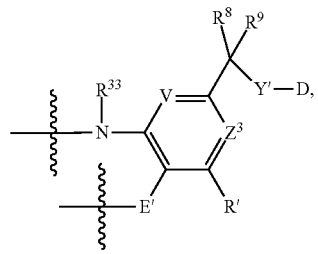

In some embodiments, —$Y_y$(W')-D, as shown in structure (2) in which subscript y is 2 and W is a Glucuronide Unit of formula —Y(W')— have structures of:

wherein J' is an optionally substituted heteroatom where permitted, including O, S and optionally substituted —NH—, and the wavy line to J' indicates the site of stable covalent bonding (i.e., is not processed or is stable at the targeted site) to $L_R$, which is preferably $L_{SS}$ or $L_S$, or the remainder of the secondary linker through said heteroatom or a functional group comprised of that heteroatom; E', independently selected from J', is an electron donating moiety such as —O—, —S—, or —N($R^{33}$)—, wherein $R^{33}$ is as defined above, wherein the electron donating ability of E' is attenuated by its bonding to the carbohydrate moiety (Su) of W', wherein W' is -E'-Su, as indicated by the wavy line adjacent to E', wherein Su boned to E' provides for a cleavage site for a glycosidase, and E' and the benzylic carbon of the —C($R^8$)($R^9$)—Y'-D moiety are bonded to the central (hetero)arylene at positions defined by V, $Z^1$, $Z^2$ or $Z^3$, requiring at least two of V, $Z^1$, $Z^2$, $Z^3$ to be =C($R^{24}$)— in which one $R^{24}$ substituent is the —C($R^8$)($R^9$)—Y'-D moiety and the other is W', such that W' and the —C($R^8$)($R^9$)—Y'-D moiety are in a 1,2 or 1,4 relationship so as to permit the 1,4- or 1,6-fragmentation on cleavage to release D or Y'-D, or a precursor thereto, as a NAMPTi compound or derivative thereof; and the remaining variable groups are as previously defined for PAB or PAB-related self-immolative Spacer Units that are bonded to a Peptide Cleavable Unit. In preferred embodiments J' is —O—, —N($R^{33}$)— wherein $R^{33}$ is preferably hydrogen or $C_1$-$C_4$ alkyl. In other preferred embodiments one or both of the remaining V, $Z^1$, $Z^2$, $Z^3$ variable groups not bonded to W' and —C($R^8$)($R^9$)—Y'-D is =CH—. In still other preferred embodiments R' is hydrogen or an electron withdrawing group, including —CN, —$NO_2$ or halogen, or one of $R^8$, $R^9$ is hydrogen and the other is hydrogen or $C_1$-$C_4$ alkyl. In more preferred embodiments both remaining variable groups from V, $Z^1$, $Z^2$, $Z^3$ are =CH—. Without being bound by theory it is believed when R' is an electron withdrawing group in a Glucuronide Unit, that group makes the glycosidic bond of W' more susceptible to glycosidase cleavage thereby assisting in the release of D, from a Ligand Drug Conjugate compound reliant on that cleavage.

In some embodiments, for a secondary linker-D moiety of structure (2), a self-immolative Spacer Unit having a PAB or PAB-type moiety bound to Y'-D has the structure of:

wherein the variable groups are as previously defined. In preferred embodiments both of V, $Z^3$ are =CH—. In other preferred embodiments $R^{33}$ is hydrogen. In still other more preferred embodiments, $R^8$ and $R^9$ are each hydrogen and R' is hydrogen or —$NO_2$.

The central (hetero)arylene of a self-immolative moiety may be further substituted to affect the kinetics of the 1,2- or 1,4-elimination in order to modulate the release of D, to improve the physiochemical properties of the Ligand Drug Conjugate (e.g., reduce hydrophobicity) into which it is incorporated and/or increase the sensitivity of the bond to protease or glycosidase cleavage. For example, to increase sensitivity to glycosidase cleavage R' can be an electron withdrawing group such halogen, —CN or —$NO_2$, as when E' of W' is an oxygen atom of a glycosidic bond within a Glucuronide Unit that is cleavable by a glycosidase.

Exemplary and non-limiting examples of self-immolative structures are provided by Alouane et al. "Self-immolative spacers: Kinetic aspects, structure-property relationships, and applications" *Angew. Chem. Int. Ed.* (2015): 54: 7492-7509; Blencowe et al. "Self-immolative linkers in polymeric delivery systems" *Polym. Chem.* (2011) 2: 773-790; Greenwald et al. "Drug delivery systems employing 1,4- or 1,6-elimination: poly(ethylene glycol) prodrugs of amine-containing compounds" *J. Med. Chem.* (1999) 42: 3657-3667; and in U.S. Pat. Nos. 7,091,186; 7,754,681; 7,553, 816; and 7,989,434, all of which are incorporated by reference herein in their entireties with the structures and variable groups provided therein specifically incorporated by reference.

In preferred embodiments Y' represents a carbamate functional group shared with D so that Y' is a second self-immolative Spacer Unit that spontaneously decomposes to $CO_2$ and D in the form of a NAMPTi compound or derivative thereof, in the manner as shown above, and occurs subsequent to 1,6-fragmentation of the PAB or PAB-type moiety of the first self-immolative Spacer Unit. In other preferred embodiments Y' is a methylene carbamate unit having the structure when bonded to D of:

heteroatom from that functional group that becomes incorporated into the methylene carbamate unit; $R^{51}$, $R^{52}$ and $R^{53}$ independently are hydrogen, optionally substituted $C_1$-$C_{12}$ alkyl, optionally substituted $C_6$-$C_{24}$ aryl, or optionally substituted C-linked $C_5$-$C_{24}$ heteroaryl, or $R^{51}$ and $R^{52}$ together with the nitrogen and carbon atoms to which they are attached define an optionally substituted $C_3$-$C_{20}$ heterocyclo and $R^{53}$ is hydrogen or optionally substituted $C_1$-$C_{12}$ alkyl.

Without being bound by theory, the sequential self-immolation of Y and Y' is illustrated as follows for Ligand Drug Conjugates and Drug Linker compounds having a Glucuronide Unit in which $R^{33}$ is —H and E' of W' is an oxygen atom (O') of a glycosidic bond:

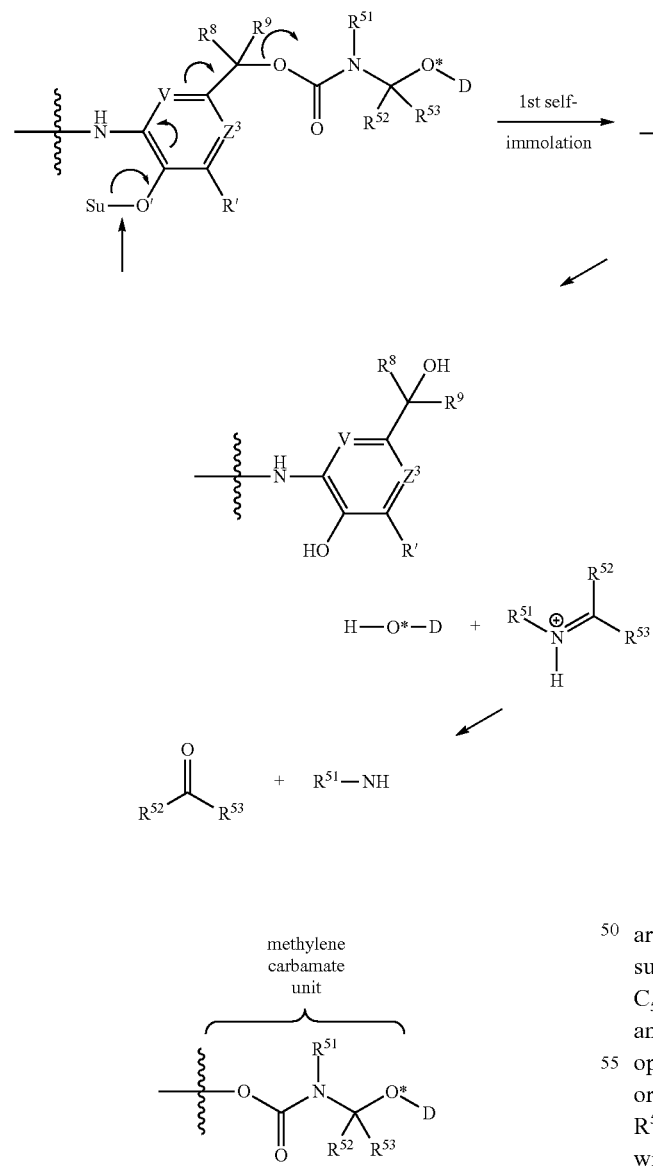

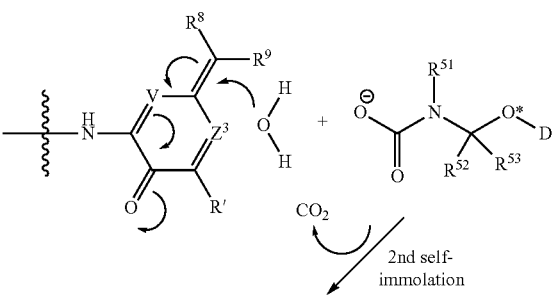

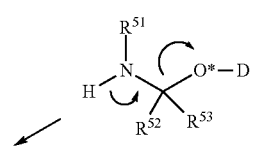

methylene carbamate unit

or a pharmaceutically acceptable salt thereof, wherein the wavy line indicates covalent attachment of the methylene carbamate unit to a first self-immolative Spacer Unit (Y); D is a Drug Unit of a NAMPTi compound or derivative thereof having a hydroxyl functional group that has been incorporated into the methylene carbamate unit; O* is the oxygen In preferred embodiments $R^{51}$, $R^{52}$ and $R^{53}$ independently are hydrogen, optionally substituted $C_1$-$C_6$ alkyl, optionally substituted $C_6$-$C_{10}$ aryl, or optionally substituted C-linked $C_5$-$C_{10}$ heteroaryl, or $R^{51}$ and $R^{52}$ together with the nitrogen and carbon atoms to which they are attached define an optionally substituted azetidinyl, pyrrolodinyl, piperidinyl, or homopiperidinyl moiety. In more preferred embodiments $R^{51}$, $R^{52}$ and $R^{53}$ are each hydrogen or $R^{5'}$ and $R^{52}$ together with the nitrogen and carbon atoms to which they are attached define an optionally substituted pyrrolodinyl or piperidinyl moiety and $R^{53}$ is hydrogen.

Embodiments of Ligand Drug Conjugates of Formula 1 and/or Formula 2 having a Peptide Cleavable Unit and incorporating a MAC Unit as a second self-immolative moiety, are represented by the structure of Formula 3 and/or Formula 4:

(Formula 3)

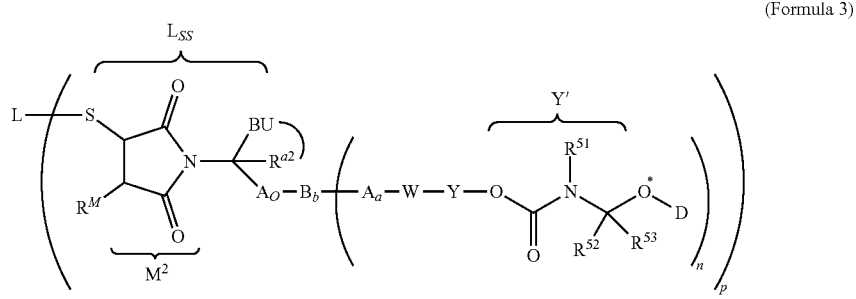

(Formula 4)

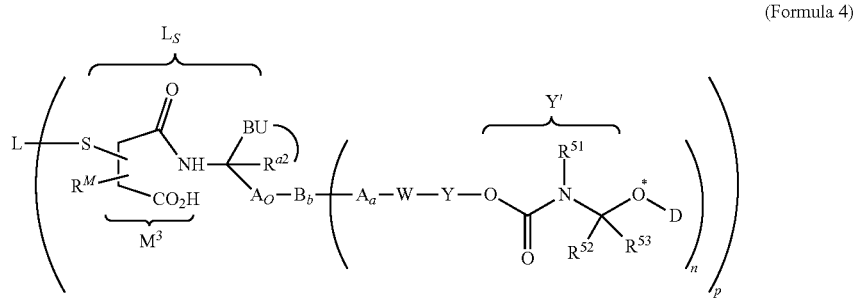

or a pharmaceutically acceptable salt thereof, and corresponding embodiments for Drug Linker Compounds are represented by Formula III, (Formula III)

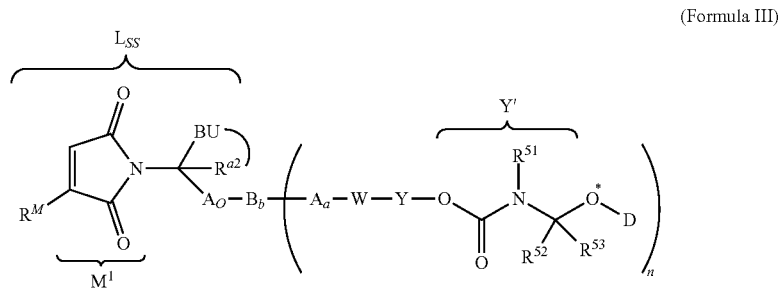

or a pharmaceutically acceptable salt thereof, wherein W is a Peptide Cleavable Unit and Y is a first self-immolative Spacer Unit and the indicated second self-immolative Spacer Unit is the MAC Unit so that subscript y is 2 in Formula 1 and Formula 2; and the remaining variable groups are as previously defined.

Embodiments of Ligand Drug Conjugates of Formula 1 and/or Formula 2 and Drug Linker Compounds of Formula I having a Glucuronide Unit and incorporating a MAC Unit as a second self-immolative moiety have structures analogous to Formula 3, Formula 4, and Formula III in which —W—Y— in these formulae are replaced by —Y(W')—, wherein Y is a first self-immolative Spacer attached to W' through a glycosidic bond as described by embodiments for Glucuronide Units.

1.4 NAMPT Drug Unit

A NAMPT Drug Unit (D) is covalently attached to $L_R$ or $L_O$ of a Linker Unit, depending on the absence of presence of $L_O$, respectively, of a Formula land/or Formula 2 Ligand Drug Conjugate compound or the Linker Unit of a Drug Linker compound of Formula I through a component of D other than its head group component, wherein that component is capable of interacting with enzymatically competent NAMPT homodimer at its nicotinamide binding site when the NAMPT Drug Unit is released from the Ligand Drug Conjugate compound or Drug Linker compound as a NAMPTi compound or derivative. That release occurs subsequent to enzymatic or non-enzymatic processing of the Linker Unit in the Conjugate compound or Drug Linker compound. In one preferred group of embodiments that processing occurs in a secondary linker of the Ligand Unit to either cleave off the NAMPT Drug Unit with or without retention of some fragment of the Linker Unit when subscript w is 0 or upon enzymatic processing of a Cleavable Unit (W), when subscript w is 1. In the latter instance, W is preferably a Peptide Cleavable Unit, which is capable of processing by a protease, preferably by cleavage of a peptide bond to Y, or W is preferably a Glucuronide Unit of formula —Y(W'), wherein Y is a self-immolative Spacer Unit and W' is attached to that Spacer Unit through a glycosidic bond that is capable of cleavage by a glycosidase.

In preferred embodiments the component of the NAMPT Drug (D) Unit, which is the site of covalent attachment to the Linker Unit of a Drug Linker compound or a Conjugate compound of a Ligand Drug Conjugate composition is the NMAPT Tail ($T_N$) Unit of a NAMPT Drug Unit having the general formula of:

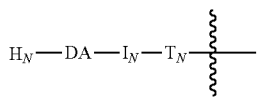

or a salt thereof, preferably one that is pharmaceutically acceptable, wherein the wavy line indicates the site of covalent attachment to $L_O$ or $L_R$ in Formula 1, Formula 2 or Formula I; $H_N$ is a NAMPT Head Unit, DA is a NAMPT Donor-Acceptor Unit, $I_N$ is a NAMPT Interconnecting Unit and $T_N$ is the aforementioned NAMPT Tail Unit. In those embodiments $T_N$ provided by a NAMPTi compound or derivative thereof has or is modified to have a functional group having an optionally substituted heteroatom that serves as handle for attachment of $T_N$ to a Linker Unit of a Drug Linker compound of Formula I or a Conjugate compound of a Ligand Drug Conjugate composition of Formula 1 and/or Formula 2 and thus becomes the site of incorporation of a NAMPTi compound or derivative thereof as a NAMPT Drug Unit into that Drug Linker or Conjugate compound. That incorporation is not limiting to the identity of the NAMPT Drug Unit since it makes no inference as to the manner of preparation of such compounds as the remainder of the NAMPT Drug Unit can be constructed subsequent to covalent attachment of $T_N$, either as a discrete component or as some intermediate comprised of $T_N$, to the Linker Unit or precursor thereof.

In one such embodiment in which subscript w is 1, initiation of release of D as a NAMPTi compound or derivative thereof occurs from protease cleavage of a Peptide Cleavable Unit in a secondary linker of the Ligand Unit. In another such embodiment initiation of D release occurs with glycosidase cleavage of a Glucuronide Unit in the secondary linker. Typically, when W is a Peptide Cleavable Unit and subscript y is 0, D is directly released as a NAMPTi compound or derivative thereof having the formula of $H-X^b-T_N-I_N-DA-H_N$, wherein $X^b$ is the optionally substituted heteroatom of the functional group of $T_N$ that was the site of covalent attachment of the NAMPT Drug Unit to the Linker Unit.

In preferred embodiments in which subscript y is 0 and the covalent bond of W-D is cleaved by the protease, $X^b$ is preferably —NH—, —O— or —S— from an amino, hydroxyl or thiol-containing functional group of $T_N$. In other preferred embodiments in which subscript y is 1 or 2 the covalent bond of W—Y is cleaved by the protease so that Y-D or Y—Y'-D is the initially released moeity, either of which may be biologically active as an inhibitor of NAMPT in its own right as a derivative of a NAMPTi compound, if Y is not a self-immolative Spacer Unit.

In other preferred embodiments in which subscript y is 1, Y is a self-immolative Spacer Unit so that initially released Y-D undergoes spontaneous fragmentation to a NAMPTi compound or derivative thereof having the formula of $H-X^a-T_N-I_N-DA-H_N$, wherein X' is the optionally substituted heteroatom of the functional group of $T_N$ and is the site of covalent attachment of the NAMPT Drug Unit to the Linker Unit and is preferably —O— or —S— from a hydroxyl or thiol-containing functional group of $T_N$.

If subscript y is 2 and W is a Peptide Cleavable Unit that is attached to a self-immolative Spacer Unit the initial release of Y—Y'-D is followed by self-immolation of Y to provide Y'-D, which itself may be biologically active as an inhibitor of NAMPT in its own right as a derivative of a NAMPTi compound, if Y' is not a self-immolative Spacer Unit. If Y' is also capable of spontaneous decomposition, as when Y' is a carbamate functional group of formula —OC(=O)—$X^b$—, or a MAC Unit as for example of formula —OC(=O)NH—CH$_2$—$X^b$—, wherein $X^b$ is the optionally substituted heteroatom of the functional group of $T_N$ and is the site of covalent attachment of the NAMPT Drug Unit to the Linker Unit, then D is eventually released as a NAMPTi compound or derivative thereof having the formula of $H-X^b-T_N-I_N-DA-H_N$, wherein $X^b$ is preferably optionally substituted —NH—, —O—, or —S—.

In another such embodiment in which subscript w is 1, initiation of release of D as a NAMPTi compound or derivative thereof occurs from glycosidase cleavage of a Glucuronide Unit of formula —Y(W)—, in which Y is a self-immolative Unit and which requires subscript y to be 1 or 2. If subscript y is 1, glycosidase action releases Y-D, which spontaneously fragments to a NAMPTi compound or derivative thereof having the formula of $H-X^a-T_N-I_N-DA-H_N$, wherein $X^a$ is the optionally substituted heteroatom of the functional group of $T_N$ and is the site of covalent attachment to the Linker Unit and is preferably —O— or —S— from a hydroxyl or thiol-containing functional group of $T_N$. If subscript y is 2, glycosidase action initially releases Y—Y'-D, which provides Y'-D after spontaneous fragmentation of Y, which itself may be biologically active as an inhibitor of NAMPT in its own right as a derivative of a NAMPTi compound, if Y' is not a self-immolative Spacer Unit. If Y' is also capable of spontaneous decomposition as when Y' is a carbamate functional group of formula —OC(=O)—$X^b$—, or a MAC Unit, as for example, of formula —OC(=O)NH—CH$_2$—$X^b$—, wherein $X^b$ is the optionally substituted heteroatom of the functional group of $T_N$ and is the site of covalent attachment to the Linker Unit, then D is eventually released as a NAMPTi compound or derivative thereof having the formula of $H-X^b-T_N-I_N-DA-H_N$, wherein $X^b$ is preferably optionally substituted —NH—, —O—, or —S—.

Preferred NAMPT Drug Units are provided by combinations of any one of the following NAMPT Head ($H_N$), NAMPT Donor Acceptor (DA), NAMPT Interconnecting ($I_N$) and NAMPT Tail ($T_N$) Units. Particularly preferred combinations provide NAMPT Drug Units of the following structures:

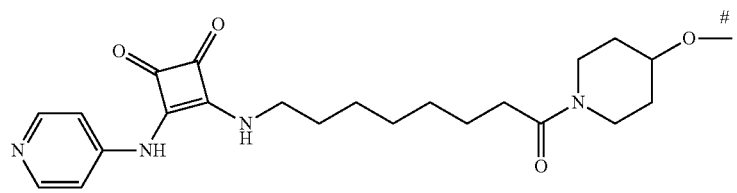

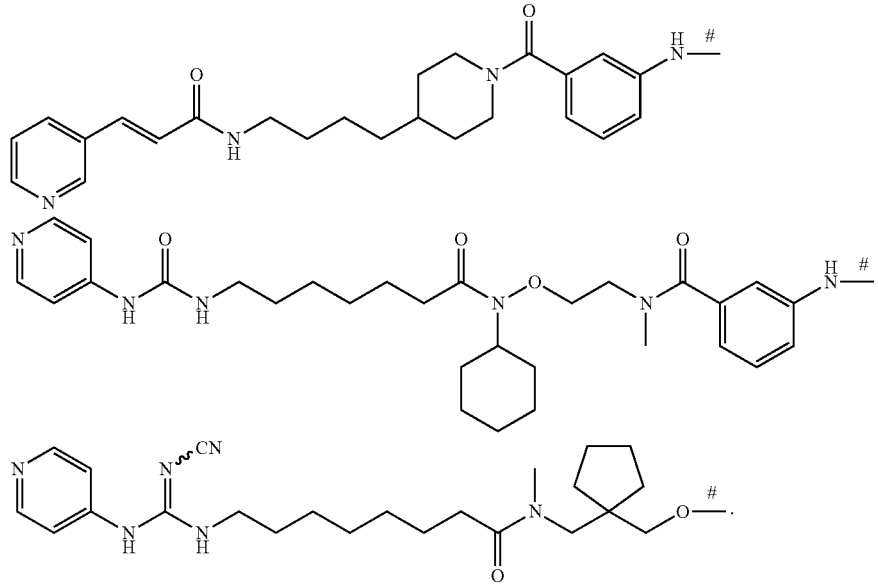

1.4.1 NAMPT Head Unit

A NAMPT Head ($H_N$) Unit is a component of NAMPTi compound or derivative thereof or a NAMPT Drug Unit of that compound or derivative that is covalently attached to or incorporates in whole or in part the NAMPT Donor Acceptor (DA) Unit of that compound and is capable of interacting with the binding site of NAMPT normally occupied by the pyridine moiety of nicotinamide prior to its enzymatic conversion to nicotinamide mononucleotide (NMN). In some embodiments the NAMPT Head ($H_N$) Unit, or a $H_N$-DA moiety in which $H_N$ incorporates the DA Unit at least in part, is a $C_5$-$C_{24}$ heteroaryl or partially aromatic $C_8$-$C_{24}$ heterocyclyl, optionally substituted, either of which is comprised of an optionally substituted 5- or 6-membered nitrogen-containing heteroaromatic ring system. In those embodiments in which the $H_N$ Unit incorporates the DA Unit at least in part, such incorporation preferably takes the form of a 5- or 6-membered aromatic or non-aromatic ring system in which the DA Unit attached to the optionally substituted 6-membered nitrogen-containing heteroaromatic ring system of $H_N$ is cyclized back to that ring system, so as to define a $H_N$-DA moiety having a partially or fully aromatic 6,5- or 6,6 fused ring system.

In preferred embodiments $H_N$ is a pyridine mimetic in which the optionally substituted $C_5$-$C_{24}$ heteroaryl or partially aromatic $C_8$-$C_{24}$ heterocyclyl of that Unit has a pKa of between about −2 to about 7, and is therefore weakly basic or remains uncharged under normal physiological conditions, and is capable of interacting with the nicotinamide binding site of enzymatically competent NAMPT dimer by one or more interactions engaged by the pyridine moiety of nicotinamide. In preferred embodiments, a pyridine mimetic is comprised of a 6-membered optionally substituted nitrogen-containing heteroaromatic ring system and is more preferably pyridin-3-yl or pyridin-4-yl, optionally substituted and/or optionally fused to an optionally substituted $C_5$ or $C_6$ heterocycle, where appropriate, wherein the pyridinyl moiety is attached by an aromatic carbon atom to the Donor Acceptor (DA) Unit. Accordingly more preferred pyridine mimetics as $H_N$ include those having the structures of:

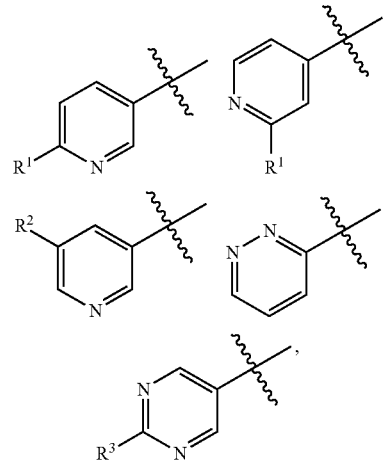

or a pharmaceutically acceptable salt thereof, wherein $R^1$ is hydrogen on an electron withdrawing group, preferably hydrogen, —$NH_2$ or chloro; $R^2$ is halogen, preferably fluoro; $R^3$ is hydrogen or an electron donating group, preferably hydrogen or —$NH_2$; and the wavy line indicates the site of covalent attachment to DA and an adjacent aromatic carbon atom thereto is the site of said optional cyclization by DA to provide $H_N$-DA in which $H_N$ incorporates at least part of DA.

In other more preferred embodiments $H_N$ is a pyridine mimetic having the structure of:

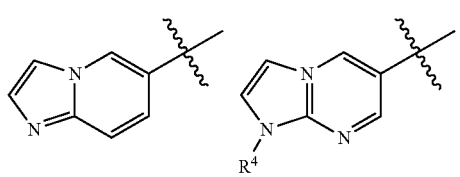

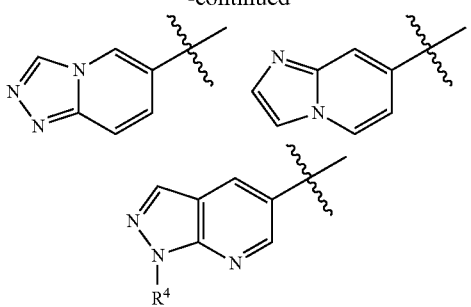

or a pharmaceutically acceptable salt thereof, wherein the wavy line indicates the site of covalent attachment to DA and an adjacent aromatic carbon atom thereto is the site of said optional cyclization by DA for $H_N$-DA in which $H_N$ incorporates at least part of DA; and $R^4$ is hydrogen or optionally substituted $C_1$-$C_4$ alkyl, preferably hydrogen methyl or ethyl, more preferably hydrogen or methyl.

In other preferred embodiments, a pyridine mimetic is comprised of a 5-membered nitrogen-containing heteroaromatic ring system, optionally substituted, wherein DA is attached to an aromatic carbon atom or nitrogen atom of that ring system. Accordingly more preferred pyridine mimetics as $H_N$ include those having the structures of:

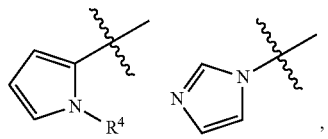

or a pharmaceutically acceptable salt thereof wherein $R^4$ is hydrogen or optionally substituted $C_1$-$C_4$ alkyl, preferably hydrogen, methyl or ethyl, more preferably hydrogen.

In more preferred embodiments DA is covalently attached to a pyridine mimetic comprised of an optionally substituted 6-membered nitrogen-containing heteroaromatic ring system at a skeletal aromatic carbon atom of that ring system without cyclization back to the pyridine mimetic. In other preferred embodiments DA is cyclized back to a pyridine mimetic having an optionally substituted 6-membered nitrogen-containing heteroaromatic ring system at an adjacent skeletal aromatic carbon of that ring system to form a $H_N$-DA moiety. In some of those preferred embodiments cyclization occurs through a heteroatom of DA or through an oxygen, sulfur or nitrogen heteroatom, optionally substituted, introduced between $H_N$ and DA, which in either instance incorporates part of the Donor Acceptor (DA) Unit into $H_N$ in the form of a 5-membered aromatic so as to define a $H_N$-DA moiety having a fully aromatic 6,5-fused ring system. In other preferred embodiments in which DA is cyclized back to the pyridine mimetic at an adjacent skeletal aromatic carbon to form a $H_N$-DA moiety in which $H_N$ incorporates part of DA, DA is cyclized back to that adjacent skeletal carbon atom through an optionally substituted methylene introduced between $H_N$ and DA in the form of a non-aromatic 5-membered ring so as to define a $H_N$-DA moiety having a partially aromatic 6,5-fused ring system. Those embodiments defining a $H_N$-DA moiety are sometimes collectively referred to as a nicotinamide moiety as further described below in embodiments of the NAMPT Donor Acceptor Unit.

In any one of the aforementioned embodiments, more preferably $H_N$ as a pyridine mimetic or $H_N$-DA as a nicotinamide mimetic is capable of interacting with Phe 193 on one monomer of NAMPT and/or Tyr 18' of the other monomer when these monomers form an enzymatically competent NAMPT homodimer and wherein each NAMPT monomer has the amino acid sequence of NCBI Reference Sequence NP_005737.1. Without being bound by theory those interactions may occur by a π-π offset stacking with one or both aromatic side chains of those two amino acid residues.

1.4.2 NAMPT Donor Acceptor Unit

A NAMPT Donor-Acceptor (DA) Unit is a component of a NAMPTi compound or derivative thereof of a NAMPT Drug Unit of that compound or its derivative that is bonded to or is incorporated into its Head Unit ($H_N$) as a $H_N$-DA moeity and is also bonded to the NAMPT Interconnecting ($I_N$) Unit of that compound or derivative. A Donor-Acceptor (DA) Unit is comprised of a hydrogen bond donor acceptor functional group, wherein a heteroatom of that functional group is attached to $H_N$, or DA is an organic moiety comprised of that functional group wherein a carbon atom of the organic moiety is attached to $H_N$, which in some embodiments is the carbon atom to which the hydrogen bond donor acceptor functional group is attached, wherein attachment of the functional group heteroatom or carbon atom of the organic moiety of DA is to a carbon skeletal atom at position 2 or 3 of the 5-membered nitrogen-containing heteroaromatic ring system of a NAMPT Head ($H_N$) Unit or at position 3 or 4 of the 6-membered nitrogen-containing heteroaromatic ring system of $H_N$, with optional cyclization of DA Unit back to an adjacent skeletal carbon atom of the nitrogen-containing heteroaromatic ring system through a heteroatom of DA or through an optionally substituted non-aromatic carbon atom or an aromatic optionally substituted nitrogen, oxygen or sulfur atom resulting in a $H_N$-DA moiety having an optionally substituted, partially aromatic or fully aromatic fused ring system, wherein said bonding of DA is in relation to a skeletal nitrogen atom of the 5- or 6-membered nitrogen-containing aromatic ring system and wherein said optional cyclization to the adjacent aromatic carbon atom of the nitrogen-containing heteroaromatic ring system substantially retains the hydrogen bonding ability of the donor acceptor functional group of DA.

In preferred embodiments $H_N$ is a pyrimidine mimetic so that the $H_N$-DA moiety with or without cyclization of DA back to the pyridine mimetic is a nicotinamide mimetic. In those embodiment in which DA is cyclized back to the pyridine moeity it does so to form a partially or fully aromatic 6,5- or 6,6-fused ring system, which incorporates at least in part the DA Unit.

In other preferred embodiments, DA is comprised of an optionally substituted amide functional group, which is the hydrogen bond donor acceptor functional group of DA, and is capable of interacting at the nicotinamide binding site with one or more of the same interactions as the amide functional group of NMN. DA in a NAMPT Drug Unit is thus capable of interacting with Ser 275 of an NAMPT monomer of an enzymatically competent NAMPT homodimer when released from a Ligand Drug Conjugate compound or Drug Linker compound, wherein each NAMPT monomer has the amino acid sequence of NCBI Reference Sequence NP_005737.1. In some of those embodiments, the amide functional group of DA is capable of interacting with Ser 275 at the hydroxyl side chain of that amino acid residue through hydrogen bonding, and/or is also capable of interacting with one or more amino acid residues selected from the group consisting of Asp 219, Ser 241, and Val 242 either directly by hydrogen bonding or indirectly through hydrogen bonding network(s) involving the intermediacy of water molecule(s).

Accordingly preferred DA Units have or are comprised of an optionally substituted amide functional group, with preferred embodiments comprising or having the structure of:

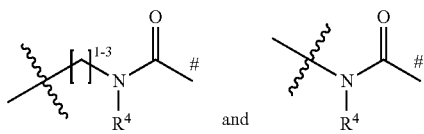

wherein $R^4$ is hydrogen or optionally substituted $C_1$-$C_4$ alkyl, preferably hydrogen, methyl or ethyl, more preferably hydrogen, wherein the nitrogen atom bonded to $R^4$ is the site of optional cyclization to $H_N$ so that $R^4$ is replaced by a bond and the wavy line indicates the site of covalent attachment to $H_N$ or to the remainder of DA, which is bonded to $H_N$; and the pound sign (#) indicates the site of covalent attachment to $I_N$.

Other DA Units have or are comprised of an amide bioisosteres structure with preferred embodiments comprising or having the structures of:

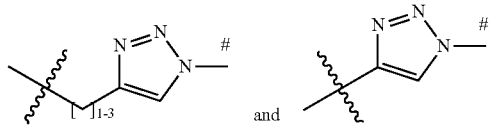

and salts thereof, including but not limiting to pharmaceutically acceptable salts, wherein the wavy line indicates the site of covalent attachment to $H_N$ or the remainder of DA; and the pound sign (#) indicates the site of covalent attachment to $I_N$, and other preferred embodiments in which DA has or is comprised of an amide bioisostere is comprised of or have the structures of:

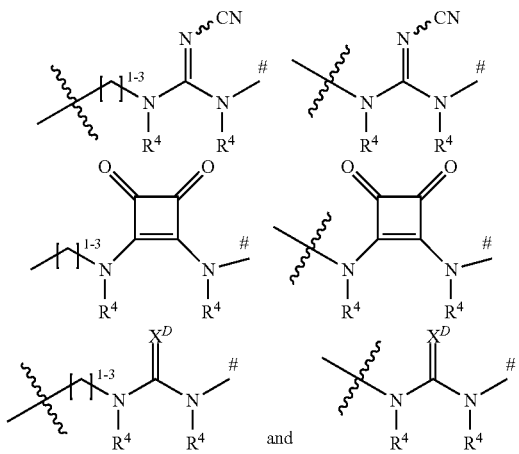

and salts thereof, including but not limiting to pharmaceutically acceptable salts, wherein $X^D$ is O, S or $NR^{4D}$; $R^4$ and $R^{4D}$ are independently selected from the group consisting of hydrogen and optionally substituted $C_1$-$C_4$ alkyl or both $R^4$ together with the nitrogen atoms to which they are attached along with the intervening carbon atom(s) define an optionally substituted 5- or 6-membered heterocyclo; and the wavy line indicates the site of covalent attachment to $H_N$ or the remainder of DA that is bonded to $H_N$; and the pound sign (#) indicates the site of covalent attachment to $I_N$, and wherein a nitrogen atom bonded to one of $R^4$ or the nitrogen atom bonded to $R^{4D}$ is the site for optional cyclization of those amide bioisosteres to $H_N$ so that one of $R^4$ or $R^{4D}$ is replaced by a bond to the pyridine mimetic through an intervening optionally substituted carbon atom or an optionally substituted heteroatom, such NH, O or —S(=O)$_{0-2}$. Preferred embodiments in which there is internal cyclization within DA or cyclization of a DA amide bioisostere to $H_N$ pyridine mimetic include structures of:

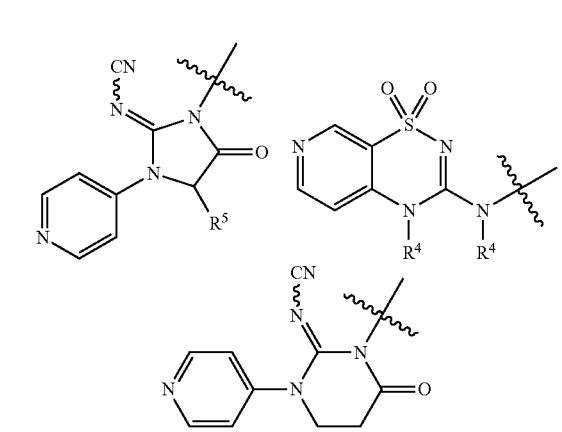

and salts thereof, including but not limiting to pharmaceutically acceptable salts, wherein $R^4$ is as previously described and $R^5$ is optionally substituted $C_6$-$C_{24}$ aryl or $C_5$-$C_{24}$ heteroaryl, preferably optionally substituted phenyl; and the wavy line indicates the site of covalent attachment to $I_N$.

In more preferred embodiments DA is an acrylamide Donor Acceptor Unit characterized by an optionally substituted amide functional group, which serves as the hydrogen bond donor acceptor, and an optionally substituted $C_2$-$C_{20}$ alkenylene and in which one of the sp² carbons of the alkenylene is bonded to the carbonyl carbon of the amide functional group, the nitrogen atom of which is the site of attachment to the NAMPT Interconnecting ($I_N$) Unit, and in which another sp² carbon of the alkenylene not attached to the amide functional group is the site of covalent attachment of that DA Unit to the optionally substituted 5- or 6-membered nitrogen-containing heteroaromatic ring system of $H_N$. In other more preferred embodiments DA is a bioisostere of that acrylamide Donor Acceptor Unit. A acrylamide bioisostere of an acrylamide DA Unit is an organic moiety that is sterically and functionally equivalent to that type of DA Unit by joining together the $H_N$ and $I_N$ Units while retaining a plurality of interactions attributable to the parent compound within the interface of an enzymatically competent NAMPT dimer.

Particularly preferred acrylamide DA Units have or are comprised of the structure of:

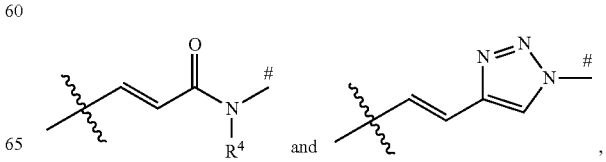

wherein the pound sign (#) indicates the site of covalent attachment of DA to I$_N$; the wavy line indicates the site of covalent attachment to H$_N$ or the remainder of DA, which is bonded to H$_N$, and the carbon atom adjacent thereto is the site of said optional cyclization to H$_N$ by the acrylamide DA Unit; and R$^4$ is hydrogen or optionally substituted C$_1$-C$_4$ alkyl, preferably hydrogen, methyl or ethyl, more preferably hydrogen, and other particularly preferred acrylamide DA Units have the structures of:

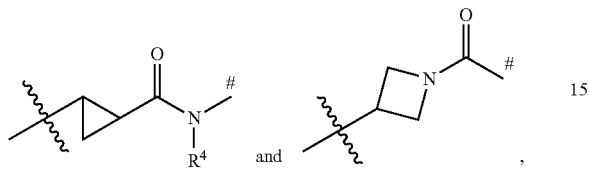

and wherein the pound sign (#) indicates the site of covalent attachment of DA to I$_N$; the wavy line indicates the site of covalent attachment to H$_N$ or the remainder of DA, which is bonded to H$_N$; and R$^4$ is hydrogen or optionally substituted C$_1$-C$_4$ alkyl, preferably hydrogen, methyl or ethyl, more preferably hydrogen.

When an acrylamide DA Unit is cyclized back to an adjacent skeletal carbon atom of the optionally substituted nitrogen-containing heteroaromatic ring system of H$_N$ it does so in particularly preferred embodiments to a 6-membered optionally substituted nitrogen-containing heteroaromatic ring system through the sp$^2$ carbon atom of the alkenylene moiety proximal to the amide functional group through an oxygen, sulfur or nitrogen heteroatom, optionally substituted, introduced between that proximal sp$^2$ carbon atom and the adjacent carbon atom so as to define a 5-membered heteroaromatic ring system fused to the 6-membered nitrogen-containing heteroaromatic ring system of H$_N$. When the 6-membered optionally substituted nitrogen-containing heteroaromatic ring system is a pyridine mimetic and DA bonded thereto is an acrylamide DA Unit, the H$_N$-DA moeity in which DA is optionally cyclized back to H$_N$ in the manner so described is sometimes referred to as a nicotinamide mimetic. Other H$_N$-DA moieties or nicotinamide mimetics have or are comprised of an amide functional group or a bioisostere thereof as described above, with optional cyclization back to H$_N$ or the pyridine mimetic where sterically permitted.

Particularly preferred H$_N$-DA or nicotinamide mimetics in which DA is not cyclized back to H$_N$ have the structure of:

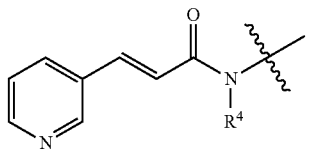

or a pharmaceutically acceptable salt thereof, wherein R$^4$ is hydrogen or optionally substituted C$_1$-C$_4$ alkyl, preferably hydrogen, methyl or ethyl, more preferably hydrogen; and the wavy line indicates the site of covalent attachment to I$_N$. Other such H$_N$-DA or nicotinamide mimetics that are particularly preferred have the structures of:

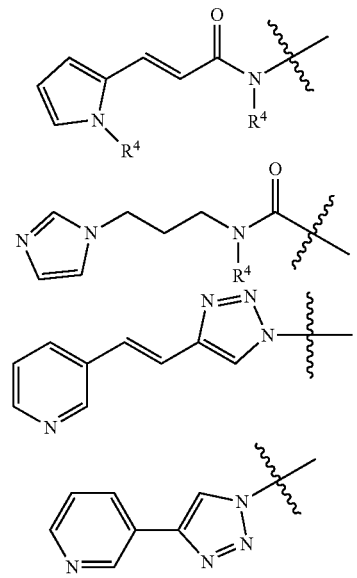

and salts thereof, including but not limiting to pharmaceutically acceptable salts, wherein R$^4$ is independently selected from the group consisting of hydrogen and optionally substituted C$_1$-C$_4$ alkyl, preferably hydrogen, methyl and ether, more preferably R$^4$ is hydrogen, and the wavy line indicates the site of covalent attachment to I$_N$.

Particularly preferred H$_N$-DA or nicotinamide mimetics in which DA is cyclized at least in part back to H$_N$ have the structures of:

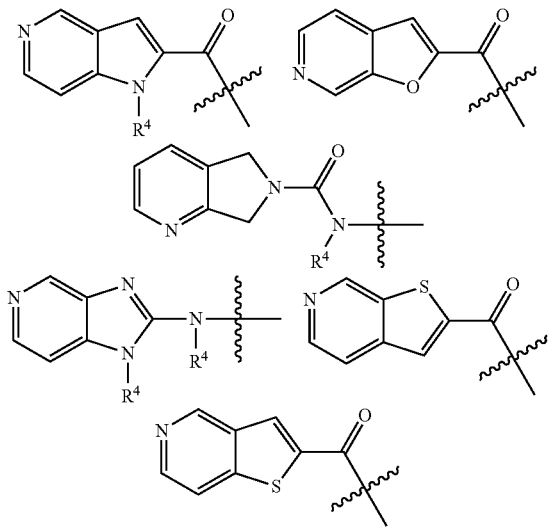

and salts thereof, including but not limiting to pharmaceutically acceptable salts, wherein R$^4$ is independently selected from the group consisting of hydrogen and optionally substituted C$_1$-C$_4$ alkyl, preferably hydrogen, methyl and ethyl, more preferably hydrogen or methyl, or two of R$^4$ together with the nitrogen atoms to which they are attached along with the intervening carbon atom defines a optionally substituted 5- or 6-membered heterocyclo; and the wavy line indicates the site of covalent attachment to I$_N$.

Particularly preferred $H_N$-DA or nicotinamide mimetics in which DA is an amide functional group have the structures of:

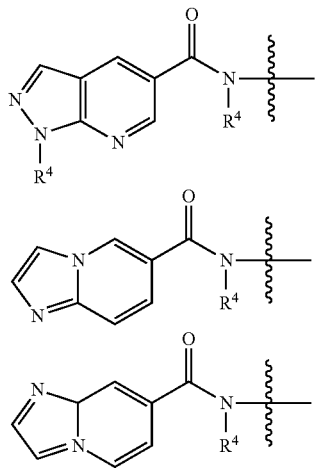

and salts thereof, including but not limiting to pharmaceutically acceptable salts, wherein $R^4$ is independently selected from the group consisting of hydrogen and optionally substituted $C_1$-$C_4$ alkyl, preferably hydrogen, methyl and ethyl, more preferably hydrogen or methyl; and the wavy line indicates the site of covalent attachment to $I_N$.

Other $H_N$-DA or nicotinamide mimetics not specifically enumerated above, which are formally derivable by various combinations of $H_N$ and DA Units described herein with or without cyclization of DA back to $H_N$ are contemplated with preferred combination that have a distance between the weakly basic or uncharged nitrogen that is not bonded to DA of the 5- or 6-membered nitrogen heteroaromatic ring system of $H_N$ and the atom of DA most distal from that nitrogen atom in a range of about 7.0 to about 7.3 angstroms, more preferably from about 7.1 to about 7.2 angstroms, when the NAMPTi compound or derivative thereof is in its MM2 minimized conformation. In other preferred combinations the distance between the atom of $H_N$ bonded to DA and the atom of the NAMPT Interconnecting ($I_N$) Unit to which the NAMPT Tail ($T_N$) Unit is attached in that minimized conformation is in the range from about 8.0 angstroms to about 9.5 angstroms, more preferably from about 8.3 angstroms to about 9.2 angstroms.

1.4.3 NAMPT Interconnector Unit

A NAMPT Interconnector ($I_N$) Unit is a component of a NAMPTi compound or derivative thereof, or of a NAMPT Drug Unit of that compound or derivative, that interconnects its Donor Acceptor (DA) and Tail ($T_N$) Units. In some embodiments, $I_N$ is capable of engaging in Van der Waals interactions with hydrophobic side amino acid side chains that line the tunnel in the region between the DA and Tail Units in an enzymatically competent NAMPT enzyme and allows for the Tail Unit to engage in one or more of the aforementioned interactions to anchor the NAMPTi compound into the dimer interface. Typically, the length of the Interconnecting Unit is also selected to allow projection of the hydroxyl or amino residue substituent of $T_N$ towards solvent accessible space on binding of a NAMPTi compound in order for that moiety, when introduced as a handle for its conjugation as a NAMPTi Drug Unit in a Ligand Drug Conjugate, does not unduly interfere with binding of the NAMPTi compound. For that purpose preferred embodiments of $I_N$ are comprised of a hydrophobic residue selected from the group consisting of optionally substituted $C_1$-$C_8$ alkylene, optionally substituted $C_6$-$C_{24}$ arylene, or a combination thereof, in which the terminus of the hydrophobic residue distal to site of attachment to $H_N$-DA is optionally functionalized for attachment to the NAMPT Tail ($T_N$) Unit. In other preferred embodiments, $I_N$ is additional comprised of an optionally substituted $C_2$-$C_{12}$ heteroalkylene or an optionally substituted $C_5$-$C_{20}$ heterocyclo that is optionally functionalized for attachment to $T_N$.

In preferred combinations of $H_N$, DA and $I_N$ in NAMPT Drug Units, $I_N$ or $I_N$-$T_N$ of the NAMPTi compound or derivative thereof from release of that Drug Unit from a Ligand Drug Conjugate compound or Drug Linker compound is capable of interacting with one or more, preferably two or more, amino acid residues of a NAMPT monomer of an enzymatically competent NAMPT homodimer selected from the group consisting of Val 242, Ile 309, Ile 351, and His 191 of NAMPT, wherein the NAMPT monomer has the amino acid sequence of NCBI Reference Sequence NP_005737.1.

In other preferred embodiments an $I_N$ Unit is or is comprised of —$X^1$—[C(=O)]$_{0,1}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$—, —$X^2$—$C_6$-$C_{24}$ arylene-O—, —$X^2$—$C_5$-$C_{24}$ heteroarylene-[C(=O)$_{0,1}$]—, —$X^2$—$C_5$-$C_{24}$ heteroarylene-[S(=O)$_{1,2}$]$_{0,1}$-, —$X^2$—$C_5$-$C_{24}$ heteroarylene-O— or —$X^2$—$C_3$-$C_{20}$ heterocyclo-[C(=O)$_{0,1}$]—, wherein the arylene, heteroarylene and heterocyclo are optionally substituted, wherein $X^1$ is optionally substituted $C_5$-$C_7$ alkylene and $X^2$ is absent or is an optionally substituted $C_1$-$C_4$ alkylene. In more preferred embodiments $I_N$ is —CH$_2$4CH$_2$)$_{3-7}$—CH$_2$—, —CH$_2$—(CH$_2$)$_{3-7}$—CH$_2$—O—, —CH$_2$—(CH$_2$)$_{3-7}$—C(=O)—, —CH$_2$—(CH$_2$)$_{3-7}$—S(=O)$_2$— or —CH$_2$—(CH$_2$)$_{3-7}$—S(=O)—. In some of those embodiments a carbon atom of $X_1$ or $X_2$ is the site of optional cyclization of $T_N$ back to $I_N$.

In other more preferred embodiments $I_N$ has or is comprised of the structure of:

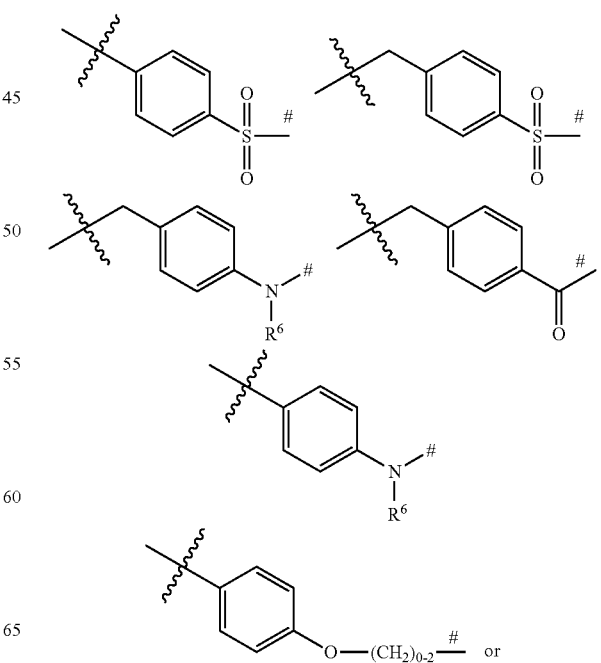

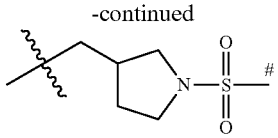

wherein the wavy line indicates the site of covalent attachment to DA or the remainder of $I_N$, which is bonded to DA and the pound sign (#) indicates the site of covalent attachment to $T_N$; and $R^6$ is hydrogen or optionally substituted saturated or unsaturated $C_1$-$C_6$ alkyl, preferably $C_1$-$C_4$ alkyl, —$CH_2CH$=$C(CH_3)_2$, or —$CH_2$—C≡CH.

1.4.4 NAMPT Tail Unit

A NAMPT Tail ($T_N$) Unit is a component of a NAMPTi compound or derivative thereof, or of a NAMPT Drug Unit of that compound or derivative, that is bonded to its Interconnecting ($I_N$) Unit. For a NAMPTi compound or its derivative in preferred embodiments $T_N$ provides a functional group capable of forming a covalent bond to a Linker Unit of a Ligand Drug Conjugate or Drug Linker compound for incorporation of the NAMPTi compound or its derivative as a NAMPT Drug Unit. A NAMPT Tail ($T_N$) Unit for that purpose in one group of preferred embodiments is comprised of an optionally substituted amino-alcohol residue or a an optionally substituted carboxylic acid-alcohol residue, the amino nitrogen or carbonyl carbon atom of which is bonded to $I_N$ or the remainder of $T_N$, which is bonded to $I_N$.

In another group of preferred embodiments, $T_N$ is comprised of an optionally substituted benzamide moiety, the amide nitrogen atom of which is bonded to $I_N$ or the remainder of $T_N$ that is bonded to $I_N$, with optional cyclization of that atom back to $I_N$ or the remainder of $T_N$ wherein said optional cyclization is included within the formula of $I_N$-$T_N$. In some embodiments that optional cyclization is to a carbon atom of $X^1$ or $X^2$ of $I_N$ as defined herein. In either instance the aromatic ring of the benzamide moeity is at least substituted with hydroxyl, thiol or an amino residue at position 3 or 4 relative to the site at which the amide carbonyl carbon atom is attached.

In yet another group of preferred embodiments $T_N$ is or is comprised of an aryl or biaryl moiety, an aromatic atom of which is bonded to $I_N$ or the remainder of $T_N$ that is bonded to $I_N$, and an aromatic ring of which is at least substituted with a hydroxyl, thiol or amino residue; and wherein the hydroxyl oxygen atom of the amino alcohol or carboxylic acid-alcohol residue, or the oxygen, sulfur or nitrogen atom of the hydroxyl, thiol or amino residue of the benzamide, aryl or biaryl moiety, is the site of covalent attachment of $T_N$ to $L_R$ or $L_O$, depending on the absence or present of $L_O$, respectively.

In any one of the above preferred groups of embodiments of $T_N$, a remainder of $T_N$ for bonding to $I_N$ is preferably an optionally substituted $C_2$-$C_4$ heteroalkylene or an optionally substituted $C_3$-$C_{20}$ heterocyclo or a combination thereof.

More preferred $T_N$ Units are or are comprised of amino alcohol residues having the structures of:

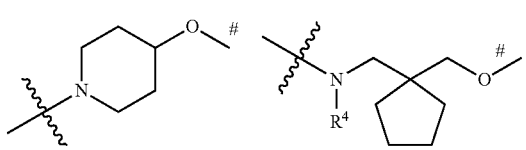

and salts thereof, including but not limited to pharmaceutically acceptable salts, $R^4$ is hydrogen or optionally substituted $C_1$-$C_4$ alkyl, preferably hydrogen or methyl; the wavy line indicates the site of covalent attachment to the remainder of $T_N$, which is bonded to $I_N$ or to $I_N$; and the pound sign (#) indicates the site of covalent to $L_O$ or $L_R$, depending on the presence or absence of $L_O$, of a drug linker moeity within a Ligand Drug Conjugate compound of Formula 1 or Formula 2 or of a Drug Linker compound of Formula I.

Other preferred embodiments $T_N$ Units are or are comprised of benzamide moieties having or comprised of the following structures:

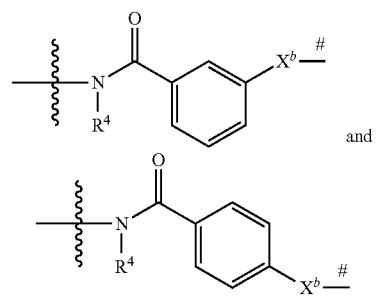

wherein $X^b$ is optionally substituted —NH—, —S— or —O—, preferably —NH—, —N(CH$_3$)—, —N(CH$_2$CH$_3$)— or —O—; $R^4$ is hydrogen or optionally substituted $C_1$-$C_4$ alkyl, preferably hydrogen, methyl or ethyl, more preferably hydrogen; and wherein the wavy line indicates the site of covalent attachment to $I_N$ or the remainder of $T_N$, which is bonded to $I_N$; the amide nitrogen of the benzamide moiety is the site of optional cyclization of $T_N$ to $I_N$ or the remainder of $T_N$, which is bonded to $I_N$; and the pound sign (#) indicates the site of covalent attachment to $L_O$ or $L_R$, depending on the presence or absence of $L_O$, in a drug linker moeity within a Ligand Drug Conjugate compound of Formula 1 or Formula 2 or of a Drug Linker compound of Formula I.

Still other preferred embodiments $T_N$ Units are or are comprised of aryl or biaryl moieties having or comprised of the following structures:

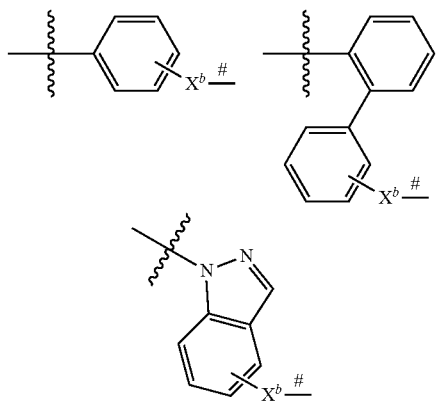

and salts thereof, including but not limited to pharmaceutically acceptable salts, wherein $X^b$ is optionally substituted —NH—, —S—, or —O—, the wavy line indicates the site of covalent attachment to $I_N$ or the remainder of $T_N$, which is bonded to $I_N$; and the pound sign (#) indicates the site of covalent attachment to $L_O$ or $L_R$, depending on the presence or absence of $L_O$, in a drug linker moeity within a Ligand Drug Conjugate compound of Formula 1 or Formula 2 or of a Drug Linker compound of Formula I.

Preferred combinations of $T_N$ and $I_N$ Units (i.e., $—I_N-T_N-$) have the structures of:

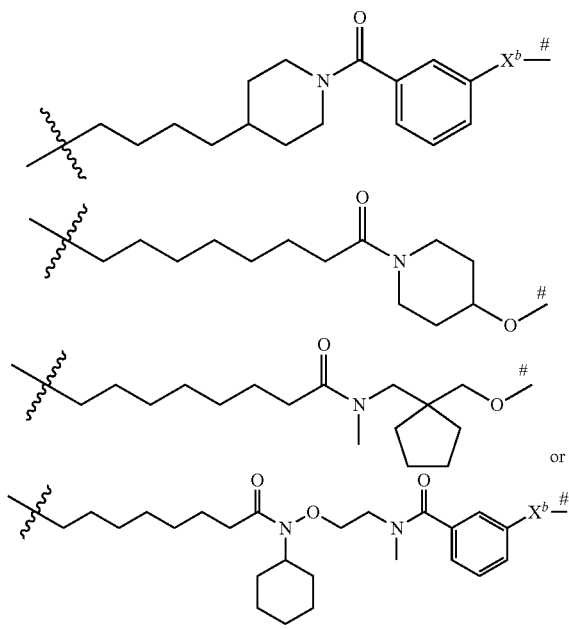

wherein $X^b$ is optionally substituted —NH—, —O— or —S—; the wavy line indicates the site of covalent attachment to DA; and the pound sign (#) indicates the site of covalent attachment to $L_O$ or $L_R$, depending on the presence or absence of $L_O$, of a drug linker moeity within a Ligand Drug Conjugate compound of Formula 1 or Formula 2 or of a Drug Linker compound of Formula I.

$T_N$ Units in combinations with any one of the above $H_N$, DA and $I_N$ Units are also contemplated. In preferred combinations $T_N$ of a released NAMPT Drug Unit from a Ligand Drug Conjugate compound or Drug Linker compound is capable of interacting with one or more, preferably two or more and more preferably three or more, amino acid residues of a NAMPT monomer of an enzymatically competent NAMPT homodimer selected from the group consisting of Ile 309, Pro 307, Val 350, Ile 378 and Ala 379, wherein the NAMPT monomer has the amino acid sequence of NCBI Reference Sequence NP_005737.1. Other preferred embodiments of $T_N$ are those of a released NAMPT Drug Unit from a Ligand Drug Conjugate compound or Drug Linker compound in which $T_N$ or $I_N-T_N$ is capable of interacting with one or more, preferably two or more and more preferably three or more, amino acid residues of a NAMPT monomer of an enzymatically competent NAMPT homodimer selected from the group consisting of Tyr 188, Lys 189, Ala 379, Asn 377, Glu 376, Val 350, Arg 349 and Pro 307, wherein the NAMPT monomer has the amino acid sequence of NCBI Reference Sequence NP_005737.1.

Other $T_N$ Units in a NAMPTi compound or derivative thereof or in a NAMPT Drug Unit of that compound or derivative in a Ligand Drug Conjugate compound or Drug Linker compound not specifically enumerated above preferably have a distance from the heteroatom that serves as the conjugation site of that compound or derivative, or from the site of conjugation of its corresponding NAMPT Drug Unit, to the atom of $T_N$ that is attached to $I_N$ when the NAMPTi compound or derivative thereof is in its MM2 minimized conformation in a range from about 5.5 to about 7.0 angstroms or more preferably at about 5.9 angstroms.

1.5 Treatment of Hyper-Proliferating Conditions

The Ligand-Drug Conjugates are useful for inhibiting the multiplication of a tumor cell or cancer cell, causing apoptosis in a tumor cancer cell, or for treating cancer in a patient. The Ligand-Drug Conjugates can be used accordingly in a variety of settings for the treatment of cancers. The Ligand-Drug Conjugates can be used to deliver a drug to a tumor cell or cancer cell. Without being bound by theory, in one embodiment, the Ligand unit of a Ligand-Drug Conjugate binds to or associates with a cell-surface cancer-cell or a tumor-cell-associated antigen or receptor, and upon binding the Ligand-Drug Conjugate can be taken up (internalized) inside a tumor cell or cancer cell through antigen- or receptor-mediated endocytosis or other internalization mechanism. The antigen can be attached to a tumor cell or cancer cell or can be an extracellular matrix protein associated with the tumor cell or cancer cell. Once inside the cell, via a enzymatic or non-enzymatic cleavable mechanism, depending upon the components of the linker system, the drug is released within the cell. In an alternative embodiment, the Drug or Drug unit is cleaved from the Ligand-Drug Conjugate within the vicinity of the tumor cell or cancer cell, and the Drug or Drug unit subsequently penetrates the cell.

The Ligand-Drug Conjugates can provide conjugation-specific tumor or cancer drug targeting, thus reducing general toxicity of the drug.

In some embodiments, the Linker Units stabilize the Ligand-Drug Conjugates in blood, yet are capable of liberating drug once inside the cell.

In one embodiment, the Ligand Unit binds to the tumor cell or cancer cell.

In another embodiment, the Ligand Unit binds to a tumor cell or cancer cell antigen which is on the surface of the tumor cell or cancer cell.

In another embodiment, the Ligand Unit binds to a tumor cell or cancer cell antigen which is an extracellular matrix protein associated with the tumor cell or cancer cell.

The specificity of the Ligand Unit for a particular tumor cell or cancer cell can be important for determining those tumors or cancers that are most effectively treated. For example, a ligand drug conjugate having a BR96 Ligand unit can be useful for treating antigen positive carcinomas including those of the lung, breast, colon, ovaries, and pancreas. Ligand-Drug Conjugates having an anti-CD30 or an anti-CD70 binding Ligand unit can be useful for treating hematologic malignancies.

Other particular types of cancers that can be treated with a Ligand Drug Conjugates include, but are not limited to the following solid tumors, blood-borne cancers, acute and chronic leukemias, and lymphomas.

Solid tumors include but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Blood-borne cancers include but are not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, and multiple myeloma.

Acute and chronic leukemias include but are not limited to lymphoblastic, myelogenous, lymphocytic, and myelocytic leukemias.

Lymphomas include but are not limited to Hodgkin's disease, non-Hodgkin's Lymphoma, Multiple myeloma, Waldenström's macroglobulinemia, Heavy chain disease, and Polycythemia vera.

Cancers, including, but not limited to, a tumor, metastasis, or other diseases or disorders characterized by hyper-proliferating cells, can be treated or its progression inhibited by administration of an ADC composition.

In other embodiments, methods for treating cancer are provided, including administering to a patient in need thereof an effective amount of a Ligand Drug Conjugate composition and a chemotherapeutic agent. In one embodiment the cancer to be treated with a chemotherapeutic in combination with a Ligand Drug Conjugate has not been found to be refractory to the chemotherapeutic agent. In another embodiment, the cancer to be treated with a chemotherapeutic in combination with a Ligand Drug Conjugate is refractory to the chemotherapeutic agent. The Ligand Drug Conjugate compositions can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior subsequent to administration of a ligand drug conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a Ligand Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

1.6 Pharmaceutical Compositions Comprising an LDC

The present invention provides pharmaceutical compositions comprising an Ligand Drug Conjugate composition described herein and a pharmaceutically acceptable carrier. The pharmaceutical compositions can be in any form that allows for an Ligand Drug Conjugate to be administered to a patient for treatment of a disorder associated with expression of the antigen to which the Ligand Unit binds. For example, the pharmaceutical compositions can be in the form of a liquid or a lyophilized solid. The preferred route of administration is parenteral. Parenteral administration includes subcutaneous injections, intravenous, intramuscular, and intrasternal injection or infusion techniques. In preferred embodiments, a pharmaceutical composition comprising a Ligand Drug Conjugate is administered intravenously in the form of a liquid solution.

Pharmaceutical compositions can be formulated so as to allow a compound to be bioavailable upon administration of the composition to a patient. Such compositions can take the form of one or more dosage units, where for example, a lyophilized solid may provide a single dosage unit when reconstituted as a solution or suspension on addition of a suitable liquid carrier.

Materials used in preparing the pharmaceutical compositions are preferably non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the pharmaceutical composition, the manner of administration, and the Ligand Drug Conjugate composition employed.

The pharmaceutical composition can be, for example, in the form of a liquid. The liquid can be useful for delivery by injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable pharmaceutical composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The pharmaceutical composition comprises an effective amount of an LDC composition such that a suitable dosage will be obtained for administration to a subject in need thereof. Typically, this amount is at least about 0.01% by weight of the pharmaceutical composition.

For intravenous administration, the pharmaceutical composition can comprise from about 0.01 to about 100 mg of an Ligand Drug Conjugate composition per kg of the animal's body weight. In one aspect, the pharmaceutical composition can include from about 1 to about 100 mg of a Ligand Drug Conjugate composition per kg of the animal's body weight. In another aspect, the amount administered will be in the range from about 0.1 to about 25 mg/kg of body weight of an Ligand Drug Conjugate composition.

Generally, the dosage of a Ligand Drug Conjugate composition administered to a patient is typically about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, preferably 0.1 to 3.2 mg/kg, or more preferably 0.1 to 2.7 mg/kg of the subject's body weight over a treatment cycle.

An Ligand Drug Conjugate can be administered by any convenient route, for example by infusion or bolus injection, by absorption through epithelial or mucocutaneous linings (e.g., oral mucosa, rectal and intestinal mucosa). Administration can be systemic or local. Various delivery systems are known, e.g., encapsulation in liposomes, microparticles, microcapsules, capsules, and can be used to administer a compound. In certain embodiments, more than one compounds or composition is administered to a patient.

In an embodiment, the Ligand Drug Conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where a Ligand Drug Conjugate is to be administered by infusion, it can be dispensed, for example, with an infusion bottle containing sterile pharmaceutical grade water or saline. Where the Ligand Drug Conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

1.7 Numbered Embodiments

The following numbered embodiments further exemplify the invention without limitation thereto.

1. A Ligand Drug Conjugate (LDC) composition, wherein the composition is represented by the structure of:

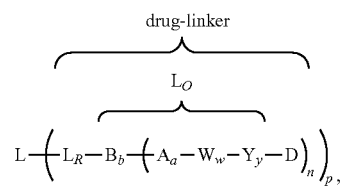

or a pharmaceutically acceptable salt thereof, wherein L is a Ligand Unit; D is a NAMPT Drug Unit covalently attached to the Formula 1 and/or Formula 2 composition structure(s) through a component of that Unit other than its head group, which corresponds to the heterocycle of nicotinamide, wherein that component remains capable of interacting with enzymatically competent NAMPT homodimer at its nicotinamide mononucleotide binding site when the NAMPT Drug Unit is released from a Ligand Drug Conjugate compound of the composition as a NAMPT inhibitor (NAMPTi) compound or derivative thereof; $L_R$ is a primary linker, which interconnects the Ligand Unit and Drug Unit optionally through $L_O$, which is an optional secondary linker; subscripts a and b independently are 0 or 1, indicating the absence or presence, respectively, of A or B; subscript n is 1, 2, 3 or 4; A is an first optional Stretcher; and B is a Branching Unit, when subscript b is 1 and subscript n is 2, 3 or 4, or B is absent, so that subscript b is 0, when subscript n is 1, wherein each of A and B is an independently selected single unit or is optionally comprised or consists of two, three or four independently selected subunits; subscript;

y is 0, 1 or 2, indicating the absence or presence of one or two of Y, respectively; Y is a Spacer Unit, or an optionally substituted heteroatom or functional group, provided that when subscript y is 0, $Y_y$ is replaced by an optionally substituted heteroatom of the distal terminal component selected from the group consisting of optionally substituted —NH—, —O— and —S—; and provided that when subscript y is 1, Y is a Spacer Unit covalently attached to an optionally substituted heteroatom of the distal terminal component selected from the group consisting optionally substituted —NH—, O and S; and provided that when subscript y is 2 so that $Y_y$ is —Y—Y'—, then Y is a first Spacer Unit and Y' is a functional group comprised of an optionally substituted heteroatom of the distal terminal component selected from the group consisting optionally substituted —NH—, O and S, or a second Spacer Unit; and subscript w is 0 or 1, indicating the absence or presence, respectively, of W; wherein when subscript w is 1, W is a Peptide Cleavable Unit or a Glucuronide Unit of formula —Y(W')—, wherein W' represents a carbohydrate moiety with glycosidic bonding to Y through a optionally substituted heteroatom, provided Y bonded to W' is required to be a first self-immolative Spacer Unit; subscript y is 0, 1 or 2, provided subscript y is 1 or 2, when W is a Glucuronide Unit, in which instance subscript y is inclusive of the required self-immolative Spacer Unit; and wherein when subscript w is 1, which indicates the presence of a Cleavable Unit, enzymatic or non-enzymatic cleavage of that Unit initiates release of the NAMPT Drug Unit as a NAMPTi compound or derivative thereof from a Conjugate compound of a Ligand Drug Conjugate composition; and when subscript w is 0, which indicates the absence of a Cleavable Unit, enzymatic or non-enzymatic cleavage of the bond between the indicated $L_R$ and $L_O$ moieties, when $L_O$ is present, or the bond between $L_R$ and D, when $L_O$ is absent, initiates release of the NAMPT Drug Unit as a NAMPTi compound or derivative;

subscript p is an average drug linker moiety loading when subscript n is other than 1 or an average drug loading when subscript n is 1, wherein subscript p in either instance is a number ranging from 1 to 24; and wherein a compound of the Ligand Drug Conjugate composition corresponds in structure(s) to that of Formula 1and/or Formula 2 in which p is replaced by p', wherein p' is an integer ranging from 1 to 24.

2. The Ligand Drug Conjugate composition of embodiment 1 wherein the NAMPTi Drug Unit is represented by the general structure of:

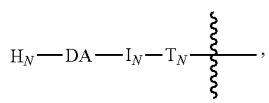

or a pharmaceutically acceptable salt thereof, wherein the wavy line indicates the site of covalent attachment to $L_O$ or $L_R$, depending on the presence or absence of $L_O$, respectively; $H_N$ is a NAMPT Head Unit, wherein the NAMPT Head Unit is a $C_5$-$C_{24}$ heteroaryl or partially aromatic $C_9$-$C_{24}$ heterocyclyl, optionally substituted and comprised of an optionally substituted 5- or 6-membered nitrogen-containing heteroaromatic ring system;

DA is a Donor-Acceptor Unit wherein the Donor-Acceptor Unit is or is comprised of a hydrogen bond donor acceptor functional group and is bonded to a carbon skeletal atom at position 2 or 3 of the 5-membered nitrogen-containing heteroaromatic ring system or at position 3 or 4 of the 6-membered nitrogen-containing heteroaromatic ring system, with optional formal cyclization of DA back to an adjacent skeletal carbon atom of the 6-membered nitrogen-containing heteroaromatic ring system through an introduced optionally substituted non-aromatic carbon atom or an optionally substituted nitrogen, oxygen or sulfur atom resulting in a partially aromatic or fully aromatic fused 6,5- or 6,6-ring system, wherein said bonding of DA is in relation to a skeletal nitrogen atom of the 5- or 6 membered nitrogen-containing heteroaromatic ring system and wherein said formal cyclization to the adjacent carbon atom of the 6-membered nitrogen-containing heteroaromatic ring system substantially retains the hydrogen bonding ability of the donor acceptor functional group of DA in absence of said cyclization;

$I_N$ is an Interconnecting Unit, wherein the Interconnecting Unit is or is comprised of —$X^1$—[C(=O)]$_{0,1}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$, —$X^2$—$C_6$-$C_{24}$ arylene-O—, —$X^2$—$C_5$-$C_{24}$ heteroarylene-[C(=O)]$_{0,1}$]—, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]—, wherein the arylene, heteroarylene and heterocyclo are optionally substituted; $X^1$ is optionally substituted $C_5$-$C_7$ alkylene; $X^2$ is absent or is an optionally substituted $C_1$-$C_4$ alkylene;

$T_N$ is a NAMPT Tail Unit, wherein the NAMPT Tail Unit is or is comprised of an optionally substituted amino-alcohol residue or a carboxylic acid-alcohol residue, the amino nitrogen or carbonyl carbon of which is bonded to $I_N$, or $T_N$ is or is comprised of an optionally substituted benzamide moiety, the amide nitrogen atom of which is bonded to $I_N$ with optional cyclization of that atom back to $I_N$ or to the remainder of $T_N$, and the aromatic ring of which is at least substituted with a hydroxyl, thiol or amino residue at position 3 or 4 relative to the site at which the amide carbonyl carbon atom is attached, or $T_N$ is or is comprised of an optionally substituted aryl or biaryl moiety, an aromatic skeletal atom of which is bonded to $I_N$, or to the remainder of $T_N$, and wherein an aromatic ring of which is at least substituted with a hydroxyl, thiol or an amino residue; and wherein $T_N$ or the remainder thereof is bond to $I_N$, wherein said remainder is an optionally substituted $C_2$-$C_7$ heteroalkylene or an optionally substituted $C_5$-$C_6$ heterocyclo, and the hydroxyl oxygen atom of the amino alcohol or carboxylic acid-alcohol residue, or the oxygen, sulfur or nitrogen atom of the hydroxyl, thiol or amino residue of the benzamide, aryl or biaryl moiety is the site of covalent attachment of $T_N$ to $L_O$ or $L_R$, depending on the presence or absence of $L_O$, respectively, of a drug linker moiety of a Ligand Drug Conjugate compound of Formula 1 or Formula 2 of the composition.

3. The Drug Conjugate composition of embodiment 2 wherein the NAMPT Head ($H_N$) Unit is a pyridine mimetic.

4. The Ligand Drug Conjugate composition of embodiment 2 or 3, wherein the Donor Acceptor (DA) Unit is comprised of an optionally substituted amide functional group or bioisostere thereof.

5. The Ligand Drug Conjugate composition of embodiment 2 or 3, wherein $H_N$-DA is a nicotinamide mimetic.

6. The Ligand Drug Conjugate composition of embodiment 2 wherein the 6-membered nitrogen-containing heteroaromatic ring system of $H_N$ is that of pyridine with optional cyclization of DA back to the pyridine aromatic ring system through an introduced aromatic oxygen, sulfur or an optionally substituted nitrogen atom so that $H_N$ contains a 6-5 fused aromatic ring system.

7. The Ligand Drug Conjugate composition of any one of embodiments 2 to 6, wherein $H_N$ of the released NAMPT Drug Unit is capable of interacting with Phe 193 on one monomer of an enzymatically competent NAMPT homodimer and/or Tyr 18' of the other monomer, wherein the NAMPT monomers have the amino acid sequence of NCBI Reference Sequence NP_005737.1.

8. The Ligand Drug Conjugate composition of embodiment 7 wherein said NAMPT Head Unit interaction(s) is through π-π stacking with the aromatic side chain(s) of Phe 193 and/or Tyr 18'.

9. The Ligand Drug Conjugate composition of embodiment 2 wherein the NAMPT Head Unit has the structure of:

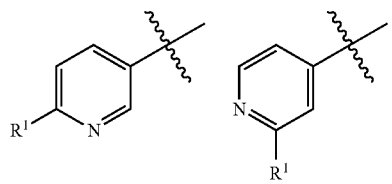

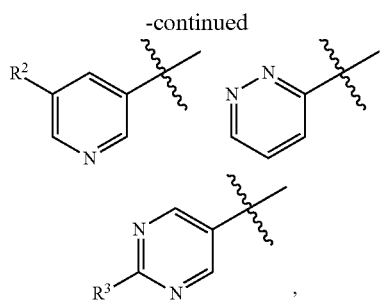

or a pharmaceutically acceptable salt thereof, wherein $R^1$ is hydrogen, —$NH_2$ or chloro; $R^2$ is fluoro; $R^3$ is hydrogen or —$NH_2$; and the wavy line indicates the site of covalent attachment to DA and an adjacent aromatic carbon atom thereto is the site of said optional cyclization by DA to $H_N$.

10. The Ligand Drug Conjugate composition of embodiment 2 wherein the NAMPT Head Unit has the structure of:

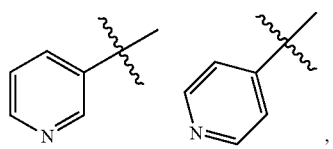 [SMILES: *c1cccnc1 ; *c1ccncc1]

or a pharmaceutically acceptable salt thereof, wherein the wavy line indicates the site of covalent attachment to DA and an adjacent aromatic carbon atom thereto is the site of said optional cyclization by DA to $H_N$.

11. The Ligand Drug Conjugate composition of embodiment 2 wherein the NAMPT Head Unit has the structure of:

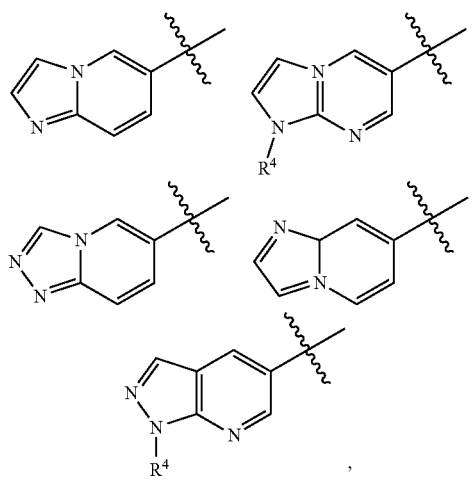

or a pharmaceutically acceptable salt thereof, wherein the wavy line indicates the site of covalent attachment to DA and an adjacent aromatic carbon atom thereto is the site of said optional cyclization by DA to $H_N$; and $R^4$ is hydrogen or optionally substituted $C_1$-$C_4$ alkyl.

12. The Ligand Drug Conjugate composition of any one of embodiments 2 to 11, wherein the Donor Acceptor Unit is an acrylamide DA Unit, optionally cyclized to an adjacent skeletal carbon atom of the nitrogen-containing aromatic ring system of $H_N$ to which it is attached.

13. The Ligand Drug Conjugate composition of any one of embodiments 2 to 12, wherein the Donor Acceptor Unit of the released NAMPT Drug Unit is capable of interacting with one or more amino acid residues of an NAMPT monomer of an enzymatically competent NAMPT homodimer selected from the group consisting of Asp 219, Ser 241, Val 242 and Ser 275, wherein the NAMPT monomer has the amino acid sequence of NCBI Reference Sequence NP_005737.1.

14. The Ligand Drug Conjugate composition of embodiment 13 wherein said DA interaction(s) is hydrogen bonding either directly or indirectly through hydrogen bonding network(s) involving the intermediacy of water molecule(s).

15. The Ligand Drug Conjugate composition of any one of embodiments 2 to 12, wherein the Donor-Acceptor Unit has the structure of:

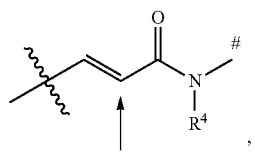

wherein $R^4$ is hydrogen or optionally substituted $C_1$-$C_4$ alkyl; DA is optionally cyclized to $H_N$, wherein said cyclization is to the $sp^2$ carbon atom proximal to the carbonyl carbon (as indicated) through an introduced optionally substituted non-aromatic carbon atom or an optionally substituted aromatic heteroatom; the wavy line indicates the site of covalent attachment to $H_N$, and the carbon atom adjacent thereto is the site of said optional cyclization by DA; and the pound sign (#) indicates the site of covalent attachment to $I_N$.

16. The Ligand Drug Conjugate composition of any one of embodiments 2 to 12, wherein the Donor-Acceptor Unit has the structure of

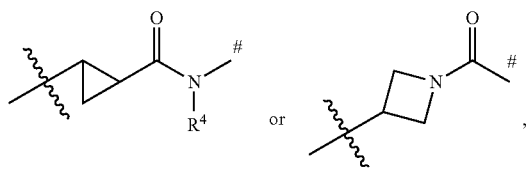

wherein $R^4$ is hydrogen or optionally substituted $C_1$-$C_4$ alkyl; and the wavy line indicates the site of covalent attachment to the NAMPT Head Unit; and the pound sign (#) indicates the site of covalent attachment to $I_N$.

17. The Ligand Drug Conjugate composition of any one of embodiments 2 to 12, wherein the Donor-Acceptor Unit has the structure of:

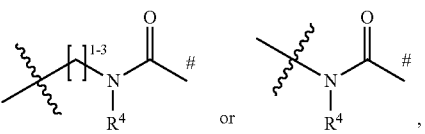

wherein $R^4$ is hydrogen or optionally substituted $C_1$-$C_4$ alkyl; and the wavy line indicates the site of covalent attachment to $H_N$; and wherein the pound sign (#) indicates the site of covalent attachment to $I_N$.

18. The Ligand Drug Conjugate composition of any one of embodiments 2 to 12, wherein the Donor-Acceptor Unit has the structure of:

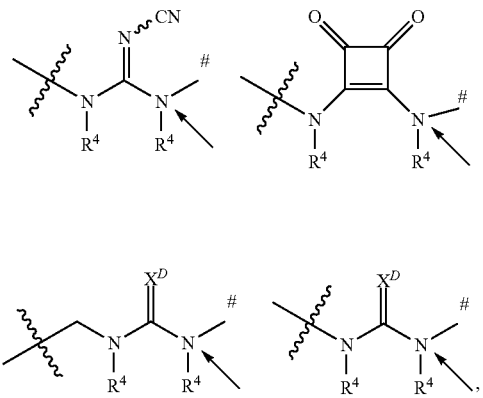

or a pharmaceutically acceptable salt thereof, wherein $X^D$ is O, S or $NR^D$, wherein the nitrogen atom is optionally protonated and $R^D$ is hydrogen or optionally substituted $C_1$-$C_4$ alkyl; each $R^4$ is independently selected from the group consisting of hydrogen and optionally substituted $C_1$-$C_4$ alkyl, or both $R^4$ together with the nitrogen atoms to which they are attached and the intervening carbon atom(s) define an optionally substituted $C_5$-$C_6$ heterocyclo; the pound sign (#) indicates the site of covalent attachment to $I_N$; and the wavy line indicates the site of covalent attachment to $H_N$, wherein DA is optionally cyclized back to an adjacent site of $H_N$, wherein said cyclization is from the indicated nitrogen atom so that $R^4$ bonded thereto is replaced by a covalent bond or from $X^D$ when $X^D$ is —$NR^D$, either directly or through an introduced —$S(=O)_{0-2}$ moeity, in which either instance $R^D$ is replaced by a bond.

19. The Ligand Drug Conjugate composition of embodiment 18 wherein the Donor-Acceptor Unit has the structure of:

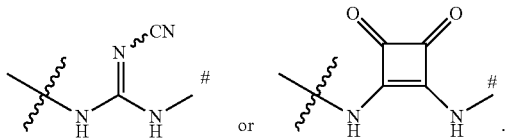

20. The Ligand Drug Conjugate composition of any one of embodiments 2 to 12, wherein the Donor-Acceptor Unit has the structure of:

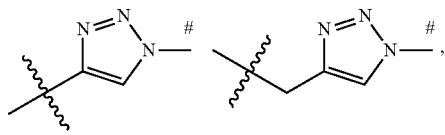

or a pharmaceutically acceptable salt thereof, wherein the wavy line indicates the site of covalent attachment to the NAMPT Head Unit; and the pound sign (#) indicates the site of covalent attachment to $I_N$.

21. The Ligand Drug Conjugate composition of embodiment 2 wherein $H_N$-DA- has the structure of:

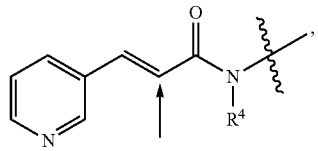

or a pharmaceutically acceptable salt thereof, wherein $R^4$ is hydrogen or optionally substituted $C_1$-$C_4$ alkyl; and the wavy line indicates the site of covalent attachment to $I_N$, and wherein the $sp^2$ carbon atom proximal to the carbonyl carbon is the site (as indicated) of optional cyclization to $H_N$ through an introduced optionally substituted non-aromatic carbon atom or an optionally substituted aromatic heteroatom.

22. The Ligand Drug Conjugate composition of embodiment 2 wherein $H_N$-DA- has the structure of:

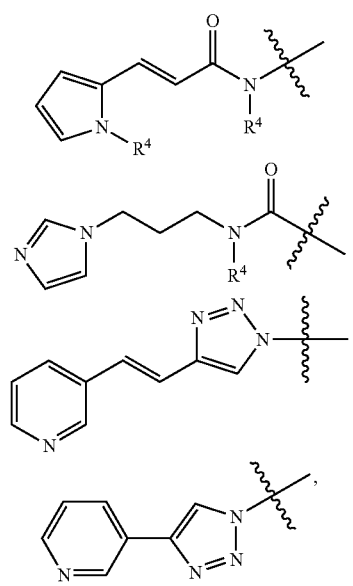

or a pharmaceutically acceptable salt thereof, wherein $R^4$ are independently selected from the group consisting of hydrogen and optionally substituted $C_1$-$C_4$ alkyl; and the wavy line indicates the site of covalent attachment to $I_N$.

23. The Ligand Drug Conjugate composition of embodiment 2 wherein $H_N$-DA- has the structure of:

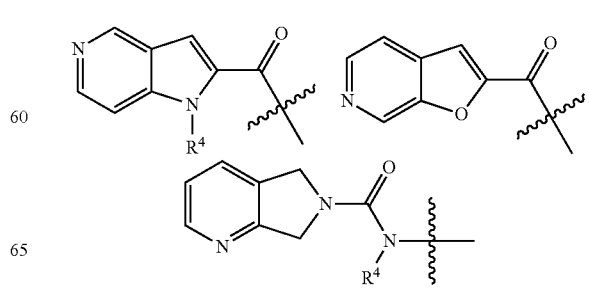

157

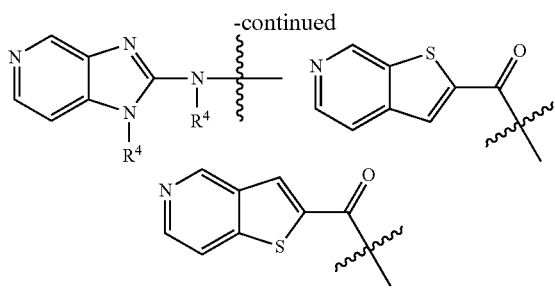

or a pharmaceutically acceptable salt thereof, wherein $R^4$ is hydrogen or optionally substituted $C_1$-$C_4$ alkyl, or both $R^4$ together with the nitrogen atoms to which they are attached and the intervening carbon atom define a $C_5$-$C_6$ heterocycle; and the wavy line indicates the site of covalent attachment to $I_N$.

24. The Ligand Drug Conjugate composition of embodiment 2 wherein $H_N$-DA- has the structure of

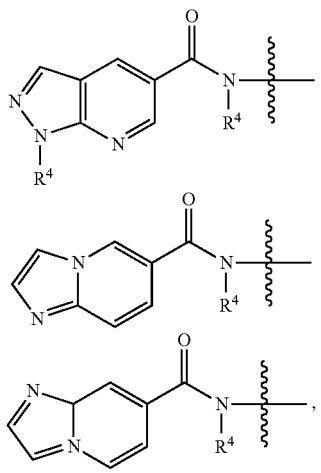

or a pharmaceutically acceptable salt thereof, wherein $R^4$ is independently selected from the group consisting of hydrogen and optionally substituted $C_1$-$C_4$ alkyl; and the wavy line indicates the site of covalent attachment to $I_N$.

25. The Ligand Drug Conjugate composition of embodiment 2 wherein $H_N$-DA- has the structure of:

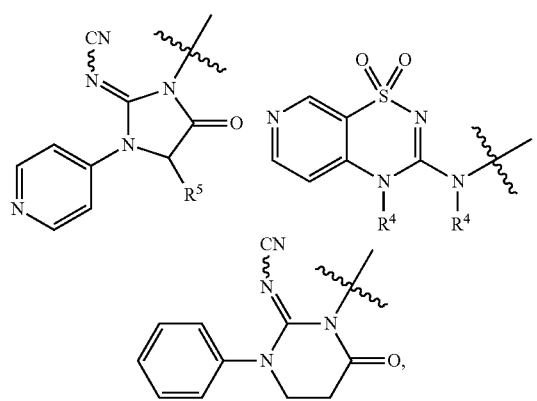

158 or a pharmaceutically acceptable salt thereof, wherein $R^4$ is independently selected from the group consisting of hydrogen and optionally substituted $C_1$-$C_4$ alkyl; $R^5$ is optionally substituted $C_6$-$C_{24}$ aryl or optionally substituted $C_5$-$C_{24}$ heteroaryl; and the wavy line indicates the site of covalent attachment to $I_N$.

26. The Ligand Drug Conjugate composition of any one of embodiments 2 to 25, wherein the NAMPT Tail ($T_N$) Unit or —$I_N$-$T_N$- of the released NAMPT Drug Unit is capable of interacting with one or more amino acid residues of a NAMPT monomer of an enzymatically competent NAMPT homodimer selected from the group consisting of Ile 309, Pro 307, Val 350, Ile 378 and Ala 379, wherein the NAMPT monomer has the amino acid sequence of NCBI Reference Sequence NP_005737.1.

27. The Ligand Drug Conjugate composition of any one of embodiments 2 to 26, wherein $T_N$ or —$I_N$-$T_N$- of the released NAMPT Drug Unit is capable of interacting with one or more amino acid residues of a NAMPT monomer of an enzymatically competent NAMPT homodimer selected from the group consisting of Tyr 188, Lys 189, Ala 379, Asn 377, Glu 376, Val 350, Arg 349 and Pro 307, wherein the NAMPT monomer has the amino acid sequence of NCBI Reference Sequence NP_005737.1.

28. The Ligand Drug Conjugate composition of any one of embodiments 2 to 25 wherein the NAMPT Tail Unit is or is comprised of an optionally substituted amino alcohol moiety wherein the oxygen atom of the alcohol is the site of covalent attachment to $L_O$ or $L_R$, depending on the presence or absence of $L_O$, respectively.

29. The Ligand Drug Conjugate composition of embodiment 28 wherein the NAMPT Tail Unit is an amino alcohol moiety having the structure of:

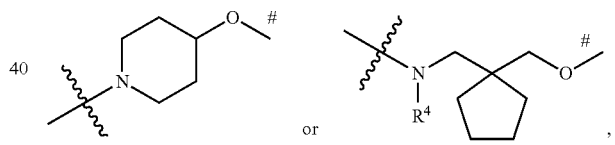

or a pharmaceutically acceptable salt thereof, wherein $R^4$ is hydrogen or optionally substituted $C_1$-$C_4$ alkyl; the wavy line indicates the site of covalent attachment to $I_N$; and the pound sign (#) indicates the site of covalent to $L_O$ or $L_R$, depending on the presence or absence of $L_O$, respectively.

30. The Ligand Drug Conjugate composition of any one of embodiments 2 to 25 wherein the Tail Unit is or is comprised of an optionally substituted benzamide moiety having a functional group providing a heteroatom that is the site of covalent attachment to $L_O$ or $L_R$, depending on the presence or absence of $L_O$, respectively.

31. The Ligand Drug Conjugate composition of embodiment 30 wherein the NAMPT Tail Unit is a benzamide moiety having the structure of:

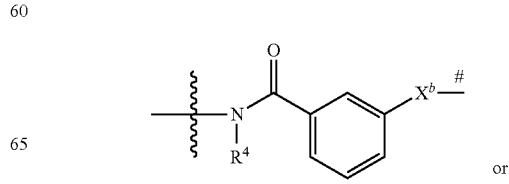

or

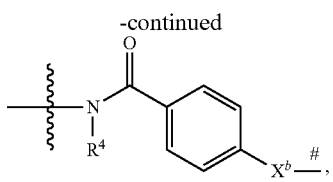

wherein $X^b$ is —S—, —O— or —NH—, optionally substituted; $R^4$ is hydrogen or optionally substituted $C_1$-$C_4$ alkyl; and the wavy line indicates the site of covalent attachment to $I_N$; the pound sign (#) indicates the site of covalent attachment to $L_O$ or $L_R$, depending on the presence or absence of $L_O$, respectively, and wherein the benzamide moeity is optionally cyclized to $I_N$ wherein the amide nitrogen of the benzamide moiety is the site of said cyclization so that $R^4$ is replaced by a covalent bond.

32. The Ligand Drug Conjugate composition of embodiment 31 wherein the NAMPT Tail Unit is a benzamide moiety having the structure of:

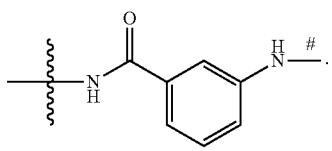 [SMILES: *NC(=O)c1cccc(NC)c1]

33. The Ligand Drug Conjugate of any one of embodiments 2 to 25, wherein the NAMPT Tail Unit is or is comprised of an optionally substituted aryl, heteroaryl or biaryl moiety having a functional group providing a heteroatom that is the site of covalent attachment to $L_O$ or $L_R$, depending on the presence or absence of $L_O$, respectively.

34. The Ligand Drug Conjugate of embodiment 33 wherein the NAMPT Tail Unit is a biaryl or aryl moiety having a having the structure of:

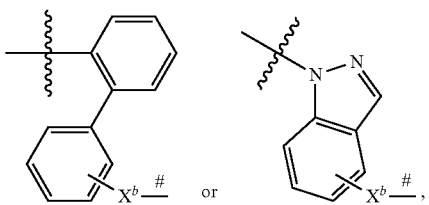

wherein $X^b$ is —S—, —O— or NH—, optionally substituted; the wavy line indicates the site of covalent attachment to $I_N$; and the pound sign (#) indicates the site of covalent attachment to $L_O$ or $L_R$, depending on the presence or absence of $L_O$, respectively.

35. The Ligand Drug Conjugate of embodiment 33 wherein the NAMPT Tail Unit is an aryl moiety having the structure of:

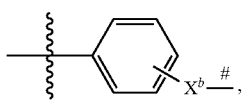

wherein $X^b$ is —S—, —O— or NH—, optionally substituted, wherein $X^b$ is at the meta or para position relative to the site of covalent attachment to $I_N$ as indicated by the wavy line; and the pound sign (#) indicates the site of covalent attachment to $L_O$ or $L_R$, depending on the presence or absence of $L_O$, respectively.

36. The Ligand Drug Conjugate composition of any one of embodiments 2 to 35, wherein $I_N$ of the released NAMPT Drug Unit is capable of interacting with one or more amino acids of a NAMPT monomer of an enzymatically competent NAMPT homodimer selected from the group consisting of Val 242, Ile 309, Ile 351, and His 191 of NAMPT, wherein the NAMPT monomer has the amino acid sequence of NCBI Reference Sequence NP_005737.1

37. The Ligand Drug Conjugate composition of any one of embodiments 2 to 35 wherein $I_N$ is —$CH_2$—$(CH_2)_{3-7}$—$CH_2$—, —$CH_2$—$(CH_2)_{3-7}$—$CH_2$—O—, —$CH_2$—$(CH_2)_{3-7}$—C(=O)—, —$CH_2$—$(CH_2)_{3-7}$—S(=O)$_2$— or —$CH_2$—$(CH_2)_{3-7}$—S(=O)—.

38. The Ligand Drug Conjugate composition of any one of embodiments 2 to 35 wherein $I_N$ has the structure of:

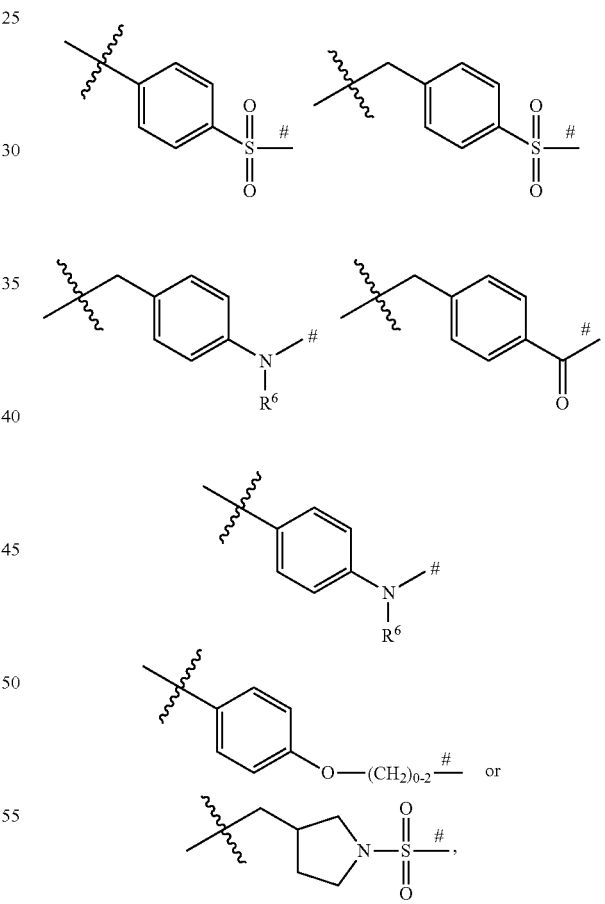

wherein the wavy line indicates the site of covalent attachment to DA and the pound sign (#) indicates the site of covalent attachment to $T_N$; and $R^6$ is hydrogen, $C_1$-$C_4$ alkyl, —$CH_2CH$=$C(CH_3)_2$, or —$CH_2$—C≡CH.

39. The Ligand Drug Conjugate composition of any one of embodiments 2 to 25, wherein —$I_N$-$T_N$- has the structure of:

161

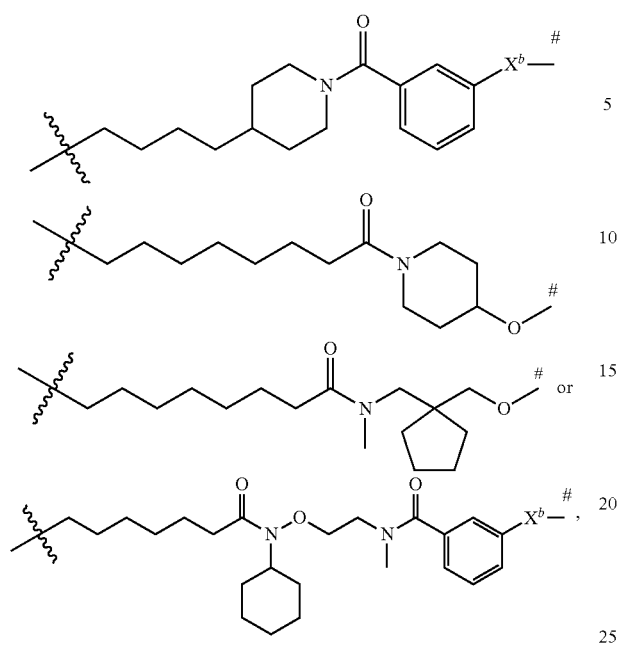

wherein
X[b] is —NH—, —O— or —S—; the wavy line indicates the site of covalent attachment to DA; and the pound sign (#) indicates the site of covalent attachment to L[O] or L[R], depending on the presence or absence of L[O], respectively.

162

40. The Ligand Drug Conjugate composition of any one of embodiments 2 to 25, wherein —I[N]-T[N]- has the structure of:

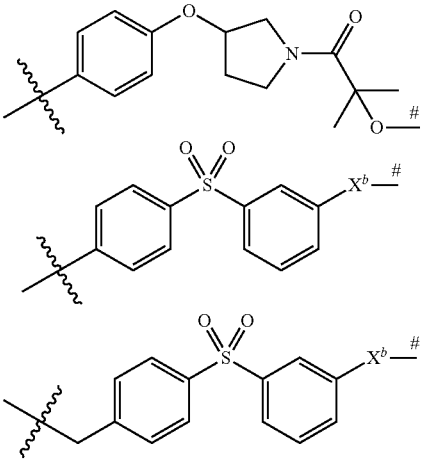

wherein X[b] is —O—, —S— or NH—, optionally substituted; the wavy line indicates the site of covalent attachment to DA; and the pound sign (#) indicates the site of covalent attachment to L[O] or L[R], depending on the presence or absence of L[O], respectively.

41. The Ligand Drug Conjugate composition of embodiment 1 wherein the NAMPT Drug Unit has the structure of:

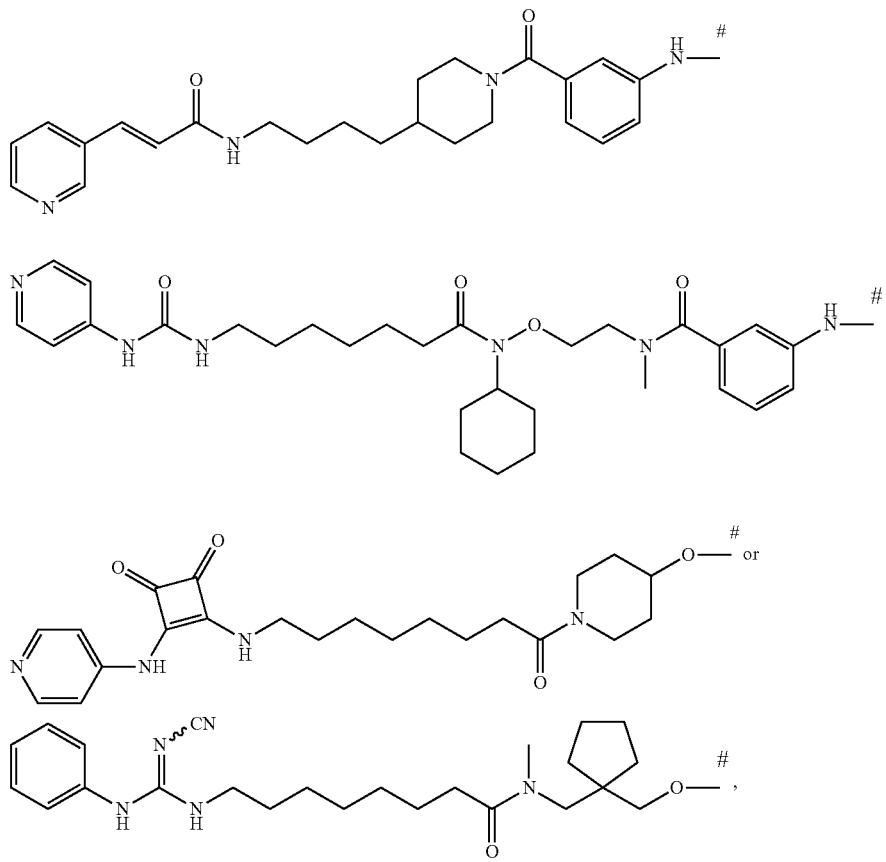

or a pharmaceutically acceptable salt thereof, wherein the pound sign (#) indicates the site of covalent attachment to $L_O$ or $L_R$, depending on the presence or absence of $L_O$, respectively.

42. The Ligand Drug Conjugate composition of any one of embodiments 1 to 41, wherein $L$-$L_R$- has the structure of:

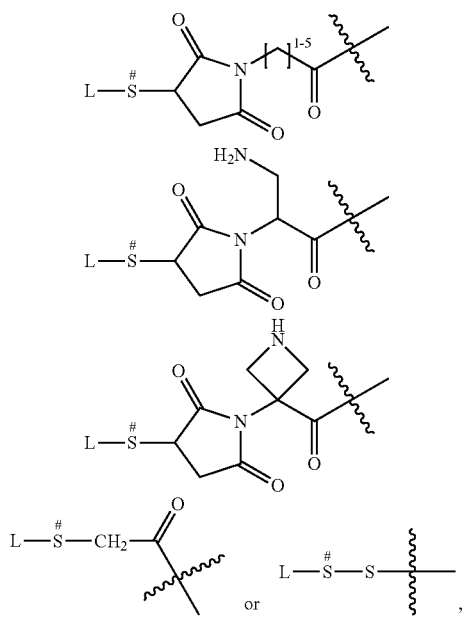

or a pharmaceutically acceptable salt thereof, wherein L is a Ligand Unit and the indicated (#) sulfur atom is from the Ligand Unit; and wherein the wavy line indicates the site of covalent attachment to the remainder of the Conjugate structure.

43. The Ligand Drug Conjugate composition of any one of embodiments 1 to 41, wherein $L$-$L_R$- has the structure of:

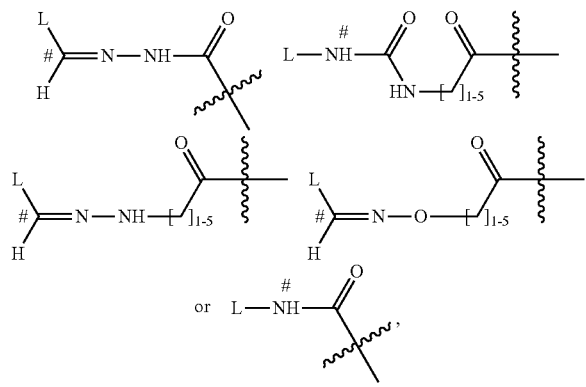

or a pharmaceutically acceptable salt thereof, wherein L is a Ligand Unit and the indicated (#) atom is from the Ligand Unit; and wherein the wavy line indicates the site of covalent attachment to the remainder of the Conjugate structure.

44. The Ligand Drug Conjugate composition of any one of embodiments 1 to 41 wherein the composition is represented by the structure(s) of Formula 1 and/or Formula 2:

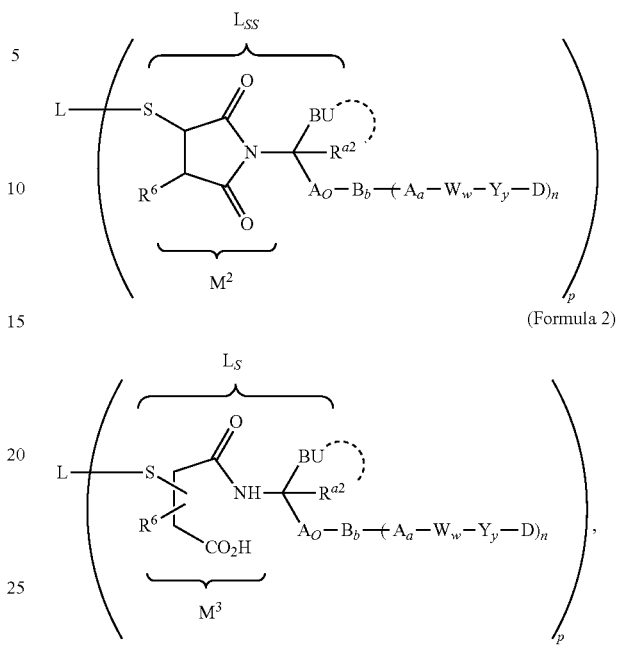

or a pharmaceutically acceptable salt thereof, wherein L is a Ligand Unit; S is a sulfur atom of the Ligand Unit, which in Formula 2 is bonded to the carbon atom α or β to the carboxylic acid functional group of the indicated succinic acid amide ($M^3$) moiety; $R^6$ is hydrogen or an optionally substituted $C_1$-$C_6$ alkyl, which in Formula 2 is bonded to the saturated carbon atom adjacent to the carbon substituted by L-S—; $A_O$ is a second optional Stretcher Unit; BU is a Basic Unit and R is an optionally substituted $C_1$-$C_{12}$ alkyl group; and the dotted curved line indicates optional cyclization so that in the absence of said cyclization BU is an acyclic Basic Unit or in the presence of said cyclization BU is a cyclized Basic Unit in which R and BU together with the carbon atom to which both are attached, define an optionally substituted spiro $C_3$-$C_{20}$ heterocyclo containing a skeletal basic nitrogen atom of a secondary or tertiary amine functional group of BU, wherein the basic nitrogen atom of the acyclic Basic Unit or cyclic Basic Unit is optionally suitably protected by a nitrogen protecting group, dependent on the degree of substitution of the basic nitrogen atom, or is optionally protonated.

45. The Ligand Drug Conjugate (LDC) composition of embodiment 44 wherein the composition is represented by the structure(s) of:

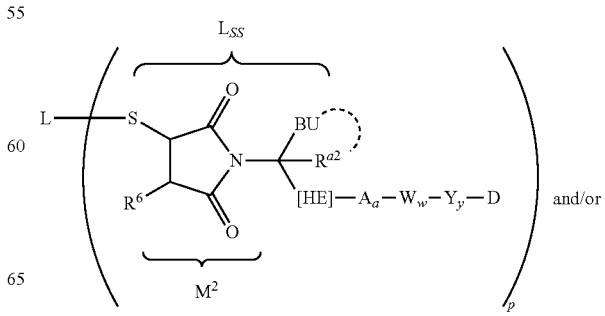

and/or

-continued

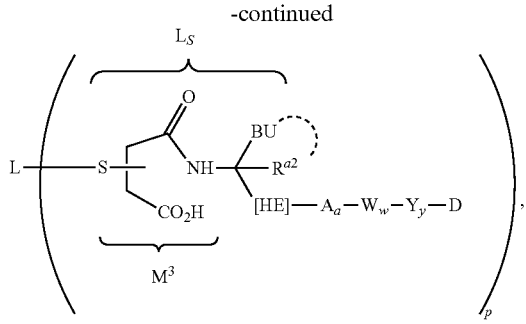

wherein

[HE] as $A_O$ is an optional Hydrolysis Enhancing Unit; subscript w is 1; W is Peptide Cleavable Unit, wherein protease action on the Peptide Cleavable Unit resulting in cleavage of the W-J' bond within a compound of the Ligand Drug Conjugate composition initiates release of the NAMPT Drug Unit as NAMPTi compound or derivative thereof from that Ligand Drug Conjugate compound, or W is a Glucuronide Unit of formula —Y(W')— having the structure of:

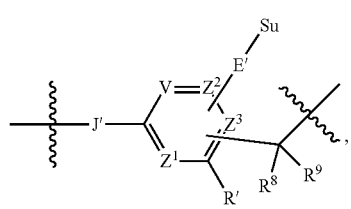

wherein

Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W'; J' is an independently selected heteroatom, optionally substituted; V, $Z^1$, $Z^2$ and $Z^3$ are independently =N— or c)=($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)— moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the C($R^8$)($R^9$)— and -E'-Su moieties are ortho or para to each other;

$R^8$ and $R^9$ independently are hydrogen, or $C_1$-$C_{12}$, alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$-$C_6$ alkyl, or other electron donating group; and wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the site of covalent attachment of the Glucuronide Unit to Y' when subscript y is 2, or to D when subscript y is 1; and wherein glycosidase action on the Glucuronide Unit resulting in cleavage of its glycosidic bond initiates release of the NAMPT Drug Unit as NAMPTi compound or derivative thereof from that Ligand Drug Conjugate compound.

46. The Ligand-Drug Conjugate composition of embodiment 45 wherein W is a Glucuronide Unit for which —W—$Y_y$-D has the structure of:

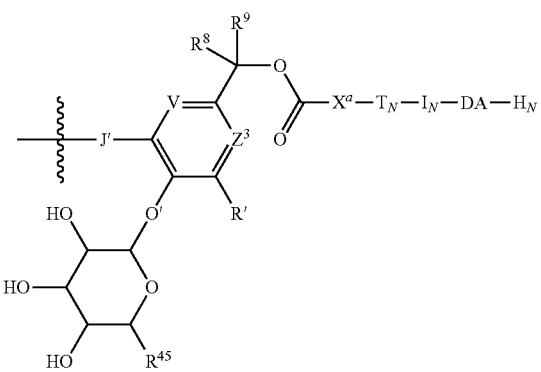

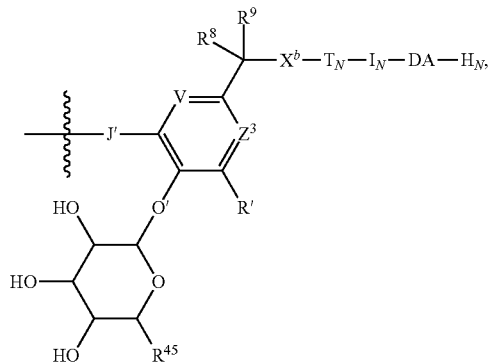

or a pharmaceutically acceptable salt thereof, wherein $X^a$ is a nitrogen atom from a primary or secondary amine functional group of $T_N$; $X^b$ is an oxygen atom from an alcohol functional group or a sulfur atom from a thiol functional group of $T_N$; R' is hydrogen or —$NO_2$ or other electron withdrawing group; $R^{45}$ is $CH_2OH$ or —$CO_2H$; wherein —O'— represents the oxygen heteroatom of an O-glycosidic bond cleavable by a glycosidase, wherein said cleavage within a compound of the Ligand Drug Conjugate composition initiates release of the NAMPT Drug Unit as a NAMPTi compound or derivative thereof from that Ligand Drug Conjugate compound.

47. The Ligand-Drug Conjugate composition of embodiment 45 wherein W is a Glucuronide Unit for which —W—$Y_y$-D has the structure of:

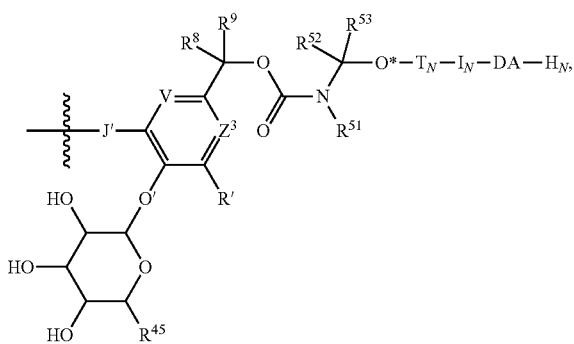

or a pharmaceutical acceptable salt thereof, wherein O* is an oxygen atom from a from an alcohol functional group of $T_N$; R' is hydrogen or —$NO_2$ or other electron withdrawing group; $R^{51}$, $R^{52}$ and $R^{53}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^{51}$ and $R^{52}$ together with the nitrogen and carbon atoms to which both are attached define an azetidine, pyrrolidine, piperidine or homopiperidine heterocyclo, and $R^{53}$ is hydrogen; $R^{45}$ is —$CH_2OH$ or —$CO_2H$; wherein O* represents the oxygen atom from an alcohol functional group of $T_N$ and O' represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative from that Ligand Drug Conjugate compound.

48. The Ligand-Drug Conjugate composition of embodiment 45 wherein W is a Peptide Cleavable Unit and —$Y_y$-D- has the structure of:

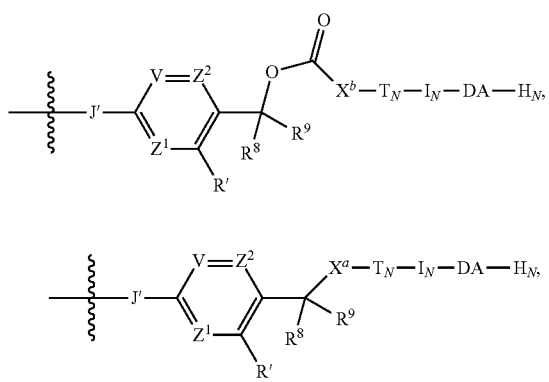

or a pharmaceutical acceptable salt thereof, wherein $X^a$ is an oxygen atom from an alcohol functional group or a sulfur atom of a thiol functional group of $T_N$; $X^b$ is a nitrogen atom from a primary or secondary amine functional group of $T_N$; R' is hydrogen or —$OC_1$-$C_6$ alkyl or other electron donating group; J' is an optionally substituted heteroatom bonded to W as indicated by the wavy line, wherein cleavage of that bond within a compound of the Ligand Drug Conjugate composition initiates release of the NAMPT Drug Unit as a NAMPTi compound or derivative thereof from that Ligand Drug Conjugate compound.

49. The Ligand-Drug Conjugate composition of embodiment 45 wherein W is a Peptide Cleavable Unit and —$Y_y$-D- has the structure of:

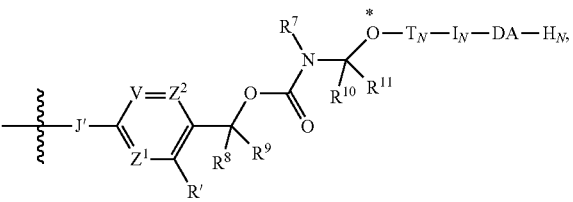

or a pharmaceutical acceptable salt thereof, wherein

R' is hydrogen or —$OC_1$-$C_6$ alkyl or other electron donating group; $R^7$, $R^{10}$ and $R^{11}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^7$ and $R^{10}$ together with the nitrogen and carbon atoms to which both are attached define an azetidine, pyrrolidine, piperidine or homopiperidine heterocyclo, and $R^{11}$ is hydrogen; $R^{45}$ is —$CH_2OH$ or —$CO_2H$; O* represents the oxygen atom from an alcohol functional group of $T_N$; and J' is an optionally substituted heteroatom bonded to W as indicated by the wavy line, wherein cleavage of that bond within a compound of the Ligand Drug Conjugate composition initiates release of the NAMPT Drug Unit as a NAMPTi compound or derivative thereof from that Ligand Drug Conjugate compound.

50. The Ligand Drug Conjugate composition of embodiment 45 wherein the composition is represented by the structure(s) of:

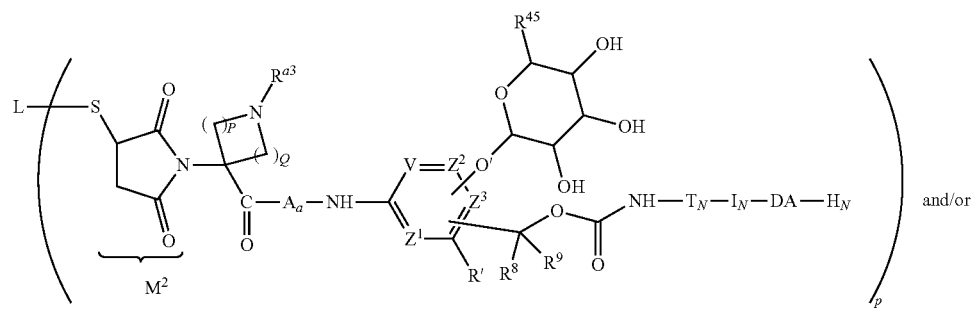

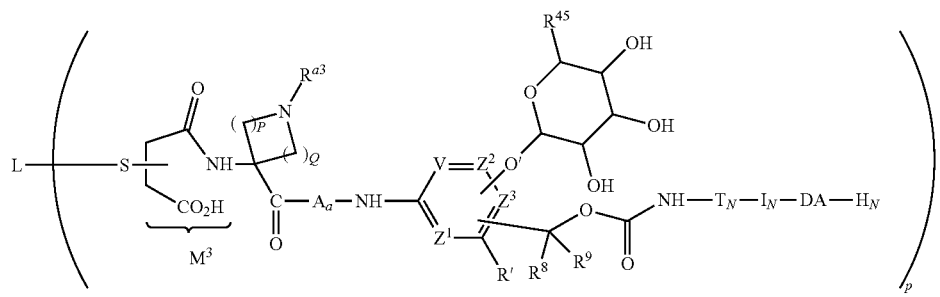

or a pharmaceutical acceptable salt thereof, wherein subscript P is 1, 2 or 3; subscript Q ranges from 1 to 6; R' is hydrogen or —$NO_2$ or other electron withdrawing group; $R^{45}$ is —$CH_2OH$ or —$CO_2H$; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2$O)$_{1-36}$—$R^{PEG2}$, wherein $R^{PEG1}$ $C_1$-$C_4$ alkylene, and $R^{PEG2}$ is —H or $C_1$-$C_4$ alkyl; and wherein the basic nitrogen atom bonded to $R^{a3}$ is optionally protonated, and wherein —O'— represents the oxygen heteroatom of an O-glycosidic bond cleavable by a glycosidase, wherein said cleavage within a compound of the Ligand Drug Conjugate composition initiates release of the NAMPT Drug Unit as a NAMPTi compound or derivative thereof that Ligand Drug Conjugate compound.

51. The Ligand Drug Conjugate composition of embodiment 45 wherein the composition is represented by the structure(s) of:

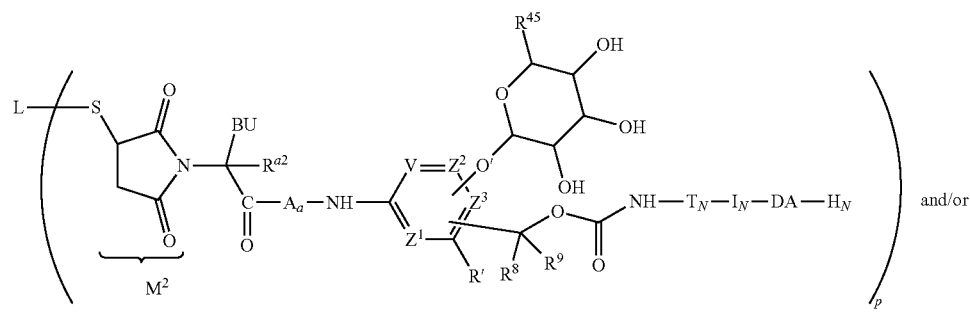 and/or

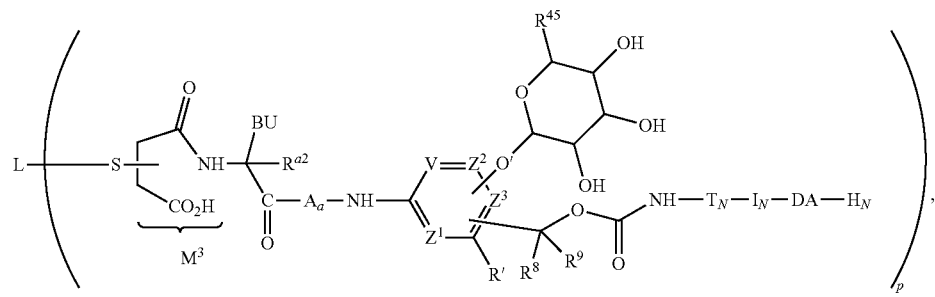

or a pharmaceutical acceptable salt thereof, wherein subscript P is 1, 2 or 3; subscript Q ranges from 1 to 6; R' is hydrogen or —$NO_2$ or other electron withdrawing group; $R^{45}$ is —$CH_2OH$ or —$CO_2H$; $R^{a2}$ is hydrogen or $C_1$-$C_6$ alkyl; BU has the structure of $[C(R^{a1})(R^{a1})]$—$[C(R^{a1})(R^{a1})]_{0-3}$—$N(R^{a3})(R^{a3})$, each $R^{a3}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a3}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; wherein the basic nitrogen atom of BU bonded to $R^{a1}$ is optionally protonated; and wherein —O'— represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof from that Ligand Drug Conjugate compound.

52. The Ligand Drug Conjugate composition of embodiment 45 wherein the composition is represented by the structure(s) of:

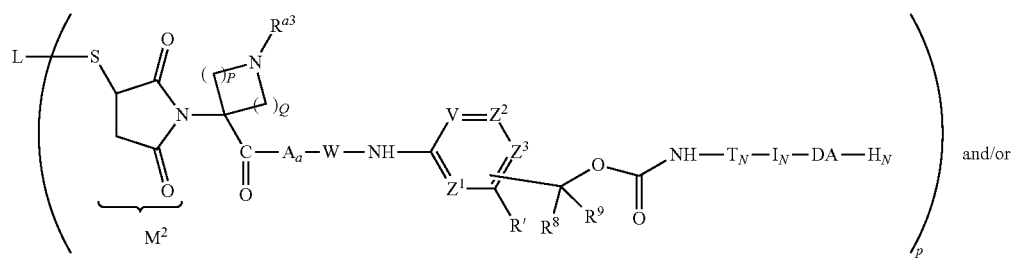

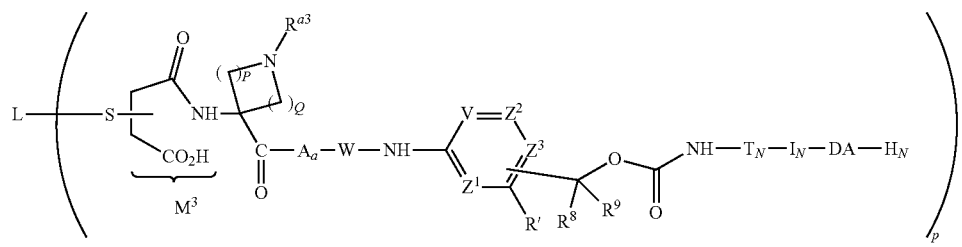

or a pharmaceutical acceptable salt thereof, wherein W is a Peptide Cleavable Unit; subscript P is 1, 2 or 3; subscript Q ranges from 1 to 6; R' is hydrogen or —$OC_1$-$C_6$ alkyl or other electron donating group; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^{a3}$ is optionally protonated, and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

53. The Ligand Drug Conjugate composition of embodiment 45 wherein the composition is represented by the structure(s) of:

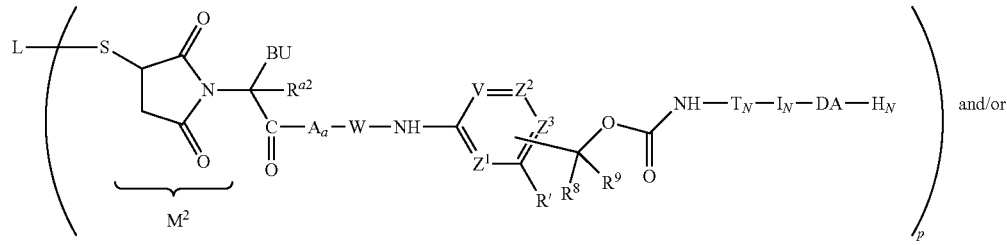

-continued

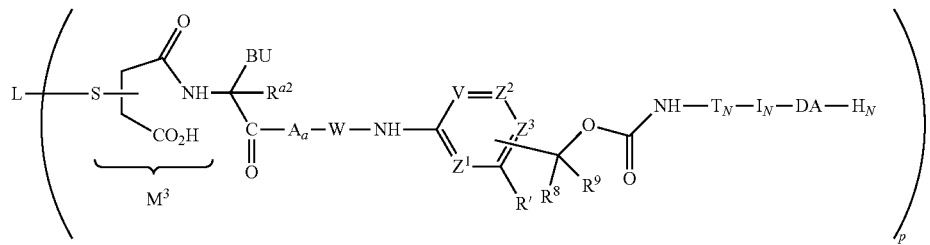

or a pharmaceutical acceptable salt thereof, wherein

W is a Peptide Cleavable Unit; subscript P is 1, 2 or 3; subscript Q ranges from 1 to 6; R' is hydrogen or —$OC_1$-$C_6$ alkyl or other electron donating group; $R^{a2}$ is hydrogen or $C_1$-$C_6$ alkyl; BU has the structure of —[$C(R^{a1})(R^{a1})$]—[$C(R^{a1})(R^{a1})$]$_{0-3}$—$N(R^{a3})(R^{a3})$, each $R^{a3}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl;

wherein the basic nitrogen atom of BU bonded to $R^{a1}$ is optionally protonated; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

54. The Ligand Drug Conjugate composition of embodiment 45 wherein the composition is represented by the structure(s) of:

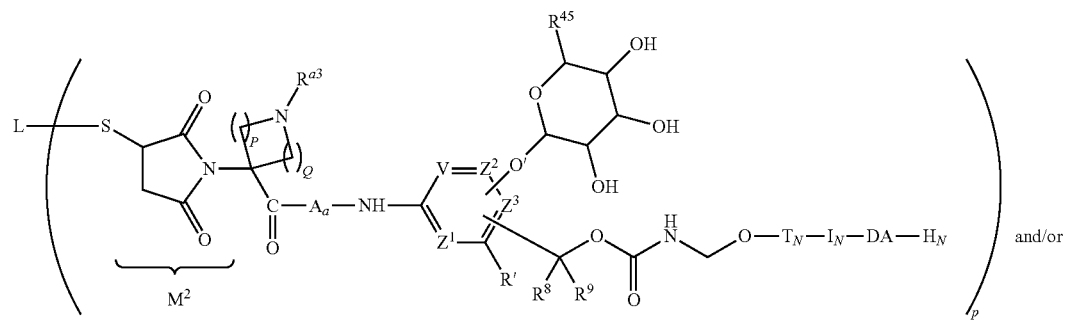 and/or

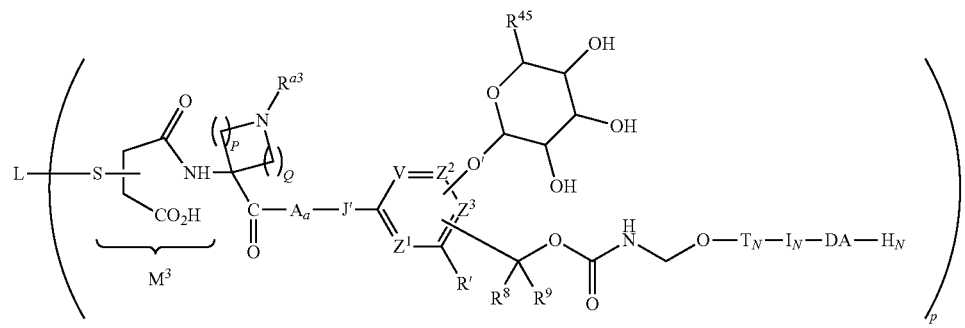

or a pharmaceutical acceptable salt thereof, wherein
subscript P is 1, 2 or 3; subscript Q ranges from 1 to 6; R' is hydrogen or —$NO_2$ or other electron withdrawing group; $R^{45}$ is —$CH_2OH$ or —$CO_2H$; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O$)$_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^{a1}$ is optionally protonated, and wherein —O'— represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof that Ligand Drug Conjugate compound.

55. The Ligand Drug Conjugate composition of embodiment 45 wherein the composition is represented by the structure(s) of:

alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; wherein the basic nitrogen atom of BU bonded to $R^{a1}$ is optionally protonated; and wherein —O'-represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof from that Ligand Drug Conjugate compound.

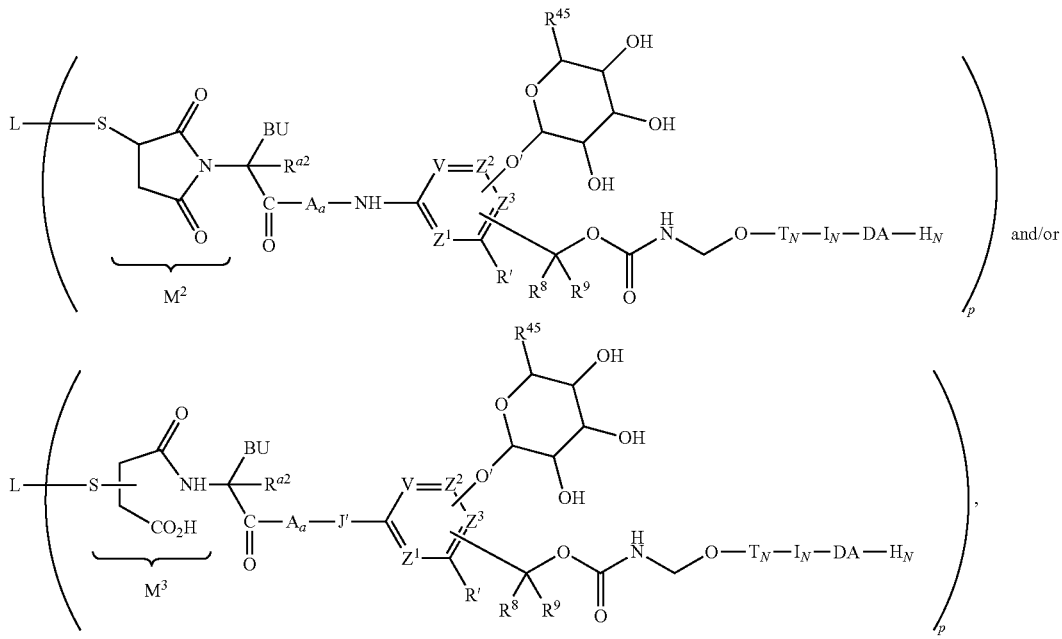

or a pharmaceutical acceptable salt thereof, wherein
subscript P is 1, 2 or 3; subscript Q ranges from 1 to 6; R' is hydrogen or —$NO_2$ or other electron withdrawing group; $R^{45}$ is —$CH_2OH$ or —$CO_2H$; $R^{a2}$ is hydrogen or $C_1$-$C_6$ 56. The Ligand Drug Conjugate composition of embodiment 45 wherein the composition is represented by the structure(s) of:

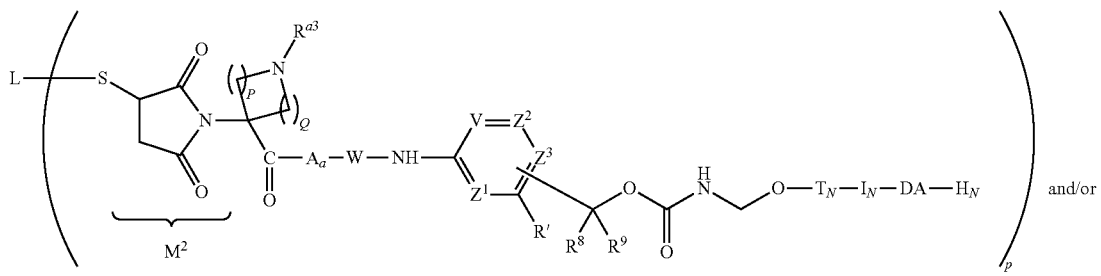

-continued

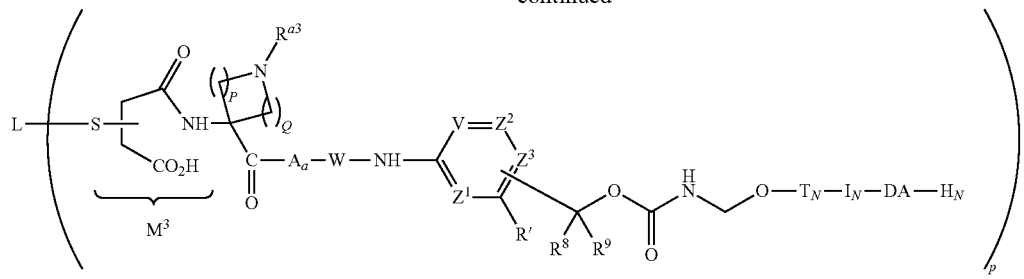

or a pharmaceutical acceptable salt thereof, wherein
W is a Peptide Cleavable Unit; subscript P is 1, 2 or 3; subscript Q ranges from 1 to 6; R' is hydrogen or —$OC_1$-$C_6$ alkyl or other electron donating group; $R^{a1}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O$)$_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^{a1}$ is optionally protonated; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

57. The Ligand Drug Conjugate composition of embodiment 45 wherein the composition is represented by the structure(s) of:

alkyl or other electron donating group; $R^{a2}$ is hydrogen or $C_1$-$C_6$ alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a3}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; wherein the basic nitrogen atom of BU bonded to $R^{a3}$ is optionally protonated; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

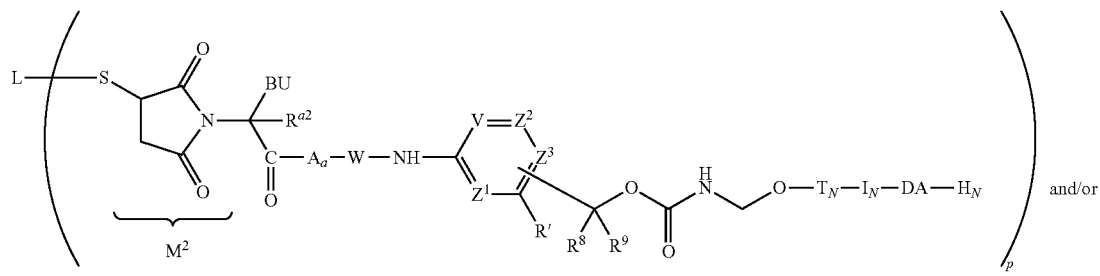 and/or

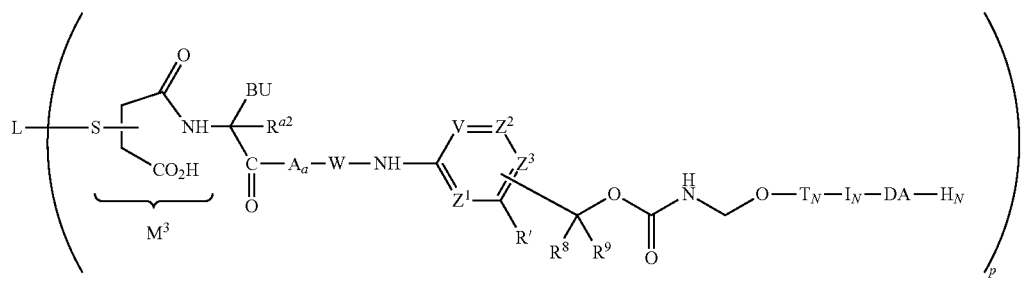

or a pharmaceutical acceptable salt thereof, wherein
W is a Peptide Cleavable Unit; subscript P is 1, 2 or 3; subscript Q ranges from 1 to 6; R' is hydrogen or —$OC_1$-$C_6$

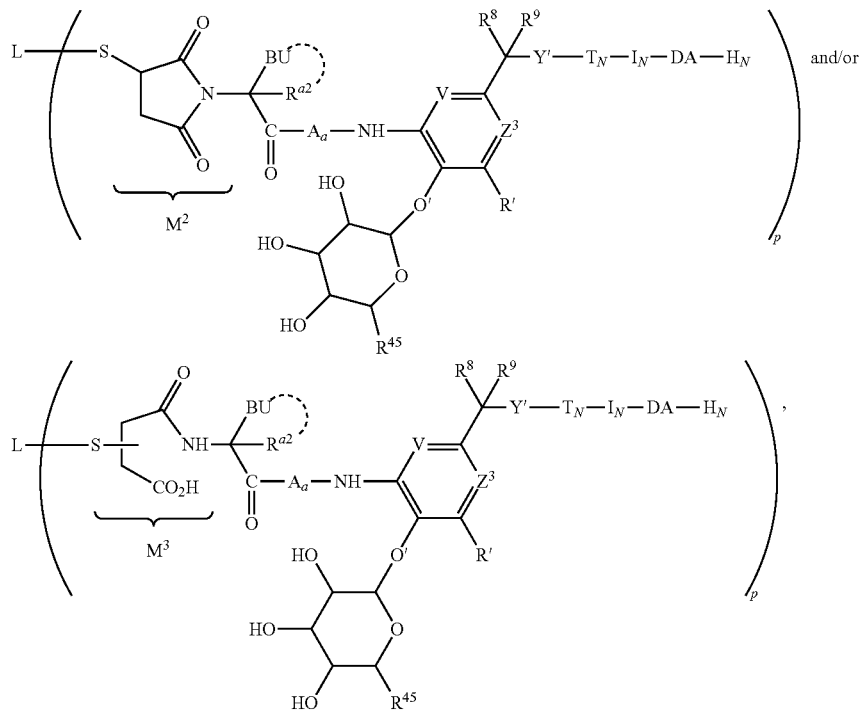

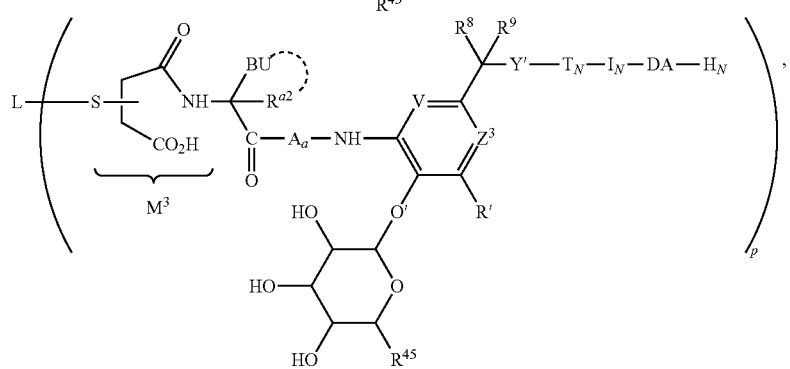

or a pharmaceutical acceptable salt thereof, wherein

Y' is $-X^a-$, $-O-C(=O)-X^b-$ or $-OC(=O)NH-CH_2-X^a-$, wherein $-X^a-$ is O and $X^b$ is $-NH-$; R' is hydrogen or $-NO_2$ or other electron withdrawing group; $R^{45}$ is $-CH_2OH$ or $CO_2H$; BU has the structure of $-[C(R^{a1})(R^{a1})]-[C(R^{a1})(R^{a1})]_{0-3}-N(R^{a3})(R^{a3})$, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a3}$ together with the carbon(s) to which they are attached and any intervening carbons define an optionally substituted $C_3$-$C_6$ cycloalkyl; $R^{a1}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; $R^{a2}$ is hydrogen or $C_1$-$C_6$ alkyl, optionally cyclized to BU, as indicated by the dotted curved line, wherein one of $R^{a1}$ or one of $R^{a3}$ is replaced with a bond to a carbon atom of $R^{a2}$ when $R^{a2}$ is $C_1$-$C_6$ alkyl; wherein the basic nitrogen atom of BU bonded to $R^{a3}$ is optionally protonated; and wherein $-O'-$ represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof that Ligand Drug Conjugate compound.

59. The Ligand-Drug Conjugate composition of embodiment 45 wherein the composition is represented by the structure(s) of:

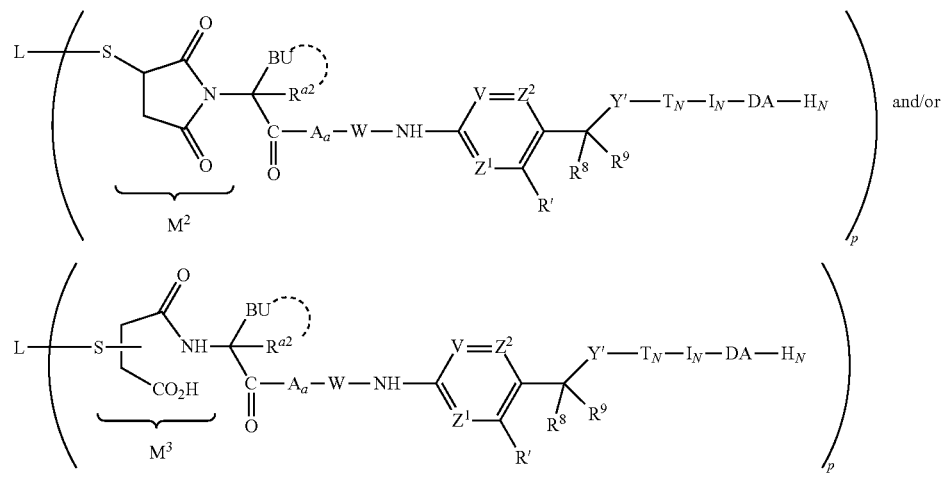

or a pharmaceutical acceptable salt thereof, wherein

W is a Peptide Cleavable Unit; Y' is —$X^a$—, —O—C(=O)—$X^b$— or —OC(=O)NH—$CH_2$—$X^a$—, wherein —$X^a$— is O and $X^b$ is —NH—; R' is hydrogen or —$OC_1$-$C_6$ alkyl or other electron donating group; $R^{45}$ is —$CH_2OH$ or —$CO_2H$; BU has the structure of —[C($R^{a1}$)($R^{a1}$)]—[C($R^{a1}$)($R^{a1}$)]$_{0-3}$—N($R^{a3}$)($R^{a3}$), each $R^{a2}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a3}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; $R^{a2}$ is hydrogen or $C_1$-$C_6$ alkyl, optionally cyclized to BU, as indicated by the dotted curved line, wherein one of $R^{a1}$ or one of $R^{a3}$ is replaced with a bond to a carbon atom of $R^{a2}$ when $R^{a2}$ is $C_1$-$C_6$ alkyl; wherein the basic nitrogen atom of BU bonded to $R^{a3}$ is optionally protonated; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

60. The Ligand-Drug Conjugate composition of embodiment 45 wherein the composition is represented by the structure(s) of:

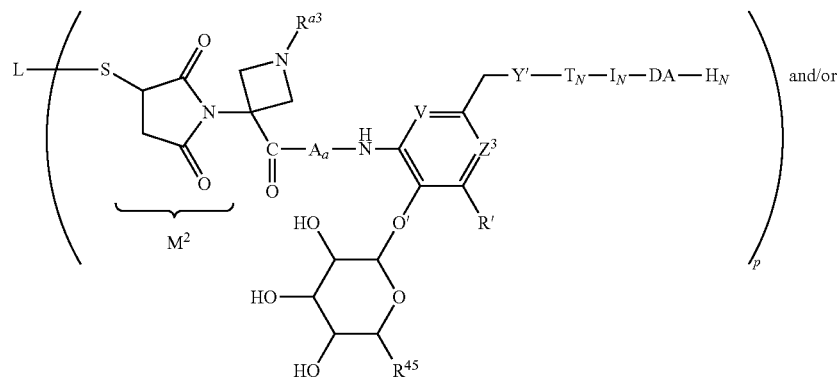

and/or

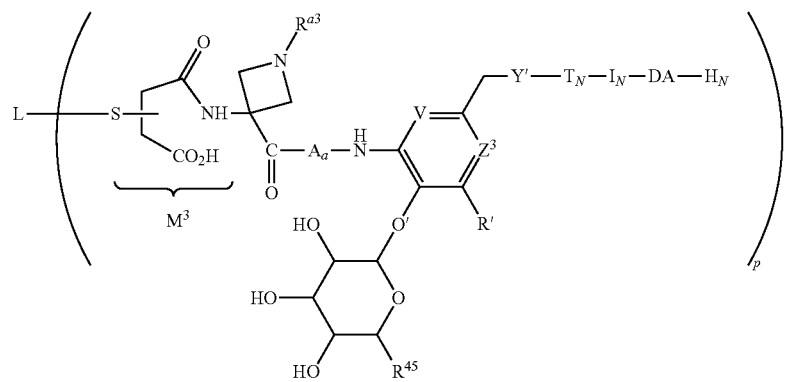

or a pharmaceutical acceptable salt thereof, wherein Y' is —$X^a$—, —O—C(=O)—$X^b$— or —OC(=O)NH—$CH_2$—$X^a$—, wherein —$X^a$— is O and $X^b$ is —NH—; $R^{45}$ is —$CH_2OH$ or —$CO_2H$; $R^{a1}$ is —H, or optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^{a1}$ is optionally protonated; and wherein —O'— represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof that Ligand Drug Conjugate compound.

61. The Ligand-Drug Conjugate composition of embodiment 45 wherein the composition is represented by the structure of:

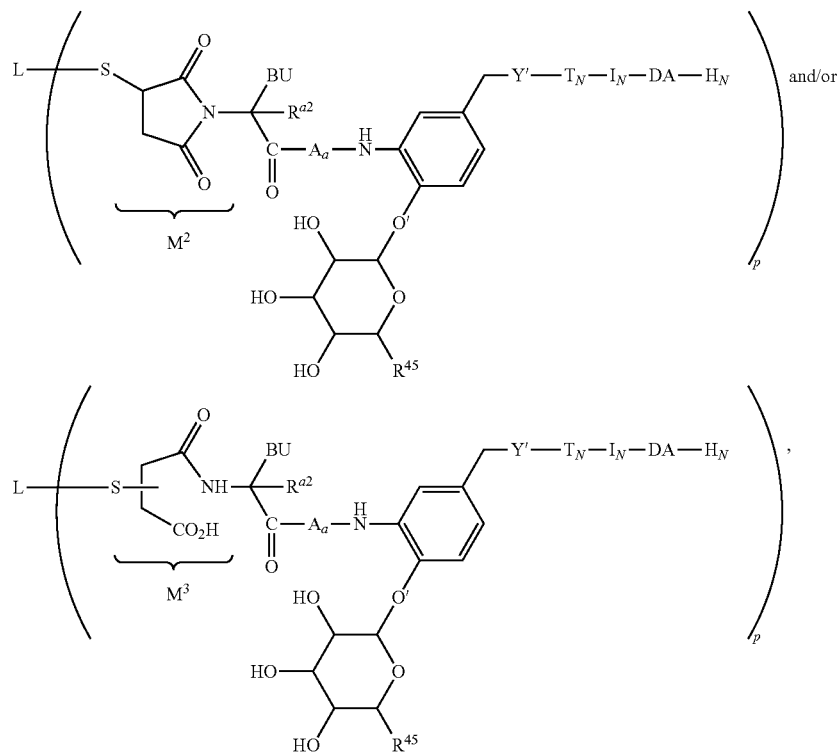

or a pharmaceutical acceptable salt thereof, wherein Y' is —$X^a$—, —O—C(=O)—$X^b$— or —OC(=O)NH—$CH_2$—$X^a$—, wherein —$X^a$— is O and $X^b$ is —NH—; $R^{45}$ is —$CH_2OH$ or —$CO_2H$; BU is —$CH_2$—$NH_2$, optionally protonated; $R^{a2}$ is hydrogen; and wherein —O'— represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof that Ligand Drug Conjugate compound.

62. The Ligand-Drug Conjugate composition of embodiment 45 wherein the composition is represented by the structure(s) of:

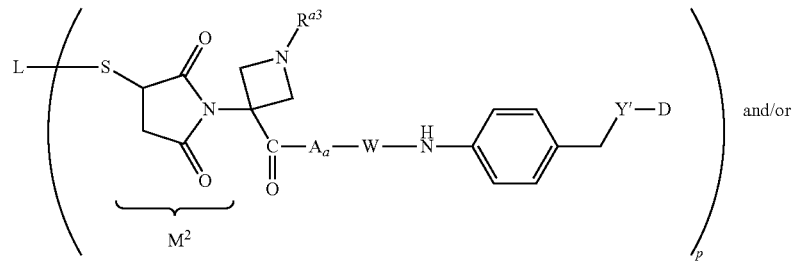

-continued

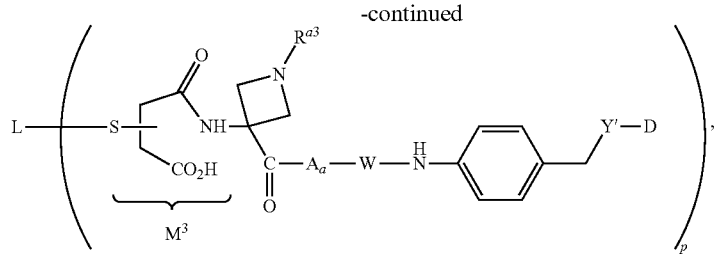

or a pharmaceutical acceptable salt thereof, wherein

W is a Peptide Cleavable Unit; Y' is —$X^a$—, —O—C(=O)—$X^b$— or —OC(=O)NH—$CH_2$—$X^a$—, wherein —$X^a$— is O and $X^b$ is —NH—; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2$O)$_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^{a3}$ is optionally protonated; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

63. The Ligand-Drug Conjugate composition of embodiment 45 wherein the composition is represented by the structure(s) of:

or a pharmaceutical acceptable salt thereof, wherein

W is a Peptide Cleavable Unit; Y' is —$X^a$—, —O—C(=O)—$X^b$— or —OC(=O)NH—$CH_2$—$X^a$—, wherein —$X^a$— is O and $X^b$ is —NH—; BU is —$CH_2$—$NH_2$, optionally protonated; $R^{a2}$ is hydrogen; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

64. The Ligand-Drug Conjugate composition of any one of the preceding embodiments in which W is a Peptide Cleavable Unit that Unit is comprised of a dipeptide, wherein the dipeptide provides for a recognition site for a regulatory or lysosomal protease for cleavage by said protease of the W-J' bond or the W—NH bond when J' is —NH within a compound of the Ligand Drug Conjugate composition so as to initiate release of the NAMPT Drug Unit as NAMPTi compound or derivative thereof from that Ligand Drug Conjugate compound.

65. The Ligand-Drug Conjugate composition of embodiment 64 wherein the W has the structure of:

wherein $R^{34}$ is benzyl, methyl, isopropyl, isobutyl, sec-butyl, —CH(OH)$CH_3$ or has the structure of wherein the asterisk indicates the site of covalent attachment to the dipeptide backbone; and $R^{35}$ is methyl, —($CH_2$)$_4$—$NH_2$, —($CH_2$)$_3$NH(C=O)$NH_2$, —($CH_2$)$_3$NH(C=NH)$NH_2$, or, —($CH_2$)$_2$$CO_2$H; and wherein the wavy lines indi cate the points of covalent attachment of the dipeptide into the structure representing the Ligand-Drug Conjugate composition.

66. The Ligand-Drug Conjugate composition of embodiment 65 wherein W is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

67. The Ligand-Drug Conjugate composition of any one of embodiments 1 to 66, wherein A or a subunit thereof is $-L^P(PEG)-$.

68. The Ligand-Drug Conjugate composition of embodiment 67 wherein $-L^P-$ or a subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form.

69. The Ligand-Drug Conjugate composition of embodiment 67 wherein $-L^P-$ or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

70. The Ligand-Drug Conjugate composition of embodiment 67 wherein $L_P$ or a subunit thereof is selected from the group consisting of lysine, glutamic acid, aspartic acid, cysteine, penicillamine, serine or threonine in its D- or L-stereochemical configuration.

71. The Ligand-Drug Conjugate composition of embodiment 67 wherein $-L^P-$ or a subunit thereof has the structure of Formula $L^P$-1 or $L^P$-2:

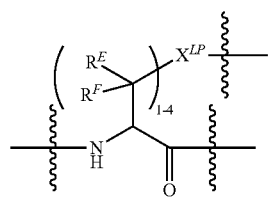

(Formula $L^P$-1)

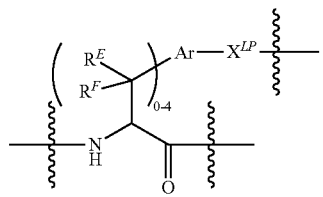

(Formula $L^P$-2)

or a pharmaceutical acceptable salt thereof, wherein $X^{LP}$ is selected from the group consisting of —O—, —$NR^{LP}$—, —S—, —S(=O)—, —S(=O)$_2$—, —C(=O)—, —C(=O)N($R^{LP}$)—, —N($R^{LP}$)C(=O)N ($R^{LP}$)—, —N($R^{LP}$)C(=N$R^{LP}$)N($R^{LP}$)—, and $C_3$-$C_8$ heterocyclo; wherein each $R^{LP}$ is independently selected from the group consisting of hydrogen and optionally substituted $C_1$-$C_6$ alkyl, or two of $R^{LP}$ together along with the carbons atoms to which they are attached and their intervening atoms define a $C_5$-$C_6$ heterocyclo and any remaining $R^{LP}$ are as previously defined; Ar is a $C_6$-$C_{10}$ arylene or a $C_5$-$C_{10}$ heteroarylene, optionally substituted; each $R^E$ and $R^F$ is independently selected from the group consisting of —H, optionally substituted $C_1$-$C_6$ alkyl, optionally substituted $C_2$-$C_6$ alkylene, optionally substituted $C_6$-$C_{10}$ arylene and optionally substituted $C_5$-$C_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined; and wherein one of the wavy lines indicates the site of covalent attachment of a PEG Unit and the other wavy lines indicates covalent attachment of Formula $L^P$-1 or Formula $L^P$-2 within the structure representing the Ligand Drug Conjugate composition.

72. The Ligand-Drug Conjugate composition of embodiment 67 wherein $-L^P(PEG)-$ has the structure of Formula $L^P$-3 or Formula $L^P$-4:

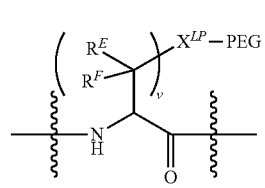

(Formula $L^P$-3)

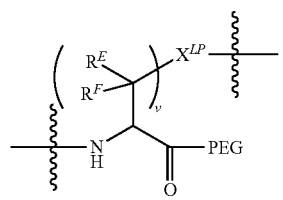

(Formula $L^P$-4)

or a pharmaceutical acceptable salt thereof, wherein subscript v is an integer ranging from 1 to 4; $X^{LP}$ is selected from the group consisting of —O—, —$NR^{LP}$—, —S—, —S(=O)—, —S(=O)$_2$—, —C(=O)—, —C(=O) N($R^{LP}$)—, —N($R^{LP}$)C(=O)N($R^{LP}$)—, —N($R^{LP}$)C (=N$R^{LP}$)N($R^{LP}$)—, and $C_3$-$C_8$ heterocyclo; wherein each $R^{LP}$ is independently selected from the group consisting of hydrogen and optionally substituted $C_1$-$C_6$ alkyl, or two of $R^{LP}$ together along with the carbons atoms to which they are attached and their intervening atoms define a $C_5$-$C_6$ heterocyclo and any remaining $R^{LP}$ are as previously defined; Ar is a $C_6$-$C_{10}$ arylene or a $C_5$-$C_{10}$ heteroarylene, optionally substituted;

each $R^E$ and $R^F$ is independently selected from the group consisting of —H, optionally substituted $C_1$-$C_6$ alkyl, optionally substituted $C_2$-$C_6$ alkylene, optionally substituted $C_6$-$C_{10}$ arylene and optionally substituted $C_5$-$C_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined, or wherein the side chain of $-[C(R^E)(R^F)]_v-X^{LP}-$ is provided by a natural or un-natural amino acid side chain; and wherein one of the wavy lines indicate the site of covalent attachment of a PEG Unit and the other wavy lines indicates covalent attachment of Formula $L^P$-1 or Formula $L^P$-2 within the structure representing the Ligand Drug Conjugate composition.

73. The Ligand-Drug Conjugate composition of embodiment 71 or 72 wherein $R^E$ and $R^F$ are independently selected from the group consisting of —H, and —$C_1$-$C_4$ alkyl.

74. The Ligand-Drug Conjugate composition of claim 71, 72 or 73 wherein $X^{LP}$ is selected from the group consisting of —O—, —NH, —S— and —C(=O)—.

75. The Ligand-Drug Conjugate composition of any one of claims 67 to 74 wherein PEG has the structure selected from the group consisting of

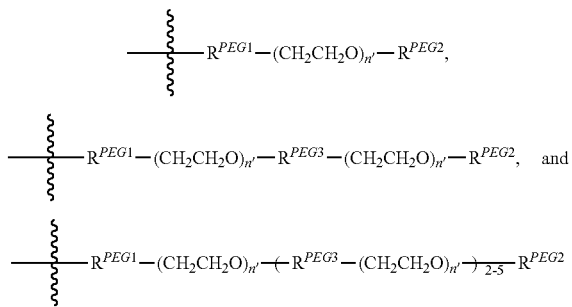

wherein the wavy line indicates site of attachment to $X^{LP}$ of the Parallel Connector Unit ($L^P$); subscript n' independently ranges from 1 to 72; $R^{PEG1}$ is an optional PEG Attachment Unit; $R^{PEG2}$ is a PEG Capping Unit; and $R^{PEG3}$ is an PEG Coupling Unit.

76. The Ligand-Drug Conjugate composition of any one of embodiments 71 to 75 wherein —$X^{LP}$-PEG has the structure of:

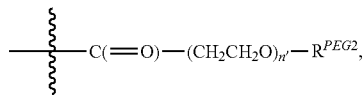

wherein subscript n' is 8, 12 or 24 and $R^{PEG2}$ is H or —CH$_3$.

77. The Ligand-Drug Conjugate composition of any one of embodiments 1 to 76 wherein A, $A_O$ or a subunit thereof has the structure of formula (3) or formula (4)

wherein the wavy lines indicated covalent attachment within the composition structure; wherein K and L' independently are C, N, O or S, provided that when K or L' is O or S, $R^{41}$ and $R^{42}$ to K or $R^{43}$ and $R^{44}$ to L' are absent, and when K or L' are N, one of $R^{41}$, $R^{42}$ to K or one of $R^{42}$, $R^{43}$ to L' are absent, and provided that no two adjacent L' are independently selected as N, O, or S; wherein subscripts e and f are independently selected integers that range from 0 to 12, and subscript g is an integer ranging from 1 to 12, wherein G is hydrogen, optionally substituted $C_1$-$C_6$ alkyl, —OH, —OR', —CO$_2$H, CO$_2R^{PR}$, wherein $R^{PR}$ is a suitable protecting, or G is —N($R^{PR}$)($R^{PR}$), wherein $R^{PR}$ are independently a protecting group or $R^{PR}$ together form a suitable protecting group, or G is —N($R^{45}$)($R^{46}$), wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl; $R^{39}$-$R^{44}$ are independently selected from the group consisting of hydrogen, optionally substituted $C_1$-$C_6$ alkyl, optionally substituted aryl, and optionally substituted heteroaryl, or $R^{39}$, $R^{40}$ together with the carbon atom to which both are attached, or $R^{41}$, $R^{42}$ together with K to which both are attached when K is a carbon atom, define a $C_3$-$C_6$ carbocyclo, and $R^{41}$-$R^{44}$ are as defined herein, or $R^{43}$, $R^{44}$ together with L' to which both are attached when L' is a carbon atom define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^{44}$ are absent, and when L' is N, one of $R^{43}$, $R^{44}$ is absent, or A, $A_O$ or a subunit thereof is an alpha-amino, beta-amino or another amine-containing acid residue.

78. The Ligand-Drug Conjugate composition of embodiment 77 wherein formula (3) or formula (4) has the structure of formula (3a) or formula (4a):

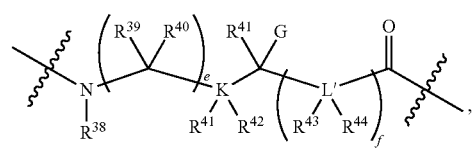

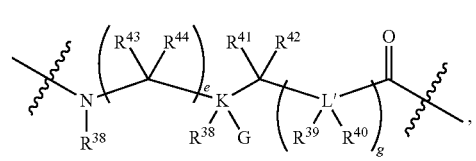

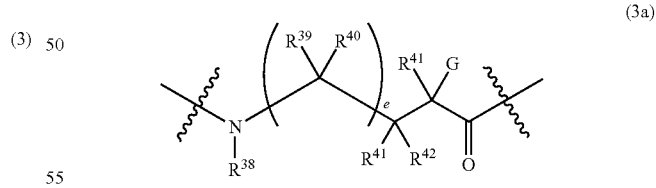

wherein subscript e and f are independently 0 or 1.

79. The Ligand-Drug Conjugate composition of any one of embodiments 1 to 78 wherein the Ligand Unit is an antibody, thereby defining an antibody Ligand Unit of an antibody drug conjugate (ADC), wherein the moiety targeted by the antibody Ligand Unit is an accessible cell-surface antigen of abnormal cells that is capable of cellular internalization when bound to ADC compound of the composition and is present in greater copy number on the abnormal cells in comparison to normal cells distant from the site of the abnormal cells.

80. The Ligand-Drug Conjugate composition of anyone of embodiments 1 to 78 wherein the Ligand Unit is a cognate ligand of an accessible cell-surface receptor on abnormal cell that is capable of cellular internalization when bound to a Ligand Drug Conjugate compound of the composition, and wherein the receptor is present in greater copy number on the abnormal cells in comparison to normal cells.

81. The Ligand-Drug Conjugate composition of any one of embodiments 1-78 wherein the Ligand Unit is an antibody, thereby defining an antibody Ligand Unit of an antibody drug conjugate (ADC), wherein the moiety targeted by the antibody Ligand Unit is an accessible cell-surface antigen of a vascular epithelial cell in the vicinity of abnormal cells, wherein said antigen is capable of cellular internalization of bound ADC and is present in greater copy number on said cells in comparison to normal epithelial cells distant from the site of the abnormal cells.

82. The Ligand Drug Conjugate composition of any one of embodiments 1 to 81 wherein subscript p is about 2, about 4, or about 8.

83. The Ligand Drug Conjugate composition of any one of the preceding embodiments in which a succinimide ($M^2$) or succinic acid amide ($M^3$) moeity is present the Ligand Unit is that of an antibody or antigen-binding fragment thereof, thereby defining an antibody Ligand Unit, wherein the sulfur atom of the antibody Ligand Unit bonded to the succinic acid ($M^2$) moiety or succinic acid amide ($M^3$) moiety is that of a cysteine residue of the antibody or antigen-binding fragment thereof.

84. The Ligand Drug Conjugate composition of embodiment 83 wherein the cysteine residue is an introduced cysteine residue in the heavy chain or light chain of the antibody or antigen binding-fragment thereof.

85. The Ligand Drug Conjugate composition of embodiment 1 wherein the composition is represented by the structure(s) of:

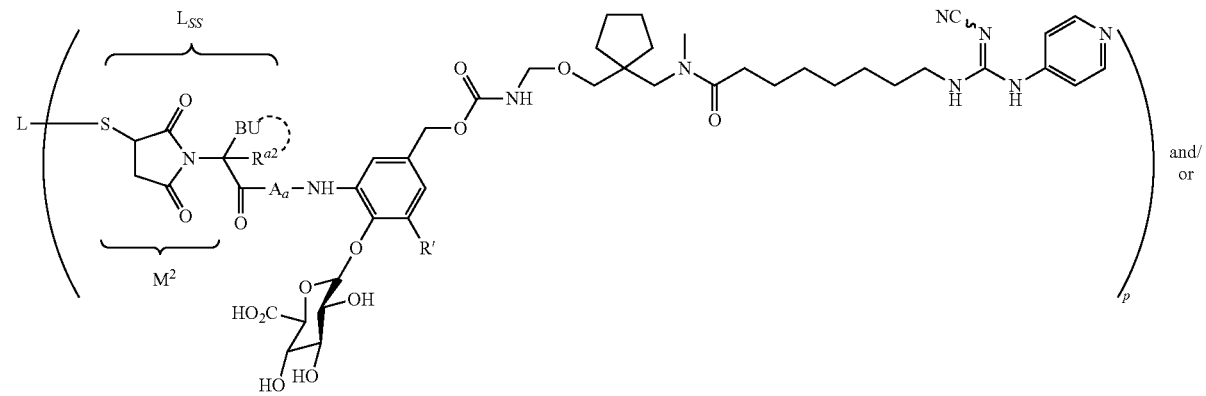

or pharmaceutical acceptable salt(s) thereof, wherein

L is an antibody, thereby defining an antibody Ligand Unit of an antibody drug conjugate (ADC), and S is a sulfur atom of the antibody; subscript a is 1 and A is an amino acid residue; BU is a acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$.

86. The Ligand Drug Conjugate composition of embodiment 1 wherein the composition is represented by the structure(s) of:

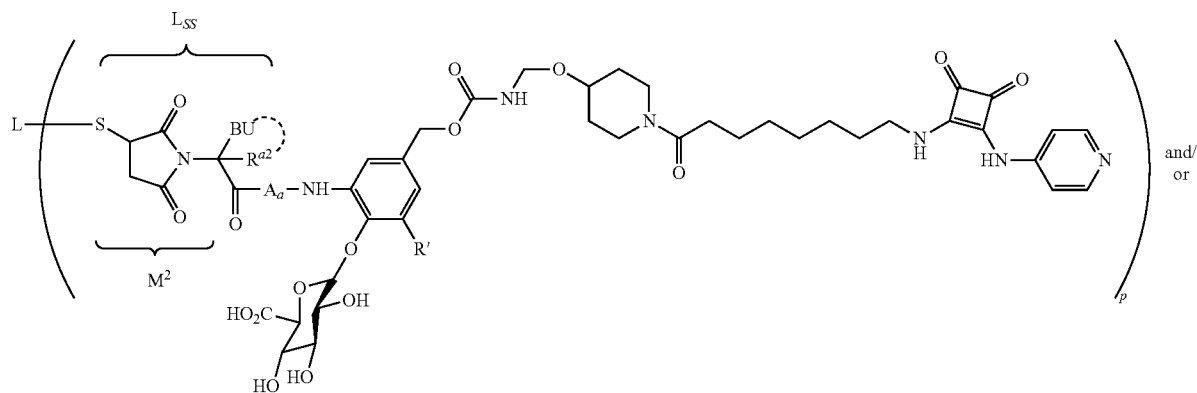

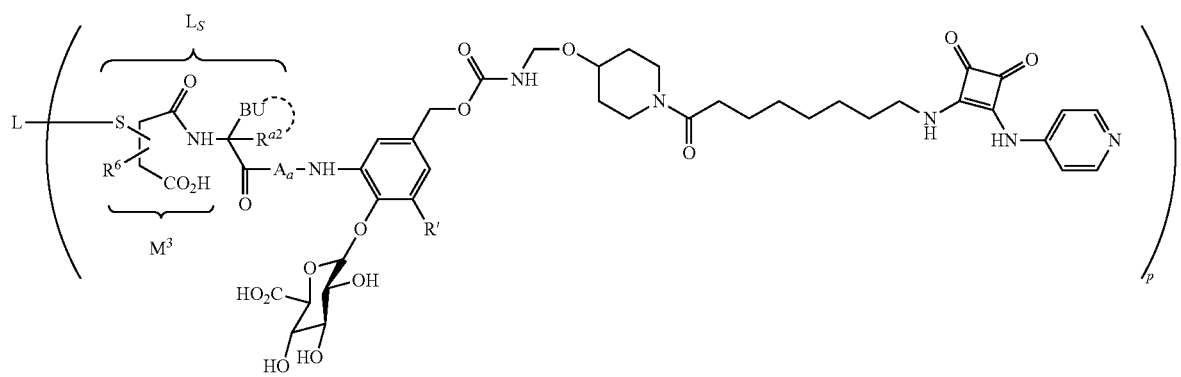

or pharmaceutical acceptable salt(s) thereof, wherein L is an antibody, thereby defining an antibody Ligand Unit of an antibody drug conjugate (ADC), and S is a sulfur atom of the antibody; subscript a is 1 and A is an amino acid residue; BU is a acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$.

87. The Ligand Drug Conjugate composition of embodiment 1 wherein the composition is represented by the structure(s) of:

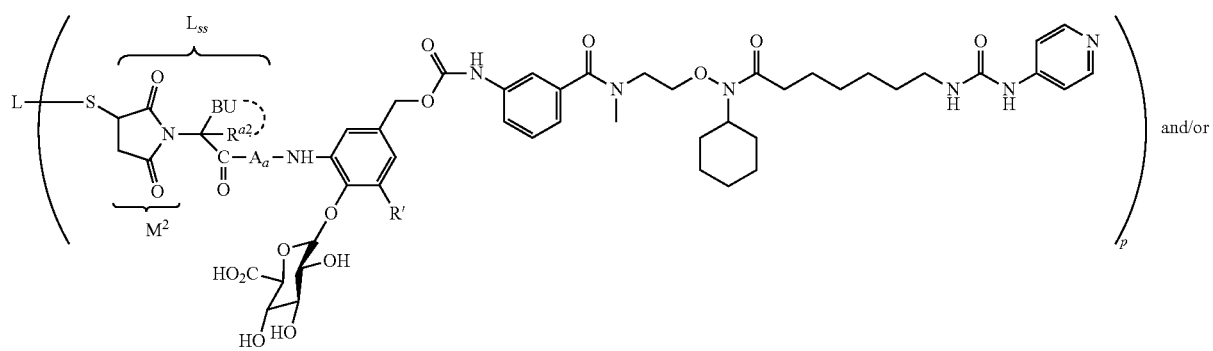

-continued

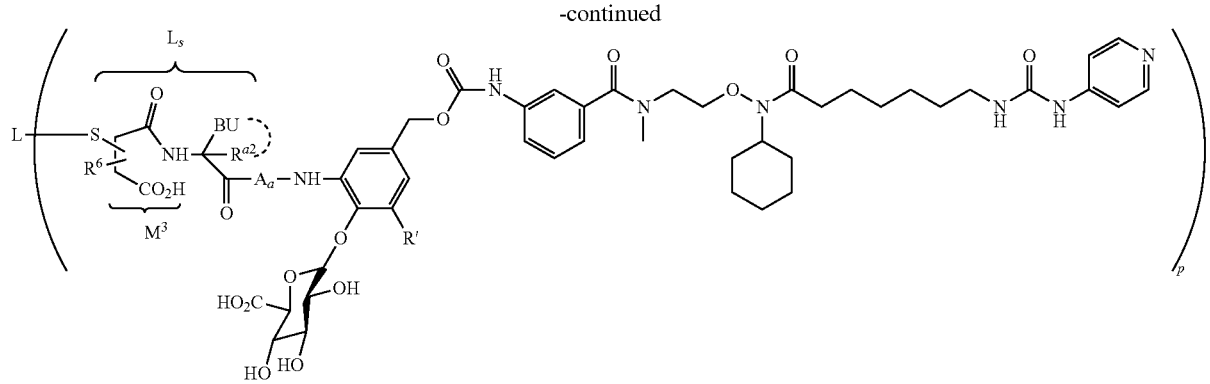

or pharmaceutical acceptable salt(s) thereof, wherein

L is an antibody, thereby defining an antibody Ligand Unit of an antibody drug conjugate (ADC), and S is a sulfur atom of the antibody; subscript a is 1 and A is an amino acid residue; BU is a acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$.

88. The Ligand Drug Conjugate composition of embodiment 1 wherein the composition is represented by the structure(s) of:

or pharmaceutical acceptable salt(s) thereof, wherein

L is an antibody, thereby defining an antibody Ligand Unit of an antibody drug conjugate (ADC), and S is a sulfur atom of the antibody; subscript a is 1 and A is an amino acid residue; BU is a acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$.

89. The Ligand Drug Conjugate composition of embodiment 1 wherein the composition is represented by the structure(s) of:

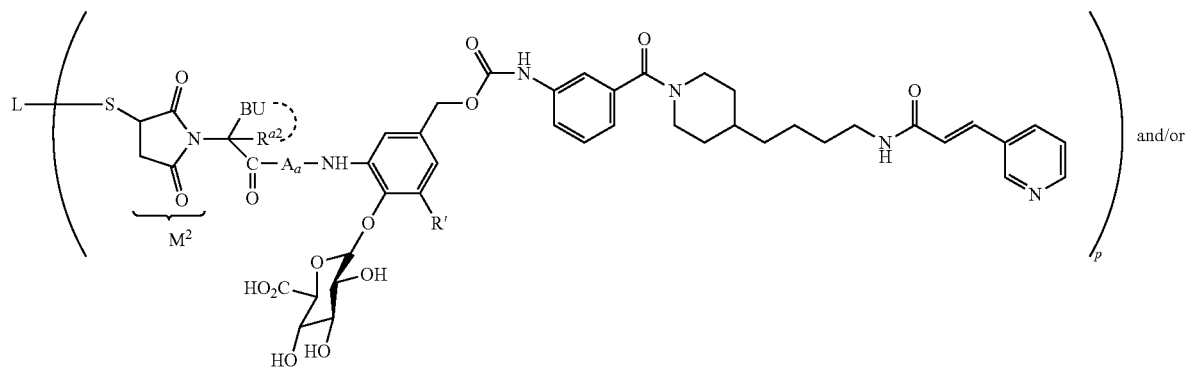

and/or

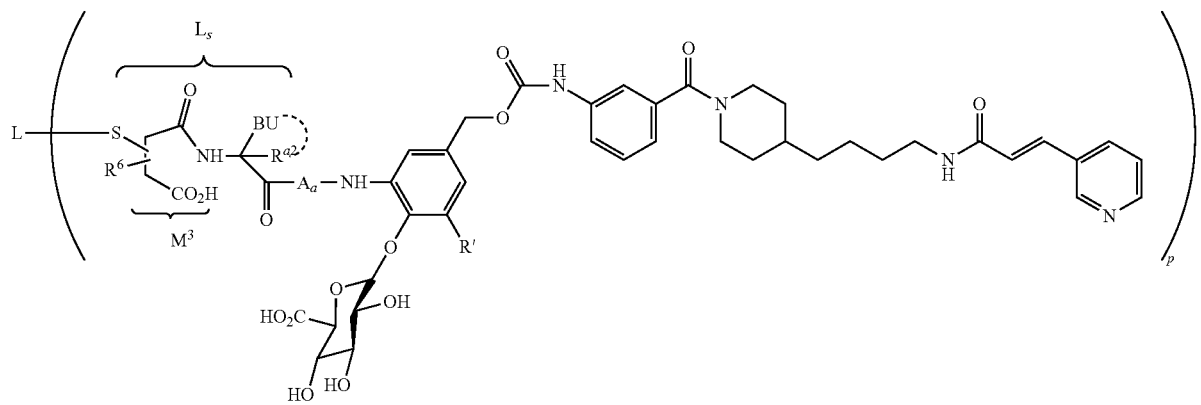

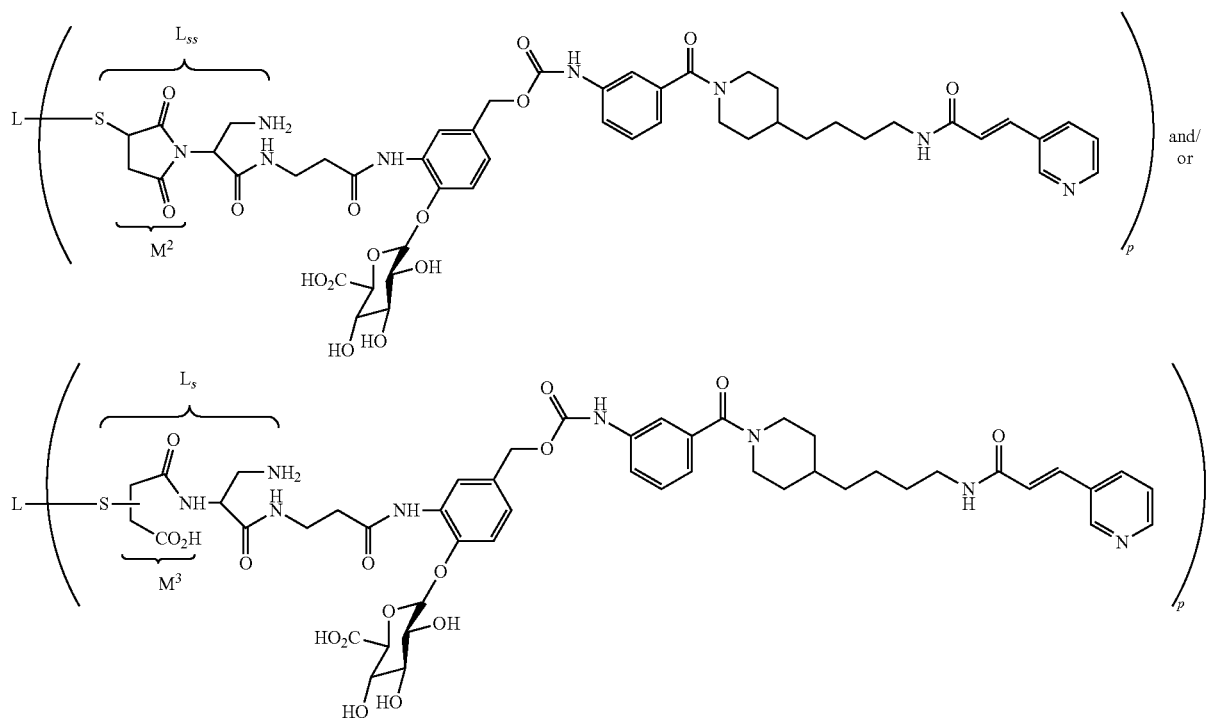

or pharmaceutical acceptable salt(s) thereof, wherein
L is an antibody, thereby defining an antibody Ligand Unit of an antibody drug conjugate (ADC), and S is a sulfur atom of the antibody, wherein the antibody is a monoclonal antibody or a chimeric antibody.

90. The Ligand Drug Conjugate composition of embodiment 1 wherein the composition is represented by the structure(s) of:

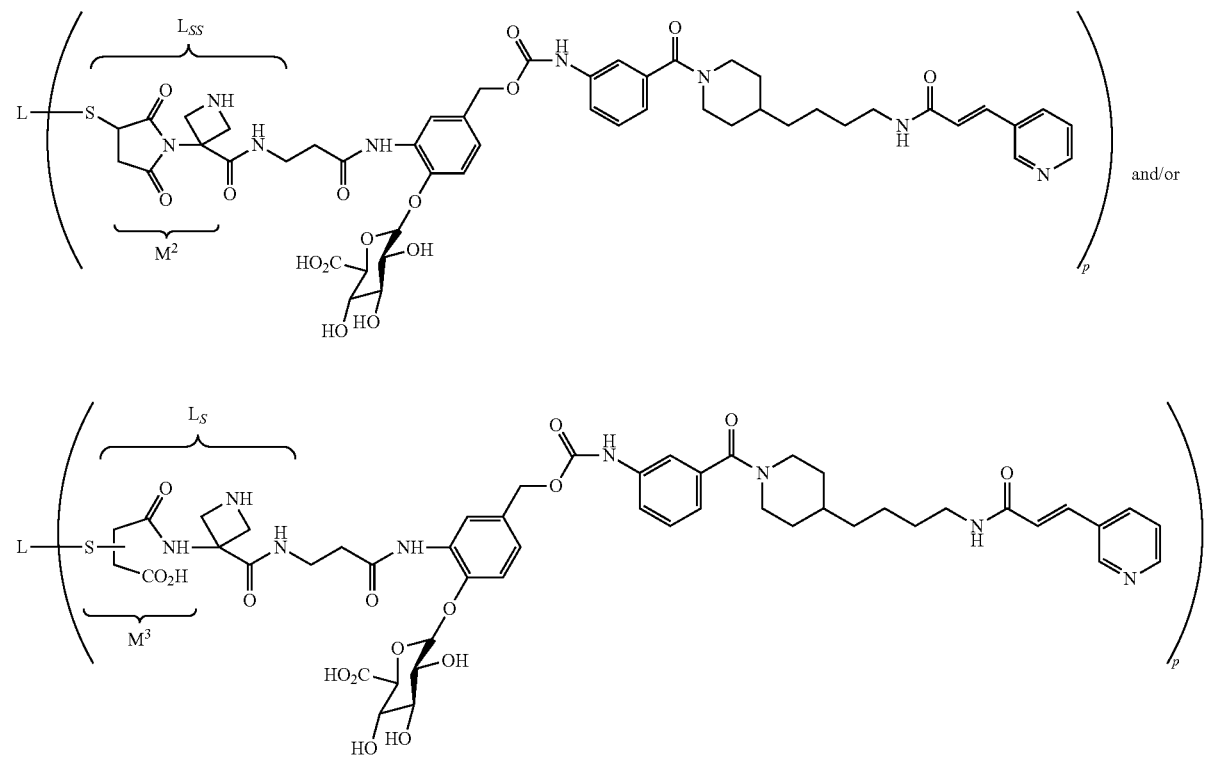

or pharmaceutical acceptable salt(s) thereof, wherein

L is an antibody, thereby defining an antibody Ligand Unit of an antibody drug conjugate (ADC), and S is a sulfur atom of the antibody, wherein the antibody is a monoclonal antibody or a chimeric antibody.

91. A formulation comprising a Ligand Drug Conjugate composition of any one of embodiments 1 to 90 and one, two, three or more excipients.

92. The formulation of embodiment 91 wherein the formulation is a pharmaceutically acceptable formulation or a precursor thereof.

93. The formulation of embodiment 92 wherein the pharmaceutically acceptable formulation precursor is a solid suitable for reconstitution as a solution for intravenous injection to a subject.

94. The formulation of embodiment 92 wherein the pharmaceutically acceptable formulation is a liquid suitable for intravenous injection to a subject.

95. The formulation of any one of embodiments 91 to 94 wherein the Ligand Drug Conjugate composition is present in the formulation in an effective amount for treatment of a hyperproliferative disease or condition.

96. A method of treating a hyperproliferative disease or condition comprising the step of administering to a patient having said disease or condition an effective amount of a Ligand Drug Conjugate composition of any one of embodiments 1 to 90.

97. The method of embodiment 96 wherein the hyperproliferative disease or condition is a cancer.

98. The method of embodiment 97 wherein the cancer is a leukemia or lymphoma.

99. A method of inhibiting the multiplication of a tumor cell or cancer cell, or causing apoptosis in a tumor cancer cell, by exposing said cell with an effective amount of a Ligand Drug Conjugate composition of any one of embodiments 1 to 90.

100. A Drug Linker compound wherein the compound is represented by the structure of:

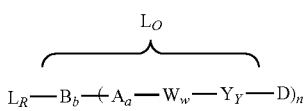

or a salt thereof, wherein

D is a NAMPT Drug Unit covalently attached to the Formula 1and/or Formula 2 composition structure(s) through a component of that Unit other than its head group, which corresponds to the heterocycle of nicotinamide, wherein that component remains capable of interacting with enzymatically competent NAMPT homodimer at its nicotinamide mononucleotide binding site when the NAMPT Drug Unit is released from the Drug Linker compound, or from a Conjugate compound of a Ligand Drug Conjugate composition prepared from the Drug Linker compound, as a NAMPTi compound or derivative thereof; $L_R$ is a primary linker having a functional group capable interacting with a targeting agent to form a covalent bond to the targeting agent as a Ligand Unit in a Ligand Drug Conjugate composition; subscripts a and b independently are 0 or 1, indicating the absence or presence, respectively, of A or B; subscript n is 1, 2, 3 or 4; A is an first optional Stretcher; and B is a Branching Unit, when subscript b is 1 and subscript n is 2, 3 or 4, or B is absent, so that subscript b is 0, when subscript n is 1, wherein each of A and B is an independently selected single unit or is optionally comprised or consists of two, three or four independently selected subunits;

subscript y is 0, 1 or 2, indicating the absence or presence of one or two of Y, respectively; Y is a Spacer Unit, or an optionally substituted heteroatom or functional group, provided that when subscript y is 0, $Y_y$ is replaced by an optionally substituted heteroatom of the distal terminal component selected from the group consisting optionally substituted —NH—, O and S; and provided that when subscript y is 1, Y is a Spacer Unit covalently attached to an optionally substituted heteroatom of the distal terminal component selected from the group consisting optionally substituted —NH—, O and S; and provided that when subscript y is 2 so that $Y_y$ is —Y—Y'—, then Y is a first Spacer Unit and Y' is a functional group comprised of an optionally substituted heteroatom of the distal terminal component selected from the group consisting optionally substituted —NH—, O and S, or a second Spacer Unit; and subscript w is 0 or 1, indicating the absence or presence, respectively, of W;

wherein when subscript w is 1, W is a Peptide Cleavable Unit or a Glucuronide Unit of formula —Y(W')—, wherein W' represents a carbohydrate moiety with glycosidic bonding to Y through a optionally substituted heteroatom, provided Y bonded to W' is required to be a first self-immolative Spacer Unit; subscript y is 0, 1 or 2, provided subscript y is 1 or 2, when W is a Glucuronide Unit, in which instance subscript y is inclusive of the required self-immolative Spacer Unit; and wherein when subscript w is 1, which indicates the presence of a Cleavable Unit, enzymatic or non-enzymatic cleavage of that Unit initiates release of the NAMPT Drug Unit as a NAMPTi compound or derivative thereof from the Drug Linker compound or from a Conjugate compound of a Ligand Drug Conjugate composition prepared from the Drug Linker compound; and when subscript w is 0, which indicates the absence of a Cleavable Unit, enzymatic or non-enzymatic cleavage of the bond between the indicated $L_R$ and $L_O$ moieties, when $L_O$ is present, or the bond between $L_R$ and D, when $L_O$ is absent, initiates release of the NAMPT Drug Unit as a NAMPTi compound or derivative thereof from the Drug Linker compound or from a Conjugate compound of a Ligand Drug Conjugate composition prepared from the Drug Linker compound.

101. The Drug Linker compound of embodiment 100 wherein the NAMPT Drug Unit is represented by the general structure of:

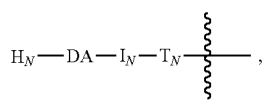

or a salt thereof, wherein the wavy line indicates the site of covalent attachment to $L_O$ or $L_R$, depending on the presence or absence of $L_O$, respectively; $H_N$ is a NAMPT Head Unit, wherein the NAMPT Head Unit is a $C_5$-$C_{24}$ heteroaryl or partially aromatic $C_9$-$C_{24}$ heterocyclyl, optionally substituted and comprised of an optionally substituted 5- or 6-membered nitrogen-containing heteroaromatic ring system;

DA is a Donor-Acceptor Unit wherein the Donor-Acceptor Unit is or is comprised of a hydrogen bond donor acceptor functional group and is bonded to a carbon skeletal atom at position 2 or 3 of the 5-membered nitrogen-containing heteroaromatic ring system or at position 3 or 4 of the 6-membered nitrogen-containing heteroaromatic ring system, with optional formal cyclization of DA back to an adjacent skeletal carbon atom of the 6-membered nitrogen-containing heteroaromatic ring system through an introduced optionally substituted non-aromatic carbon atom or an optionally substituted nitrogen, oxygen or sulfur atom resulting in a partially aromatic or fully aromatic fused 6,5- or 6,6-ring system, wherein said bonding of DA is in relation to a skeletal nitrogen atom of the 5- or 6 membered nitrogen-containing heteroaromatic ring system and wherein said formal cyclization to the adjacent carbon atom of the 6-membered nitrogen-containing heteroaromatic ring system substantially retains the hydrogen bonding ability of the donor or acceptor functional group of DA in absence of said cyclization;

$I_N$ is an Interconnecting Unit, wherein the Interconnecting Unit is or is comprised of —$X^1$—[C(=O)]$_{0,1}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$—, —$X^2$—$C_6$-$C_{24}$ arylene-O—, —$X^2$—$C_5$-$C_{24}$ heteroarylene-[C(=O)$_{0,1}$]—, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]—, wherein the arylene, heteroarylene and heterocyclo are optionally substituted; $X^1$ is optionally substituted $C_5$-$C_7$ alkylene; $X^2$ is absent or is an optionally substituted $C_1$-$C_4$ alkylene;

$T_N$ is a NAMPT Tail Unit, wherein the NAMPT Tail Unit is or is comprised of an optionally substituted amino-alcohol residue or a carboxylic acid-alcohol residue, the amino nitrogen or carbonyl carbon of which is bonded to $I_N$, or $T_N$ is or is comprised of an optionally substituted benzamide moiety, the amide nitrogen atom of which is bonded to $I_N$ with optional cyclization of that atom back to $I_N$ or to the remainder of $T_N$, and the aromatic ring of which is at least substituted with a hydroxyl, thiol or amino residue at position 3 or 4 relative to the site at which the amide carbonyl carbon atom is attached, or $T_N$ is or is comprised of an optionally substituted aryl or biaryl moiety, an aromatic skeletal atom of which is bonded to $I_N$, or to the remainder of $T_N$, and wherein an aromatic ring of which is at least substituted with a hydroxyl, thiol or an amino residue; and wherein $T_N$ or the remainder thereof is bond to $I_N$, wherein said remainder is an optionally substituted $C_2$-$C_7$ heteroalkylene or an optionally substituted $C_5$-$C_6$ heterocyclo, and the hydroxyl oxygen atom of the amino alcohol or carboxylic acid-alcohol residue, or the oxygen, sulfur or nitrogen atom of the hydroxyl, thiol or amino residue of the benzamide, aryl or biaryl moiety is the site of covalent attachment of $T_N$ to $L_O$ or $L_R$, depending on the presence or absence of $L_O$, respectively.

102. The Drug Linker compound of embodiment 101 wherein the NAMPT Head ($H_N$) Unit is a pyridine mimetic.

103. The Drug Linker compound of embodiment 101 or 102 wherein the Donor Acceptor (DA) Unit is comprised of an optionally substituted amide functional group or bioisostere thereof.

104. The Drug Linker compound of embodiment 101 or 102 wherein $H_N$-DA is a nicotinamide mimetic.

105. The Drug Linker compound of embodiment 101 wherein the 6-membered nitrogen-containing heteroaromatic ring system of $H_N$ is that of pyridine with optional cyclization of DA back to the pyridine aromatic ring system through an introduced aromatic oxygen, sulfur or an optionally substituted nitrogen atom so that $H_N$ contains a 6-5 fused aromatic ring system.

106. The Drug Linker compound of any one of embodiments 101 to 105 wherein $H_N$ of the released NAMPT Drug Unit is capable of interacting with Phe 193 on one monomer of an enzymatically competent NAMPT homodimer and/or Tyr 18' of the other monomer wherein the NAMPT monomers have the amino acid sequence of NCBI Reference Sequence NP_005737.1.

107. The Drug Linker compound of embodiment 106 wherein said NAMPT Head Unit interaction(s) is through pi-pi stacking with the aromatic side chain(s) of Phe 193 and/or Tyr 18'.

108. The Drug Linker compound of embodiment 101 wherein the NAMPT Head Unit has the structure of:

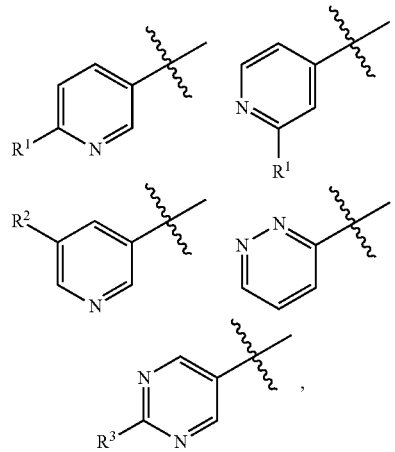

or a pharmaceutically acceptable salt thereof, wherein $R^1$ is hydrogen, —$NH_2$ or chloro; $R^2$ is fluoro; $R^3$ is hydrogen or —$NH_2$; and the wavy line indicates the site of covalent attachment to DA and an adjacent aromatic carbon atom thereto is the site of said optional cyclization by DA 109. The Drug Linker compound of embodiment 101 wherein the NAMPT Head Unit has the structure of:

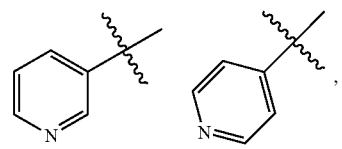 [SMILES: *c1cccnc1 ; *c1ccncc1]

or a salt thereof, wherein
the wavy line indicates the site of covalent attachment to DA and an adjacent aromatic carbon atom thereto is the site of said optional cyclization by DA.

110. The Drug Linker compound of embodiment 101 wherein the NAMPT Head Unit has the structure of:

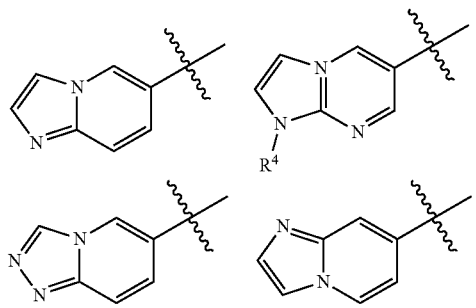

-continued

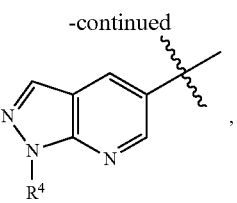

or a salt thereof, wherein the wavy line indicates the site of covalent attachment to DA and an adjacent aromatic carbon atom thereto is the site of said optional cyclization by DA; and wherein $R^4$ is hydrogen or optionally substituted $C_1$-$C_4$ alkyl.

111. The Drug Linker compound of any one of embodiments 101 to 110 wherein the Donor Acceptor Unit is an acrylamide DA Unit, optionally cyclized to an adjacent skeletal carbon atom of the nitrogen-containing aromatic ring system of $H_N$ to which it is attached.

112. The Drug Linker compound of any one of embodiments 101 to 111 wherein the Donor Acceptor Unit of the released NAMPT Drug Unit is capable of interacting with one or more amino acid residues of an NAMPT monomer of an enzymatically competent NAMPT homodimer selected from the group consisting of Asp 219, Ser 241, Val 242 and Ser 275, wherein the NAMPT monomer has the amino acid sequence of NCBI Reference Sequence NP_005737.1.

113. The Drug Linker compound of embodiment 112 wherein said DA interaction(s) is hydrogen bonding either directly or indirectly through hydrogen bonding network(s) involving the intermediacy of water molecule(s).

114. The Drug Linker compound of any one of embodiments 101 to 111 wherein the Donor-Acceptor Unit has the structure of:

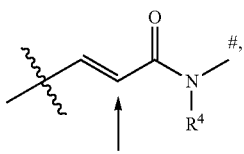

wherein $R^4$ is hydrogen or optionally substituted $C_1$-$C_4$ alkyl; DA is optionally cyclized to $H_N$, wherein said cyclization is to the sp$^2$ carbon atom proximal to the carbonyl carbon (as indicated) through an introduced optionally substituted non-aromatic carbon atom or an optionally substituted aromatic heteroatom; the wavy line indicates the site of covalent attachment to the $H_N$, and the carbon atom adjacent thereto is the site of said optional cyclization by DA; and the pound sign (#) indicates the site of covalent attachment to $I_N$.

115. The Drug Linker compound of any one of embodiments 101 to 111 wherein the Donor-Acceptor Unit has the structure of:

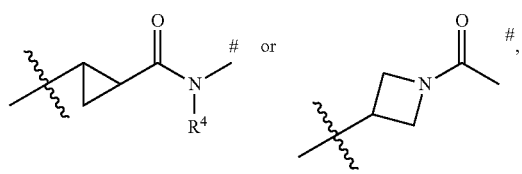

wherein $R^4$ is hydrogen or optionally substituted $C_1$-$C_4$ alkyl; and the wavy line indicates the site of covalent attachment to $H_N$; and the pound sign (#) indicates the site of covalent attachment to $I_N$.

116. The Drug Linker compound of any one of embodiments 101 to 111, wherein the Donor-Acceptor Unit has the structure of:

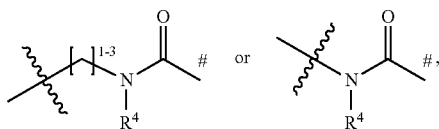

wherein $R^4$ is hydrogen or optionally substituted $C_1$-$C_4$ alkyl; and the wavy line indicates the site of covalent attachment to $H_N$; and wherein the pound sign (#) indicates the site of covalent attachment to $I_N$.

117. The Drug Linker compound of any one of embodiments 101 to 111, wherein the Donor-Acceptor Unit has the structure of:

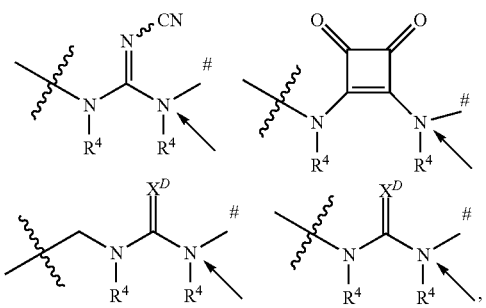

or a salt thereof, wherein $X^D$ is O, S or $NR^D$, wherein the nitrogen atom is optionally protonated and $R^D$ is hydrogen or optionally substituted $C_1$-$C_4$ alkyl; each $R^4$ is independently selected from the group consisting of hydrogen and optionally substituted $C_1$-$C_4$ alkyl, or both $R^4$ together with the nitrogen atoms to which they are attached and the intervening carbon atom(s) define an optionally substituted $C_5$-$C_6$ heterocyclo; the pound sign (#) indicates the site of covalent attachment to $I_N$; and the wavy line indicates the site of covalent attachment to $H_N$, wherein DA is optionally cyclized back to an adjacent site of $H_N$, wherein said cyclization is from the indicated nitrogen atom so that $R^4$ bonded thereto is replaced by a covalent bond or from $X^D$ when $X^D$ is —$NR^D$, either directly or through an introduced —S(=O)$_{0-2}$ moeity, in which either instance $R^D$ is replaced by a bond.

118. The Drug Linker compound of embodiment 117 wherein the Donor-Acceptor Unit has the structure of:

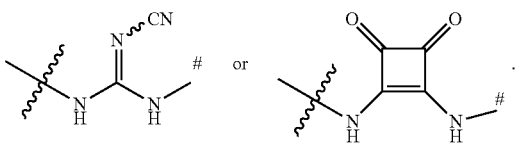

119. The Drug Linker compound of any one of embodiments 101 to 111, wherein the Donor-Acceptor Unit has the structure of:

205

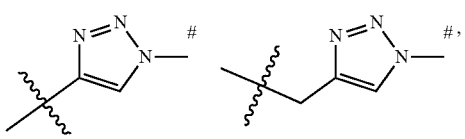

or a salt thereof, wherein
the wavy line indicates the site of covalent attachment to the NAMPT Head Unit; and the pound sign (#) indicates the site of covalent attachment to $I_N$.

120. The Drug Linker compound of embodiment 101 wherein $H_N$-DA- has the structure of:

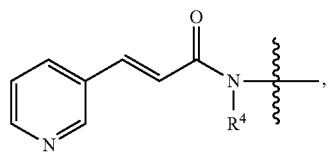

or a salt thereof, wherein
$R^4$ is independently hydrogen or $C_1$-$C_4$ alkyl; and the wavy line indicates the site of covalent attachment to $I_N$.

121. The Drug Linker compound of embodiment 101 wherein $H_N$-DA- has the structure of:

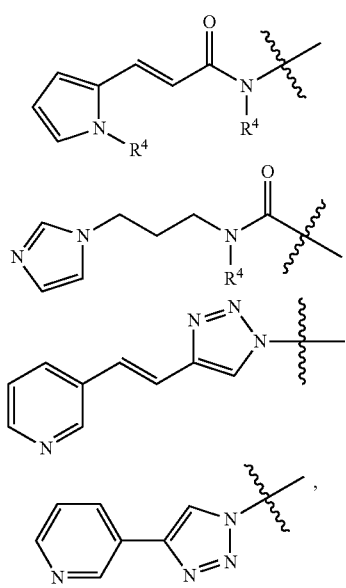

or a salt thereof,
wherein $R^4$ is independently selected from the group consisting of hydrogen and $C_1$-$C_4$ alkyl; and the wavy line indicates the site of covalent attachment to $I_N$.

122. The Drug Linker compound of embodiment 101 wherein $H_N$-DA- has the structure of:

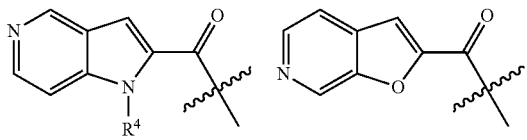

206
-continued

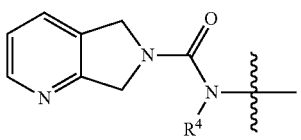

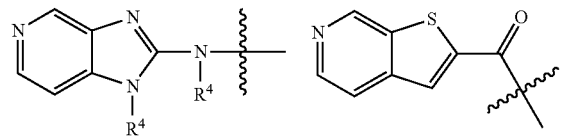

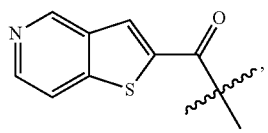

or a salt thereof, wherein $R^4$ is hydrogen or optionally substituted $C_1$-$C_4$ alkyl, or both $R^4$ together with the nitrogen atoms to which they are attached and the intervening carbon atom define a $C_5$-$C_6$ heterocyclo; and the wavy line indicates the site of covalent attachment to $I_N$.

123. The Drug Linker compound of embodiment 101 wherein $H_N$-DA- has the structure of:

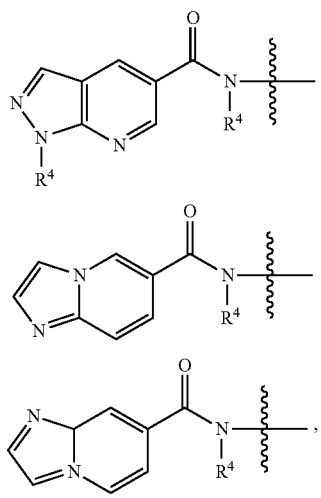

or a salt thereof, wherein $R^4$ is independently selected from the group consisting of hydrogen and optionally substituted $C_1$-$C_4$ alkyl; and the wavy line indicates the site of covalent attachment to $I_N$.

124. The Drug Linker compound of embodiment 101 wherein $H_N$-DA- has the structure of:

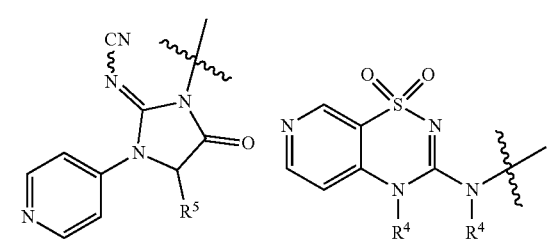

-continued

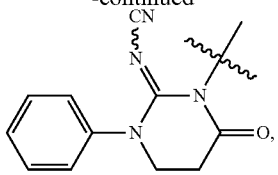

or a salt thereof, wherein $R^4$ is independently selected from the group consisting of hydrogen and optionally substituted $C_1$-$C_4$ alkyl; $R^5$ is optionally substituted $C_6$-$C_{24}$ aryl or optionally substituted $C_5$-$C_{24}$ heteroaryl; and the wavy line indicates the site of covalent attachment to $I_N$.

125. The Drug Linker compound of any one of embodiments 101 to 124, wherein the NAMPT Tail ($T_N$) Unit or —$I_N$-$T_N$- of the released NAMPT Drug Unit is capable of interacting with one or more amino acid residues of a NAMPT monomer of an enzymatically competent NAMPT homodimer selected from the group consisting of Ile 309, Pro 307, Val 350, Ile 378 and Ala 379, wherein the NAMPT monomer has the amino acid sequence of NCBI Reference Sequence NP_005737.1.

126. The Drug Linker compound of any one of embodiments 101 to 125, wherein $T_N$ or —$I_N$-$T_N$- of the released NAMPT Drug Unit is capable of interacting with one or more amino acid residues of a NAMPT monomer of an enzymatically competent NAMPT homodimer selected from the group consisting of Tyr 188, Lys 189, Ala 379, Asn 377, Glu 376, Val 350, Arg 349 and Pro 307, wherein the NAMPT monomer has the amino acid sequence of NCBI Reference Sequence NP_005737.1.

127. The Drug Linker compound of any one of embodiments 101 to 124 wherein the NAMPT Tail Unit is an amino alcohol moiety wherein the oxygen atom of the alcohol is the site of covalent attachment to $L_O$ or $L_R$, depending on the presence or absence of $L_O$.

128. The Drug Linker compound of embodiment 127 wherein the NAMPT Tail Unit is an amino alcohol moiety having the structure of:

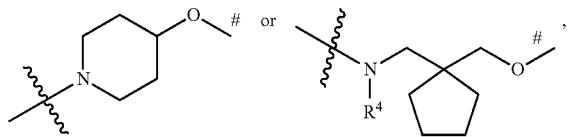

or a salt thereof, wherein $R^4$ is hydrogen or optionally substituted $C_1$-$C_4$ alkyl; the wavy line indicates the site of covalent attachment to $I_N$; and the pound sign (#) indicates the site of covalent to $L_O$ or $L_R$, depending on the presence or absence of $L_O$, respectively.

129. The Drug Linker compound of any one of embodiments 101 to 124 wherein the Tail Unit is a benzamide moiety having a functional group providing a heteroatom that is the site of covalent attachment to $L_O$ or $L_R$, depending on the presence or absence of $L_O$.

130. The Drug Linker compound of embodiment 129 wherein the NAMPT Tail Unit is a benzamide moiety having the structure of:

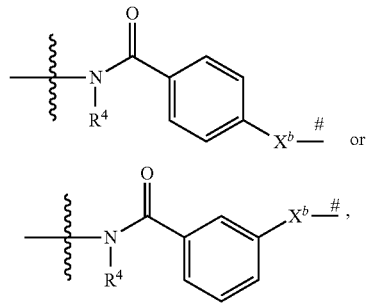

wherein $X^b$ is —S—, —O— or —NH—, optionally substituted; $R^4$ is hydrogen or optionally substituted $C_1$-$C_4$ alkyl; and the wavy line indicates the site of covalent attachment to $I_N$; the pound sign (#) indicates the site of covalent attachment to $L_O$ or $L_R$, depending on the presence or absence of $L_O$, respectively, and wherein the benzamide moiety is optionally cyclized to $I_N$ wherein the amide nitrogen of the benzamide moiety is the site of said cyclization so that $R^4$ is replaced by a covalent bond.

131. The Drug Linker compound of embodiment 130 wherein the NAMPT Tail Unit is a benzamide moiety having the structure of:

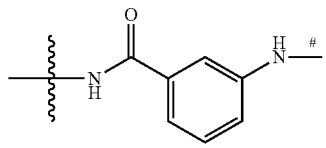

132. The Drug Linker compound of any one of embodiments 101 to 124 wherein the NAMPT Tail Unit is an aryl, heteroaryl or biaryl moiety having a functional group providing a heteroatom that is the site of covalent attachment to the Linker Unit.

133. The Drug Linker compound of embodiment 132 wherein the NAMPT Tail Unit is a biaryl or heteroaryl moiety having a having the structure of:

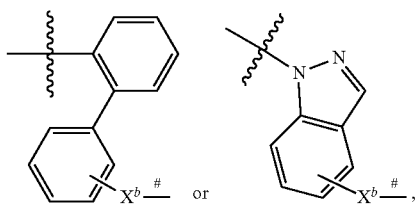

wherein $X^b$ is —S—, —O— or NH—, optionally substituted; the wavy line indicates the site of covalent attachment to $I_N$; and the pound sign (#) indicates the site of covalent attachment to $L_O$ or $L_R$, depending on the presence or absence of $L_O$, respectively.

134. The Drug Linker compound of embodiment 123 wherein the NAMPT Tail Unit is an aryl moiety having the structure of:

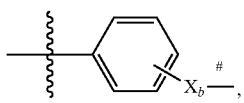

wherein $X^b$ is —S—, —O— or NH—, optionally substituted, wherein $X^b$ is at the meta or para position relative to the site of covalent attachment to $I_N$ as indicated by the wavy line; and the pound sign (#) indicates the site of covalent attachment to $L_O$ or $L_R$, depending on the presence or absence of $L_O$, respectively.

135. The Drug Linker compound of any one of embodiments 101 to 134 wherein $I_N$ of the released NAMPT Drug Unit is capable of interacting with one or more amino acids of a NAMPT monomer of an enzymatically competent NAMPT homodimer selected from the group consisting of Val 242, Ile 309, Ile 351, and His 191 of NAMPT, wherein the NAMPT monomer has the amino acid sequence of NCBI Reference Sequence NP_005737.1.

136. The Drug Linker compound of any one of embodiments 101 to 134, wherein $I_N$ is —CH$_2$—(CH$_2$)$_{3-7}$—CH$_2$—, —CH$_2$—(CH$_2$)$_{n1}$—CH$_2$—O—, —CH$_2$—(CH$_2$)$_{3-7}$—C(=O)—, —CH$_2$—(CH$_2$)$_{3-7}$—S(=O)$_2$— or —CH$_2$—(CH$_2$)$_{3-7}$—S(=O)—.

137. The Drug Linker compound of any one of embodiments 101 to 134 wherein $I_N$ has the structure of:

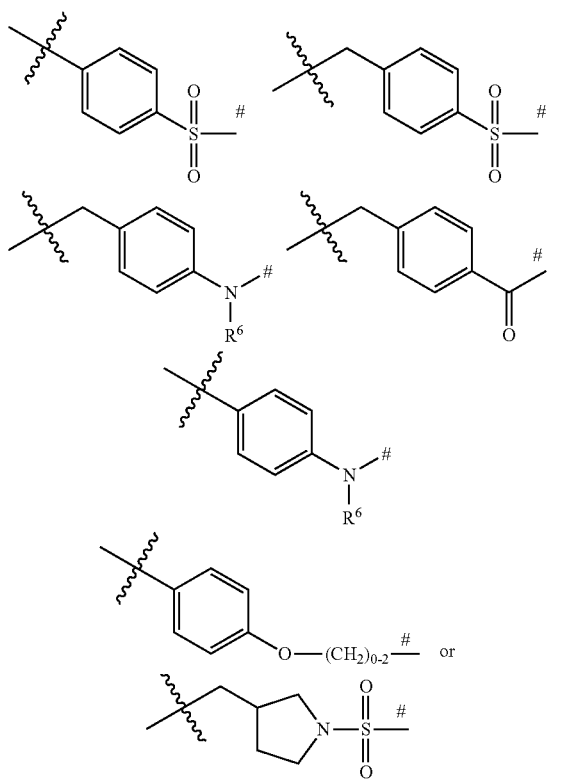

wherein the wavy line indicates the site of covalent attachment to DA and the pound sign (#) indicates the site of covalent attachment to $T_N$; and $R^6$ is hydrogen, $C_1$-$C_4$ alkyl, —CH$_2$CH=C(CH$_3$)$_2$, or —CH$_2$—C≡CH.

138. The Drug Linker compound of any one of embodiments 101 to 124, wherein —$I_N$-$T_N$- has the structure of:

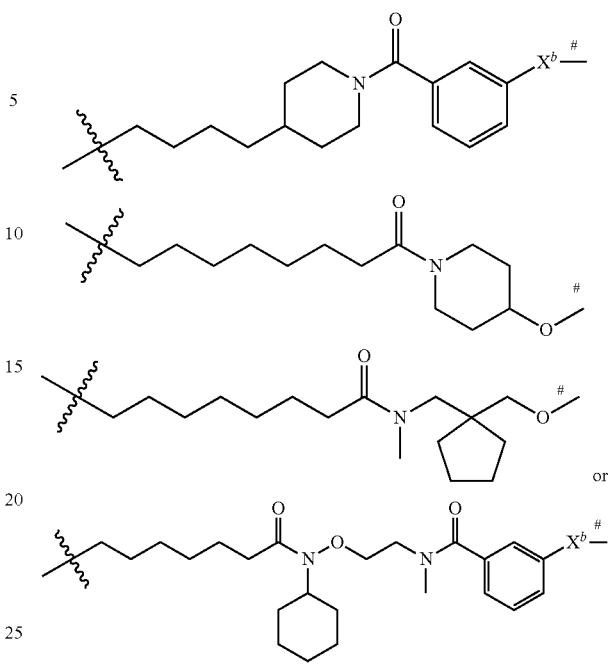

wherein $X^b$ is —O—, —S— or NH—, optionally substituted; the wavy line indicates the site of covalent attachment to DA; and the pound sign (#) indicates the site of covalent attachment to $L_O$ or $L_R$, depending on the presence or absence of $L_O$, respectively.

139. The Drug Linker compound of any one of embodiments 101 to 124, wherein —$I_N$-$T_N$- has the structure of:

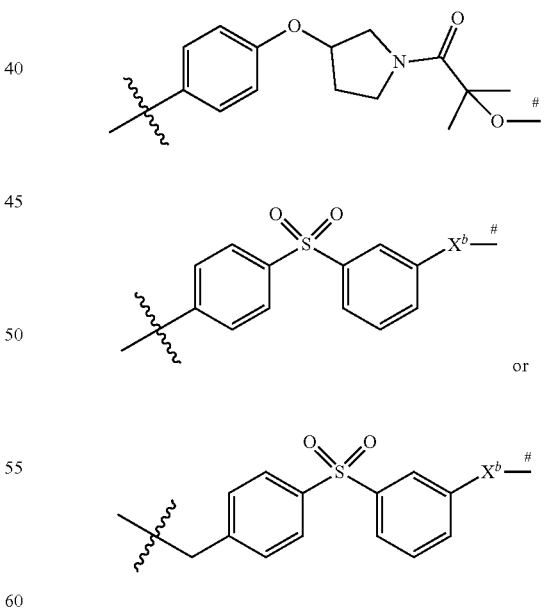

wherein the wavy line indicates the site of covalent attachment to DA and the pound sign (#) indicates the site of covalent attachment to $L_O$ or $L_R$, depending on the presence or absence of $L_O$; and $X^b$ is —O—, —S— or NH—, optionally substituted.

140. The Drug Linker compound of claim 100 wherein the NAMPT Drug Unit has the structure of:

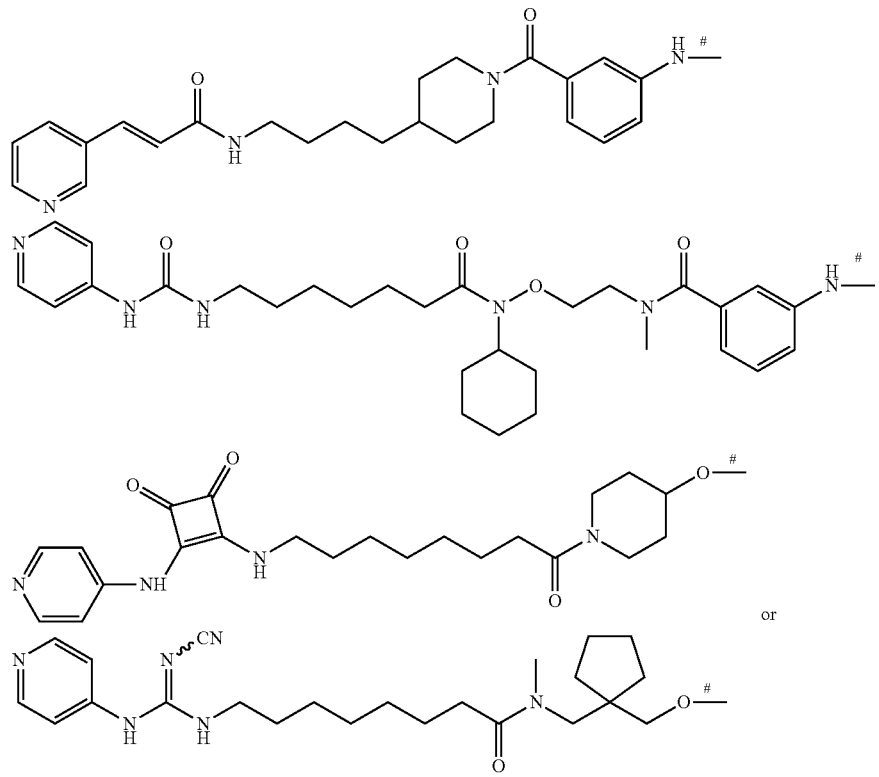

or a salt thereof, wherein the pound sign (#) indicates the site of covalent attachment to $L_O$ or $L_R$, depending on the presence or absence of $L_O$.

141. The Drug Linker compound of any one of embodiments 100 to 140 wherein $L_{R^-}$ has the structure of:

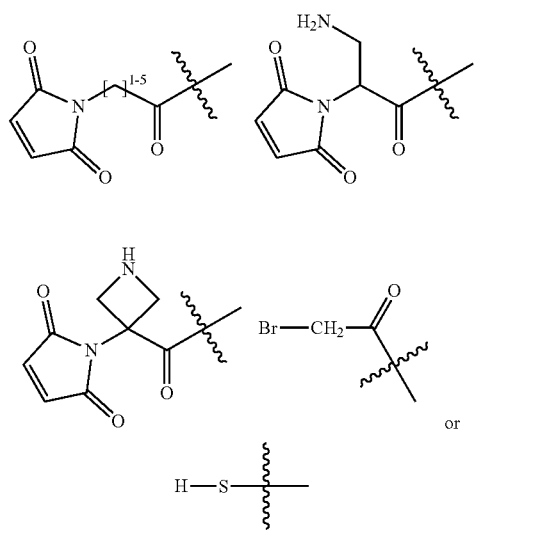

or a salt thereof, wherein the wavy line indicates the site of covalent attachment to the remainder of the Drug Linker compound.

142. The Drug Linker compound of any one of embodiments 100 to 140 wherein $L_{R^-}$ has the structure of:

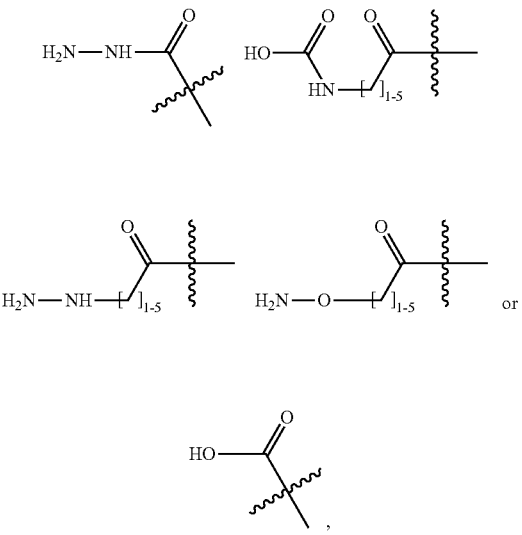

or a salt thereof, wherein the wavy line indicates the site of covalent attachment to the remainder of the Drug Linker compound.

143. The Drug Linker compound of any one of embodiments 100 to 140 wherein the compound is represented by the structure of Formula I:

(Formula I)

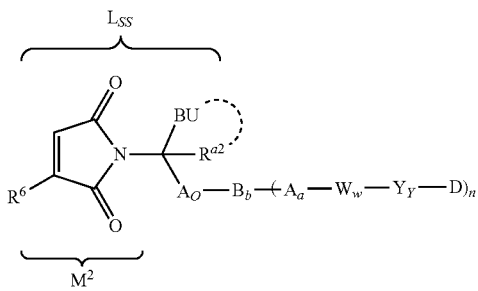

or a salt thereof, wherein $R^6$ is hydrogen or an optionally substituted $C_1$-$C_6$ alkyl, which in Formula 2 is bonded to the saturated carbon atom adjacent to the carbon substituted by L-S—; $A_O$ is a second optional Stretcher Unit; BU is a Basic Unit and $R^{a2}$ is an optionally substituted $C_1$-$C_{12}$ alkyl group; and the dotted curved line indicates optional cyclization so that in the absence of said cyclization BU is an acyclic Basic Unit or in the presence of said cyclization BU is a cyclized Basic Unit in which $R^{a2}$ and BU together with the carbon atom to which both are attached define an optionally substituted spiro $C_3$-$C_{20}$ heterocycle containing a skeletal basic nitrogen atom of a secondary or tertiary amine functional group of BU, wherein the basic nitrogen atom of the acyclic Basic Unit or cyclic Basic Unit is optionally suitably protected by a nitrogen protecting group, dependent on the degree of substitution of the basic nitrogen atom, or is optionally protonated.

144. The Drug Linker compound of embodiment 143 wherein the compound is represented by the structure of:

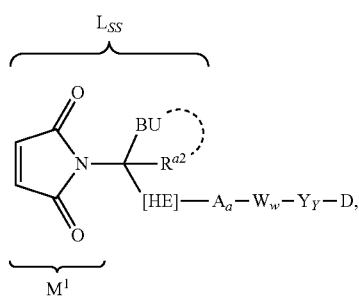

or a salt thereof, wherein

[HE] as $A_O$ is an optional Hydrolysis Enhancing Unit; subscript w is 1; W is Peptide Cleavable Unit, wherein protease action on the Peptide Cleavable Unit resulting in cleavage of the W-J' bond within the Drug Linker compound, or within Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound, or W is a Glucuronide Unit of formula —Y(W')— having the structure of:

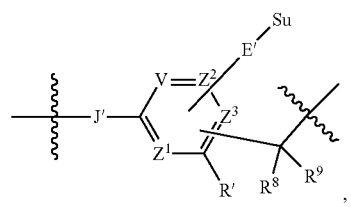

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W'; J' is an independently selected heteroatom, optionally substituted;

V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)— moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$-$C_6$ alkyl, or other electron donating group;

wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the site of covalent attachment of the Glucuronide Unit to Y' when subscript y is 2, or to D when subscript y is 1; and wherein glycosidase action on the Glucuronide Unit resulting in cleavage of its glycosidic bond within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

145. The Drug Linker compound of embodiment 144 wherein W is a Glucuronide Unit for which —W—$Y_y$-D has the structure of:

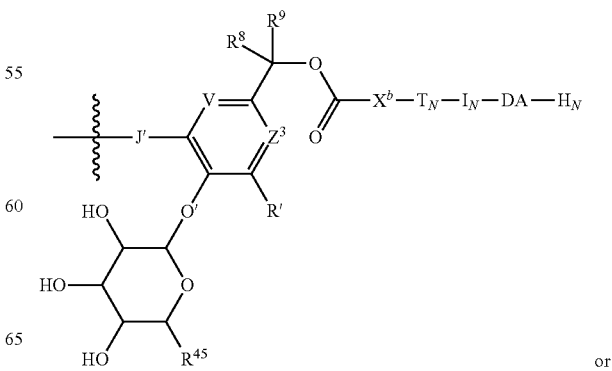

or

-continued

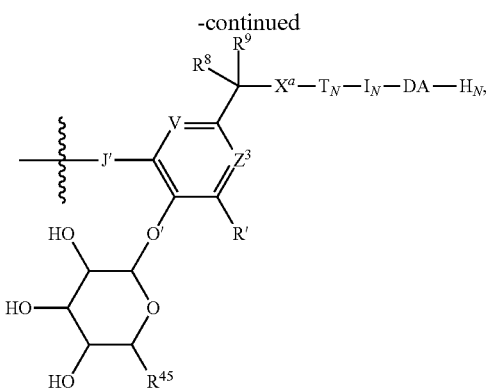

or a salt thereof, wherein $X^a$ is an oxygen atom from an alcohol functional group or a sulfur atom from a thiol functional group of $T_N$; $X^b$ is a nitrogen atom from a primary or secondary amine functional group of $T_N$; R' is hydrogen or —$NO_2$ or other electron withdrawing group; $R^{45}$ is —$CH_2OH$ or —$CO_2H$; wherein —O'— represents the oxygen heteroatom of an O-glycosidic bond cleavable by a glycosidase, wherein said cleavage within the Drug Linker Compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

146. The Drug Linker compound of embodiment 144 wherein W is a Glucuronide Unit for which —W—$Y_y$-D has the structure of:

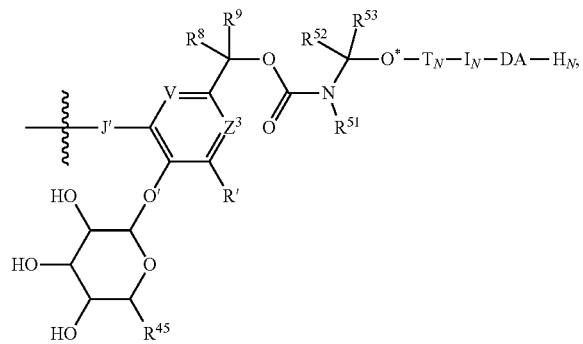

or a salt thereof, wherein R' is hydrogen or —$NO_2$ or other electron withdrawing group; $R^{51}$, $R^{52}$ and $R^{53}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^{51}$ and $R^{52}$ together with the nitrogen and carbon atoms to which both are attached define an azetidine, pyrrolidine, piperidine or homopiperidine heterocyclo, and $R^{53}$ is hydrogen; $R^{45}$ is —$CH_2OH$ or —$CO_2H$; wherein O* represents the oxygen atom from an alcohol functional group of $T_N$ and O' represents the oxygen atom of an O-glycosidic bond cleavable by a glycosidase, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative from that Drug Linker or Ligand Drug Conjugate compound.

147. The Drug Linker compound of embodiment 144 wherein W is a Peptide Cleavable Unit and —$Y_y$-D- has the structure of:

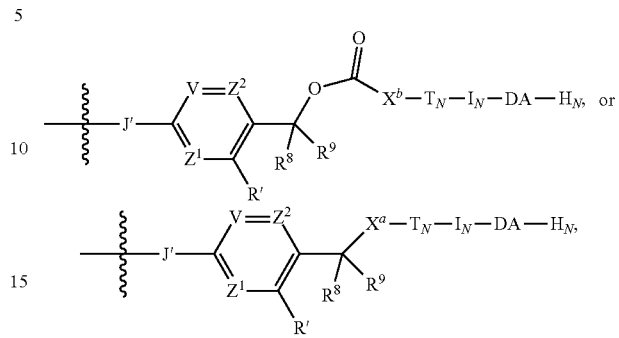

or a salt thereof, wherein $X^a$ is an oxygen atom from an alcohol functional group or a sulfur atom of a thiol functional group of $T_N$;

$X^b$ is a nitrogen atom from a primary or secondary amine functional group of $T_N$; R' is hydrogen or —$OC_1$-$C_6$ alkyl or other electron donating group; J' is an optionally substituted heteroatom bonded to W as indicated by the wavy line, wherein cleavage of that bond within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

148. The Drug Linker compound of embodiment 144 wherein W is a Peptide Cleavable Unit and —$Y_y$-D- has the structure of:

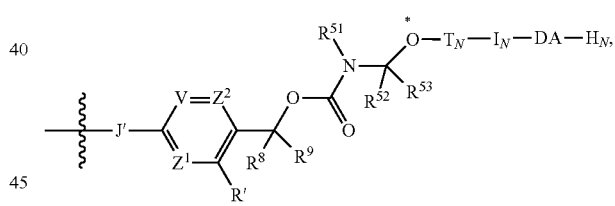

or a salt thereof, wherein R' is hydrogen or —$OC_1$-$C_6$ alkyl or other electron donating group; $R^{51}$, $R^{52}$ and $R^{53}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^{51}$ and $R^{52}$ together with the nitrogen and carbon atoms to which both are attached define an azetidine, pyrrolidine, piperidine or homopiperidine heterocyclo, and $R^{53}$ is hydrogen; $R^{45}$ is —$CH_2OH$ or —$CO_2H$; O* represents the oxygen atom from an alcohol functional group of $T_N$; and J' is an optionally substituted heteroatom bonded to W as indicated by the wavy line, wherein cleavage of that bond within the Drug Linker compound, or within a Conjugate compound prepared from the Drug Linker compound, initiates release of the NAMPT Drug Unit as a NAMPTi compound or derivative thereof from that Drug Linker or Ligand Drug Conjugate compound.

149. The Drug Linker compound of embodiment 144 wherein the compound is represented by the structure of:

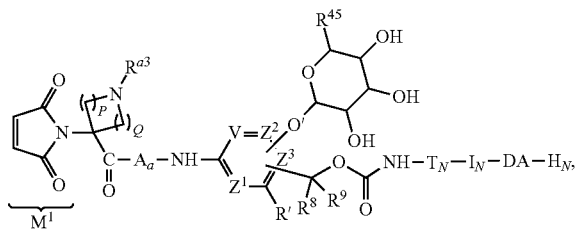

or a salt thereof, wherein subscript P is 1, 2 or 3; subscript Q ranges from 1 to 6; R' is hydrogen or —NO$_2$ or other electron withdrawing group; R$^{45}$ is —CH$_2$OH or —CO$_2$H; R$^{a3}$ is —H, or optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene, and R$^{PEG2}$ is —H or C$_1$-C$_4$ alkyl; and wherein the basic nitrogen atom bonded to R$^{a3}$ is optionally protonated, and wherein —O'— represents the oxygen heteroatom of an O-glycosidic bond cleavable by a glycosidase, wherein said cleavage within the Drug Linker compound, or within a Conjugate compound of a Ligand Drug Conjugate composition prepared from the Drug Linker Compound, initiates release of the NAMPT Drug Unit as a NAMPTi compound or derivative thereof from that Drug Linker or Ligand Drug Conjugate compound.

150. The Drug Linker compound of embodiment 144 wherein the compound is represented by the structure of:

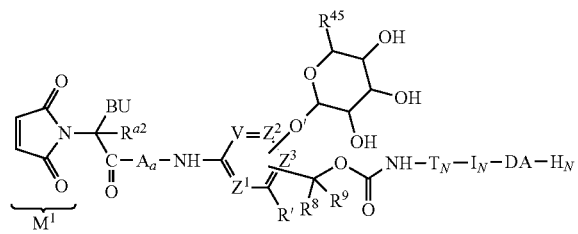

or a salt thereof, wherein subscript P is 1, 2 or 3; subscript Q ranges from 1 to 6; R' is hydrogen or —NO$_2$ or other electron withdrawing group; R$^{45}$ is —CH$_2$OH or —CO$_2$H; R$^{a2}$ is hydrogen or C$_1$-C$_6$ alkyl;

BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^{a3}$ independently are hydrogen, optionally substituted C$_1$-C$_6$ alkyl or R$^{a3}$ together with the nitrogen atom to which both are attached define a C$_3$-C$_6$ heterocyclyl in which the basic nitrogen is a skeletal atom; wherein the basic nitrogen atom of BU bonded to R$^{a3}$ is optionally protonated; and wherein —O'— represents the oxygen atom of an O-glycosidic bond cleavable by a glycosidase, wherein said cleavage within The Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

151. The Drug Linker compound of embodiment 144 wherein the compound is represented by the structure of:

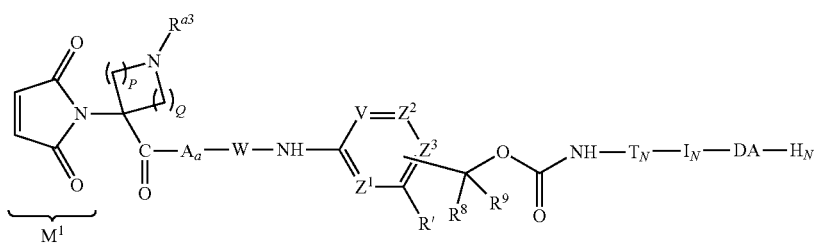

or a salt thereof, wherein W is a Peptide Cleavable Unit; subscript P is 1, 2 or 3; subscript Q ranges from 1 to 6; R' is hydrogen or —OC$_1$-C$_6$ alkyl or other electron donating group; R$^{a1}$ is —H, or optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene, and R$^{PEG2}$ is —H or C$_1$-C$_4$ alkyl; and wherein the basic nitrogen atom bonded to R$^{a1}$ is optionally protonated, wherein protease action on the Peptide Cleavable Unit cleaves the W—NH bond, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

152. The Drug Linker compound of embodiment 144 wherein the compound is represented by the structure of:

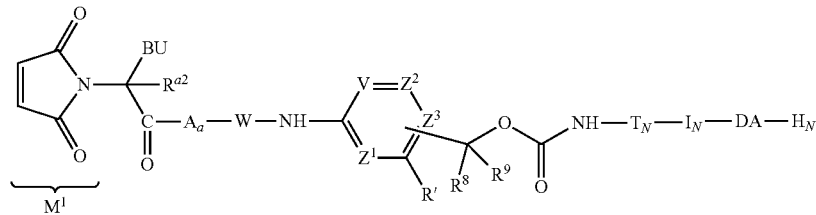

or a salt thereof, wherein W is a Peptide Cleavable Unit; subscript P is 1, 2 or 3; subscript Q ranges from 1 to 6; R' is hydrogen or —$OC_1$-$C_6$ alkyl or other electron donating group; $R^{a2}$ is hydrogen or $C_1$-$C_6$ alkyl;

BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; wherein the basic nitrogen atom of BU bonded to $R^{a1}$ is optionally protonated; and wherein protease action on the Peptide Cleavable Unit cleaves the W—NH bond, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

153. The Drug Linker compound of embodiment 144 wherein the compound is represented by the structure of:

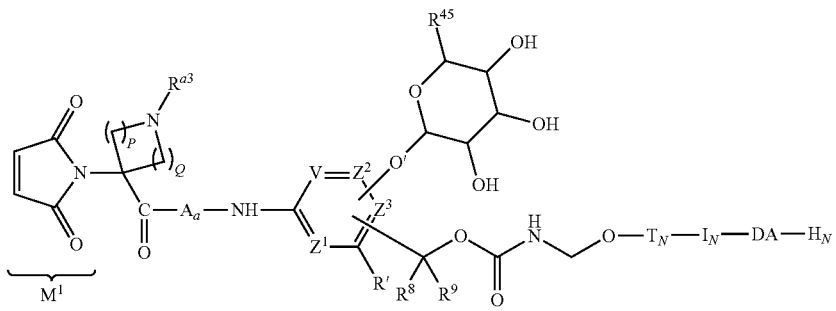

or a salt thereof, wherein subscript P is 1, 2 or 3; subscript Q ranges from 1 to 6; R' is hydrogen or —NO$_2$ or other electron withdrawing group; R$^{45}$ is —CH$_2$OH or —CO$_2$H; R$^{a1}$ is —H, or optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene, and R$^{PEG2}$ is —H or C$_1$-C$_4$ alkyl; and wherein the basic nitrogen atom bonded to R$^{a3}$ is optionally protonated, and wherein —O'— represents the oxygen atom of an O-glycosidic bond cleavable by a glycosidase, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

154. The Drug Linker compound of embodiment 144 wherein the compound is represented by the structure of:

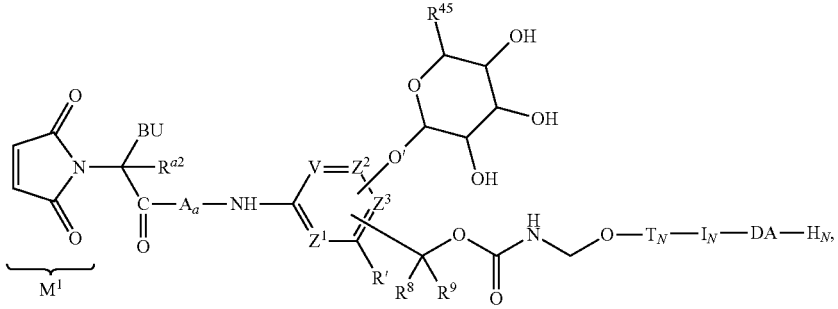

or a salt thereof, wherein subscript P is 1, 2 or 3; subscript Q ranges from 1 to 6; R' is hydrogen or —NO$_2$ or other electron withdrawing group; R$^{45}$ is —CH$_2$OH or —CO$_2$H; R$^{a2}$ is hydrogen or C$_1$-C$_6$ alkyl;

BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a3}$ together with the carbon(s) to which they are attached and any intervening carbons define an optionally substituted C$_3$-C$_6$ cycloalkyl; R$^{a1}$ independently are hydrogen, optionally substituted C$_1$-C$_6$ alkyl or R$^{a3}$ together with the nitrogen atom to which both are attached define a C$_3$-C$_6$ heterocyclyl in which the basic nitrogen is a skeletal atom; wherein the basic nitrogen atom of BU bonded to R$^{a3}$ is optionally protonated; and wherein —O'— represents the oxygen atom of an O-glycosidic bond cleavable by a glycosidase, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

155. The Drug Linker compound of embodiment 144 wherein the compound is represented by the structure of:

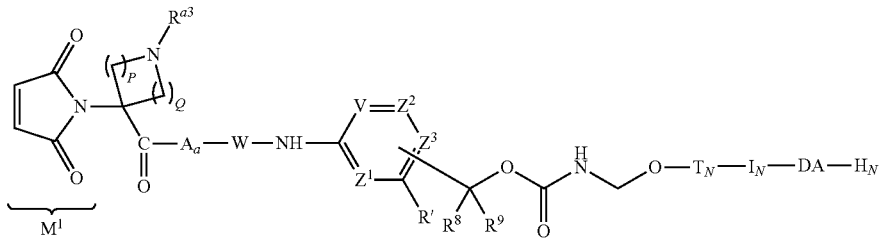

or a salt thereof, wherein W is a Peptide Cleavable Unit; subscript P is 1, 2 or 3; subscript Q ranges from 1 to 6; R' is hydrogen or —O$C_1$-$C_6$ alkyl or other electron donating group; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to R is optionally protonated; and wherein protease action on the Peptide Cleavable Unit cleaves the W—NH bond, wherein said cleavage within The Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

156. The Drug Linker compound of embodiment 144 wherein the compound is represented by the structure of:

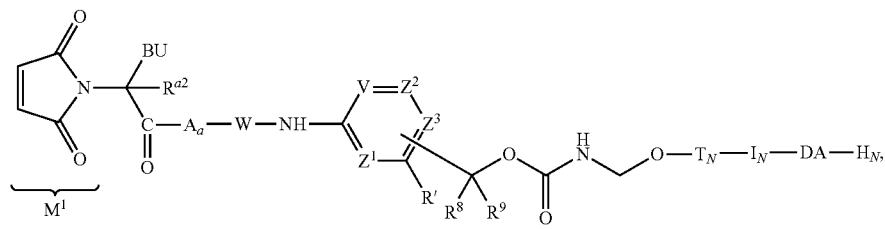

or a salt thereof, wherein W is a Peptide Cleavable Unit: subscript P is 1, 2 or 3; subscript Q ranges from 1 to 6; R' is hydrogen or —O$C_1$-$C_6$ alkyl or other electron donating group; $R^{a2}$ is hydrogen or $C_1$-$C_6$ alkyl;

BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom;

wherein the basic nitrogen atom of BU bonded to $R^{a3}$ is optionally protonated; and wherein protease action on the Peptide Cleavable Unit cleaves the W—NH bond, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

157. The Drug Linker compound of embodiment 144 wherein the compound is represented by the structure of:

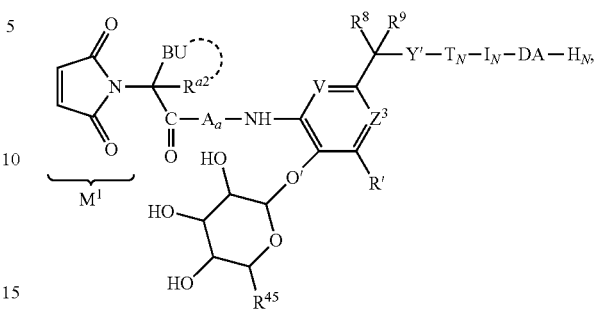

or a salt thereof, wherein Y' is —$X^a$—, —O—C(=O)—$X^b$— or —OC(=O)NH—$CH_2$—$X^a$—, wherein —$X^a$— is O and $X^b$ is —NH—; R' is hydrogen or —$NO_2$ or other electron withdrawing group; $R^{45}$ is —$CH_2$OH or —$CO_2$H;

BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a1}$ independently are hydrogen, optionally substituted $C_1$-$C_6$ alkyl or $R^{a1}$ together with the nitrogen atom to which both are attached define a $C_3$-$C_6$ heterocyclyl in which the basic nitrogen is a skeletal atom;

$R^{a2}$ is hydrogen or $C_1$-$C_6$ alkyl, optionally cyclized to BU, as indicated by the dotted curved line, wherein one of $R^{a1}$ or one of $R^{a1}$ is replaced with a bond to a carbon atom of $R^{a2}$ when $R^{a2}$ is $C_1$-$C_6$ alkyl; wherein the basic nitrogen atom of BU bonded to $R^{a3}$ is optionally protonated; and wherein —O'— represents the oxygen atom of an O-glycosidic bond cleavable by a glycosidase, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

158. The Drug Linker compound of embodiment 144 wherein the compound is represented by the structure of:

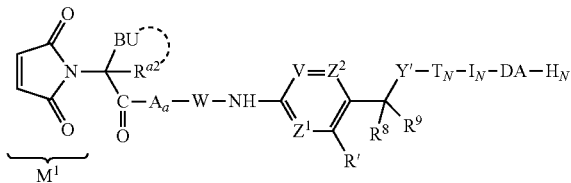

or a salt thereof, wherein W is a Peptide Cleavable Unit; Y' is —$X^a$—, —O—C(=O)—$X^b$— or —OC(=O)NH—$CH_2$—$X^a$—, wherein —$X^a$— is O and $X^b$ is —NH—; R' is hydrogen or —$OC_1$-$C_6$ alkyl or other electron donating group; $R^{45}$ is —$CH_2OH$ or —$CO_2H$;

BU has the structure of —[C($R^{a1}$)($R^{a1}$)]—[C($R^{a1}$)($R^{a1}$)]$_{0-3}$—N($R^{a3}$)($R^{a3}$), each $R^{a3}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a1}$ independently are hydrogen, optionally substituted $C_1$-$C_6$ alkyl or $R^{a1}$ together with the nitrogen atom to which both are attached, as indicated by the dotted curved line, define a $C_3$-$C_6$ heterocyclyl in which the basic nitrogen is a skeletal atom; $R^{a2}$ is hydrogen or $C_1$-$C_6$ alkyl, optionally cyclized to BU, as indicated by the dotted curved line, wherein one of $R^{a1}$ or one of $R^{a3}$ is replaced with a bond to a carbon atom of $R^{a2}$ when $R^{a2}$ is $C_1$-$C_6$ alkyl; wherein the basic nitrogen atom of BU bonded to $R^{a3}$ is optionally protonated; and wherein protease action on the Peptide Cleavable Unit cleaves the W—NH bond, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

159. The Drug Linker compound of embodiment 144 wherein the compound is represented by the structure of:

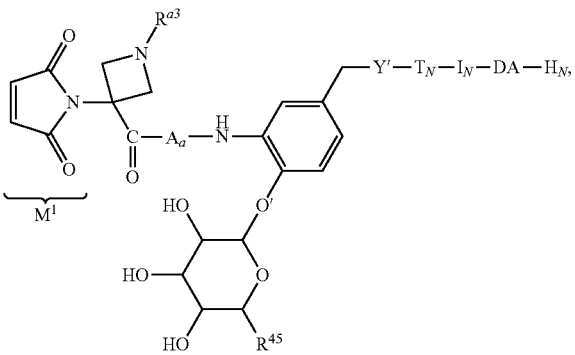

or a salt thereof, wherein Y' is —$X^a$—, —O—C(=O)—$X^b$— or —OC(=O)NH—$CH_2$—$X^a$—, wherein —$X^a$— is O and $X^b$ is —NH—; $R^{45}$ is —$CH_2OH$ or —$CO_2H$; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^{a3}$ is optionally protonated; and wherein —O'O'— represents the oxygen atom of an O-glycosidic bond cleavable by a glycosidase, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

160. The Drug Linker compound of embodiment 144 wherein the compound is represented by the structure of:

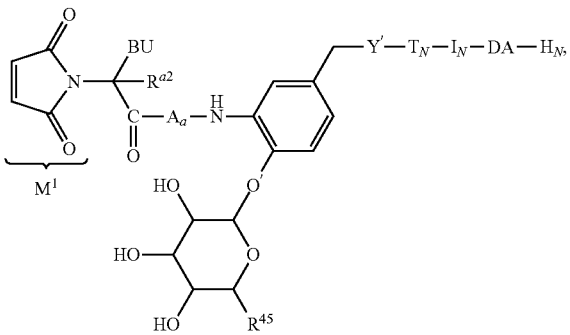

or a salt thereof, wherein Y' is —$X^a$—, —O—C(=O)—$X^b$— or —OC(=O)NH—$CH_2$—$X^a$—, wherein —$X^a$— is O and $X^b$ is —NH—; $R^{45}$ is —$CH_2OH$ or —$CO_2H$; BU is —$CH_2$—$NH_2$, optionally protonated; $R^{a2}$ is hydrogen; and wherein —O'— represents the oxygen atom of an O-glycosidic bond cleavable by a glycosidase, wherein said cleavage within The Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

161. The Drug Linker compound of embodiment 144 wherein the compound is represented by the structure of:

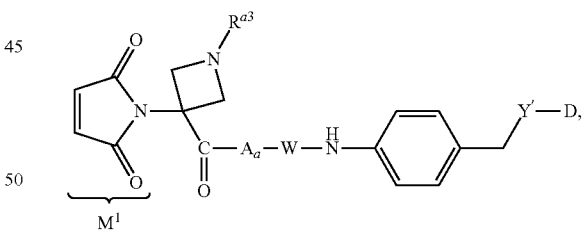

or a salt thereof, wherein W is a Peptide Cleavable Unit; Y' is —$X^a$—, —O—C(=O)—$X^b$— or —OC(=O)NH—$CH_2$—$X^a$—, wherein —$X^a$— is O and $X^b$ is —NH—; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^{a1}$ is optionally protonated; and wherein protease action on the Peptide Cleavable Unit cleaves the W—NH bond, wherein said cleavage within the Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

162. The Drug Linker compound of embodiment 144 wherein the compound is represented by the structure of:

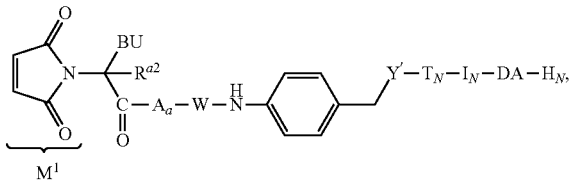

or a salt thereof, wherein W is a Peptide Cleavable Unit; Y' is —$X^a$—, —O—C(=O)—$X^b$— or —OC(=O)NH—CH$_2$—$X^a$—, wherein —$X^a$— is O and $X^b$ is —NH—; BU is —CH$_2$—NH$_2$, optionally protonated; $R^{a2}$ is hydrogen; and wherein protease action on the Peptide Cleavable Unit cleaves the W—NH bond, wherein said cleavage within The Drug Linker compound, or within a Conjugate compound of a Ligand Drug Conjugate composition prepared from the Drug Linker compound, initiates release of the NAMPT Drug Unit as a NAMPTi compound or derivative thereof from that Drug Linker or Ligand Drug Conjugate compound.

163. The Drug Linker compound of any one of the preceding embodiments in which W is a Peptide Cleavable Unit that Unit is comprised of a dipeptide wherein the dipeptide provides for a recognition site for a regulatory or lysosomal protease for cleavage by said protease of the W-J' bond or the W—NH bond when J' is —NH within the Drug Linker compound, or within a Conjugate compound of a Ligand Drug Conjugate composition prepared from the Drug Linker compound, so as to initiate release of the NAMPT Drug Unit as NAMPTi compound or derivative thereof from that Drug Linker or Ligand Drug Conjugate compound.

164. The Drug Linker compound of embodiment 163 wherein the W has the structure of:

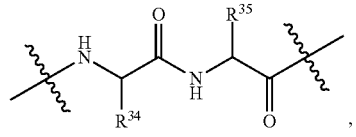

wherein $R^{34}$ is benzyl, methyl, isopropyl, isobutyl, sec-butyl, —CH(OH)CH$_3$ or has the structure of

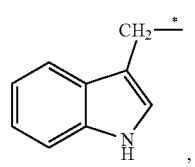

wherein the asterisk indicates the site of covalent attachment to the dipeptide backbone; and $R^{35}$ is methyl, —(CH$_2$)$_4$—NH$_2$, —(CH$_2$)$_3$NH(C=O)NH$_2$, —(CH$_2$)$_3$NH(C=NH)NH$_2$, or, —(CH$_2$)$_2$CO$_2$H; and wherein the wavy lines indicate the points of covalent attachment of the dipeptide into the structure representing the Drug Linker compound.

165. The Drug Linker compound of claim 164 wherein W is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

166. The Drug Linker compound of any one of embodiments 100 to 165, wherein A or a subunit thereof is -$L^P$ (PEG)-.

167. The Drug Linker compound of embodiment 166 wherein -$L^P$- or a subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form.

168. The Drug Linker compound of embodiment 166 wherein -$L^P$- or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

169. The Drug Linker compound of embodiment 166 wherein $L_P$ or a subunit thereof is selected from the group consisting of lysine, glutamic acid, aspartic acid, cysteine, penicillamine, serine or threonine in its D- or L-stereochemical configuration.

170. The Drug Linker compound of embodiment 166 wherein -$L^P$- or a subunit thereof has the structure of Formula $L^P$-1 or $L^P$-2:

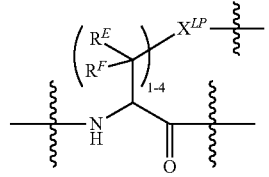
(Formula $L^P$-1)

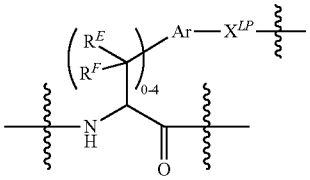
(Formula $L^P$-2)

or a pharmaceutical acceptable salt thereof, wherein $X^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, —N(R$^{LP}$)C(=NR$^{LP}$)N(R')—, and C$_3$-C$_8$ heterocyclo; wherein each R$^{LP}$ is independently selected from the group consisting of hydrogen and optionally substituted C$_1$-C$_6$ alkyl, or two of R$^{LP}$ together along with the carbons atoms to which they are attached and their intervening atoms define a C$_5$-C$_6$ heterocyclo and any remaining R$^{LP}$ are as previously defined; Ar is a C$_6$-C$_{10}$ arylene or a C$_5$-C$_{10}$ heteroarylene, optionally substituted;

each R$^E$ and R$^F$ is independently selected from the group consisting of —H, optionally substituted C$_1$-C$_6$ alkyl, optionally substituted C$_2$-C$_6$ alkylene, optionally substituted $C_6$-$C_{10}$ arylene and optionally substituted $C_5$-$C_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined; and wherein one of the wavy lines indicate the site of covalent attachment of a PEG Unit and the other wavy lines indicates covalent attachment of Formula $L^P$-1 or Formula $L^P$-2 within the structure representing the Drug Linker compound.

171. The Drug Linker compound of embodiment 166 wherein -$L^P$(PEG)- has the structure of Formula $L^P$-3 or Formula $L^P$-4:

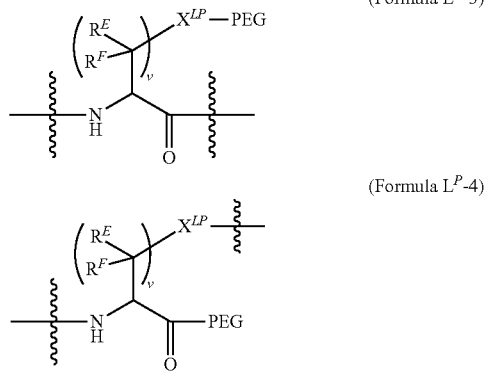

(Formula $L^P$-3)

(Formula $L^P$-4)

or a pharmaceutical acceptable salt thereof, wherein subscript v is an integer ranging from 1 to 4; $X^{LP}$ is selected from the group consisting of —O—, —$NR^{LP}$—, —S—, —S(=O)—, —S(=O)$_2$—, —C(=O)—, —C(=O)N($R^{LP}$)—, —N($R^{LP}$)C(=O)N($R^{LP}$)—, —N($R^{LP}$)C(=N$R^{LP}$)N($R^{LP}$)—, and $C_3$-$C_8$ heterocyclo; wherein each $R^{LP}$ is independently selected from the group consisting of hydrogen and optionally substituted $C_1$-$C_6$ alkyl, or two of $R^{LP}$ together along with the carbons atoms to which they are attached and their intervening atoms define a $C_5$-$C_6$ heterocyclo and any remaining $R^{LP}$ are as previously defined; Ar is a $C_6$-$C_{10}$ arylene or a $C_5$-$C_{10}$ heteroarylene, optionally substituted;

each $R^E$ and $R^F$ is independently selected from the group consisting of —H, optionally substituted $C_1$-$C_6$ alkyl, optionally substituted $C_2$-$C_6$ alkylene, optionally substituted $C_6$-$C_{10}$ arylene and optionally substituted $C_5$-$C_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined, or wherein the side chain of —[C($R^E$)($R^F$)]$_v$—$X^{LP}$— is provided by a natural or un-natural amino acid side chain; and wherein one of the wavy lines indicate the site of covalent attachment of a PEG Unit and the other wavy lines indicates covalent attachment of Formula $L^P$-1 or Formula $L^P$-2 within the structure representing the Drug Linker compound.

172. The Drug Linker compound of embodiment 170 or 171 wherein $R^E$ and $R^F$ are independently selected from the group consisting of —H, and —$C_1$-$C_4$ alkyl.

173. The Drug Linker compound of embodiment 170, 171 or 172 wherein $X^{LP}$ is selected from the group consisting of —O—, —NH, —S— and —C(=O)—.

174. The Drug Linker compound of any one of embodiments 166 to 173 wherein PEG has the structure selected from the group consisting of:

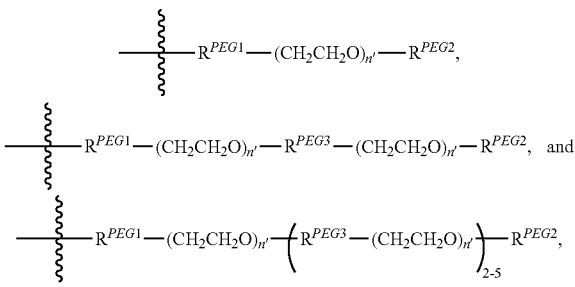

wherein the wavy line indicates site of attachment to $X^{LP}$ of the Parallel Connector Unit ($L^P$); subscript n' independently ranges from 1 to 72; $R^{PEG1}$ is an optional PEG Attachment Unit; $R^{PEG2}$ is a PEG Capping Unit; and $R^{PEG3}$ is an PEG Coupling Unit.

175. The Drug Linker compound of any one of embodiments 170 to 174 wherein —$X^{LP}$-PEG has the structure of:

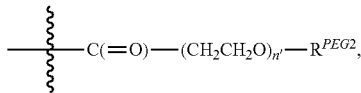

wherein subscript n' is 8, 12 or 24 and $R^{PEG2}$ is H or —$CH_3$.

176. The Drug Linker compound of any one of embodiments 100 to 175 wherein A, $A_O$, or a subunit thereof has the structure of formula (3) or formula (4):

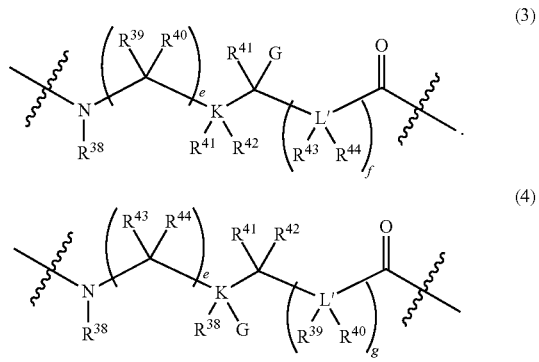

wherein the wavy lines indicated covalent attachment within the structure representing the Drug Linker compound; wherein K and L' independently are C, N, O or S, provided that when K or L' is O or S, $R^{41}$ and $R^{42}$ to K or $R^{43}$ and $R^{44}$ to L' are absent, and when K or L' are N, one of $R^{41}$, $R^{42}$ to K or one of $R^{42}$, $R^{43}$ to L' are absent, and provided that no two adjacent L' are independently selected as N, O, or S; wherein subscripts e and f are independently selected integers that range from 0 to 12, and subscript g is an integer ranging from 1 to 12;

wherein G is hydrogen, optionally substituted $C_1$-$C_6$ alkyl, —OH, —$OR^{PR}$, —$CO_2H$, $CO_2R^{PR}$, wherein $R^{PR}$ is a suitable protecting, or G is —N($R^{PR}$)($R^{PR}$), wherein $R^{PR}$ are independently a protecting group or $R^{PR}$ together form a suitable protecting group, or G is —N($R^{45}$)($R^{46}$), wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl;

$R^{39}$-$R^{44}$ are independently selected from the group consisting of hydrogen, optionally substituted $C_1$-$C_6$ alkyl, optionally substituted aryl, and optionally substituted heteroaryl, or $R^{39}$, $R^{40}$ together with the carbon atom to which both are attached, or $R^{41}$, $R^{42}$ together with K to which both are attached when K is a carbon atom, define a $C_3$-$C_6$ carbocyclo, and $R^{41}$-$R^{44}$ are as defined herein, or $R^{43}$, $R^{44}$ together with L' to which both are attached when L' is a carbon atom define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^{44}$ are absent, and when L' is N, one of $R^{43}$, $R^{44}$ is absent, or A or a subunit thereof is an alpha-amino, beta-amino or another amine-containing acid residue.

177. The Drug Linker compound of embodiment 176 wherein formula (3) or formula (4) has the structure of formula (3a) or formula (4a):

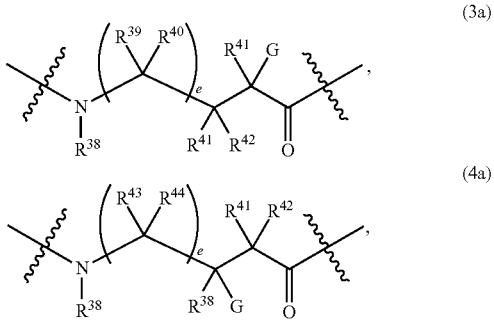

wherein
subscript e and f are independently 0 or 1.

1A. A Ligand Drug Conjugate (LDC) composition, wherein the composition is represented by the structure of:

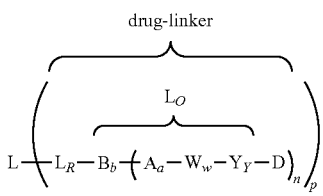

or a pharmaceutically acceptable salt thereof, wherein L is a Ligand Unit; D is a NAMPT Drug Unit represented by the general structure of:

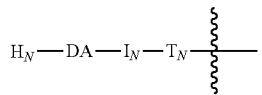

or a pharmaceutically acceptable salt thereof, wherein the wavy line indicates the site of covalent attachment to $L_O$ or $L_R$, depending on the presence or absence of $L_O$, respectively; $H_N$ is a NAMPT Head Unit, wherein the NAMPT Head Unit is a $C_5$-$C_{24}$ heteroaryl or partially aromatic $C_9$-$C_{24}$ heterocyclyl, optionally substituted, wherein the $C_5$-$C_{24}$ heteroaryl or partially aromatic $C_9$-$C_{24}$ heterocyclyl is comprised of an optionally substituted 5- or 6-membered nitrogen-containing heteroaromatic ring system corresponding to the heterocycle of nicotinamide, and is capable of interacting with enzymatically competent NAMPT homodimer at its nicotinamide mononucleotide binding site when the NAMPT Drug Unit is released from a Ligand Drug Conjugate compound of the composition as a NAMPT inhibitor (NAMPTi) compound or derivative thereof;

DA is a Donor-Acceptor Unit wherein the Donor-Acceptor Unit is or is comprised of a hydrogen bond donor acceptor functional group and is bonded to a carbon skeletal atom at position 2 or 3 of the 5-membered nitrogen-containing heteroaromatic ring system or at position 3 or 4 of the 6-membered nitrogen-containing heteroaromatic ring system, with optional formal cyclization of DA back to an adjacent skeletal carbon atom of the 6-membered nitrogen-containing heteroaromatic ring system through an introduced optionally substituted non-aromatic carbon atom or an optionally substituted nitrogen, oxygen or sulfur atom resulting in a partially aromatic or fully aromatic fused 6,5- or 6,6-ring system, wherein said bonding of DA is in relation to a skeletal nitrogen atom of the 5- or 6 membered nitrogen-containing heteroaromatic ring system and wherein said formal cyclization to the adjacent carbon atom of the 6-membered nitrogen-containing heteroaromatic ring system substantially retains the hydrogen bonding capability of the donor acceptor functional group of DA in absence of said cyclization;

$I_N$ is an Interconnecting Unit, wherein the Interconnecting Unit is or is comprised of —$X^1$—[C(=O)]$_{0,1}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$—, —$X^2$—$C_6$-$C_{24}$ arylene-O—, —$X^2$—$C_5$-$C_{24}$ heteroarylene-[C(=O)$_{0,1}$]—, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]—, wherein the arylene, heteroarylene and heterocyclo are optionally substituted; $X^1$ is optionally substituted $C_5$-$C_7$ alkylene; $X^2$ is absent or is an optionally substituted $C_1$-$C_4$ alkylene;

$T_N$ is a NAMPT Tail Unit, wherein the NAMPT Tail Unit is or is comprised of an optionally substituted amino-alcohol residue or a carboxylic acid-alcohol residue, the —O— or optionally substituted nitrogen of which is the site of covalent attachment to $L_O$, or $L_R$, depending on the presence or absence of $L_O$, or $T_N$ is or is comprised of an optionally substituted benzamide moiety, the amide nitrogen atom of which is bonded to $I_N$ with optional cyclization of that atom back to $I_N$ or to the remainder of $T_N$, and the aromatic ring of which is at least substituted with a hydroxyl, thiol or amino residue, the —O—, —S— or optionally substituted nitrogen of which at position 3 or 4 relative to the site at which the amide carbonyl carbon atom is attached is the site of covalent attachment to $L_O$ or $L_R$, depending on the presence or absence of $L_O$, or $T_N$ is or is comprised of an optionally substituted aryl or biaryl moiety, an aromatic skeletal atom of which is bonded to $I_N$, or to the remainder of $T_N$, and wherein an aromatic ring of which is at least substituted with a hydroxyl, thiol or an amino residue, the —O—, —S— or optionally substituted nitrogen of which is the site of covalent attachment to $L_O$ or $L_R$, depending on the presence or absence of $L_O$; and wherein $T_N$ or the remainder thereof is bonded to $I_N$, wherein said remainder is an optionally substituted $C_2$-heteroalkylene or an optionally substituted $C_5$-$C_6$ heterocyclo;

$L_R$ is a primary linker, which interconnects the Ligand Unit and Drug Unit optionally through $L_O$, as indicated, which is an optional secondary linker; subscripts a and b independently are 0 or 1, indicating the absence or presence, respectively, of A or B; subscript n is 1, 2, 3 or 4; A is an first optional Stretcher; and B is a Branching Unit, when subscript b is 1 and subscript n is 2, 3 or 4, or B is absent, so that subscript b is 0, when subscript n is 1, wherein each of A and B is an independently selected single unit or is optionally comprised or consists of at least two, three or four independently selected subunits;

subscript y is 0, 1 or 2, indicating the absence or presence of one or two of Y, respectively; Y is a Spacer Unit, provided that when subscript y is 1, Y is a Spacer Unit covalently attached to an optionally substituted heteroatom of $T_N$ selected from the group consisting of —O—, —S— and optionally substituted nitrogen; and provided that when subscript y is 2 so that $Y_y$ is —Y—Y'—, then Y is a first Spacer Unit and Y' is a functional group comprised of the optionally substituted heteroatom of $T_N$, or Y' is a second Spacer Unit; and subscript w is 0 or 1, indicating the absence or presence, respectively, of W; wherein when subscript w is 1, W is a Peptide Cleavable Unit or a Glucuronide Unit of formula —Y(W')—, wherein W' represents a carbohydrate moiety with glycosidic bonding to Y through a optionally substituted heteroatom, provided Y bonded to W' is required to be a first self-immolative Spacer Unit; subscript y is 0, 1 or 2, provided subscript y is 1 or 2 when W is a Glucuronide Unit, in which instance subscript y is inclusive of the required self-immolative Spacer Unit; and wherein when subscript w is 1, which indicates the presence of a Cleavable Unit, enzymatic or non-enzymatic cleavage of that Unit initiates release of the NAMPT Drug Unit as a NAMPTi compound or derivative thereof from a Conjugate compound of a Ligand Drug Conjugate composition; and when subscript w is 0, which indicates the absence of a Cleavable Unit, enzymatic or non-enzymatic cleavage of the bond between the indicated $L_R$ and $L_O$ moieties, when $L_O$ is present, or the bond between $L_R$ and D, when $L_O$ is absent, initiates release of the NAMPT Drug Unit as a NAMPTi compound or derivative thereof;

subscript p is an average drug linker moiety loading when subscript n is other than 1 or an average drug loading when subscript n is 1, wherein subscript p in either instance is a number ranging from about 1 to about 24; and wherein a compound of the Ligand Drug Conjugate composition corresponds in structure(s) to that of Formula for Formula 2 in which p is replaced by p', wherein p' is an integer ranging from 1 to 24.

2A. The Ligand Drug Conjugate composition of embodiment 1A, wherein the NAMPT Head ($H_N$) Unit is a pyridine mimetic.

3A. The Ligand Drug Conjugate composition of embodiment 1A or 2A, wherein the Donor Acceptor (DA) Unit is comprised of an optionally substituted amide functional group or bioisostere thereof.

4A. The Ligand Drug Conjugate composition of embodiment 1A, wherein $H_N$-DA is a nicotinamide mimetic.

5A. The Ligand Drug Conjugate composition of embodiment 1A, wherein the 6-membered nitrogen-containing heteroaromatic ring system of $H_N$ is that of pyridine with optional cyclization of DA back to the pyridine aromatic ring system through an introduced aromatic oxygen, sulfur or an optionally substituted nitrogen atom so that $H_N$ contains a 6-5 fused aromatic ring system.

6A. The Ligand Drug Conjugate composition of any one of embodiment 1A-5A, wherein each of the NAMPT homodimers of the enzymatically competent NAMPT homodimer has the amino acid sequence of NCBI Reference Sequence NP_005737.1.

7A. The Ligand Drug Conjugate composition of any one of embodiment 1A-5A, wherein the NAMPT Head Unit has the structure of:

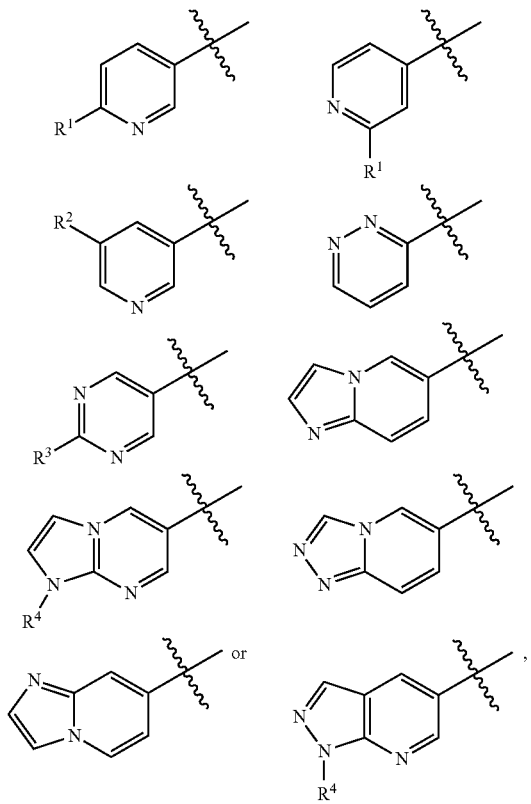

or a pharmaceutically acceptable salt thereof, in particular, having the structure of:

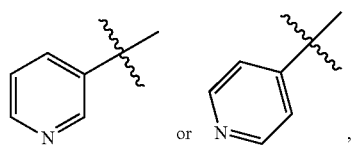 [SMILES: *c1cccnc1 ; *c1ccncc1]

or a pharmaceutically acceptable salt thereof, wherein $R^1$ is hydrogen, —NH$_2$ or chloro; $R^2$ is fluoro; $R^3$ is hydrogen or —NH$_2$; and the wavy line indicates the site of covalent attachment to DA and an adjacent aromatic carbon atom thereto is the site of said optional cyclization by DA to $H_N$.

8A. The Ligand Drug Conjugate composition of any one of embodiments 1A-7A, wherein the Donor-Acceptor Unit has the structure of:

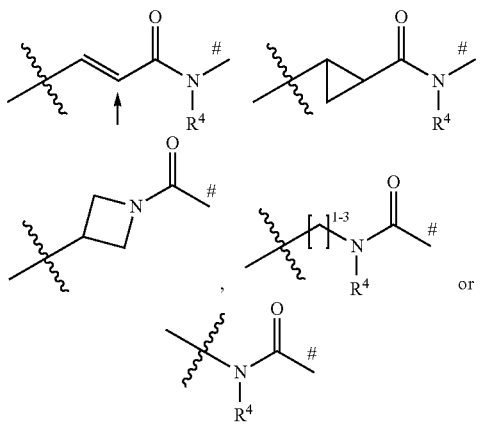

in particular, having the structure of:

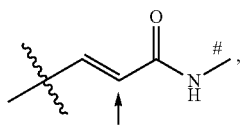

wherein $R^4$ is hydrogen or optionally substituted $C_1$-$C_4$ alkyl; DA is optionally cyclized to $H_N$, wherein said cyclization is to the $sp^2$ carbon atom proximal to the carbonyl carbon (as indicated) through an introduced optionally substituted non-aromatic carbon atom or an optionally substituted aromatic heteroatom; the wavy line indicates the site of covalent attachment to $H_N$, and the carbon atom adjacent thereto is the site of said optional cyclization by DA; and the pound sign (#) indicates the site of covalent attachment to $I_N$, or wherein the Donor-Acceptor Unit has the structure of:

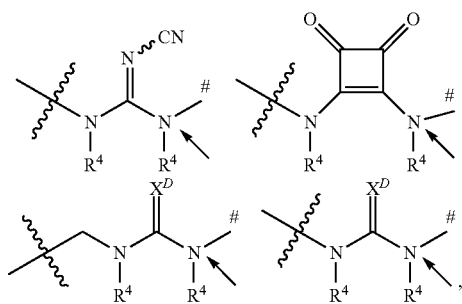

or a pharmaceutically acceptable salt thereof, in particular, having the structure of:

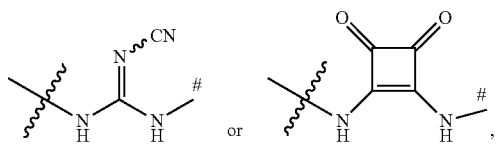

or a pharmaceutically acceptable salt thereof, wherein $X^D$ is O, S or $NR^D$, wherein the nitrogen atom is optionally protonated and $R^D$ is hydrogen or optionally substituted $C_1$-$C_4$ alkyl; each $R^4$ is independently selected from the group consisting of hydrogen and optionally substituted $C_1$-$C_4$ alkyl, or both $R^4$ together with the nitrogen atoms to which they are attached and the intervening carbon atom(s) define an optionally substituted $C_5$-$C_6$ heterocyclo; the pound sign (#) indicates the site of covalent attachment to $I_N$; and the wavy line indicates the site of covalent attachment to $H_N$, wherein DA is optionally cyclized back to an adjacent site of $H_N$, wherein said cyclization is from the indicated nitrogen atom so that $R^4$ bonded thereto is replaced by a covalent bond or from $X^D$ when $X^D$ is —$NR^D$, either directly or through an introduced —$S(=O)_{0-2}$ moeity, in which either instance $R^D$ is replaced by a bond.

9A. The Ligand Drug Conjugate composition of any one of embodiments 1A-8A, wherein $H_N$-DA- has the structure of:

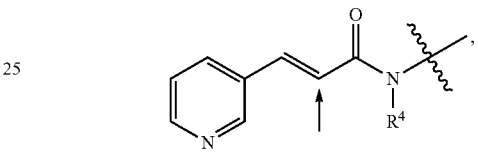

or a pharmaceutically acceptable salt thereof, wherein $R^4$ is hydrogen or optionally substituted $C_1$-$C_4$ alkyl; and the wavy line indicates the site of covalent attachment to $I_N$, and wherein the $sp^2$ carbon atom proximal to the carbonyl carbon is the site (as indicated) of optional cyclization to $H_N$ through an introduced optionally substituted non-aromatic carbon atom or an optionally substituted aromatic heteroatom.

10A. The Ligand Drug Conjugate composition of any one of embodiments 1A to 9A wherein the NAMPT Tail Unit is or is comprised of an optionally substituted amino alcohol moiety, wherein the oxygen atom of the alcohol is the site of covalent attachment to $L_O$ or $L_R$, depending on the presence or absence of $L_O$, respectively, in particular having the structure of.

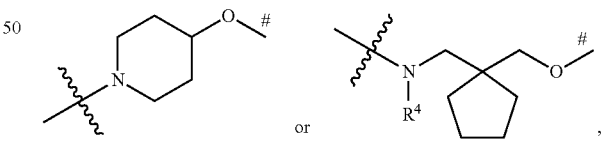

or a pharmaceutically acceptable salt thereof, wherein $R^4$ is hydrogen or optionally substituted $C_1$-$C_4$ alkyl; the wavy line indicates the site of covalent attachment to $I_N$; and the pound sign (#) indicates the site of covalent to $L_O$ or $L_R$, depending on the presence or absence of $L_O$, respectively, or wherein the Tail Unit is or is comprised of an optionally substituted benzamide moeity having a functional group providing a heteroatom that is the site of covalent attachment to $L_O$ or $L_R$, depending on the presence or absence of $L_O$, respectively, in particular having the structure of:

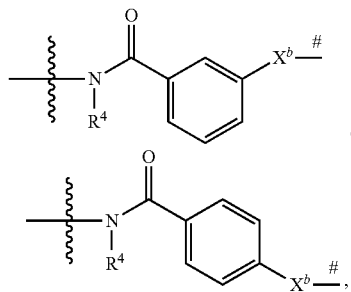

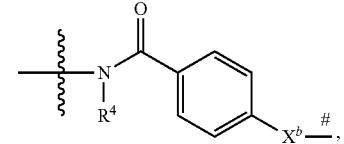

or wherein $X^b$ is —S—, —O— or —NH—, optionally substituted; and $R^4$ is hydrogen or optionally substituted $C_1$-$C_4$ alkyl, wherein the benzamide moeity is optionally cyclized to $I_N$ wherein the amide nitrogen of the benzamide moiety is the site of said cyclization so that $R^4$ is replaced by a covalent bond, more particularly, having the structure of:

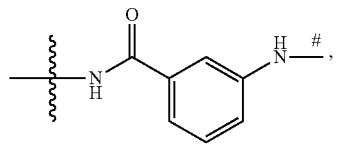 [SMILES: *NC(=O)c1cccc(NC)c1]

wherein the wavy line indicates the site of covalent attachment to $I_N$; and the pound sign (#) indicates the site of covalent attachment to $L_O$ or $L_R$, depending on the presence or absence of $L_O$, respectively.

11A. The Ligand Drug Conjugate composition of any one of embodiments 1A-10A, wherein $I_N$ is —CH$_2$—(CH$_2$)$_{3-7}$—CH$_2$—, —CH$_2$—(CH$_2$)$_{3-7}$—CH$_2$—O—, —CH$_2$—(CH$_2$)$_{3-7}$—C(=O)—, —CH$_2$—(CH$_2$)$_{3-7}$—S(=O)$_2$— or —CH$_2$—(CH$_2$)$_{3-7}$—S(=O)—.

12A. The Ligand Drug Conjugate composition of embodiment 11A, wherein —$I_N$-$T_N$- has the structure of:

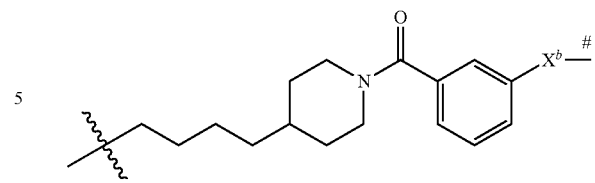

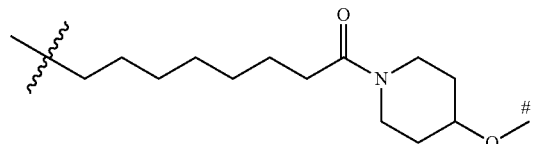

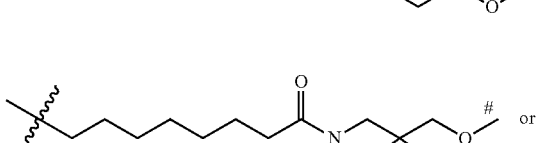

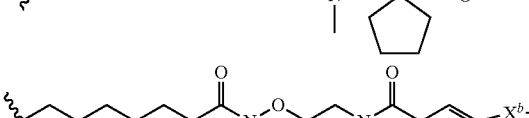

or

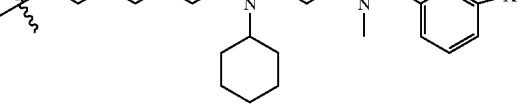

wherein $X^b$ is —NH—, —O— or —S—; the wavy line indicates the site of covalent attachment to DA; and the pound sign (#) indicates the site of covalent attachment to $L_O$ or $L_R$, depending on the presence or absence of $L_O$, respectively.

13A. The Ligand Drug Conjugate composition of any one of embodiments 1A-12A, wherein the NAMPT Drug Unit has the structure of:

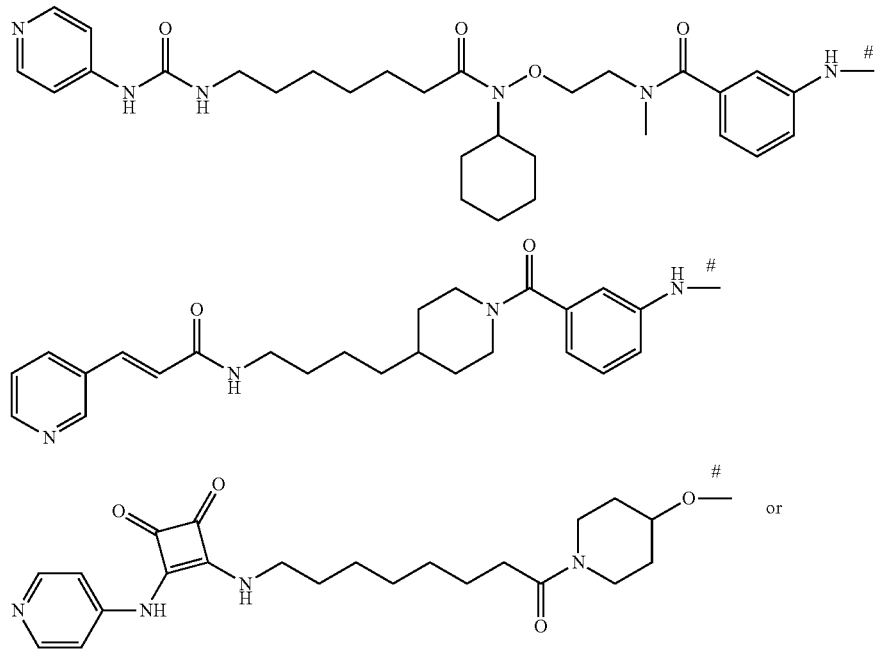

-continued

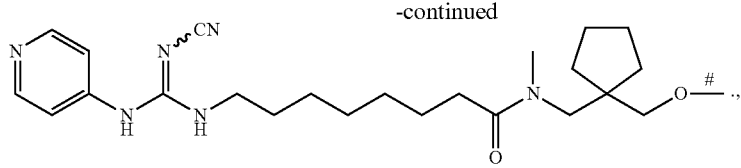

or a pharmaceutically acceptable salt thereof, wherein the pound sign (#) indicates the site of covalent attachment to $L_O$ or $L_R$, depending on the presence or absence of $L_O$, respectively.

14A. The Ligand Drug Conjugate composition of any one of embodiments 1A-13A, wherein L-$L_R$- has the structure of:

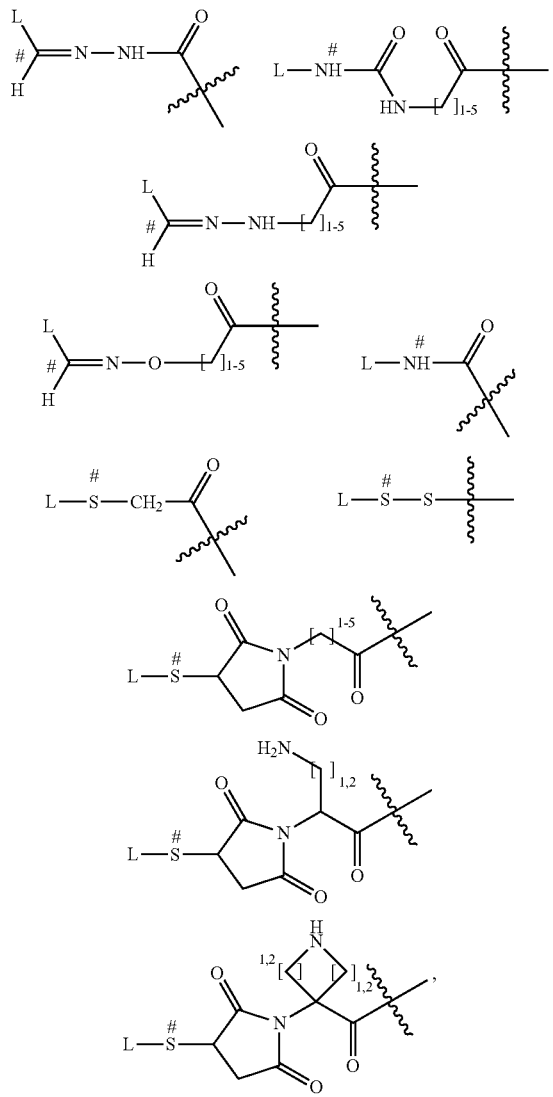

or a pharmaceutically acceptable salt thereof, wherein the indicated (#) nitrogen, carbon or sulfur atom is from the Ligand Unit; and wherein the wavy line indicates the site of covalent attachment to the remainder of the Conjugate structure.

15A. The Ligand Drug Conjugate composition of embodiment 1A, wherein the composition is represented by the structure(s) of Formula 1 and/or Formula 2:

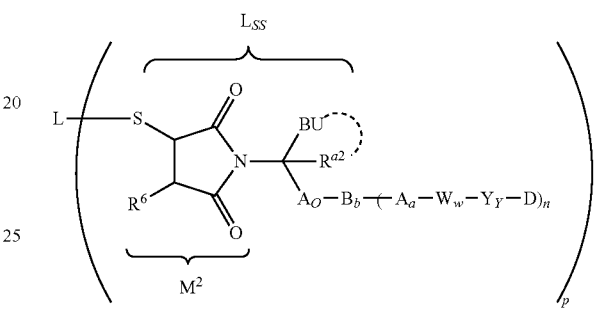
(Formula 1)

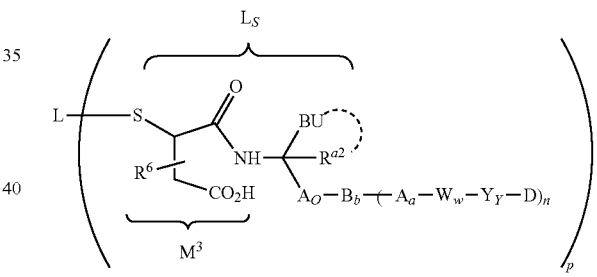
(Formula 2)

or a pharmaceutically acceptable salt thereof, wherein S is a sulfur atom of the Ligand Unit, which in Formula 2 is bonded to the carbon atom α or β to the carboxylic acid functional group of the indicated succinic acid amide ($M^3$) moiety; $R^6$ is hydrogen or an optionally substituted $C_1$-$C_6$ alkyl, which in Formula 2 is bonded to the saturated carbon atom adjacent to the carbon substituted by L-S—; $A_O$ is a second optional Stretcher Unit; BU is a Basic Unit and $R^{a2}$ is an optionally substituted $C_1$-$C_{12}$, alkyl group; and the dotted curved line indicates optional cyclization so that in the absence of said cyclization BU is an acyclic Basic Unit or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group of BU, wherein the basic nitrogen atom of the acyclic Basic Unit or cyclic Basic Unit is optionally suitably protected by a nitrogen protecting group, dependent on the degree of substitution of the basic nitrogen atom, or is optionally protonated, in particular, having the structure of:

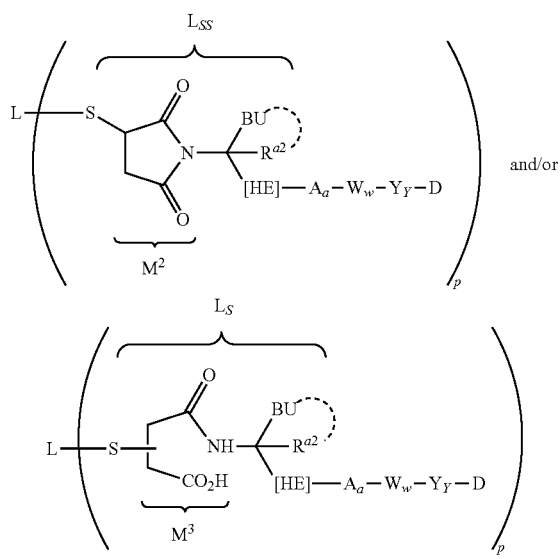

wherein [HE] as $A_O$ is an optional Hydrolysis Enhancing Unit; subscript w is 1; W is Peptide Cleavable Unit, wherein protease action on the Peptide Cleavable Unit resulting in cleavage of the W-J' bond within a compound of the Ligand Drug Conjugate composition initiates release of the NAMPT Drug Unit as NAMPTi compound or derivative thereof from that Ligand Drug Conjugate compound, or W is a Glucuronide Unit of formula —Y(W')— having the structure of:

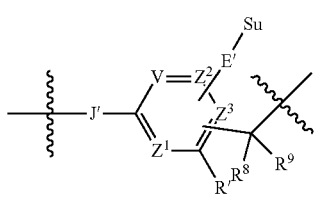

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W'; J' is an independently selected heteroatom, optionally substituted; V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)— moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$-$C_6$ alkyl, or other electron donating group; and wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the site of covalent attachment of the Glucuronide Unit to Y' when subscript y is 2, or to D when subscript y is 1, and the remaining variable groups retain their previous meanings; and wherein glycosidase action on the Glucuronide Unit resulting in cleavage of its glycosidic bond initiates release of the NAMPT Drug Unit as NAMPTi compound or derivative thereof from that Ligand Drug Conjugate compound.

16A. The Ligand-Drug Conjugate composition of embodiment 15A, wherein W is a Glucuronide Unit for which —W—$Y_y$-D has the structure of:

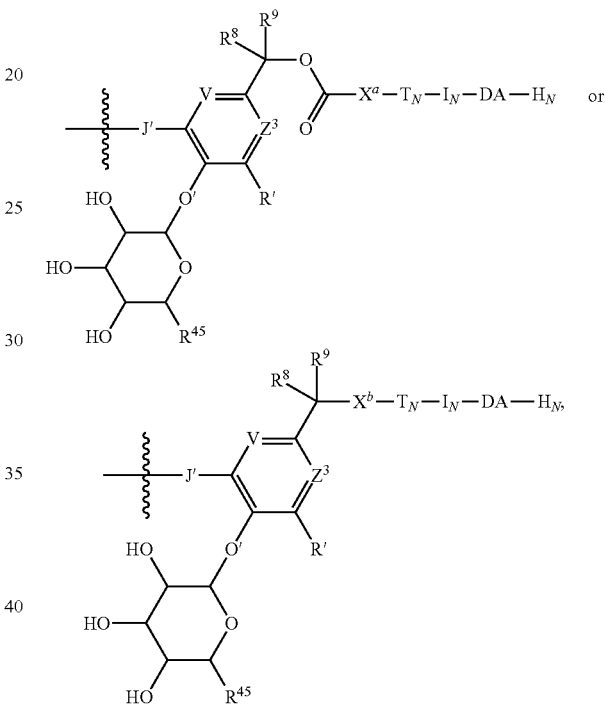

or a pharmaceutically acceptable salt thereof, wherein $X^a$ is a nitrogen atom from a primary or secondary amine functional group of $T_N$; $X^b$ is an oxygen atom from an alcohol functional group or a sulfur atom from a thiol functional group of $T_N$, or —W—$Y_y$-D has the structure of:

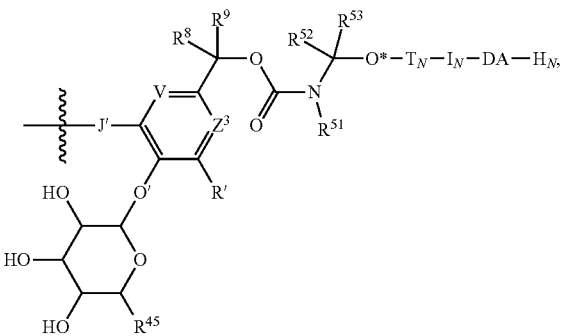

or a pharmaceutical acceptable salt thereof, wherein $R^{51}$, $R^{52}$ and $R^{53}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^{51}$ and $R^{52}$ together with the nitrogen and carbon atoms to which both are attached define an azetidine, pyrrolidine, piperidine or homopiperidine heterocyclo, and $R^{53}$ is hydrogen; and R' is hydrogen or —$NO_2$ or other electron withdrawing group; and wherein O* represents the oxygen atom from an alcohol functional group of $T_N$ and O' represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative from that Ligand Drug Conjugate compound, or wherein W is a Peptide Cleavable Unit for which —$Y_y$-D- has the structure of:

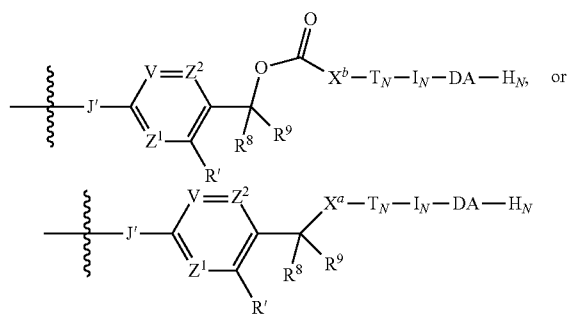

or a pharmaceutical acceptable salt thereof, wherein $X^a$ is an oxygen atom from an alcohol functional group or a sulfur atom of a thiol functional group of $T_N$; $X^b$ is a nitrogen atom from a primary or secondary amine functional group of $T_N$, or has the structure of:

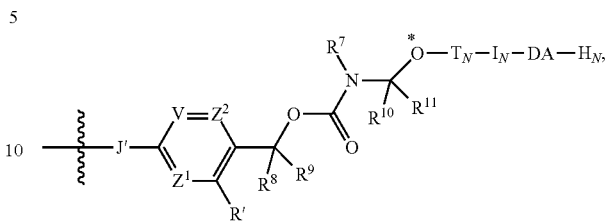

or a pharmaceutical acceptable salt thereof, wherein R' is hydrogen or —$OC_1$-$C_6$ alkyl or other electron donating group; $R^7$, $R^{10}$ and $R^{11}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^7$ and $R^{10}$ together with the nitrogen and carbon atoms to which both are attached define an azetidine, pyrrolidine, piperidine or homopiperidine heterocyclo, and $R^{11}$ is hydrogen;

$R^{45}$ is —$CH_2OH$ or —$CO_2H$; O* represents the oxygen atom from an alcohol functional group of $T_N$; and J' is an optionally substituted heteroatom bonded to W as indicated by the wavy line, wherein cleavage of that bond within a compound of the Ligand Drug Conjugate composition initiates release of the NAMPT Drug Unit as a NAMPTi compound or derivative thereof from that Ligand Drug Conjugate compound.

17A. The Ligand Drug Conjugate composition of embodiment 15A, wherein W is a Glucuronide Unit for which the composition is represented by the structure(s) of:

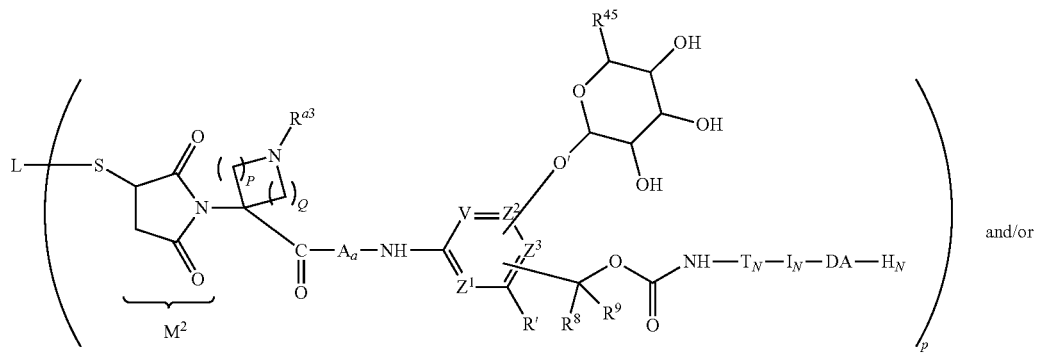

and/or

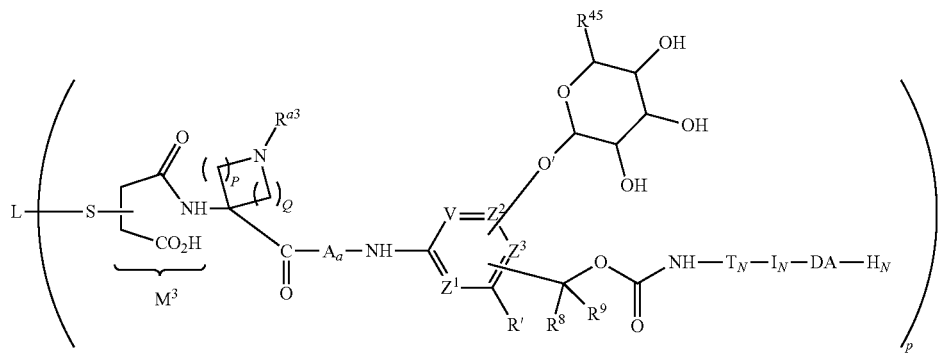

or a pharmaceutical acceptable salt thereof, wherein subscript P is 1, 2 or 3; and subscript Q ranges from 1 to 6,
or by the structure(s) of:

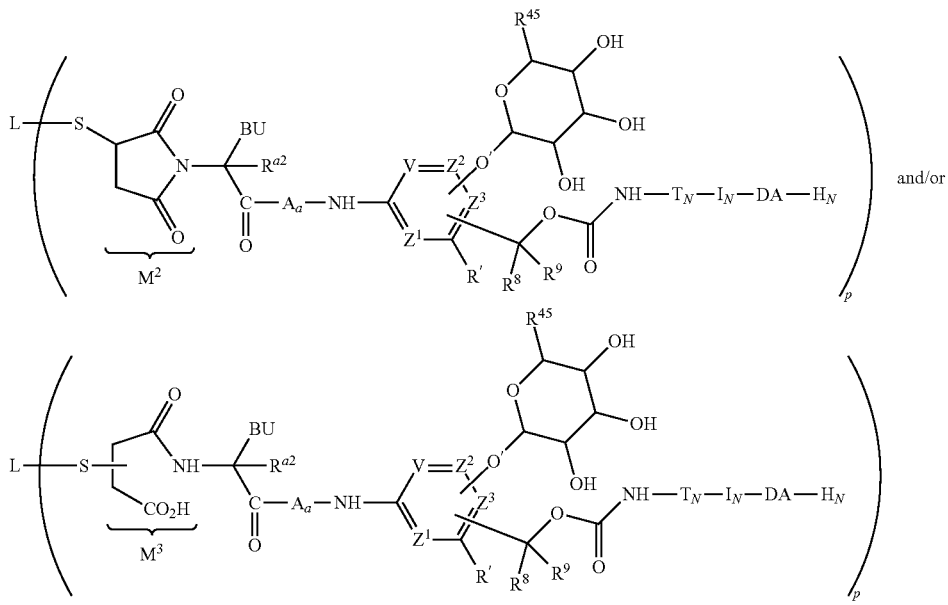

or a pharmaceutical acceptable salt thereof, wherein $R^{a3}$ is hydrogen or $C_1$-$C_6$ alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; and wherein R' is hydrogen or —$NO_2$ or other electron withdrawing group; $R^{45}$ is —$CH_2OH$ or —$CO_2H$; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl, wherein the basic nitrogen atom bonded to $R^{a3}$ is optionally protonated, and wherein —O'— represents the oxygen heteroatom of an O-glycosidic bond cleavable by a glycosidase, wherein said cleavage within a compound of the Ligand Drug Conjugate composition initiates release of the NAMPT Drug Unit as a NAMPTi compound or derivative thereof that Ligand Drug Conjugate compound, or wherein the W is a Peptide Cleavable Unit for which the composition is represented by the structure(s) of:

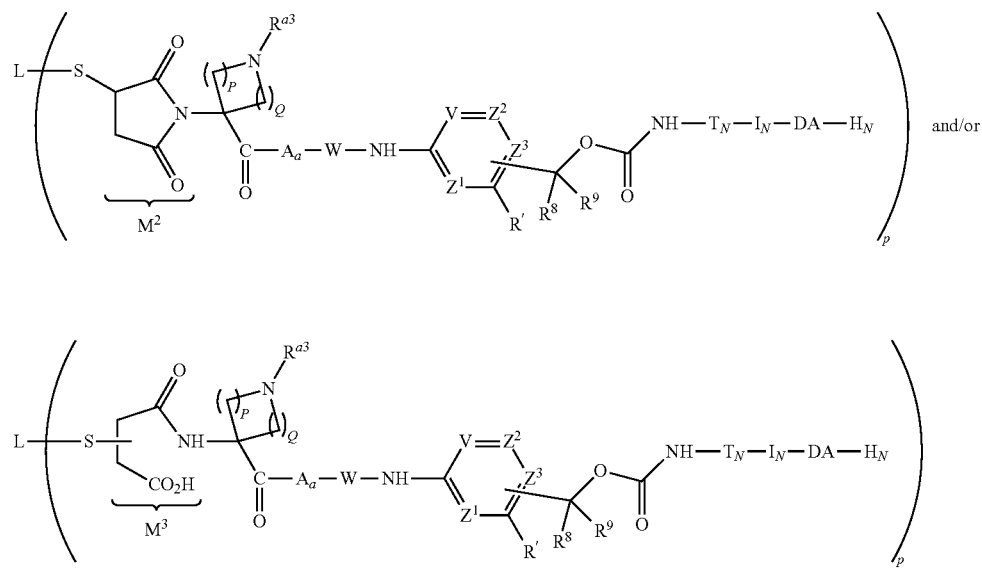

or a pharmaceutical acceptable salt thereof, wherein subscript P is 1, 2 or 3; and subscript Q ranges from 1 to 6, or is represented by the structure(s) of:

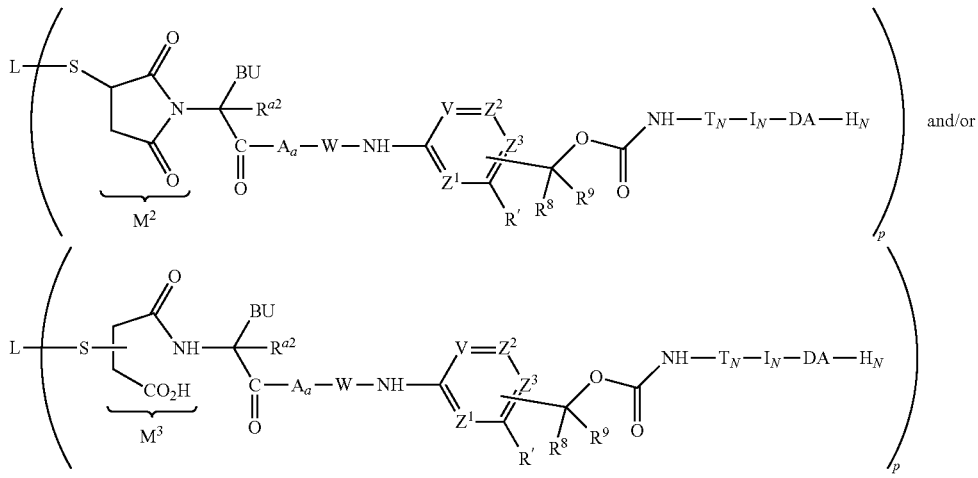 and/or or a pharmaceutical acceptable salt thereof, wherein $R^{a2}$ is hydrogen or $C_1$-$C_6$ alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a3}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; and wherein $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—)$CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and the basic nitrogen atom bonded to $R^{a3}$ is optionally protonated; and R' is hydrogen or —$OC_1$-$C_6$ alkyl or other electron donating group; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

18A. The Ligand Drug Conjugate composition of embodiment 15A, wherein W is a Glucuronide Unit for which the composition is represented by the structure(s) of:

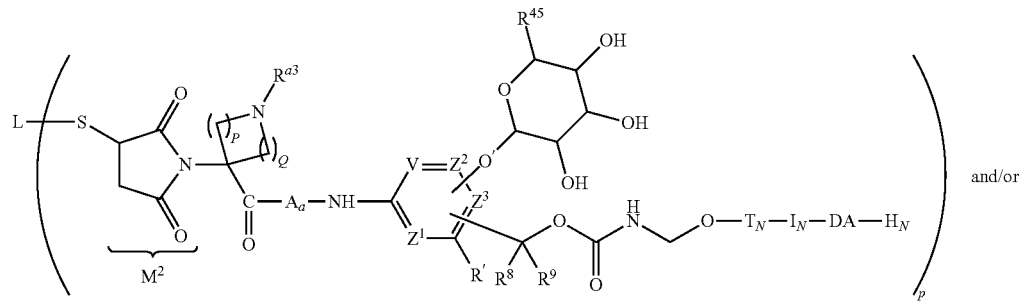 and/or

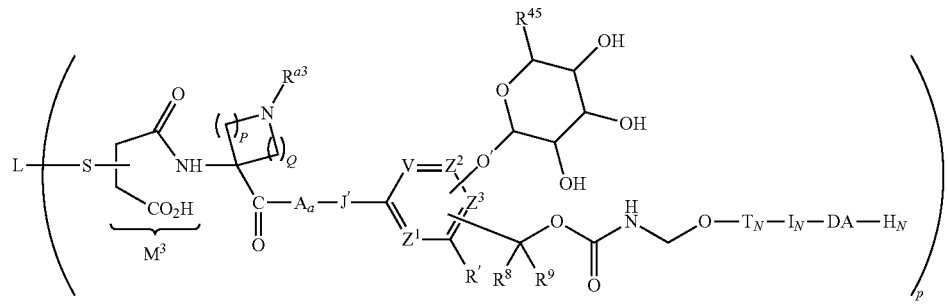

or a pharmaceutical acceptable salt thereof, wherein subscript P is 1, 2 or 3; and subscript Q ranges from 1 to 6, or is represented by the structure(s) of:

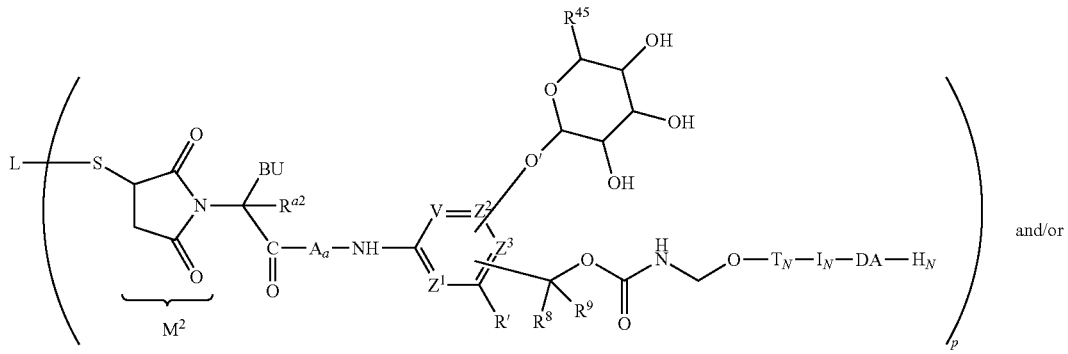

and/or

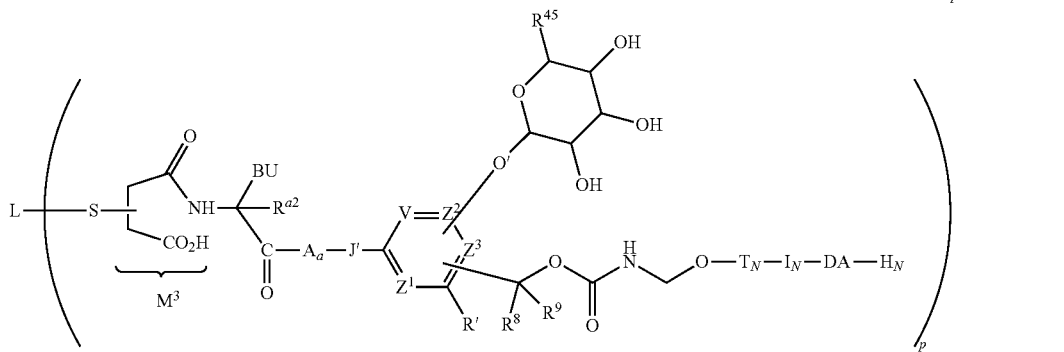

or a pharmaceutical acceptable salt thereof, wherein $R^{a3}$ is hydrogen or $C_1$-$C_6$ alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a3}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; and wherein R' is hydrogen or —$NO_2$ or other electron withdrawing group; $R^{45}$ is —$CH_2OH$ or —$CO_2H$; and —O'— represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof from that Ligand Drug Conjugate compound, or wherein W is a Peptide Cleavable Unit for which the composition is represented by the structure(s) of:

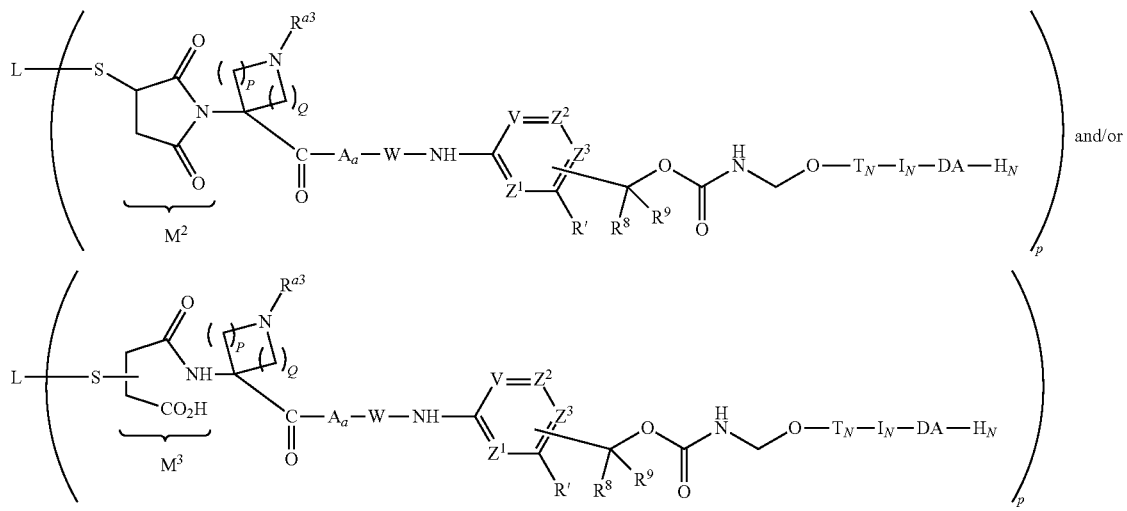

or a pharmaceutical acceptable salt thereof, wherein subscript P is 1, 2 or 3; subscript Q ranges from 1 to 6, or is represented by the structure(s) of:

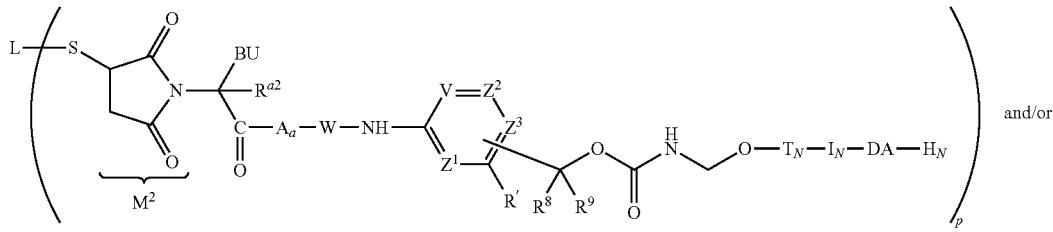

and/or

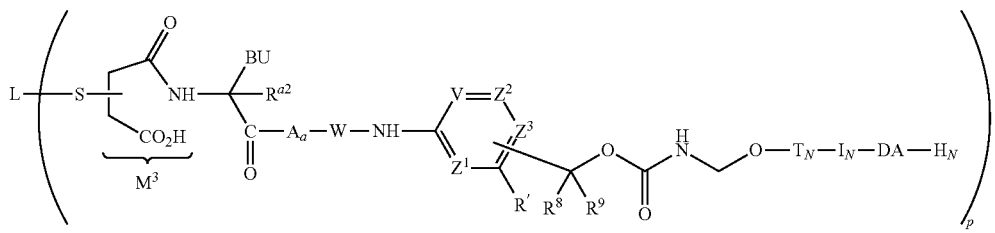

or a pharmaceutical acceptable salt thereof, wherein $R^{a2}$ is hydrogen or $C_1$-$C_6$ alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a1}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; and wherein the basic nitrogen atom of BU is optionally protonated; and wherein R' is hydrogen or —O$C_1$-$C_6$ alkyl or other electron donating group; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—(CH$_2$CH$_2$O)$_{1-36}$—$R^{PEG2}$, wherein $R^{PEG1}$ is $C_1$-$C_4$ alkylene, and $R^{PEG2}$ is —H or $C_1$-$C_4$ alkyl, wherein the basic nitrogen atom bonded to $R^{a3}$ is optionally protonated; and wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

19A. The Ligand-Drug Conjugate composition of embodiment 15A, wherein W is a Glucuronide Unit for which the composition is represented by the structure(s) of:

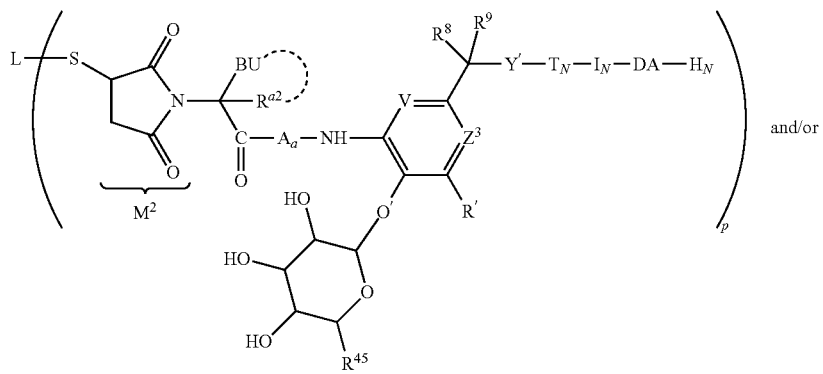

and/or

-continued

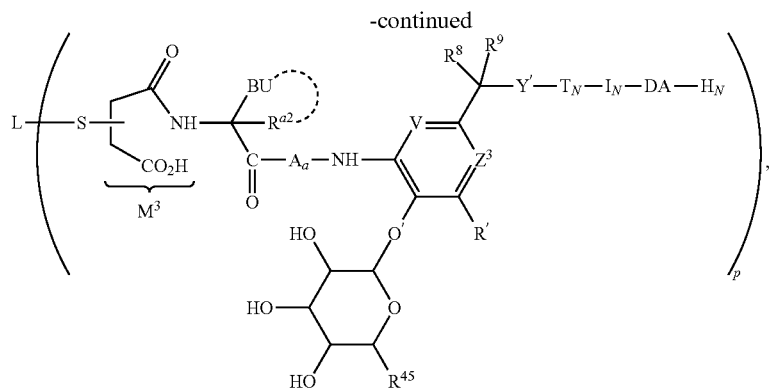

or a pharmaceutical acceptable salt thereof, wherein R' is hydrogen or —$NO_2$ or other electron withdrawing group; $R^{a2}$ is hydrogen or $C_1$-$C_6$ alkyl, optionally cyclized to BU, as indicated by the dotted curved line; BU has the structure of —$[C(R^{a1})(R^{a1})]$—$[C(R^{a1})(R^{a1})]_{0-3}$—$N(R^{a3})(R^{a3})$, wherein in the absence of cyclization to $R^{a2}$, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a3}$ together with the carbon(s) to which they are attached and any intervening carbons define an optionally substituted $C_3$-$C_6$ cycloalkyl; and $R^{a3}$ independently are hydrogen, optionally substituted $C_1$-$C_6$ alkyl or $R^{a1}$ together with the nitrogen atom to which both are attached define a $C_3$-$C_6$ heterocyclyl in which the basic nitrogen is a skeletal atom; and wherein the basic nitrogen atom of BU is optionally protonated, and in the presence of cyclization one of $R^{a1}$ or one of $R^{a3}$ is replaced with a bond to a carbon atom of $R^{a2}$ in which $R^{a2}$ is $C_1$-$C_6$ alkyl and the remaining $R^{a1}$ and $R^{a3}$ are as previously defined, in particular, by the structure(s) of:

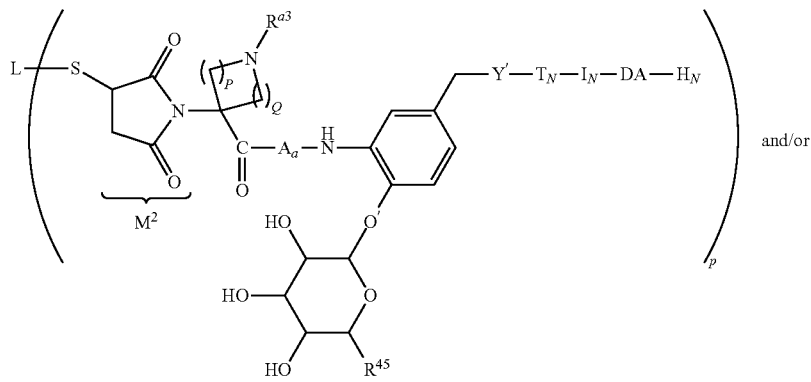

and/or

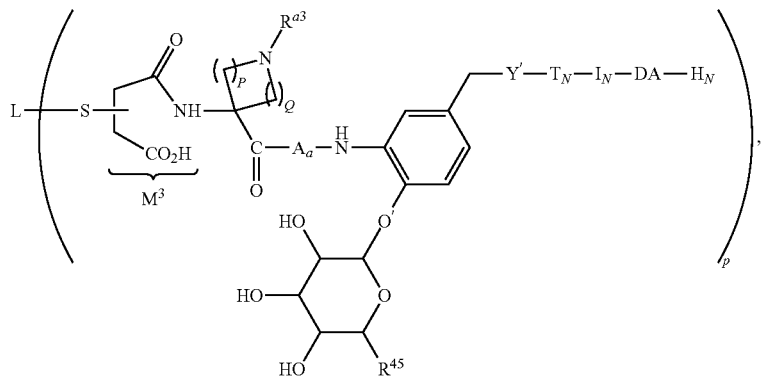

or a pharmaceutically acceptable salt thereof, more particularly, by the structure(s) of:
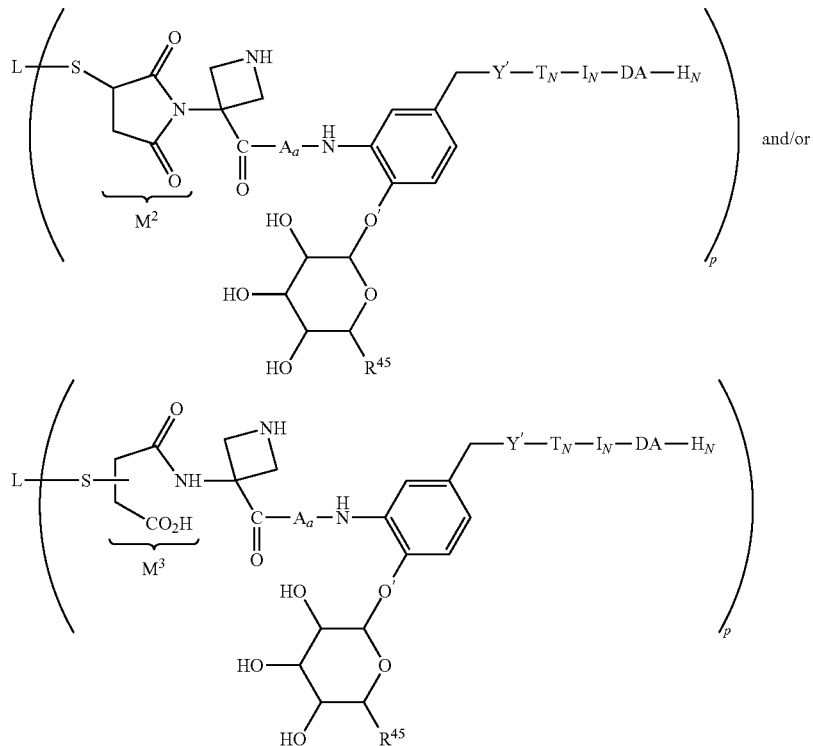
or a pharmaceutically acceptable salt thereof, or in particular by the structure(s) of:
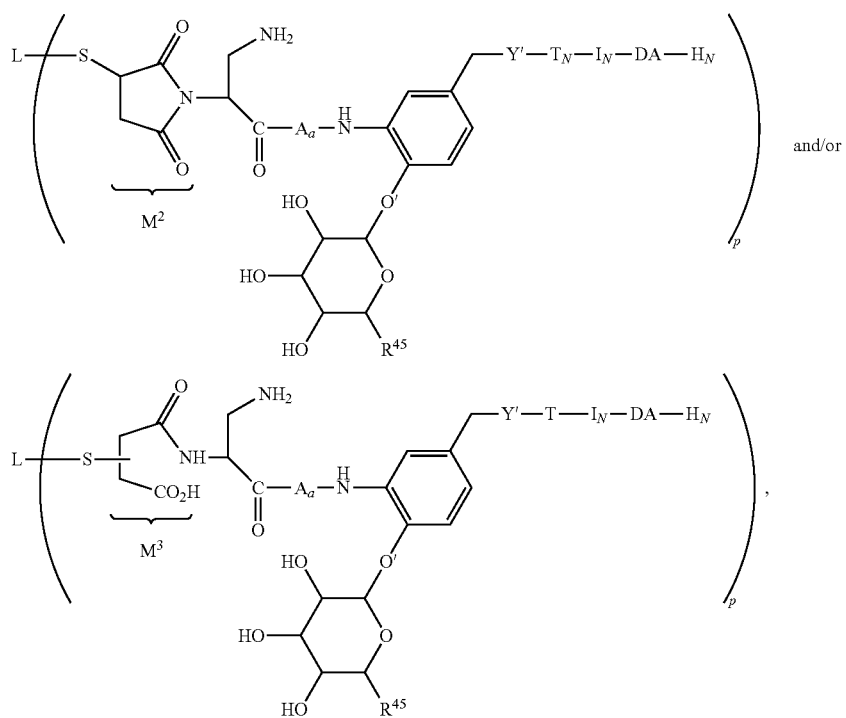

or a pharmaceutical acceptable salt thereof, and
wherein Y' is —$X^a$—, —O—C(=O)—$X^b$— or —OC(=O)NH—CH$_2$—$X^a$—, wherein $X^a$ or $X^b$ are from $T_N$, wherein —$X^a$— is O and $X^b$ is —NH—; and $R^{45}$ is —CH$_2$OH or —CO$_2$H; and wherein —O'— represents the oxygen atom of an O-glycosidic bond cleavable by a glycosidase, wherein said cleavage within a compound of the Ligand Drug Conjugate composition initiates release of the NAMPT Drug Unit as a NAMPTi compound or derivative thereof that Ligand Drug Conjugate compound, or wherein W is a Peptide Cleavable Unit for which the composition is represented by the structure(s) of:

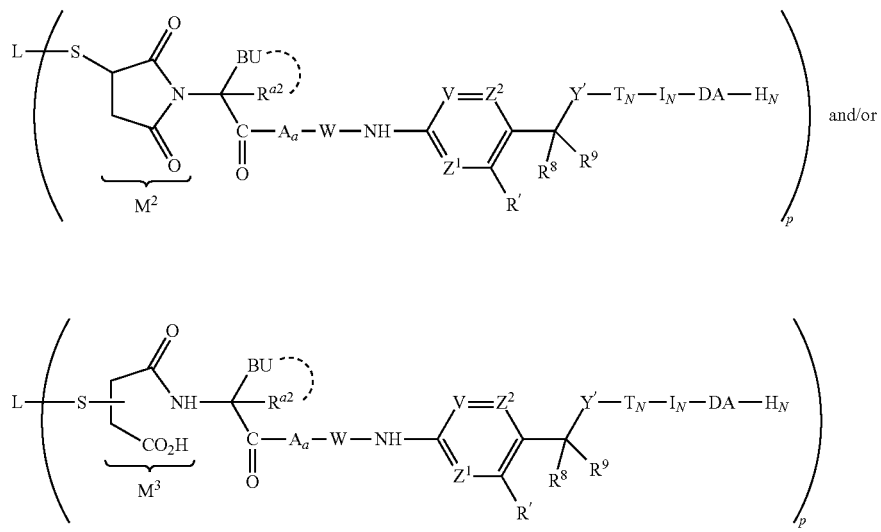

or a pharmaceutically acceptable salt thereof, wherein R' is hydrogen or —OC$_1$-C$_6$ alkyl or other electron donating group; $R^{a2}$ is hydrogen or C$_1$-C$_6$ alkyl, optionally cyclized to BU, as indicated by the dotted curved line; BU has the structure of —[C($R^{a1}$)($R^{a1}$)]—[C($R^{a1}$)($R^{a1}$)]$_{0-3}$—N($R^{a3}$)($R^{a3}$), wherein in the absence of cyclization to $R^{a2}$, each $R^{a3}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two $R^{a1}$ together with the carbon(s) to which they are attached and any intervening carbons define an optionally substituted C$_3$-C$_6$ cycloalkyl; and $R^{a3}$ independently are hydrogen, optionally substituted C$_1$-C$_6$ alkyl or $R^{a1}$ together with the nitrogen atom to which both are attached define a C$_3$-C$_6$ heterocyclyl in which the basic nitrogen is a skeletal atom; and wherein the basic nitrogen atom of BU is optionally protonated, and in the presence of cyclization one of $R^{a1}$ or one of $R^{a3}$ is replaced with a bond to a carbon atom of $R^{a2}$ in which $R^{a2}$ is C$_1$-C$_6$ alkyl and the remaining $R^{a1}$ and $R^{a3}$ are as previously defined, in particular by the structure(s) of:

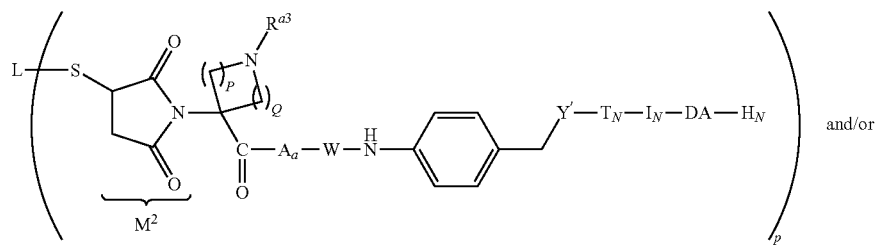

-continued

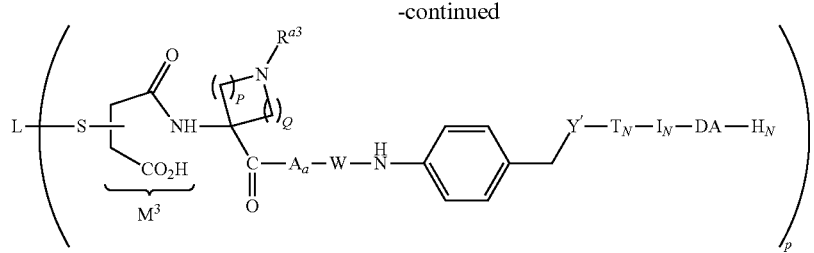

or a pharmaceutically acceptable salt thereof, more particularly by the structure(s) of:

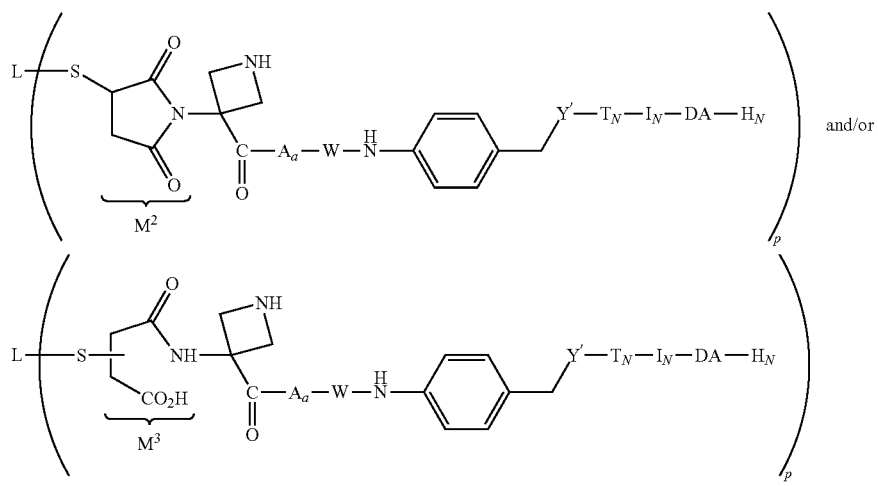

or a pharmaceutically acceptable salt thereof, or particularly by the structure(s) of:

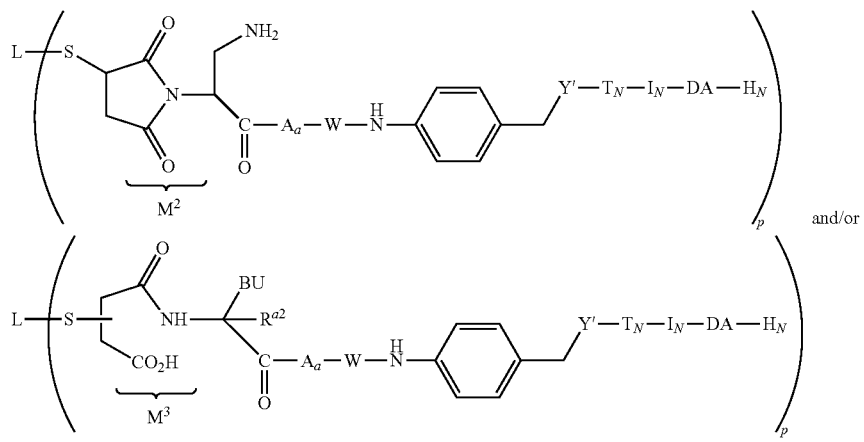

or a pharmaceutically acceptable salt thereof; and wherein Y' is —$X^a$—, —O—C(=O)—$X^b$— or —OC(=O)NH—CH$_2$—$X^a$—, wherein $X^a$ and $X^b$ are from $T_N$, wherein —$X^a$— is O and $X^b$ is —NH—; and R' is hydrogen or —OC$_1$-C$_6$ alkyl or other electron donating group, wherein protease action on the Peptide Cleavable Unit cleaves the W—NH bond, wherein said cleavage within a compound of the Ligand Drug Conjugate composition initiates release of the NAMPT Drug Unit as a NAMPTi compound or derivative thereof from that Ligand Drug Conjugate compound.

20A. The Ligand-Drug Conjugate composition of any one of embodiments 1A-19A in which W is a Peptide Cleavable Unit that Unit is comprised of a dipeptide wherein the dipeptide provides for a recognition site for a regulatory or lysosomal protease for cleavage by said protease of the W-J' bond or the W—NH bond when J' is —NH within a compound of the Ligand Drug Conjugate composition so as

261 to initiate release of the NAMPT Drug Unit as NAMPTi compound or derivative thereof from that Ligand Drug Conjugate compound.

21A. The Ligand-Drug Conjugate composition of embodiment 20A, wherein the W has the structure of:

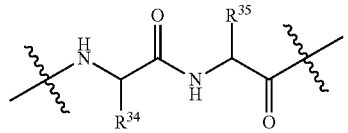

wherein $R^{34}$ is benzyl, methyl, isopropyl, isobutyl, sec-butyl, —CH(OH)CH$_3$ or has the structure of

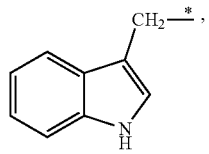

wherein the asterisk indicates the site of covalent attachment to the dipeptide backbone;

and $R^{35}$ is methyl, —(CH$_2$)$_4$—NH$_2$, —(CH$_2$)$_3$NH(C=O)NH$_2$, —(CH$_2$)$_3$NH(C=NH)NH$_2$, or, —(CH$_2$)$_2$CO$_2$H; and wherein the wavy lines indicate the points of covalent attachment of the dipeptide into the structure representing the Ligand-Drug Conjugate composition, in particular W is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

22A. The Ligand-Drug Conjugate composition of any one of claims 1A-21A, wherein A or a subunit thereof is -L$^P$(PEG)-, wherein -L$^P$- or a subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form, or -L$^P$- or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration, or wherein -L$^P$(PEG)- has the structure of:

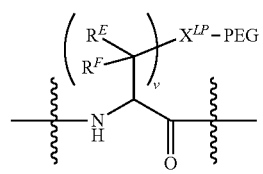

(Formula L$^P$-3)

262

-continued

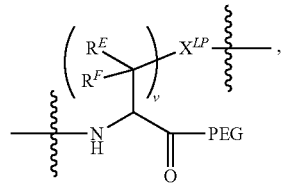

(Formula L$^P$-4)

or a pharmaceutical acceptable salt thereof, wherein subscript v is an integer ranging from 1 to 4; X$^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, —N(R$^{LP}$)C(=NR$^{LP}$)N(R$^{LP}$)—, and C$_3$-C$_8$ heterocyclo, in particular —O—, —NH—, —S— and —C(=O)—; wherein each R$^{LP}$ is independently selected from the group consisting of hydrogen and optionally substituted C$_1$-C$_6$ alkyl, or two of R$^{LP}$ together along with the carbons atoms to which they are attached and their intervening atoms define a C$_5$-C$_6$ heterocyclo and any remaining R$^{LP}$ are as previously defined; Ar is a C$_6$-C$_{10}$ arylene or a C$_5$-C$_{10}$ heteroarylene, optionally substituted;

each R$^E$ and R$^F$ is independently selected from the group consisting of —H, optionally substituted C$_1$-C$_6$ alkyl, optionally substituted C$_2$-C$_6$ alkylene, optionally substituted C$_6$-C$_{10}$ arylene and optionally substituted C$_5$-C$_{10}$ heteroarylene, in particular hydrogen and C$_1$-C$_4$ alkyl, or R$^E$ and R$^F$ together with the carbon atom to which both are attached defines an optionally substituted spiro C$_3$-C$_6$ carbocyclo, or R$^E$ and R$^F$ from adjacent carbon atoms together with these atoms and any intervening carbon atoms defines an optionally substituted C$_5$-C$_6$ carbocyclo with any remaining R$^E$ and R$^F$ as previously defined, or wherein the side chain of —[C(R$^E$)(R$^F$)]$_v$—X$^{LP}$— is provided by a natural or un-natural amino acid side chain; and wherein the wavy lines indicate the sites of covalent attachments within the remainder of the Conjugate structure, in particular having the PEG Unit represented by:

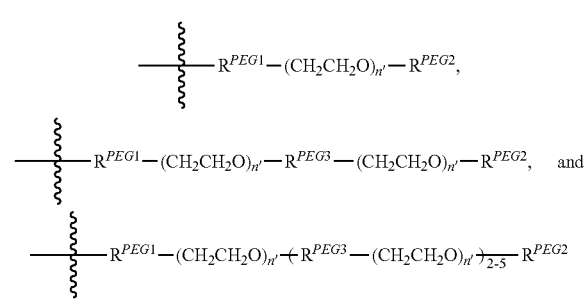

wherein the wavy line indicates site of attachment to X$^{LP}$ of the Parallel Connector Unit (L$^P$); subscript n' independently ranges from 1 to 72; R$^{PEG1}$ is an optional PEG Attachment Unit; R$^{PEG2}$ is a PEG Capping Unit; and R$^{PEG3}$ is an PEG Coupling Unit, or having X$^{LP}$-PEG with the structure of:

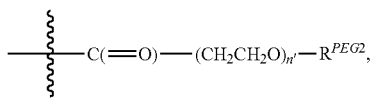

wherein subscript n' is 8, 12 or 24 and $R^{PEG2}$ is H or —$CH_3$.

23A. The Ligand-Drug Conjugate composition of any one of claims 1A-22A, wherein A or a subunit thereof has the structure of formula (3) or formula (4):

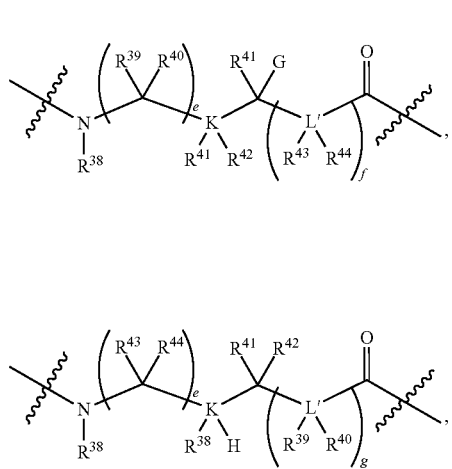

(3)

(4)

wherein the wavy lines indicated covalent attachment within the composition structure; wherein K and L' independently are C, N, O or S, provided that when K or L' is O or S, $R^{41}$ and $R^{42}$ to K or $R^{43}$ and $R^{44}$ to L' are absent, and when K or L' are N, one of $R^{41}$, $R^{42}$ to K or one of $R^{42}$, $R^{43}$ to L' are absent, and provided that no two adjacent L' are independently selected as N, O, or S; wherein subscripts e and f are independently selected integers that range from 0 to 12, and subscript g is an integer ranging from 1 to 12;

wherein G is hydrogen, optionally substituted $C_1$-$C_6$ alkyl, —OH, —$OR^{PR}$, —$CO_2H$, $CO_2R^{PR}$, wherein $R^{PR}$ is a suitable protecting, or G is —$N(R^{PR})(R^{PR})$, wherein $R^{PR}$ are independently a protecting group or $R^{PR}$ together form a suitable protecting group, or G is —$N(R^{45})(R^{46})$ wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

$R^{38}$ is hydrogen or optionally substituted $C_1$-$C_6$ alkyl; $R^{39}$-$R^{44}$ are independently selected from the group consisting of hydrogen, optionally substituted $C_1$-$C_6$ alkyl, optionally substituted aryl, and optionally substituted heteroaryl, or $R^{30}$, $R^{40}$ together with the carbon atom to which both are attached, or $R^{41}$, $R^{42}$ together with K to which both are attached when K is a carbon atom, define a $C_3$-$C_6$ carbocyclo, and $R^{41}$-$R^{44}$ are as defined herein, or $R^{43}$, $R^{44}$ together with L' to which both are attached when L' is a carbon atom define a $C_3$-$C_6$ carbocyclo, and $R^{30}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^{44}$ are absent, and when L' is N, one of $R^{43}$, $R^{44}$ is absent, or A or a subunit thereof is an alpha-amino, beta-amino or another amine-containing acid residue, in particular, wherein formula (3) or formula (4) has the structure of formula (3a) or formula (4a):

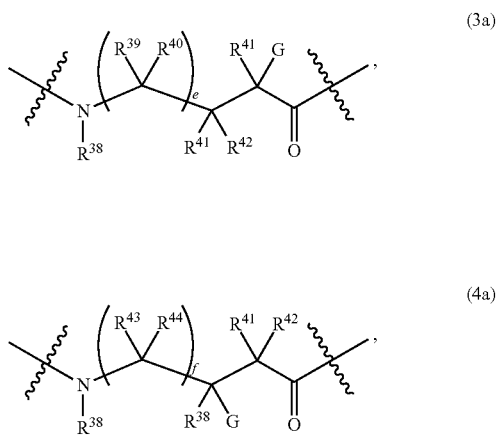

(3a)

(4a)

wherein subscript e and f are independently 0 or 1. 24A. The Ligand-Drug Conjugate composition of any one of embodiments 1A-23A wherein the Ligand Unit is an antibody or an antigen-binding fragment thereof, thereby defining an antibody Ligand Unit of an antibody drug conjugate (ADC), wherein the antigen targeted by the antibody Ligand Unit is an accessible cell-surface antigen of abnormal cells that is capable of cellular internalization when bound to an ADC compound of the composition and is present in greater copy number on the abnormal cells in comparison to normal cells distant from the site of the abnormal cells, or an accessible cell-surface antigen of a vascular epithelial cell in the vicinity of abnormal cells, wherein said antigen is capable of cellular internalization of bound ADC and is present in greater copy number on said cells in comparison to normal epithelial cells distant from the site of the abnormal cells.

25A. The Ligand Drug Conjugate composition embodiment 24A, wherein subscript p is about 2, about 4, or about 8.

26A. The Ligand Drug Conjugate composition of any one of embodiments 15A-19A, wherein the sulfur atom attached to the succinimide ($M^2$) or succinic acid amide ($M^3$) moiety of a drug linker moiety of the Conjugate structure is that of an antibody or antigen-binding fragment thereof, thereby defining an antibody Ligand Unit, wherein the sulfur atom of the antibody Ligand Unit bonded to the succinic acid ($M^2$) moiety or succinic acid amide ($M^3$) moiety is that of a cysteine residue native to the antibody or antigen-binding fragment thereof or an introduced cysteine residue in the heavy chain or light chain of the antibody or antigen binding-fragment thereof.

27A. The Ligand Drug Conjugate composition of embodiment 1A, wherein the composition is represented by the structure(s) of:

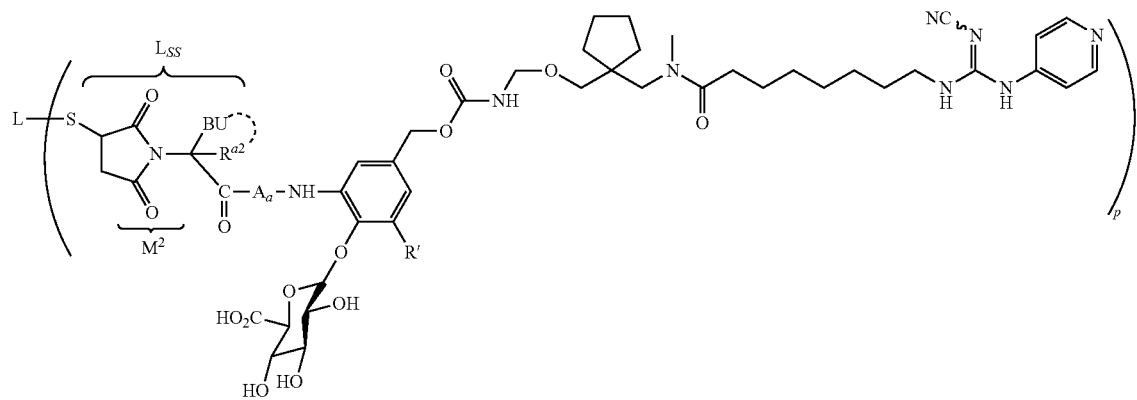
and/or
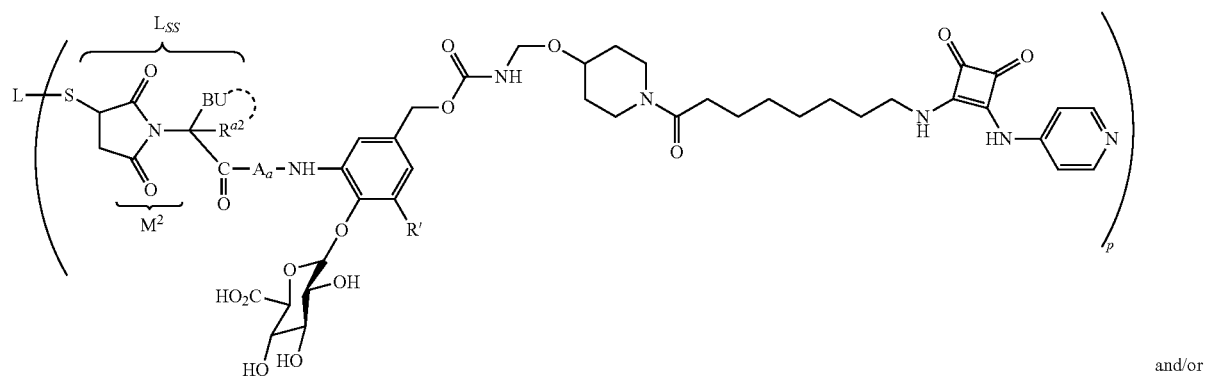
or pharmaceutical acceptable salt(s) thereof, or
the composition is represented by the structure(s) of:
and/or

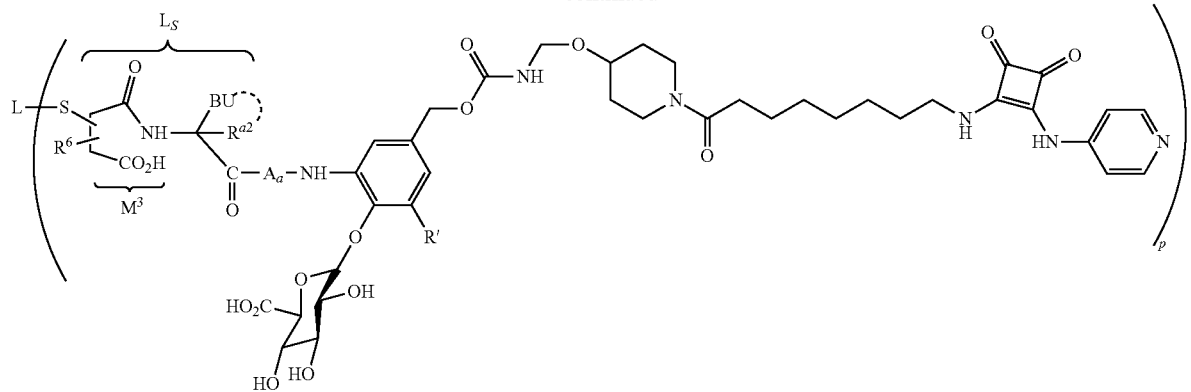
or pharmaceutical acceptable salt(s) thereof, or the composition is represented by the structure(s) of:
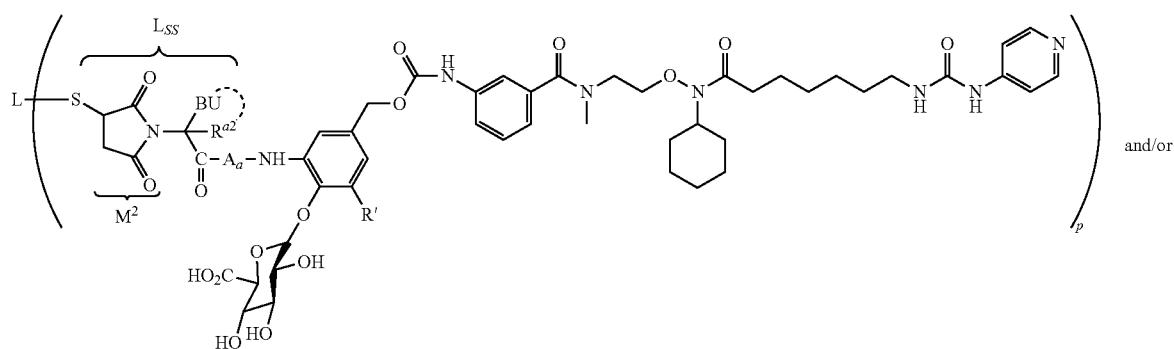
and/or
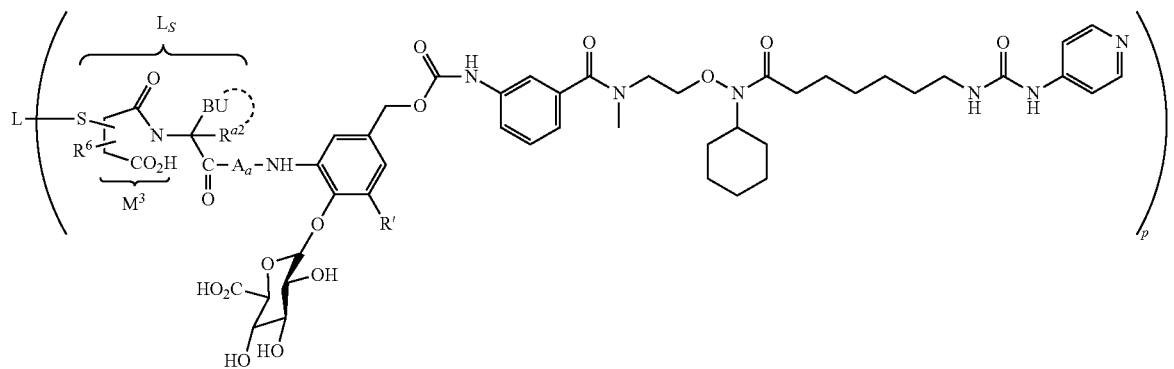

or pharmaceutical acceptable salt(s) thereof, in particular by:

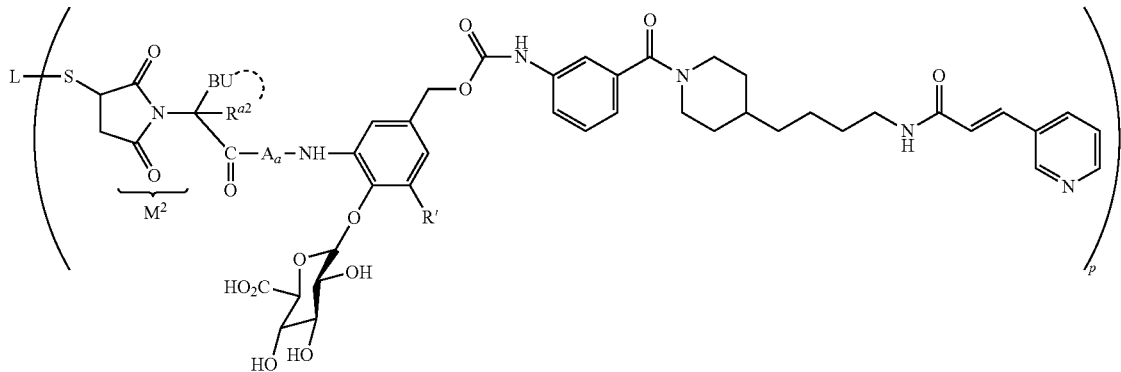

and/or

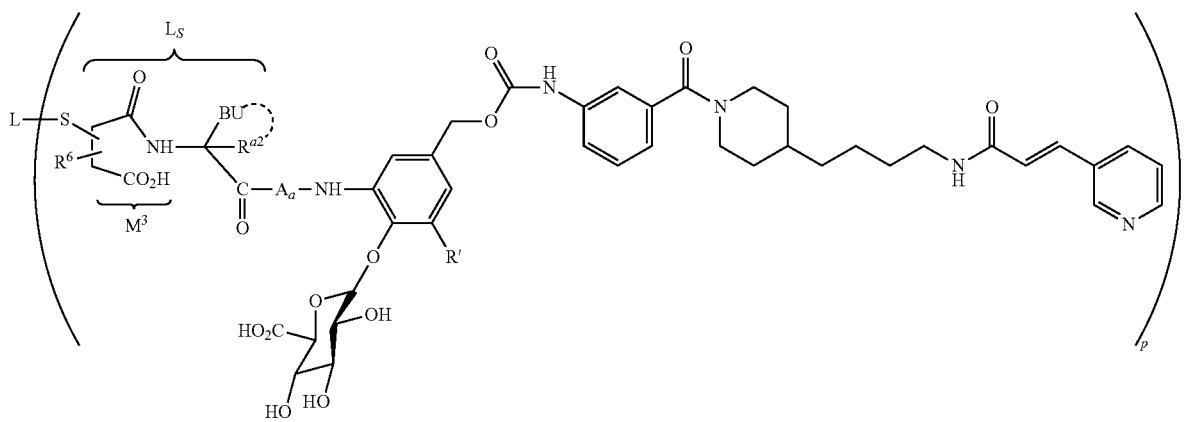

or pharmaceutical acceptable salt(s) thereof,
wherein subscript a is 1 and A is an amino acid residue; BU is a acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$,
more particularly by:

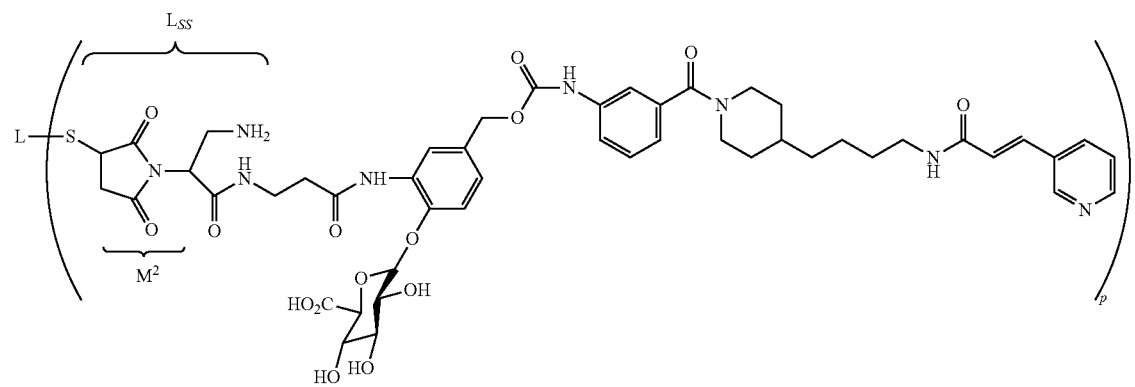

and/or

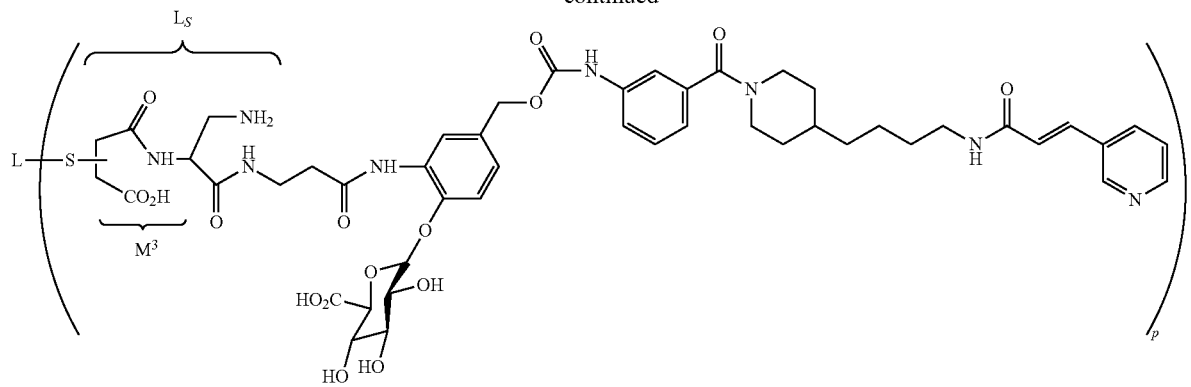

or pharmaceutical acceptable salt(s) thereof, or by:

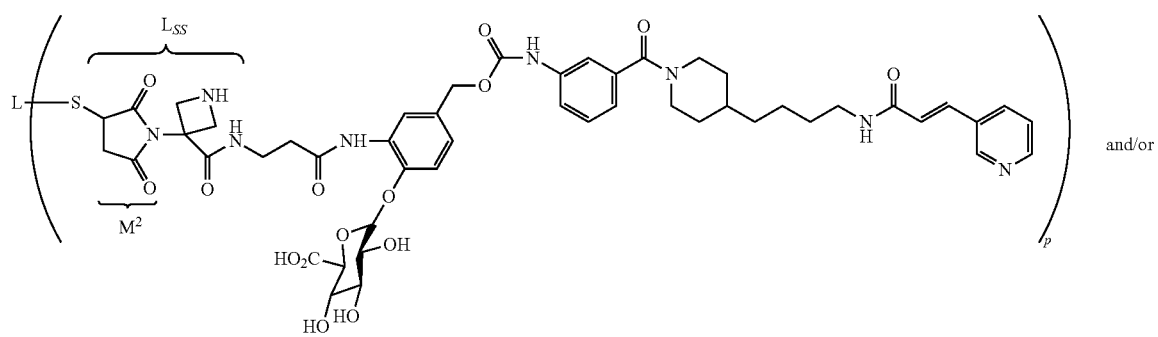

and/or

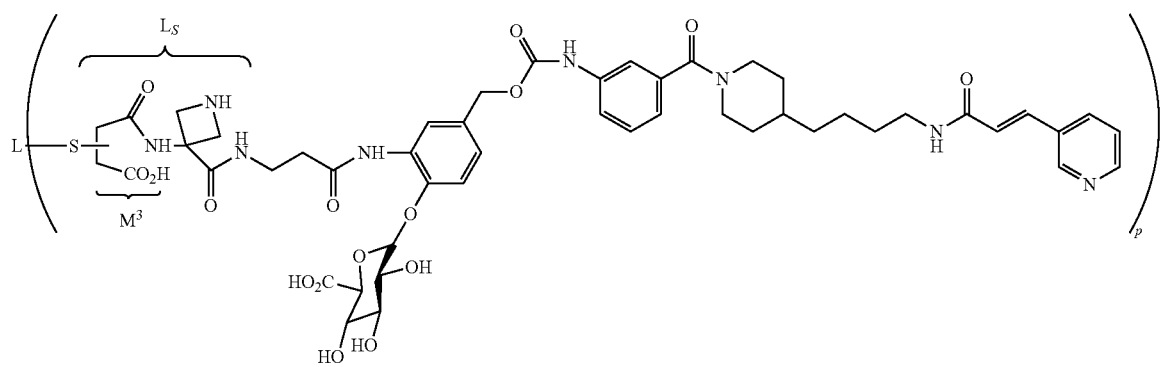

or pharmaceutical acceptable salt(s) thereof, wherein L is an antibody, thereby defining an antibody Ligand Unit of an antibody drug conjugate (ADC), and S is a sulfur atom of the antibody, wherein the antibody is a monoclonal antibody or a chimeric antibody.

28A. A formulation comprising a Ligand Drug Conjugate composition of any one of embodiments 1A-27A and at least one, two, three or more excipients, in particular, wherein the formulation is a pharmaceutically acceptable formulation or a precursor thereof particularly wherein the pharmaceutically acceptable formulation precursor is a solid suitable for reconstitution as a solution for intravenous injection to a subject in need thereof, or the pharmaceutically acceptable formulation is a liquid suitable for intravenous injection to a subject in need thereof, more particularly in which the Ligand Drug Conjugate composition is present in an effective amount for treatment of a hyperproliferative disease or condition.

29A. A method of treating a hyperproliferative disease or condition comprising the step of administering to a subject in need thereof having said disease or condition, in particular having a cancer, more particularly a leukemia or lymphoma, an effective amount of a Ligand Drug Conjugate composition of any one of claims 1-13, 15-19 and 27.

30A. A method of inhibiting the multiplication of a tumor cell or cancer cell, or causing apoptosis in a tumor cancer cell by exposing said cell to an effective amount of a Ligand Drug Conjugate composition or a compound thereof of any one of embodiments 1A-27A.

31A. A Drug Linker compound, wherein the Drug Linker compound is represented by the structure of:

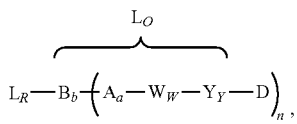

or a salt thereof, wherein $L_R$ is a primary linker having a functional group capable interacting with a targeting agent to form a covalent bond to a Ligand Unit corresponding to or incorporating the targeting agent in a Ligand Drug Conjugate composition;

D is a NAMPT Drug Unit represented by the general structure of:

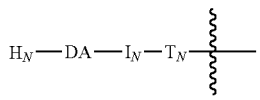

or a salt thereof, wherein the wavy line indicates the site of covalent attachment to $L_O$, as indicated, which is an optional secondary linker, or $L_R$, depending on the presence or absence of $L_O$, respectively;

$H_N$ is a NAMPT Head Unit, wherein the NAMPT Head Unit is a $C_5$-$C_{24}$ heteroaryl or partially aromatic $C_9$-$C_{24}$ heterocyclyl, optionally substituted, wherein the $C_5$-$C_{24}$ heteroaryl or partially aromatic $C_9$-$C_{24}$ heterocyclyl is comprised of an optionally substituted 5- or 6-membered nitrogen-containing heteroaromatic ring system corresponding to the heterocycle of nicotinamide, and is capable of interacting with enzymatically competent NAMPT homodimer at its nicotinamide mononucleotide binding site when the NAMPT Drug Unit is released from a Ligand Drug Conjugate compound of the composition as a NAMPT inhibitor (NAMPTi) compound or derivative thereof;

DA is a Donor-Acceptor Unit wherein the Donor-Acceptor Unit is or is comprised of a hydrogen bond donor acceptor functional group and is bonded to a carbon skeletal atom at position 2 or 3 of the 5-membered nitrogen-containing heteroaromatic ring system or at position 3 or 4 of the 6-membered nitrogen-containing heteroaromatic ring system, with optional formal cyclization of DA back to an adjacent skeletal carbon atom of the 6-membered nitrogen-containing heteroaromatic ring system through an introduced optionally substituted non-aromatic carbon atom or an optionally substituted nitrogen, oxygen or sulfur atom resulting in a partially aromatic or fully aromatic fused 6,5- or 6,6-ring system, wherein said bonding of DA is in relation to a skeletal nitrogen atom of the 5- or 6 membered nitrogen-containing heteroaromatic ring system and wherein said formal cyclization to the adjacent carbon atom of the 6-membered nitrogen-containing heteroaromatic ring system substantially retains the hydrogen bonding capability of the donor acceptor functional group of DA in absence of said cyclization;

$I_N$ is an Interconnecting Unit, wherein the Interconnecting Unit is or is comprised of —$X^1$—[C(=O)]$_{0,1}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$, —$X^2$—$C_6$-$C_{24}$ arylene-O—, —$X^2$—$C_5$-$C_{24}$ heteroarylene-[C(=O)]$_{0,1}$—, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]—, wherein the arylene, heteroarylene and heterocyclo are optionally substituted; $X^1$ is optionally substituted $C_5$-$C_7$ alkylene; $X^2$ is absent or is an optionally substituted $C_1$-$C_4$ alkylene;

$T_N$ is a NAMPT Tail Unit, wherein the NAMPT Tail Unit is or is comprised of an optionally substituted amino-alcohol residue or a carboxylic acid-alcohol residue, the —O— or optionally substituted nitrogen of which is the site of covalent attachment to $L_O$, or $L_R$, depending on the presence or absence of $L_O$, or $T_N$ is or is comprised of an optionally substituted benzamide moiety, the amide nitrogen atom of which is bonded to $I_N$ with optional cyclization of that atom back to $I_N$ or to the remainder of $T_N$, and the aromatic ring of which is at least substituted with a hydroxyl, thiol or amino residue, the —O—, —S— or optionally substituted nitrogen of which at position 3 or 4 relative to the site at which the amide carbonyl carbon atom is attached is the site of covalent attachment to $L_O$ or $L_R$, depending on the presence or absence of $L_O$, or $T_N$ is or is comprised of an optionally substituted aryl or biaryl moiety, an aromatic skeletal atom of which is bonded to $I_N$, or to the remainder of $T_N$, and wherein an aromatic ring of which is at least substituted with a hydroxyl, thiol or an amino residue, the —O—, —S— or optionally substituted nitrogen of which is the site of covalent attachment to $L_O$ or $L_R$, depending on the presence or absence of $L_O$; and wherein $T_N$ or the remainder thereof is bonded to $I_N$, wherein said remainder is an optionally substituted $C_2$-heteroalkylene or an optionally substituted $C_5$-$C_6$ heterocyclo, subscripts a and b independently are 0 or 1, indicating the absence or presence, respectively, of A or B; subscript n is 1, 2, 3 or 4; A is an first optional Stretcher; and B is a Branching Unit, when subscript b is 1 and subscript n is 2, 3 or 4, or B is absent, so that subscript b is 0, when subscript n is 1, wherein each of A and B is an independently selected single unit or is optionally comprised or consists of at least two, three or four independently selected subunits;

subscript y is 0, 1 or 2, indicating the absence or presence of one or two of Y, respectively; Y is a Spacer Unit, provided that when subscript y is 1, Y is a Spacer Unit covalently attached to an optionally substituted heteroatom of $T_N$ selected from the group consisting of —O—, —S— and optionally substituted nitrogen; and provided that when subscript y is 2 so that $Y_y$ is —Y—Y'—, then Y is a first Spacer Unit and Y' is a functional group comprised of the optionally substituted heteroatom of $T_N$, or Y' is a second Spacer Unit; and subscript w is 0 or 1, indicating the absence or presence, respectively, of W; wherein when subscript w is 1, W is a Peptide Cleavable Unit or a Glucuronide Unit of formula —Y(W')—, wherein W' represents a carbohydrate moiety with glycosidic bonding to Y through a optionally substituted heteroatom, provided Y bonded to W' is required to be a first self-immolative Spacer Unit; subscript y is 0, 1 or 2, provided subscript y is 1 or 2 when W is a Glucuronide Unit, in which instance subscript y is inclusive of the required self-immolative Spacer Unit; and wherein when subscript w is 1, which indicates the presence of a Cleavable Unit, enzymatic or non-enzymatic cleavage of that Unit in the Drug Linker Compound, or in a drug linker moiety of a Ligand Drug Conjugate compound or a N-acetyl-cysteine (NAC) conjugate prepared from the Drug Linker compound initiates release of the NAMPT Drug Unit as a NAMPTi compound or derivative therefrom, and when subscript w is 0, which indicates the absence of a Cleavable Unit, wherein enzymatic or non-enzymatic cleavage of the bond between the indicated $L_R$ and $L_O$ moieties, when $L_O$ is present, or the bond between $L_R$ and D, when $L_O$ is absent, initiates release of the NAMPT Drug Unit as a NAMPTi compound or derivative thereof from the Drug Linker compound or said drug linker moiety or NAC conjugate.

32A. The Drug Linker compound of embodiment 31A, wherein the NAMPT Head ($H_N$) Unit is a pyridine mimetic.

33A. The Drug Linker compound of embodiment 31A or 32A, wherein the Donor Acceptor (DA) Unit is comprised of an optionally substituted amide functional group or bioisostere thereof.

34A. The Drug Linker compound of embodiment 31A, wherein $H_N$-DA is a nicotinamide mimetic.

35A. The Drug Linker compound of embodiment 31A, wherein the 6-membered nitrogen-containing heteroaromatic ring system of $H_N$ is that of pyridine with optional cyclization of DA back to the pyridine aromatic ring system through an introduced aromatic oxygen, sulfur or an optionally substituted nitrogen atom so that $H_N$ contains a 6-5 fused aromatic ring system.

36A. The Drug Linker compound of embodiment 31A, wherein each of the NAMPT homodimers of the enzymatically competent NAMPT homodimer has the amino acid sequence of NCBI Reference Sequence NP-005737.1.

37A. The Drug Linker compound of any one of embodiments 31A-36A, wherein the NAMPT Head Unit has the structure of:

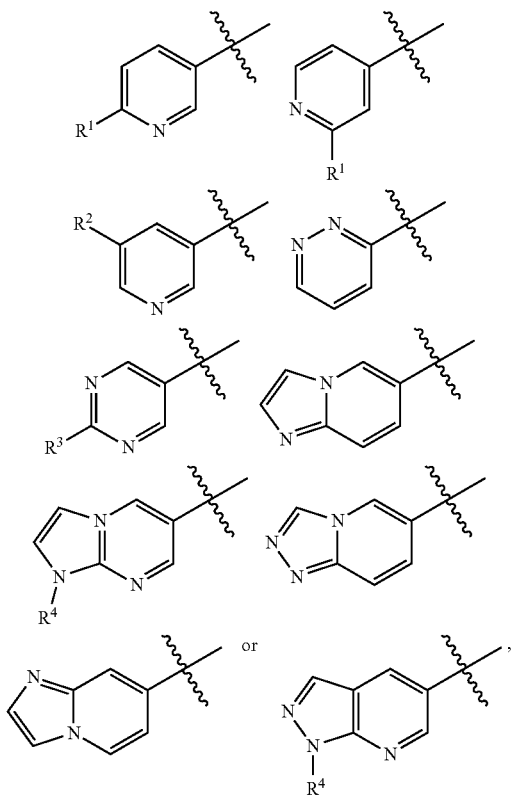

or a salt thereof, in particular, having the structure of:

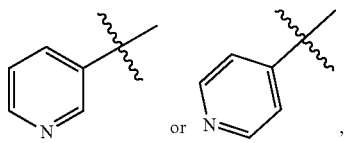 [SMILES: *c1cccnc1 ; *c1ccncc1]

or a salt thereof, wherein R' is hydrogen, —$NH_2$ or chloro; $R^2$ is fluoro; $R^3$ is hydrogen or —$NH_2$; and the wavy line indicates the site of covalent attachment to DA and an adjacent aromatic carbon atom thereto is the site of said optional cyclization by DA to $H_N$.

38A. The Drug Linker compound of any one of embodiments 31A-37A, wherein the Donor-Acceptor Unit has the structure of:

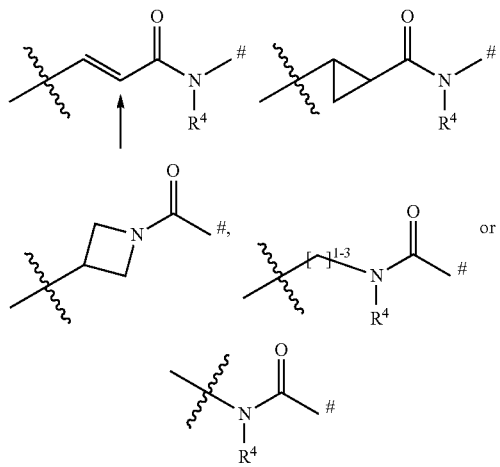

in particular, having the structure of:

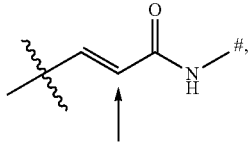

wherein $R^4$ is hydrogen or optionally substituted $C_1$-$C_4$ alkyl; DA is optionally cyclized to $H_N$, wherein said cyclization is to the $sp^2$ carbon atom proximal to the carbonyl carbon (as indicated) through an introduced optionally substituted non-aromatic carbon atom or an optionally substituted aromatic heteroatom; the wavy line indicates the site of covalent attachment to $H_N$, and the carbon atom adjacent thereto is the site of said optional cyclization by DA; and the pound sign (#) indicates the site of covalent attachment to $I_N$, or wherein the Donor-Acceptor Unit has the structure of:

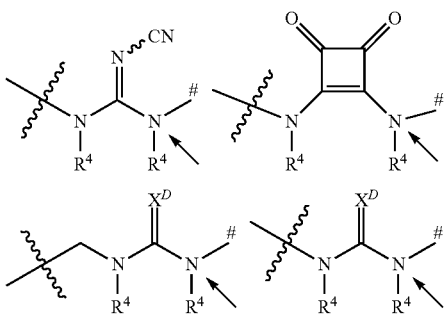

or a salt thereof, in particular, having the structure of:

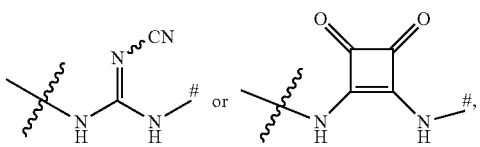

or a salt thereof, wherein $X^D$ is O, S or $NR^D$, wherein the nitrogen atom is optionally protonated and $R^D$ is hydrogen or optionally substituted $C_1$-$C_4$ alkyl; each $R^4$ is independently selected from the group consisting of hydrogen and optionally substituted $C_1$-$C_4$ alkyl, or both $R^4$ together with the nitrogen atoms to which they are attached and the intervening carbon atom(s) define an optionally substituted $C_5$-$C_6$ heterocyclo; the pound sign (#) indicates the site of covalent attachment to $I_N$; and the wavy line indicates the site of covalent attachment to $H_N$, wherein DA is optionally cyclized back to an adjacent site of $H_N$, wherein said cyclization is from the indicated nitrogen atom so that $R^4$ bonded thereto is replaced by a covalent bond or from $X^D$ when $X^D$ is —$NR^D$, either directly or through an introduced —S(=O)$_{0-2}$ moiety, in which either instance $R^D$ is replaced by a bond.

39. The Drug Linker compound of any one of embodiments 31A-36A, wherein $H_N$-DA- has the structure of:

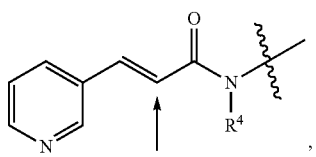

or a salt thereof, wherein $R^4$ is hydrogen or optionally substituted $C_1$-$C_4$ alkyl; and the wavy line indicates the site of covalent attachment to $I_N$, and wherein the sp$^2$ carbon atom proximal to the carbonyl carbon is the site (as indicated) of optional cyclization to $H_N$ through an introduced optionally substituted non-aromatic carbon atom or an optionally substituted aromatic heteroatom.

40. The Drug Linker compound of any one of embodiments 31A to 39A, wherein the NAMPT Tail Unit is or is comprised of an optionally substituted amino alcohol moiety, wherein the oxygen atom of the alcohol is the site of covalent attachment to $L_O$ or $L_R$, depending on the presence or absence of $L_O$, respectively, in particular having the structure of:

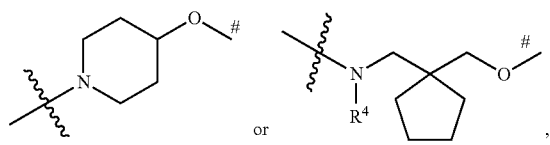

or a pharmaceutically acceptable salt thereof, wherein $R^4$ is hydrogen or optionally substituted $C_1$-$C_4$ alkyl; the wavy line indicates the site of covalent attachment to $I_N$; and the pound sign (#) indicates the site of covalent to $L_O$ or $L_R$, depending on the presence or absence of $L_O$, respectively, or wherein the Tail Unit is or is comprised of an optionally substituted benzamide moeity having a functional group providing a heteroatom that is the site of covalent attachment to $L_O$ or $L_R$, depending on the presence or absence of $L_O$, respectively, in particular, having the structure of:

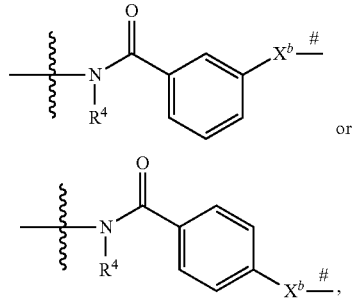

wherein $X^b$ is —S— —O— or —NH—, optionally substituted; and $R^4$ is hydrogen or optionally substituted $C_1$-$C_4$ alkyl, wherein the benzamide moiety is optionally cyclized to $I_N$ wherein the amide nitrogen of the benzamide moiety is the site of said cyclization so that $R^4$ is replaced by a covalent bond, more particularly, having the structure of:

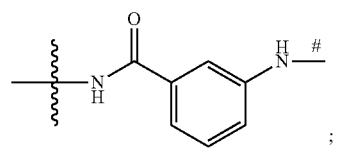 [SMILES: *NC(=O)c1cccc(NC)c1]

wherein the wavy line indicates the site of covalent attachment to $I_N$; the pound sign (#) indicates the site of covalent attachment to $L_O$ or $L_R$, depending on the presence or absence of $L_O$, respectively.

41. The Drug Linker compound of any one of embodiments 31A-40A, wherein $I_N$ is —CH$_2$—(CH$_2$)$_{3-7}$—CH$_2$—, —CH$_2$—(CH$_2$)$_{3-7}$—CH$_2$—O—, —CH$_2$—(CH$_2$)$_{3-7}$—C(=O)—, —CH$_2$—(CH$_2$)$_{3-7}$—S(=O)$_2$— or —CH$_2$—(CH$_2$)$_{3-7}$—S(=O)—.

42. The Drug Linker compound of any one of embodiments 31A-39A, wherein —$I_N$-$T_N$- has the structure of:

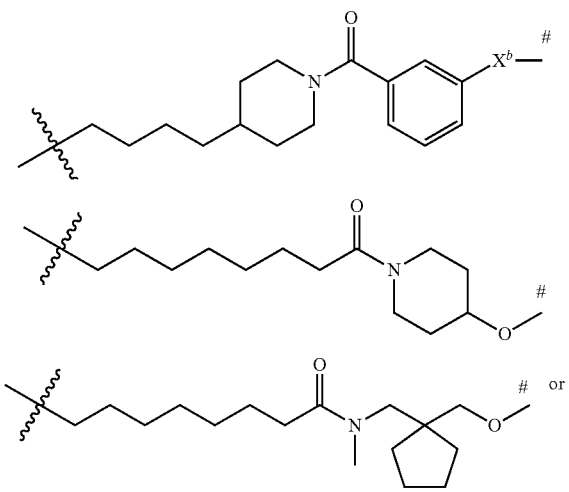

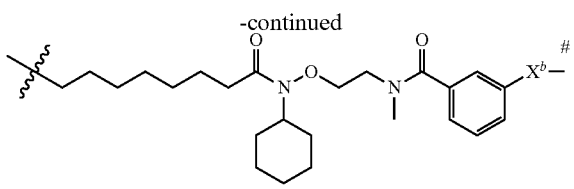

wherein $X^b$ is —NH—, —O— or —S—; the wavy line indicates the site of covalent attachment to DA; and the pound sign (#) indicates the site of covalent attachment to $L_O$ or $L_R$, depending on the presence or absence of $L_O$, respectively.

43A. The Drug Linker compound of embodiment 31A, wherein the NAMPT Drug Unit has the structure of:

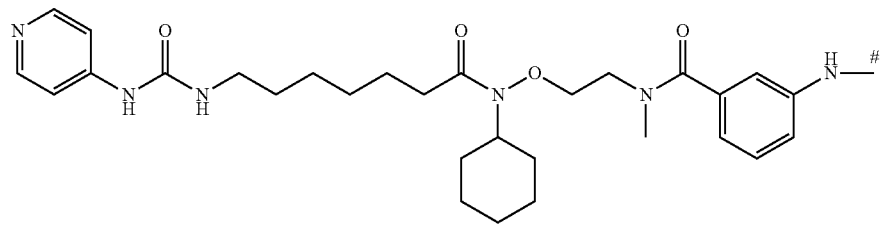

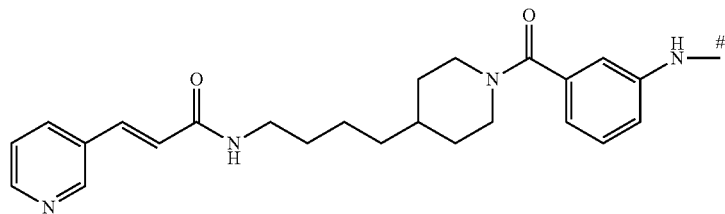

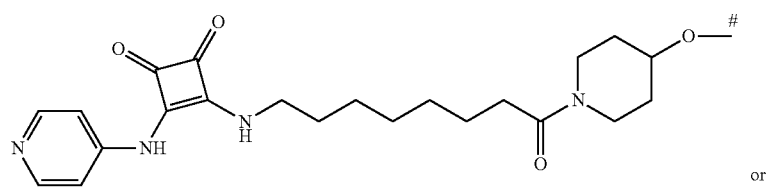

or

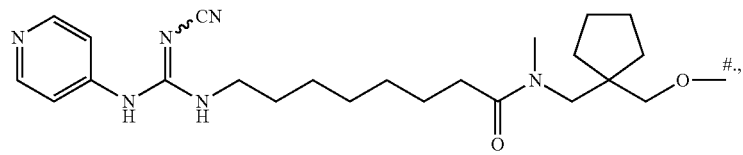

or a salt thereof, wherein the pound sign (#) indicates the site of covalent attachment to $L_O$ or $L_R$, depending on the presence or absence of $L_O$, respectively.

44A. The Drug Linker compound of embodiment 31A, wherein the Drug Linker compound is represented by the structure of:

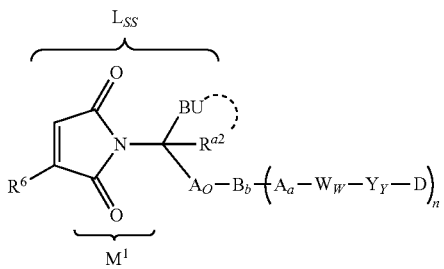

or a salt thereof, wherein $R^6$ is hydrogen or an optionally substituted $C_1$-$C_6$ alkyl, which in Formula 2 is bonded to the saturated carbon atom adjacent to the carbon substituted by L-S—; $A_O$ is a second optional Stretcher Unit; BU is a Basic Unit and $R^{a2}$ is an optionally substituted $C_1$-$C_{12}$ alkyl group; and the dotted curved line indicates optional cyclization so that in the absence of said cyclization BU is an acyclic Basic Unit or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group of BU, wherein the basic nitrogen atom of the acyclic Basic Unit or cyclic Basic Unit is optionally suitably protected by a nitrogen protecting group, dependent on the degree of substitution of the basic nitrogen atom, or is optionally protonated, in particular, having the structure of:

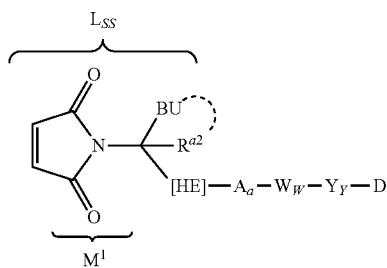

wherein [HE] as $A_O$ is an optional Hydrolysis Enhancing Unit; subscript w is 1; W is Peptide Cleavable Unit, wherein protease action on the Peptide Cleavable Unit resulting in cleavage of the W-J' bond within the Drug Linker compound, or from the drug linker moiety of the Ligand Drug Conjugate compound or N-acetyl-cysteine (NAC) conjugate prepared from the Drug Linker compound initiates release of the NAMPT Drug Unit as NAMPTi compound or derivative thereof from that Ligand Drug Conjugate compound, or W is a Glucuronide Unit of formula —Y(W')— having the structure of:

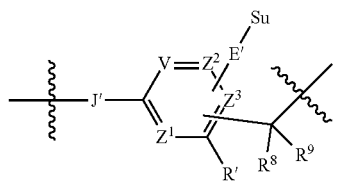

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W'; J' is an independently selected heteroatom, optionally substituted;

V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)— moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$-$C_6$ alkyl, or other electron donating group; and wherein the wavy line adjacent to J' indicates the site of covalent attachment of the Glucuronide Unit to A when subscript a is 1 or to the indicated $L_{SS}$ primary linker when subscript a is 0; and the wavy line adjacent to the —C($R^8$)($R^9$)— moiety indicates the site of covalent attachment of the Glucuronide Unit to Y' when subscript y is 2, or to D when subscript y is 1, and the remaining variable groups retain their previous meanings;

and wherein glycosidase action on the Glucuronide Unit resulting in cleavage of its glycosidic bond initiates release of the NAMPT Drug Unit as NAMPTi compound or derivative thereof from the Drug Linker compound or from the drug linker moiety of the Ligand Drug Conjugate compound or N-acetyl-cysteine (NAC) conjugate prepared from the Drug Linker compound.

45A. The Drug Linker compound of embodiment 44A, wherein W is a Glucuronide Unit for which —W—$Y_y$-D has the structure of:

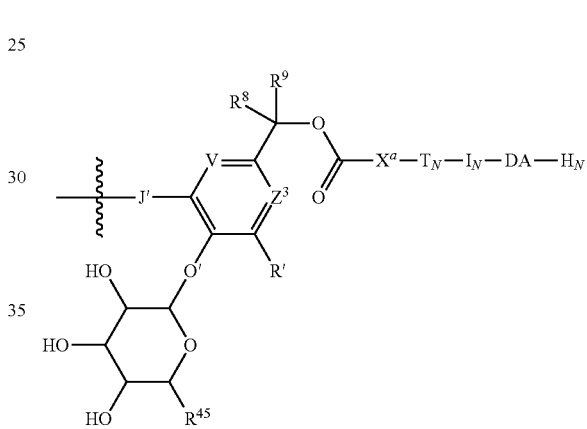

or

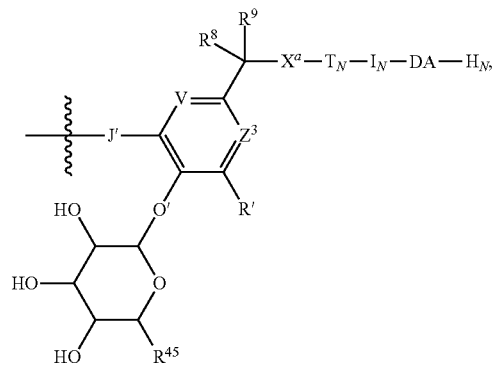

or a salt thereof, wherein $X^a$ is a nitrogen atom from a primary or secondary amine functional group of $T_N$; $X^b$ is an oxygen atom from an alcohol functional group or a sulfur atom from a thiol functional group of $T_N$, or —W—$Y_y$-D has the structure of:

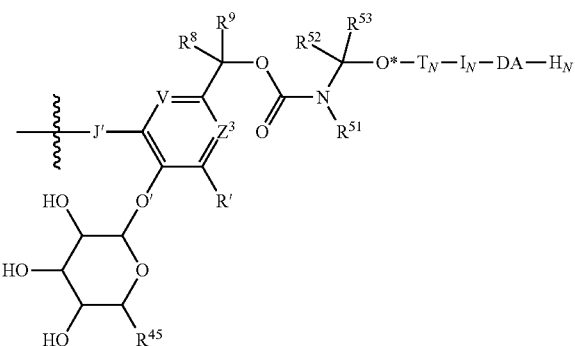

or a salt thereof, $R^{51}$, $R^{52}$ and $R^{53}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^{51}$ and $R^{52}$ together with the nitrogen and carbon atoms to which both are attached define an azetidine, pyrrolidine, piperidine or homopiperidine heterocyclo, and $R^{53}$ is hydrogen; and R' is hydrogen or —$NO_2$ or other electron withdrawing group; and O* represents the oxygen atom from an alcohol functional group of $T_N$ and O' represents the oxygen atom of an O-glycosidic bond cleavable by a glycosidase, wherein said cleavage initiates release of the NAMPT Drug Unit as a NAMPTi compound or derivative from the Drug Linker compound or from the drug linker moiety of the Ligand Drug Conjugate compound or N-acetyl-cysteine (NAC) conjugate prepared from the Drug Linker compound, or wherein W is a Peptide Cleavable Unit for which —$Y_y$-D- has the structure of:

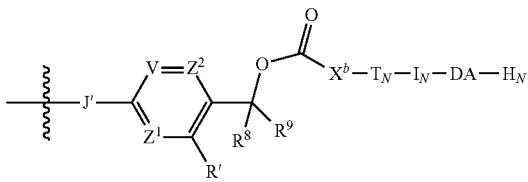

or

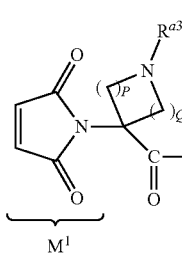

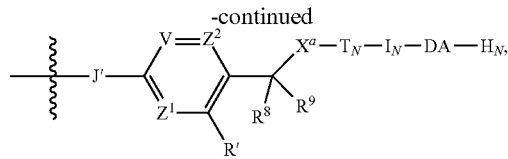

or a salt thereof, wherein $X^a$ is an oxygen atom from an alcohol functional group or a sulfur atom of a thiol functional group of $T_N$; $X^b$ is a nitrogen atom from a primary or secondary amine functional group of $T_N$, or has the structure of:

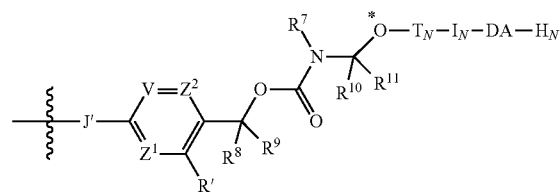

or a salt thereof, wherein R' is hydrogen or —$OC_1$-$C_6$ alkyl or other electron donating group; $R^7$, $R^{10}$ and $R^{11}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^7$ and $R^{10}$ together with the nitrogen and carbon atoms to which both are attached define an azetidine, pyrrolidine, piperidine or homopiperidine heterocyclo, and $R^{11}$ is hydrogen; and $R^{45}$ is —$CH_2OH$ or —$CO_2H$;

O* represents the oxygen atom from an alcohol functional group of $T_N$; and J' is an optionally substituted heteroatom bonded to W as indicated by the wavy line, wherein cleavage of that bond initiates release of the NAMPT Drug Unit as a NAMPTi compound or derivative from the Drug Linker compound or from the drug linker moiety of the Ligand Drug Conjugate compound or N-acetyl-cysteine (NAC) conjugate prepared from the Drug Linker compound.

46A. The Drug Linker compound of embodiment 44A, wherein W is a Glucuronide Unit for which the Drug linker compound is represented by the structure of:

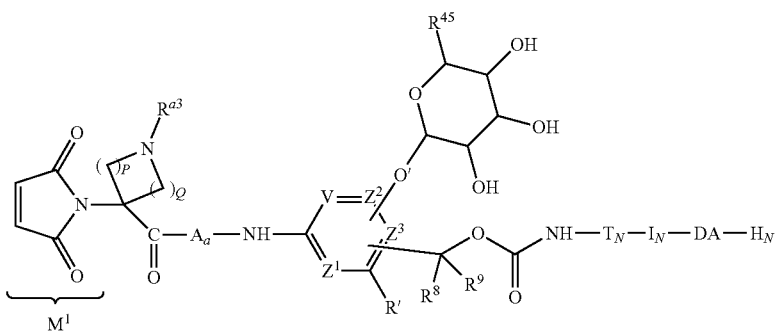

or a salt thereof, wherein subscript P is 1, 2 or 3; and subscript Q ranges from 1 to 6, or by the structure of:

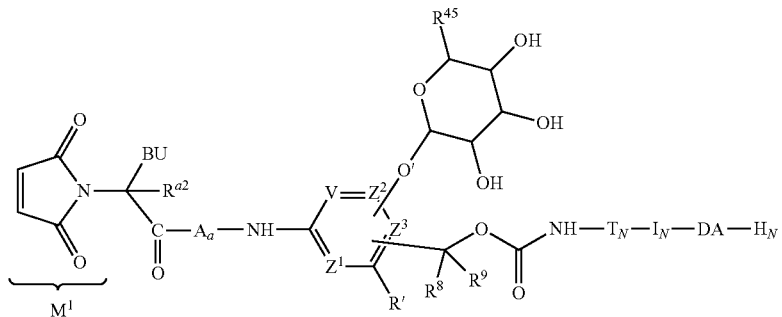

or a salt thereof, wherein $R^{a2}$ is hydrogen or $C_1$-$C_6$ alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$—$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; and wherein R' is hydrogen or —$NO_2$ or other electron withdrawing group; $R^{45}$ is —$CH_2OH$ or —$CO_2H$; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl, wherein the basic nitrogen atom bonded to $R^{a3}$ is optionally protonated, and wherein —O'— represents the oxygen heteroatom of an O-glycosidic bond cleavable by a glycosidase, wherein said cleavage within initiates release of the NAMPT Drug Unit as a NAMPTi compound or derivative from the Drug Linker compound or from the drug linker moiety of the Ligand Drug Conjugate compound or N-acetyl-cysteine (NAC) conjugate prepared from the Drug Linker compound, or wherein the W is a Peptide Cleavable Unit for which the composition is represented by the structure of:

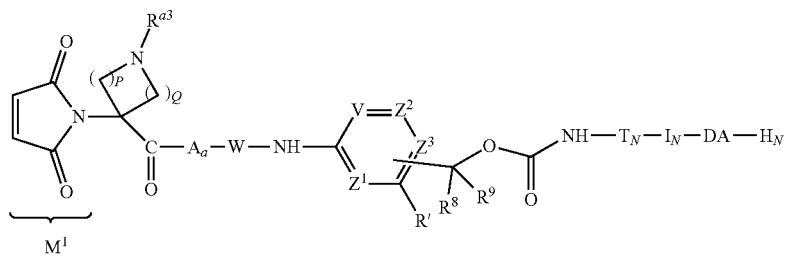

or a salt thereof, wherein subscript P is 1, 2 or 3; and subscript Q ranges from 1 to 6, or is represented by the structure of:

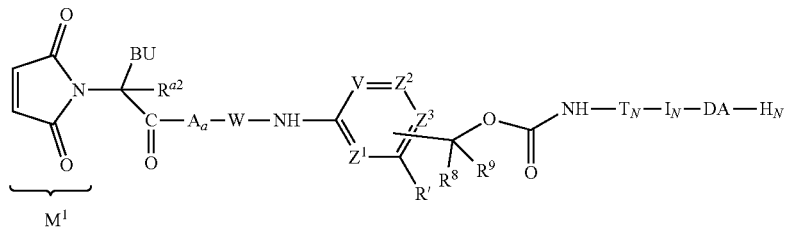

or a salt thereof, wherein $R^{a2}$ is hydrogen or $C_1$-$C_6$ alkyl; BU has the structure of —[C($R^{a1}$)($R^{a1}$)]—[C($R^{a1}$)($R^{a1}$)]$_{0-3}$N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; and wherein $R^{a3}$ is —H, or optionally substituted $C_1$-$C_6$ alkyl, optionally substituted $C_1$-$C_4$ alkylene-($C_6$-$C_{10}$ aryl), or —$R^{PEG1}$—O—(CH$_2$CH$_2$O)$_{1-36}$—$R^{PEG2}$, wherein $R^{PEG1}$ is $C_1$-$C_4$ alkylene, and $R^{PEG2}$ is —H or $C_1$-$C_4$ alkyl; and the basic nitrogen atom bonded to $R^{a3}$ is optionally protonated or optionally protected by a suitable nitrogen protecting group when one or both of $R^{a3}$ is hydrogen; and R' is hydrogen or —O$C_1$-$C_6$ alkyl or other electron donating group; and wherein protease action on the Peptide Cleavable Unit cleaves the W—NH bond, wherein said cleavage initiates release of the NAMPT Drug Unit as a NAMPTi compound or derivative from the Drug Linker compound or from the drug linker moiety of the Ligand Drug Conjugate compound or N-acetyl-cysteine (NAC) conjugate prepared from the Drug Linker compound.

47A. The Drug Linker compound of embodiment 44A, wherein W is a Glucuronide Unit for which the Drug Linker compound is represented by the structure of:

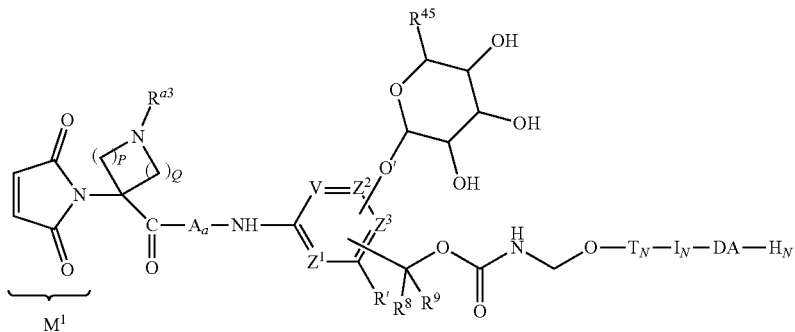

or a salt thereof, wherein subscript P is 1, 2 or 3; and subscript Q ranges from 1 to 6, or is represented by the structure of:

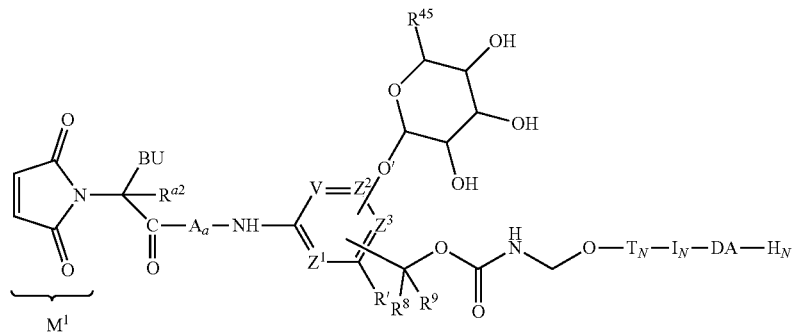

or a salt thereof, wherein $R^{a2}$ is hydrogen or $C_1$-$C_6$ alkyl; BU has the structure of —[C($R^{a1}$)($R^{a1}$)]—[C($R^{a1}$)($R^{a1}$)]$_{0-3}$—N($R^{a3}$)($R^{a3}$), each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a1}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; and wherein R' is hydrogen or —NO$_2$ or other electron withdrawing group; $R^{45}$ is —CH$_2$OH or —CO$_2$H; and —O'— represents the oxygen atom of an O-glycosidic bond cleavable by a glycosidase, wherein said cleavage initiates release of the NAMPT Drug Unit as a NAMPTi compound or derivative thereof from the Drug Linker compound or from the drug linker moiety of the Ligand Drug Conjugate compound or N-acetyl-cysteine (NAC) conjugate prepared from the Drug Linker compound, or wherein W is a Peptide Cleavable Unit for which the Drug Linker compound is represented by the structure of:

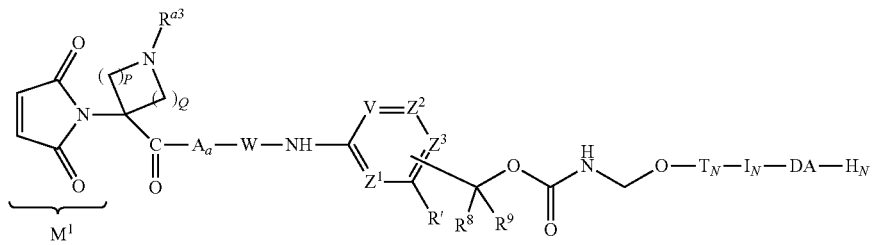

or a salt thereof, wherein subscript P is 1, 2 or 3; subscript Q ranges from 1 to 6, or is represented by the structure of:

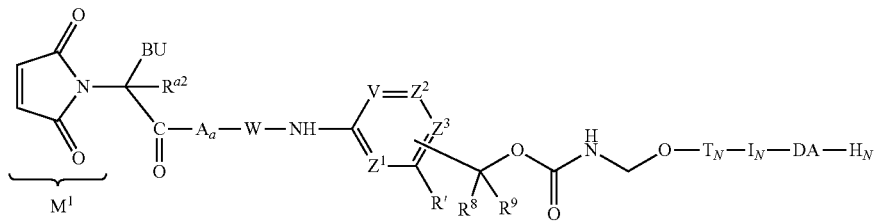

wherein $R_{a2}$ is hydrogen or $C_1$-$C_6$ alkyl; BU has the structure of $—[C(R^{a1})(R^{a1})]—[C(R^{a1})(R^{a1})]_{0\text{-}3}—N(R^{a3})(R^{a3})$, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a1}$ independently are hydrogen, optionally substituted $C_1$-$C_6$ alkyl, or $R^{a1}$ together with the nitrogen atom to which both are attached define a $C_3$-$C_6$ heterocyclyl in which the basic nitrogen is a skeletal atom; and wherein the basic nitrogen atom of BU is optionally protonated; and wherein R' is hydrogen or $—OC_1$-$C_6$ alkyl or other electron donating group; $R^{a3}$ is $—H$, or optionally substituted $C_1$-$C_6$ alkyl, optionally substituted $—C_1$-$C_4$ alkylene-($C_6$-$C_{10}$ aryl), or $—R^{PEG1}—O—(CH_2CH_2O)_{1\text{-}36}—R^{PEG2}$, wherein $R^{PEG1}$ is $C_1$-$C_4$ alkylene, and $R^{PEG2}$ is $—H$ or $C_1$-$C_4$ alkyl, wherein the basic nitrogen atom bonded to $R^{a3}$ is optionally protonated; and wherein protease action on the Peptide Cleavable Unit cleaves the W—NH bond, wherein said cleavage initiates release of the NAMPT Drug Unit as a NAMPTi compound or derivative thereof from the Drug Linker compound or from the drug linker moiety of the Ligand Drug Conjugate compound or N-acetyl-cysteine (NAC) conjugate prepared from the Drug Linker compound.

48A. The Drug Linker compound of embodiment 44A, wherein W is a Glucuronide Unit for which the Drug Linker compound is represented by the structure of:

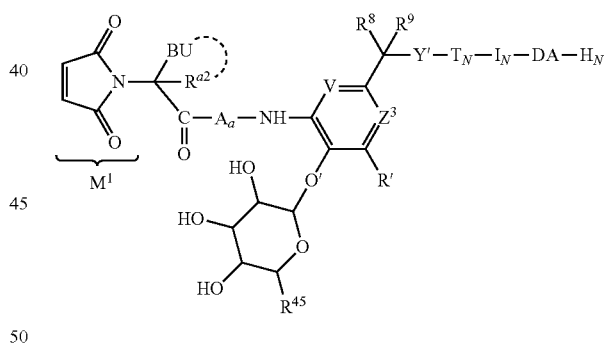

or a salt thereof, wherein R' is hydrogen or $—NO_2$ or other electron withdrawing group; $R^{a2}$ is hydrogen or $C_1$-$C_6$ alkyl, optionally cyclized to BU, as indicated by the dotted curved line, BU has the structure of $—[C(R^{a1})(R^{a1})]—[C(R^{a1})(R^{a1})]_{0\text{-}3}—N(R^{a3})(R^{a3})$, wherein in the absence of cyclization to $R^{a2}$, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; and $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; and wherein the basic nitrogen atom of BU is optionally protonated, and in the presence of cyclization one of $R^{a1}$ or one of $R^{a3}$ is replaced with a bond to a carbon atom of $R^{a1}$ in which $R^{a1}$ is $C_1$-$C_6$ alkyl and the remaining $R^{a1}$ and $R^{a3}$ are as previously defined, in particular, by the structure of:

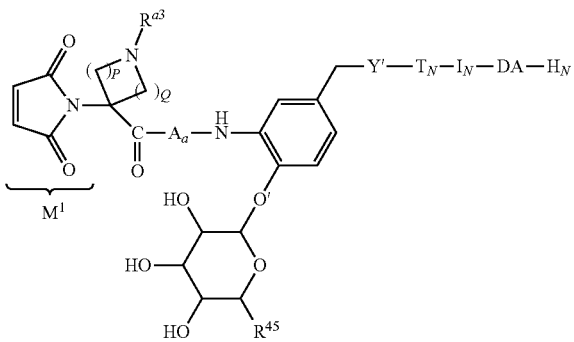

or a salt thereof, more particularly, by the structure of:

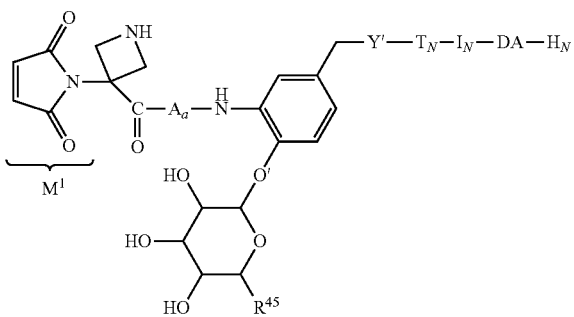

or a salt thereof, or in particular by the structure of:

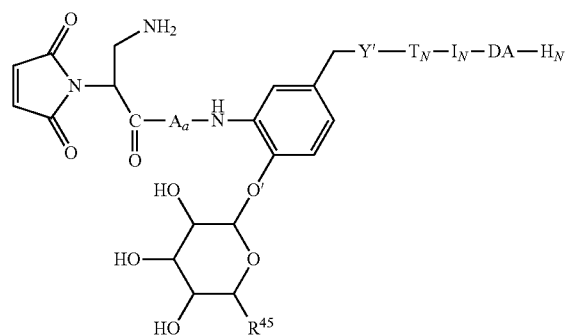

or a salt thereof, and wherein Y' is —$X^a$—, —O—C(=O)—$X^b$— or —OC(=O)NH—CH$_2$—$X^a$—, wherein $X^a$ or $X^b$ are from $T_N$, wherein —$X^a$— is O and $X^b$ is —NH—; and $R^{45}$ is —CH$_2$OH or —CO$_2$H; and wherein —O'— represents the oxygen atom of an O-glycosidic bond cleavable by a glycosidase, wherein said cleavage initiates release of the NAMPT Drug Unit as a NAMPTi compound or derivative thereof from the Drug Linker compound or from the drug linker moiety of the Ligand Drug Conjugate compound or N-acetyl-cysteine (NAC) conjugate prepared from the Drug Linker compound, or wherein W is a Peptide Cleavable Unit for which the Drug Linker compound is represented by the structure of:

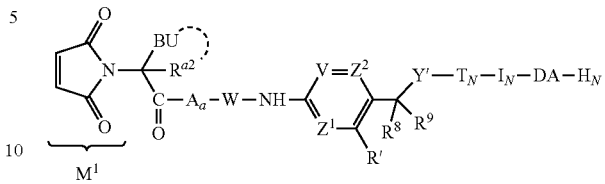

or a salt thereof, wherein R' is hydrogen or —OC$_1$-C$_6$ alkyl or other electron donating group; $R^{a2}$ is hydrogen or $C_1$-$C_6$ alkyl, optionally cyclized to BU, as indicated by the dotted curved line; BU has the structure of —[C($R^{a1}$)($R^{a1}$)]—[C($R^{a1}$)($R^{a1}$)]$_{0-3}$—N($R^{a3}$)($R^{a3}$), wherein in the absence of cyclization to $R^{a2}$, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; and $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen is a skeletal atom; and wherein the basic nitrogen atom of BU is optionally protonated, and in the presence of cyclization one of $R^{a1}$ or one of $R^{a3}$ is replaced with a bond to a carbon atom of $R^{a1}$ in which $R^{a1}$ is $C_1$-$C_6$ alkyl and the remaining $R^{a1}$ and $R^{a3}$ are as previously defined, in particular by the structure of:

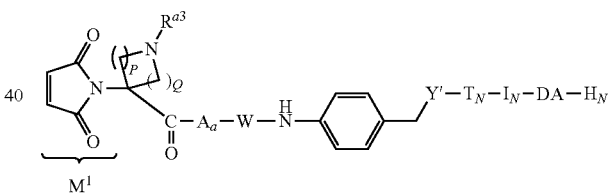

or a salt thereof, more particularly by the structure of:

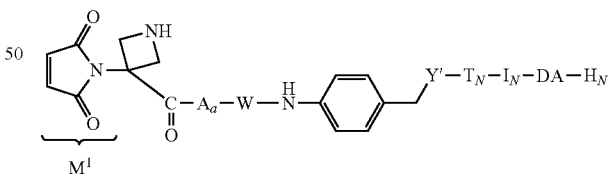

or a salt thereof, or particular by the structure of:

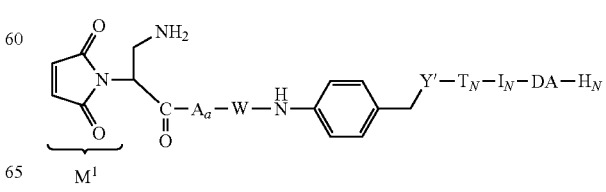

or a salt thereof; and wherein Y' is —$X^a$—, —O—C(=O)—$X^b$— or —OC(=O)NH—CH$_2$—$X^a$—, wherein $X^a$ and $X^b$ are from $T_N$, wherein —$X^a$— is O and $X^b$ is —NH—; and R' is hydrogen or —OC$_1$-C$_6$ alkyl or other electron donating group, wherein protease action on the Peptide Cleavable Unit cleaves the W—NH bond, wherein said cleavage initiates release of the NAMPT Drug Unit as a NAMPTi compound or derivative thereof from the Drug Linker compound or from the drug linker moiety of the Ligand Drug Conjugate compound or N-acetyl-cysteine (NAC) conjugate prepared from the Drug Linker compound.

49A. The Drug Linker compound of any one of embodiments 31A to 48A in which W is a Peptide Cleavable Unit that Unit is comprised of a dipeptide wherein the dipeptide provides for a recognition site for a regulatory or lysosomal protease for cleavage by said protease of the W-J' bond or the W—NH bond when J' is —NH within the Drug Linker compound or the drug linker moiety of the Ligand Drug Conjugate compound or N-acetyl-cysteine (NAC) conjugate prepared from the Drug Linker compound so as to initiate release of the NAMPT Drug Unit as NAMPTi compound or derivative from that Drug Linker compound, drug linker moiety or NAC conjugate.

50A. The Drug Linker compound of claim 4A9, wherein the W has the structure of:

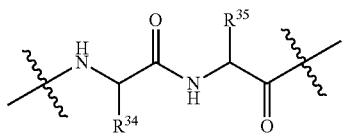

wherein $R^{34}$ is benzyl, methyl, isopropyl, isobutyl, sec-butyl, —CH(OH)CH$_3$ or has the structure of

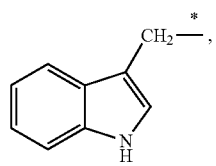

wherein the asterisk indicates the site of covalent attachment to the dipeptide backbone; and $R^{35}$ is methyl, —(CH$_2$)$_4$—NH$_2$, —(CH$_2$)$_3$NH(C=O)NH$_2$, —(CH$_2$)$_3$NH(C=NH)NH$_2$, or, —(CH$_2$)$_2$CO$_2$H; and wherein the wavy lines indicate the points of covalent attachment of the dipeptide into the structure representing the Ligand-Drug Conjugate composition, in particular W is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

51A. The Drug Linker compound of any one of embodiments 31A-50A, wherein A or a subunit thereof is -$L^P$(PEG)-, wherein -$L^P$- or a subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form, or -$L^P$- or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration, or wherein -$L^P$(PEG)- has the structure of:

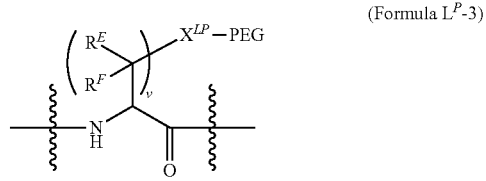
(Formula $L^P$-3)

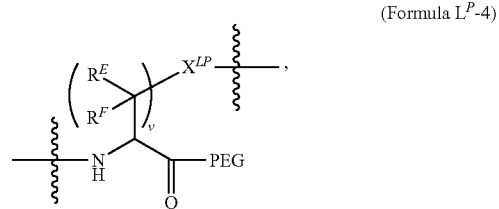
(Formula $L^P$-4)

or a pharmaceutical acceptable salt thereof, wherein subscript v is an integer ranging from 1 to 4; $X^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, —N(R$^{LP}$)C(=NR$^{LP}$)N(R$^{LP}$)—, and C$_3$-C$_8$ heterocyclo, in particular —O—, —NH, —S— and —C(=O)—;

wherein each R$^{LP}$ is independently selected from the group consisting of hydrogen and optionally substituted C$_1$-C$_6$ alkyl, or two of R$^{LP}$ together along with the carbons atoms to which they are attached and their intervening atoms define a C$_5$-C$_6$ heterocyclo and any remaining R$^{LP}$ are as previously defined; Ar is a C$_6$-C$_{10}$ arylene or a C$_5$-C$_{10}$ heteroarylene, optionally substituted;

each R$^E$ and R$^F$ is independently selected from the group consisting of —H, optionally substituted C$_1$-C$_6$ alkyl, optionally substituted C$_2$-C$_6$ alkylene, optionally substituted C$_6$-C$_{10}$ arylene and optionally substituted C$_5$-C$_{10}$ heteroarylene, in particular hydrogen and C$_1$-C$_4$ alkyl or R$^E$ and R$^F$ together with the carbon atom to which both are attached defines an optionally substituted spiro C$_3$-C$_6$ carbocyclo, or R$^E$ and R$^F$ from adjacent carbon atoms together with these atoms and any intervening carbon atoms defines an optionally substituted C$_5$-C$_6$ carbocyclo with any remaining R$^E$ and R$^F$ as previously defined, or wherein the side chain of —[C(R$^E$)(R$^F$)]$_v$—$X^{LP}$— is provided by a natural or un-natural amino acid side chain; and wherein the wavy lines indicate the sites of covalent attachments within the remainder of the Conjugate structure, in particular having the PEG Unit represented by:

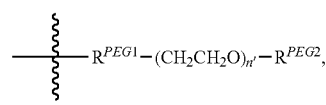

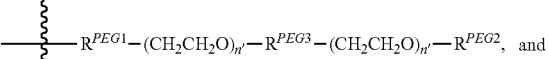 and

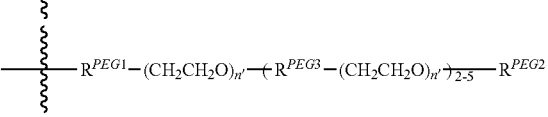

wherein the wavy line indicates site of attachment to $X^{LP}$ of the Parallel Connector Unit ($L^P$); subscript n' independently ranges from 1 to 72; $R^{PEG1}$ is an optional PEG Attachment Unit; $R^{PEG2}$ is a PEG Capping Unit; and $R^{PEG3}$ is an PEG Coupling Unit, or having $X^{LP}$-PEG with the structure of:

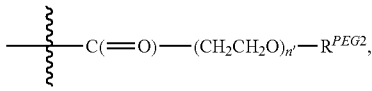

wherein subscript n' is 8, 12 or 24 and $R^{PEG2}$ is H or —CH$_3$.

52A. The Drug Linker compound of any one of embodiment 31A-51A, wherein A or a subunit thereof has the structure of formula (3) or formula (4):

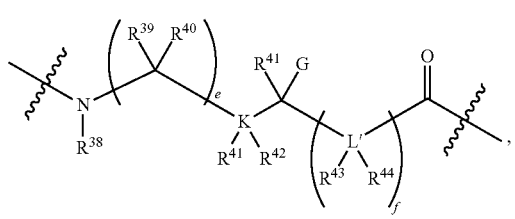 (3)

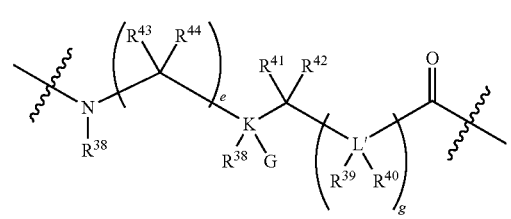 (4)

wherein the wavy lines indicated covalent attachment within the composition structure; wherein K and L' independently are C, N, O or S, provided that when K or L' is O or S, $R^{41}$ and $R^{42}$ to K or $R^{43}$ and $R^{44}$ to L' are absent, and when K or L' are N, one of $R^{41}$, $R^{42}$ to K or one of $R^{42}$, $R^{43}$ to L' are absent, and provided that no two adjacent L' are independently selected as N, O, or S; wherein subscripts e and f are independently selected integers that range from 0 to 12, and subscript g is an integer ranging from 1 to 12;

wherein G is hydrogen, optionally substituted $C_1$-$C_6$ alkyl, —OH, —OR', —CO$_2$H, CO$_2$R$^{PR}$, wherein R$^{PR}$ is a suitable protecting, or G is —N(R$^{PR}$)(R$^{PR}$), wherein R$^{PR}$ are independently a protecting group or R$^{PR}$ together form a suitable protecting group, or G is —N(R$^{45}$)(R$^{46}$ wherein one of R$^{45}$, R$^{46}$ is hydrogen or R$^{PR}$, wherein R$^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl; $R^{39}$-$R^{44}$ are independently selected from the group consisting of hydrogen, optionally substituted $C_1$-$C_6$ alkyl, optionally substituted aryl, and optionally substituted heteroaryl, or $R^{30}$, $R^{40}$ together with the carbon atom to which both are attached, or $R^{41}$, $R^{42}$ together with K to which both are attached when K is a carbon atom, define a $C_3$-$C_6$ carbocyclo, and $R^{41}$-$R^{44}$ are as defined herein, or $R^{43}$, $R^{44}$ together with L' to which both are attached when L' is a carbon atom define a $C_3$-$C_6$ carbocyclo, and $R^{30}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^{44}$ are absent, and when L' is N, one of $R^{43}$, $R^{44}$ is absent, or A or a subunit thereof is an alpha-amino, beta-amino or another amine-containing acid residue, in particular, wherein formula (3) or formula (4) has the structure of formula (3a) or formula (4a):

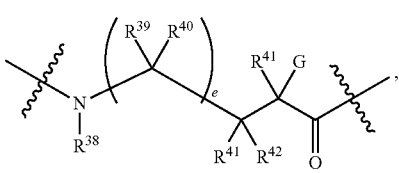 (3a)

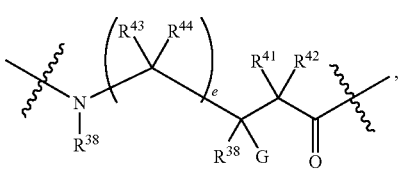 (4a)

wherein subscript e and f are independently 0 or 1.

53A. The Drug Linker compound of embodiment 31A, wherein the Drug Linker compound is represented by the structure of:

297
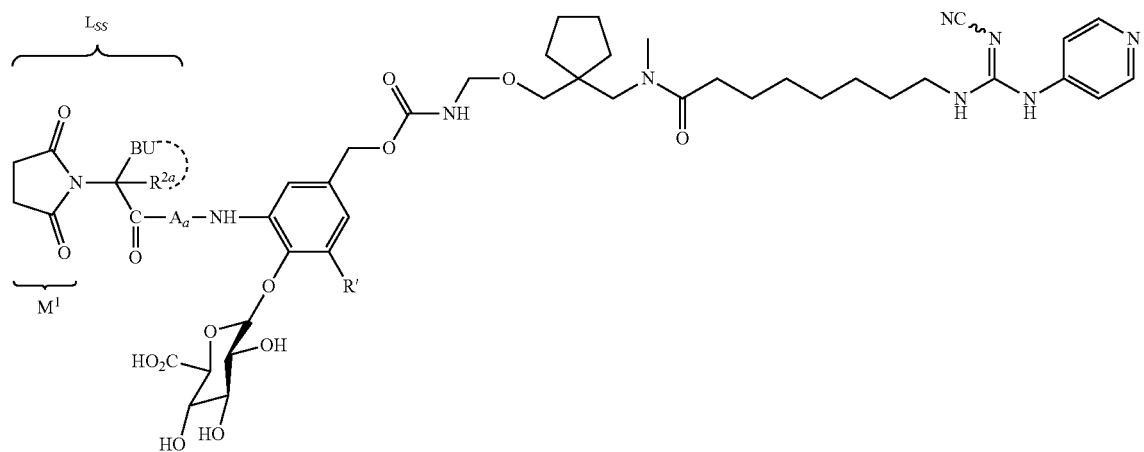
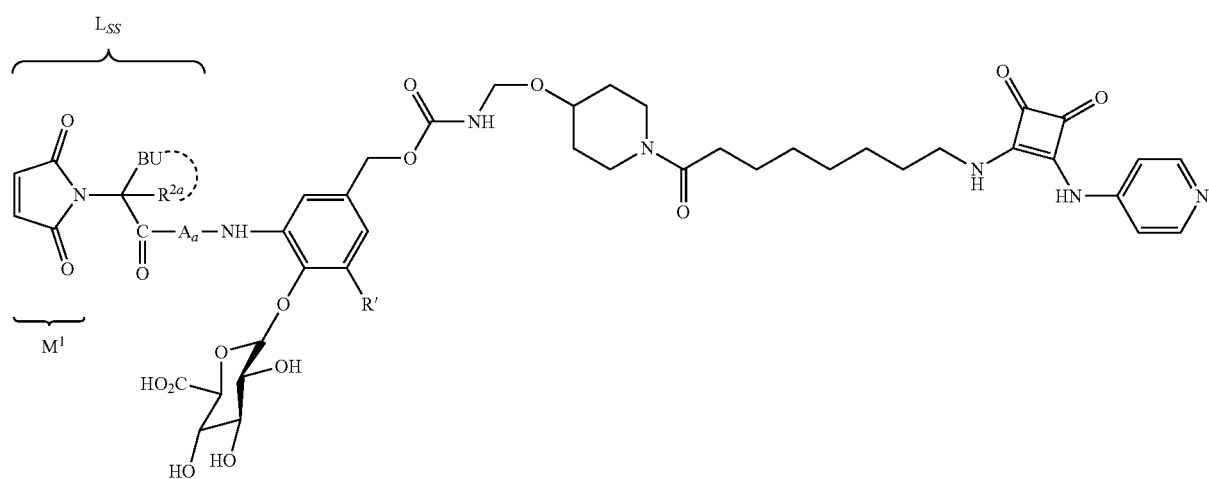
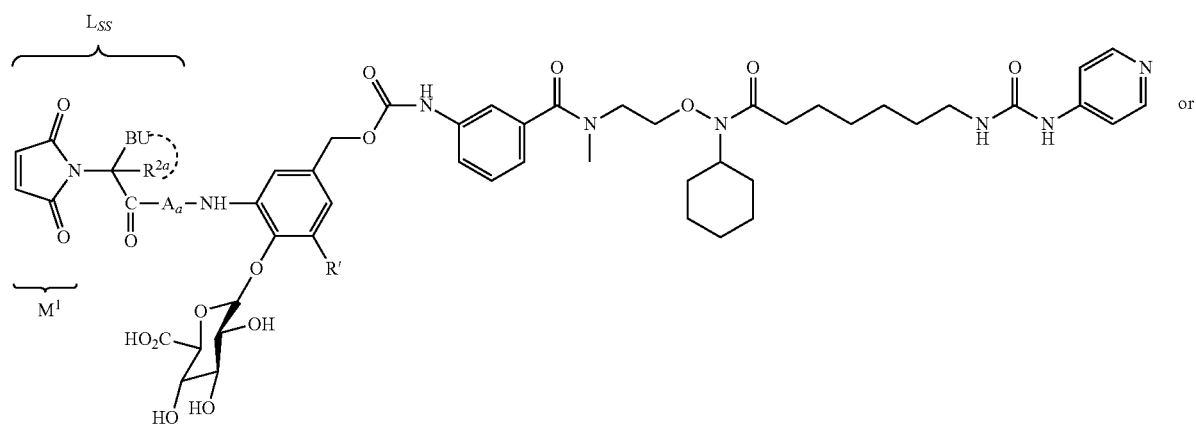 or

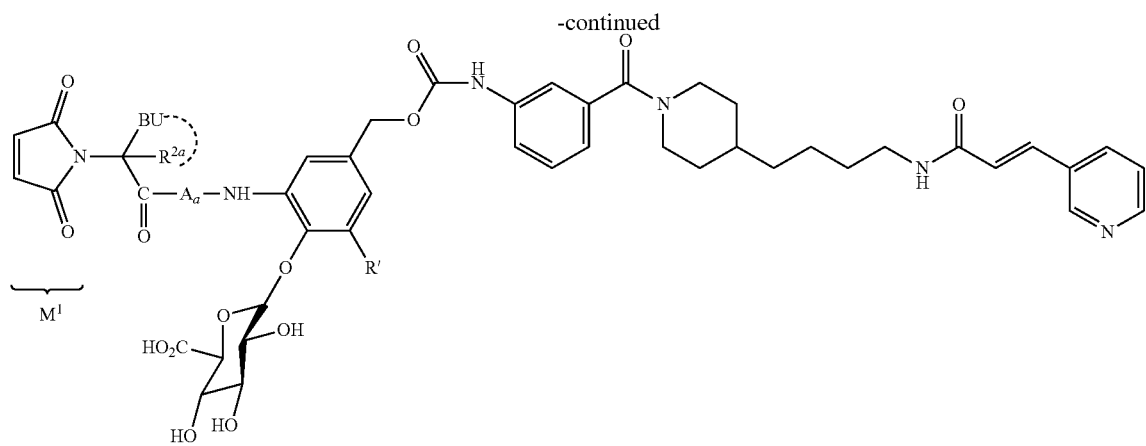

or a salt thereof, wherein subscript a is 1 and A is an amino acid residue; BU is a acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$, in particular by:

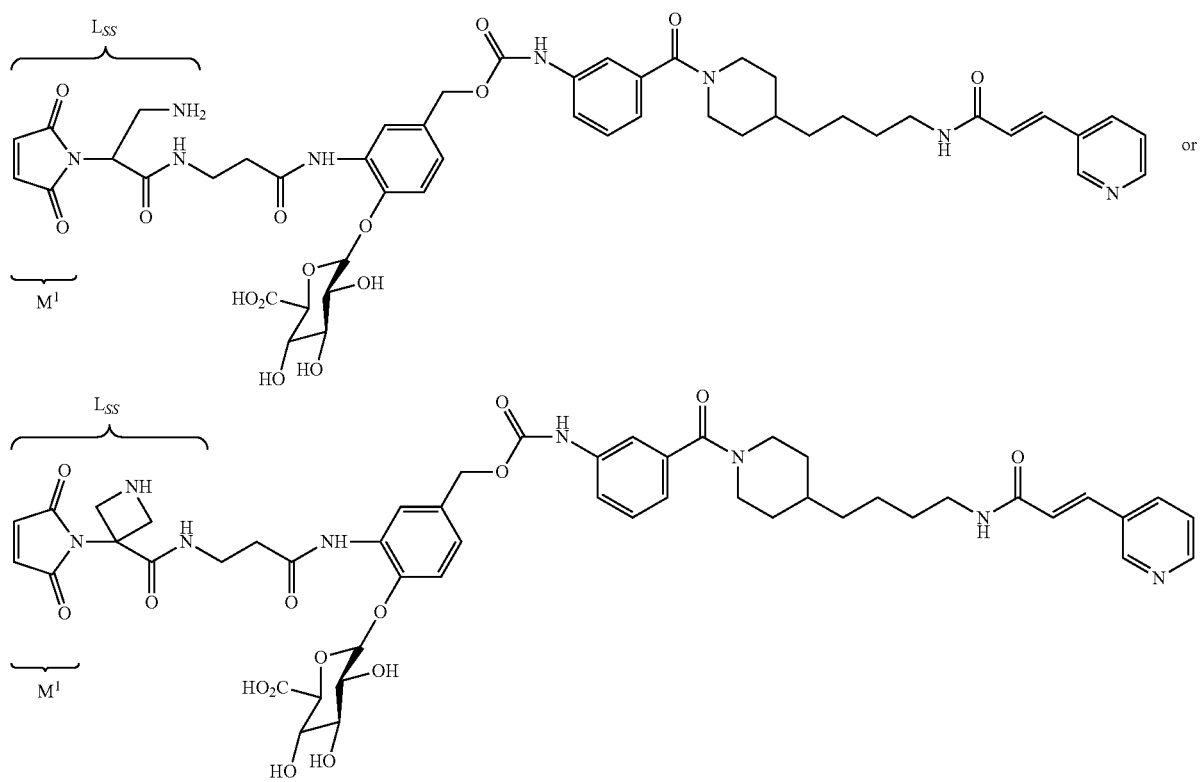

or a salt thereof.

54A. A method of preparing a Ligand Drug Conjugate composition or compound thereof of embodiment 1A, the method comprising the step of: contacting a Drug Linker compound of embodiment 31A with a targeting agent having a reactive function group capable of interacting with the reactive functional group of the primary linker of the Drug Linker compound so as to form a covalent bond to between the Ligand Unit corresponding to the targeting agent and the primary linker of the Ligand Drug Conjugate corresponding in structure to the primary linker of the Drug Linker compound.

55A. The method of embodiment MA, wherein the reactive functional group of the targeting agent is a cysteine thiol of an antibody, either native to the antibody through interchain disulfide bond reduction or introduced by genetic engineering into the antibody and the reactive functional group of the primary linker of the Ligand Drug Conjugate is a maleimide ($M^1$) moiety comprising the Stretcher Unit of that primary linker, whereby said contacting of said reactive functional groups provides the Ligand Drug Conjugate composition or compound of embodiment 1A in which L is an antibody Ligand Unit.

EXAMPLES

General Information.

All commercially available anhydrous solvents were used without further purification. Silica gel chromatography was performed on a Biotage Isolera One flash purification system (Charlotte, N.C.). UPLC-MS was performed on a Waters Xevo G2 ToF mass spectrometer interfaced to a Waters Acquity H-Class Ultra Performance LC equipped with an Acquity UPLC BEH C18 2.1×50 mm, 1.7 μm reverse phase column. The acidic mobile phase (0.1% formic acid) consisted of a gradient of 3% to 95% acetonitrile in water over 1.43 min (flow rate=0.7 mL/min) with a return to baseline conditions over 0.36 min. Where "hydrophobic method" is specified, the composition of eluent increased to a maximum of 97% acetonitrile in water with a return to baseline conditions over 3.57 min. Where "polar method" is specified, an ACQUITY UPLC HSS T3 Column (100 Å, 1.8 μm, 2.1 mm×150 mm) was used, and the composition of eluent increased to from 3% to a maximum of 95% acetonitrile in water with a return to baseline conditions over 1.79 min.

Preparative HPLC was carried out on a Waters 2545 solvent delivery system configured with a Waters 2998 PDA detector. Products were purified over a $C_{12}$ Phenomenex Synergi reverse phase column (10.0-50 mm diameter×250 mm length, 4 μm, 80 Å) eluting with 0.05% trifluoroacetic acid in water (solvent A) and 0.05% trifluoroacetic acid in acetonitrile (solvent B). The purification methods generally consisted of linear gradients of solvent A to solvent B, ramping from 5% aqueous solvent B to 95% solvent B; flow rate was varied depending on column diameter. NMR spectral data were collected on a Varian Mercury 400 MHz spectrometer. Coupling constants (J) are reported in hertz.

NAMPT Enzyme Preparation.

NAMPT containing a C-terminal 6×His tag was expressed in *E. coli* using the pET28a vector (Novagen). The protein was purified by nickel affinity chromatography, then buffer-exchanged into 50 mM Tris, 100 mM NaCl, pH 7 and flash frozen.

Fluorescence Polarization Assay.

A fluorescent probe molecule for use in FP assay was prepared by reaction of compound 10 with the diacetate of fluorescein-5-carbonyl azide (via Curtius rearrangement), followed by saponification of the acetate groups. The product was purified by preparative HPLC. Assays were run in 384-well plate with 30 μl per well. Assay buffer consisted of 50 mM HEPES, 50 mM KCl, 5 mM MgCl2, 125 μM ATP, 0.5 mM beta-mercaptoethanol, and 0.005% BSA. NAMPT was used at 120 nM and fluorescent probe molecule at 30 nM. Test articles were added as a dilution series from ~1000 nM to 0.5 nM. After incubating at room temp for 4 hours, fluorescence polarization was measured on Envision plate reader. Curve fitting was performed in GraphPad Prism using a 4-parameter log(inhibitor concentration) vs response model.

In Vitro NAD Assays.

Cells cultured in log-phase growth were seeded for 24 h in 96-well plates containing 150 μL RPMI 1640 supplemented with 20% FBS. Serial dilutions of free drugs or antibody-drug conjugates in cell culture media were prepared at 4× working concentrations; 50 μL of each dilution was added to the 96-well plates. Following addition of ADC, cells were incubated with test articles for 2-4 d at 37° C. NAD levels were assessed NAD-Glo® (Promega, Madison, Wis.) and luminescence was measured on a plate reader. The $IC_{50}$ value is defined here as the concentration that results in a 50% reduction in NAD levels relative to untreated controls.

In Vivo Xenograft Models.

All experiments were conducted in concordance with the Animal Care and Use Committee in a facility fully accredited by the Association for Assessment and Accreditation of Laboratory Animal Care. Efficacy experiments were conducted in the L540cy Hodgkin's lymphoma model. Tumor cells, as a cell suspension, were implanted sub-cutaneous in immune-compromised SCID mice. Upon tumor engraftment, mice were randomized to study groups (5 mice per group) when the average tumor volume reached about 100 mm3. The ADC or controls were dosed once via intraperitoneal injection. Tumor volume as a function of time was determined using the formula (L×W2)/2. Animals were euthanized when tumor volumes reached 750 mm3 Mice showing durable regressions were terminated after 10-12 weeks post implant.

Scheme 1: Exemplary preparation of a NAMPTi compound derivative in which $H_N$-DA is a pyridyl-vinylogous amide moeity and the NAMPT Tail Unit is a derivitized benzamide moeity.

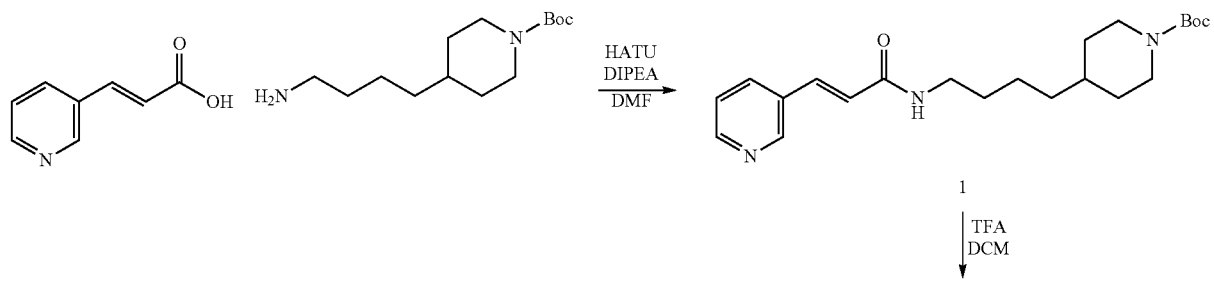

303 304
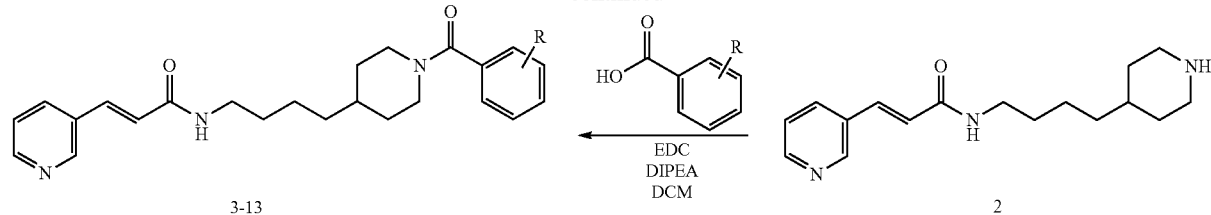

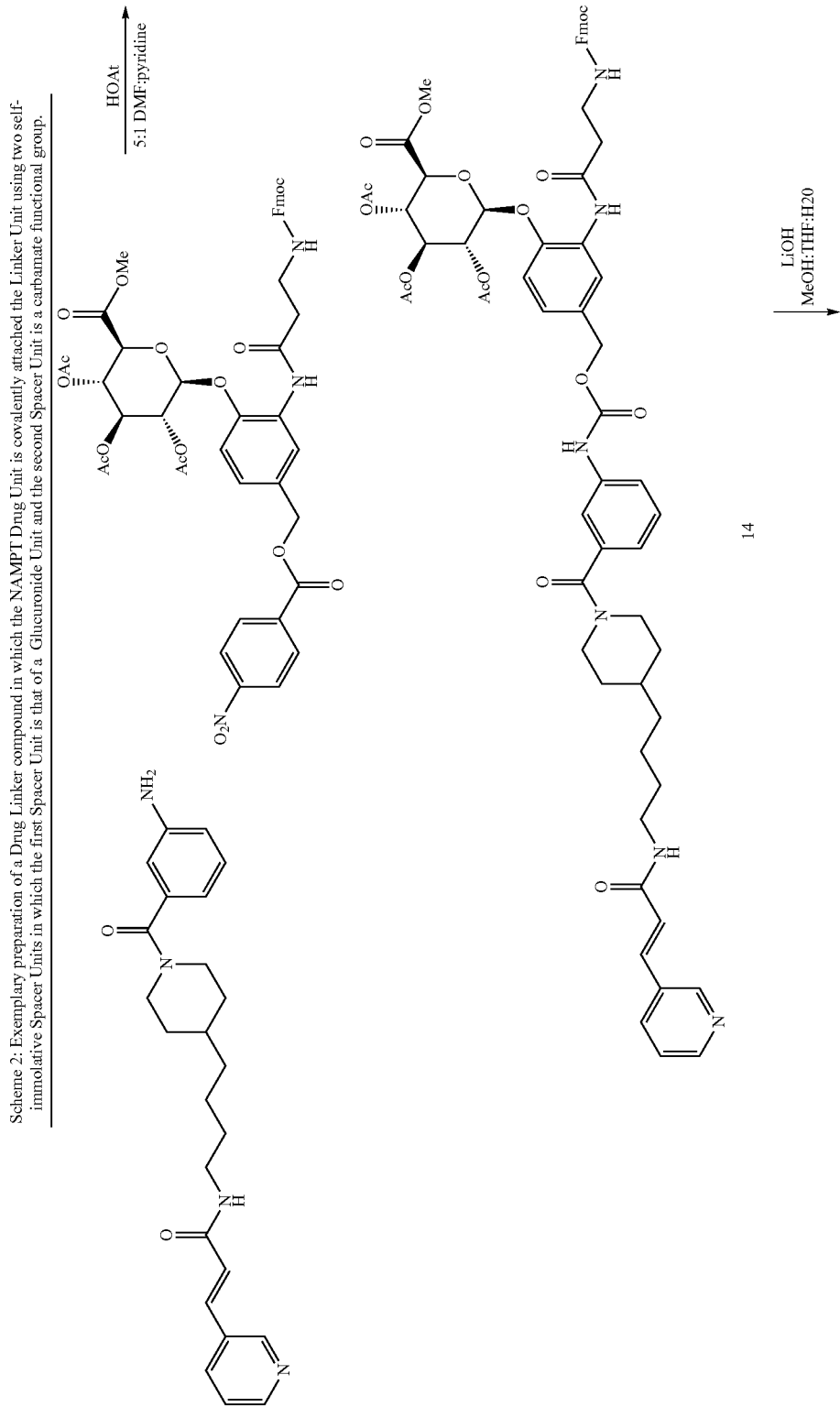
Scheme 2: Exemplary preparation of a Drug Linker compound in which the NAMPT Drug Unit is covalently attached the Linker Unit using two self-immolative Spacer Units in which the first Spacer Unit is that of a Glucuronide Unit and the second Spacer Unit is a carbamate functional group.

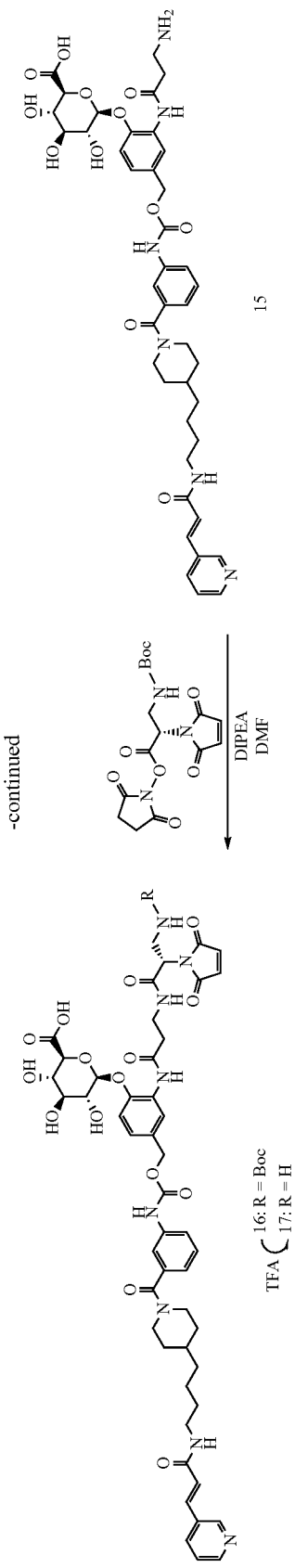

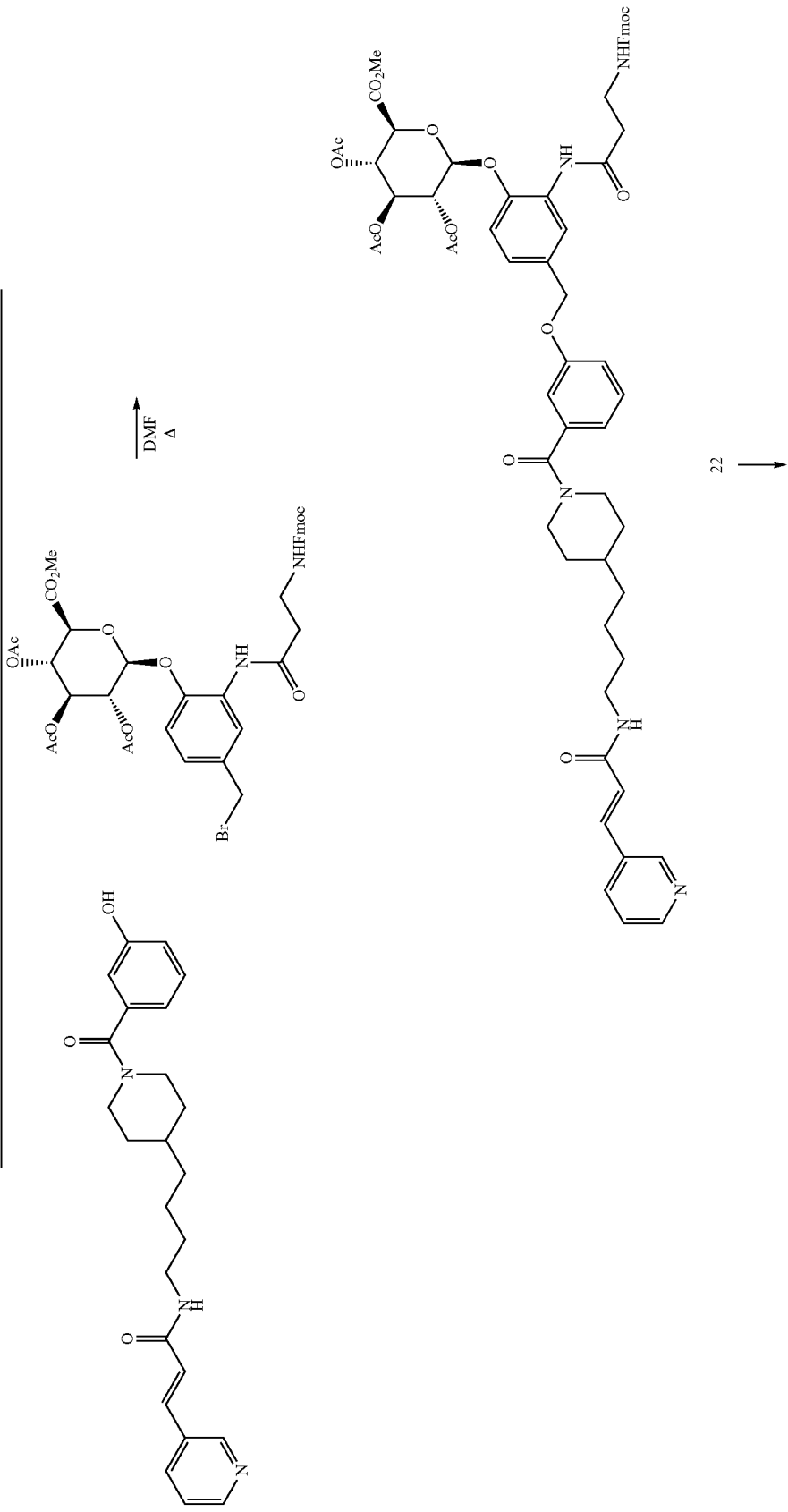
Scheme 3: Exemplary preparation of Drug Linker compound in which the NAMPT Drug Unit is covalently attached directly to the Linker Unit through the self-immolative Spacer Unit of a Glucuronide Unit using a benzyl-ether functional group.

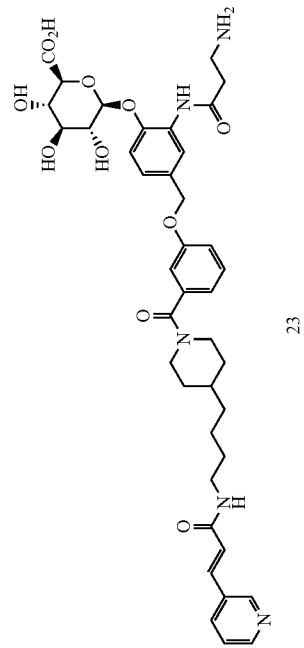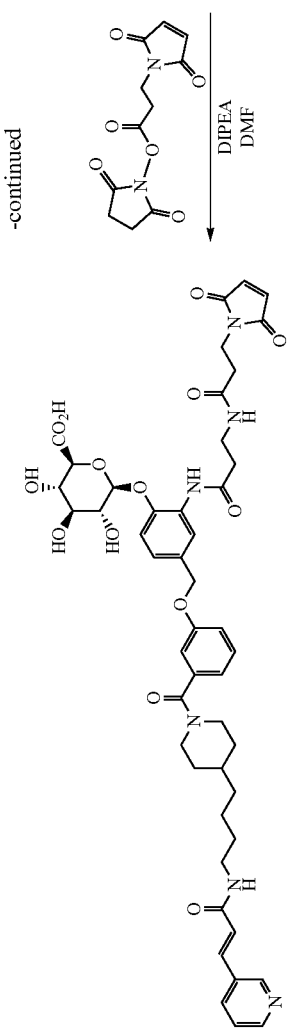

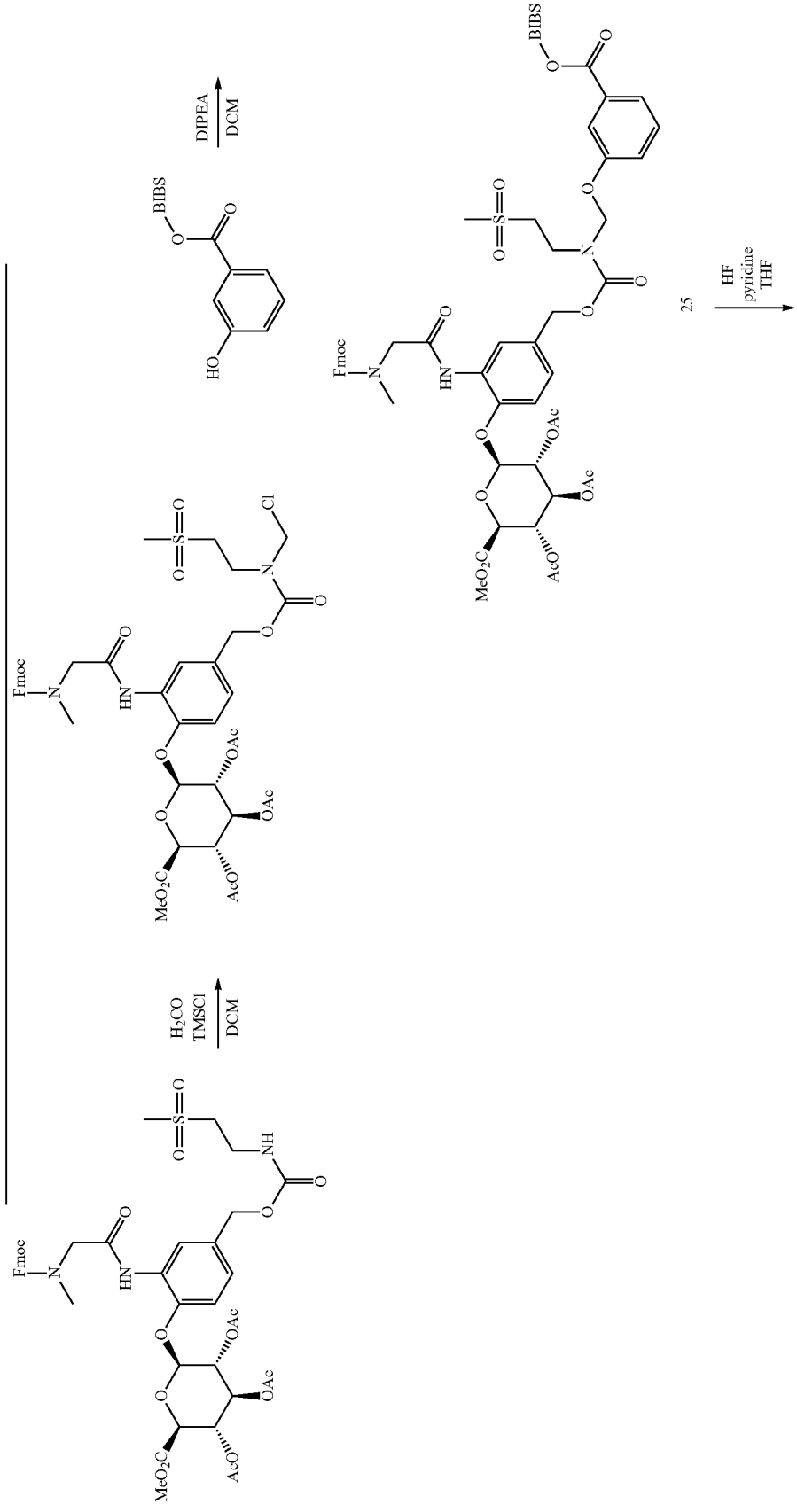
Scheme 4: Exemplary preparation of NAMPT Drug Linker in which the NAMPT Drug Unit is covalently attached the Linker Unit using two self-immolative Spacer Units in which the first Spacer Unit is that of a Glucuronide Unit and the second Spacer Unit is a MAC Unit.

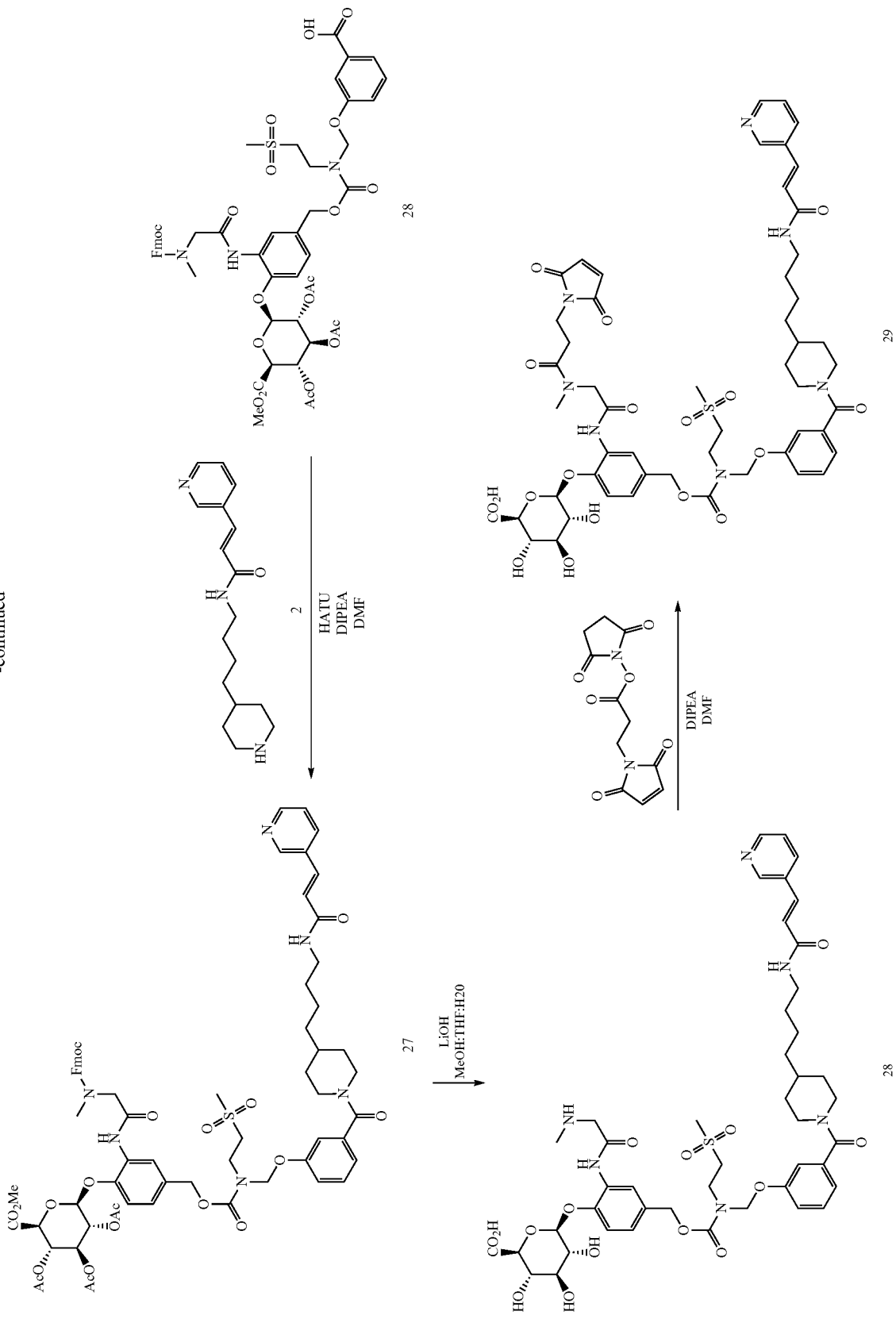

Scheme 5: Exemplary preparation of an NAMPTi derivative compound in which H$_N$-DA is a pyridyl-urea moeity and the NAMPT Tail Unit is a derivitized benzamide moeity.
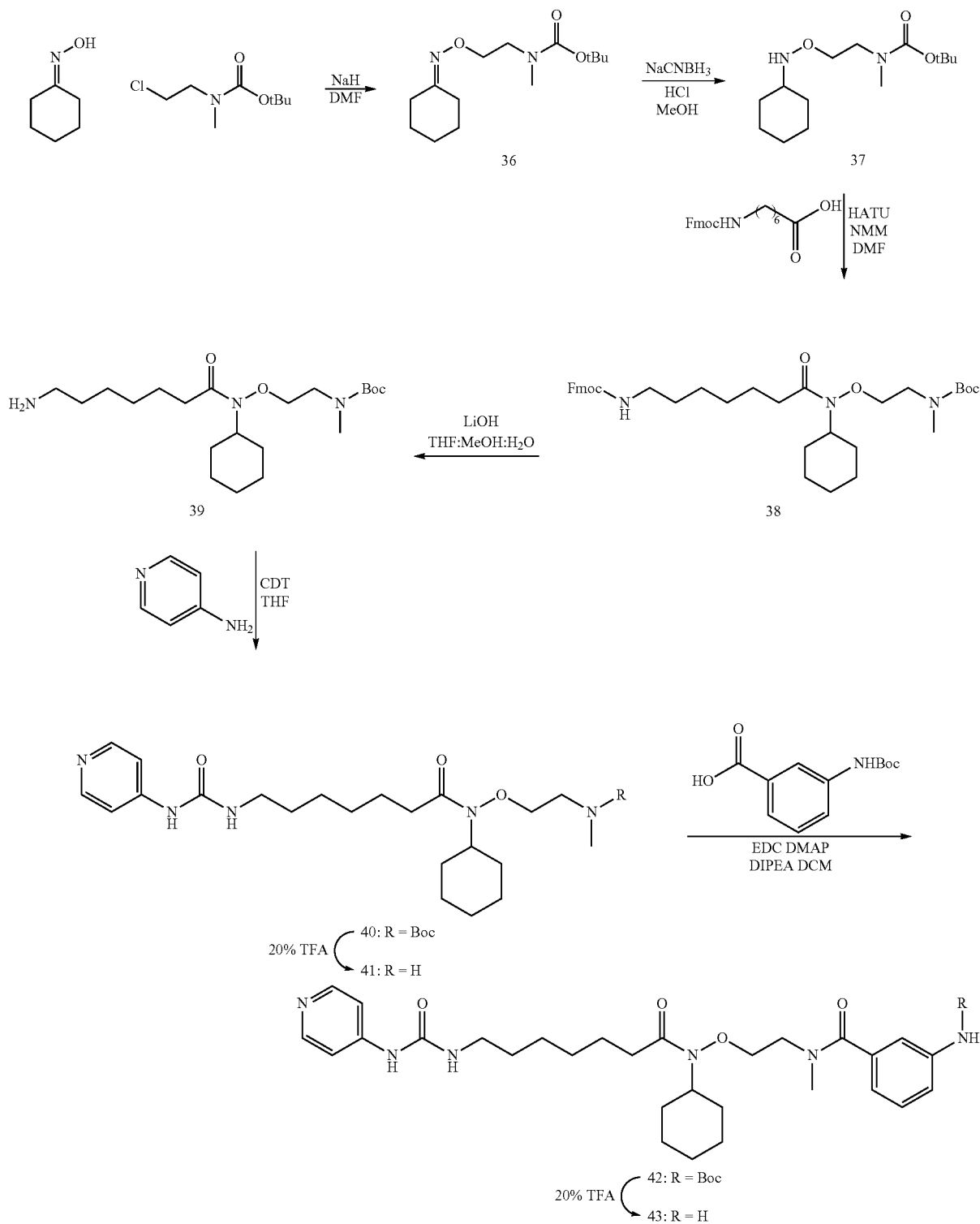

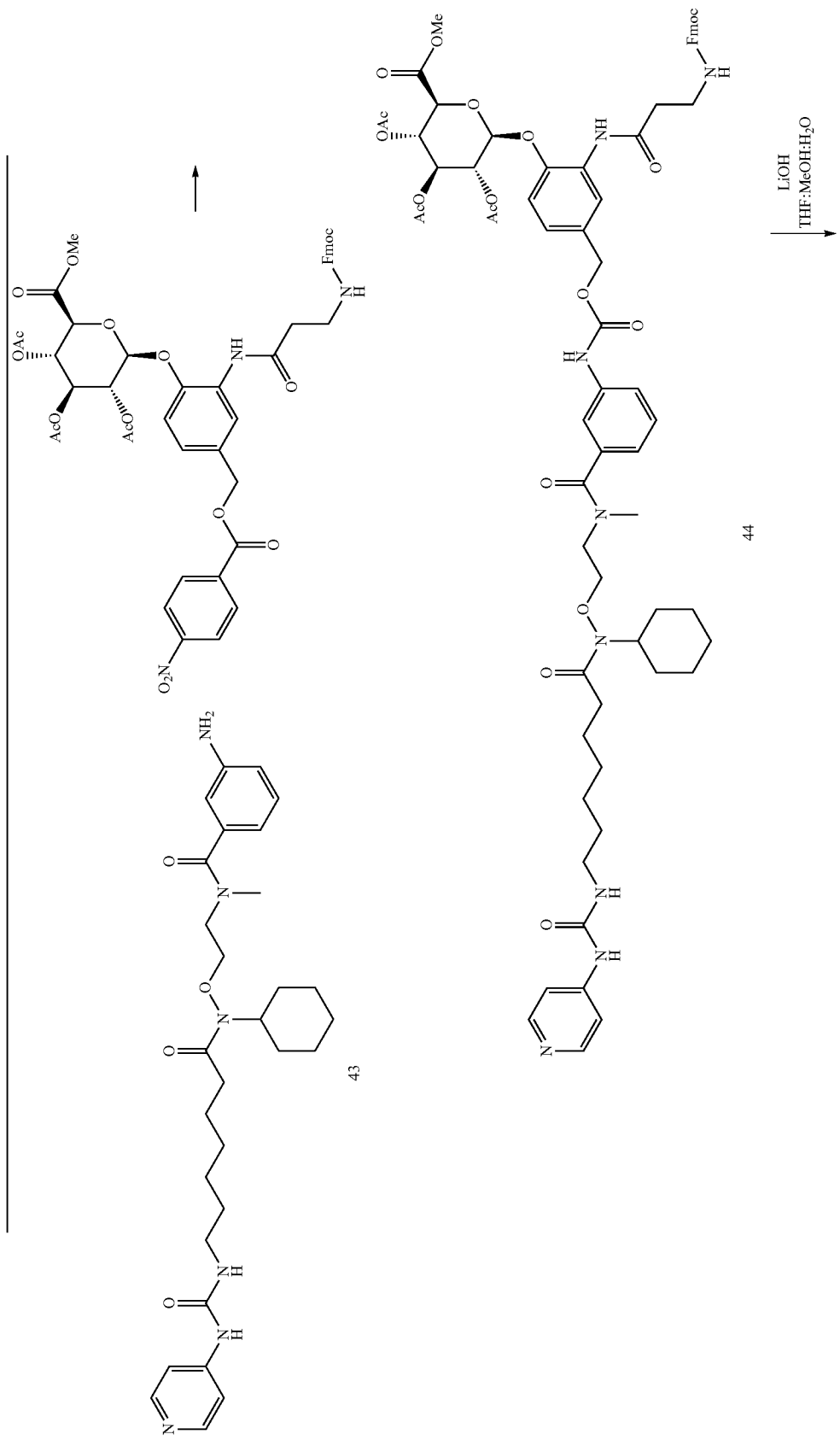
Scheme 6: Exemplary preparation of a Drug Linker compound in which the NAMPT Drug Unit contains a pyridyl urea H$_N$-DA moeity and is covalently attached to the Linker Unit using two self-immolative Spacer Unit in which the first Spacer Unit is that of a Glucuronide Unit the second Spacer Unit is a carbamate functional group.

-continued
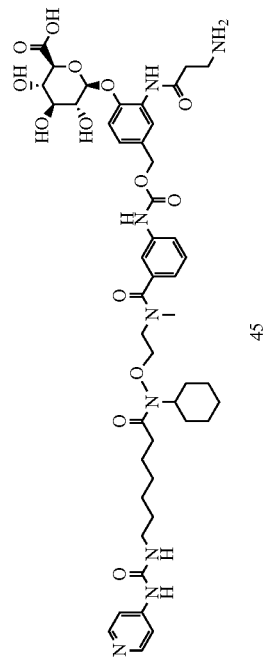
45
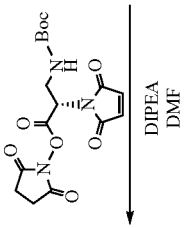
DIPEA
DMF
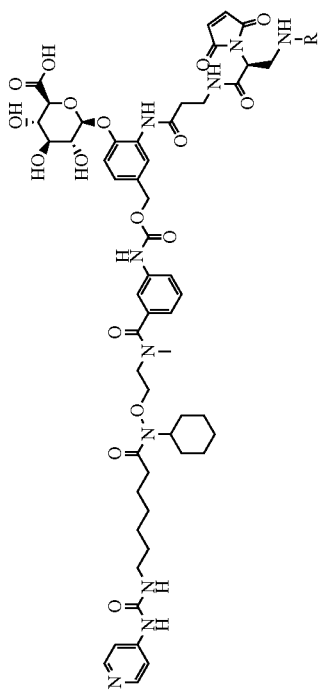
46: R = Boc
47: R = H
20% TFA Scheme 7: Exemplary preparation of an NAMPTi derivative compound in which H$_N$-DA is a pyridyl-squaramide moeity and the NAMPT Tail Unit is a derivitized benzamide moeity.
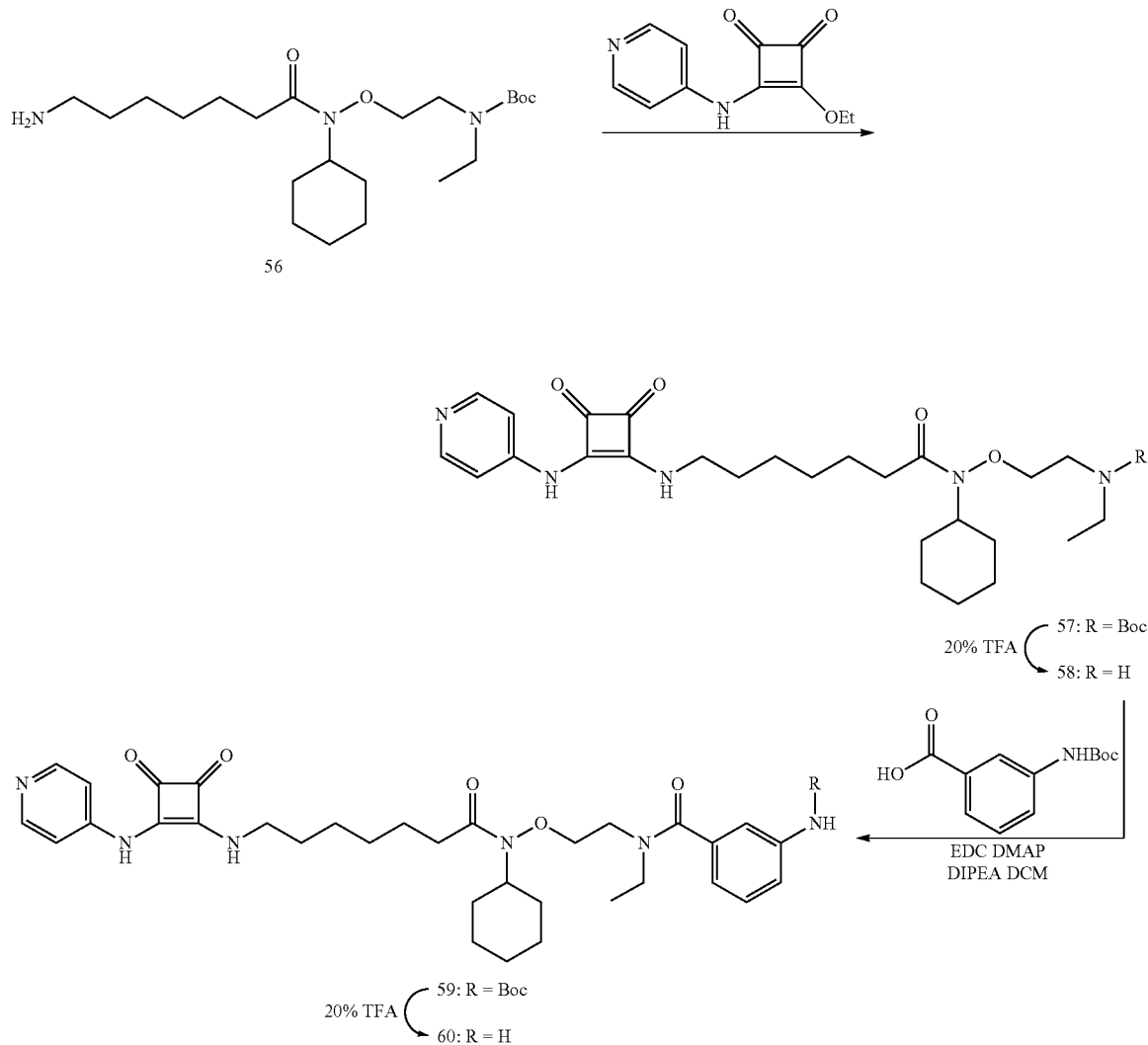
Scheme 8: Alternative exemplary preparation of an NAMPTi derivative compound in which H$_N$-DA is a pyridyl-squaramide moeity and the NAMPT Tail Unit is a derivitized benzamide moeity.
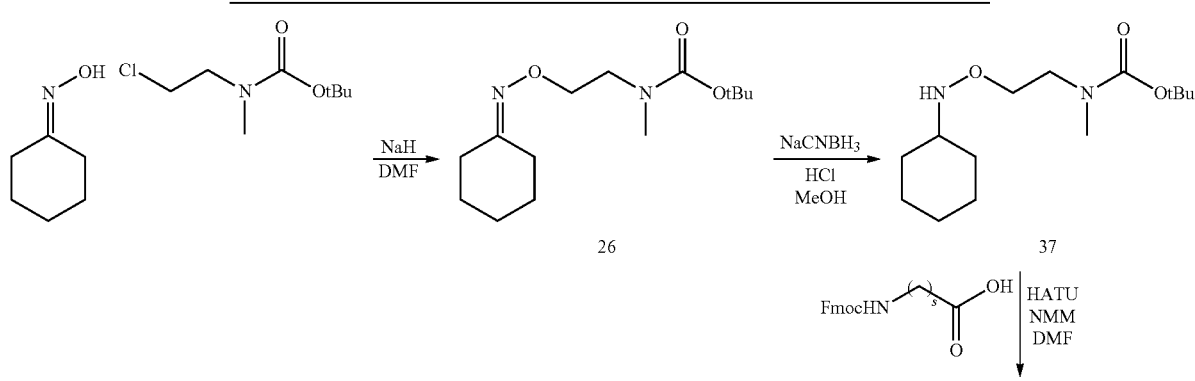

325
326
-continued
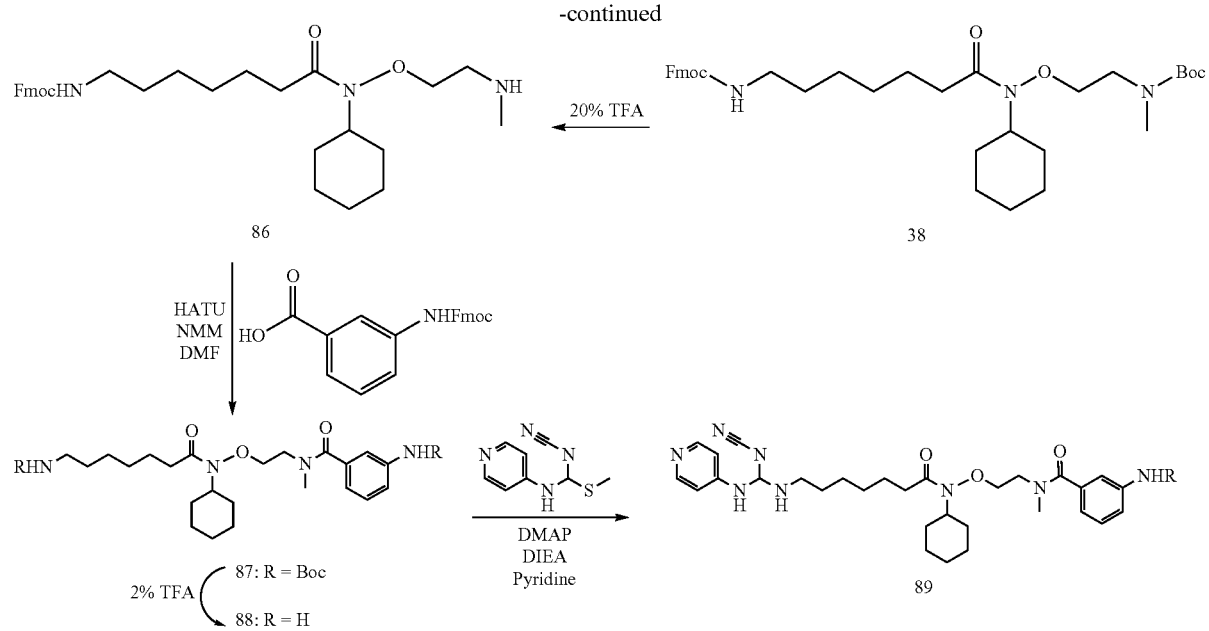

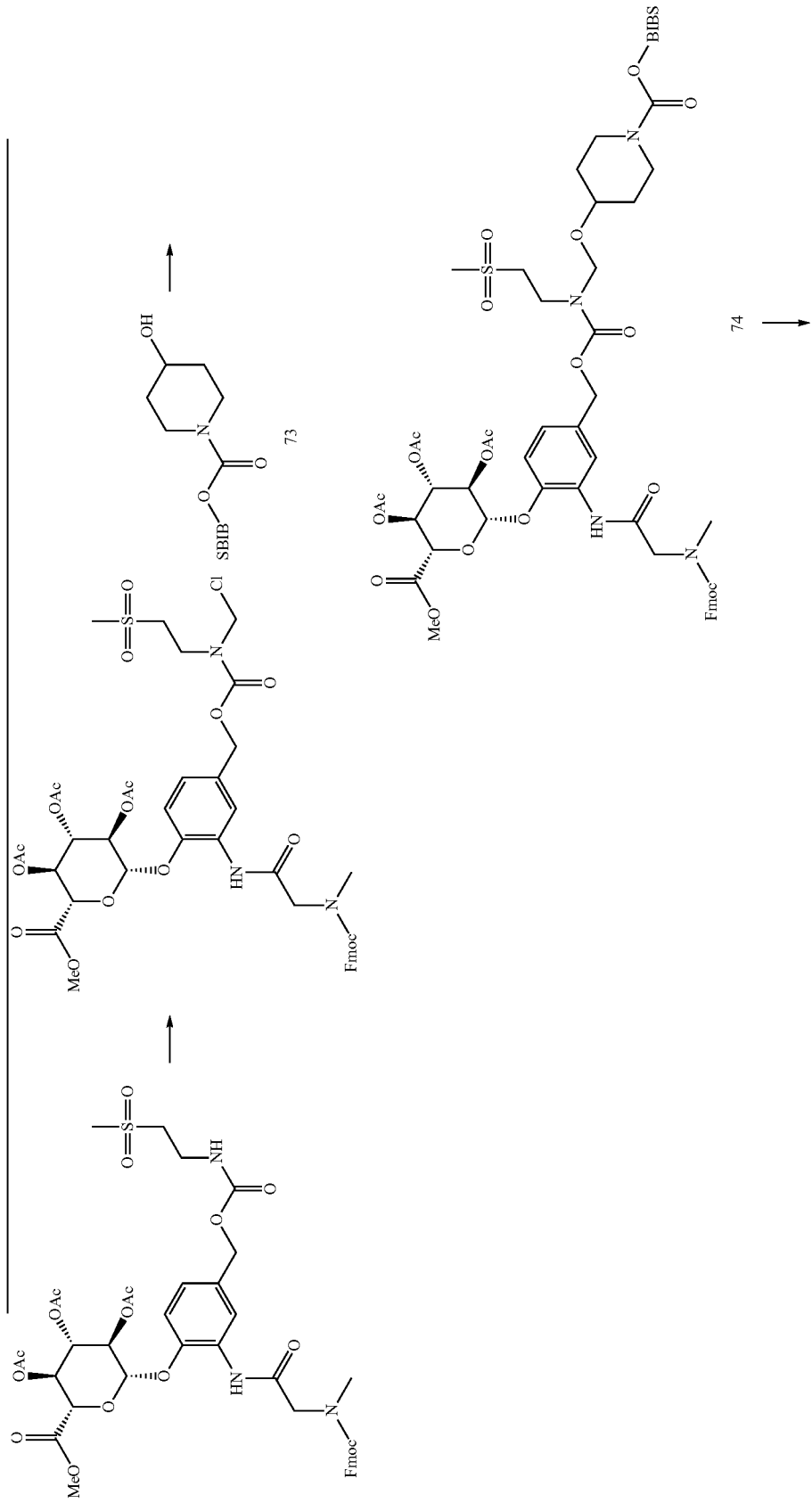
Scheme 9: Exemplary preparation of a Drug Linker compound in which the NAMPT Drug Unit contains a pyridyl-squaramide H$_N$-DA moeity and is covalently attached to the Linker Unit using two self-immolative Spacer Unit in which the first Spacer Unit is that of a Glucuronide Unit the second Spacer Unit is a carbamate functional group.

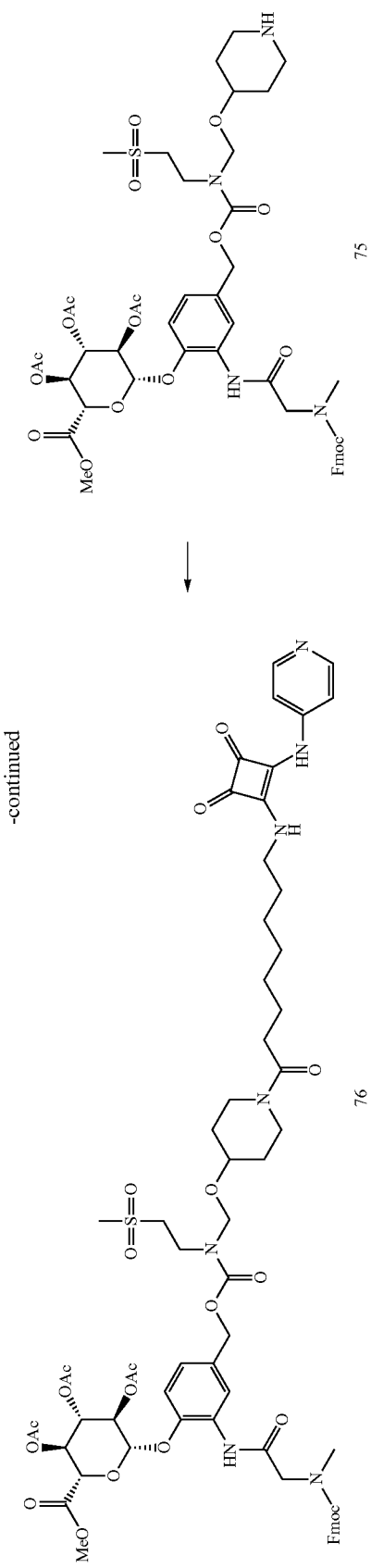
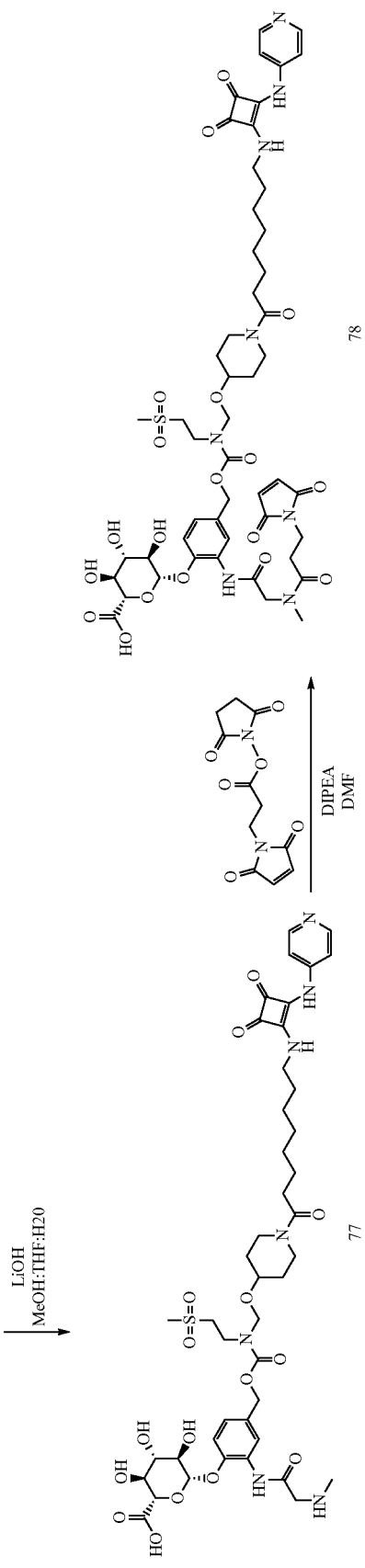

Example 1: tert-butyl (E)-4-(4-(3-(pyridin-3-yl)acrylamido)butyl)piperidine-1-carboxylate (1)

(2E)-3-(pyridin-3-yl)prop-2-enoic acid (698 mg, 4.68 mmol) was dissolved in DMF (24 mL) and treated with DIPEA (2 mL, 11.7 mmol) and HATU (1.80 g, 4.68 mmol). After 5 minutes, tert-butyl 4-(4-aminobutyl)piperidine-1-carboxylate (1.00 g, 3.90 mmol) was added as a solution in DMF (8 mL). The reaction was stirred at room temperature overnight. The reaction solvent was removed in vacuo, and the residue redissolved in EtOAc then washed once with water, twice with saturated NaHCO$_3$, and once with brine. The organic layer was dried over Na$_2$SO$_4$ and concentrated. The crude product was purified by silica gel chromatography (EtOAc/hexanes) to provide the title compound (1.16 g, 3.00 mmol, 77%). LCMS: $t_R$=1.22 min; m/z=388.3 [M+H]$^+$. $^1$H NMR (400 MHz, Chloroform-d) δ 8.78-8.71 (m, 1H), 8.57 (dd, J=4.8, 1.6 Hz, 1H), 7.83-7.75 (m, 1H), 7.62 (d, J=15.7 Hz, 1H), 7.35-7.29 (m, 1H), 6.45 (d, J=15.7 Hz, 1H), 5.68 (t, 1H), 4.18-3.90 (m, 2H), 3.40 (td, J=7.2, 5.9 Hz, 2H), 2.76-2.55 (m, 2H), 1.70-1.51 (m, 4H), 1.45 (s, 9H), 1.43-1.31 (m, 3H), 1.31-1.20 (m, 2H), 1.07 (qd, J=12.5, 4.4 Hz, 2H).

Example 2. (E)-N-(4-(piperidin-4-yl)butyl)-3-(pyridin-3-yl)acrylamide (2)

Compound 1 (1.06 g, 2.75 mmol) was dissolved in dichloromethane (15 mL) and treated with TFA (3 mL) for 90 minutes. The reaction was concentrated in vacuo, redissolved in 1:1 MeCN:H$_2$O, and concentrated again to the title compound as the di-TFA salt (1.30 g, 2.69 mmol, 98%). LCMS: $t_R$=0.46 min; m/z=288.2 [M+H]$^+$. $^1$H NMR (400 MHz, Methanol-d4) δ 9.01-8.93 (m, 1H), 8.74 (dd, J=5.5, 1.4 Hz, 1H), 8.60 (dtt, J=8.2, 1.5, 0.6 Hz, 1H), 7.99-7.87 (m, 1H), 7.61 (d, J=15.8 Hz, 1H), 6.88 (d, J=15.8 Hz, 1H), 3.40-3.28 (m, 6H), 2.95 (td, m, 2H), 2.02-1.86 (m, 2H), 1.69-1.53 (m, 3H), 1.50-1.24 (m, 6H).

Example 3. (E)-N-(4-(1-(3-aminobenzoyl)piperidin-4-yl)butyl)-3-(pyridin-3-yl)acrylamide (3)

3

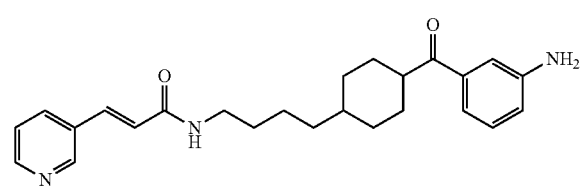

To a reaction vessel containing compound 2 (30 mg, 0.058 mmol) and 3-((tert-butoxycarbonyl)amino)benzoic acid (14 mg, 0.058 mmol) was added a 0.25 M solution of EDC in DCM (350 μL, 0.087 mmol) followed by a 0.25 M solution of DMAP in DCM (350 μL, 0.087 mmol) and DIPEA (51 μL, 0.29 mmol). The reaction was stirred for 3 hours, then concentrated in vacuo. The crude material was redissolved in EtOAc and washed twice with water, once with saturated NH$_4$Cl, and once with brine. The organic layer was dried over Na$_2$SO$_4$ and concentrated. The resulting intermediate product was treated with 30% TFA in DCM for 30 minutes, then concentrated in vacuo. Purification by preparative HPLC afforded the title compound (22.1 mg, 0.042 mmol, 73%). LCMS: $t_R$=0.66 min; m/z=407.3 [M+H]$^+$.

Example 5. (E)-N-(4-(1-(4-aminobenzoyl)piperidin-4-yl)butyl)-3-(pyridin-3-yl)acrylamide (4)

4

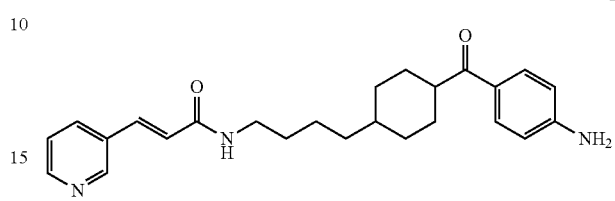

The title compound was prepared according to the method for compound 3 using 4-((tert-butoxycarbonyl)amino)benzoic acid as the starting acid. LCMS: $t_R$=0.67 min; m/z=407.3 [M+H]$^+$.

Example 6. (E)-N-(4-(1-(2-aminobenzoyl)piperidin-4-yl)butyl)-3-(pyridin-3-yl)acrylamide (5)

5

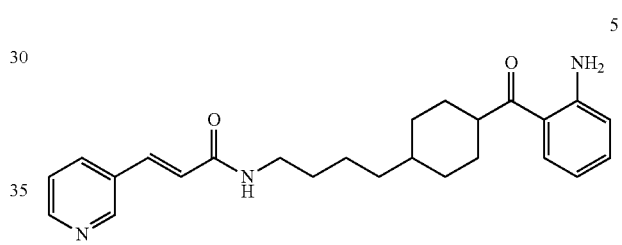

The title compound was prepared according to the method for compound 3 using 2-((tert-butoxycarbonyl)amino)benzoic acid as the starting acid. LCMS: $t_R$=0.88 min; m/z=407.3 [M+H]$^+$.

Example 7. (E)-N-(4-(1-(3-hydroxybenzoyl)piperidin-4-yl)butyl)-3-(pyridin-3-yl)acrylamide (6)

6

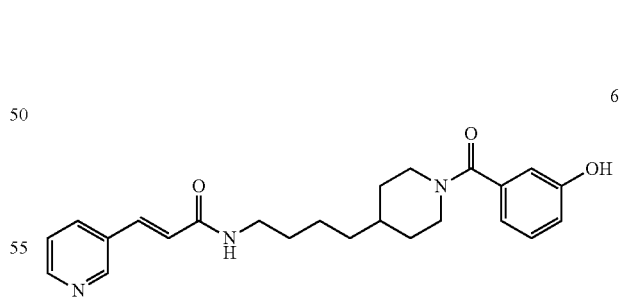

To a reaction vessel containing Compound 2 (30 mg, 0.058 mmol) and 3-hydroxybenzoic acid (8.0 mg, 0.058 mmol) was added a 0.25 M solution of EDC in DCM (350 μL, 0.087 mmol) followed by a 0.25 M solution of DMAP in DCM (350 μL, 0.087 mmol) and DIPEA (51 μL, 0.29 mmol). The reaction was stirred for 3 hours, then concentrated in vacuo. Purification by preparative HPLC afforded the title compound (12.1 mg, 0.023 mmol, 40%). LCMS: $t_R$=0.79 min; m/z=408.3 [M+H]$^+$.

Example 8. (E)-N-(4-(1-(4-hydroxybenzoyl)piperidin-4-yl)butyl)-3-(pyridin-3-yl)acrylamide (7)

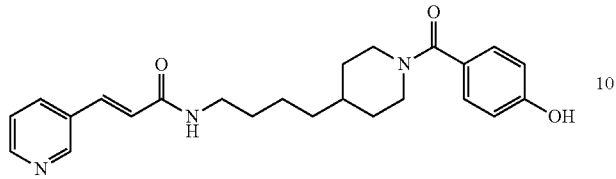

7

The title compound was prepared according to the method for compound 6 using 4-hydroxybenzoic acid as the starting acid. LCMS: $t_R$=0.74 min; m/z=408.3 [M+H]$^+$.

Example 9. (E)-N-(4-(1-(2-hydroxybenzoyl)piperidin-4-yl)butyl)-3-(pyridin-3-yl)acrylamide (8)

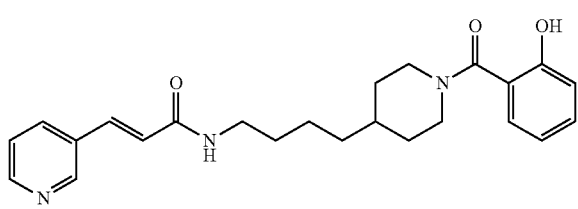

8

The title compound was prepared according to the method of compound 6 using 2-hydroxybenzoic acid as the starting acid. LCMS: $t_R$=1.18 min; m/z=408.2 [M+H]$^+$.

Example 10. (E)-N-(4-(1-(3-(2-hydroxyethoxy)benzoyl)piperidin-4-yl)butyl)-3-(pyridin-3-yl)acrylamide (9)

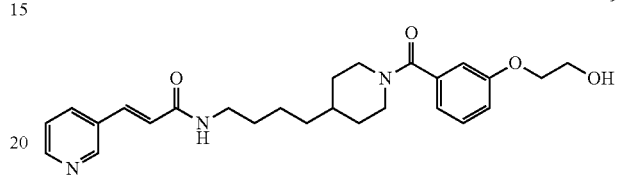

9

The title compound was prepared according to the method of compound 6 using 3-(2-hydroxyethoxy)benzoic acid as the starting acid LCMS: $t_R$=0.79 min; m/z=452.3 [M+H]$^+$.

Example 11. (E)-N-(4-(1-(4-(2-hydroxyethoxy)benzoyl)piperidin-4-yl)butyl)-3-(pyridin-3-yl)acrylamide (10)

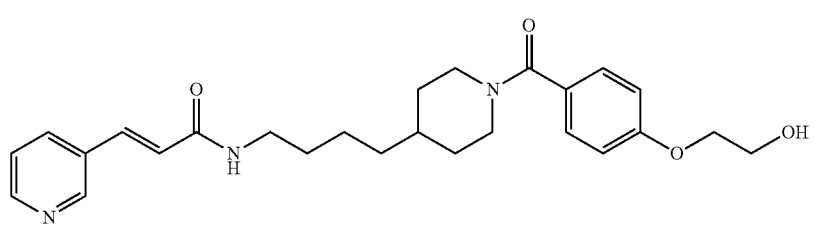

10

The title compound was prepared according to the method for compound 6 using 4-(2-hydroxyethoxy)benzoic acid as the starting acid. LCMS: $t_R$=0.74 min; m/z=452.3[M+H]$^+$.

Example 12. Methyl (E)-3-nitro-5-(4-(4-(3-(pyridin-3-yl)acrylamido)butyl)-piperidine-1-carbonyl)benzoate (11)

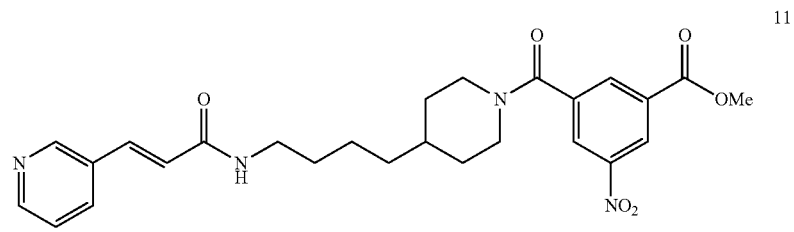 [SMILES: COC(=O)c1cc(N)cc(C(=O)N2CCC(CCCCNC(=O)/C=C/c3cccnc3)CC2)c1]

11

The title compound was prepared according to the method of compound 6 using 3-(methoxycarbonyl)-5-nitrobenzoic acid as the starting acid. LCMS: $t_R$=1.10 min; m/z=495.4 [M+H]$^+$.

Example 13. Methyl (E)-3-amino-5-(4-(4-(3-(pyridin-3-yl)acrylamido)butyl)-piperidine-1-carbonyl)benzoate (12)

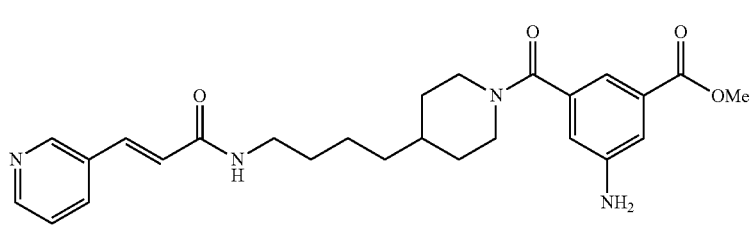

To a stirred solution of 11 (35 mg, 0.057 mmol) in 10:1 MeOH:AcOH was added Zn dust (~40 mg) in portions. After 2 hours, the reaction was filtered through a Celite plug and concentrated in vacuo. The residue was redissolved in DMSO and purified by preparative HPLC to provide the title compound (24 mg, 0.052 mmol, 91%). LCMS: $t_R$=0.89 min; m/z=465.4 [M+H]$^+$.

Example 14. (E)-3-amino-5-(4-(4-(3-(pyridin-3-yl)acrylamido)butyl)-piperidine-1-carbonyl)benzoic acid (13)

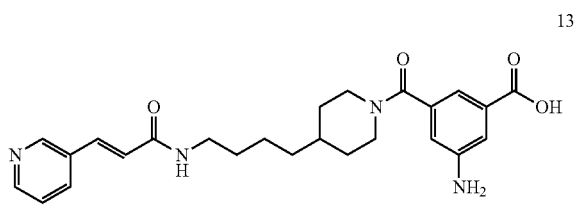 [SMILES: Nc1cc(C(=O)O)cc(C(=O)N2CCC(CCCCNC(=O)/C=C/c3cccnc3)CC2)c1]

To a stirred solution of 12 (5.0 mg, 0.011 mmol) in 1:1 MeOH:THF (500 µL) was added a 0.2 M solution of LiOH (269 µl, 0.054 mmol). The reaction was stirred at room temperature for 6 hours, then quenched with 1M HCl. The reaction was concentrated in vacuo, then redissolved in DMSO and purified by preparative HPLC to provide the title compound (3.9 mg, 0.007 mmol, 64%). LCMS: $t_R$=0.75 min; m/z=451.4 [M+H]$^+$.

Example 15. (2S,3R,4S,5S,6S)-2-(2-(3-((((9H-fluoren-9-yl)methoxy)carbonyl)amino)propanamido)-4-((((3-(4-(4-((E)-3-(pyridin-3-yl)acrylamido)butyl)piperidine-1-carbonyl)phenyl)carbamoyl)oxy)methyl)phenoxy)-6-(methoxycarbonyl)tetrahydro-2H-pyran-3,4,5-triyl triacetate (14)

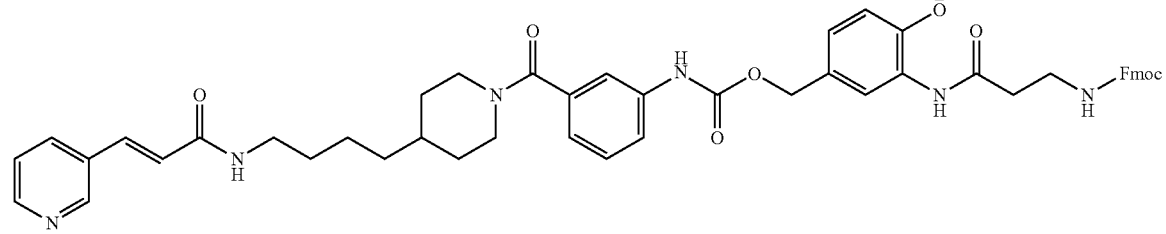

Compound 3 (241 mg, 0.59 mmol) and methyl (2S,3S,4S,5R,6S)-3,4,5-tris(acetyloxy)-6-[2-(3-{[(9H-fluoren-9-yl-methoxy)carbonyl]amino}propanamido)-4-{[(4-nitrophenoxycarbonyl)oxy]methyl}phenoxy]oxane-2-carboxylate (596 mg, 0.65 mmol, prepared according to the procedure of *Bioconjugate Chem.* 2006, 17, 831-840) were dissolved in DMF (4 mL) and pyridine (1 mL). HOAc (32 mg, 0.24 mmol) was added as a solution in DMF, and the reaction stirred at room temperature overnight. The reaction was poured into EtOAc, and the organic layer washed 2× water, 3× saturated NaHCO₃, and 3×5% LiCl. The organic layer was dried over Na₂SO₄ and concentrated in vacuo. The crude product was purified by silica gel chromatography to provide the title compound (550 mg, 0.47 mmol, 79%). LCMS: $t_R$=1.48 min; m/z=1181.5 [M+H]⁺.

Example 16. (2S,3S,4S,5R,6S)-6-(2_(3-aminopropanamido)-4-((((3-(4-(4-((E)-3-(pyridin-3-yl)acrylamido)butyl)piperidine-1-carbonyl)phenyl)carbamoyl)oxy)-methyl)phenoxy)-3,4,5-trihydroxytetrahydro-2H-pyran-2-carboxylic acid (15)

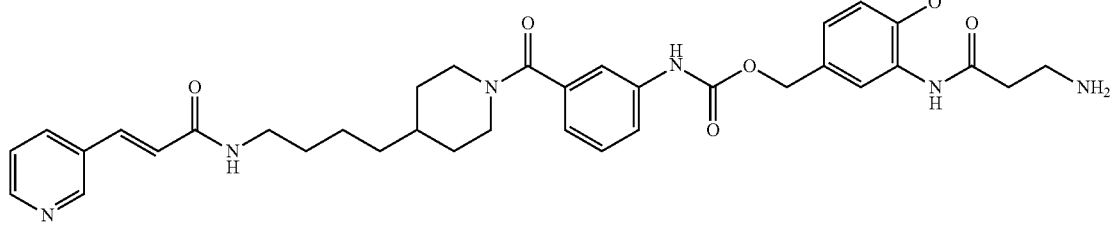

Compound 14 (550 mg, 0.47 mmol) was dissolved in THF (12 mL) and MeOH (12 mL) and cooled on ice. A solution of LiOH (0.2M, 23 ml, 4.6 mmol) was slowly added. After 30 minutes, the reaction was removed from ice and allowed to warm to room temperature. After 4 hours, the reaction was washed three times with EtOAc, and the aqueous phase concentrated to provide crude product which was further purified by preparative HPLC to give the title compound (78 mg, 0.075 mmol, 16%). LCMS: $t_R$=0.78 min; m/z=819.4 [M+H]⁺.

Example 17. (2S,3S,4S,5R,6S)-6-(2-(3-((S)-3-((tert-butoxycarbonyl)-amino)-2-(2,5-dioxo-2,5-dihydro-1H-pyrrol-1-yl)propanamido)propanamido)-4-((((3-(4_(4-((E)-3-(pyridin-3-yl)acrylamido)butyl)piperidine-1-carbonyl)phenyl)-carbamoyl)oxy)methyl)-phenoxy)-3,4,5-trihydroxytetrahydro-2H-pyran-2-carboxylic acid (16)

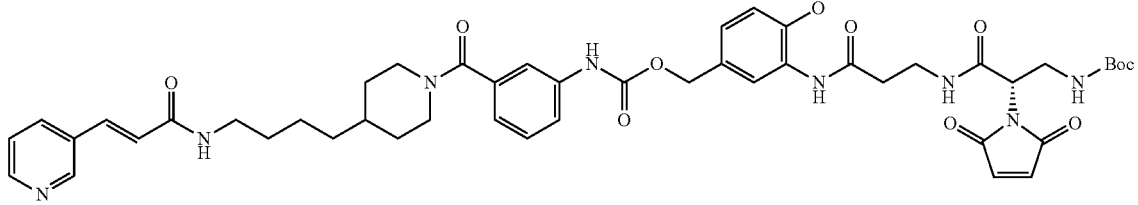

Compound 15 (78 mg, 0.075 mmol) was dissolved in DMF (0.7 μl) and DIPEA (39 μl, 0.22 mmol) followed by addition of 2,5-dioxopyrrolidin-1-yl (2S)-3-[(tert-butoxycarbonyl)amino]-2-(2,5-dioxopyrrol-1-yl)propanoate (30 mg, 0.078 mmol). After 3 hours, the reaction was diluted with DMSO and purified by preparative HPLC to give the title compound (80 mg, 0.067 mmol, 90%). LCMS: $t_R$=1.02 min; m/z=1085.5 [M+H]$^+$.

Example 18. (2S,3S,4S,5R,6S)-6-(2-(3-((S)-3-amino-2-(2,5-dioxo-2,5-dihydro-1H-pyrrol-1-yl)propanamido)propanamido)-4-((((3-(4-(4-((E)-3-(pyridin-3-yl)acrylamido)butyl)piperidine-1-carbonyl)phenyl)carbamoyl)oxy)methyl)phenoxy)-3,4,5-trihydroxytetrahydro-2H-pyran-2-carboxylic acid (17)

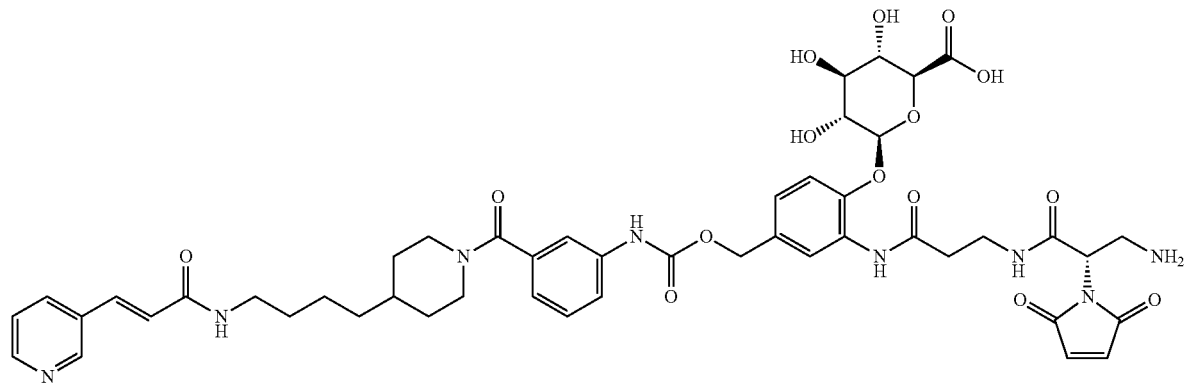

17

Compound 16 (80 mg, 0.067 mmol) was treated with 20% TFA in DCM (6 mL) for 1 hour. The solvent was removed in vacuo, and the residue dissolved in DMSO and purified by preparative HPLC to provide the title compound (66.5 mg, 0.055 mmol, 82%). LCMS: $t_R$=0.81 min; m/z=985.4 [M+H]$^+$.

Example 19. (2S,3S,4S,5R,6S)-6-(2-((S)-44-((((9H-fluoren-9-yl)methoxy)carbonyl)amino)-38,45-dioxo-2,5,8,11,14,17,20,23,26,29,32,35-dodecaoxa-39,46-diazanonatetracontan-49-amido)-4-((((3-(4-(4-((E)-3-(pyridin-3-yl)acrylamido)-butyl)piperidine-1-carbonyl)phenyl)carbamoyl)oxy)methyl)phenoxy)-3,4,5-trihydroxy-tetrahydro-2H-pyran-2-carboxylic acid (18)

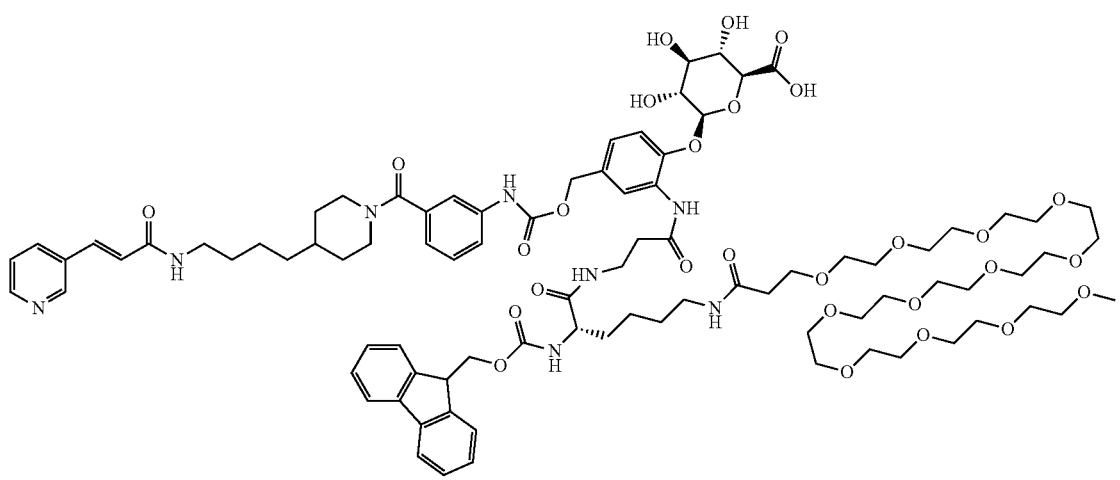

18

A solution of Fmoc-Lys(PEG12)-OSu (70 mg, 0.068 mmol) in DMF (1 mL) was added to compound 15 (55.4 mg, 0.068 mmol). DIPEA (47 μL, 0.27 mmol) was added and the reaction stirred at room temperature for 4 hours. The reaction was purified by preparative HPLC to give the title compound (88.8 mg, 0.051 mmol, 75%). LCMS: $t_r$=1.22 min; m/z=1740.9 [M+H]$^+$.

Example 20. (2S,3S,4S,5R,6S)-6-(2-((S)-44-amino-38,45-dioxo-2,5,8,11,14,17,20,23,26,29,32,35-dodecaoxa-39,46-diazanonatetracontan-49-amido)-4-((((3-(4-(4-((E)-3-(pyridin-3-yl)acrylamido)butyl)piperidine-1-carbonyl)phenyl)-carbamoyl)oxy)methyl)phenoxy)-3,4,5-trihydroxytetrahydro-2H-pyran-2-carboxylic acid (19)

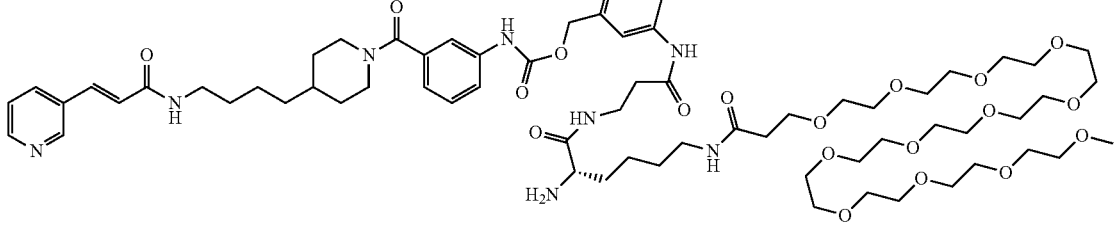

19

Compound 19 was prepared from compound 18 by the method of Compound 15. LCMS: $t_R$=0.88 min; m/z=1517.8 [M+H]$^+$.

Example 21. (2S,3S,4S,5R,6S)-6-(2-((S)-44-((S)-3-((tert-butoxycarbonyl)-amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontan-49-amido)-4-((((3-(4-(4-((E)-3-(pyridin-3-yl)acrylamido)butyl)piperidine-1-carbonyl)phenyl)-carbamoyl)oxy)methyl)phenoxy)-3,4,5-trihydroxytetrahydro-2H-pyran-2-carboxylic acid (20)

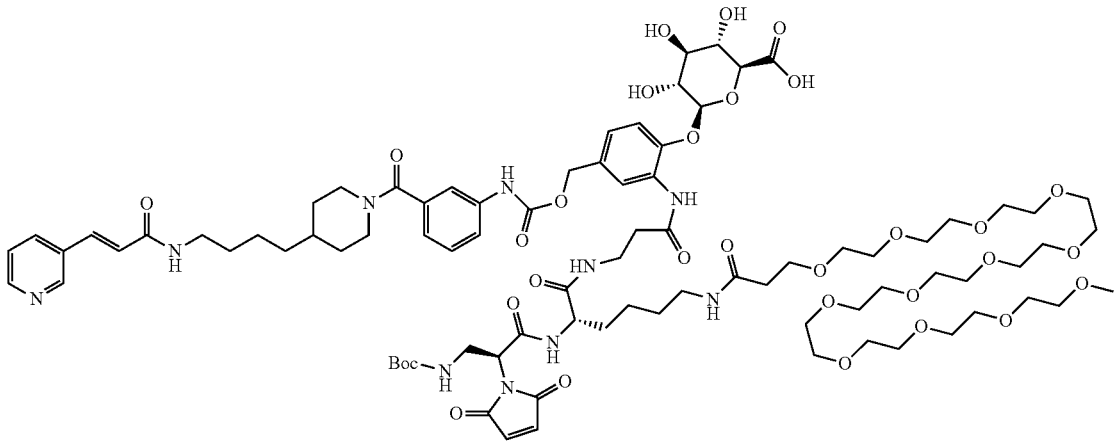

20

Compound 20 prepared from compound 19 by the method of Compound 16. LCMS: $t_R$=1.04 min; m/z=1784.9 [M+H]$^+$.

Example 22. (2S,3S,4S,5R,6S)-6-(2-((S)-44-((S)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontan-49-amido)_4-((((3-(4_(4-((E)-3-(pyridin-3-yl)acrylamido)butyl)piperidine-1-carbonyl)phenyl)carbamoyl)oxy)methyl)phenoxy)-3,4,5-trihydroxytetrahydro-2H-pyran-2-carboxylic acid (21)

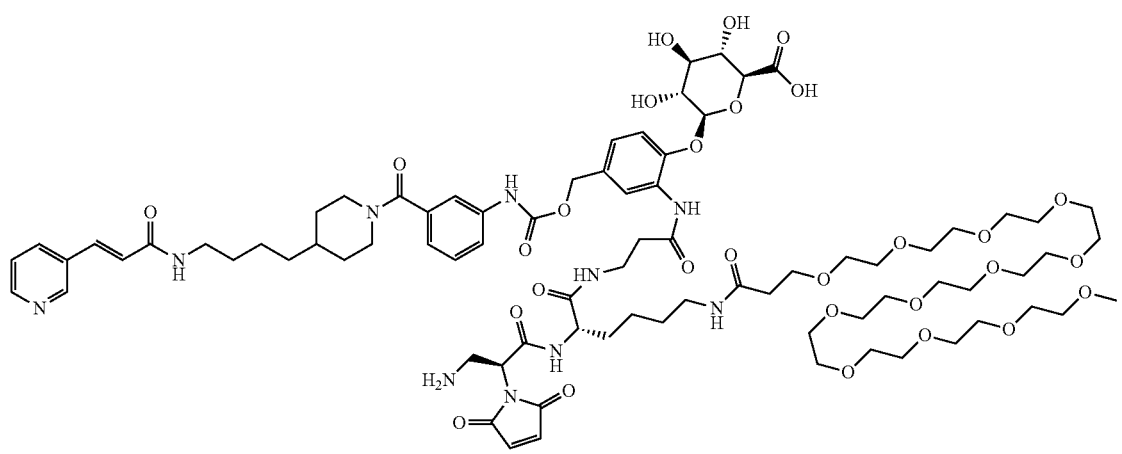

Compound 21 was prepared by the method of compound 17. LCMS: $t_R$=0.86 min; m/z=1683.8 [M+H]$^+$.

Example 23. (2S,3R,4S,5S,6S)-2-(2-(3-(((((9H-fluoren-9-yl)methoxy)-carbonyl)amino)propanamido)-4-((3-(4-(4-((E)-3-(pyridin-3-yl)acrylamido)butyl)-piperidine-1-carbonyl)phenoxy)methyl)phenoxy)-6-(methoxycarbonyl)tetrahydro-2H-pyran-3,4,5-triyl triacetate (22)

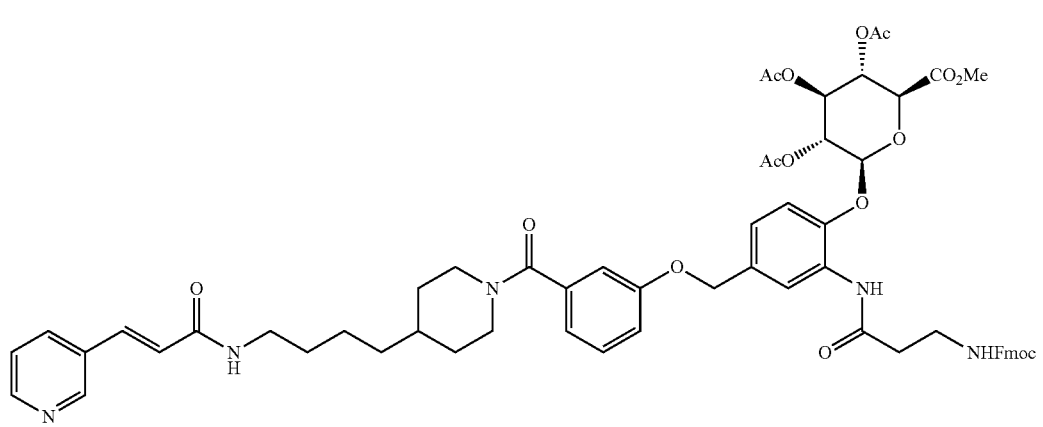

Compound 6 (27.5 mg, 0.053 mmol) and (2S,3R,4S,5S,6S)-2-(2-(3-(((((9H-fluoren-9-yl)methoxy)carbonyl)amino)propanamido)-4-(bromomethyl)phenoxy)-6-(methoxycarbonyl)tetrahydro-2H-pyran-3,4,5-triyl triacetate (43 mg, 0.053 mmol), prepared according to *Mol. Cancer Ther.* 15(5): 938-945, were dissolved in DMF. K$_2$CO$_3$ (15 mg, 0.11 mmol) was added and the reaction stirred at 40° C. After 45 minutes, the reaction was quenched by addition of acetic acid (30 μL). The product was purified by preparative HPLC to give the title compound (6.2 mg, 0.005 mmol, 13%). LCMS: t$_R$=1.44 min; m/z=1138.7 [M+H]$^+$.

Example 24. (2S,3S,4S,5R,6S)-6-(2_(3-aminopropanamido)-4-((3-(4-(4-((E)-3-(pyridin-3-yl)acrylamido)butyl)piperidine-1-carbonyl)phenoxy)methyl)phenoxy)-3,4,5-trihydroxytetrahydro-2H-pyran-2-carboxylic acid (23)

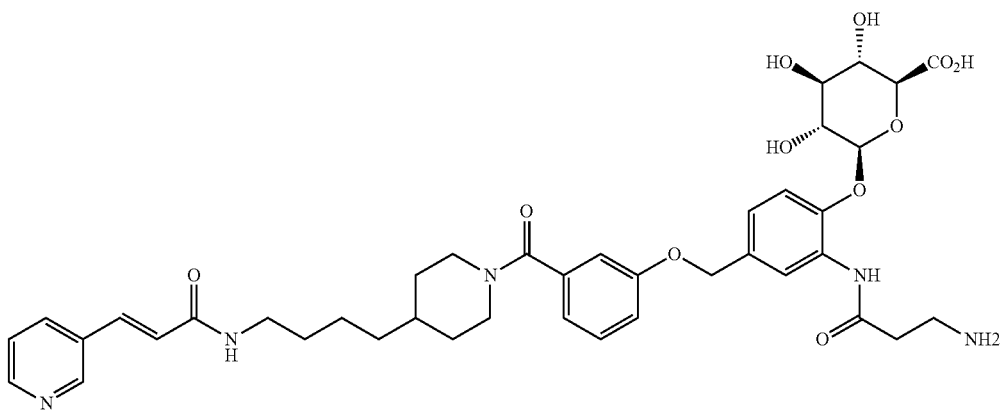

Compound 23 was prepared from compound 22 by the method of Compound 15. LCMS: t$_R$=0.75 min; m/z=776.5 [M+H]$^+$.

Example 25. (2S,3S,4S,5R,6S)-6-(2-(3-(3-(2,5-dioxo-2,5-dihydro-1H-pyrrol-1-yl)propanamido)propanamido)-4-((3-(4-(4-((E)-3-(pyridin-3-yl)acrylamido)butyl)-piperidine-1-carbonyl)phenoxy)methyl)phenoxy)-3,4,5-trihydroxytetrahydro-2H-pyran-2-carboxylic acid (24)

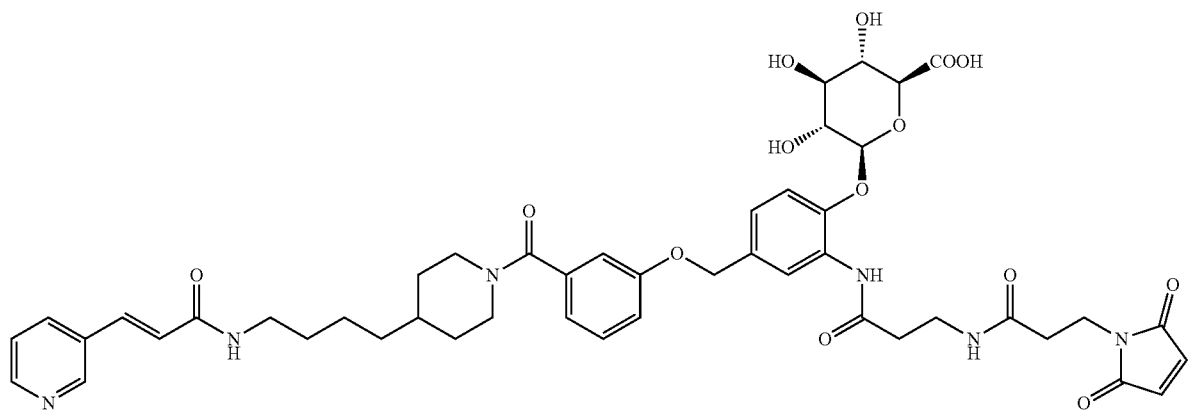

Compound 23 (1.9 mg, 0.002 mmol) was treated with 2,5-dioxopyrrolidin-1-yl 3-(2,5-dioxo-2,5-dihydro-1H-pyrrol-1-yl)propanoate (0.7 mg, 0.003 mmol) and DIPEA (1.3 µl, 0.007 mmol) in DMF (72 µl). After 45 minutes, the reaction was diluted with DMSO and purified by preparative HPLC to give the title compound (1.6 mg, 71%). LCMS: $t_R$=0.86 min, m/z=927.6 [M+H]$^+$.

Example 26. (2S,3R,4S,5S,6S)-2-(2-(2-((((9H-fluoren-9-yl)methoxy)-carbonyl)(methyl)amino)acetamido)-4-(((((3-(((di-tert-butyl(isobutyl)silyl)oxy)carbonyl)-phenoxy)methyl)(2-(methylsulfonyl)ethyl)carbamoyl)-oxy)methyl)phenoxy)-6-(methoxycarbonyl)-tetrahydro-2H-pyran-3,4,5-triyl triacetate (25)

Example 27. 3-(((((3-(2-((((9H-fluoren-9-yl)methoxy)carbonyl)(methyl-)amino)acetamido)-4-(((2S,3R,4S,5S,6S)-3,4,5-triacetoxy-6-(methoxycarbonyl)tetrahydro-2H-pyran-2-yl)oxy)benzyl)oxy)carbonyl)(2-(methylsulfonyl)ethyl)amino)methoxy)benzoic acid (26)

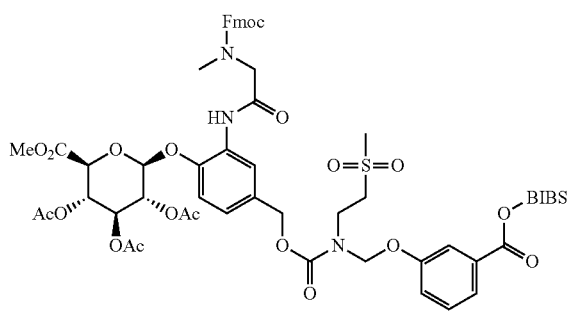

25

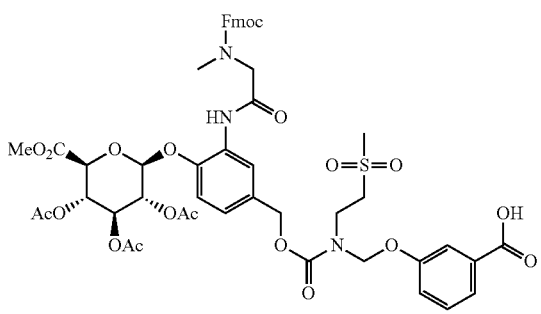

26

(2S,3R,4S,5S,6S)-2-(2-(2-(((((9H-fluoren-9-yl)methoxy)carbonyl)(methyl)-amino)acetamido)-4-(((((2-(methylsulfonyl)ethyl)carbamoyl)oxy)methyl)phenoxy)-6-(methoxycarbonyl)tetrahydro-2H-pyran-3,4,5-triyl triacetate (131 mg, 0.146 mmol), prepared according to *Angew. Chem. Int. Ed.* 2016, 55, 7948, was dissolved in DCM (1.5 mL) and treated with paraformaldehyde (131 mg, 4.4 mmol), TMSCl (500 µL), and water (1 µL) in succession. After 90 minutes, the reaction was filtered through a 0.45 micron syringe filter. Anhydrous toluene (3 mL) was added to the filtrate prior to concentration. This activated intermediate was dried under high vacuum for one hour. Di-tert-butyl(isobutyl)silyl 3-hydroxybenzoate was dried by azeotroping three times from anhydrous toluene. The activated intermediate and phenol derivative were combined in anhydrous DCM (1 mL) and treated with DIPEA (76 µL, 0.44 mmol). After one hour, the reaction was diluted with EtOAc and washed three times with saturated $NH_4C_1$. The organic layer was dried over $Na_2SO_4$ and concentrated. The crude material was purified by silica gel chromatography to provide the title compound (108 mg, 0.087 mmol, 59%). LCMS: $t_R$=2.07 min (hydrophobic method), m/z=1268.5 [M+Na]$^+$.

Compound 25 (108 mg, 0.087 mmol) was dissolved in 10:1 THF:pyridine (900 µL) and treated with HF:pyridine (50 µL). After 90 minutes, the reaction was quenched by addition of excess TMSOEt. The crude material was concentrated in vacuo, redissolved in DMSO, and purified by preparative HPLC to provide the titled compound (9 mg, 0.009 mmol, 10%). LCMS: $t_R$=1.52 min (hydrophobic method); m/z=1070.4 [M+Na]$^+$.

Example 28. (2S,3R,4S,5S,6S)-2-(2-(2-(((((9H-fluoren-9-yl)methoxy)-carbonyl)(methyl)amino)acetamido)-4-(((((2-(methylsulfonyl)ethyl)((3-(4-(4-((E)-3-(pyridin-3-yl)acrylamido)butyl)piperidine-1-carbonyl)phenoxy)methyl-)carbamoyl)-oxy)methyl)phenoxy)-6-(methoxycarbonyl)tetrahydro-2H-pyran-3,4,5-triyl triacetate (27)

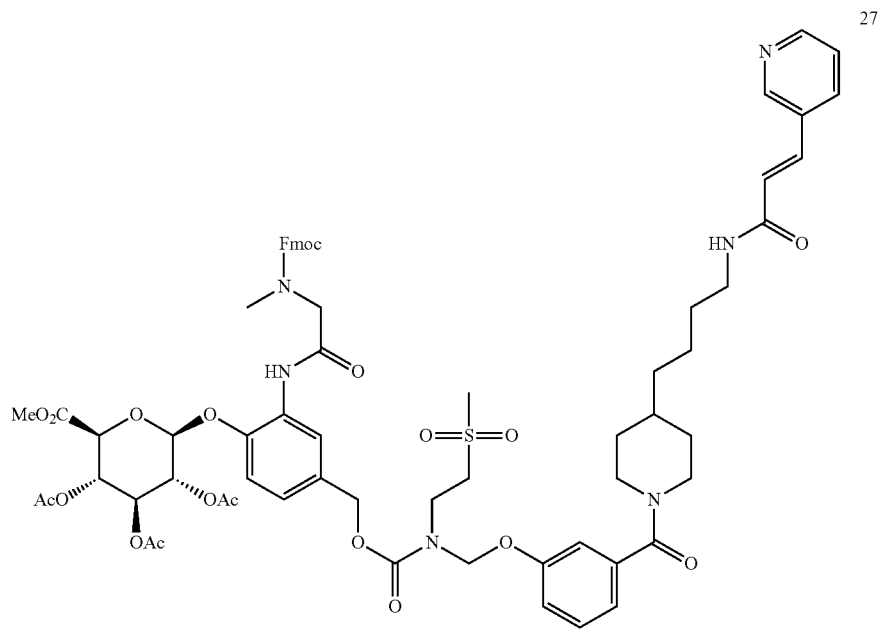

Compound 26 (9 mg, 0.009 mmol) was treated with HATU (3.6 mg, 0.009 mmol) and DIPEA (4.5 µL, 0.026 mmol) for 5 min in DMF (100 µl). Compound 2 (2.7 mg, 0.009 mmol) was then added. After 5 minutes, the reaction as diluted with DMF and purified by preparative HPLC to give the title compound (8.3 mg, 0.006 mmol, 73%). LCMS: $t_R$=1.45 min (hydrophobic method); m/z=1317.6 [M+H]$^+$.

Example 29. (2S,3S,4S,5R,6S)-3,4,5-trihydroxy-6-(2-(2-(methylamino)-acetamido)-4-((((2-(methylsulfonyl)ethyl)((3-(4-(4-((E)-3-(pyridin-3-yl)acrylamido)butyl-)piperidine-1-carbonyl)phenoxy)methyl)carbamoyl)oxy)methyl)-phenoxy)tetrahydro-2H-pyran-2-carboxylic acid (28)
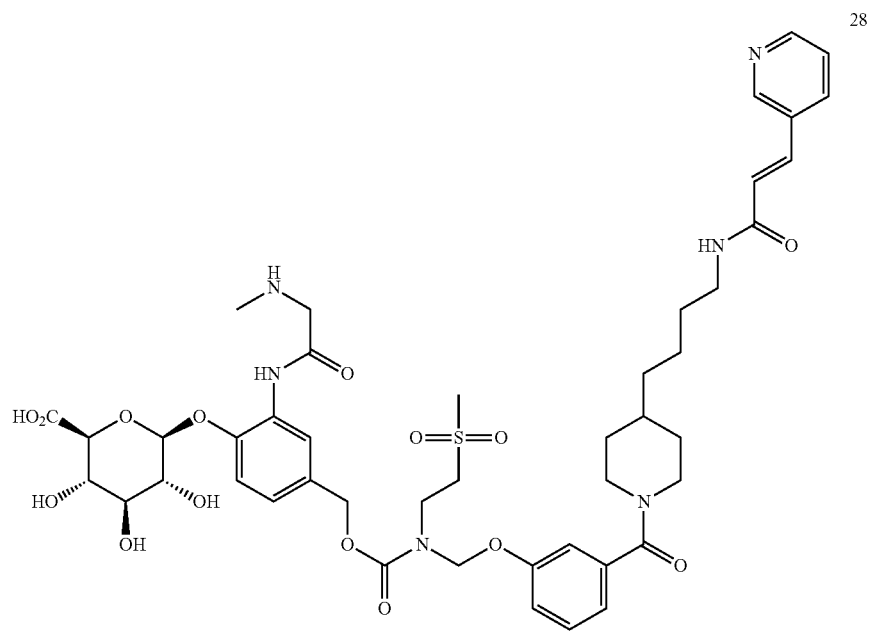 [SMILES: CNCC(=O)Nc1cc(COC(=O)N(CCS(C)(=O)=O)COc2cccc(C(=O)N3CCC(CCCCNC(=O)/C=C/c4cccnc4)CC3)c2)ccc1O[C@@H]1O[C@H](C(=O)O)[C@@H](O)[C@H](O)[C@H]1O]
Compound 28 was prepared from compound 27 according to the method for Compound 15. LCMS: $t_R$=0.74 min; m/z=955.5 [M+H]$^+$.

Example 30. (2S,3S,4S,5R,6S)-6-(2-(2-(3-(2,5-dioxo-2,5-dihydro-1H-pyrrol-1-yl)-N-methylpropanamido)acetamido)-4-((((2-(methylsulfonyl)ethyl)((3-(4-(4-((E)-3-(pyridin-3-yl)acrylamido)butyl)piperidine-1-carbonyl)phenoxy)methyl)carbamoyl)oxy-)methyl)phenoxy)-3,4,5-trihydroxytetrahydro-2H-pyran-2-carboxylic acid (29)

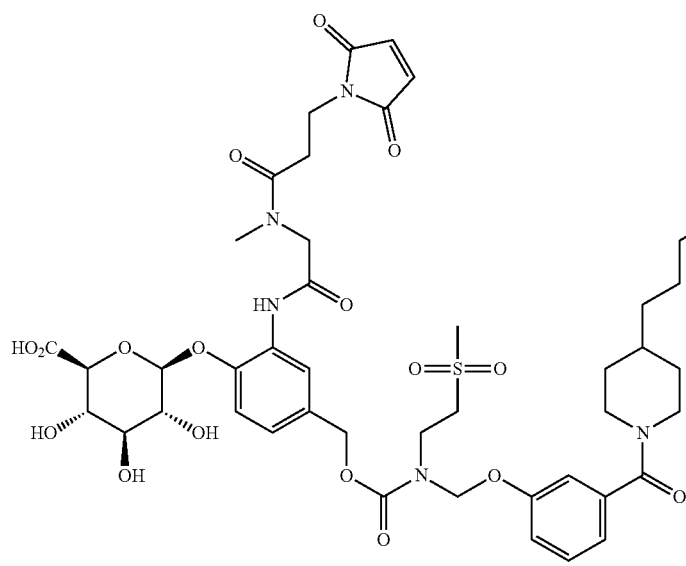

Compound 28 (4.7 mg, 0.005 mmol) was treated with 2,5-dioxopyrrolidin-1-yl 3-(2,5-dioxo-2,5-dihydro-1H-pyrrol-1-yl)propanoate (5.2 mg, 0.020 mmol) and DIPEA (6.9 μL, 0.039 mmol) in DMF (100 μL). After 3 hours, the reaction was diluted with DMSO and purified by preparative HPLC to provide the title compound (0.78 mg, 0.001 mmol, 14%). LCMS: $t_R$=0.90 min; m/z=1106.5[M+H]$^+$.

Example 31. tert-butyl (2-((cyclohexylideneamino)oxy)ethyl)(methyl)-carbamate (36)

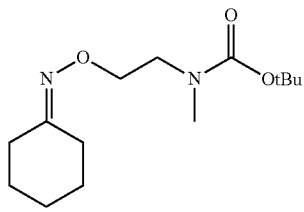

Cyclohexanone oxime (478 mg, 4.22 mmol) taken up in 8 mL DMF and chilled in an ice bath. NaH (338 mg, 14.08 mmol, 60% dispersion in mineral oil) added portion-wise, and the reaction mixture stirred at 0° C. for 1 h under argon, after which point tert-butyl (2-chloroethyl)(methyl)carbamate (818 mg, 4.22 mmol) in 2 mL DMF was added, the ice bath removed, and the reaction mixture stirred at room temp 20 h, then heated for 3 h at 60° C. The mixture was cooled, filtered, the filtrate concentrated in vacuo, and the residue partitioned between sat'd NH$_4$Cl and ether. The aqueous extract was extracted an additional time with ether, and the combined organic extracts washed once with 0.5M NaOH, once with brine, dried over MgSO$_4$, filtered, and concentrated in vacuo to provide the title compound (696 mg, 2.57 mmol, 61%). LCMS: $t_R$=1.56 min; m/z=293.2[M+H]$^+$. $^1$HNMR (400 MHz, CDCl$_3$, δ): 1.46 (s, 9H), 1.56-1.73 (m, 6H), 2.18-2.23 (m, 2H), 2.45 (t, J=6.3 Hz, 2H), 2.91 (s, 3H), 3.40-3.54 (m, 2H), 4.05-4.17 (m, 2H).

Example 32. tert-butyl (2-((cyclohexylamino)oxy)ethyl)(methyl)carbamate (37)

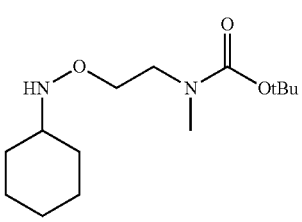

Compound 36 (696 mg, 2.57 mmol) was taken up in 10 mL MeOH and chilled in an ice bath. A small amount of methyl orange was added, then sodium cyanoborohydride (323 mg, 5.15 mmol). To the yellow solution, 2 M HCl in MeOH added until color changed to pink. Stirred 30 min on ice, then ice bath removed and stirred at room temp 4 h. The reaction mixture was concentrated in vacuo, then suspended in water, upon which the pH of mixture was adjusted to 9 with 6 N KOH, diluted with an equal volume of brine, and extracted four times with CH₂Cl₂. The combined organic extracts were washed with brine, dried over Na₂SO₄, filtered, and concentrated in vacuo. The crude product was purified by silica gel chromatography (MeOH/CH₂Cl₂) to provide compound 37 (534 mg, 1.96 mmol, 76%). LCMS: $t_R$=1.56 min; m/z=293.2 [M+H]⁺. ¹HNMR (400 MHz, CDCl₃, δ): 1.02-1.33 (m, 4H), 1.46 (s, 9H), 1.54-1.68 (m, 2H), 1.74 (dt, J=13.3, 3.9 Hz, 2H), 1.80-1.90 (m, 2H), 2.66-2.85 (m, 1H), 2.88 (s, 3H), 3.30-3.53 (m, 2H), 3.77 (t, J=5.3 Hz, 2H), 5.50 (br s, 1H).

Example 33. tert-butyl (12-cyclohexyl-1-(9H-fluoren-9-yl)-3,11-dioxo-2,13-dioxa-4,12-diazapentadecan-15-yl)(methyl)carbamate (38)

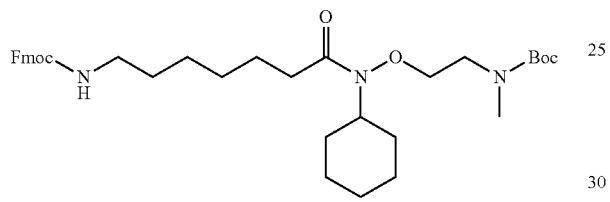

38

A solution of Fmoc-aminoheptanoic acid (720 mg, 1.96 mmol), NMM (0.26 mL, 2.36 mmol), and HATU (894 mg, 2.36 mmol) in 5 mL DMF was added to Compound 37 (534 mg, 1.96 mmol) in 5 mL DMF and the reaction mixture stirred at room temp under argon overnight. The reaction mixture was partially concentrated in vacuo, diluted with EtOAc and washed twice with saturated NaHCO₃ solution. The aqueous extract was again extracted with EtOAc, and the combined organic extracts washed once with brine, dried over MgSO₄, filtered, and concentrated in vacuo. The crude product was purified by silica gel chromatography (MeOH/CH₂Cl₂) to provide the title compound (339 mg, 0.55 mmol, 28%). LCMS: $t_R$=1.82 min; m/z=621.3 [M+H]⁺.

Example 34. tert-butyl (2-((7-amino-N-cyclohexyl-heptanamido)oxy)ethyl-(methyl)carbamate (39)

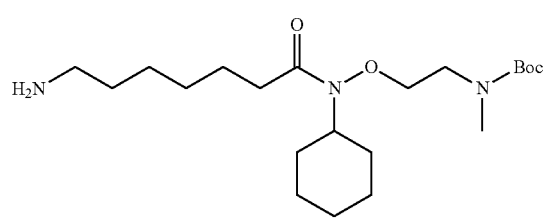

39

Compound 39 was prepared from compound 38 by the method of compound 15. LCMS: $t_r$=1.06 min; m/z=400.4 [M+H]⁺.

Example 35. tert-butyl (2-((N-cyclohexyl-7-(3-(pyridin-4-yl)ureido)-heptanamido)oxy)ethyl)(methyl)carbamate (40)

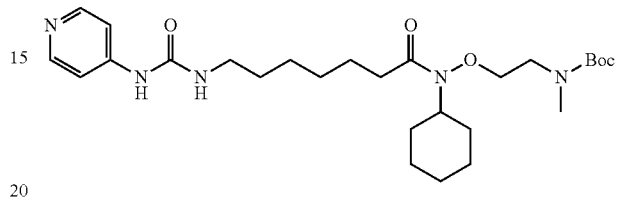

40

Carbonyl ditriazole (358 mg, 2.18 mmol) and 4-aminopyridine (68.4 mg, 0.73 mmol) stirred in 15 mL THF at room temperature overnight. The reaction mixture was diluted with EtOAc and washed once with water, dried over Na₂SO₄, filtered and concentrated in vacuo. The residue was resuspended in 10 mL THF and added to Compound 39 in 10 mL THF with DIEA (0.25 mL, 1.45 mmol) and 2 mL DMF for solubility, and the reaction stirred at room temperature under argon 2.5 h and concentrated in vacuo. The crude product was purified by preparative HPLC to give the title compound (183 mg, 0.35 mmol, 49%). LCMS: $t_R$=1.14 min; m/z=520.4 [M+H]⁺.

Example 36. N-cyclohexyl-N-(2-(methylamino)ethoxy)-7-(3-(pyridin-4-yl)ureido)heptanamide (41)

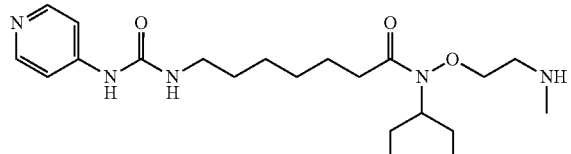

41

The title compound was prepared from compound 40 by the method of compound 17. LCMS: $t_R$=0.73 min; m/z=420.4 [M+H]⁺.

Example 37. tert-butyl (3-((2-((N-cyclohexyl-7-(3-(pyridin-4-yl)ureido)-heptanamido)oxy)ethyl)(methyl)carbamoyl)phenyl)carbamate (42)

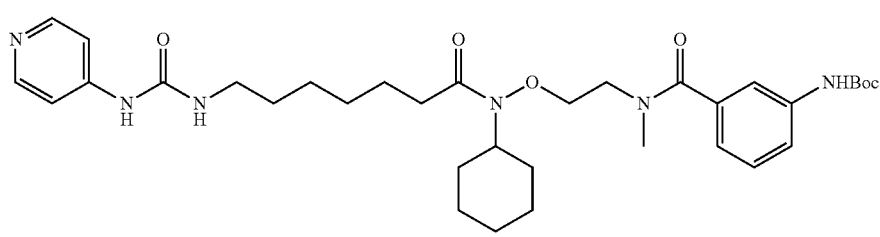

The title compound was prepared from compound 41 according to the method of compound 3 using 3-((tert-butoxycarbonyl)amino)benzoic acid as the acid component. LCMS: $t_R$=1.17 min; m/z=639.5 [M+H]$^+$.

Example 38. 3-amino-N-(2-((N-cyclohexyl-7-(3-(pyridin-4-yl)ureido)-heptanamido)oxy)ethyl)-N-methylbenzamide (43)

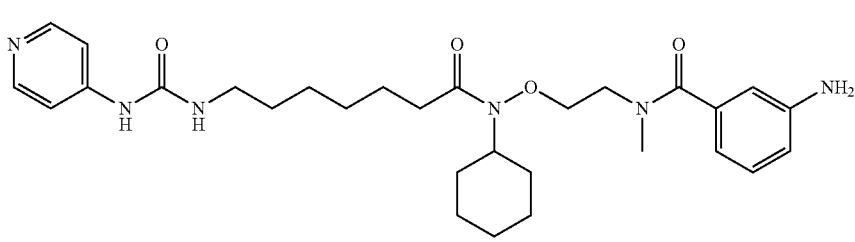

The title compound was prepared from 42 by the method of compound 17. LCMS: $t_R$=0.89 min; m/z=539.4 [M+H]$^+$.

Example 39. (2S,3R,4S,5S,6S)-2-(2-(3-((((9H-fluoren-9-yl)methoxy)-carbonyl)amino)propanamido)-4-((((3-((2-((N-cyclohexyl-7-(3-(pyridin-4-yl)ureido)-heptanamido)oxy)ethyl)(methyl)carbamoyl)phenyl)carbamoyl)oxy)methyl)phenoxy)-6-(methoxycarbonyl)tetrahydro-2H-pyran-3,4,5-triyl triacetate (44)

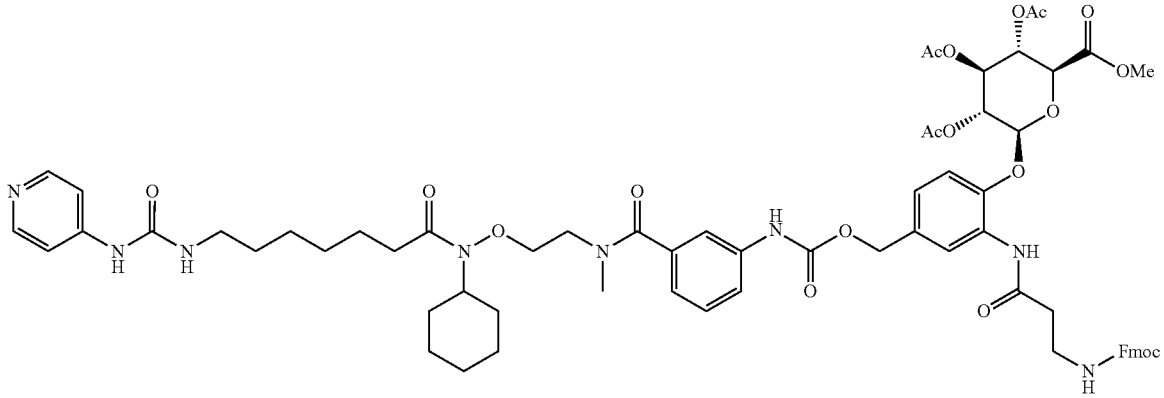

The title compound was prepared from 43 by the method of compound 14. LCMS: $t_R$=1.48 min; m/z=1313.8 [M+H]$^+$.

Example 40. (2S,3S,4S,5R,6S)-6-(2_(3-aminopropanamido)-4-((((3-((2-((N-cyclohexyl-7-(3-(pyridin-4-yl)ureido)heptanamido)oxy)ethyl)(methyl)carbamoyl)-phenyl)-carbamoyl)-oxy)-methyl)phenoxy)-3,4,5-trihydroxytetrahydro-2H-pyran-2-carboxylic acid (45)

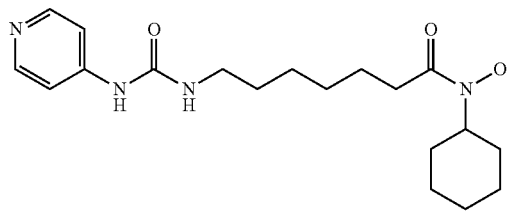
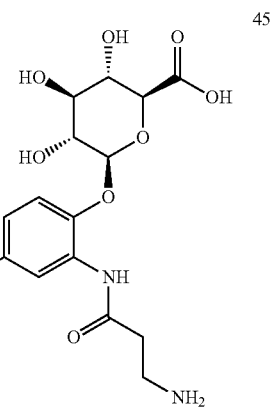

The title compound was prepared from compound 44 by the method of compound 15. LCMS: $t_R$=0.95 min; m/z=951.7 [M+H]$^+$.

Example 41. (2S,3S,4S,5R,6S)-6-(2-(3-((S)-3-((tert-butoxycarbonyl)amino)-2-(2,5-dioxo-2,5-dihydro-1H-pyrrol-1-yl)propanamido)propanamido)-4-((((3-((2-((N-cyclohexyl-7-(3-(pyridin-4-yl)ureido)heptanamido)oxy)ethyl)(methyl)carbamoyl)phenyl)-carbamoyl)oxy)-methyl)phenoxy)-3,4,5-trihydroxytetrahydro-2H-pyran-2-carboxylic acid (46)

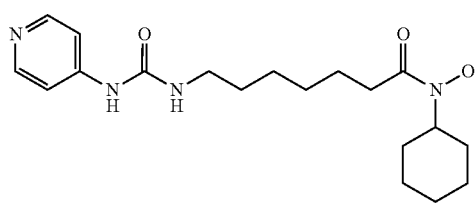
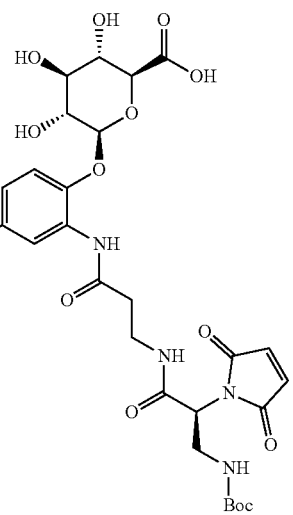

The title compound was prepared from compound 45 by the method of compound 16. LCMS: $t_R$=1.16 min; m/z=1217.8 [M+H]$^+$.

Example 42. (2S,3S,4S,5R,6S)-6-(2-(3-((S)-3-amino-2-(2,5-dioxo-2,5-dihydro-1H-pyrrol-1-yl)propanamido)propanamido)-4-((((3-((2-((N-cyclohexyl-7-(3-(pyridin-4-yl)ureido)heptanamido)oxy)ethyl)(methyl)carbamoyl)phenyl)carbamoyl)oxy)methyl)phenoxy)-3,4,5-trihydroxytetrahydro-2H-pyran-2-carboxylic acid (47)

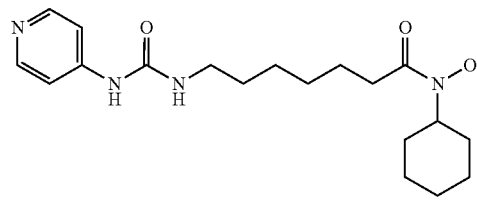
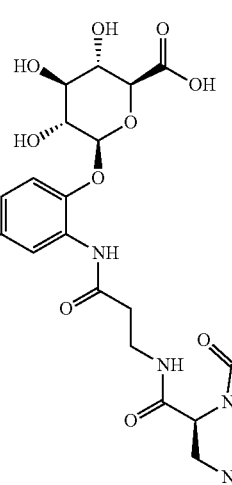

47

The title compound was prepared from compound 46 by the method of compound 17. LCMS: $t_R$=0.95 min; m/z=1117.7 [M+H]$^+$.

Example 43. (2S,3S,4S,5R,6S)-6-(3-((S)-44-((((9H-fluoren-9-yl)methoxy)-carbonyl)amino)-38,45-dioxo-2,5,8,11,14,17,20,23,26,29,32,35-dodecaoxa-39,46-diazanonatetracontan-49-amido)-4-((((3-((2-((N-cyclohexyl-7-(3-(pyridin-4-yl)ureido)-heptanamido)oxy)ethyl)(methyl)carbamoyl)phenyl)carbamoyl)oxy)methyl)phenoxy)-3,4,5-trihydroxytetrahydro-2H-pyran-2-carboxylic acid (48)

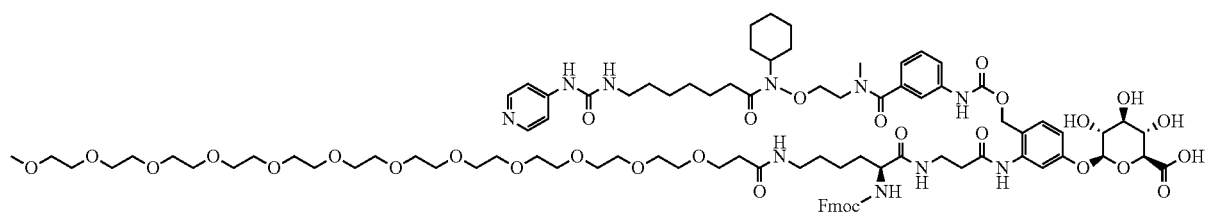

48

The title compound was prepared from compound 45 by the method of compound 18. LCMS: $t_R$=1.74 min; m/z=1872.4 [M+H]$^+$.

Example 44. (2S,3S,4S,5R,6S)-6-(3-((S)-44-amino-38,45-dioxo-2,5,8,11,14,17,20,23,26,29,32,35-dodecaoxa-39,46-diazanonatetracontan-49-amido)-4-((((3-((2-((N-cyclohexyl-7-(3-(pyridin-4-yl)ureido)heptanamido)oxy)ethyl)(methyl)-carbamoyl)phenyl)carbamoyl)oxy)methyl)phenoxy)-3,4,5-trihydroxytetrahydro-2H-pyran-2-carboxylic acid (49)

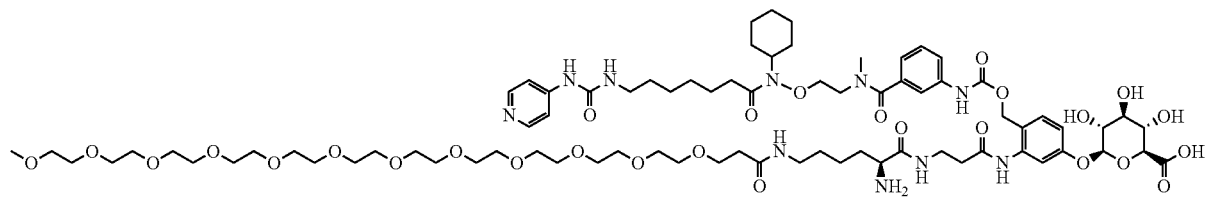

49

The title compound 49 was prepared from compound 48 by the method of compound 15. LCMS: $t_R$=1.40 min; m/z=1649.9 [M+H]$^+$.

Example 45. (2S,3S,4S,5R,6S)-6-(3-((S)-44-((S)-3-((tert-butoxycarbonyl)-amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontan-49-amido)-4-((((3-((2-((N-cyclohexyl-7-(3-(pyridin-4-yl)ureido)heptanamido)oxy)ethyl)(methyl)-carbamoyl)phenyl)carbamoyl)oxy)methyl)-phenoxy)-3,4,5-trihydroxytetrahydro-2H-pyran-2-carboxylic acid (50)

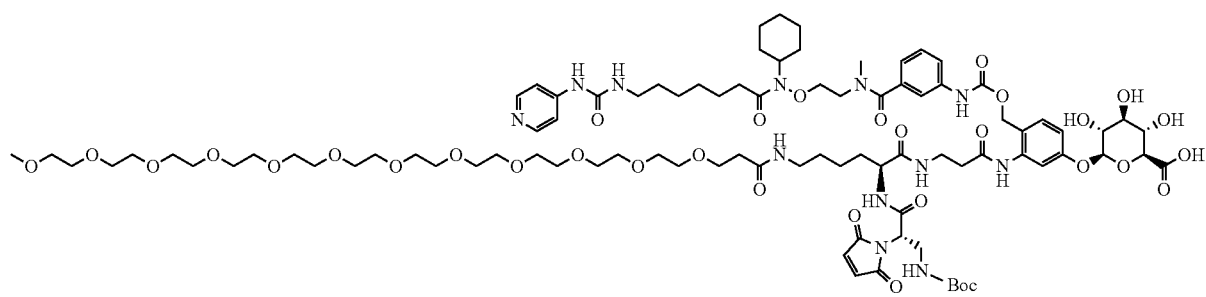

50

The title compound was prepared from 49 by the method of Compound 16. LCMS: $t_R$=1.62 min; m/z=1916.3 [M+H]$^+$.

Example 46. (2S,3S,4S,5R,6S)-6-(3-((S)-44-((S)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontan-49-amido)-4-((((3-((2-((N-cyclohexyl-7-(3-(pyridin-4-yl)ureido)heptanamido)oxy)ethyl)(methyl)carbamoyl)phenyl)carbamoyl)oxy)-methyl)phenoxy)-3,4,5-trihydroxytetrahydro-2H-pyran-2-carboxylic acid (51)

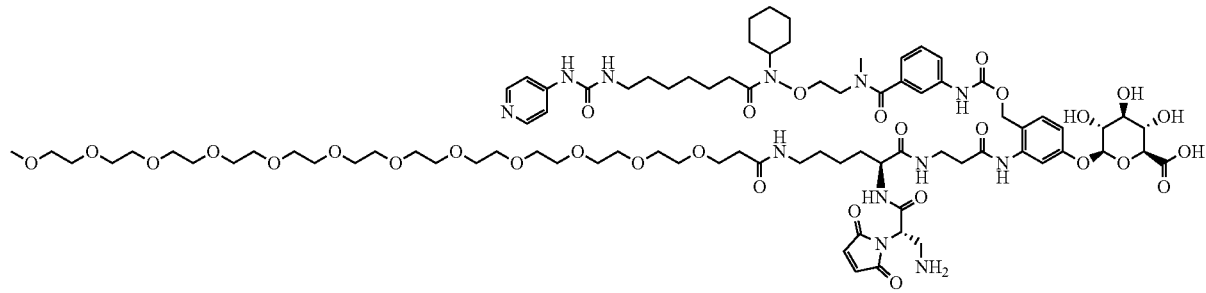

51

The title compound was prepared from compound 50 by the method of compound 17. LCMS: t$_R$=0.98 min; m/z=1816.9 [M+H]$^+$.

Example 47. N-cyclohexyl-7-((3,4-dioxo-2-(pyridin-4-ylamino)cyclobut-1-en-1-yl)amino)-N-(2-morpholinoethoxy)heptanamide (52)

The title compound was prepared according to WO2010/23307 A1.

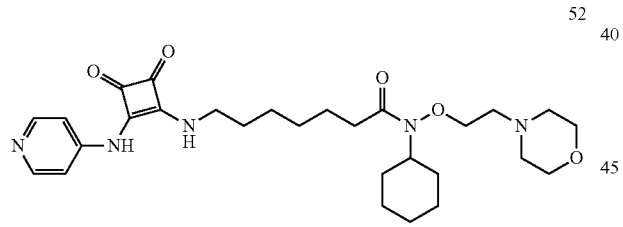

52

Example 48. tert-butyl (2-((N-cyclohexyl-7-((3,4-dioxo-2-(pyridin-4-ylamino)cyclobut-1-en-1-yl)amino)heptanamido)oxy)ethyl)(ethyl)carbamate (57)

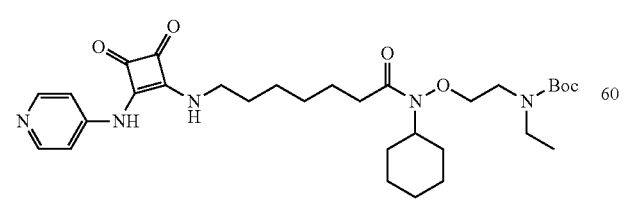

57

To a solution of the TFA salt of compound 56 (78.3 mg, 0.15 mmol) in 2 mL MeCN was added DIEA (77.5 µL, 0.45 mmol) and 3-ethoxy-4-(pyridin-4-ylamino)cyclobut-3-ene-1,2-dione (32.4 mg, 0.15 mmol) and the reaction stirred at room temp 1 h, then purified by preparative HPLC to give the title compound (49.2 mg, 0.070 mmol, 47%). LCMS: t$_R$=1.35 min; m/z=586.4 [M+H]$^+$.

Example 49. N-cyclohexyl-7-((3,4-dioxo-2-(pyridin-4-ylamino)cyclobut-1-en-1-yl)amino)-N-(2-(ethylamino)ethoxy)heptanamide (58)

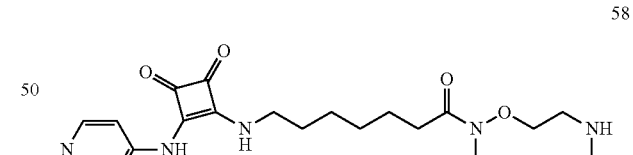

58

The title compound was prepared from compound 57 by the method of compound 17. LCMS: t$_R$=0.81 min; m/z=486.3 [M+H]$^+$.

Example 50. tert-butyl (3-((2-((N-cyclohexyl-7-((3,4-dioxo-2-(pyridin-4-ylamino)cyclobut-1-en-1-yl)amino)heptanamido)oxy)ethyl)(ethyl)carbamoyl)phenyl)-carbamate (59)

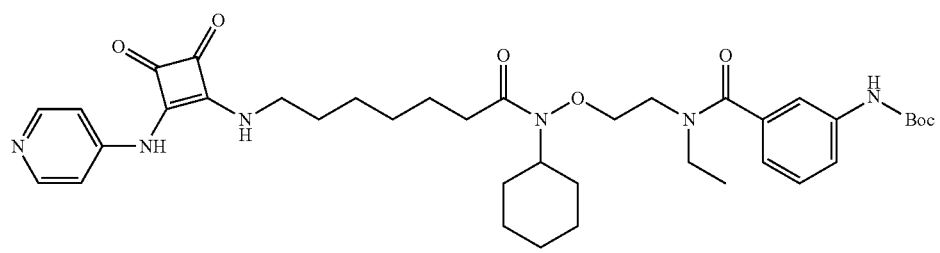

The title compound was prepared from compound 58 according to the method of compound 6 using 3-((tert-butoxycarbonyl)amino)benzoic acid as the starting acid. LCMS: $t_R$=1.36 min; m/z=705.4 [M+H]$^+$.

Example 51. 3-amino-N-(2-((N-cyclohexyl-7-((3,4-dioxo-2-(pyridin-4-ylamino)cyclobut-1-en-1-yl)amino)heptanamido)oxy)ethyl)-N-ethylbenzamide (60)

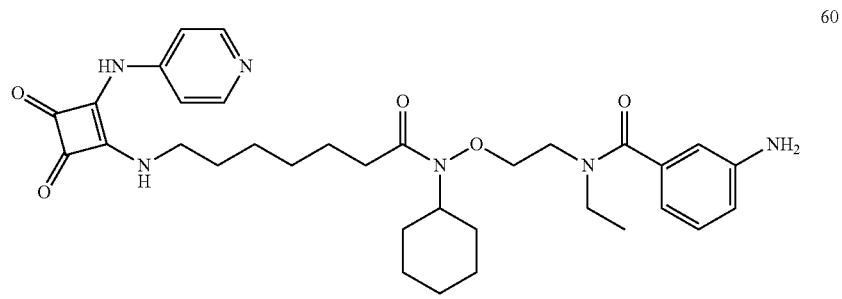 [SMILES: CCN(CCON(C(=O)CCCCCCNc1c(Nc2ccncc2)c(=O)c1=O)C1CCCCC1)C(=O)c1cccc(N)c1]

The title compound was prepared from compound 59 by the method of compound 17. LCMS: $t_R$=1.08 min; m/z=605.4 [M+H]$^+$.

Example 52. (2S,3R,4S,5S,6S)-2-(2-(3-(((((9H-fluoren-9-yl)methoxy)carbonyl)amino)propanamido)-4-((((3-((2-((N-cyclohexyl-7-((3,4-dioxo-2-(pyridin-4-ylamino)cyclobut-1-en-1-yl)amino)heptanamido)oxy)ethyl)(ethyl)carbamoyl)-phenyl)carbamoyl)oxy)methyl)phenoxy)-6-(methoxycarbonyl)tetrahydro-2H-pyran-3,4,5-triyl triacetate (61)
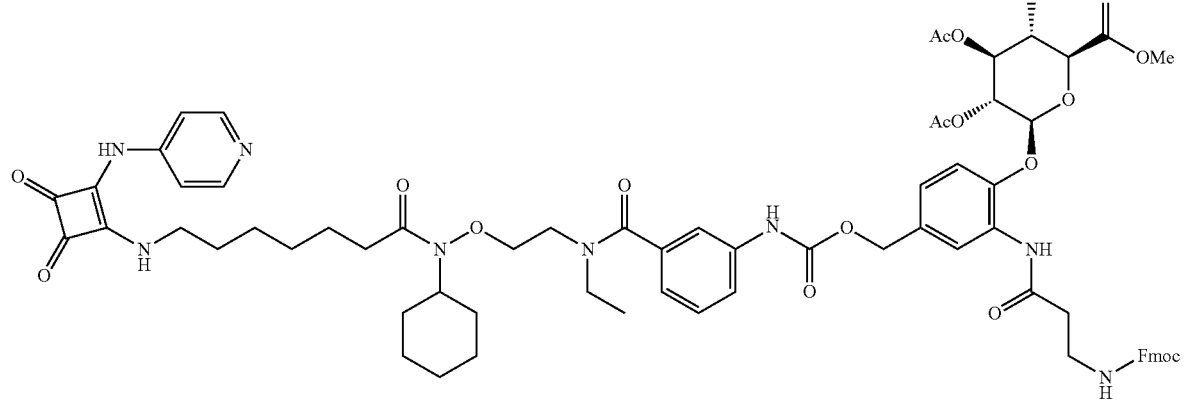
The title compound was prepared from compound 60 by the method of compound 14. LCMS: $t_R$=1.51 min; m/z=1379.7 [M+H]$^+$.
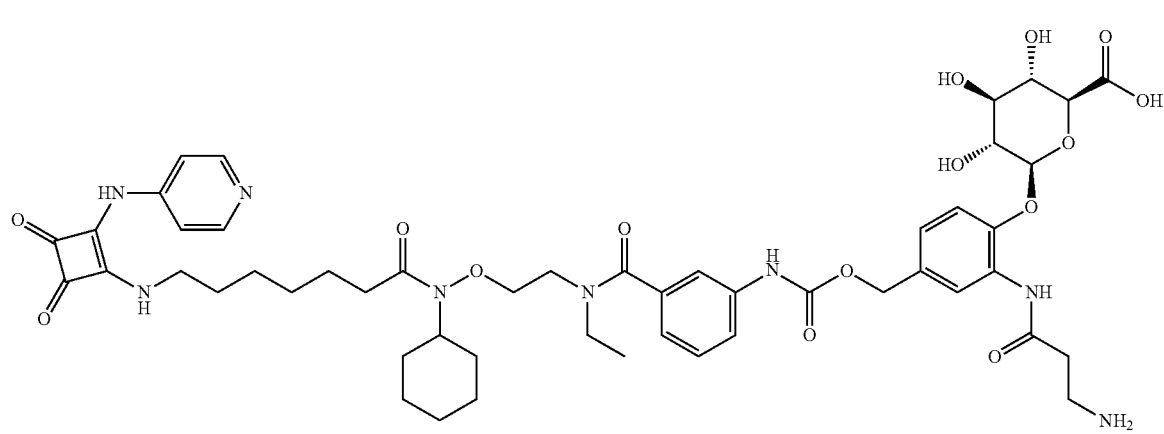

Example 53. (2S,3S,4S,5R,6S)-6-(2_(3-aminopropanamido)-4-((((3-((2-((N-cyclohexyl-7-((3,4-dioxo-2-(pyridin-4-ylamino)cyclobut-1-en-1-yl)amino)heptanamido)-oxy)ethyl)(ethyl)carbamoyl)phenyl)carbamoyl)oxy)methyl)phenoxy)-3,4,5-trihydroxy-tetrahydro-2H-pyran-2-carboxylic acid (62)

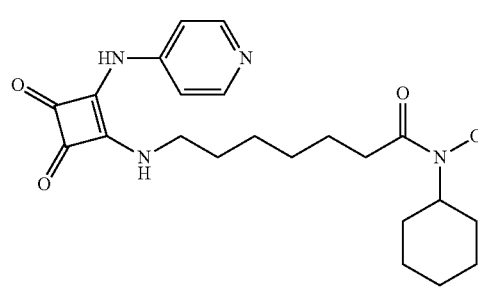
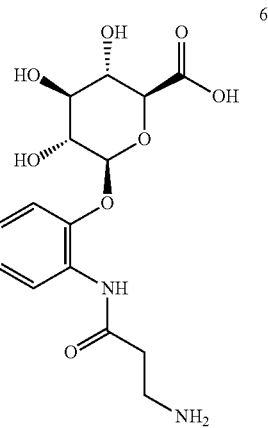

62

The title compound was prepared from compound 61 by the method of compound 15. LCMS: $t_R$=0.99 min; m/z=1017.5 [M+H]$^+$.

Example 54. (2S,3S,4S,5R,6S)-6-(2-(3-((S)-3-((tert-butoxycarbonyl)amino)-2-(2,5-dioxo-2,5-dihydro-1H-pyrrol-1-yl)propanamido)propanamido)-4-((((3-((2-((N-cyclohexyl-7-((3,4-dioxo-2-(pyridin-4-ylamino)cyclobut-1-en-1-yl)amino)heptanamido)-oxy)ethyl)(ethyl)carbamoyl)phenyl)carbamoyl)oxy)methyl)phenoxy)-3,4,5-trihydroxy-tetrahydro-2H-pyran-2-carboxylic acid (63)

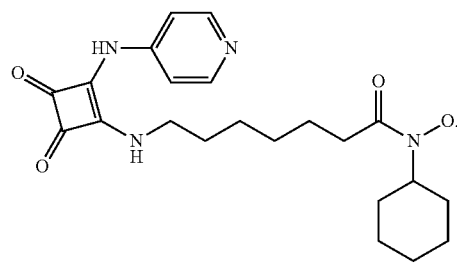
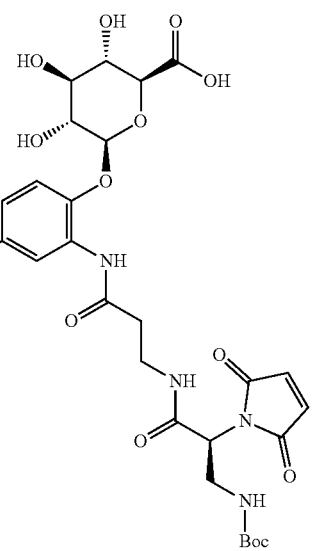

63

The title compound was prepared from compound 62 by the method of compound 16. LCMS: $t_R$=1.18 min; m/z=1283.6 [M+H]$^+$.

Example 55. (2S,3S,4S,5R,6S)-6-(2-(3-((S)-3-amino-2-(2,5-dioxo-2,5-dihydro-1H-pyrrol-1-yl)propanamido)propanamido)-4-((((3-((2-((N-cyclohexyl-7-((3,4-dioxo-2-(pyridin-4-ylamino)cyclobut-1-en-1-yl)amino)heptanamido)oxy)ethyl)(ethyl)carbamoyl)phenyl)carbamoyl)oxy)methyl)phenoxy)-3,4,5-trihydroxytetrahydro-2H-pyran-2-carboxylic acid (64)

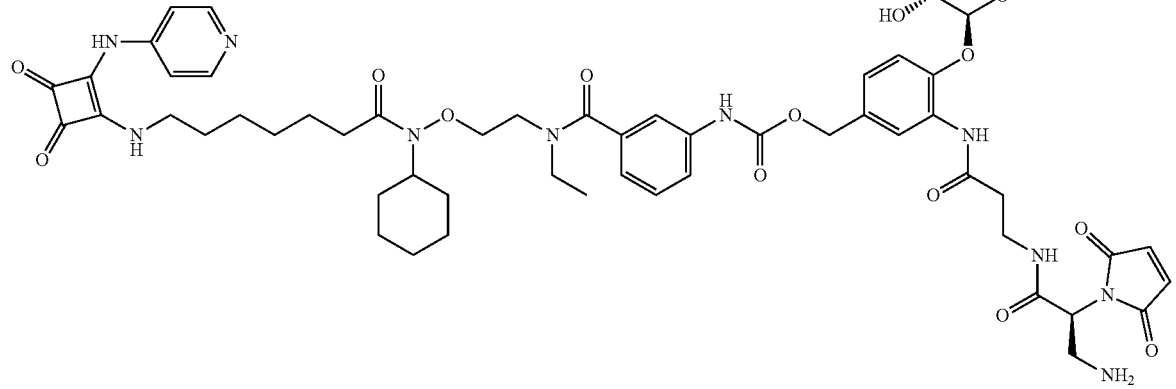

The title compound was prepared from compound 63 by the method of compound 17. LCMS: $t_R$=0.97 min; m/z=1183.5 [M+H]$^+$.

Example 56. 8-((3,4-dioxo-2-(pyridin-4-ylamino)cyclobut-1-en-1-yl)amino)octanoic acid (65)

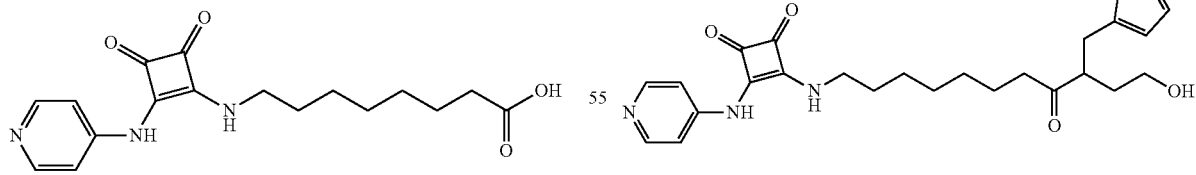

The title compound was prepared by the method of compound 57 using 8-aminooctanoic acid as the starting amine LCMS: $t_R$=0.68 min; m/z=332.2 [M+H]$^+$.

Example 57. 8-((3,4-dioxo-2-(pyridin-4-ylamino)cyclobut-1-en-1-yl)amino)-N-(furan-2-ylmethyl)-N-(2-hydroxyethyl)octanamide (66)

The title compound was prepared from compound 65 and 2-((furan-2-ylmethyl)amino)ethan-1-ol by the method of compound 1. LCMS: $t_R$=0.82 min; m/z=455.3 [M+H]$^+$.

Example 58. 3-((8-(4-hydroxypiperidin-1-yl)-8-oxooctyl)amino)-4-(pyridin-4-ylamino)cyclobut-3-ene-1,2-dione (67)

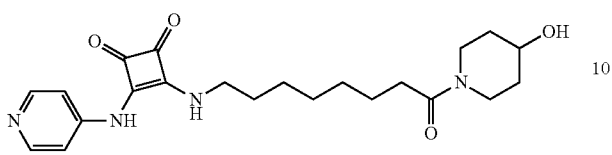

67

The title compound was prepared from compound 65 and piperidin-4-ol by the method of compound 3. LCMS: $t_R$=0.68 min; m/z=415.3 [M+H]$^+$.

Example 59. 3-((8-(3-hydroxyazetidin-1-yl)-8-oxooctyl)amino)-4-(pyridin-4-ylamino)cyclobut-3-ene-1,2-dione (68)

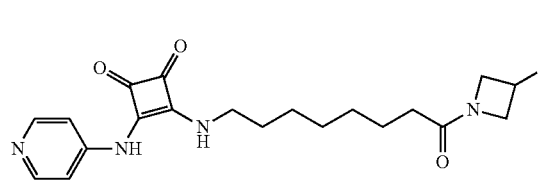

68

The title compound was prepared from compound 65 and azetidin-3-ol by the method of compound 3. LCMS: $t_R$=0.65 min; m/z=387.2 [M+H]$^+$.

Example 60. 8-((3,4-dioxo-2-(pyridin-4-ylamino)cyclobut-1-en-1-yl)amino)-N-((1-(hydroxymethyl)cyclopentyl)methyl)-N-methyloctanamide (69)

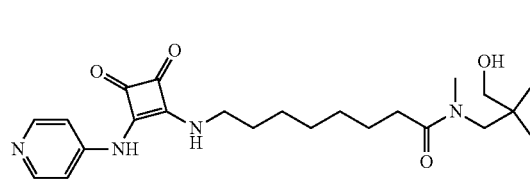

69

The title compound was prepared from compound 65 and (1-((methylamino)-methyl)cyclopentyl)methanol by the method of compound 1. LCMS: $t_R$=0.98 min; m/z=457.3 [M+H]$^+$.

Example 61. tert-butyl (8-((2-hydroxyethyl)(methyl)amino)-8-oxooctyl)carbamate (70)

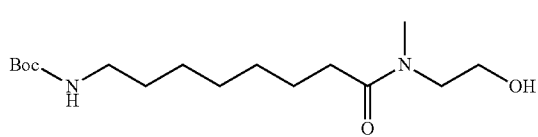

70

The title compound was prepared from 8-((tert-butoxycarbonyl)-amino)octanoic acid and 2-(methylamino)ethan-1-ol according to the method for compound 3. LCMS: $t_R$=1.13 min; m/z=339.3 [M+Na]$^+$.

Example 62. 8-amino-N-(2-hydroxyethyl)-N-methyloctanamide (71)

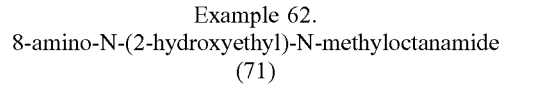

71

The title compound was prepared from compound 70 according to the method for compound 17. LCMS: $t_R$=0.44 min; m/z=217.3 [M+H]$^+$.

Example 63. 8-((3,4-dioxo-2-(pyridin-4-ylamino)cyclobut-1-en-1-yl)amino)-N-(2-hydroxyethyl)-N-methyloctanamide (72)

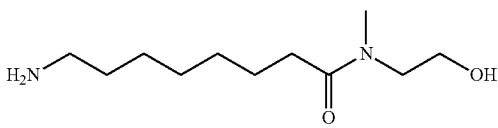

72

The title compound was prepared from compound 71 according to the method for compound 57. LCMS: $t_R$=0.70 min; m/z=389.4 [M+H]$^+$.

Example 64. di-tert-butyl(isobutyl)silyl 4-hydroxypiperidine-1-carboxylate (73)

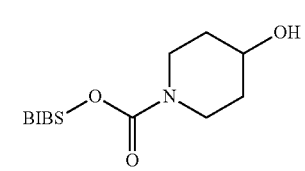

73

To a solution of 4-hydroxypiperidine (1.00 g, 9.89 mmol) in 45 mL CH$_2$Cl$_2$ in an oven-dried flask under argon was added triethylamine (3.58 mL, 25.7 mmol), CO$_2$ bubbled into the reaction, then BIBSOTf (3.58 mL, 12.85 mmol) added via syringe and the reaction stirred at room temp overnight under CO$_2$. The reaction mixture was diluted with CH$_2$Cl$_2$ and washed three times with water, dried over MgSO$_4$, filtered, and concentrated in vacuo. The crude product was purified by silica gel chromatography (MeOH/CH$_2$Cl$_2$) to provide the title compound (1.50 g, 4.37 mmol, 44%). LCMS: $t_R$=1.88 min; m/z=344.3 [M+H]$^+$.

Example 65. (2S,3R,4S,5S,6S)-2-(2-(2-((((9H-fluoren-9-yl)methoxy)-carbonyl)(methyl)amino)acetamido)-4-(((((1-(((di-tert-butyl(isobutyl)silyl)oxy)carbonyl)-piperidin-4-yl)oxy)methyl)(2-(methylsulfonyl)ethyl)carbamoyl)oxy)methyl)phenoxy)-6-(methoxy-carbonyl)tetrahydro-2H-pyran-3,4,5-triyl triacetate (74)

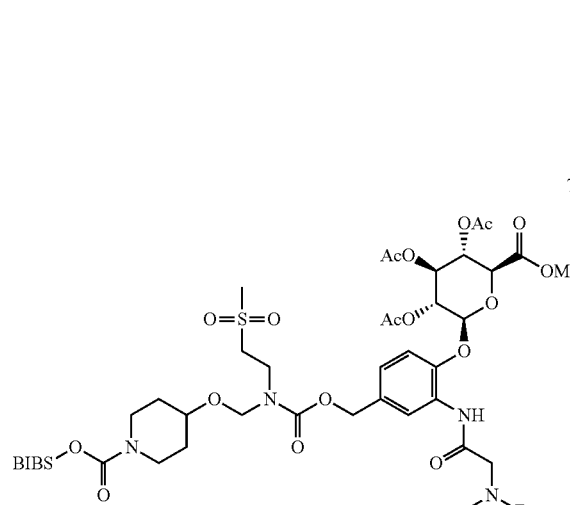

The title compound was prepared from compound 73 according to the method of compound 25. LCMS: $t_R$=1.92 min; m/z=1253.6 [M+H]⁺.

Example 66. (2S,3R,4S,5S,6S)-2-(2-(2-((((9H-fluoren-9-yl)methoxy)-carbonyl)(methyl)amino)acetamido)-4-((((2-(methylsulfonyl)ethyl)((piperidin-4-yloxy)-methyl)carbamoyl)oxy)methyl)phenoxy)-6-(methoxycarbonyl)tetrahydro-2H-pyran-3,4,5-triyl triacetate (75)

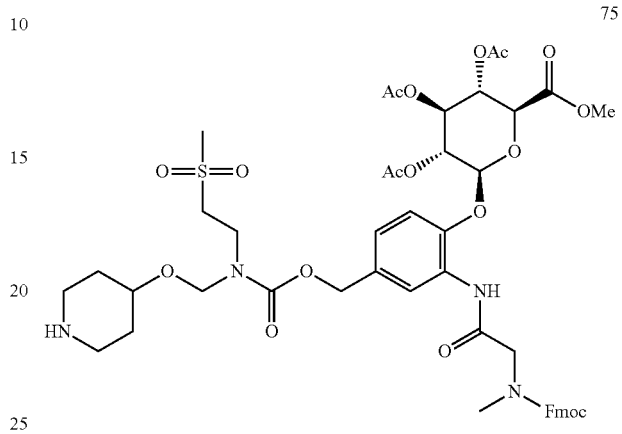

The title compound was prepared from compound 74 according to the method of compound 26. LCMS: $t_R$=1.54 min; m/z=1011.4 [M+H]⁺.

Example 67. (2S,3R,4S,5S,6S)-2-(2-(2-((((9H-fluoren-9-yl)methoxy)-carbonyl)(methyl)amino)acetamido)-4-((((((1-(8-((3,4-dioxo-2-(pyridin-4-ylamino)-cyclobut-1-en-1-yl)amino)octanoyl)piperidin-4-yl)oxy)methyl)(2-(methylsulfonyl)ethyl)-carbamoyl)oxy)methyl)phenoxy)-6-(methoxycarbonyl)tetrahydro-2H-pyran-3,4,5-triyl triacetate (76)

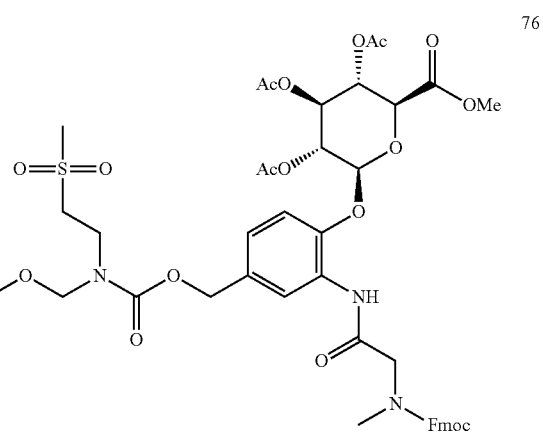

The title compound was prepared from compounds 75 and 65 according to the method of compound 1. LCMS: $t_R$=1.60 min; m/z=1324.6 [M+H]⁺.

Example 68. (2S,3S,4S,5R,6S)-6-(4-((((((1-(8-((3,4-dioxo-2-(pyridin-4-ylamino)cyclobut-1-en-1-yl)amino)octanoyl)piperidin-4-yl)oxy)methyl)(2-(methyl-sulfonyl)ethyl)carbamoyl)oxy)methyl)-2-(2-(methylamino)acetamido)phenoxy)-3,4,5-trihydroxytetrahydro-2H-pyran-2-carboxylic acid (77)

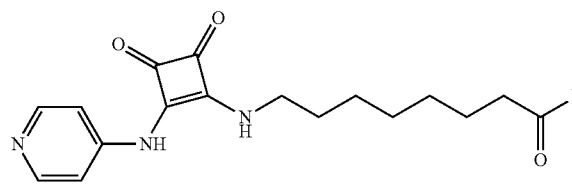
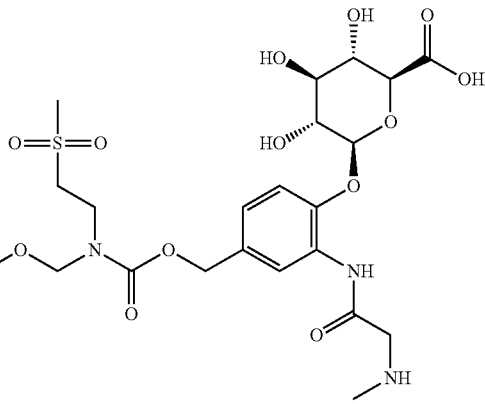

77

The title compound was prepared from compound 76 according to the method of compound 15. LCMS: $t_R$=0.90 min; m/z=962.4 [M+H]$^+$.

Example 69 (2S,3S,4S,5R,6S)-6-(2-(2-(3-(2,5-dioxo-2,5-dihydro-1H-pyrrol-1-yl)-N-methylpropanamido)acetamido)-4-((((a 1-(8-((3,4-dioxo-2-(pyridin-4-ylamino)-cyclobut-1-en-1-yl)amino)octanoyl)piperidin-4-yl)oxy)methyl)(2-(methylsulfonyl)ethyl)-carbamoyl)oxy)methyl)phenoxy)-3,4,5-trihydroxytetrahydro-2H-pyran-2-carboxylic acid (78)

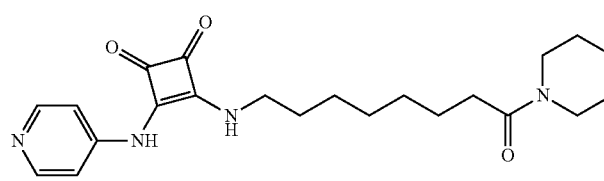
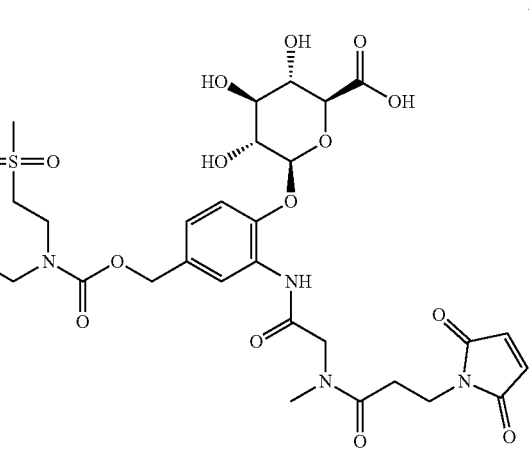

78

The title compound was prepared from compound 77 according to the method of compound 29. LCMS: $t_R$=1.05 min; m/z=1113.5 [M+H]$^+$.

Example 70. (E)-8-(2-cyano-3-(pyridin-4-yl)guanidino)octanoic acid (79)

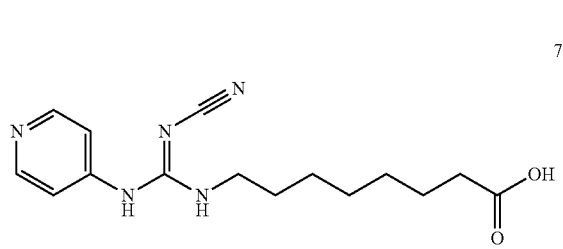

A solution of (Z)—N'-cyano-N-(pyridin-4-yl)methylsulfanylmethanimidamide (695 mg, 3.62 mmol), 8-aminooctanoic acid (576 mg, 3.62 mmol), DMAP (486 mg, 3.98 mmol), and DIEA (1.90 mL, 10.85 mmol) in 17 mL pyridine was heated at 70° C. under argon overnight, concentrated in vacuo, and purified by preparative HPLC to give the title compound (668 mg, 2.20 mmol, 61%). LCMS: $t_R$=0.63 min; m/z=304.2 [M+H]$^+$.

Example 71. (E)-8-(2-cyano-3-(pyridin-4-yl)guanidino)-N-((1-(hydroxymethyl)cyclopentyl)methyl)-N-methyloctanamide (80)

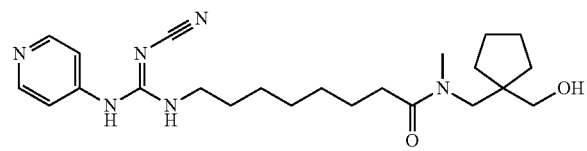

The title compound was prepared from compound 79 and (1-((methylamino)-methyl)cyclopentyl)methanol according to the method of compound 1. LCMS: $t_R$=0.92 min; m/z=429.3 [M+H]$^+$.

Example 72. (E)-8-(2-cyano-3-(pyridin-4-yl)guanidino)-N-(furan-2-ylmethyl)-N-(2-hydroxyethyl)octanamide (81)

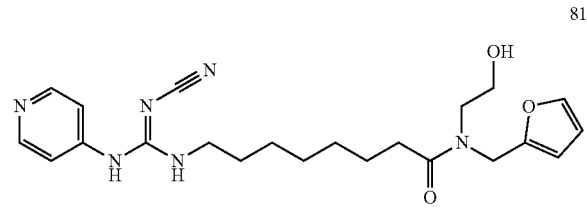 [SMILES: N#C/N=C(\NCCCCCCCC(=O)N(CCO)Cc1ccco1)Nc1ccncc1]

The title compound was prepared from compound 79 and 2-((furan-2-ylmethyl)amino)ethan-1-ol according to the method of compound 1. LCMS: $t_R$=0.79 min; m/z=427.3 [M+H]$^+$.

Example 73. (E)-2-cyano-1-(8-(4-hydroxypiperidin-1-yl)-8-oxooctyl)-3-(pyridin-4-yl)guanidine (82)

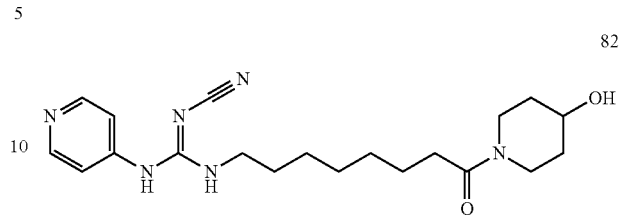

The title compound was prepared from compound 79 and piperidin-4-ol according to the method of compound 1. LCMS: $t_R$=0.95 min; m/z=387.3 [M+H]$^+$.

Example 74. (E)-8-(2-cyano-3-(pyridin-4-yl)guanidino)-N-(2-hydroxyethyl)-N-methyloctanamide (83)

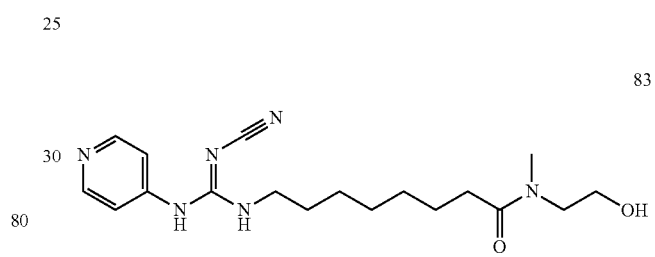

The title compound was prepared from compound 71 and (Z)—N'-cyano-N-(pyridin-4-yl)methylsulfanylmethanimidamide by the method of compound 79. LCMS: $t_R$=0.66 min; m/z=361.4 [M+H]$^+$.

Example 75. 8-((3,4-dioxo-2-(pyridin-4-ylamino)cyclobut-1-en-1-yl)amino)-N-(5-ethyl-4-hydroxypyrimidin-2-yl)octanamide (84)

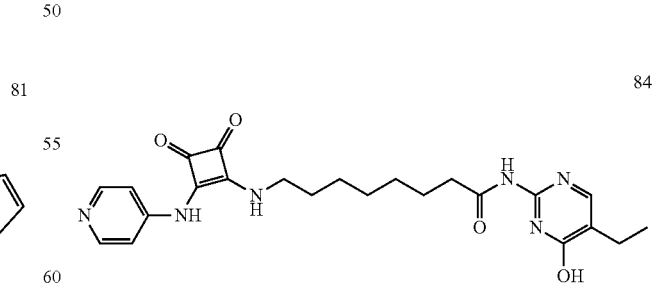

The title compound was prepared according to the method of compound 1 using compound 49 as the starting acid. LCMS: $t_R$=0.79 min; m/z=453.26 [M+H]$^+$.

Example 76. (E)-8-(2-cyano-3-(pyridin-4-yl)guanidino)-N-(5-ethyl-4-hydroxypyrimidin-2-yl)octanamide (85)

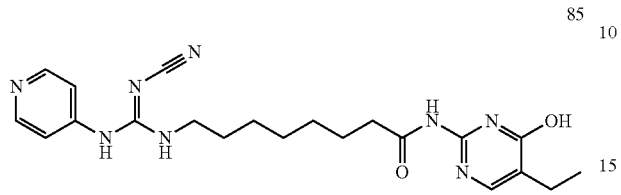

The title compound was prepared according to the method of compound 1 using compound 60 as the starting acid. LCMS: $t_R$=0.75 min; m/z=425.27 [M+H]$^+$

Example 77. (9H-fluoren-9-yl)methyl (7-(cyclohexyl(2-(methylamino)-ethoxy)amino)-7-oxoheptyl)carbamate (86)

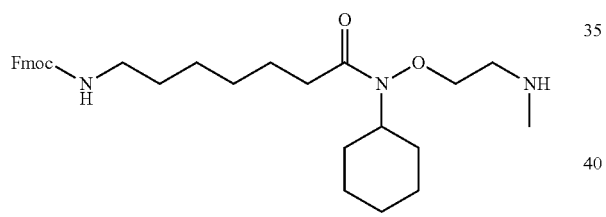

The title compound was prepared according to the method of compound 2. LCMS: $t_R$=1.18 min; m/z=522.30 [M+H]$^+$.

Example 78. (9H-fluoren-9-yl)methyl (7-((2-(3-((((9H-fluoren-9-yl)methoxy)carbonyl)amino)-N-methylbenzamido)ethoxy)(cyclohexyl)amino)-7-oxoheptyl)carbamate (87)

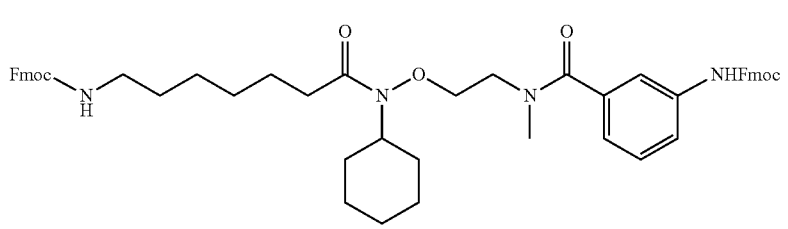

The title compound was prepared according to the method of compound 1. LCMS: $t_R$=1.82 min; m/z=864.41 [M+H]$^+$.

Example 79. 3-amino-N-(2-((7-amino-N-cyclohexylheptanamido)oxy)ethyl)-N-methylbenzamide (88)

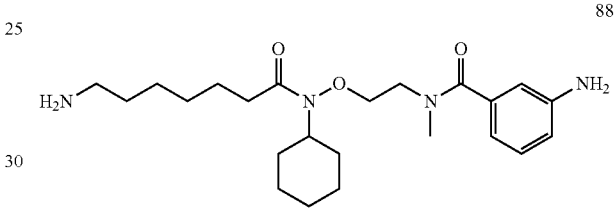

Compound 87 (42.0 mg, 0.049 mmol) taken up in 1 mL 2% piperidine in DMF and stirred at room temperature 1 h. The product was purified by preparative HPLC to provide the title compound (27.9 mg, 0.043 mmol, 88%). LCMS: $t_R$=0.77 min; m/z=419.27 [M+H]$^+$.

Example 80. (E)-3-amino-N-(1-cyano-11-cyclo-hexyl-10-oxo-2-(pyridin-4-ylamino)-12-oxa-1,3,11-triazatetradec-1-en-14-yl)-N-methylbenzamide (89)

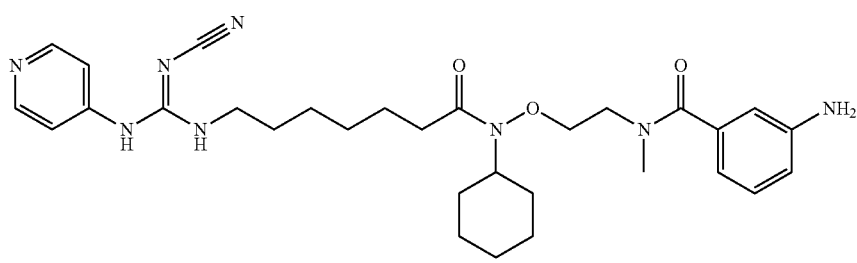

The title compound was prepared according to the method of compound 60. LCMS: t$_r$=0.86 min; m/z=563.30 [M+H]$^+$.

Example 81. tert-butyl 4-(4-((3,4-dioxo-2-(pyridin-4-ylamino)cyclobut-1-en-1-yl)amino)butyl)piperidine-1-carboxylate (90)

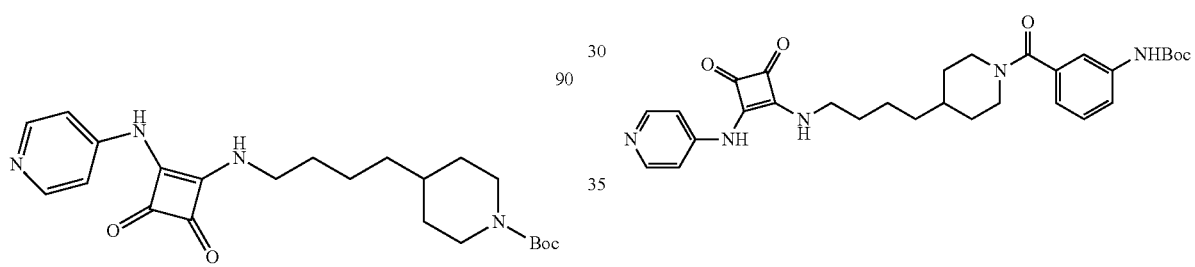

The title compound was prepared according to the method of compound 33. LCMS: t$_R$=1.00 min; m/z=429.17 [M+H]$^+$.

Example 82. 3-((4-(piperidin-4-yl)butyl)amino)-4-(pyridin-4-ylamino)-cyclobut-3-ene-1,2-dione (91)

The title compound was prepared according to the method of compound 2. LCMS: t$_R$=0.41 min; m/z=329.17 [M+H]$^+$.

Example 83. tert-butyl (3-(4-(4-((3,4-dioxo-2-(pyridin-4-ylamino)cyclobut-1-en-1-yl)amino)butyl)piperidine-1-carbonyl)phenyl)carbamatedione (92)

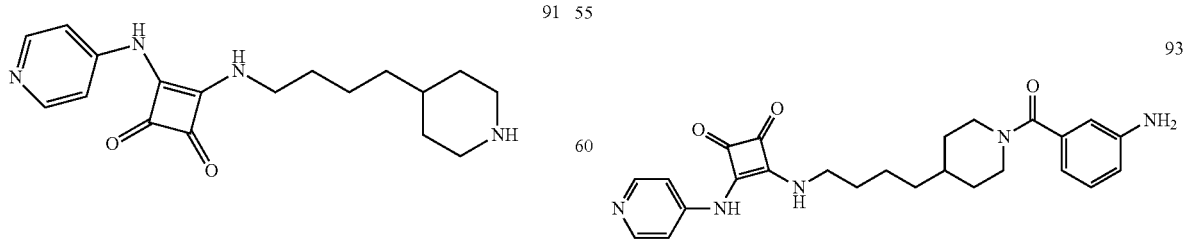

The title compound was prepared according to the method of compound 3. LCMS: t$_R$=1.00 min; m/z=548.24 [M+H]$^+$.
$^1$H NMR (400 MHz, CD$_3$OD, δ): 1.05-1.26 (m, 2H), 1.30-1.39 (m, 3H), 1.39-1.48 (m, 2H), 1.50 (s, 9H), 1.54-1.61 (m, 1H), 1.61-1.73 (m, 3H), 1.84 (br d, J=12.0 Hz, 1H), 2.81 (t, J=12.0 Hz, 1H), 3.65-3.80 (m, 3H), 4.59 (d, J=12.0 Hz, 1H), 6.97 (dt, J=8.0 Hz, 2.0 Hz, 1H), 7.31 (t, J=8.0 Hz, 1H), 7.43 (ddd, J=12.0 Hz, 2.2 Hz, 1.1 Hz, 1H), 7.52 (s, 1H), 7.55 (d, J=8.0 Hz, 2H), 8.32-8.38 (m, 2H).

Example 84. 3-((4-(1-(3-aminobenzoyl)piperidin-4-yl)butyl)amino)-4-(pyridin-4-ylamino)cyclobut-3-ene-1,2-dione (93)

The title compound was prepared according to the method of compound 2. LCMS: t$_R$=0.68 min; m/z=448.20 [M+H]$^+$.

Example 85. tert-butyl 4-(4-((((9H-fluoren-9-yl)methoxy)carbonyl)amino)-butyl)piperidine-1-carboxylate (94)

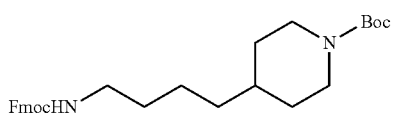

Tert-butyl 4-(4-aminobutyl)piperidine-1-carboxylate (47.2 mg, 0.18 mmol) was taken up in 3 mL saturated sodium bicarbonate solution and 1.5 mL dioxane, and a solution of Fmoc-C$_1$ (71.4 mg, 0.28 mmol) in 1.5 mL dioxane was slowly added at 0° C. The reaction mixture was allowed to warm to ambient temperature overnight under argon, then partitioned between EtOAc and 1M HCl, the organic layer washed once with brine, dried over MgSO$_4$, filtered, and concentrated in vacuo. The crude product was purified via silica gel chromatography using a gradient from 0-50% MeOH/CH$_2$Cl$_2$ (74 mg, 0.16 mmol, 84%). LCMS: t$_R$=1.76 min; m/z=501.23 [M+Na]$^+$.

Example 86. (9H-fluoren-9-yl)methyl (4-(piperidin-4-yl)butyl)carbamate (95)

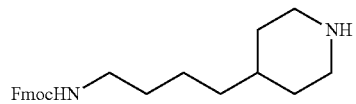

The title compound was prepared according to the method of compound 2. LCMS: t$_r$=1.69 min; m/z=379.18 [M+H]$^+$.

Example 87. (9H-fluoren-9-yl)methyl (3-(4-(4-((((9H-fluoren-9-yl)methoxy)carbonyl)amino)butyl)piperidine-1-carbonyl)phenyl)carbamate (96)

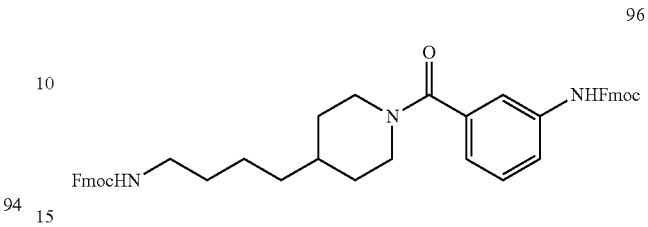

The title compound was prepared according to the method of compound 1. LCMS: t$_R$=1.91 min; m/z=720.49 [M+H]$^+$.

Example 88. (4-(4-aminobutyl)piperidin-1-yl)(3-aminophenyl)methanone (97)

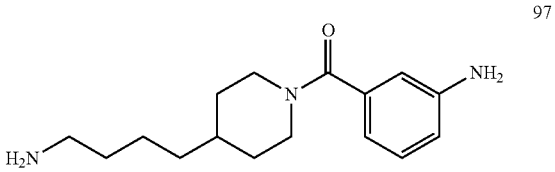 [SMILES: NCCCCC1CCN(C(=O)c2cccc(N)c2)CC1]

The title compound was prepared according to the method of compound 88. LCMS: t$_R$=0.76 min; m/z=276.24 [M+H]$^+$. $^1$HNMR (400 MHz, CD$_3$OD, δ): 1.05-1.27 (m, 2H), 1.29-1.38 (m, 2H), 1.38-1.49 (m, 2H), 1.54-1.69 (m, 4H), 1.86 (d, J=12.0 Hz, 1H), 2.83 (t, J=14.0 Hz, 1H), 2.92 (t, J=6.0 Hz, 2H), 3.10 (t, J=14.0 Hz, 1H), 3.68 (d, J=12.0 Hz, 1H), 4.61 (d, J=12.0 Hz, 1H), 7.18-7.32 (m, 3H), 7.48 (t, J=8.0 Hz, 1H).

Example 89. (Z)-1-(4-(1-(3-aminobenzoyl)piperidin-4-yl)butyl)-2-cyano-3-(pyridin-4-yl)guanidine (98)

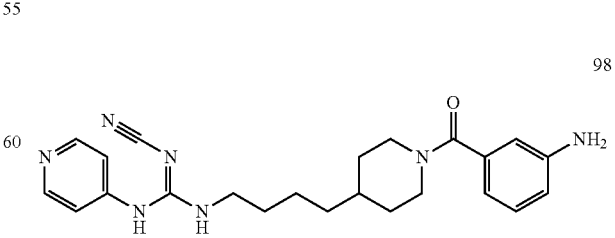

The title compound was prepared according to the method of compound 60. LCMS: t$_r$=1.02 min; m/z=420.42 [M+H]$^+$.

Example 90. (2S,3R,4S,5S,6S)-2-(2-(3-((((9H-fluoren-9-yl)methoxy)carbonyl)amino)propanamido)-4-((((3-(4-(4-((3,4-dioxo-2-(pyridin-4-ylamino)cyclobut-1-en-1-yl)amino)butyl)piperidine-1-carbonyl)phenyl)carbamoyl)oxy)-methyl)phenoxy)-6-(methoxycarbonyl)tetrahydro-2H-pyran-3,4,5-triyl triacetate (99)

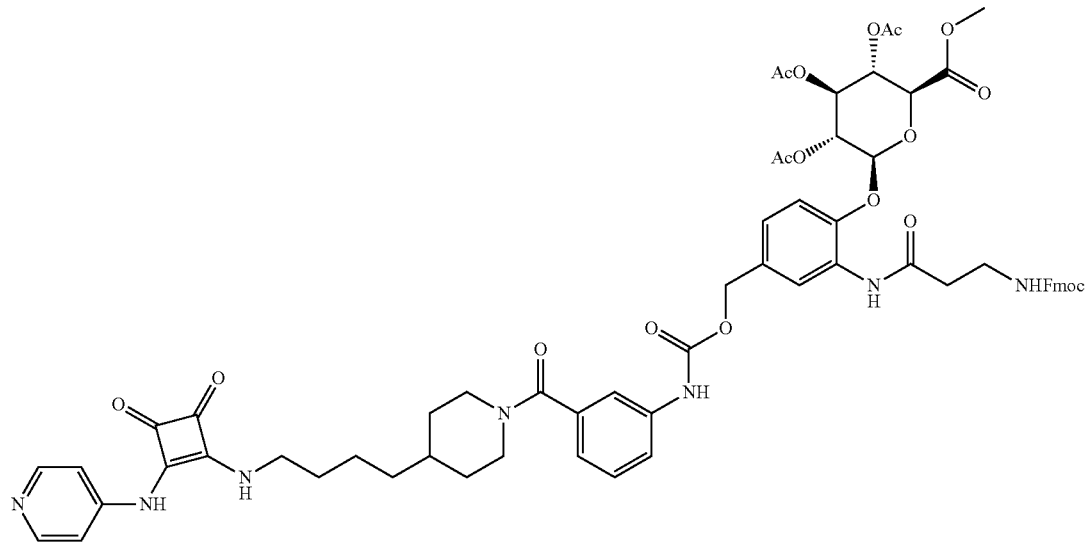

The title compound was prepared according to the method of compound 9. LCMS: $t_R$=1.38 min; m/z=1223.40 [M+H]$^+$.

Example 91. (2S,3S,4S,5R,6S)-6-(2-(3-aminopropanamido)-4-((((3-(4-(4-((3,4-dioxo-2-(pyridin-4-ylamino)cyclobut-1-en-1-yl)amino)butyl)piperidine-1-carbonyl)phenyl)carbamoyl)oxy)methyl)phenoxy)-3,4,5-trihydroxytetrahydro-2H-pyran-2-carboxylic acid (100)

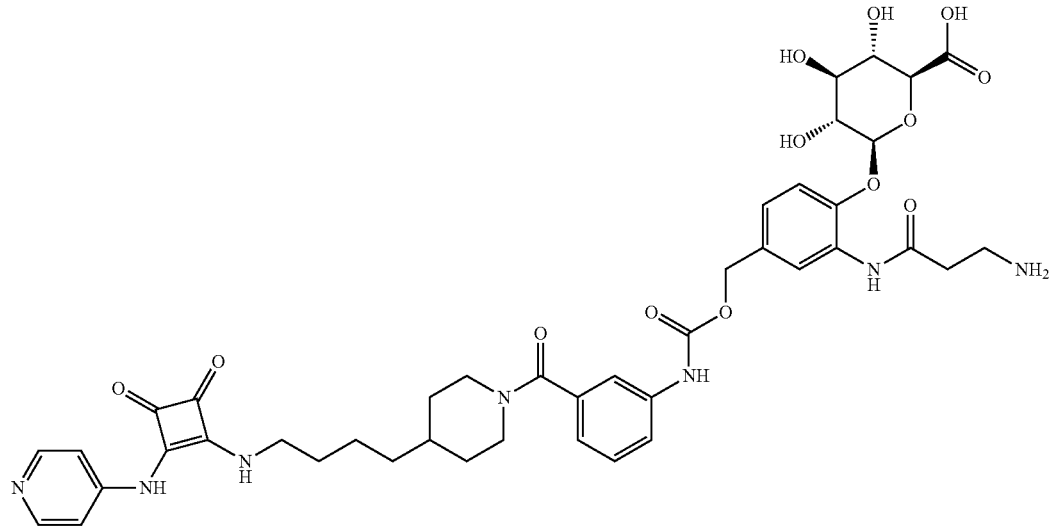

The title compound was prepared according to the methods of compound 10 and compound 88. LCMS: $t_R$=0.89 min; m/z=860.30 [M+H]$^+$.

Example 92. (2S,3S,4S,5R,6S)-6-(2-(3-(3-(2,5-di-oxo-2,5-dihydro-1H-pyrrol-1-yl)propanamido)propanamido)-4-((((3-(4-(4-((3,4-dioxo-2-(pyridin-4-ylamino)cyclobut-1-en-1-yl)amino)butyl)piperidine-1-carbonyl)phenyl)carbamoyl)oxy)methyl)phenoxy)-3,4,5-trihydroxytetrahydro-2H-pyran-2-carboxylic acid (101)

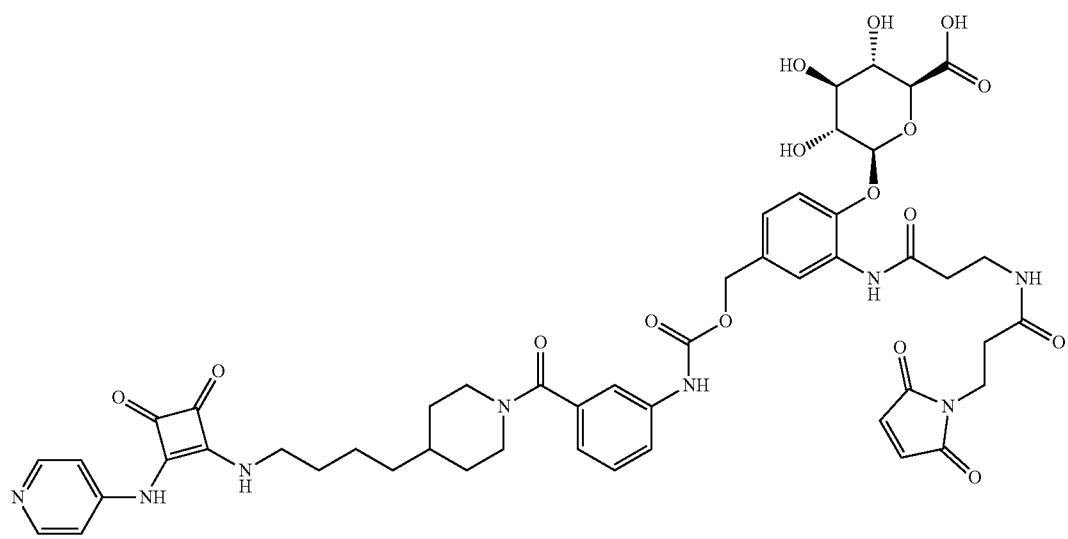

The title compound was prepared according to the method of compound 11 using 2,5-dioxopyrrolidin-1-yl 3-(2,5-dioxopyrrol-1-yl)propanoate as the starting NHS ester. LCMS: $t_R$=0.82 min; m/z=1011.32 [M+H]$^+$.

Example 93. (2S,3R,4S,5S,6S)-2-(2-(3-((((9H-fluoren-9-yl)methoxy)-carbonyl)amino)propanamido)-4-((((3-(((E)-1-cyano-11-cyclohexyl-10-oxo-2-(pyridin-4-ylamino)-12-oxa-1,3,11-triazatetradec-1-en-14-yl)(methyl)carbamoyl)phenyl)carbamoyl)-oxy)methyl)phenoxy)-6-(methoxycarbonyl)tetrahydro-2H-pyran-3,4,5-triyltriacetate (102)
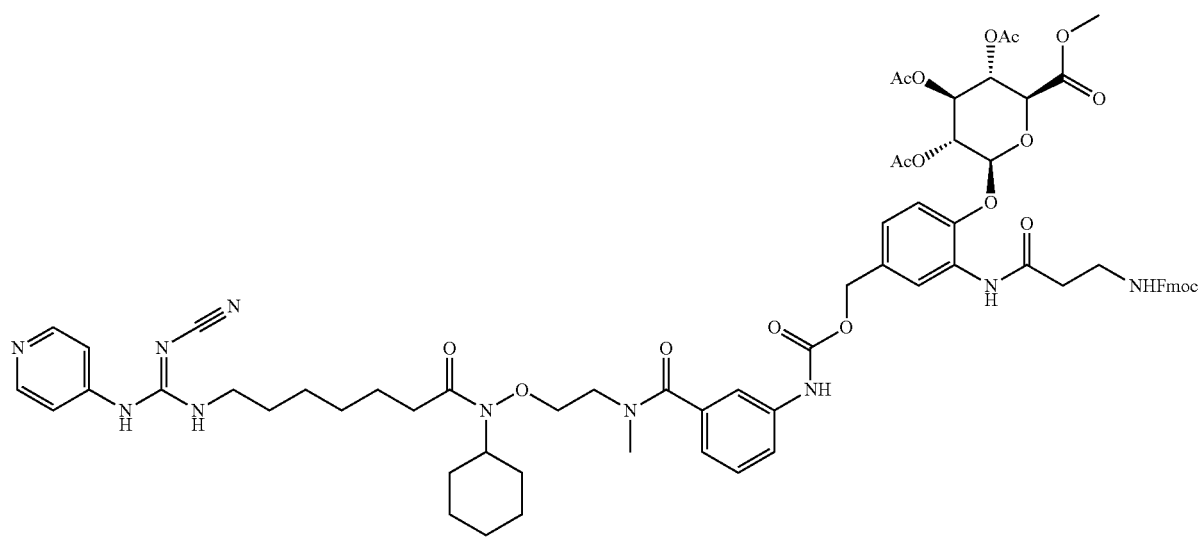
The title compound was prepared according to the method of compound 9. LCMS: $t_R$=1.39 min; m/z=1337.50 [M+H]$^+$.

Example 94. (2S,3S,4S,5R,6S)-6-(2-(3-aminopropanamido)-4-((((3-(((E)-1-cyano-11-cyclohexyl-10-oxo-2-(pyridin-4-ylamino)-12-oxa-1,3,11-triazatetradec-1-en-14-yl)(methyl)carbamoyl)phenyl)carbamoyl)oxy)methyl)phenoxy)-3,4,5-trihydroxytetrahydro-2H-pyran-2-carboxylic acid (103)
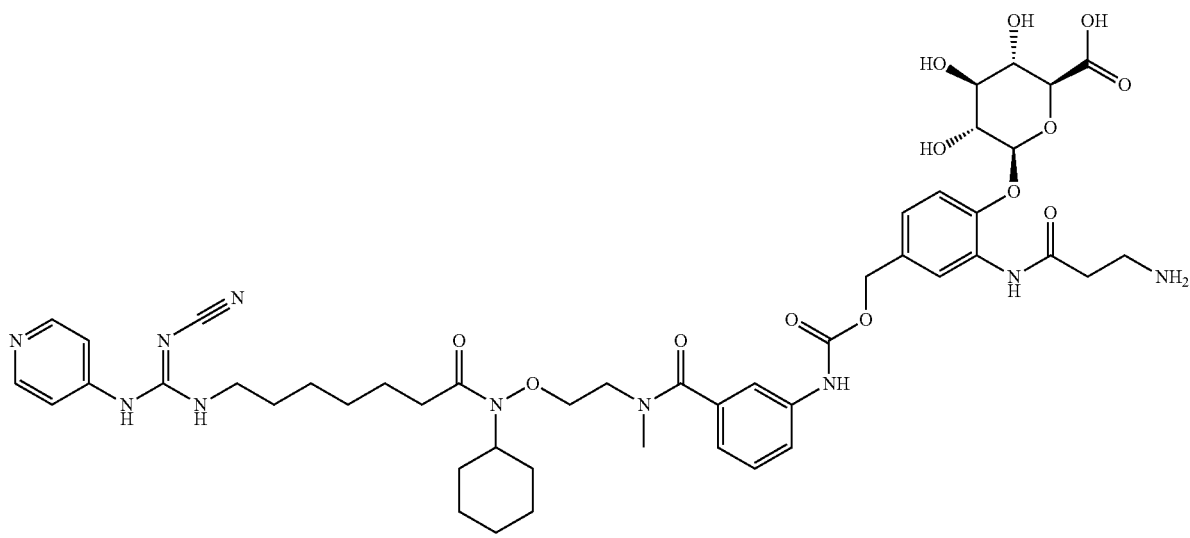
The title compound was prepared according to the methods of compound 10 and compound 88. LCMS: $t_R$=0.88 min; m/z=976.40 [M+H]$^+$.

Example 95. (2S,3S,4S,5R,6S)-6-(4-((((3-(((E)-1-cyano-11-cyclohexyl-10-oxo-2-(pyridin-4-ylamino)-12-oxa-1,3,11-triazatetradec-1-en-14-yl)(methyl)carbamoyl)-phenyl)carbamoyl)oxy)methyl)-2-(3-(3-(2,5-dioxo-2,5-dihydro-1H-pyrrol-1-yl)-propanamido)propanamido)phenoxy)-3,4,5-trihydroxytetrahydro-2H-pyran-2-carboxylic acid (104)

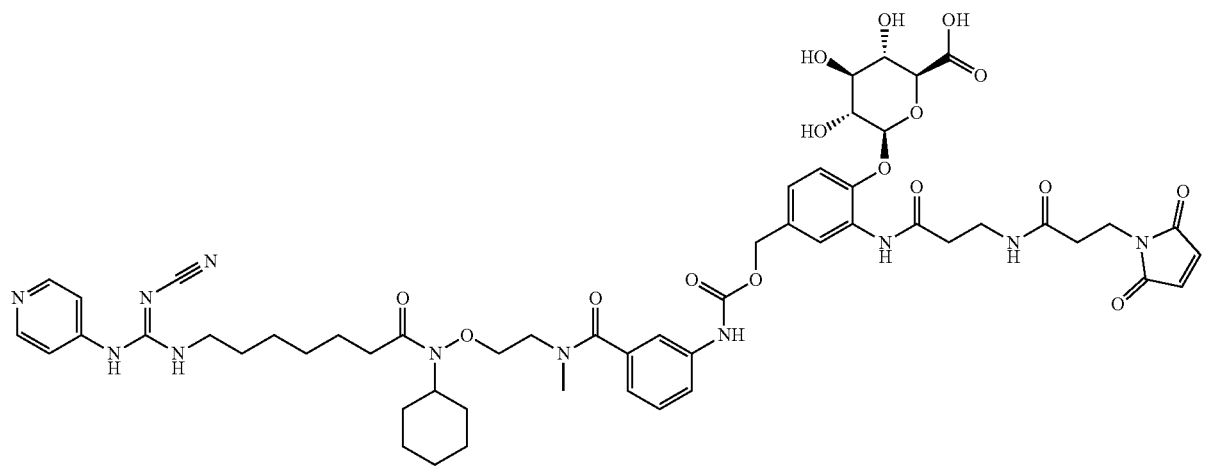

104

The title compound was prepared according to the method of compound 11 using 2,5-dioxopyrrolidin-1-yl 3-(2,5-dioxopyrrol-1-yl)propanoate as the starting NHS ester. LCMS: $t_R$=0.93 min; m/z=1126.4 [M+H]$^+$.

Example 96. (2S,3R,4S,5S,6S)-2-(2-(3-((((9H-fluoren-9-yl)methoxy)carbonyl)amino)propanamido)-4-((((3-(4-(4-((Z)-2-cyano-3-(pyridin-4-yl)guanidino)butyl)piperidine-1-carbonyl)phenyl)carbamoyl)oxy)methyl)phenoxy)-6-(methoxycarbonyl)tetrahydro-2H-pyran-3,4,5-triyl triacetate (105)

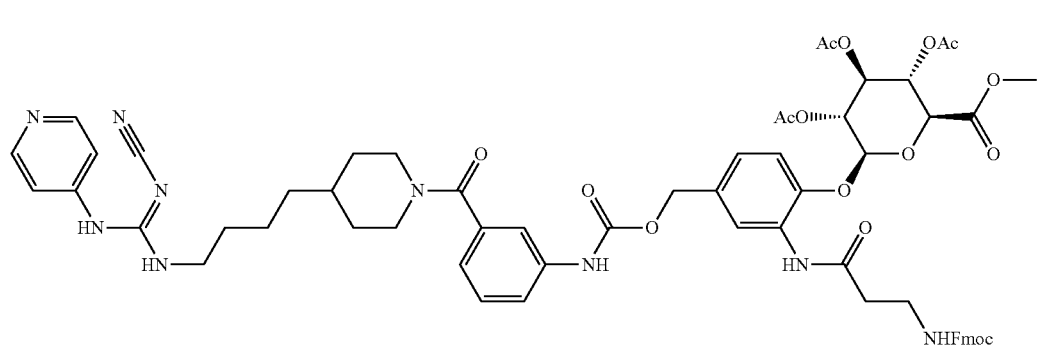

105

The title compound was prepared according to the method of compound 9. LCMS: $t_R$=1.39 min; m/z=1194.38 [M+H]$^+$.

Example 97. (2S,3S,4S,5R,6S)-6-(2-(3-aminopropanamido)-4-((((3-(4-(4-((Z)-2-cyano-3-(pyridin-4-yl)guanidino)butyl)piperidine-1-carbonyl)phenyl)carbamoyl)-oxy)methyl)phenoxy)-3,4,5-trihydroxytetrahydro-2H-pyran-2-carboxylic acid (106)

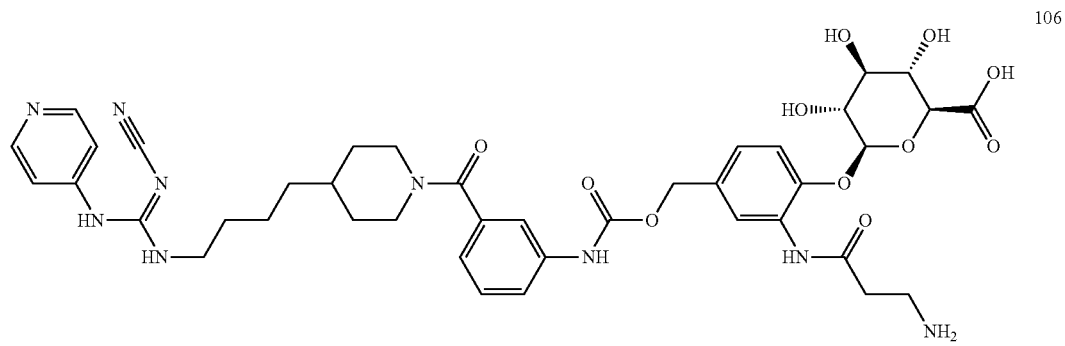 [SMILES: N#C/N=C(/NCCCCC1CCN(C(=O)c2cccc(NC(=O)OCc3ccc(O[C@@H]4O[C@H](C(=O)O)[C@@H](O)[C@H](O)[C@H]4O)c(NC(=O)CCN)c3)c2)CC1)Nc1ccncc1]

The title compound was prepared according to the method of compound 10. LCMS (polar method): $t_R$=1.42 min; m/z=832.31 [M+H]$^+$.

Example 98. (2S,3S,4S,5R,6S)-6-(4-((((3-(4-(4-((Z)-2-cyano-3-(pyridin-4-yl)guanidino)butyl)piperidine-1-carbonyl)phenyl)carbamoyl)oxy)methyl)-2-(3-(3-(2,5-dioxo-2,5-dihydro-1H-pyrrol-1-yl)propanamido)propanamido)phenoxy)-3,4,5-trihydroxytetrahydro-2H-pyran-2-carboxylic acid (107)

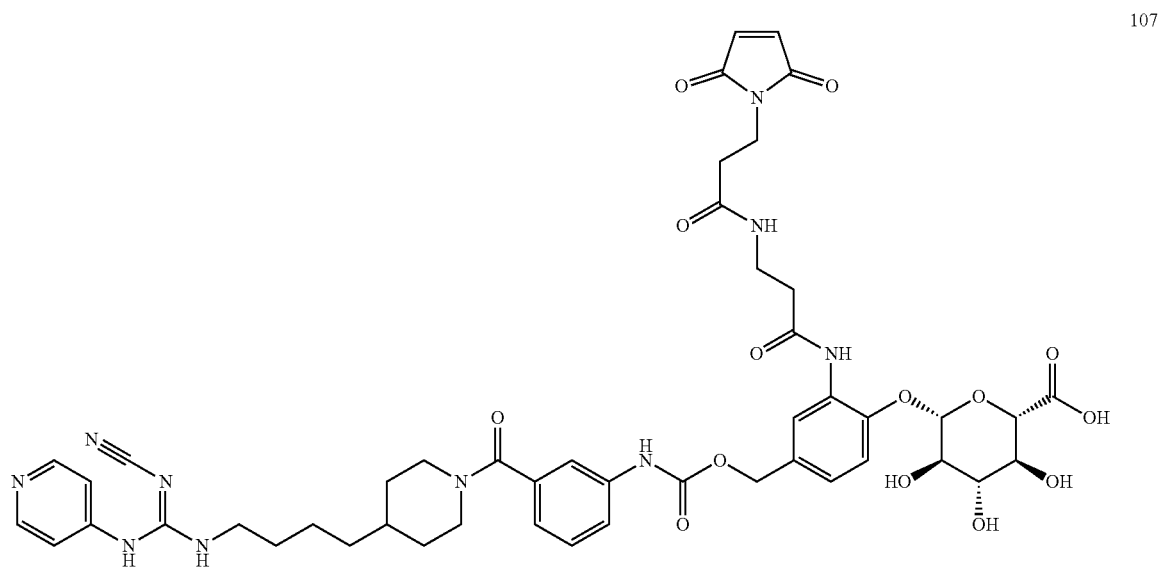 [SMILES: N#C/N=C(/NCCCCC1CCN(C(=O)c2cccc(NC(=O)OCc3ccc(O[C@@H]4O[C@H](C(=O)O)[C@@H](O)[C@H](O)[C@H]4O)c(NC(=O)CCNC(=O)CCN4C(=O)C=CC4=O)c3)c2)CC1)Nc1ccncc1]

The title compound was prepared according to the method of compound 11 using 2,5-dioxopyrrolidin-1-yl 3-(2,5-dioxopyrrol-1-yl)propanoate as the starting NHS ester. LCMS: $t_R$=0.85 min; m/z=983.33 [M+H]$^+$.

Example 99: Binding and Cytoxicity of NAMPTi Compounds

NAMPTi compounds and derivatives thereof bearing functional groups on their NAMPT Tail ($T_N$) Units for covalent attachment as a NAMPT Drug Unit to a Linker Unit of a Drug Linker compound or Ligand Drug Conjugate were evaluated for binding to enzymatically competent NAMPT using a fluorescence polarization assay as described in Example X, and for cytotoxicity using the CellTiter-Glo™ assay as described in Example XX. The results of those assays are presented in Table 1. Modifications to $T_N$ Units of NAMPTi compounds (e.g., CHS-828, FK-866, compound 30, and compound 52) to provide NAMPTi derivatives suitable for the aforementioned covalent attachment typically resulted in negligible to modest reductions in NAMPT enzyme binding, which showed with the exception of compound 43, significant improvement in binding relative to parent compound 30. In vitro cytotoxicities were more varied, with differences in membrane permeability potentially influencing the observed $IC_{50}$ values. Tighter-binding compounds determined from the polarization assay representation various NAMPT Head Unit classes were selected for further elaboration into drug linker moieties within Drug Linker compounds and Ligand Drug Conjugates. Those elaborations employed carbamate or benzyl ether functional groups or methylene-alkoxy carbamate (MAC) units for covalent attachment of the NAMPT Drug Unit to a self-immolative Spacer Unit in the Linker Units of the drug linker moieties, depending on the functional group presented by the $T_N$ Unit.

TABLE 1

$IC_{50}$ values (nM) for NAMPTi compounds and derivatives thereof in the fluorescence polarization (FP) assay for binding to purified NAMPT, and in a cytotoxicity (CellTiter-Glo) assay in 4 cell lines: BxPC-3 (pancreatic adenocarcinoma), HepG2 (hepatocellular carcinoma), L540cy (Hodgkin's lymphoma), and MOLM-13 (acute myeloid leukemia).

| Compound ID | FP | Cytotoxicity | | | |
| --- | --- | --- | --- | --- | --- |
| | | BxPC-3 | HepG2 | L540cy | MOLM-13 |
| FK-866 | 29 | 36.2 | 5.45 | 7.32 | 6.64 |
| 3 | 40 | 38.5 | 8 | 8.5 | 7 |
| 4 | 114 | ND | ND | ND | ND |
| 5 | 101 | 694 | 1000 | 35 | 40 |
| 6 | 36 | 193 | 29 | 20 | 8 |
| 7 | 79 | ND | ND | ND | ND |
| 8 | 101 | 642.65 | 220.8 | 87.27 | 98.99 |
| 9 | 80 | ND | ND | ND | ND |
| 10 | 91 | ND | ND | ND | ND |
| 30 | 335 | 12.35 | 4.15 | 4.12 | 7.25 |
| 43 | 82 | 8 | 4 | 3 | 6 |
| 52 | 41 | 39.05 | 8.75 | 4.76 | 5.26 |
| 60 | 62 | 126 | 35 | 31 | 8 |
| 66 | 24 | 209.3 | 59.76 | 22.48 | 26.85 |
| 67 | 16 | 1000 | 948 | 265 | 108 |
| 68 | 27 | 1000 | 1000 | 1000 | 811 |
| 69 | 35 | 96.88 | 12.49 | 9.12 | 18.03 |
| 72 | 29 | 1000 | 1000 | 1000 | 806.8 |
| CHS-828 | 85 | 8.02 | 1.16 | 2.22 | 4.62 |
| 80 | 17 | 6.12 | 1.08 | 0.78 | 1.63 |
| 81 | 24 | 17.73 | 6.44 | 1.6 | 2.07 |
| 82 | ND | 169 | 25 | 39 | 10 |
| 83 | 32 | 886.3 | 75.44 | 51.18 | 153.4 |

The structures of FK-866 and CHS-828 are as follows:

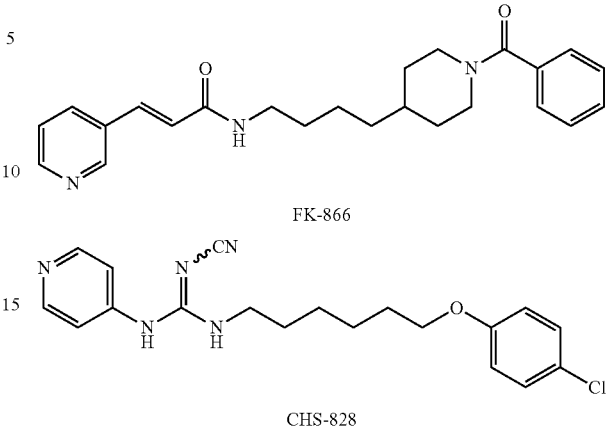

FK-866

CHS-828

Example 100: In Vitro Activity of Antibody-Drug Conjugates

ADCs were prepared by full reduction of interchain disulfides to reveal 8-conjugatable cysteines/antibody and subsequent alkylation with the maleimide-containing drug-linkers. Representative ADCs for pyridyl acrylamide, pyridyl urea, and pyridyl squaramide NAMPT Head Unit classes were prepared targeting antigen 1, antigen 2 or antigen 3. All ADCs were loaded at 8-NAMPT Drug Units/ antibody Ligand Unit and were monomeric by size-exclusion chromatography. ADC were tested for their ability to deplete NAD using the NAD-Glo assay.

Conjugates targeting antigen Ag1, which is a ubiquitous and ready internalizable antigen on cancer cells, showed strong activity against most cells lines, with poor activity against BxPC-3 reflecting the lower sensitivity of this cell lines to free drugs (Table 2). Conjugates targeting Ag2 were highly active against CD30-positive L540cy cells, while conjugates targeting antigen Ag3 were active against Hep3B and JHH-7 cells. No measurable activity for Ag2 ADCs was observed in CD30-negative cell lines, which were otherwise sensitive to targeted ADCs, indicating the high degree of immunological specificity of the constructs.

TABLE 2

$IC_{50}$ values (ng/mL) for Antibody-Drug Conjugates in the NAD-Glo assay.

| ADC ID | NAD depletion ($IC_{50}$, ng/ml) | | | | | |
| --- | --- | --- | --- | --- | --- | --- |
| | BxPC-3 | HL-60 | L540cy | MOLP-8 | Hep3B | JHH-7 |
| Ag1-17 | >1000 | 350 | 9.4 | 6.8 | 3.7 | 15.1 |
| Ag1-47 | >1000 | 322 | 13.2 | 11.7 | | |
| Ag1-64 | >1000 | | 58.6 | | | |
| Ag2-17 | >1000 (Ag+) | >1000 (Ag+) | 3.7 | >1000 (Ag+) | >1000 (Ag+) | >1000 (Ag+) |
| Ag2-47 | >1000 (Ag−) | >1000 (Ag−) | 6.1 | >1000 (Ag−) | >1000 (Ag−) | >1000 (Ag−) |
| Ag3-17 | | | | | 2.2 | 6.1 |
| Ag3-47 | | | | | 42.3 | 46.3 |
| Ag3-64 | | | | | 43.7 | 127 |

Example 101: In Vivo Xenograft Models

Figure 2:
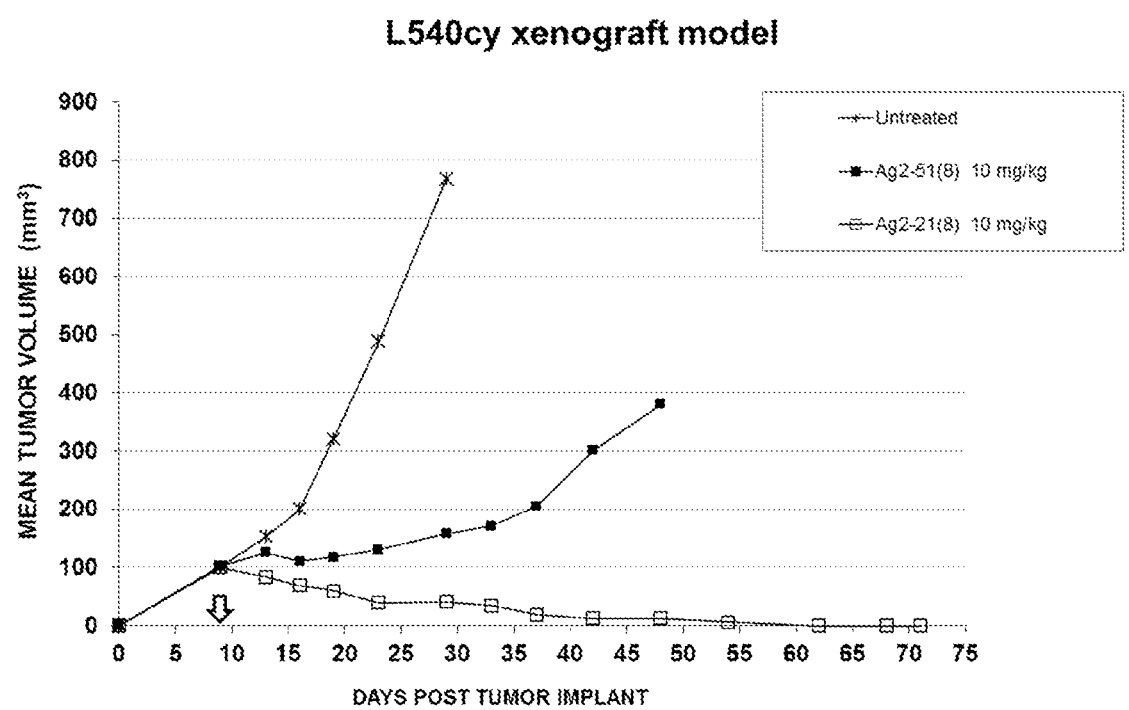
FIG. 2 shows variation over time (days) in tumor volume (mm$^3$) in a L450cy xenograft model post tumor implant in untreated SCID mice in comparison to those treated with 10 mg/Kg (i.p.) Antibody Drug Conjugates (8 NAMPT Drug Units/Ab) prepared from chimeric antibody cAC10, which targets Ag2 (CD30) expressed by the implanted L450cy tumor cells, and Drug Linker compound 21 or Drug Linker compound 51.

The anti-Ag2 chimeric antibody cAC10, which targets CD30, was conjugated to 8 NAMPT Drug Units/Ab using Drug Linker compound 21 in which the Linker Unit contains a PEG Unit and is an analog of Drug Linker compounds 17, which does not contain a PEG Unit. The Antibody Drug Conjugate so prepared is identified as Ag2-21. SCID mice were implanted with L450cy tumor cells on day 0. Tumors reached 100 mm$^3$ on day 9, whereupon the mice were treated with a single dose of 1, 3 or 10 mg/kg (ip) of Ag2-21. Tumor sizes were monitored out to 71 days, resulting in complete regressions for animals treated with Ag2-21 (FIG. 1) at 3 and 10 mg/Kg and tumor growth delay at 1 mg/Kg in comparison to mice treated with 10 mg/kg non-binding control ADC (h00-21). That dose ranging study confirms an earlier experiment involving treatment in the same xenograft model with 10 mg/Kg Ag2-21, which was done in comparison to untreated animals and animals treated with 10 mg/Kg Ag2-51 prepared from cAC10 antibody and Drug Linker compound 51 (FIG. 2). In that earlier experiment complete regression was first observed for animals treated with Ag2-21 and tumor delay growth was observed for animals treated with Ag2-51.

TABLE 3

Xenograft data for ADCs from Drug Linker compound 17

| Xenograft | Targeted Antigen | DAR | Dose mg/Kg | Dose Schedule | Median survival |
|---|---|---|---|---|---|
| L540cy | Ag2 | 8 | 3 | single | 29/>64*** |
| L-428 | Ag2 | 8 | 10 | single | 45/>61** |
| L-82 | Ag2 | 8 | 10 | single | 17/24 |
| JHH-7 | Ag3 | 8 | 10 | single | 14/24* |
| SU-DHL-8 | Ag4 | 8 | 10 | single | 15/58** |
| Ramos | Ag4 | 8 | 10 | single | 28/>35*** |
| MOLM-13 | Ag5 | 10 | 10 | q7dx3 | 19/35 |
| MOLM-13 | Ag6 | 10 | 10 | q7dx3 | 19/35 |

Complete responses (CRs) reflect number of animals in treated group in the study with no observable tumor mass at any time during the experiment relative to the total number of animals as indicated by: *CR 6/6 or 5/5; CR 4/5; *CR 1/6.

Median survival reflects the days

Example 102: Tolerability of Antibody-Drug Conjugates

Figure 3:
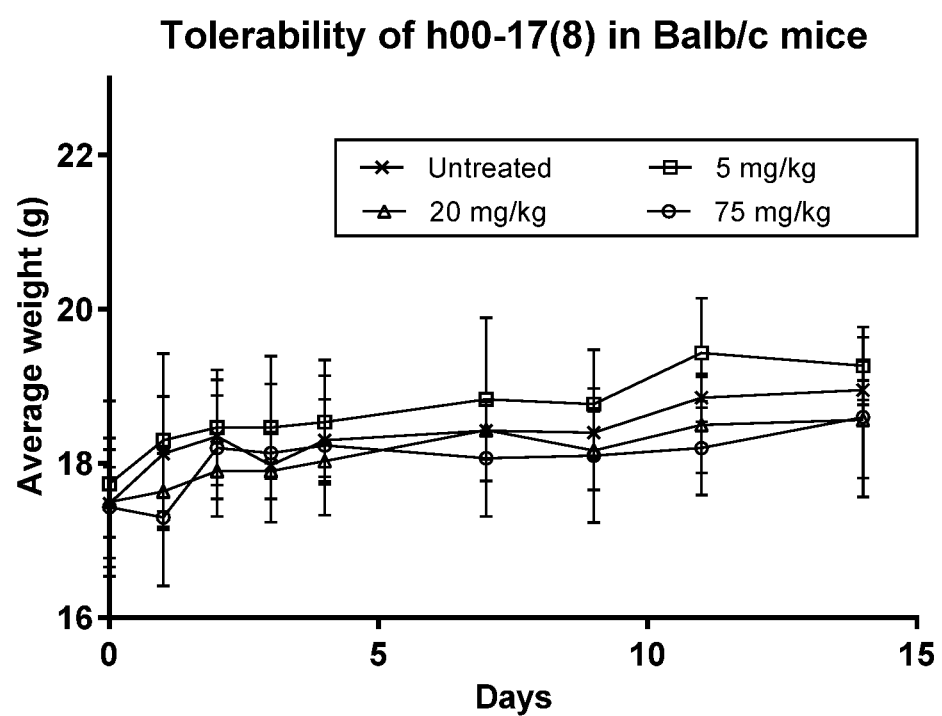
FIG. 3 shows the variation over time (days) in average weight of Balb/c mice treated at various dose levels with an Antibody Drug Conjugate conjugated to 8 NAMPT Drug Units prepared from a non-targeting antibody (h00) and Drug Linker compound 17.

Balb/c mice were administered either 5 mg/Kg, 20 mg/Kg or 75 mg/Kg Antibody Drug Conjugate identified as h00-17(8), which has a loading of 8 NAMPT Drug Units and was prepared from a non-binding control antibody (h00) and Drug Linker compound 17. Treatments with the Conjugates are well-tolerated, with no weight loss or outward signs of toxicity observed in comparison to untreated animals (FIG. 3).

---

What is claimed is:

1. A Ligand Drug Conjugate (LDC) compound, wherein the compound is represented by the structure of:

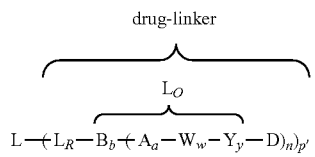

or a pharmaceutically acceptable salt thereof, wherein
L is a Ligand Unit;
D is a NAMPT Drug Unit represented by the general structure of:

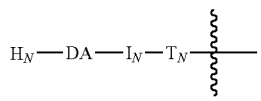

or a pharmaceutically acceptable salt thereof, wherein the wavy line indicates the site of covalent attachment to $L_O$ or $L_R$, depending on the presence or absence of $L_O$;

$H_N$ is a NAMPT Head Unit, wherein the NAMPT Head Unit is a $C_5$-$C_{24}$ heteroaryl or partially aromatic $C_9$-$C_{24}$ heterocyclyl, optionally substituted, wherein the $C_5$-$C_{24}$ heteroaryl or partially aromatic $C_9$-$C_{24}$ heterocyclyl comprises an optionally substituted 5- or 6-membered nitrogen-containing heteroaromatic ring system corresponding to the heterocycle of nicotinamide, and is capable of interacting with enzymatically competent NAMPT homodimer at its nicotinamide mononucleotide binding site when the NAMPT Drug Unit is released from a Ligand Drug Conjugate compound as a NAMPT inhibitor (NAMPTi) compound or derivative thereof;

DA is a Donor-Acceptor Unit wherein the Donor-Acceptor Unit is or comprises a hydrogen bond donor or acceptor functional group and is bonded to a carbon skeletal atom at position 2 or 3 of the 5-membered nitrogen-containing heteroaromatic ring system or at position 3 or 4 of the 6-membered nitrogen-containing heteroaromatic ring system, with optional formal cyclization of DA back to an adjacent skeletal carbon atom of the 6-membered nitrogen-containing heteroaromatic ring system through an introduced optionally substituted non-aromatic carbon atom or an optionally substituted nitrogen, oxygen or sulfur atom resulting in a partially aromatic or fully aromatic fused 6,5- or 6,6- ring system,
wherein said bonding of DA is in relation to a skeletal nitrogen atom of the 5- or 6 membered nitrogen-containing heteroaromatic ring system and wherein said formal cyclization to the adjacent carbon atom of the 6-membered nitrogen-containing heteroaromatic ring system substantially retains the hydrogen bonding capability of the donor or acceptor functional group of DA in absence of said cyclization;

$I_N$ is an Interconnecting Unit, wherein the Interconnecting Unit is or comprises —$X^1$—[C(=O)]$_{0,1}$—, —$X^1$—S(=O)$_{1,2}$—, —$X^2$—$C_6$-$C_{24}$ arylene-[C(=O)]$_{0,1}$—, —$X^2$—$C_6$-$C_{24}$ arylene-[S(=O)]$_{1,2}$]$_{0,1}$, —$X^2$—$C_6$-$C_{24}$ arylene-O—, —$X^2$—$C_5$-$C_{24}$ heteroarylene-[C(=O)]$_{0,1}$]-, —$X^2$—$C_5$-$C_{24}$ heteroarylene-[S(=O)]$_{1,2}$]$_{0,1}$, —$X^2$—$C_5$-$C_{24}$ heteroarylene-O— or —$X^2$—$C_3$-$C_{20}$ heterocyclo-[C(=O)]$_{0,1}$]-, wherein the arylene, heteroarylene and heterocyclo are optionally substituted;

$X^1$ is optionally substituted $C_5$-$C_7$ alkylene;
$X^2$ is absent or is an optionally substituted $C_1$-$C_4$ alkylene;
$T_N$ is a NAMPT Tail Unit, wherein the NAMPT Tail Unit is or comprises an optionally substituted amino-alcohol residue or a carboxylic acid-alcohol residue, the —O— or optionally substituted nitrogen of which is the site of covalent attachment to $L_O$, or $L_R$, depending on the presence or absence of $L_O$, or $T_N$ is or comprises an optionally substituted benzamide moiety, the amide nitrogen atom of which is bonded to $I_N$ with optional cyclization of that atom back to $I_N$ or to the remainder of $T_N$, and the aromatic ring of which is at least substituted with a hydroxyl, thiol or amino residue, the —O—, —S— or optionally substituted nitrogen atom of which at position 3 or 4 relative to the site at which the amide carbonyl carbon atom is attached is the site of covalent attachment to $L_O$ or $L_R$, depending on the presence or absence of $L_O$, or $T_N$ is or comprises an optionally substituted aryl or biaryl moiety, an aromatic skeletal atom of which is bonded to $I_N$, or to the remainder of $T_N$, and wherein an aromatic ring of which is at least substituted with a hydroxyl, thiol or an amino residue, the —O—, —S— or optionally substituted nitrogen of which is the site of covalent attachment to $L_O$ or $L_R$, depending on the presence or absence of $L_O$, respectively; and wherein $T_N$ or the remainder thereof is bonded to $I_N$, wherein said remainder is an optionally substituted $C_2$-$C_7$ heteroalkylene or an optionally substituted $C_5$-$C_6$ heterocyclo, $L_R$ is a primary linker, which interconnects the Ligand Unit and Drug Unit optionally through $L_O$, as indicated, which is an optional secondary linker;

subscripts a and b independently are 0 or 1, indicating the absence or presence, respectively, of A or B;
subscript n is 1, 2, 3 or 4;
A is a first optional Stretcher; and
B is a Branching Unit, when subscript b is 1 and subscript n is 2, 3 or 4, or B is absent, so that subscript b is 0, when subscript n is 1,
wherein each of A and B is an independently selected single unit or optionally comprises or consists of at least two, three or four independently selected sub-units;
subscript w is 1, indicating the presence of W;
W is a Glucuronide Unit of formula —Y(W')—, wherein W' is a carbohydrate moiety with glycosidic bonding to Y through an optionally substituted heteroatom;
Y is a Spacer Unit; and
subscript y is 1 or 2, indicating the presence of one or two of Y, respectively,
provided that when subscript y is 1, Y is covalently attached to a heteroatom of $T_N$, wherein that heteroatom is selected from the group consisting of —O—, —S— and optionally substituted nitrogen, and
provided that when subscript y is 2, $Y_y$ is —Y—Y'—, wherein Y is a first Spacer Unit and Y' is a second Spacer Unit that is covalently attached to the heteroatom of $T_N$ or a functional group comprising the heteroatom from $T_N$; and wherein the Spacer Unit to which W' is attached is a required self-immolative Spacer Unit; and wherein glycosidase cleavage of the glycosidic bond between W' and the self-immolative Spacer Unit initiates release of the NAMPT Drug Unit as a NAMPTi compound from a drug linker moiety of a Ligand Drug Conjugate compound; and wherein subscript p' is an integer ranging from 1 to 24, and wherein the released NAMPTi compound is capable of inhibiting an enzymatically competent NAMPT homodimer.

2. The Ligand Drug Conjugate compound of claim 1, wherein the Donor Acceptor (DA) Unit comprises an optionally substituted amide functional group or comprises a bioisostere of an amide functional group.

3. The Ligand Drug Conjugate compound of claim 1, wherein the 6-membered nitrogen-containing heteroaromatic ring system of $H_N$ is that of pyridine with optional cyclization of DA back to the pyridine aromatic ring system through an introduced aromatic oxygen, sulfur or an optionally substituted nitrogen atom so that $H_N$ contains a 6-5 fused aromatic ring system.

4. The Ligand Drug Conjugate compound of claim 1, wherein each of the NAMPT homodimers of the enzymatically competent NAMPT homodimer has the amino acid sequence of SEQID 1.

5. The Ligand Drug Conjugate compound of claim 1, wherein the NAMPT Head Unit has the structure of:

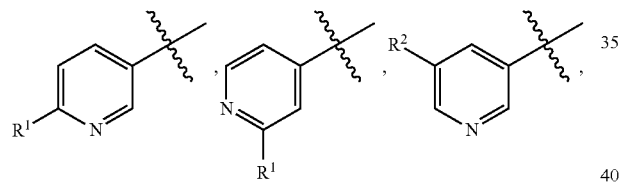

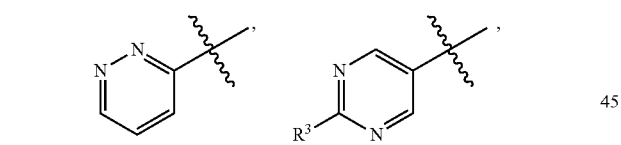

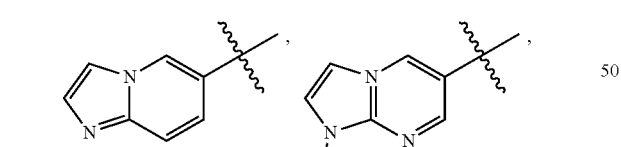

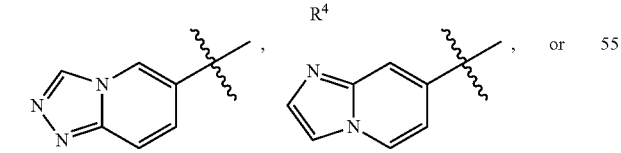

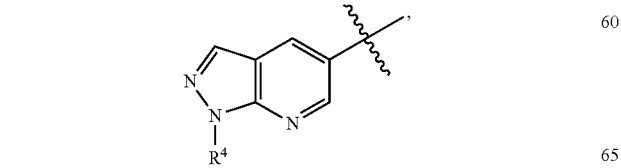

or a pharmaceutically acceptable salt thereof, or
the NAMPT Heat Unit has the structure of:

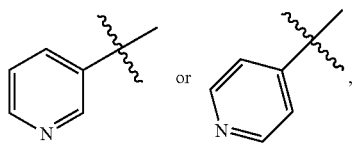 [SMILES: *c1cccnc1 ; *c1ccncc1]

or a pharmaceutically acceptable salt thereof, wherein $R^1$ is hydrogen, —$NH_2$ or chloro;

$R^2$ is fluoro;

$R^3$ is hydrogen or —$NH_2$; and the wavy line indicates the site of covalent attachment to DA and an adjacent aromatic carbon atom thereto is the site of said optional cyclization by DA to $H_N$.

6. The Ligand Drug Conjugate compound of claim 2, wherein the Donor-Acceptor Unit has the structure of:

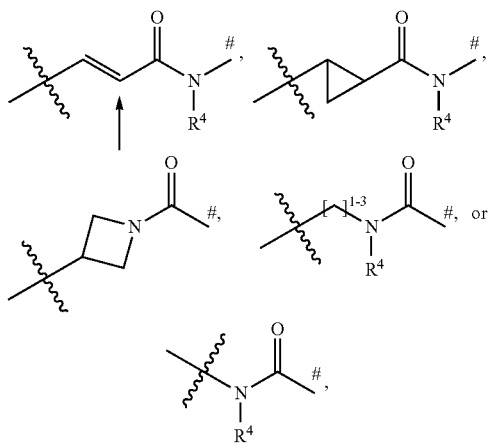

or the Donor-Acceptor Unit the structure of:

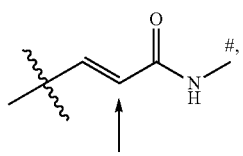

wherein $R^4$ is hydrogen or optionally substituted $C_1$-$C_4$ alkyl;

DA is optionally cyclized to $H_N$, wherein said cyclization is to the $sp^2$ carbon atom proximal to the carbonyl carbon (as indicated) through an introduced optionally substituted non-aromatic carbon atom or an optionally substituted aromatic heteroatom;

the wavy line indicates the site of covalent attachment to $H_N$, and the aromatic carbon atom adjacent thereto is the site of said optional cyclization by DA to $H_N$; and the pound sign (#) indicates the site of covalent attachment to $I_N$, or wherein the Donor-Acceptor Unit has the structure of:

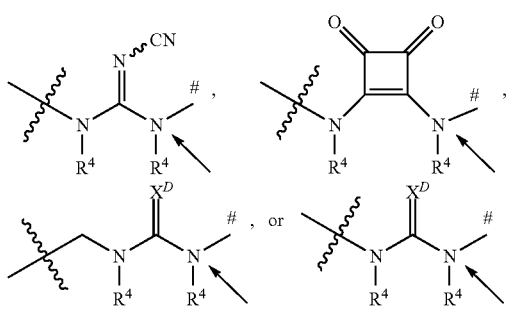

or a pharmaceutically acceptable salt thereof, or the Donor-Acceptor Unit has the structure of:

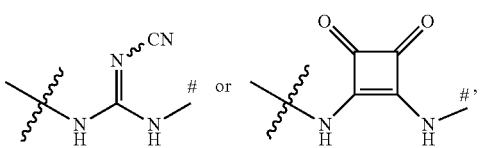

or a pharmaceutically acceptable salt thereof, wherein $X^D$ is O, S or $NR^D$, wherein the nitrogen atom is optionally protonated and $R^D$ is hydrogen or optionally substituted $C_1$-$C_4$ alkyl;

each $R^4$ is independently selected from the group consisting of hydrogen and optionally substituted $C_1$-$C_4$ alkyl, or both $R^4$ together with the nitrogen atoms to which they are attached and the intervening carbon atom(s) define an optionally substituted $C_5$-$C_6$ heterocyclo;

the pound sign (#) indicates the site of covalent attachment to $I_N$; and the wavy line indicates the site of covalent attachment to $H_N$, wherein DA is optionally cyclized back to an adjacent aromatic carbon atom of $H_N$, wherein said cyclization is from the indicated nitrogen atom so that $R^4$ bonded thereto is replaced by a covalent bond to said adjacent aromatic carbon atom, or is from $X^D$ when $X^D$ is —$NR^D$, either directly or through an introduced —S(=O)$_{0-2}$— moiety, in which either instance $R^D$ is replaced by a bond to said adjacent carbon atom or the sulfur atom of said introduced moiety.

7. The Ligand Drug Conjugate compound of claim 1, wherein $H_N$-DA- has the structure of:

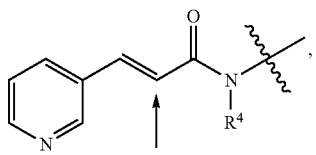

or a pharmaceutically acceptable salt thereof, wherein $R^4$ is hydrogen or optionally substituted $C_1$-$C_4$ alkyl; and the wavy line indicates the site of covalent attachment to $I_N$, and wherein the sp$^2$ carbon atom proximal to the carbonyl carbon atom is the site (as indicated) of optional cyclization to $H_N$ through an introduced optionally substituted non-aromatic carbon atom or an optionally substituted aromatic heteroatom.

8. The Ligand Drug Conjugate compound of claim 1, wherein the NAMPT Tail Unit is or comprises an optionally substituted amino alcohol moiety, wherein the oxygen atom of the alcohol is the site of covalent attachment to $L_O$ or $L_R$, depending on the presence or absence of $L_O$, respectively, or wherein the NAMPT Tail Unit is an amino alcohol moiety having the structure of:

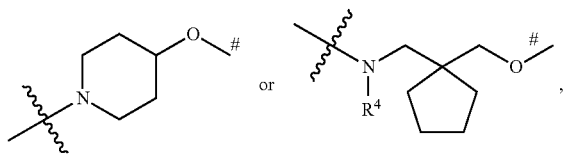

or a pharmaceutically acceptable salt thereof, wherein $R^4$ is hydrogen or optionally substituted $C_1$-$C_4$ alkyl;

the wavy line indicates the site of covalent attachment to $I_N$; and the pound sign (#) indicates the site of covalent to $L_O$ or $L_R$, depending on the presence or absence of $L_O$, respectively, or wherein the NAMPT Tail Unit is or comprises an optionally substituted benzamide moiety having a functional group providing a heteroatom that is the site of covalent attachment to $L_O$ or $L_R$, depending on the presence or absence of $L_O$, respectively, or wherein the NAMPT Tail Unit is a benzamide moiety having the structure of:

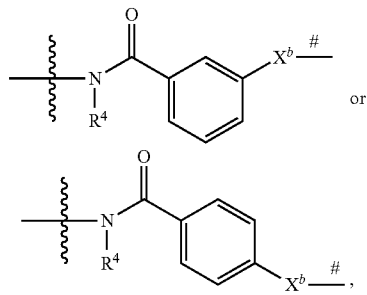

wherein $X^b$ is —S—, —O— or —NH—, optionally substituted; and $R^4$ is hydrogen or optionally substituted $C_1$-$C_4$ alkyl, wherein the benzamide moiety is optionally cyclized to $I_N$, wherein the amide nitrogen atom of the benzamide moiety is the site of said cyclization so that $R^4$ is replaced by a covalent bond to $I_N$, or wherein the NAMPT Tail Unit is a benzamide moiety having the structure of:

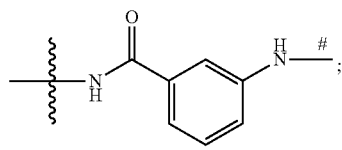 [SMILES: *NC(=O)c1cccc(NC)c1]

wherein the wavy line indicates the site of covalent attachment to $I_N$;

the pound sign (#) indicates the site of covalent attachment to $L_O$ or $L_R$, depending on the presence or absence of $L_O$, respectively.

9. The Ligand Drug Conjugate compound of claim 8, wherein $I_N$ is —CH$_2$—(CH$_2$)$_{3-7}$—CH$_2$—, —CH$_2$—(CH$_2$)$_{3-7}$—CH$_2$—O—, —CH$_2$—(CH$_2$)$_{3-7}$—C(=O)—, —CH$_2$—(CH$_2$)$_{3-7}$—S(=O)$_2$— or —CH$_2$—(CH$_2$)$_{3-7}$—S(=O)—.

10. The Ligand Drug Conjugate compound of claim 8, wherein —$I_N$-$T_N$- has the structure of:

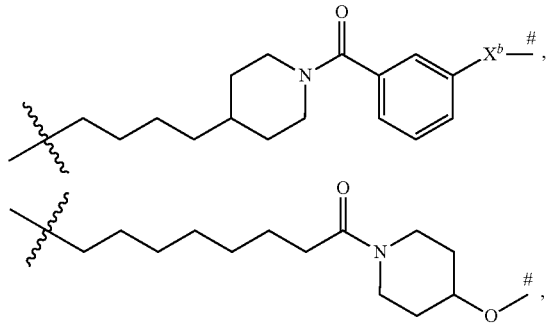

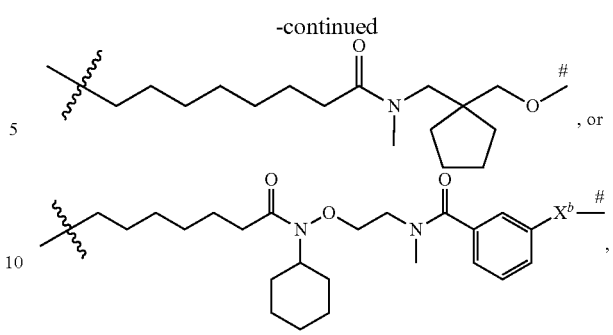

wherein $X^b$ is —NH—, —O— or —S—;
the wavy line indicates the site of covalent attachment to DA; and
the pound sign (#) indicates the site of covalent attachment to $L_O$ or $L_R$, depending on the presence or absence of $L_O$, respectively.

11. The Ligand Drug Conjugate compound of claim 1, wherein
the NAMPT Drug Unit has the structure of:

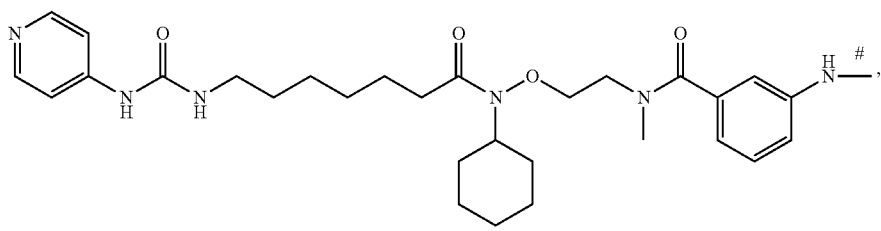

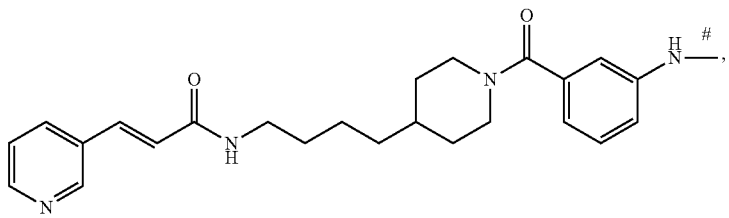

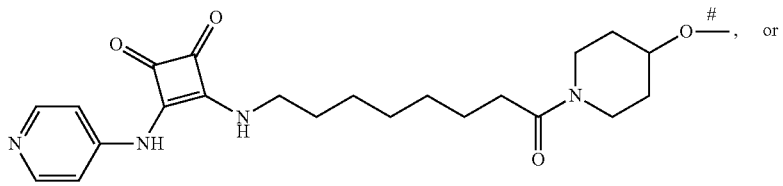

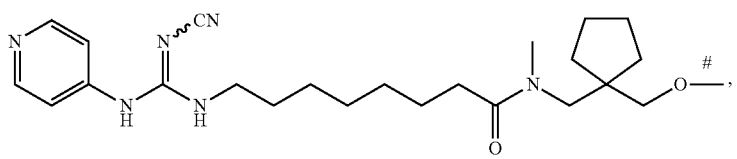

or a pharmaceutically acceptable salt thereof, wherein the pound sign (#) indicates the site of covalent attachment to $L_O$ or $L_R$, depending on the presence or absence of $L_O$, respectively.

12. The Ligand Drug Conjugate compound of claim 1, wherein $L$-$L_R$- has the structure of:

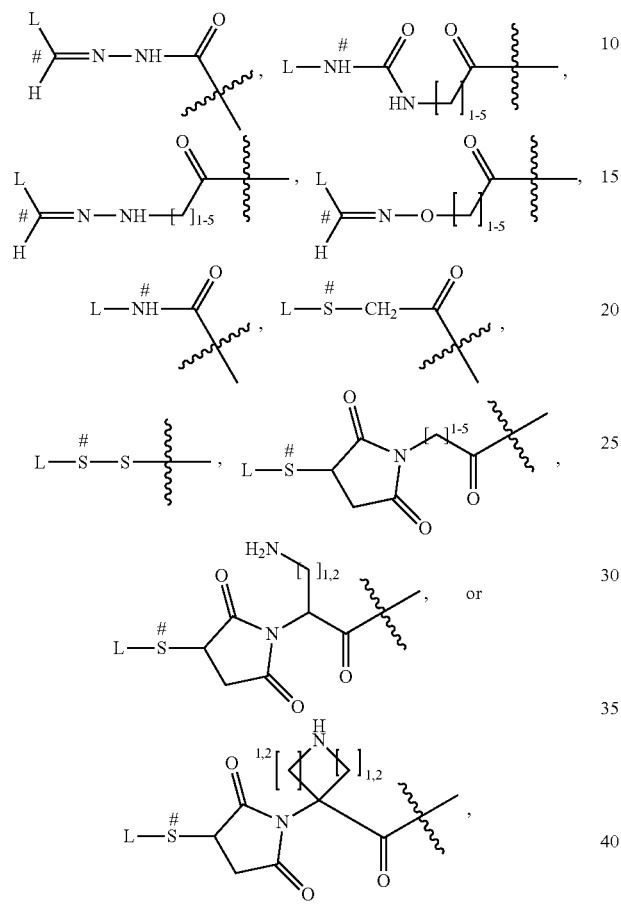

or a pharmaceutically acceptable salt thereof, wherein the indicated (#) nitrogen, carbon or sulfur atom is from the Ligand Unit; and wherein the wavy line indicates the site of covalent attachment to the remainder of the Conjugate structure.

13. The Ligand Drug Conjugate compound of claim 1, wherein the compound is represented by the structure of Formula 1 or Formula 2:

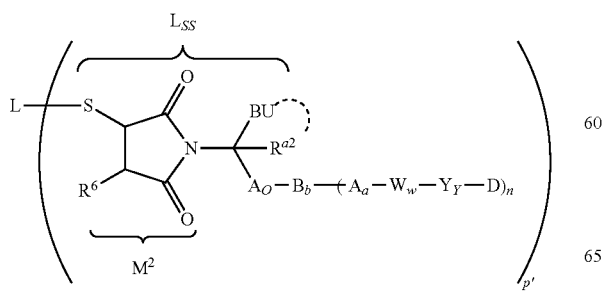
(1)

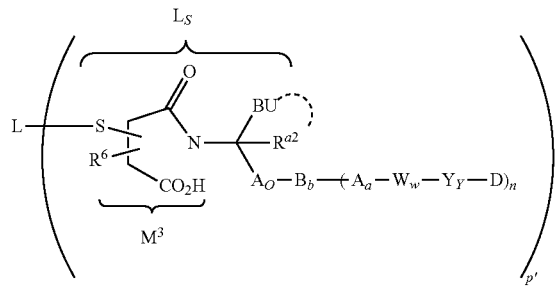
(2)

or a pharmaceutically acceptable salt thereof, wherein
S is a sulfur atom of the Ligand Unit, which in Formula 2 is bonded to the carbon atom α or β to the carboxylic acid functional group of the indicated succinic acid amide ($M^3$) moiety;
$R^6$ is hydrogen or an optionally substituted $C_1$-$C_6$ alkyl, which in Formula 2 is bonded to the saturated carbon atom adjacent to the carbon substituted by L-S—;
$A_O$ is a second optional Stretcher Unit;
BU is a Basic Unit and $R^{a2}$ is an optionally substituted $C_1$-$C_{12}$ alkyl group; and
the dotted curved line indicates optional cyclization so that in the absence of said cyclization BU is an acyclic Basic Unit or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit,
wherein the basic nitrogen atom of the acyclic Basic Unit or cyclic Basic Unit is optionally suitably protected by a nitrogen protecting group, dependent on the degree of substitution of the basic nitrogen atom, or is optionally protonated, or
wherein the compound is represented by the structure of:

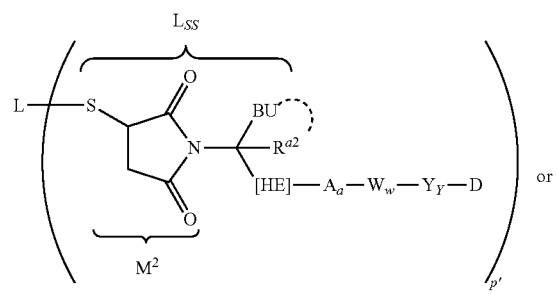 or

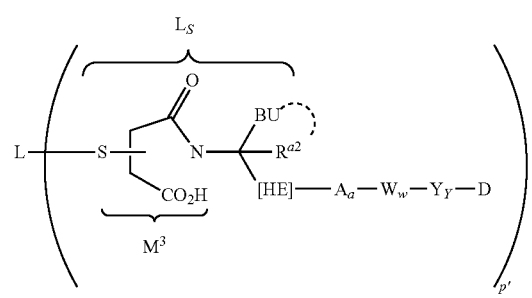

wherein [HE] as $A_O$ is an optional Hydrolysis Enhancing Unit;
the Glucuronide Unit of formula —Y(W')— has the structure of:

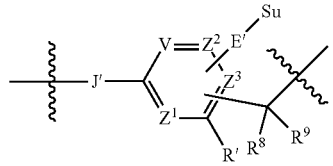

wherein Su is a carbohydrate moiety and -E'- represents an optionally substituted heteroatom of a glycosidic bond cleavable by a glycosidase so that Su-E' is W' and the remainder of the Glucuronide Unit structure is a self-immolative Spacer Unit bonded to W';
J' is an independently selected heteroatom, optionally substituted, and the wavy line thereto is the site of covalent attachment resistant to enzymatic or non-enzymatic cleavage under normal physiological conditions wherein said site of covalent attachment is to A when subscript a is 1 or to the indicated $L_{SS}$ primary linker when subscript a is 0; and
V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—,
provided that one and only one —C($R^8$)($R^9$)— moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su,
provided the —C($R^8$)($R^9$)— and -E'-Su moieties are ortho or para to each other;
$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted,
or
$R^8$ and $R^9$ together with the carbon atom to which both are attached define an optionally substituted $C_5$-$C_{20}$ carbocyclo; and
R' is hydrogen or —$NO_2$, or other electron withdrawing group and
wherein the wavy line adjacent to the —C($R^8$)($R^9$)— moiety indicates the site of covalent attachment of the Glucuronide Unit to Y' when subscript y is 2, or to D when subscript y is 1 wherein the remaining variable groups of the compound structure(s) are as previously defined for Formula 1 and Formula 2.

14. The Ligand-Drug Conjugate compound of claim 13, wherein the compound is represented by the structure of:

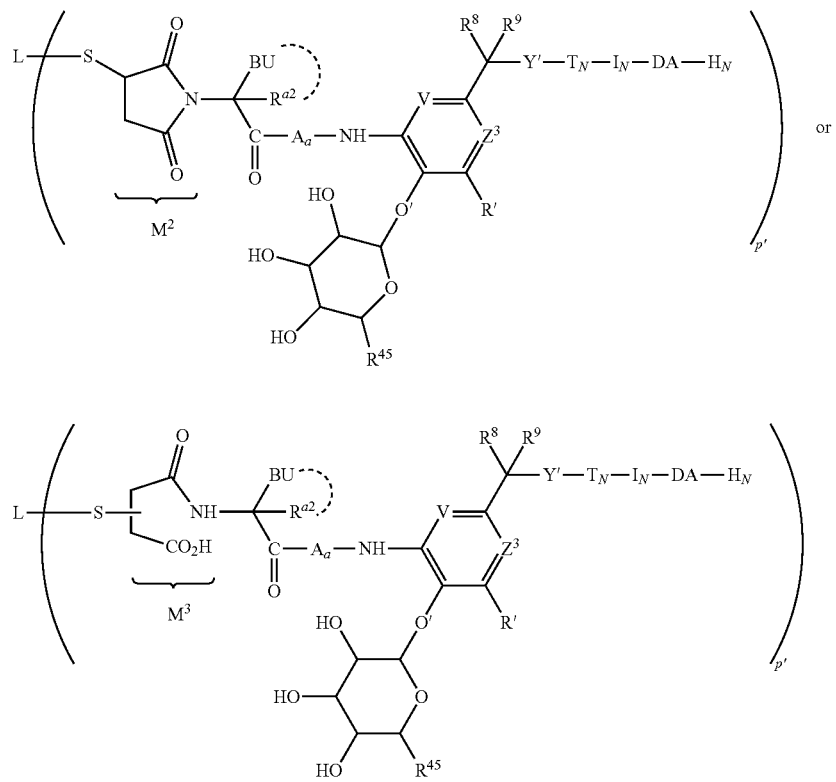

or a pharmaceutical acceptable salt thereof, wherein
R' is hydrogen or —$NO_2$ or other electron withdrawing group;
$R^{a2}$ is hydrogen or $C_1$-$C_6$ alkyl, optionally cyclized to BU, as indicated by the dotted curved line,
BU has the structure of —[C($R^{a1}$)($R^{a1}$)]—[C($R^{a1}$)($R^{a1}$)]$_{0-3}$—N($R^{a3}$)($R^{a3}$),
wherein in the absence of cyclization to $R^{a2}$, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-

$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; and $R^{a3}$ independently are hydrogen, optionally substituted $C_1$-$C_6$ alkyl or $R^{a3}$ together with the nitrogen atom to which both are attached define a $C_3$-$C_6$ heterocyclyl in which the basic nitrogen atom is a skeletal atom, or one of $R^{a3}$ is —H and the other is optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and the basic nitrogen atom bonded to $R^{a3}$ is optionally protonated; and in the presence of cyclization one of $R^{a1}$ or one of $R^{a3}$ is replaced with a bond to a carbon atom of $R^{a2}$ in which $R^{a2}$ is $C_1$-$C_6$ alkyl and the remaining $R^{a1}$ and $R^{a3}$ are as previously defined; and wherein Y' is —$X^a$—, —O—C(=O)—$X^b$— or —OC(=O)NH—$CH_2$—$X^a$—;

wherein $X^a$ or $X^b$ are from $T_N$, wherein —$X^a$— is O or S and $X^b$ is —NH—; and $R^{45}$ is —$CH_2OH$ or —$CO_2H$; and wherein —O'— represents the oxygen atom of the O-glycosidic bond cleavable by the glycosidase, or wherein the compound is represented by the structure of:

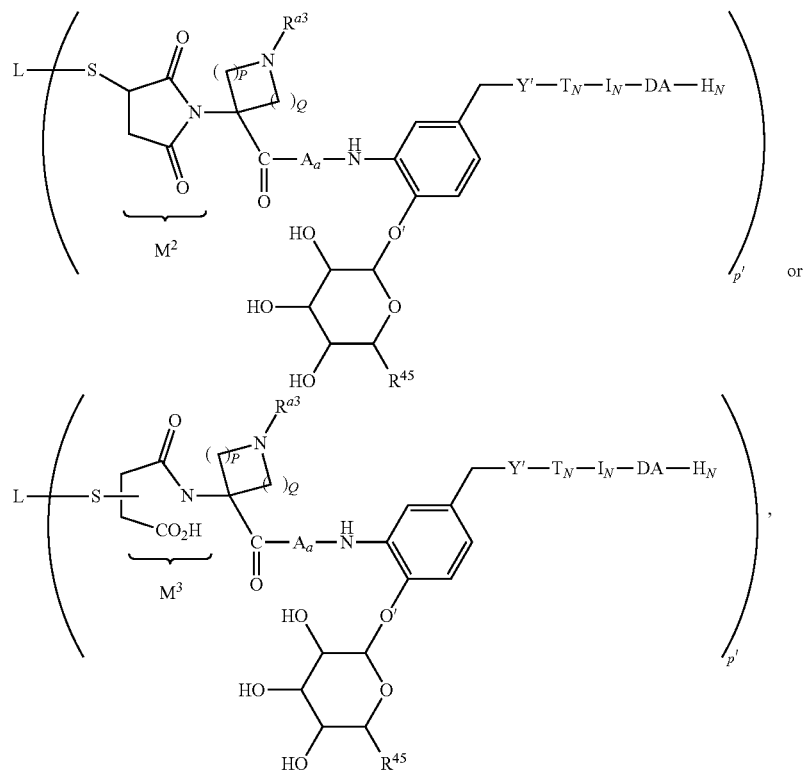

or a pharmaceutically acceptable salt thereof, wherein
subscript P is 1, 2 or 3;
subscript Q ranges from 1 to 6; and
wherein the remaining variable groups are as previously defined, or
wherein the compound is represented by the structure of:

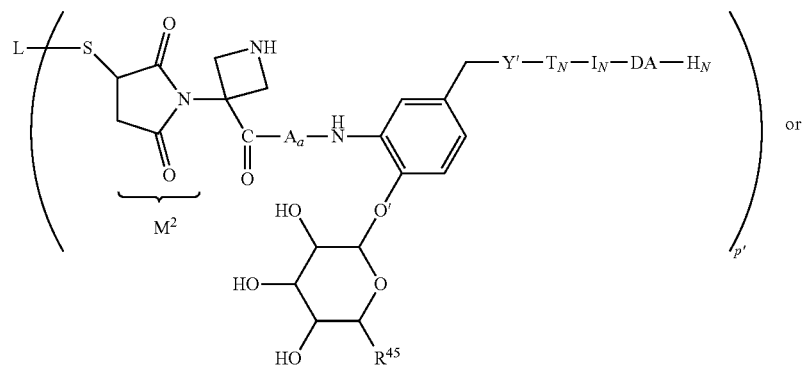

-continued

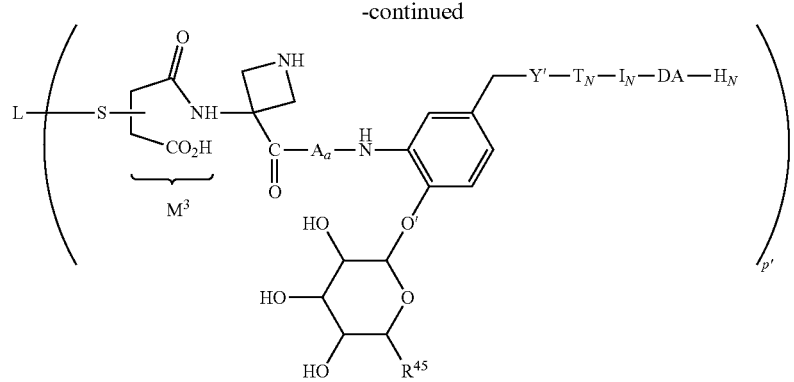

or a pharmaceutically acceptable salt thereof, wherein the variable groups are as previously defined, or wherein the compound is represented by the structure of:

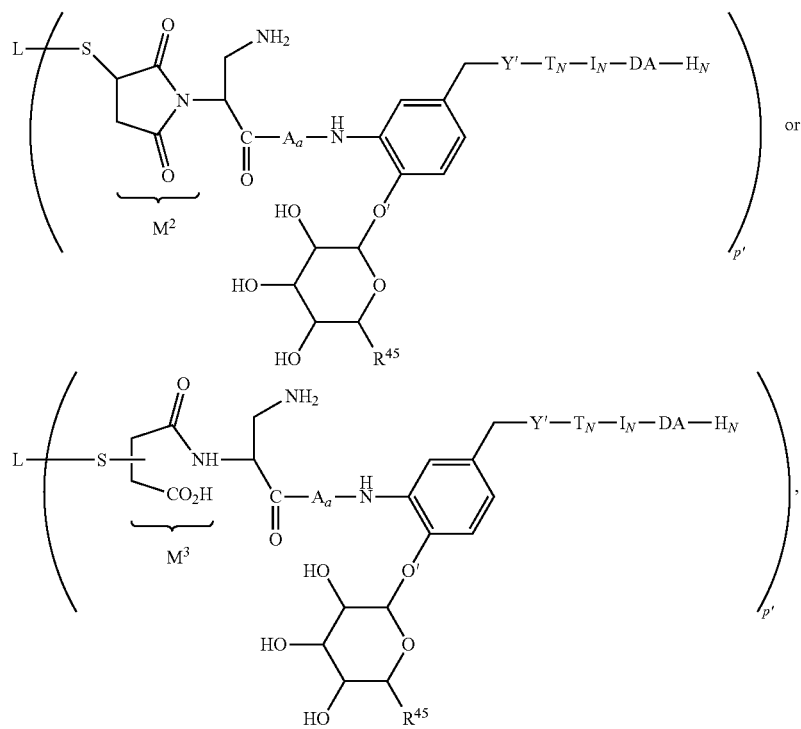

or a pharmaceutical acceptable salt thereof, wherein the variable groups are as previously defined.

15. The Ligand-Drug Conjugate compound of claim 14, wherein A or a subunit thereof has the structure of formula (3) or formula (4):

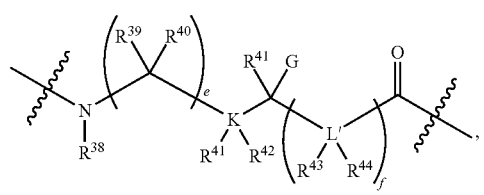

(3)

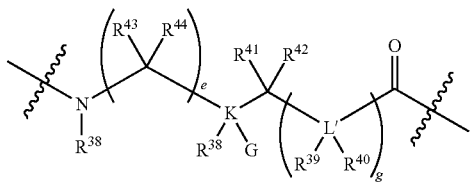

(4)

wherein the wavy lines indicated covalent attachment within the compound structure;

wherein K and L' independently are C, N, O or S, provided that when K or L' is O or S, $R^{41}$ and $R^{42}$ to K or $R^{43}$ and $R^{44}$ to L' are absent, and when K or L' are N, one of $R^{41}$, $R^{42}$ to K or one of $R^{42}$, $R^{43}$ to L' are absent, and provided that no two adjacent L' are independently selected as N, O, or S;

wherein subscripts e and f are independently selected integers that range from 0 to 12, and subscript g is an integer ranging from 1 to 12;

wherein G is hydrogen, optionally substituted $C_1$-$C_6$ alkyl, —OH, —$OR^{PR}$, —$CO_2H$, $CO_2R^{PR}$, wherein $R^{PR}$ is a suitable protecting, or G is —$N(R^{PR})(R^{PR})$, wherein $R^{PR}$ are independently a protecting group or $R^{PR}$ together form a suitable protecting group, or G is —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl;

$R^{39}$-$R^{44}$ are independently selected from the group consisting of hydrogen, optionally substituted $C_1$-$C_6$ alkyl, optionally substituted aryl, and optionally substituted heteroaryl, or $R^{39}$, $R^{40}$ together with the carbon atom to which both are attached, or $R^{41}$, $R^{42}$ together with K to which both are attached when K is a carbon atom, define a $C_3$-$C_6$ carbocyclo, and $R^{41}$-$R^{44}$ are as defined herein, or $R^{43}$, $R^4$ together with L' to which both are attached when L' is a carbon atom define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^4$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^4$ are absent, and when L' is N, one of $R^{43}$, $R^4$ is absent, or A or a subunit thereof is an alpha-amino, beta-amino or another amine-containing acid residue, or wherein A or a subunit thereof has the structure of formula (3a) or formula (4a):

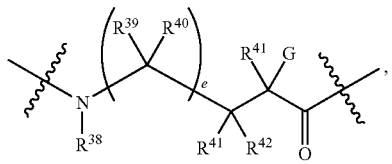

(3a)

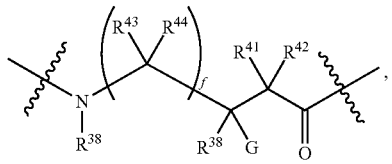

(4a)

wherein subscript e and f are independently 0 or 1.

16. The Ligand-Drug Conjugate compound of claim 14, wherein the Ligand Unit is an antibody or an antigen-binding fragment thereof, thereby defining an antibody Ligand Unit of an antibody drug conjugate (ADC),
wherein the antigen targeted by the antibody Ligand Unit is an accessible cell-surface antigen of abnormal cells that is capable of cellular internalization when bound to an ADC compound and is present in greater copy number on the abnormal cells in comparison to normal cells distant from the site of the abnormal cells, or the antigen is an accessible cell-surface antigen of a vascular epithelial cell in the vicinity of abnormal cells, wherein said antigen is capable of cellular internalization of bound ADC and is present in greater copy number on said cells in comparison to normal epithelial cells distant from the site of the abnormal cells.

17. The Ligand Drug Conjugate compound of claim 16, wherein subscript p' is 2, 4, 8, or 10.

18. The Ligand Drug Conjugate compound of claim 14, wherein the sulfur atom attached to the indicated succinimide ($M^2$) or succinic acid amide ($M^3$) moiety of a drug linker moiety of the Conjugate is that of an antibody or antigen-binding fragment thereof, thereby defining an antibody Ligand Unit, wherein the sulfur atom of the antibody Ligand Unit bonded to the succinic acid ($M^2$) moiety or succinic acid amide ($M^3$) moiety is that of a cysteine residue native to the antibody or antigen-binding fragment thereof or an introduced cysteine residue in the heavy chain or light chain of the antibody or antigen binding-fragment thereof.

19. The Ligand Drug Conjugate compound of claim 1, wherein the compound is represented by the structure of:

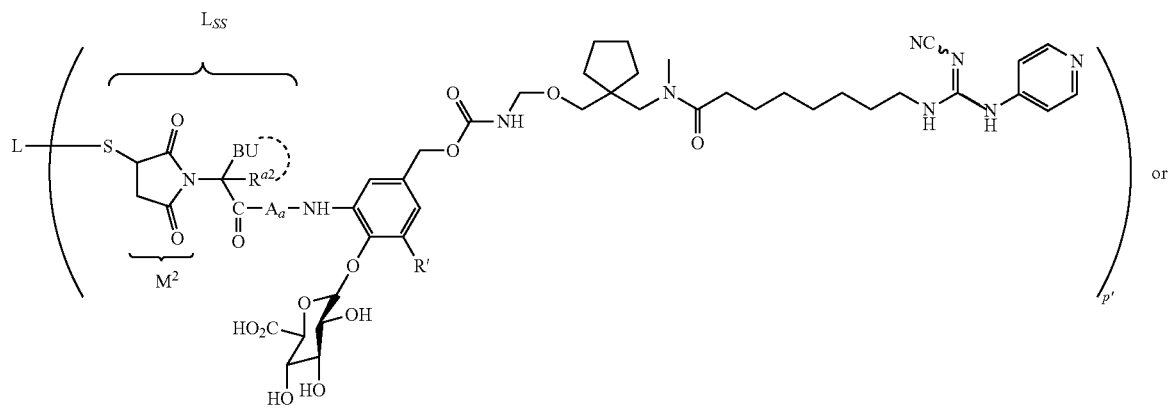

or

-continued
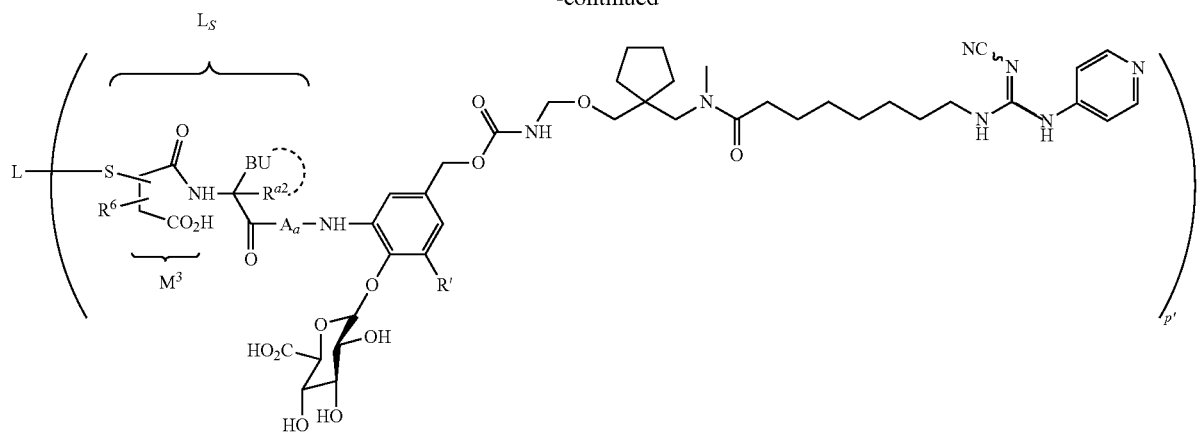
or a pharmaceutical acceptable salt thereof,
or
the compound is represented by the structure of:
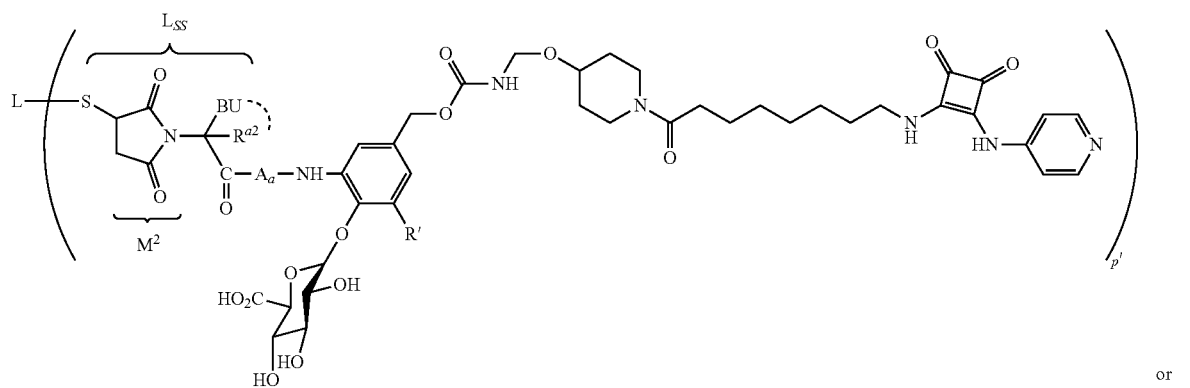
or
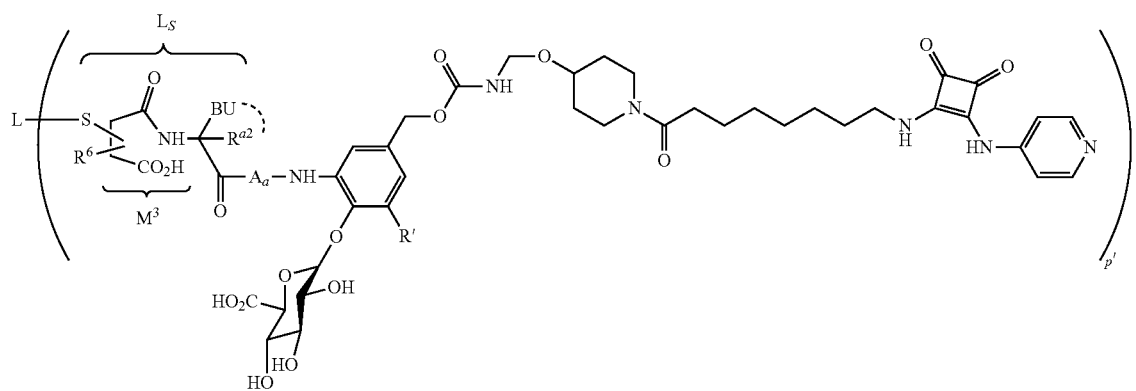

or a pharmaceutical acceptable salt thereof, wherein or
the compound is represented by the structure of:
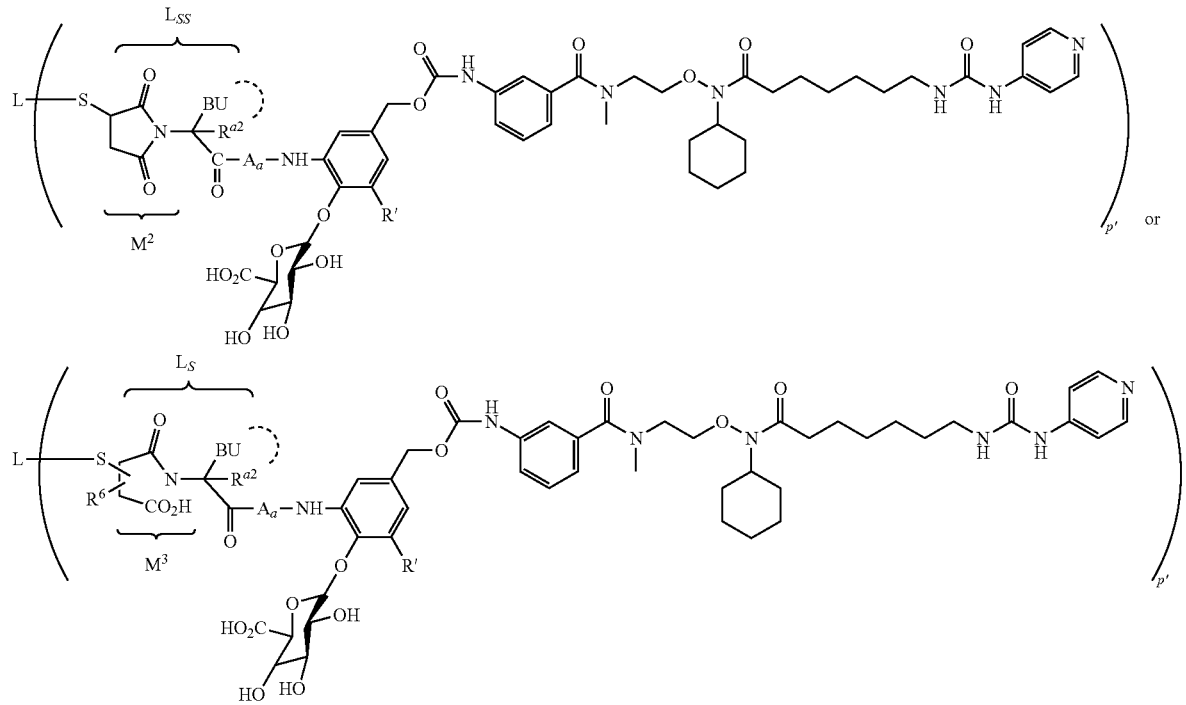
or a pharmaceutical acceptable salt thereof, or
the compound is represented by the structure of:
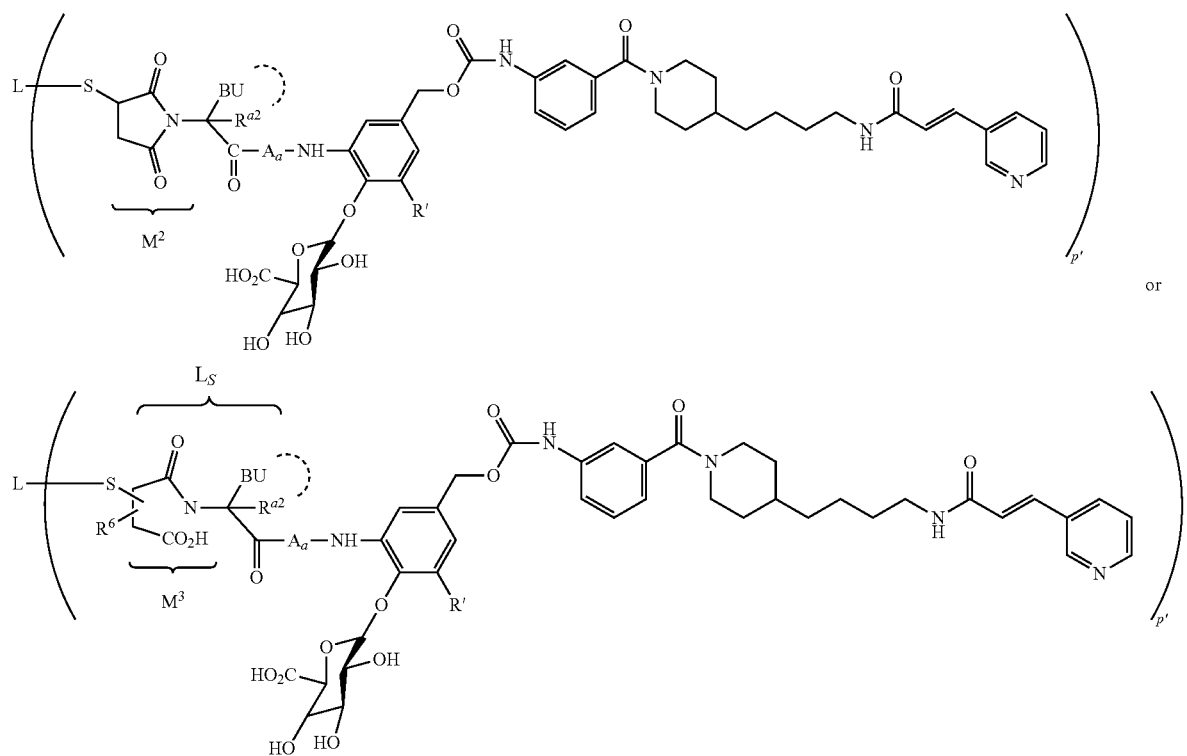
or or a pharmaceutical acceptable salt thereof,
wherein
  subscript a is 1 and A is an amino acid residue;
  BU is an acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and
  R' is hydrogen or —$NO_2$, or
  the compound is represented by the structure of:

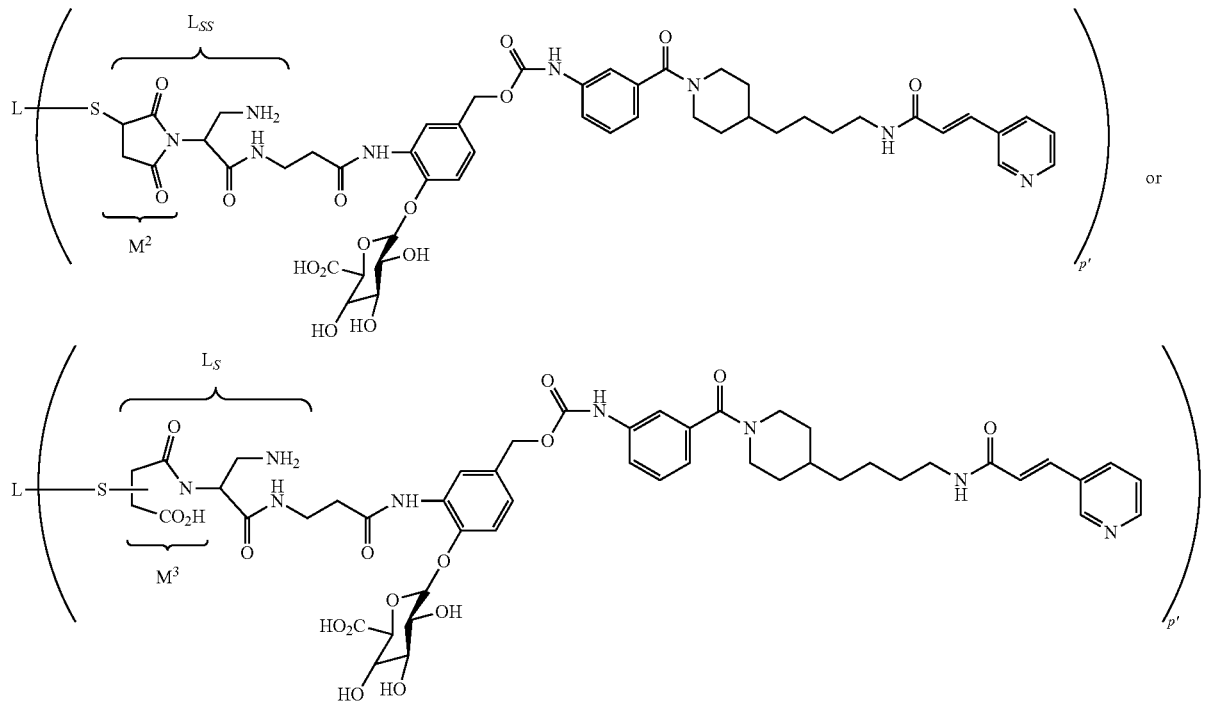

or a pharmaceutical acceptable salt thereof, or
the compound is represented by the structure of:

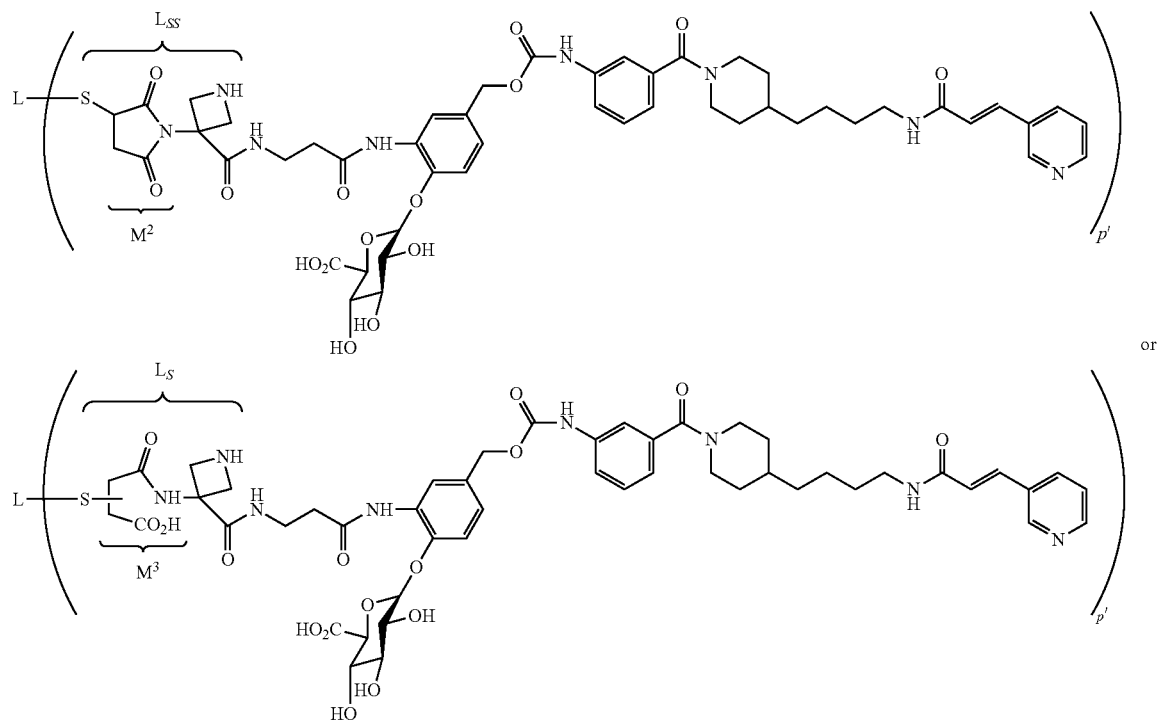

or a pharmaceutical acceptable salt thereof,
wherein
L is an antibody, thereby defining an antibody Ligand Unit of an antibody drug conjugate (ADC), and S is a sulfur atom of the antibody, wherein the antibody is a humanized or chimeric monoclonal antibody.

20. A pharmaceutically acceptable formulation comprising a Ligand Drug Conjugate compound of claim 1 and at least one, two, or three pharmaceutically acceptable excipients, or a pharmaceutically acceptable formulation precursor comprising a Ligand Drug Conjugate compound of claim 1 and at least one, two, or three pharmaceutically acceptable excipients, wherein the formulation precursor is a solid suitable for reconstitution as a liquid formulation for intravenous injection to a subject in need thereof, or a pharmaceutically acceptable formulation comprising a Ligand Drug Conjugate compound of claim 1 and at least one, two, or three pharmaceutically acceptable excipients, wherein one of the excipients is a liquid carrier so that the formulation is a liquid suitable for intravenous injection to a subject in need thereof, wherein the Ligand Drug Conjugate compound is present in an effective amount for treatment of a hyperproliferative disease or condition in said liquid formulation.

* * * * *

UNITED STATES PATENT AND TRADEMARK OFFICE
CERTIFICATE OF CORRECTION

PATENT NO. : 11,638,762 B2
APPLICATION NO. : 16/343140
DATED : May 2, 2023
INVENTOR(S) : Christopher Scott Neumann and Kathleen Olivas It is certified that error appears in the above-identified patent and that said Letters Patent is hereby corrected as shown below:

In the Claims

At Column 412, Claim number 8, Line number 44 (Approx.), delete "—S— —O—" and insert -- —S—, —O— --.

At Column 420, Claim number 14, Line 8, delete "$X^a$–;" and insert --$X^a$–,--.

At Column 423, Claim number 15, Line 29 (Approx.), delete "$R^4$" and insert --$R^{44}$--.

At Column 423, Claim number 15, Line 37, delete "$R^4$" and insert --$R^{44}$--.

At Column 423, Claim number 15, Line 41, delete "$R^4$" and insert --$R^{44}$--.

At Column 423, Claim number 15, Line 42, delete "$R^4$" and insert --$R^{44}$--.

Signed and Sealed this
Nineteenth Day of March, 2024

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 491
<212> TYPE: PRT
<213> ORGANISM: Homo sapiens

<400> SEQUENCE: 1

```
Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140
```

```
Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
    290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Ile Val Glu Gly Met
        355                 360                 365

Lys Gln Lys Met Trp Ser Ile Glu Asn Ile Ala Phe Gly Ser Gly Gly
    370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

Pro Val Ala Asp Pro Asn Lys Arg Ser Lys Lys Gly Arg Leu Ser Leu
            420                 425                 430

His Arg Thr Pro Ala Gly Asn Phe Val Thr Leu Glu Glu Gly Lys Gly
        435                 440                 445

Asp Leu Glu Glu Tyr Gly Gln Asp Leu Leu His Thr Val Phe Lys Asn
    450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490
```